US012351570B2

(12) United States Patent
Heinrich et al.

(10) Patent No.: US 12,351,570 B2
(45) Date of Patent: Jul. 8, 2025

(54) DISUBSTITUTED ALKYNE DERIVATIVES

(71) Applicants: MERCK PATENT GMBH, Darmstadt (DE); RYVU THERAPEUTICS S.A., Cracow (PL)

(72) Inventors: Timo Heinrich, Gross-Umstadt (DE); Carl Petersson, Nykvarn (SE); Mireille Krier, Muehltal (DE); Andrzej Gondela, Tychy (PL); Michal Mikolaj Galezowski, Cracow (PL); Charles-Henry Robert Yves Fabritius, Poznan (PL); Mateusz Oktawian Nowak, Cracow (PL); Marcin Krol, Cracow (PL)

(73) Assignee: MERCK PATENT GMBH, Darmstadt (DE)

( * ) Notice: Subject to any disclaimer, the term of this patent is extended or adjusted under 35 U.S.C. 154(b) by 924 days.

(21) Appl. No.: 17/311,930

(22) PCT Filed: Dec. 20, 2019

(86) PCT No.: PCT/EP2019/086662
§ 371 (c)(1),
(2) Date: Jun. 8, 2021

(87) PCT Pub. No.: WO2020/127960
PCT Pub. Date: Jun. 25, 2020

(65) Prior Publication Data
US 2023/0052586 A1 Feb. 16, 2023

(30) Foreign Application Priority Data
Dec. 21, 2018 (EP) ..................... 18461654

(51) Int. Cl.
*C07D 401/12* (2006.01)
*A61K 31/18* (2006.01)
*A61K 31/275* (2006.01)
*A61K 31/357* (2006.01)
*A61K 31/437* (2006.01)
*A61K 31/44* (2006.01)
*A61K 31/4439* (2006.01)
*A61K 31/4709* (2006.01)
*A61K 31/4985* (2006.01)
*A61K 31/5377* (2006.01)
*C07C 311/29* (2006.01)
*C07D 213/79* (2006.01)
*C07D 215/36* (2006.01)
*C07D 319/18* (2006.01)
*C07D 413/12* (2006.01)
*C07D 471/04* (2006.01)
*C07D 487/04* (2006.01)

(52) U.S. Cl.
CPC ............ *C07D 401/12* (2013.01); *A61K 31/18* (2013.01); *A61K 31/275* (2013.01); *A61K 31/357* (2013.01); *A61K 31/437* (2013.01); *A61K 31/44* (2013.01); *A61K 31/4439* (2013.01); *A61K 31/4709* (2013.01); *A61K 31/4985* (2013.01); *A61K 31/5377* (2013.01); *C07C 311/29* (2013.01); *C07D 213/79* (2013.01); *C07D 215/36* (2013.01); *C07D 319/18* (2013.01); *C07D 413/12* (2013.01); *C07D 471/04* (2013.01); *C07D 487/04* (2013.01)

(58) Field of Classification Search
None
See application file for complete search history.

(56) References Cited

FOREIGN PATENT DOCUMENTS

| EP | 0947500 A1 * | 6/1999 | ........... C07C 233/25 |
|---|---|---|---|
| TW | 201718589 A | 6/2017 | |
| WO | WO-03011868 A1 | 2/2003 | |
| WO | WO-2016081464 A1 | 5/2016 | |
| WO | WO-2016201426 A1 | 12/2016 | |

OTHER PUBLICATIONS

Fra et. al., 2016, Indole Synthesis through Sequential Electrophilic N—H and C—H Bond Activation Using Iodine(III) Reactivity, Chem. Eur. J., 22, 4351-4354 (Year: 2016).*
Ali et al. (2014) Input of Isosteric and Bioisosteric Approach in Drug Design, J. Chem. Soc. Pak., 36, p. 150-169. (Year: 2014).*
Park, S. J., et al. "An overview of MCT1 and MCT4 in GBM: small molecule transporters with large implications." American Journal of Cancer Research 8.10 (2018): 1967-1976.
Granchi, Carlotta et al. "An Update on Therapeutic Opportunities Offered by Cancer Glycolytic Metabolism." Bioorganic & medicinal chemistry letters 24.21 (2014): 4915-4925.
Fra, Laura et al. "Indole Synthesis through Sequential Electrophilic N—H and C—H Bond Activation Using Iodine (III) Reactivity." Chemistry—A European Journal 22.13 (2016): 4351-4354.
Fuentes, Noelia, et al. "Cyclization cascades via N-amidyl radicals toward highly functionalized heterocyclic scaffolds." Journal of the American Chemical Society 137.2 (2015): 964-973.
Le, Christine M., et al. "Stereoselective synthesis of methylene oxindoles via palladium (II)-catalyzed intramolecular cross-coupling of carbamoyl chlorides." Journal of the American Chemical Society 138.43 (2016): 14441-14448.
Arcadi, Antonio et al. "ChemInForm Abstract: The palladium-catalyzed reaction of o-Alkynyltrifluoracetanilides with Alkyl Halides. An entry into 2-Substituted 3-Alkylindoles.", ChemInForm, vol. 31, No. 25, Jun. 20, 2000.

(Continued)

*Primary Examiner* — Kortney L. Klinkel
*Assistant Examiner* — Dawanna Shar-Day White
(74) *Attorney, Agent, or Firm* — PERRY + CURRIER INC.

(57) ABSTRACT

The present invention relates to disubstituted alkyne derivatives. These compounds are useful for the prevention and/or treatment of several medical conditions including hyperproliferative disorders and diseases.

17 Claims, No Drawings

(56) References Cited

OTHER PUBLICATIONS

Hanzlik, Robert P. et al. "Active site dynamics of toluene hydroxylation by cytochrome P-450." The Journal of Organic Chemistry 55.13 (1990): 3992-3997.
Jarman, Michael, et al. "The deuterium isotope effect for the a-hydroxylation of tamoxifen by rat liver microsomes accounts for the reduced genotoxicity of [D5-ethyl] tamoxifen." Carcinogenesis 16.4 (1995): 683-688.
Gurrapu, Shirisha, et al. "Monocarboxylate transporter 1 inhibitors as potential anticancer agents." ACS medicinal chemistry letters 6.5 (2015): 558-561.
Gao, Yuzhen, et al. "A cascade phosphinoylation/cyclization/desulfonylation process for the synthesis of 3-phosphinoylindoles." Organic letters 18.6 (2016): 1242-1245.
Gillette, James R. et al. "Theory for the observed isotope effects on the formation of multiple products by different kinetic mechanisms of cytochrome P450 enzymes." Biochemistry 33.10 (1994): 2927-2937.
Foster, Allan B. "Deuterium isotope effects in the metabolism of drugs and xenobiotics: implications for drug design." Advances in drug Research 14 (1985): 1-40.
Wang, Hui, et al. "Synthesis and structure-activity relationships of pteridine dione and trione monocarboxylate transporter 1 inhibitors." Journal of medicinal chemistry 57.17 (2014): 7317-7324.
Quanz, Maria, et al. "Preclinical efficacy of the novel monocarboxylate transporter 1 inhibitor BAY-8002 and associated markers of resistance." Molecular Cancer Therapeutics 17.11 (2018): 2285-2296.
Reider Paul J., et al. "Synthesis of (R)-serine-2-d and its conversion to the broad-spectrum antibiotic fludalanine." The Journal of Organic Chemistry 52.15 (1987): 3326-3334.
Nancolas, Bethany et al. "Identification of key binding site residues of MCT1 for AR-C155858 reveals the molecular basis of its isoform selectivity." Biochemical Journal 466.1 (2015): 177-188.
Marchiq, Ibtissam et al., "Hypoxia, cancer metabolism and the therapeutic benefit of targeting lactate/H+ symporters." Journal of molecular medicine 94.2 (2016): 155-171.
Naganawa, Atsushi, et al. "Discovery of new chemical leads for selective EP1 receptor antagonists." Bioorganic & medicinal chemistry 14.16 (2006): 5562-5577.
Liu, Jun et al. "Silver-catalyzed cascade cyclization-stannylation of o-alkynylaniline derivatives with 2-tributylstannylfuran: an efficient synthesis of (3-indolyl) stannanes." Chemical Communications 49.100 (2013): 11794-11796.
Wu, Bin et al. "Benziodoxole Triflate as a Versatile Reagent for Iodo (III) cyclization of Alkynes." Chemistry—An Asian Journal 12.24 (2017): 3123-3127.
Xu, Wei, et al. "Gold (I)-Catalyzed Formal Intramolecular Dehydro-Diels-Alder Reaction of Ynamide-ynes: Synthesis of Functionalized Benzo [b] carbazoles." Organic letters 20.11 (2018): 3273-3277.

* cited by examiner

DISUBSTITUTED ALKYNE DERIVATIVES

FIELD OF THE INVENTION

The present invention relates to disubstituted alkyne derivatives. These compounds are useful for inhibiting monocarboxylate transporters (MCT) and for the prevention and/or treatment of several medical conditions including hyperproliferative disorders and diseases that are affected by MCT activity.

BACKGROUND OF THE INVENTION

The production of ATP (adenosine triphosphate) plays a central role in the metabolism of cells. Unlike normal, i.e. healthy cells that usually favor mitochondrial oxidative phosphorylation (OXPHPOS) to produce energy, i.e. ATP, tumor cells are heavily dependent upon glycolysis to produce ATP even under aerobic conditions. This switch of metabolism in tumor cells to the process of aerobic glycolysis by which glucose is eventually converted into lactate is also known as the "Warburg Effect" (I. Marchiq and J. Pouysségur, J. Mol. Med. (2016) 94:155-171).

When compared to a normal cell a tumor cell exhibits increased glucose uptake and enhanced conversion to lactate; thus efficient lactate transport (exclusion) is essential for the tumor cell to avoid both lactate accumulation and low intracellular pH value. It has been shown that monocarboxylate transporters (MCT) play a role in lactate transport across the plasma membrane accompanied by proton transfer. Among the several MCT isoforms (I. Marchiq and J. Pouysségur, J. Mol. Med. (2016) 94:155-171) MCT1 and MCT4 are those most frequently expressed in tumor cells. MCT1 shows a much higher affinity to lactate (Km at about 1 to 3.5 mmol/L) than MCT4 (Km at about 28 mmol/L). There is also evidence that MCT4 expression levels are higher in hypoxic cells than in well-oxygenated cells while the opposite seems true for MCT1 expression. Furthermore, since malignant tumors contain both aerobic and hypoxic regions it is believed that both MCT1 and MCT4 play a role in a metabolic mechanism called metabolic symbiosis that utilizes lactate for tumor cells of different levels of oxygen supply: A hypoxic tumor cell converts large amounts of glucose to lactate by glycolysis which lactate is then transported out of the cell via the up-regulated MCT4. A nearby aerobic tumor cell then uptakes lactate via MCT1 and utilizes the lactate for energy production via OXPHOS (I. Marchiq and J. Pouysségur, J. Mol. Med. (2016) 94:155-171).

These findings indicate that MCT may be a promising target for cancer therapy. However, there is evidence suggesting that selective inhibition of MCT1, in particular in highly glycolytic and hypoxic tumors, may be compensated by upregulating MCT4 rendering the treatment with the MCT1 inhibitor ineffective. To the contrary, there are no indications that inhibition of MCT4 in cancer cells would be compensated by MCT1 up-regulation. Thus, promising approaches for the development of an effective treatment of diseases and conditions which are affected by MCT1 and/or MCT4 activity, in particular of hyperproliferative conditions/diseases, are the selective inhibition of MCT4 or the dual inhibition of both MCT1 and MCT4. Further it is to be mentioned that upregulation of MCT4 and/or MCT1 may also play a role in the development and hence treatment of other than hyperproliferative conditions, e.g. inflammatory disorders or diseases, in particular Crohn's disease, ulcerative colitis, idiopathic pulmonary fibrosis, muscular dystrophy, rheumatoid arthritis, and systemic sclerosis (scleroderma); or neurodegenerative diseases, in particular Huntigton's disease.

PRIOR ART

EP 0 947 500 A1 discloses methyl 4-{2-[5-chloro-2-(4-chlorobenzenesulfon-amido)phenyl]ethynyl}benzoate and 4-{2-[5-chloro-2-(4-chlorobenzenesulfon-amido)phenyl]ethynyl}benzoic acid as antagonists of the prostanoid receptor $PGE_2$. The benzoic acid is further disclosed in A. Naganawa et al., Bioorg. Med. Chem., 14 (2006) 5562-5577.

Y. Gao et al., Org. Lett. 2016, 18, 1242-1245, disclose methyl 4-{2-[2-(4-methylbenzenesulfonamido)phenyl]ethynyl}benzoate as starting material for synthesizing a 3-phosphinoylindole derivative.

A. Arcadi et al., Synlett 2000, No. 3, 394-396 disclose the synthesis of methyl 4-{2-[2-(N-benzyl-2,2,2-trifluoroacetamido)phenyl]ethynyl}benzoate.

W. Xu et al., Organic Letters 2018, 20, 3273-3277, disclose the synthesis of ethyl 4-(2-{2-[N-(2-phenylethynyl)-4-methylbenzenesulfonamido]phenyl}-ethynyl)benzoate.

Both B. Wu et al., Chem. Asian J. 2017, 12, 3123-3127, and J. Liu et al., Chem. Commun. 2013, 49, 11794-11796, disclose ethyl 4-{2-[2-(4-methylbenzenesulfonamido)phenyl]ethynyl}benzoate.

DESCRIPTION OF THE INVENTION

It is an object of the present invention to provide compounds that are useful for the prevention and/or treatment of medical conditions, disorders and/or diseases, in particular of hyperproliferative disorders/diseases, which compounds are inhibitors of MCT, in particular of MCT4 or of MCT4 and MCT1.

The object has surprisingly been solved by the compounds of the present invention. This invention provides a compound of formula (I)

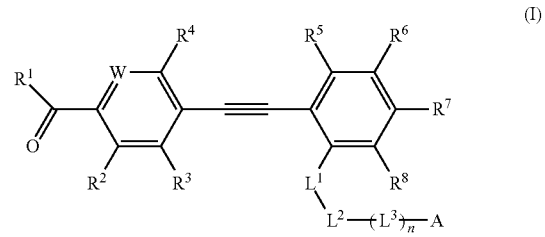

wherein
W denotes $CR^{W1}$, N;
$R^{W1}$ is H, halogen, $R^a$, —$OR^a$;
$R^1$ is —OH, —$OR^a$, —$NH_2$, —$NHR^a$, —$NR^aR^b$, —N(H)OH, —N(H)O—$R^a$, —N(H)CN, —N(H)—C(=O)—$R^a$, —N(H)—$SO_2$—$R^a$; or $R^1$ together with $R^2$ forms a divalent —O—$CH_2$— or —N—$CH_2$— radical;
$R^2$ is H, halogen, —CN, $R^a$, —OH, —$OR^a$, $NH_2$, —NH—$R^a$, —$NR^aR^b$;
$R^3$ is H, halogen, $R^a$, —OH, —$OR^a$, $NH_2$, —NH—$R^a$, —$NR^aR^b$, —$NO_2$, unsubstituted or substituted phenyl; or
$R^2$ and $R^3$ form together with the carbon atoms to which they are attached to an unsubstituted or substituted six-membered aromatic ring; or form together a divalent —NH—CH$_2$—CH$_2$—NH— radical;

$R^4$ is H, $R^a$;

$R^5$ is H, halogen;

$R^6$ is H, halogen, $R^a$, —OR$^a$, NH$_2$, —NHR$^a$, —NR$^a$R$^b$, —NO$_2$, Ar$^A$;

$R^7$ is H, halogen, $R^a$, —OR$^a$, NH$_2$, —NHR$^a$, —NR$^a$R$^b$, —N(H)—C(=O)—R$^a$, —C(=O)—NHR$^a$;

$R^8$ is H, halogen, $R^a$;

n is an integer selected from 0 and 1;

$L^1$ is a divalent —NH—, —N(R$^a$)— or —CH$_2$— radical; and $L^2$ is a divalent —SO$_2$— radical; and $L^3$ is a divalent-CH=CH— radical;

or $L^1$ is a divalent —N(CHO)—, —N(C(=O)—R$^a$)—, —N(C(=O)—NH$_2$)—, —N(C(=O)—NHR$^a$)— or —N(C(=O)—NR$^a$R$^b$)— radical; and $L^2$ is a divalent —CH$_2$— radical; and $L^3$ is a divalent —CH$_2$— radical;

or $L^1$ is a divalent —CH$_2$— radical;

$L^2$ is a divalent —N(CHO)—, —N(C(=O)—R$^a$)—, —N(C(=O)—NH$_2$)—, —N(C(=O)—NHR$^a$)— or —N(C(=O)—NR$^a$R$^b$)— radical; and $L^3$ is a single bond;

or $L^1$ is a divalent —N=radical;

$L^2$ is a divalent =S(=O)(R$^a$)— radical; and $L^3$ is a single bond;

or $L^1$ is a divalent-SO$_2$— radical;

$L^2$ is a divalent —NH— or —N(R$^a$)— radical; and $L^3$ is a single bond;

A is a ring selected from the group consisting of Ar$^A$, Hetar$^A$, Cyc$^A$ or Hetcyc$^A$;

Ar$^A$ is a mono-, bi- or tricyclic aryl with 5, 6, 7, 8, 9, 10, 11, 12, 13, 14 ring carbon atoms, wherein that aryl may be unsubstituted or substituted with substituents $R^{A1}$, $R^{A2}$, $R^{A3}$, $R^{A4}$, $R^{A5}$, $R^{A6}$ and/or $R^{A7}$ which may be the same or different, with the proviso that Ar$^A$ is not 4-methylphenyl;

Hetar$^A$ is a mono-, bi- or tricyclic heteroaryl with 5, 6, 7, 8, 9, 10, 11, 12, 13, 14 ring atoms wherein 1, 2, 3, 4, 5 of said ring atoms is/are a hetero atom(s) selected from N, O and/or S and the remaining are carbon atoms, wherein that heteroaryl may be unsubstituted or substituted with substituents $R^{A1}$, $R^{A2}$, $R^{A3}$, $R^{A4}$, $R^{A5}$, $R^{A6}$ and/or $R^{A7}$ which may be the same or different;

Cyc$^A$ is a saturated or partially unsaturated, mono-, bi- or tricyclic carbocycle with 3, 4, 5, 6, 7, 8, 9, 10, 11, 12, 13, 14, 15 ring carbon atoms, wherein that carbocycle may be unsubstituted or substituted with $R^{A8}$, $R^{A9}$, $R^{A10}$ and/or $R^{A11}$ which may be the same or different;

Hetcyc$^A$ is a saturated or partially unsaturated, mono-, bi- or tricyclic heterocycle with 3, 4, 5, 6, 7, 8, 9, 10, 11, 12, 13, 14, 15 ring atoms wherein 1, 2, 3, 4, 5 of said ring atoms is/are a hetero atom(s) selected from N, O and/or S and the remaining are carbon atoms, wherein that heterocycle may be unsubstituted or substituted with $R^{A8}$, $R^{A9}$, $R^{A10}$ and/or $R^{A11}$ which may be the same or different;

$R^{A1}$, $R^{A2}$, $R^{A3}$, $R^{A4}$, $R^{A5}$, $R^{A6}$, $R^{A7}$ are independently from each other H, halogen, $R^a$, —OR$^a$, —NH$_2$, —NHR$^a$, —NR$^a$R$^b$, —N(H)—C(=O)—R$^a$, Ar$^B$, —O—Ar$^B$, Hetar$^B$, CyC$^B$, Hetcyc$^B$.

and/or two adjacent $R^{A1}$, $R^{A2}$, $R^{A3}$, $R^{A4}$, $R^{A5}$, $R^{A6}$, $R^{A7}$ may form together a divalent —C$_{1-3}$-alkylene-O— or —O—C$_{1-3}$-alkylene-O— radical which C$_{1-3}$-alkylene may be unsubstituted or mono- or disubstituted with R$^a$ or halogen; or may form together with the ring atoms to which they are attached to a Cyc$^C$;

$R^{A8}$, $R^{A9}$, $R^{A10}$, $R^{A11}$ are independently from each other H, R$^a$; or a pair of $R^{A8}$, $R^{A9}$, $R^{A10}$ and/or $R^{A11}$ form a =O radical;

Ar$^B$ is a phenyl ring, wherein that phenyl ring may be unsubstituted or substituted with substituents $R^{B1}$, $R^{B2}$ and/or $R^{B3}$ which may be the same or different;

Hetar$^B$ is a monocyclic heteroaryl with 5, 6, 7 ring atoms wherein 1, 2, 3, 4 of said ring atoms is/are a hetero atom(s) selected from N, O and/or S and the remaining are carbon atoms, wherein that heteroryl may be unsubstituted or substituted with substituents $R^{B1}$, $R^{B2}$ and/or $R^{B3}$ which may be the same or different;

Cyc$^B$ is a mono- or bicyclic saturated or partially unsaturated carbocycle with 5, 6, 7, 8, 9, 10 ring carbon atoms wherein that carbocycle may be unsubstituted or mono-, di- or trisubstituted with $R^{B4}$, $R^{B5}$ and/or $R^{B6}$ which may be the same or different;

Hetcyc$^B$ is a saturated or partially unsaturated monocyclic heterocycle with 3, 4, 5, 6, 7 ring atoms wherein 1, 2 of said ring atoms is/are a hetero atom(s) selected from N, O and/or S and the remaining are carbon atoms, wherein that heterocycle may be unsubstituted or mono-, di- or trisubstituted with $R^{B4}$, $R^{B5}$ and/or $R^{B6}$ which may be the same or different;

Cyc$^C$ is a mono- or bicyclic saturated or partially unsaturated carbocycle with 5, 6, 7, 8, 9, 10 ring carbon atoms wherein that carbocycle is fused to Ar$^A$ or Hetar$^A$ via 2 adjacent ring atoms of said Ar$^A$ or Hetar$^A$ and wherein that carbocycle may be unsubstituted or substituted with $R^{C1}$, $R^{C2}$, $R^{C3}$, $R^{C4}$, $R^{C5}$, $R^{C6}$ which may be the same or different;

$R^{B1}$, $R^{B2}$ and/or $R^{B3}$ are independently from each other H, halogen, $R^a$, —OR$^a$, —SR$^a$;

$R^{B4}$, $R^{B5}$, $R^{B6}$, $R^{C1}$, $R^{C2}$, $R^{C3}$, $R^{C4}$, $R^{C5}$, $R^{C6}$ are independently from each other H, R$^a$;

$R^a$, $R^b$ are independently from each other unsubstituted or substituted, straight-chain or branched C$_{1-6}$-aliphatic or may form together with the nitrogen atom to which they are attached to an unsubstituted or substituted saturated, partially unsaturated or aromatic heterocycle with 4, 5, 6, 7 ring atoms wherein 1, 2 of said ring atoms is/are a hetero atom(s) selected from N, O and/or S and the remaining are carbon atoms;

or derivatives, N-oxides, prodrugs, solvates, tautomers or stereoisomers thereof and/or the pharmaceutically acceptable salts of each of the foregoing, including mixtures thereof in all ratios;

with the proviso that (a) 4-{2-[5-chloro-2-(4-chlorobenzenesulfonamido)phenyl]ethynyl}-benzoic acid;

(b) methyl 4-{2-[5-chloro-2-(4-chlorobenzenesulfonamido)phenyl]ethynyl}-benzoate;

(c) methyl 4-{2-[2-(4-methylbenzenesulfonamido)phenyl]ethynyl}benzoate; and (d) methyl 4-{2-[2-(N-benzyl-2,2,2-trifluoroacetamido)phenyl]ethynyl}-benzoate are excluded.

In general, all residues, radicals, substituents, groups, moieties, etc. which occur more than once may be identical or different, i.e. are independent of one another. Above and below, the residues and parameters have the meanings indicated for formula (I), unless expressly indicated otherwise. Accordingly, the invention relates, in particular, to the compounds of formula (I) in which at least one of the said residues radicals, substituents has one of the preferred meanings indicated below.

Any of those particular or even preferred embodiments of the present invention as specified below and in the claims do not only refer to the specified compounds of formula (I) but to derivatives, N-oxides, prodrugs, solvates, tautomers or stereoisomers thereof as well as the pharmaceutically acceptable salts of each of the foregoing, including mixtures thereof in all ratios, too, unless indicated otherwise.

In a particular embodiment, PE0, the compound of the present invention is a compound of formula (I) or derivatives, N-oxides, prodrugs, solvates, tautomers or stereoisomers thereof and/or the pharmaceutically acceptable salts of each of the foregoing, including mixtures thereof in all ratios, in which W denotes $CR^{W1}$, N;

$R^{W1}$ is H, halogen, $R^a$, —$OR^a$;

$R^1$ is —OH, —$OR^a$, —$NH_2$, —$NHR^a$, —$NR^aR^b$, —N(H)OH, —N(H)O—$R^a$, —N(H)CN, —N(H)—C(=O)—$R^a$, —N(H)—$SO_2$—$R^a$; or $R^1$ together with $R^2$ forms a divalent —O—$CH_2$— or —N—$CH_2$— radical;

$R^2$ is H, halogen, —CN, $R^a$, —OH, —$OR^a$, $NH_2$, —NH—$R^a$, —$NR^aR^b$;

$R^3$ is H, halogen, $R^a$, —OH, —$OR^a$, $NH_2$, —NH—$R^a$, —$NR^aR^b$, —$NO_2$, unsubstituted or substituted phenyl; or $R^2$ and $R^3$ form together with the carbon atoms to which they are attached to an unsubstituted or substituted six-membered aromatic ring; or form together a divalent —NH—$CH_2$—$CH_2$—NH— radical;

$R^4$ is H, $R^a$;

$R^5$ is H, halogen;

$R^6$ is H, halogen, $R^a$, —$OR^a$, $NH_2$, —$NHR^a$, —$NR^aR^b$, —$NO_2$, $Ar^A$;

$R^7$ is H, halogen, $R^a$, —$OR^a$, $NH_2$, —$NHR^a$, —$NR^aR^b$, —N(H)—C(=O)—$R^a$, —C(=O)—$NHR^a$;

$R^8$ is H, halogen, $R^a$;

n is an integer selected from 0 and 1;

$L^1$ is a divalent —NH—, —N($R^a$)— or —$CH_2$— radical; and $L^2$ is a divalent —$SO_2$— radical; and $L^3$ is a divalent-CH=CH— radical;

or $L^1$ is a divalent —N(CHO)—, —N(C(=O)—$R^a$)—, —N(C(=O)—$NH_2$)—, —N(C(=O)—$NHR^a$)— or —N(C(=O)—$NR^aR^b$)— radical; and $L^2$ is a divalent —$CH_2$— radical; and $L^3$ is a divalent —$CH_2$— radical;

or $L^1$ is a divalent —$CH_2$— radical;

$L^2$ is a divalent —N(CHO)—, —N(C(=O)—$R^a$)—, —N(C(=O)—$NH_2$)—, —N(C(=O)—$NHR^a$)— or —N(C(=O)—$NR^aR^b$)— radical; and $L^3$ is a single bond;

A is a ring selected from the group consisting of $Ar^A$, $Hetar^A$, $Cyc^A$ or $Hetcyc^A$;

$Ar^A$ is a mono-, bi- or tricyclic aryl with 5, 6, 7, 8, 9, 10, 11, 12, 13, 14 ring carbon atoms, wherein that aryl may be unsubstituted or substituted with substituents $R^{A1}$, $R^{A2}$, $R^{A3}$, $R^{A4}$, $R^{A5}$, $R^{A6}$ and/or $R^{A7}$ which may be the same or different, with the proviso that $Ar^A$ is not 4-methylphenyl;

$Hetar^A$ is a mono-, bi- or tricyclic heteroaryl with 5, 6, 7, 8, 9, 10, 11, 12, 13, 14 ring atoms wherein 1, 2, 3, 4, 5 of said ring atoms is/are a hetero atom(s) selected from N, O and/or S and the remaining are carbon atoms, wherein that heteroaryl may be unsubstituted or substituted with substituents $R^{A1}$, $R^{A2}$, $R^{A3}$, $R^{A4}$, $R^{A5}$, $R^{A6}$ and/or $R^{A7}$ which may be the same or different;

$Cyc^A$ is a saturated or partially unsaturated, mono-, bi- or tricyclic carbocycle with 3, 4, 5, 6, 7, 8, 9, 10, 11, 12, 13, 14, 15 ring carbon atoms, wherein that carbocycle may be unsubstituted or substituted with $R^{A8}$, $R^{A9}$, $R^{A10}$ and/or $R^{A11}$ which may be the same or different;

$Hetcyc^A$ is a saturated or partially unsaturated, mono-, bi- or tricyclic heterocycle with 3, 4, 5, 6, 7, 8, 9, 10, 11, 12, 13, 14, 15 ring atoms wherein 1, 2, 3, 4, 5 of said ring atoms is/are a hetero atom(s) selected from N, O and/or S and the remaining are carbon atoms, wherein that heterocycle may be unsubstituted or substituted with $R^{A8}$, $R^{A9}$, $R^{A10}$ and/or $R^{A11}$ which may be the same or different;

$R^{A1}$, $R^{A2}$, $R^{A3}$, $R^{A4}$, $R^{A5}$, $R^{A6}$, $R^{A7}$ are independently from each other H, halogen, $R^a$, —$OR^a$, —$NH_2$, —$NHR^a$, —$NR^aR^b$, —N(H)—C(=O)—$R^a$, $Ar^B$, —O—$Ar^B$, $Hetar^B$, $Cyc^B$, $Hetcyc^B$;

and/or two adjacent $R^{A1}$, $R^{A2}$, $R^{A3}$, $R^{A4}$, $R^{A5}$, $R^{A6}$, $R^{A7}$ may form together a divalent —$C_{1-3}$-alkylene-O— or —O—$C_{1-3}$-alkylene-O— radical which $C_{1-3}$-alkylene may be unsubstituted or mono- or disubstituted with $R^a$ or halogen; or may form together with the ring atoms to which they are attached to a $Cyc^c$;

$R^{A8}$, $R^{A9}$, $R^{A10}$, $R^{A11}$ are independently from each other H, $R^a$; or a pair of $R^{A8}$, $R^{A9}$, $R^{A10}$ and/or $R^{A11}$ form a =O radical;

$Ar^B$ is a phenyl ring, wherein that phenyl ring may be unsubstituted or substituted with substituents $R^{B1}$, $R^{B2}$ and/or $R^{B3}$ which may be the same or different;

$Hetar^B$ is a monocyclic heteroaryl with 5, 6, 7 ring atoms wherein 1, 2, 3, 4 of said ring atoms is/are a hetero atom(s) selected from N, O and/or S and the remaining are carbon atoms, wherein that heteroryl may be unsubstituted or substituted with substituents $R^{B1}$, $R^{B2}$ and/or $R^{B3}$ which may be the same or different;

$Cyc^B$ is a mono- or bicyclic saturated or partially unsaturated carbocycle with 5, 6, 7, 8, 9, 10 ring carbon atoms wherein that carbocycle may be unsubstituted or mono-, di- or trisubstituted with $R^{B4}$, $R^{B5}$ and/or $R^{B6}$ which may be the same or different;

$Hetcyc^B$ is a saturated or partially unsaturated monocyclic heterocycle with 3, 4, 5, 6, 7 ring atoms wherein 1, 2 of said ring atoms is/are a hetero atom(s) selected from N, O and/or S and the remaining are carbon atoms, wherein that heterocycle may be unsubstituted or mono-, di- or trisubstituted with $R^{B4}$, $R^{B5}$ and/or $R^{B6}$ which may be the same or different;

$Cyc^C$ is a mono- or bicyclic saturated or partially unsaturated carbocycle with 5, 6, 7, 8, 9, 10 ring carbon atoms wherein that carbocycle is fused to $Ar^A$ or $Hetar^A$ via 2 adjacent ring atoms of said $Ar^A$ or $Hetar^A$ and wherein that carbocycle may be unsubstituted or substituted with $R^{C1}$, $R^{C2}$, $R^{C3}$, $R^{C4}$, $R^{C5}$, $R^{C6}$ which may be the same or different;

$R^{B1}$, $R^{B2}$ and/or $R^{B3}$ are independently from each other H, halogen, $R^a$, —$OR^a$, —$SR^a$;

$R^{B4}$, $R^{B5}$, $R^{B6}$, $R^{C1}$, $R^{C2}$, $R^{C3}$, $R^{C4}$, $R^{C5}$, $R^{C6}$ are independently from each other H, $R^a$;

$R^a$, $R^b$ are independently from each other unsubstituted or substituted, straight-chain or branched $C_{1-6}$-aliphatic or may form together with the nitrogen atom to which they are attached to an unsubstituted or substituted saturated, partially unsaturated or aromatic heterocycle with 4, 5, 6, 7 ring atoms wherein 1, 2 of said ring atoms is/are a hetero atom(s) selected from N, O and/or S and the remaining are carbon atoms;

or derivatives, N-oxides, prodrugs, solvates, tautomers or stereoisomers thereof and/or the pharmaceutically acceptable salts of each of the foregoing, including mixtures thereof in all ratios;

with the proviso that (a) 4-{2-[5-chloro-2-(4-chlorobenzenesulfonamido)phenyl]ethynyl}-benzoic acid;

(b) methyl 4-{2-[5-chloro-2-(4-chlorobenzenesulfonamido)phenyl]ethynyl}-benzoate;

(c) methyl 4-{2-[2-(4-methylbenzenesulfonamido)phenyl]ethynyl}benzoate; and (d) methyl 4-{2-[2-(N-benzyl-2,2,2-trifluoroacetamido)phenyl]ethynyl}-benzoate are excluded.

In a particular embodiment, PE1, the compound of the present invention is a compound of formula (I) or derivatives, N-oxides, prodrugs, solvates, tautomers or stereoisomers thereof and/or the pharmaceutically acceptable salts of each of the foregoing, including mixtures thereof in all ratios, in which $R^5$ is H;

$R^6$ is H, halogen, $R^a$, —$OR^a$, —$NH_2$, —$NHR^a$, —$NR^aR^b$;

$R^7$ is H, halogen, $R^a$, —$OR^a$;

$R^8$ is H, halogen;

and in which the radicals/residues/substituents/groups not designated in greater detail have the meaning indicated for the compound of formula (I) above, i.e. in its most general meaning.

In a further particular embodiment of PE1, designated as PE1a, PE1 is also part of particular embodiment PE0.

A further particular embodiment of the present invention, designated as PE2, is a compound of formula (I), or derivatives, N-oxides, prodrugs, solvates, tautomers or stereoisomers thereof and/or the pharmaceutically acceptable salts of each of the foregoing, including mixtures thereof in all ratios, in which W denotes $CR^{W1}$, N;

$R^{W1}$ is H, $R^a$, —$OR^a$;

$R^1$ is —OH, $OR^a$, $NHR^a$, NH—OH;

$R^2$ is H, halogen, $R^a$, —$OR^a$, —$NH_2$, —$NHR^a$, —$NR^aR^b$;

$R^3$ is H, halogen, $R^a$, —$OR^a$, —$NH_2$, —$NHR^a$, —$NR^aR^b$, —$NO_2$, phenyl;

or $R^2$ and $R^3$ form together with the carbon atoms to which they are attached to a benzo ring;

$R^4$ is H; and in which the radicals/residues/substituents/groups not designated in greater detail have the meaning indicated for the compound of formula (I) above, i.e. in its most general meaning. In a further particular embodiment of PE2—designated as PE2a —, PE2 is also a part of particular embodiment PE1. In other words, PE2a is a compound of formula (I)—or derivatives, N-oxides, prodrugs, solvates, tautomers or stereoisomers thereof and/or the pharmaceutically acceptable salts of each of the foregoing, including mixtures thereof in all ratios— in which W denotes $CR^{W1}$, N;

$R^{W1}$ is H, $R^a$, —$OR^a$;

$R^1$ is —OH, $OR^a$, $NHR^a$, NH—OH;

$R^2$ is H, halogen, $R^a$, —$OR^a$, —$NH_2$, —$NHR^a$, —$NR^aR^b$;

$R^3$ is H, halogen, $R^a$, —$OR^a$, —$NH_2$, —$NHR^a$, —$NR^aR^b$, —$NO_2$, phenyl;

or $R^2$ and $R^3$ form together with the carbon atoms to which they are attached to a benzo ring;

$R^4$ is H;

$R^5$ is H;

$R^6$ is H, halogen, $R^a$, —$OR^a$, —$NH_2$, —$NHR^a$, —$NR^aR^b$;

$R^7$ is H, halogen, $R^a$, —$OR^a$;

$R^8$ is H, halogen.

In a further particular embodiment of PE2, designated as PE2b, PE2 or even PE2a is also part of particular embodiment PE0.

Another particular embodiment of the invention, PE3, is a compound of formula (I) or derivatives, N-oxides, prodrugs, solvates, tautomers or stereoisomers thereof and/or the pharmaceutically acceptable salts of each of the foregoing, including mixtures thereof in all ratios, in which W is N;

and the remaining radicals/residues/groups/substituents are as defined for the general formula (I) or for particular embodiments PE0, PE1, PE1a, PE2, PE2a or PE2b.

One preferred embodiment of PE3, designated as PE3a, is a compound of formula (I-a)—or derivatives, N-oxides, prodrugs, solvates, tautomers or stereoisomers thereof and/or the pharmaceutically acceptable salts of each of the foregoing, including mixtures thereof in all ratios —:

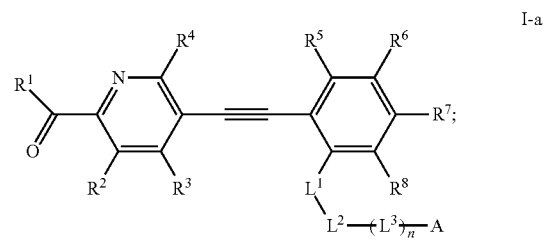

wherein $R^2$ is H, halogen, $R^a$, —$OR^a$, —$NH_2$, —$NHR^a$, —$NR^aR^b$;

$R^3$ is H, halogen, $R^a$, —$OR^a$, —$NH_2$, —$NHR^a$, —$NR^aR^b$, —$NO_2$, phenyl; and $R^1$, $R^4$, $R^5$, $R^6$, $R^1$, $R^8$, $R^a$, $R^b$, n, $L^1$, $L^2$, $L^3$ and A are as defined for the general formula (I) above or for particular embodiments PE0, PE1, PE1a, PE2, PE2a or PE2b.

Another preferred embodiment of PE3, designated as PE3b, is a compound of formula (I)—or derivatives, N-oxides, prodrugs, solvates, tautomers or stereoisomers thereof and/or the pharmaceutically acceptable salts of each of the foregoing, including mixtures thereof in all ratios—in which $R^2$ and $R^3$ form together with the carbon atoms to which they are attached to an unsubstituted benzo ring thereby forming a compound of formula (I-b)

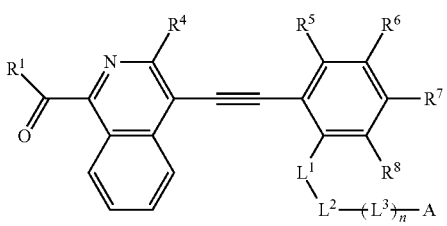

wherein
R¹, R⁴, R⁵, R⁶, R⁷, R⁸, n, L¹, L², L³ and A are as defined for the general formula (I) above or for particular embodiments PE0, PE1, PE1a, PE2, PE2a or PE2b.

In a further particular embodiment of PE3, designated as PE3c, PE3 or even PE3a or PE3b is also part of particular embodiment PE0.

A further particular embodiment, embodiment PE4, is a compound of formula (I)—or derivatives, N-oxides, prodrugs, solvates, tautomers or stereoisomers thereof and/or the pharmaceutically acceptable salts of each of the foregoing, including mixtures thereof in all ratios—in which
L¹ is a divalent —NH— radical; and
L² is a divalent —SO₂— radical;
while R¹, R², R³, R⁴, R⁵, R⁶, R⁷, R⁸, n, L³ and A are as defined for the general formula (I) above or for any of the particular embodiments mentioned above, i.e. PE0, PE1, PE1a, PE2, PE2a, PE2b, PE3, PE3a, PE3b. PE3c.

A particular preferred embodiment PE4a of these sulfonamide compounds of the present invention and of PE4 is a compound of formula (I)—or derivatives, N-oxides, prodrugs, solvates, tautomers or stereoisomers thereof and/or the pharmaceutically acceptable salts of each of the foregoing, including mixtures thereof in all ratios—in which n is 0 (zero) so that L³ is absent.

Still another particular embodiment, PE5, is a compound of formula (I)—or derivatives, N-oxides, prodrugs, solvates, tautomers or stereoisomers thereof and/or the pharmaceutically acceptable salts of each of the foregoing, including mixtures thereof in all ratios—in which
L¹ is a divalent —N(CHO)— radical; and
L² is a divalent —CH₂— radical;
wherein R¹, R², R³, R⁴, R⁵, R⁶, R⁷, R⁸, n, L³ and A are as defined for the general formula (I) above or for any of the particular embodiments mentioned above, i.e. PE0, PE1, PE1a, PE2, PE2a, PE2b, PE3, PE3a, PE3b, PE3c.

A particular preferred embodiment PE5a of these formamido compounds of the present invention and of PE5 is a compound of formula (I)—or derivatives, N-oxides, prodrugs, solvates, tautomers or stereoisomers thereof and/or the pharmaceutically acceptable salts of each of the foregoing, including mixtures thereof in all ratios—in which n is 0 (zero) so that L³ is absent.

In another particular embodiment of the present invention, PE6, the compound of formula (I)—or derivatives, N-oxides, prodrugs, solvates, tautomers or stereoisomers thereof and/or the pharmaceutically acceptable salts of each of the foregoing, including mixtures thereof in all ratios—is selected from compounds of formula (I) in which
A is a ring selected from the group consisting of $Ar^4$, $Hetar^4$, $Hetcyc^4$ or $Cyc^4$;
$Ar^4$ is a phenyl or naphthyl radical which radical may be unsubstituted or substituted with substituents $R^{A1}$, $R^{A2}$, $R^{A3}$, $R^{A4}$, $R^{A5}$, $R^{A6}$ and/or $R^{A7}$ which may be the same or different, with the proviso that $Ar^4$ is not 4-methylphenyl;
$Hetar^4$ is a monocyclic heteroaryl with 5 or 6 ring atoms, a bicyclic heteroaryl with 9 or 10 ring atoms or a tricyclic heteroaryl with 13 ring atoms wherein 1, 2 or 3 of said ring atoms is/are a hetero atom(s) selected from N, O and/or S and the remaining are carbon atoms, wherein that heteroryl may be unsubstituted or substituted with substituents $R^{A1}$, $R^{A2}$, $R^{A3}$, $R^{A4}$, $R^{A5}$, $R^{A6}$ and/or $R^{A7}$ which may be the same or different;
$Cyc^4$ is a saturated or partially unsaturated, monocyclic carbocycle with 5, 6 or 7 ring carbon atoms or a bicyclic carbocycle with 9 or 10 ring carbon atoms, wherein that carbocycle may be unsubstituted or substituted with $R^{A8}$, $R^{A9}$, $R^{A10}$ and/or $R^{A11}$ which may be the same or different;
$Hetcyc^4$ is a saturated or partially unsaturated, monocyclic heterocycle with 5 or 6 ring atoms or a saturated or partially unsaturated, bicyclic heterocycle with 9 or 10 ring atoms wherein 1 or 2 of said ring atoms is/are a hetero atom(s) selected from N, O and/or S and the remaining are carbon atoms, wherein that heterocycle may be unsubstituted or substituted with $R^{A8}$, $R^{A9}$, $R^{A10}$ and/or $R^{A11}$ which may be the same or different;
$R^{A1}$, $R^{A2}$, $R^{A3}$, $R^{A4}$, $R^{A5}$, $R^{A6}$, $R^{A7}$ are independently from each other H, halogen, $R^a$, —$OR^a$, —$NH_2$, —$NHR^a$, —$NR^aR^b$, —N(H)—C(=O)—$R^a$, $Ar^B$, $Hetar^B$, $Cyc^B$; and/or
two adjacent $R^{A1}$, $R^{A2}$, $R^{A3}$, $R^{A4}$, $R^{A5}$, $R^{A6}$, $R^{A7}$ may form together a divalent —$C_{1-3}$-alkylen-O— or —O—$C_{1-3}$-alkylene-O— radical; or may form together with the ring atoms to which they are attached to a $Cyc^c$;
$R^{A8}$, $R^{A9}$, $R^{A10}$ and/or $R^{A11}$ are independently from each other H, $R^a$; or a pair of $R^{A8}$, $R^{A9}$, $R^{A10}$ and $R^{A11}$ form a =O (oxo) radical;
$Ar^B$ is a phenyl ring, wherein that phenyl ring may be unsubstituted or substituted with substituents $R^{B1}$, $R^{B2}$ and/or $R^{B3}$ which may be the same or different;
$Hetar^B$ is a monocyclic heteroaryl with 5 or 6 ring atoms wherein 1 or 2 of said ring atoms is/are a hetero atom(s) selected from N, O and/or S and the remaining are carbon atoms, wherein that heteroryl may be unsubstituted or substituted with substituents $R^{B1}$, $R^{B2}$ and/or $R^{B3}$ which may be the same or different;
$Cyc^B$ is a monocyclic 6-membered or bicyclic 9-membered saturated or partially unsaturated carbocycle wherein that carbocycle is unsubstituted;
$Cyc^c$ is a monocyclic 6-membered or bicyclic 9-membered carbocycle wherein that carbocycle is fused to a $Ar^4$ or $Hetar^4$ via 2 adjacent ring atoms of said $Ar^4$ or $Hetar^4$;
$R^{B1}$, $R^{B2}$ and/or $R^{B3}$ are independently from each other H, $R^a$, —$OR^a$, —$SR^a$;
$R^a$ is unsubstituted or substituted, straight-chain or branched $C_{1-6}$-aliphatic; wherein the remaining radicals, residues, groups or substituents are as defined for the general formula above or for any other preferred embodiments mentioned above, i.e. PE0, PE1, PE1a, PE2, PE2a, PE2b, PE3, PE3a, PE3b, PE3c, PE4, PE4a, PE5, PE5a.

In a preferred particular embodiment, PE6a, of PE6
A is a ring selected from the group consisting of $Ar^4$, $Hetar^4$, $Hetcyc^4$ or $Cyc^4$;
$Ar^4$ is selected from the group consisting of
phenyl or naphthyl each of which is unsubstituted or substituted with 1, 2, 3 or 4 substituents independently from each other selected from the group consisting of $R^{A1}$, $R^{A2}$, $R^{A3}$, $R^{A4}$, $R^{A5}$, $R^{A6}$, $R^{A7}$, with the proviso that $Ar^A$ is not 4-methylphenyl;

5,6,7,8-tetrahydronaphthyl (tetralinyl) or 9H-fluorenyl each of which is unsubstituted or substituted with 1, 2 or 3 substituents on the aromatic part of said tetrahydronaphthyl or fluorenyl radical independently from each other selected from the group consisting of $R^{A1}$, $R^{A2}$, $R^{A3}$, $R^{A4}$, $R^{A5}$, $R^{A6}$, $R^{A7}$ and/or 1, 2 or 3 substituents on the non-aromatic part of said tetrahydronaphthyl or fluorenyl radical independently from each other selected from the group consisting of $R^{C1}$, $R^{C2}$, $R^{C3}$, $R^{C4}$, $R^{C5}$, $R^{C6}$;

Hetar$^A$ is selected from the group consisting of pyrrolyl, furanyl, thienyl, pyrazolyl, imidazolyl, pyridinyl, indolyl, benzofuranyl, benzothienyl, benzothiazolyl, benzooxadiazolyl, benzofuranzanyl, benzothiadiazolyl, imidazopyridinyl, quinolinyl, isoquinolinyl, quinoxalinyl, dibenzofuranyl, 9H-carbazolyl and azatricyclotridecapentaendionyl each of which is unsubstituted or substituted with 1, 2 or 3 substituents independently from each other selected from the group consisting of $R^{A1}$, $R^{A2}$, $R^{A3}$, $R^{A4}$, $R^{A5}$, $R^{A6}$, $R^{A7}$;

Cyc$^A$ is selected from the group consisting of cyclohexenyl, 1,4-dihydronaphth-1-yl 1,4-dihydronaphth-2-yl, 2,3-dihydronaphth-1-yl, 2,3-dihydronaphth-2-yl, 2,3-dihydronaphth-3-yl, 2,3-dihydronaphth-4-yl, indan-1-yl, indan-2-yl each of which is unsubstituted or substituted with 1, 2 or 3 substituents independently from each other selected from the group consisting of $R^{A8}$, $R^{A9}$, $R^{A10}$ and $R^{A11}$;

Hetcyc$^A$ is selected from the group consisting of decahydroquinolinyl, decahydroisoquinolinyl, octahydro-1H-indolyl, 2,3-dihydro-1H-indolyl, 1H,2H,3H-pyrrolopyridinyl, 1,2,3,4-tetrahydroisoquinolinyl, 1,2,3,4-tetrahydronaphthridinyl each of which is unsubstituted or substituted with 1, 2 or 3 substituents independently from each other selected from the group consisting of $R^{A8}$, $R^{A9}$, $R^{A10}$ and $R^{A11}$;

$R^{A1}$, $R^{A2}$, $R^{A3}$, $R^{A4}$, $R^{A5}$, $R^{A6}$, $R^{A7}$ are independently from each other H, halogen, $R^a$, —$OR^a$, —$NR^aR^b$, —N(H)—C(=O)—$R^a$, $Ar^B$, —O—$Ar^B$, Hetar$^B$, Cyc$^B$; and/or two adjacent $R^{A1}$, $R^{A2}$, $R^{A3}$, $R^{A4}$, $R^{A5}$, $R^{A6}$, $R^{A7}$ may form together a divalent —$C_{1-3}$-alkylene-O— or —O—$C_{1-3}$-alkylene-O— radical which $C_{1-3}$-alkylene may be unsubstituted or mono- or disubstituted with $R^a$;

$R^{A8}$, $R^{A9}$, $R^{A10}$, $R^{A11}$ are independently from each other H, $R^a$; or a pair of $R^{A8}$, $R^{A9}$, $R^{A10}$ and/or $R^{A11}$ form a =O radical;

$Ar^B$ is phenyl which is unsubstituted or substituted with 1, 2 or 3 substituents independently from each other selected from the group consisting of $R^{B1}$, $R^{B2}$ and/or $R^{B3}$;

Hetar$^B$ is pyrrolyl, furanyl, thienyl, pyrazolyl, imidazolyl, pyridinyl, pyrimidinyl, each of which is unsubstituted or substituted with 1, 2 or 3 substituents independently from each other selected from the group consisting of $R^{B1}$, $R^{B2}$ and/or $R^{B3}$;

Cyc$^B$ is cyclohexenyl;

$R^{B1}$, $R^{B2}$ and/or $R^{B3}$ are independently from each other H, $R^a$, —$OR^a$, —$SR^a$;

$R^a$ is unsubstituted or substituted, straight-chain or branched $C_{1-6}$-aliphatic; halogen is F, Cl, Br.

A yet another particular embodiment of the present invention, PE7, is represented by compounds of formula (I)—or derivatives, N-oxides, prodrugs, solvates, tautomers or stereoisomers thereof and/or the pharmaceutically acceptable salts of each of the foregoing, including mixtures thereof in all ratios—in which W denotes $CR^{W1}$, N;

$R^{W1}$ is H, —$OCH_3$;

$R^1$ is —OH, —$OC_{1-4}$-alkyl, —$OCH_2CH(OH)$—$CH_2OH$, —$O(CH_2)_2O(CH_2)_2OH$, —$O(CH_2)_2OCH_3$,

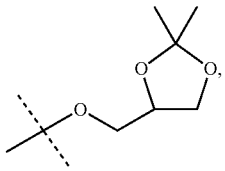

$OCH_2$-phenyl, —$NHCH(CH_3)_2$;

$R^2$ is H, F, Cl, $CH_3$, $C_2H_5$, —$CH_2OH$, —$OCH_3$, —$OC_2H_5$, —$NH_2$, —$NHCH_3$, —$NHC_2H_5$;

$R^3$ is H, F, Cl, $CH_3$, —C(=$CH_2$)$CH_3$, —$OCH_3$, —$OC_2H_5$, phenyl, —N($CH_3$)$_2$, —$NO_2$; or $R^2$ and $R^3$ form together with the carbon atoms to which they are attached to a benzo ring;

$R^4$ is H;

$R^5$ is H;

$R^6$ is H, F, Cl, Br, I, —$CH_3$, —$C_2H_5$, —$CH(CH_3)_2$, —$OCH_3$, —N($CH_3$)$_2$;

$R^7$ is H, F, Cl, Br, $CH_3$, $CF_3$, —$OCH_3$;

$R^8$ is H, F;

n is 0;

$L^1$ is a divalent —NH— or —N($CH_3$)— radical; and $L^2$ is a divalent —$SO_2$— radical;

or $L^1$ is a divalent —N(CHO)— radical; and $L^2$ is a divalent —$CH_2$— radical; and A is a ring selected from the group consisting of Ar$^A$, Hetar$^A$, Cyc$^A$ or Hetcyc$^A$;

Ar$^A$ is selected from the group consisting of 4-methoxyphenyl, 4-methoxy-2-methylphenyl, 4-methoxy-3-methylphenyl, 2,3-dimethyl-4-methoxyphenyl, 2,3,6-trimethyl-4-methoxyphenyl, 2,3-dichloro-4-methoxyphenyl, 3-acetamido-4-ethoxyphenyl, 4-(cyclohex-1-en-1-yl)phenyl, 1,1'-biphenyl-2-yl, 1,1'-biphenyl-3-yl, 1,1'-biphenyl-4-yl, 2'-methyl-1,1'-biphenyl-4-yl, 2-methoxy-1,1'-biphenyl-4-yl, 3-methoxy-1,1'-biphen-4-yl, 2'-methoxy-1,1'-biphenyl-2-yl, 2'-methoxy-1,1'-biphenyl-3-yl, 2'-methoxy-1,1'-biphenyl-4-yl, 3-phenoxyphenyl, 4-(1H-pyrazol-1-yl)phenyl, 3-(pyridin-2-yl)phenyl, 3-(pyridin-3-yl)phenyl, 3-(6-methoxypyridin-2-yl)phenyl, 3-(2,6-dimethoxypyridin-3-yl)phenyl, naphth-1-yl, naphth-2-yl, 4-bromonaphth-1-yl, 4-methylnaphth-1-yl, 1-methylnaphth-2-yl, 4-methoxynaphth-1-yl, 4-methoxynaphth-2-yl, 4-ethoxynaphth-1-yl, 4-propan-2-yloxynaphth-1-yl, 5-chloronaphth-1-yl, 6-chloronaphth-2-yl, 5,6,7,8-tetrahydronaphth-2-yl, 4-methoxy-5,6,7,8-tetrahydronaphth-1-yl, 9H-fluoren-2-yl;

Hetar$^A$ is selected from the group consisting of 5-bromo-6-methoxypyridin-3-yl, 6-phenylpyridin-3-yl, 1-methylindol-4-yl, 1-benzofuran-2-yl, 1-benzothiophen-3-yl, 5-chloro-1-benzothiophen-2-yl, 5-chloro-3-methyl-1-benzothiophen-2-yl, 1,3-benzothiazol-4-yl, quinolin-2-yl, quinolin-8-yl, 2-methylquinolin-8-yl, 3-methylquinolin-8-yl, 4-methylquinolin-8-yl, 6-methylquinolin-8-yl, 7-methylquinolin-8-yl, 4,7-dimethylquinolin-8-yl, 5,7-dimethylquinolin-8-yl, 5,6,7-trimethylquinolin-8- yl, 5-ethylquinolin-8-yl, 5-(n-propyl-)quinolin-8-yl, 2-methoxyquinolin-8-yl, 4-methoxyquinolin-8-yl, 5-methoxyquinolin-8-yl, 5-trifluormethoxy-quinolin-8-yl, 5-ethoxyquinolin-8-yl, 7-ethoxyquinolin-8-yl, 5-(propan-2-yloxy)quinolin-8-yl, 7-(propan-2-yloxy) quinolin-8-yl, 4-prop-2-yn-1-oxy-quinolin-8-yl, 3-chloroquinolin-8-yl, 4-chloroquinolin-8-yl, 6-fluoroquinolin-8-yl, 2,4-dichloroquinolin-8-yl, 3,4-dichloroquinolin-8-yl, 4,7-dichloroquinolin-8-yl, 5,7-dichloroquinolin-8-yl, 7-bromo-2-chloroquinolin-8-yl, 4-chloro-7-fluoroquinolin-8-yl, 7-bromo-4-chloroquinolin-8-yl, 6-chloro-2-methylquinolin-8-yl, 4-dimethylamino-quinolin-8-yl, 9H-carbazol-2-yl, 9-methyl-9H-carbazol-3-yl, 9-methyl-9H-carbazol-4-yl, dibenzofuran-2-yl, dibenzofuran-3-yl;

$Cyc^4$ is 3,4-dihydronaphth-2-yl;

$Hetcyc^4$ is selected from the group consisting of 2,3-dihydro-1H-indol-1-yl, octahydro-1H-indol-1-yl, decahydroquinolin-1-yl, 4a,8a-trans-decahydroquinolin-1-yl, 4aR,8aS-decahydroquinolin-1-yl, decahydroquinolin-2-yl, 4-methyldecahydroquinolin-1-yl, 1,2,3,4-tetrahydro-1,8-naphthyridin-1-yl.

One preferred embodiment, PE7a, of PE7 are particular sulfonamide compounds, i.e. compounds of PE7 in which n is 0;

$L^1$ is a divalent —NH— or —N(CH$_3$)— radical; and $L^2$ is a divalent —SO$_2$— radical;

or derivatives, N-oxides, prodrugs, solvates, tautomers or stereoisomers thereof and/or the pharmaceutically acceptable salts of each of the foregoing, including mixtures thereof in all ratios.

Another preferred embodiment, PE7b, of PE7 are particular formamido compounds, i.e. compounds of PE7 in which n is 0;

$L^1$ is a divalent —N(CHO)— radical; and $L^2$ is a divalent —CH$_2$— radical;

or derivatives, N-oxides, prodrugs, solvates, tautomers or stereoisomers thereof and/or the pharmaceutically acceptable salts of each of the foregoing, including mixtures thereof in all ratios It is still another particular embodiment, PE8, of the present invention that comprises a compound selected from the following group, N-oxides thereof and pharmaceutically acceptable salts either of the compound or any of its N-oxides, the group consisting of:

4-methoxy-5-{2-[2-(7-methylquinoline-8-sulfonamido)phenyl]ethynyl}pyridine-2-carboxylic acid 5-(2-{2-[N-({[1,1'-biphenyl]-4-yl}methyl)formamido] phenyl}ethynyl)-4-methoxy-pyridine-2-carboxylic acid 3-(methylamino)-5-{2-[2-(7-methylquinoline-8-sulfonamido)phenyl]ethynyl}-pyridine-2-carboxylic acid 5-{2-[2-(5-methoxyquinoline-8-sulfonamido)phenyl]ethynyl}-3-(methylamino)-pyridine-2-carboxylic acid 5-{2-[5-iodo-2-(5-methoxyquinoline-8-sulfonamido)phenyl]ethynyl}pyridine-2-carboxylic acid 4-methoxy-5-(2-{2-[N-({2'-methoxy-[1,1'-biphenyl]-4-yl}methyl)formamido]-phenyl}ethynyl)pyridine-2-carboxylic acid 5-[2-(2-{[(4a,8a-trans)-decahydroquinoline-1-sulfonyl] amino}phenyl)ethynyl]-4-methoxypyridine-2-carboxylic acid 4-{2-[5-bromo-2-(5-methoxyquinoline-8-sulfonamido)phenyl]ethynyl}-isoquinoline-1-carboxylic acid 5-{2-[5-chloro-2-(7-methylquinoline-8-sulfonamido)phenyl]ethynyl}-3-(methyl-amino)pyridine-2-carboxylic acid 5-{2-[5-chloro-2-(5-methoxyquinoline-8-sulfonamido)phenyl]ethynyl}-3-(methylamino)pyridine-2-carboxylic acid 5-{2-[5-chloro-2-(4-methoxy-2,3-dimethylbenzenesulfonamido)phenyl]-ethynyl}-4-methoxypyridine-2-carboxylic acid 5-{2-[5-bromo-4-fluoro-2-(5-methoxyquinoline-8-sulfonamido)phenyl]ethynyl}-pyridine-2-carboxylic acid 5-{2-[5-bromo-2-(5-methoxyquinoline-8-sulfonamido)phenyl]ethynyl}pyridine-2-carboxylic acid 5-{2-[5-bromo-2-(5-methoxyquinoline-8-sulfonamido)phenyl]ethynyl}-4-methoxypyridine-2-carboxylic acid 5-{2-[5-bromo-4-fluoro-2-(5-methoxyquinoline-8-sulfonamido)phenyl]ethynyl}-4-methoxypyridine-2-carboxylic acid 5-{2-[5-chloro-2-(5-methoxyquinoline-8-sulfonamido)phenyl]ethynyl}pyridine-2-carboxylic acid 5-{2-[5-chloro-2-(5-methoxyquinoline-8-sulfonamido)phenyl]ethynyl}-4-methoxypyridine-2-carboxylic acid 5-{2-[5-chloro-2-(7-methylquinoline-8-sulfonamido)phenyl]ethynyl}-4-methoxypyridine-2-carboxylic acid 5-{2-[5-chloro-2-(5-ethoxyquinoline-8-sulfonamido)phenyl]ethynyl}-4-methoxypyridine-2-carboxylic acid 5-[2-(5-Methoxy-quinoline-8-sulfonylamino)-5-methyl-phenylethynyl]-pyridine-2-carboxylic acid 4-Methoxy-5-[2-(5-trifluoromethoxy-quinoline-8-sulfonylamino)-phenyl-ethynyl]-pyridine-2-carboxylic acid 5-[5-Methyl-2-(7-methyl-quinoline-8-sulfonylamino)-phenylethynyl]-pyridine-2-carboxylic acid 3-(ethylamino)-5-{2-[2-(quinoline-8-sulfonamido)phenyl] ethynyl}pyridine-2-carboxylic acid 2,3-dihydroxypropyl 5-{2-[2-(7-methylquinoline-8-sulfonamido)phenyl]-ethynyl}pyridine-2-carboxylate 5-{2-[5-ethyl-2-(7-methylquinoline-8-sulfonamido)phenyl] ethynyl}pyridine-2-carboxylic acid 5-{2-[2-(7-methylquinoline-8-sulfonamido)phenyl] ethynyl}pyridine-2-carboxylic acid 5-{2-[2-(5-methoxyquinoline-8-sulfonamido)phenyl]ethynyl}-3-methylpyridine-2-carboxylic acid 5-{2-[2-(9H-fluorene-2-sulfonamido)phenyl] ethynyl}pyridine-2-carboxylic acid 3-methyl-5-{2-[2-(7-methylquinoline-8-sulfonamido)phenyl]ethynyl}pyridine-2-carboxylic acid 4-methyl-5-{2-[2-(7-methylquinoline-8-sulfonamido)phenyl]ethynyl}pyridine-2-carboxylic acid 5-[2-(2-{8-oxatricyclo[7.4.0.0$^{2,7}$]trideca-1(9),2(7),3,5,10,12-hexaene-6-sulfon-amido}phenyl)ethynyl]pyridine-2-carboxylic acid 5-{2-[2-(5-methoxyquinoline-8-sulfonamido)phenyl]ethynyl}-4-methylpyridine-2-carboxylic acid 5-{2-[5-fluoro-2-(7-methylquinoline-8-sulfonamido)phenyl]ethynyl}pyridine-2-carboxylic acid methyl 5-{2-[2-(5-methoxyquinoline-8-sulfonamido)phenyl]ethynyl}-4-methyl-pyridine-2-carboxylate methyl 5-{2-[2-(5-methoxyquinoline-8-sulfonamido)phenyl]ethynyl}pyridine-2-carboxylate methyl 5-{2-[2-(9H-fluorene-2-sulfonamido)phenyl] ethynyl}pyridine-2-carboxylate methyl 5-{2-[5-fluoro-2-(7-methylquinoline-8-sulfonamido)phenyl]ethynyl}-pyridine-2-carboxylate methyl 5-{2-[2-(7-methylquinoline-8-sulfonamido)phenyl] ethynyl}pyridine-2-carboxylate 5-(2-{2-[(decahydroquinoline-1-sulfonyl)amino] phenyl}ethynyl)pyridine-2-carboxylic acid methyl 5-{2-[5-fluoro-2-(7-methylquinoline-8-sulfonamido)phenyl]ethynyl}-4-methylpyridine-2-carboxylate 5-{2-[5-fluoro-2-(7-methylquinoline-8-sulfonamido)phenyl]ethynyl}-4-methyl-pyridine-2-carboxylic acid 4-chloro-5-{2-[2-(7-methylquinoline-8-sulfonamido)phenyl]ethynyl}pyridine-2-carboxylic acid
methyl 4-chloro-5-{2-[2-(7-methylquinoline-8-sulfonamido)phenyl]ethynyl}-pyridine-2-carboxylate
methyl 4-chloro-5-{2-[2-(5-methoxyquinoline-8-sulfonamido)phenyl]ethynyl}-pyridine-2-carboxylate
5-{2-[2-(7-methylquinoline-8-sulfonamido)phenyl]ethynyl}-4-(prop-1-en-2-yl)pyridine-2-carboxylic acid
4-chloro-5-{2-[2-(5-methoxyquinoline-8-sulfonamido)phenyl]ethynyl}pyridine-2-carboxylic acid
4-{2-[2-(7-methylquinoline-8-sulfonamido)phenyl]ethynyl}benzoic acid
5-[2-(2-{[(4aR,8aS)-decahydroquinoline-1-sulfonyl]amino}phenyl)ethynyl]-pyridine-2-carboxylic acid
ethyl 5-{2-[2-(5-methoxyquinoline-8-sulfonamido)phenyl]ethynyl}pyridine-2-carboxylate
propyl 5-{2-[2-(5-methoxyquinoline-8-sulfonamido)phenyl]ethynyl}pyridine-2-carboxylate
propan-2-yl 5-[2-[2-(5-methoxyquinoline-8-sulfonamido)phenyl]ethynyl]-pyridine-2-carboxylate
butyl 5-{2-[2-(5-methoxyquinoline-8-sulfonamido)phenyl]ethynyl}pyridine-2-carboxylate
4-methoxy-5-{2-[2-(5-methoxyquinoline-8-sulfonamido)phenyl]ethynyl}-pyridine-2-carboxylic acid
benzyl 5-{2-[2-(5-methoxyquinoline-8-sulfonamido)phenyl]ethynyl}pyridine-2-carboxylate
4-ethoxy-5-{2-[2-(5-methoxyquinoline-8-sulfonamido)phenyl]ethynyl}pyridine-2-carboxylic acid
4-ethoxy-5-{2-[2-(7-methylquinoline-8-sulfonamido)phenyl]ethynyl}pyridine-2-carboxylic acid
5-(2-{2-[N-({[1,1'-biphenyl]-4-yl}methyl)formamido]phenyl}ethynyl)pyridine-2-carboxylic acid
5-{2-[5-fluoro-2-(5-methoxyquinoline-8-sulfonamido)phenyl]ethynyl}pyridine-2-carboxylic acid
5-{2-[4,5-dichloro-2-(5-methoxyquinoline-8-sulfonamido)phenyl]ethynyl}-pyridine-2-carboxylic acid
5-(2-{2-[N-({2'-methoxy-[1,1'-biphenyl]-4-yl}methyl)formamido]phenyl}-ethynyl)pyridine-2-carboxylic acid
5-{2-[4-chloro-2-(5-methoxyquinoline-8-sulfonamido)phenyl]ethynyl}pyridine-2-carboxylic acid
5-(2-{2-[N-({2-methoxy-[1,1'-biphenyl]-4-yl}methyl)formamido]phenyl}-ethynyl)pyridine-2-carboxylic acid
5-[2-(2-{[N-(naphthalen-2-yl)formamido]methyl}phenyl)ethynyl]pyridine-2-carboxylic acid
5-{2-[4,5-dichloro-2-(7-methylquinoline-8-sulfonamido)phenyl]ethynyl}-pyridine-2-carboxylic acid
5-{2-[2-(5-methoxyquinoline-8-sulfonamido)phenyl]ethynyl}-3-(methylamino)pyridine-2-carboxylic acid
5-{2-[2-(7-ethoxyquinoline-8-sulfonamido)phenyl]ethynyl}pyridine-2-carboxylic acid
5-(2-{2-[7-(propan-2-yloxy)quinoline-8-sulfonamido]phenyl}ethynyl)pyridine-2-carboxylic acid
5-(2-{2-[N-({3-methoxy-[1,1'-biphenyl]-4-yl}methyl)formamido]phenyl}ethynyl)-pyridine-2-carboxylic acid
4-methoxy-5-[2-(2-{[(4-methyl-decahydroquinolin-1-yl)sulfonyl]amino}phenyl)-ethynyl]pyridine-2-carboxylic acid
5-[2-(2-{[(4a,8a-trans)-decahydroquinoline-1-sulfonyl]amino}phenyl)ethynyl]-3-methylpyridine-2-carboxylic acid
5-{2-[2-(7-methylquinoline-8-sulfonamido)phenyl]ethynyl}-4-phenylpyridine-2-carboxylic acid
5-{2-[2-(9-methyl-9H-carbazole-3-sulfonamido)phenyl]ethynyl}pyridine-2-carboxylic acid
5-[2-(2-{[(4-methyl-decahydroquinolin-1-yl)sulfonyl]amino}phenyl)ethynyl]-pyridine-2-carboxylic acid
4-{2-[5-bromo-2-(7-methylquinoline-8-sulfonamido)phenyl]ethynyl}-isoquinoline-1-carboxylic acid
4-{2-[5-chloro-2-(7-methylquinoline-8-sulfonamido)phenyl]ethynyl}-isoquinoline-1-carboxylic acid
4-{2-[5-chloro-2-(5-methoxyquinoline-8-sulfonamido)phenyl]ethynyl}-isoquinoline-1-carboxylic acid
2-(methylamino)-4-{2-[2-(7-methylquinoline-8-sulfonamido)phenyl]ethynyl}-benzoic acid
4-methoxy-5-{2-[2-(4-methoxy-2,3-dimethylbenzenesulfonamido)phenyl]-ethynyl}pyridine-2-carboxylic acid
methyl 5-{2-[2-(7-methylquinoline-8-sulfonamido)-5-nitrophenyl]ethynyl}-pyridine-2-carboxylate
5-{2-[5-methoxy-2-(7-methylquinoline-8-sulfonamido)phenyl]ethynyl}pyridine-2-carboxylic acid
5-[2-(4-Chloro-quinoline-8-sulfonylamino)-phenylethynyl]-pyridine-2-carboxylic acid
5-{2-[2-(4-ethoxynaphthalene-1-sulfonamido)phenyl]ethynyl}pyridine-2-carboxylic acid
5-[2-(2-{[1,1'-biphenyl]-4-sulfonamido}phenyl)ethynyl]pyridine-2-carboxylic acid
5-(2-{2-[4-(propan-2-yloxy)naphthalene-1-sulfonamido]phenyl}ethynyl)-pyridine-2-carboxylic acid
5-{2-[2-(3,4-dichloroquinoline-8-sulfonamido)phenyl]ethynyl}pyridine-2-carboxylic acid
5-{2-[2-(4,7-dichloroquinoline-8-sulfonamido)phenyl]ethynyl}pyridine-2-carboxylic acid
5-{2-[2-(5,6,7-trimethylquinoline-8-sulfonamido)phenyl]ethynyl}pyridine-2-carboxylic acid
5-{2-[2-(5,7-dichloroquinoline-8-sulfonamido)phenyl]ethynyl}pyridine-2-carboxylic acid
5-{2-[5-fluoro-2-(7-methylquinoline-8-sulfonamido)phenyl]ethynyl}-3-methylpyridine-2-carboxylic acid
5-{2-[2-(4,7-dimethylquinoline-8-sulfonamido)phenyl]ethynyl}pyridine-2-carboxylic acid
5-{2-[2-(7-bromo-2-chloroquinoline-8-sulfonamido)phenyl]ethynyl}pyridine-2-carboxylic acid
5-{2-[2-(7-bromo-4-chloroquinoline-8-sulfonamido)phenyl]ethynyl}pyridine-2-carboxylic acid
5-{2-[2-(4-chloro-7-fluoroquinoline-8-sulfonamido)phenyl]ethynyl}pyridine-2-carboxylic acid
5-{2-[2-(5-ethoxyquinoline-8-sulfonamido)phenyl]ethynyl}pyridine-2-carboxylic acid
3-Ethyl-5-[2-(quinoline-8-sulfonylamino)-phenylethynyl]-pyridine-2-carboxylic acid
5-{2-[5-bromo-4-fluoro-2-(7-methylquinoline-8-sulfonamido)phenyl]ethynyl}-4-methoxypyridine-2-carboxylic acid
4-methoxy-5-{2-[2-(quinoline-8-sulfonamido)phenyl]ethynyl}pyridine-2-carboxylic acid
3-Methyl-5-[2-(5-trifluoromethoxy-quinoline-8-sulfonylamino)-phenylethynyl]-pyridine-2-carboxylic acid
5-[2-(5-Trifluoromethoxy-quinoline-8-sulfonylamino)-phenylethynyl]-pyridine-2-carboxylic acid
5-[5-Chloro-2-(4-methoxy-2,3-dimethyl-benzenesulfonylamino)-phenyl-ethynyl]-pyridine-2-carboxylic acid
5-[5-Chloro-2-(4-methoxy-benzenesulfonylamino)-phenyl-ethynyl]-4-methoxy-pyridine-2-carboxylic acid
5-[5-Methoxy-2-(5-methoxy-quinoline-8-sulfonylamino)-phenylethynyl]-pyridine-2-carboxylic acid
4-{2-[5-bromo-2-(4-methoxy-2,3-dimethylbenzenesulfonamido)phenyl]-ethynyl}isoquinoline-1-carboxylic acid
4-[5-Chloro-2-(4-methoxy-2,3-dimethyl-benzenesulfonylamino)-phenyl-ethynyl]-isoquinoline-1-carboxylic acid
7-methyl-N-[2-(2-{7-oxo-5H,7H-furo[3,4-b]pyridin-3-yl}ethynyl)phenyl]-quinoline-8-sulfonamide 3-amino-5-{2-[2-(4-methoxy-2,3-dimethylbenzenesulfonamido)phenyl]-ethynyl}pyridine-2-carboxylic acid
5-{2-[5-chloro-2-(4-methoxy-2,3-dimethylbenzenesulfonamido)phenyl]-ethynyl}-3-(methylamino)pyridine-2-carboxylic acid
(2,2-dimethyl-1,3-dioxolan-4-yl)methyl 4-methoxy-5-{2-[2-(7-methylquinoline-8-sulfonamido)phenyl]ethynyl}pyridine-2-carboxylate
2,3-dihydroxypropyl 4-methoxy-5-{2-[2-(7-methylquinoline-8-sulfonamido)-phenyl]ethynyl}pyridine-2-carboxylate
5-{2-[2-(4-methoxy-2,3-dimethylbenzenesulfonamido)-5-methylphenyl]-ethynyl}pyridine-2-carboxylic acid
5-{2-[2-(5-propylquinoline-8-sulfonamido)phenyl]ethynyl}pyridine-2-carboxylic acid
3-{2-[2-(naphthalene-2-sulfonamido)phenyl]ethynyl}benzoic acid
4-{2-[2-(naphthalene-2-sulfonamido)phenyl]ethynyl}benzoic acid
4-{2-[2-(N-methylnaphthalene-2-sulfonamido)phenyl]ethynyl}benzoic acid
4-(2-{2-[(naphthalene-2-sulfonyl)methyl]phenyl}ethynyl)benzoic acid
4-{2-[2-(5,6,7,8-tetrahydronaphthalene-2-sulfonamido)phenyl]ethynyl}benzoic acid
4-{2-[2-(4-methoxynaphthalene-1-sulfonamido)phenyl]ethynyl}benzoic acid
2-methyl-4-{2-[2-(naphthalene-2-sulfonamido)phenyl]ethynyl}benzoic acid
4-{2-[2-(4-methoxy-5,6,7,8-tetrahydronaphthalene-1-sulfonamido)-phenyl]ethynyl}benzoic acid
2-fluoro-4-{2-[2-(naphthalene-2-sulfonamido)phenyl]ethynyl}benzoic acid
4-{2-[5-fluoro-2-(naphthalene-2-sulfonamido)phenyl]ethynyl}benzoic acid
4-{2-[2-(naphthalene-2-sulfonamido)-4-(trifluoromethyl)phenyl]ethynyl}-benzoic acid
4-{2-[2-(4-methoxynaphthalene-1-sulfonamido)phenyl]ethynyl}-2-methyl-benzoic acid
4-{2-[4-methoxy-2-(naphthalene-2-sulfonamido)phenyl]ethynyl}benzoic acid
4-{2-[2-(5-chloro-3-methyl-1-benzothiophene-2-sulfonamido)phenyl]ethynyl}-benzoic acid
4-{2-[2-(2,3-dichloro-4-methoxybenzenesulfonamido)phenyl]ethynyl}benzoic acid
4-{2-[5-fluoro-2-(4-methoxynaphthalene-1-sulfonamido)phenyl]ethynyl}-benzoic acid
4-{2-[2-(5-methoxyquinoline-8-sulfonamido)phenyl]ethynyl}benzoic acid
2-chloro-4-{2-[2-(naphthalene-2-sulfonamido)phenyl]ethynyl}benzoic acid
3-fluoro-4-{2-[2-(naphthalene-2-sulfonamido)phenyl]ethynyl}benzoic acid
5-{2-[2-(4-methoxynaphthalene-1-sulfonamido)phenyl]ethynyl}pyridine-2-carboxylic acid
4-{2-[3-fluoro-2-(naphthalene-2-sulfonamido)phenyl]ethynyl}benzoic acid
2-methoxy-4-{2-[2-(4-methoxynaphthalene-1-sulfonamido)phenyl]ethynyl}-benzoic acid
5-{2-[5-fluoro-2-(4-methoxynaphthalene-1-sulfonamido)phenyl]ethynyl}-pyridine-2-carboxylic acid
4-{2-[2-(quinoline-8-sulfonamido)phenyl]ethynyl}benzoic acid
4-{2-[6-methyl-2-(naphthalene-2-sulfonamido)pyridin-3-yl]ethynyl}benzoic acid
5-{2-[2-(4-methoxy-2,3-dimethylbenzenesulfonamido)phenyl]ethynyl}pyridine-2-carboxylic acid
4-{2-[2-(6-chloronaphthalene-2-sulfonamido)phenyl]ethynyl}benzoic acid
5-{2-[2-(5-methoxyquinoline-8-sulfonamido)phenyl]ethynyl}pyridine-2-carboxylic acid
2-fluoro-4-{2-[2-(4-methoxynaphthalene-1-sulfonamido)phenyl]ethynyl}-benzoic acid
4-{2-[4-methyl-2-(naphthalene-2-sulfonamido)phenyl]ethynyl}benzoic acid
4-{2-[2-(4-methoxy-2-methylbenzenesulfonamido)phenyl]ethynyl}benzoic acid
4-{2-[2-(5-bromo-6-methoxypyridine-3-sulfonamido)phenyl]ethynyl}benzoic acid
3-methyl-5-{2-[2-(naphthalene-2-sulfonamido)phenyl]ethynyl}pyridine-2-carboxylic acid
5-{2-[2-(quinoline-8-sulfonamido)phenyl]ethynyl}pyridine-2-carboxylic acid
4-{2-[2-(naphthalene-1-sulfonamido)phenyl]ethynyl}benzoic acid
4-{2-[2-(4-methoxy-3-methylbenzenesulfonamido)phenyl]ethynyl}benzoic acid
2-ethoxy-4-{2-[2-(4-methoxynaphthalene-1-sulfonamido)phenyl]ethynyl}-benzoic acid
3-methyl-5-{2-[2-(quinoline-8-sulfonamido)phenyl]ethynyl}pyridine-2-carboxylic acid
4-methyl-5-{2-[2-(quinoline-8-sulfonamido)phenyl]ethynyl}pyridine-2-carboxylic acid
2-methoxy-4-{2-[2-(naphthalene-1-sulfonamido)phenyl]ethynyl}benzoic acid
5-{2-[2-(4-methoxynaphthalene-1-sulfonamido)phenyl]ethynyl}-3-methyl-pyridine-2-carboxylic acid
2-methoxy-4-{2-[2-(4-methoxy-2-methylbenzenesulfonamido)phenyl]ethynyl}-benzoic acid
4-{2-[5-fluoro-2-(naphthalene-1-sulfonamido)phenyl]ethynyl}benzoic acid
2-fluoro-4-{2-[2-(naphthalene-1-sulfonamido)phenyl]ethynyl}benzoic acid
5-{2-[2-(naphthalene-1-sulfonamido)phenyl]ethynyl}pyridine-2-carboxylic acid
4-{2-[2-(1-benzofuran-2-sulfonamido)phenyl]ethynyl}benzoic acid
3-methyl-5-{2-[2-(naphthalene-1-sulfonamido)phenyl]ethynyl}pyridine-2-carboxylic acid
4-{2-[2-(4-methylnaphthalene-1-sulfonamido)phenyl]ethynyl}benzoic acid
4-{2-[2-(3,4-dihydronaphthalene-2-sulfonamido)phenyl]ethynyl}benzoic acid
2-methyl-4-{2-[2-(naphthalene-1-sulfonamido)phenyl]ethynyl}benzoic acid
5-{2-[2-(3,4-dihydronaphthalene-2-sulfonamido)phenyl]ethynyl}pyridine-2-carboxylic acid
4-{2-[2-(1-benzothiophene-3-sulfonamido)phenyl]ethynyl}benzoic acid
4-{2-[2-(9H-fluorene-2-sulfonamido)phenyl]ethynyl}benzoic acid
4-methyl-5-{2-[2-(naphthalene-1-sulfonamido)phenyl]ethynyl}pyridine-2-carboxylic acid
5-[2-(2-{[1,1'-biphenyl]-3-sulfonamido}phenyl)ethynyl]pyridine-2-carboxylic acid
5-{2-[2-(1-methylnaphthalene-2-sulfonamido)phenyl]ethynyl}pyridine-2-carboxylic acid
5-(2-{2-[(decahydroisoquinoline-2-sulfonyl)amino]phenyl}ethynyl)pyridine-2-carboxylic acid
5-{2-[2-(1-benzothiophene-3-sulfonamido)phenyl]ethynyl}pyridine-2-carboxylic acid
5-{2-[2-(1,3-benzothiazole-4-sulfonamido)phenyl]ethynyl}pyridine-2-carboxylic acid 5-{2-[5-fluoro-2-(quinoline-8-sulfonamido)phenyl]
ethynyl}pyridine-2-carboxylic acid
5-[2-(2-{2'-methoxy-[1,1'-biphenyl]-3-
sulfonamido}phenyl)ethynyl]pyridine-2-carboxylic acid
5-[2-(2-{N-[(naphthalen-2-yl)methyl]formamido}phenyl)
ethynyl]pyridine-2-carboxylic acid
5-[2-(2-{N-[(naphthalen-2-yl)methyl]acetamido}phenyl)
ethynyl]pyridine-2-carboxylic acid
5-{2-[2-(2-methoxyquinoline-8-sulfonamido)phenyl]
ethynyl}pyridine-2-carboxylic acid
5-{2-[2-(9H-fluorene-2-sulfonamido)phenyl]ethynyl}-3-
methylpyridine-2-carboxylic acid
5-{2-[2-(9H-fluorene-2-sulfonamido)phenyl]ethynyl}-4-
methylpyridine-2-carboxylic acid
5-[2-(2-{N-[(quinolin-2-yl)methyl]acetamido}phenyl)ethy-
nyl]pyridine-2-carboxylic acid
5-[2-[2-(9H-carbazole-2-sulfonamido)phenyl]
ethynyl}pyridine-2-carboxylic acid
5-(2-{2-[3-(2,6-dimethoxypyridin-3-yl)benzenesulfona-
mido]phenyl}ethynyl)-pyridine-2-carboxylic acid
5-(2-{2-[(2,3-dihydro-1H-indole-1-sulfonyl)amino]
phenyl}ethynyl)pyridine-2-carboxylic acid
5-(2-{2-[3-(6-methoxypyridin-2-yl)benzenesulfonamido]
phenyl}ethynyl)-pyridine-2-carboxylic acid
5-{2-[2-(4-bromonaphthalene-1-sulfonamido)phenyl]
ethynyl}pyridine-2-carboxylic acid
methyl 5-(2-{2-[3-(pyridin-3-yl)benzenesulfonamido]
phenyl}ethynyl)pyridine-2-carboxylate
methyl 5-(2-{2-[4-(1H-pyrazol-1-yl)benzenesulfonamido]
phenyl}ethynyl)-pyridine-2-carboxylate
methyl 5-[2-(2-{[1,1'-biphenyl]-2-sulfonamido}phenyl)
ethynyl]pyridine-2-carboxylate
methyl 4-methyl-5-{2-[2-(7-methylquinoline-8-sulfona-
mido)phenyl]ethynyl}-pyridine-2-carboxylate
5-[2-(2-{[1,1'-biphenyl]-4-sulfonamido}-5-fluorophenyl)
ethynyl]-4-methyl-pyridine-2-carboxylic acid
methyl 5-[2-(2-{[1,1'-biphenyl]-4-sulfonamido}-5-fluoro-
phenyl)ethynyl]-4-methylpyridine-2-carboxylate
methyl 5-[2-(2-{carbamoyl[(naphthalen-2-yl)methyl]
amino}phenyl)ethynyl]-pyridine-2-carboxylate
5-[2-(2-{[1,1'-biphenyl]-2-sulfonamido}phenyl)ethynyl]
pyridine-2-carboxylic acid
5-(2-{2-[4-(1H-pyrazol-1-yl)benzenesulfonamido]
phenyl}ethynyl)pyridine-2-carboxylic acid
5-[2-(2-{carbamoyl[(naphthalen-2-yl)methyl]
amino}phenyl)ethynyl]pyridine-2-carboxylic acid
5-{2-[2-(9-methyl-9H-carbazole-2-sulfonamido)phenyl]
ethynyl}pyridine-2-carboxylic acid
5-(2-{2-[(1,2,3,4-tetrahydro-1,8-naphthyridine-1-carbonyl)
amino]phenyl}-ethynyl)pyridine-2-carboxylic acid
4-[2-(2-{[1,1'-biphenyl]-4-sulfonamido}phenyl)ethynyl]
benzoic acid
5-[2-(2-{[N-(naphthalen-1-yl)acetamido]methyl}phenyl)
ethynyl]pyridine-2-carboxylic acid
3-(dimethylamino)-5-{2-[2-(7-methylquinoline-8-sulfona-
mido)phenyl]ethynyl}-pyridine-2-carboxylic acid
3-methoxy-5-{2-[2-(7-methylquinoline-8-sulfonamido)phe-
nyl]ethynyl}pyridine-2-carboxylic acid
5-(2-{2-[4-(cyclohex-1-en-1-yl)benzenesulfonamido]
phenyl}ethynyl)pyridine-2-carboxylic acid
5-(2-{2-{N-[(quinolin-8-yl)methyl]formamido}phenyl)
ethynyl]pyridine-2-carboxylic acid
5-(2-{2-[N-({2'-methoxy-[1,1'-biphenyl]-3-yl}methyl)for-
mamido]phenyl}ethynyl)pyridine-2-carboxylic acid
5-(2-{2-[N-({[1,1'-biphenyl]-3-yl}methyl)formamido]
phenyl}ethynyl)pyridine-2-carboxylic acid
5-{2-[4-bromo-2-(5-methoxyquinoline-8-sulfonamido)phe-
nyl]ethynyl}pyridine-2-carboxylic acid
5-{2-[4-bromo-2-(7-methylquinoline-8-sulfonamido)phe-
nyl]ethynyl}pyridine-2-carboxylic acid
4-(dimethylamino)-5-{2-[2-(7-methylquinoline-8-sulfona-
mido)phenyl]ethynyl}-pyridine-2-carboxylic acid
3-ethoxy-5-{2-[2-(7-methylquinoline-8-sulfonamido)phe-
nyl]ethynyl}pyridine-2-carboxylic acid
5-(2-{2-[N-({2'-methoxy-[1,1'-biphenyl]-2-yl}methyl)for-
mamido]phenyl}-ethynyl)pyridine-2-carboxylic acid
5-(2-{2-[N-({[1,1'-biphenyl]-4-yl}methyl)formamido]
phenyl}ethynyl)-3-methyl-pyridine-2-carboxylic acid
3-methyl-5-[2-(2-{N-[(naphthalen-2-yl)methyl]
formamido}phenyl)ethynyl]-pyridine-2-carboxylic acid
5-{2-[4-methoxy-2-(5-methoxyquinoline-8-sulfonamido)
phenyl]ethynyl}-pyridine-2-carboxylic acid
5-{2-[2-(9-methyl-9H-carbazole-4-sulfonamido)phenyl]
ethynyl}pyridine-2-carboxylic acid
5-[2-(2-{N-[2-(naphthalen-1-yl)ethyl]formamido}phenyl)
ethynyl]pyridine-2-carboxylic acid
N-(2-{2-[6-(3-hydroxyoxetan-3-yl)pyridin-3-yl]
ethynyl}phenyl)-7-methylquinoline-8-sulfonamide
5-[2-(2-{N-[(3-phenoxyphenyl)methyl]formamido}phenyl)
ethynyl]pyridine-2-carboxylic acid
4-{2-[2-(7-methylquinoline-8-sulfonamido)phenyl]
ethynyl}isoquinoline-1-carboxylic acid
4-{2-[2-(5-methoxyquinoline-8-sulfonamido)phenyl]
ethynyl}isoquinoline-1-carboxylic acid
N-hydroxy-5-{2-[2-(5-methoxyquinoline-8-sulfonamido)
phenyl]-ethynyl}pyridine-2-carboxamide
5-{2-[4-methoxy-2-(7-methylquinoline-8-sulfonamido)phe-
nyl]ethynyl}pyridine-2-carboxylic acid
4-methoxy-5-(2-{2-[(octahydro-1H-indole-1-sulfonyl)
amino]phenyl}ethynyl)-pyridine-2-carboxylic acid
5-[2-(2-{N-[(6-phenylpyridin-3-yl)methyl]
formamido}phenyl)ethynyl]pyridine-2-carboxylic acid
N-hydroxy-4-methoxy-5-{2-[2-(5-methoxyquinoline-8-
sulfonamido)phenyl]-ethynyl}pyridine-2-carboxamide
2-methoxy-4-{2-[2-(7-methylquinoline-8-sulfonamido)phe-
nyl]ethynyl}benzoic acid
2-methoxy-4-{2-[2-(5-methoxyquinoline-8-sulfonamido)
phenyl]ethynyl}-benzoic acid
4-{2-[2-(5-methoxyquinoline-8-sulfonamido)phenyl]ethy-
nyl}-2-(methylamino)-benzoic acid
5-{2-[5-(dimethylamino)-2-(7-methylquinoline-8-sulfona-
mido)phenyl]ethynyl}-pyridine-2-carboxylic acid
4-[2-(4-Methoxy-2,3-dimethyl-benzenesulfonylamino)-
phenylethynyl]-benzoic acid
4-Methoxy-naphthalene-1-sulfonic acid [4-fluoro-2-(6-
methanesulfonylamino-carbonyl-pyridin-2-ylethynyl)-
phenyl]-amide
4-[2-(4-Methoxy-naphthalene-2-sulfonylamino)-phenyl-
ethynyl]-benzoic acid
5-[2-(3-Methyl-quinoline-8-sulfonylamino)-phenylethy-
nyl]-pyridine-2-carboxylic acid
5-[2-(4-Methyl-quinoline-8-sulfonylamino)-phenylethy-
nyl]-pyridine-2-carboxylic acid
5-[2-(6-Methyl-quinoline-8-sulfonylamino)-phenylethy-
nyl]-pyridine-2-carboxylic acid
5-[2-(2-Methyl-quinoline-8-sulfonylamino)-phenylethy-
nyl]-pyridine-2-carboxylic acid
4-[2-(3-Chloro-quinoline-8-sulfonylamino)-phenylethy-
nyl]-benzoic acid
5-[2-(3-Chloro-quinoline-8-sulfonylamino)-phenylethy-
nyl]-pyridine-2-carboxylic acid
5-{2-[2-(4-methoxy-2,3,6-trimethylbenzenesulfonamido)
phenyl]ethynyl}-pyridine-2-carboxylic acid 4-{2-[2-(5-chloro-1-benzothiophene-2-sulfonamido)phenyl]ethynyl}benzoic acid
5-[2-[4-fluoro-2-(naphthalene-1-sulfonamido)phenyl]ethynyl}pyridine-2-carboxylic acid
5-[2-(2-{8-oxatricyclo[7.4.0.0]trideca-1(9),2(7),3,5,10,12-hexaene-4-sulfonamido}phenyl)ethynyl]pyridine-2-carboxylic acid
5-{2-[2-(5-chloronaphthalene-1-sulfonamido)phenyl]ethynyl}pyridine-2-carboxylic acid
5-[2-(2-{2'-methyl-[1,1'-biphenyl]-4-sulfonamido}phenyl)ethynyl]pyridine-2-carboxylic acid
5-{2-[2-(6-fluoroquinoline-8-sulfonamido)phenyl]ethynyl}pyridine-2-carboxylic acid
5-{2-[2-(3-acetamido-4-ethoxybenzenesulfonamido)phenyl]ethynyl}pyridine-2-carboxylic acid
5-[2-(2-{8-oxatricyclo[7.4.0.0$^{2,7}$]trideca-1(9),2(7),3,5,10,12-hexaene-5-sulfonamido}phenyl)ethynyl]pyridine-2-carboxylic acid
5-{2-[2-(1-methyl-1H-indole-4-sulfonamido)phenyl]ethynyl}pyridine-2-carboxylic acid
5-[2-(2-{[1,1'-biphenyl]-4-sulfonamido}-5-fluorophenyl)ethynyl]-3-methylpyridine-2-carboxylic acid
5-[2-(5-fluoro-2-{8-oxatricyclo[7.4.0.0$^{2,7}$]trideca-1(9),2(7),3,5,10,12-hexaene-5-sulfonamido}phenyl)ethynyl]-3-methylpyridine-2-carboxylic acid
5-{2-[5-fluoro-2-(5-methoxyquinoline-8-sulfonamido)phenyl]ethynyl}-3-methylpyridine-2-carboxylic acid
5-{2-[2-(2,4-dichloroquinoline-8-sulfonamido)phenyl]ethynyl}pyridine-2-carboxylic acid
5-{2-[2-(6-chloro-2-methylquinoline-8-sulfonamido)phenyl]ethynyl}pyridine-2-carboxylic acid
5-{2-[2-(4-methoxyquinoline-8-sulfonamido)phenyl]ethynyl}pyridine-2-carboxylic acid
5-[5-Ethoxy-2-(quinoline-8-sulfonylamino)-phenylethynyl]-pyridine-2-carboxylic acid
4-(2-{2-[(E)-2-phenylethenesulfonamido]phenyl}ethynyl)benzoic acid
5-(2-{2-[4-(prop-2-yn-1-yloxy)quinoline-8-sulfonamido]phenyl}-ethynyl)pyridine-2-carboxylic acid
2-methoxy-5-methyl-4-{2-[2-(7-methylquinoline-8-sulfonamido)phenyl]-ethynyl}benzoic acid
5-[5-Chloro-2-(4-methoxy-benzenesulfonylamino)-phenylethynyl]-pyridine-2-carboxylic acid
4-Methoxy-5-[2-(4-methoxy-benzenesulfonylamino)-phenylethynyl]-pyridine-2-carboxylic acid
5-[2-(5-Methoxy-quinoline-8-sulfonylamino)-phenylethynyl]-pyridine-2-carboxylic acid isopropylamide
4-[2-(4-Methoxy-2,3-dimethyl-benzenesulfonylamino)-phenylethynyl]-isoquinoline-1-carboxylic acid
3-(hydroxymethyl)-5-{2-[2-(7-methylquinoline-8-sulfonamido)phenyl]-ethynyl}pyridine-2-carboxylic acid
(2,2-dimethyl-1,3-dioxolan-4-yl)methyl 5-{2-[2-(7-methylquinoline-8-sulfonamido)phenyl]ethynyl}pyridine-2-carboxylate
2-methoxyethyl 4-methoxy-5-{2-[2-(5-methoxyquinoline-8-sulfonamido)-phenyl]ethynyl}pyridine-2-carboxylate
2-(2-hydroxyethoxy)ethyl 5-{2-[2-(7-methylquinoline-8-sulfonamido)-phenyl]ethynyl}pyridine-2-carboxylate
2-methoxyethyl 5-{2-[2-(7-methylquinoline-8-sulfonamido)phenyl]ethynyl}-pyridine-2-carboxylate
5-{2-[2-(5-ethylquinoline-8-sulfonamido)phenyl]ethynyl}pyridine-2-carboxylic acid
8-{2-[2-(7-methylquinoline-8-sulfonamido)phenyl]ethynyl}-1H,2H,3H,4H-pyrido[3,4-b]pyrazine-5-carboxylic acid
5-{2-[2-(7-methylquinoline-8-sulfonamido)-5-(propan-2-yl)phenyl]ethynyl}-pyridine-2-carboxylic acid
5-[2-(4-Dimethylamino-quinoline-8-sulfonylamino)-phenylethynyl]-4-methoxy-pyridine-2-carboxylic acid
5-(2-{2-[5-(propan-2-yloxy)quinoline-8-sulfonamido]phenyl}ethynyl)pyridine-2-carboxylic acid
5-{2-[5-bromo-2-(7-methylquinoline-8-sulfonamido)phenyl]ethynyl}pyridine-2-carboxylic acid
5-{2-[5-bromo-4-fluoro-2-(7-methylquinoline-8-sulfonamido)phenyl]ethynyl}-pyridine-2-carboxylic acid
5-{2-[2-(7-ethylquinoline-8-sulfonamido)phenyl]ethynyl}pyridine-2-carboxylic acid
5-{2-[5-chloro-2-(5-methoxyquinoline-8-sulfonamido)-3-methylphenyl]-ethynyl}pyridine-2-carboxylic acid
5-{2-[2-(7-methoxyquinoline-8-sulfonamido)phenyl]ethynyl}pyridine-2-carboxylic acid
5-{2-[2-(4-ethoxyquinoline-8-sulfonamido)phenyl]ethynyl}pyridine-2-carboxylic acid
5-(2-{2-[4-(propan-2-yloxy)quinoline-8-sulfonamido]phenyl}ethynyl)pyridine-2-carboxylic acid
5-{2-[4-(5-methoxyquinoline-8-sulfonamido)-[1,1'-biphenyl]-3-yl]ethynyl}pyridine-2-carboxylic acid
5-{2-[2-chloro-6-(5-methoxyquinoline-8-sulfonamido)phenyl]ethynyl}pyridine-2-carboxylic acid
5-{2-[5-bromo-2-(7-methylquinoline-8-sulfonamido)phenyl]ethynyl}-4-methoxypyridine-2-carboxylic acid
5-{2-[2-(5-ethoxyquinoline-8-sulfonamido)phenyl]ethynyl}-4-methoxypyridine-2-carboxylic acid
5-{2-[5-chloro-2-(7-methylquinoline-8-sulfonamido)phenyl]ethynyl}pyridine-2-carboxylic acid
3-Ethyl-5-[2-(7-ethyl-quinoline-8-sulfonylamino)-phenylethynyl]-pyridine-2-carboxylic acid
3-(ethylamino)-5-{2-[2-(4-methoxy-2,3-dimethylbenzenesulfonamido)phenyl]-ethynyl}pyridine-2-carboxylic acid
5-{2-[2-(7-ethylquinoline-8-sulfonamido)phenyl]ethynyl}-3-(methylamino)-pyridine-2-carboxylic acid
5-{2-[2-(5,7-dimethylquinoline-8-sulfonamido)phenyl]ethynyl}pyridine-2-carboxylic acid
2-methoxyethyl 4-methoxy-5-{2-[2-(7-methylquinoline-8-sulfonamido)phenyl]-ethynyl}pyridine-2-carboxylate
4-Methoxy-5-[2-(4-methylamino-quinoline-8-sulfonylamino)-phenylethynyl]-pyridine-2-carboxylic acid
5-[2-(4-Dimethylamino-quinoline-8-sulfonylamino)-phenylethynyl]-4-methyl-pyridine-2-carboxylic acid
5-[2-(2-{[(3-methoxyphenyl)(methyl)oxo-A6-sulfanylidene]amino}phenyl)-ethynyl]pyridine-2-carboxylic acid
4-{2-[2-(4-chloroquinoline-8-sulfonamido)phenyl]ethynyl}isoquinoline-1-carboxylic acid
4-{2-[2-(5-ethoxyquinoline-8-sulfonamido)phenyl]ethynyl}isoquinoline-1-carboxylic acid
4-{2-[2-(5,7-dimethylquinoline-8-sulfonamido)phenyl]ethynyl}isoquinoline-1-carboxylic acid
4-(2-{2-[5-(propan-2-yloxy)quinoline-8-sulfonamido]phenyl}ethynyl)-isoquinoline-1-carboxylic acid
4-[2-(2-{[methyl(oxo)(quinolin-8-yl)-A6-sulfanylidene]amino}phenyl)ethynyl]-isoquinoline-1-carboxylic acid
3-Ethyl-5-[2-(5-methoxy-quinoline-8-sulfonylamino)-phenylethynyl]-pyridine-2-carboxylic acid
3-Ethyl-5-[2-(2-methyl-quinoline-8-sulfonylamino)-phenylethynyl]-pyridine-2-carboxylic acid
5-[2-(5-Trifluoromethoxy-quinoline-8-sulfonylamino)-phenylethynyl]-pyridine-2-carboxylic acid
4-Methoxy-5-[2-(5-trifluoromethoxy-quinoline-8-sulfonylamino)-phenyl-ethynyl]-pyridine-2-carboxylic acid
5-{2-[5-(2,2,2-Trifluoro-ethoxy)-quinoline-8-sulfonylamino]-phenylethynyl}-pyridine-2-carboxylic acid 5-{5-Chloro-2-[5-(2,2,2-trifluoro-ethoxy)-quinoline-8-sulfonylamino]-phenyl-ethynyl}-pyridine-2-carboxylic acid 4-Methoxy-5-{2-[5-(2,2,2-trifluoro-ethoxy)-quinoline-8-sulfonylamino]-phenyl-ethynyl}-pyridine-2-carboxylic acid 5-{5-Chloro-2-[5-(2,2,2-trifluoro-ethoxy)-quinoline-8-sulfonylamino]-phenyl-ethynyl}-4-methoxy-pyridine-2-carboxylic acid 3-Ethyl-5-[2-(7-methyl-quinoline-8-sulfonylamino)-phenylethynyl]-pyridine-2-carboxylic acid.

Preferably, these compounds of PE8 are selected from the group consisting of (PE8a):

4-methoxy-5-{2-[2-(7-methylquinoline-8-sulfonamido)phenyl]ethynyl}pyridine-2-carboxylic acid 5-(2-{2-[N-({[1,1'-biphenyl]-4-yl}methyl)formamido]phenyl}ethynyl)-4-methoxypyridine-2-carboxylic acid 3-(methylamino)-5-{2-[2-(7-methylquinoline-8-sulfonamido)phenyl]-ethynyl}pyridine-2-carboxylic acid 5-{2-[2-(5-methoxyquinoline-8-sulfonamido)phenyl]ethynyl}-3-(methylamino)-pyridine-2-carboxylic acid 5-{2-[5-iodo-2-(5-methoxyquinoline-8-sulfonamido)phenyl]ethynyl}pyridine-2-carboxylic acid 4-methoxy-5-(2-{2-[N-({2'-methoxy-[1,1'-biphenyl]-4-yl}methyl)formamido]phenyl}ethynyl)pyridine-2-carboxylic acid 5-[2-(2-{[(4a,8a-trans)-decahydroquinoline-1-sulfonyl]amino}phenyl)ethynyl]-4-methoxypyridine-2-carboxylic acid 4-{2-[5-bromo-2-(5-methoxyquinoline-8-sulfonamido)phenyl]-ethynyl}isoquinoline-1-carboxylic acid 5-{2-[5-chloro-2-(7-methylquinoline-8-sulfonamido)phenyl]ethynyl}-3-(methylamino)pyridine-2-carboxylic acid 5-{2-[5-chloro-2-(5-methoxyquinoline-8-sulfonamido)phenyl]ethynyl}-3-(methylamino)pyridine-2-carboxylic acid 5-{2-[5-chloro-2-(4-methoxy-2,3-dimethylbenzenesulfonamido)phenyl]ethynyl}-4-methoxypyridine-2-carboxylic acid 5-{2-[5-bromo-4-fluoro-2-(5-methoxyquinoline-8-sulfonamido)phenyl]ethynyl}pyridine-2-carboxylic acid 5-{2-[5-bromo-2-(5-methoxyquinoline-8-sulfonamido)phenyl]ethynyl}pyridine-2-carboxylic acid 5-{2-[5-bromo-2-(5-methoxyquinoline-8-sulfonamido)phenyl]ethynyl}-4-methoxypyridine-2-carboxylic acid 5-{2-[5-bromo-4-fluoro-2-(5-methoxyquinoline-8-sulfonamido)phenyl]ethynyl}-4-methoxypyridine-2-carboxylic acid 5-{2-[5-chloro-2-(5-methoxyquinoline-8-sulfonamido)phenyl]ethynyl}pyridine-2-carboxylic acid 5-{2-[5-chloro-2-(5-methoxyquinoline-8-sulfonamido)phenyl]ethynyl}-4-methoxypyridine-2-carboxylic acid 5-{2-[5-chloro-2-(7-methylquinoline-8-sulfonamido)phenyl]ethynyl}-4-methoxypyridine-2-carboxylic acid 5-{2-[5-chloro-2-(5-ethoxyquinoline-8-sulfonamido)phenyl]ethynyl}-4-methoxypyridine-2-carboxylic acid 5-[2-(5-Methoxy-quinoline-8-sulfonylamino)-5-methyl-phenylethynyl]-pyridine-2-carboxylic acid 4-Methoxy-5-[2-(5-trifluoromethoxy-quinoline-8-sulfonylamino)-phenyl-ethynyl]-pyridine-2-carboxylic acid 5-[5-Methyl-2-(7-methyl-quinoline-8-sulfonylamino)-phenylethynyl]-pyridine-2-carboxylic acid 3-(ethylamino)-5-{2-[2-(quinoline-8-sulfonamido)phenyl]ethynyl}pyridine-2-carboxylic acid 2,3-dihydroxypropyl 5-{2-[2-(7-methylquinoline-8-sulfonamido)phenyl]ethynyl}pyridine-2-carboxylate 5-{2-[5-ethyl-2-(7-methylquinoline-8-sulfonamido)phenyl]ethynyl}pyridine-2-carboxylic acid 5-{2-[2-(7-methylquinoline-8-sulfonamido)phenyl]ethynyl}pyridine-2-carboxylic acid 5-{2-[2-(5-methoxyquinoline-8-sulfonamido)phenyl]ethynyl}-3-methylpyridine-2-carboxylic acid 5-{2-[2-(9H-fluorene-2-sulfonamido)phenyl]ethynyl}pyridine-2-carboxylic acid 3-methyl-5-{2-[2-(7-methylquinoline-8-sulfonamido)phenyl]ethynyl}pyridine-2-carboxylic acid 4-methyl-5-{2-[2-(7-methylquinoline-8-sulfonamido)phenyl]ethynyl}pyridine-2-carboxylic acid 5-[2-(2-{8-oxatricyclo[7.4.0.0$^{2,7}$]trideca-1 (9),2(7),3,5,10,12-hexaene-6-sulfonamido}phenyl)ethynyl]pyridine-2-carboxylic acid 5-{2-[2-(5-methoxyquinoline-8-sulfonamido)phenyl]ethynyl}-4-methylpyridine-2-carboxylic acid 5-{2-[5-fluoro-2-(7-methylquinoline-8-sulfonamido)phenyl]ethynyl}pyridine-2-carboxylic acid methyl 5-{2-[2-(5-methoxyquinoline-8-sulfonamido)phenyl]ethynyl}-4-methylpyridine-2-carboxylate methyl 5-{2-[2-(5-methoxyquinoline-8-sulfonamido)phenyl]ethynyl}pyridine-2-carboxylate methyl 5-{2-[2-(9H-fluorene-2-sulfonamido)phenyl]ethynyl}pyridine-2-carboxylate methyl 5-{2-[5-fluoro-2-(7-methylquinoline-8-sulfonamido)phenyl]ethynyl}-pyridine-2-carboxylate methyl 5-{2-[2-(7-methylquinoline-8-sulfonamido)phenyl]ethynyl}pyridine-2-carboxylate 5-(2-{2-[(decahydroquinoline-1-sulfonyl)amino]phenyl}ethynyl)pyridine-2-carboxylic acid methyl 5-{2-[5-fluoro-2-(7-methylquinoline-8-sulfonamido)phenyl]ethynyl}-4-methylpyridine-2-carboxylate 5-{2-[5-fluoro-2-(7-methylquinoline-8-sulfonamido)phenyl]ethynyl}-4-methylpyridine-2-carboxylic acid 4-chloro-5-{2-[2-(7-methylquinoline-8-sulfonamido)phenyl]ethynyl}pyridine-2-carboxylic acid methyl 4-chloro-5-{2-[2-(7-methylquinoline-8-sulfonamido)phenyl]ethynyl}-pyridine-2-carboxylate methyl 4-chloro-5-{2-[2-(5-methoxyquinoline-8-sulfonamido)phenyl]ethynyl}-pyridine-2-carboxylate 5-{2-[2-(7-methylquinoline-8-sulfonamido)phenyl]ethynyl}-4-(prop-1-en-2-yl)pyridine-2-carboxylic acid 4-chloro-5-{2-[2-(5-methoxyquinoline-8-sulfonamido)phenyl]ethynyl}pyridine-2-carboxylic acid 4-{2-[2-(7-methylquinoline-8-sulfonamido)phenyl]ethynyl}benzoic acid 5-[2-(2-{[(4aR,8aS)-decahydroquinoline-1-sulfonyl]amino}phenyl)ethynyl]-pyridine-2-carboxylic acid ethyl 5-{2-[2-(5-methoxyquinoline-8-sulfonamido)phenyl]ethynyl}pyridine-2-carboxylate propyl 5-{2-[2-(5-methoxyquinoline-8-sulfonamido)phenyl]ethynyl}pyridine-2-carboxylate propan-2-yl 5-{2-[2-(5-methoxyquinoline-8-sulfonamido)phenyl]ethynyl}-pyridine-2-carboxylate butyl 5-{2-[2-(5-methoxyquinoline-8-sulfonamido)phenyl]ethynyl}pyridine-2-carboxylate 4-methoxy-5-{2-[2-(5-methoxyquinoline-8-sulfonamido)phenyl]ethynyl}-pyridine-2-carboxylic acid benzyl 5-{2-[2-(5-methoxyquinoline-8-sulfonamido)phenyl]ethynyl}pyridine-2-carboxylate 4-ethoxy-5-{2-[2-(5-methoxyquinoline-8-sulfonamido)phenyl]ethynyl}pyridine-2-carboxylic acid 4-ethoxy-5-{2-[2-(7-methylquinoline-8-sulfonamido)phenyl]ethynyl}pyridine-2-carboxylic acid 5-(2-{2-[N-({[1,1'-biphenyl]-4-yl}methyl)formamido]phenyl}ethynyl)pyridine-2-carboxylic acid 5-{2-[5-fluoro-2-(5-methoxyquinoline-8-sulfonamido)phenyl]ethynyl}pyridine-2-carboxylic acid 5-{2-[4,5-dichloro-2-(5-methoxyquinoline-8-sulfonamido)phenyl]ethynyl}-pyridine-2-carboxylic acid 5-(2-{2-[N-({2'-methoxy-[1,1'-biphenyl]-4-yl}methyl)formamido]phenyl}-ethynyl)pyridine-2-carboxylic acid 5-{2-[4-chloro-2-(5-methoxyquinoline-8-sulfonamido)phenyl]ethynyl}-pyridine-2-carboxylic acid 5-(2-{2-[N-({2-methoxy-[1,1'-biphenyl]-4-yl}methyl)formamido]phenyl}ethynyl)-pyridine-2-carboxylic acid 5-[2-(2-{[N-(naphthalen-2-yl)formamido]methyl}phenyl)ethynyl]pyridine-2-carboxylic acid 5-{2-[4,5-dichloro-2-(7-methylquinoline-8-sulfonamido)phenyl]ethynyl}-pyridine-2-carboxylic acid 5-{2-[2-(5-methoxyquinoline-8-sulfonamido)phenyl]ethynyl}-3-(methylamino)-pyridine-2-carboxylic acid 5-{2-[2-(7-ethoxyquinoline-8-sulfonamido)phenyl]ethynyl}pyridine-2-carboxylic acid 5-(2-{2-[7-(propan-2-yloxy)quinoline-8-sulfonamido]phenyl}ethynyl)pyridine-2-carboxylic acid 5-(2-{2-[N-({3-methoxy-[1,1'-biphenyl]-4-yl}methyl)formamido]phenyl}ethynyl)-pyridine-2-carboxylic acid 4-methoxy-5-[2-(2-{[(4-methyl-decahydroquinolin-1-yl)sulfonyl]amino}phenyl)-ethynyl]pyridine-2-carboxylic acid 5-[2-(2-{[(4a,8a-trans)-decahydroquinoline-1-sulfonyl]amino}phenyl)ethynyl]-3-methylpyridine-2-carboxylic acid 5-{2-[2-(7-methylquinoline-8-sulfonamido)phenyl]ethynyl}-4-phenylpyridine-2-carboxylic acid 5-{2-[2-(9-methyl-9H-carbazole-3-sulfonamido)phenyl]ethynyl}pyridine-2-carboxylic acid 5-[2-(2-{[(4-methyl-decahydroquinolin-1-yl)sulfonyl]amino}phenyl)ethynyl]-pyridine-2-carboxylic acid 4-{2-[5-bromo-2-(7-methylquinoline-8-sulfonamido)phenyl]ethynyl}-isoquinoline-1-carboxylic acid 4-{2-[5-chloro-2-(7-methylquinoline-8-sulfonamido)phenyl]ethynyl}-isoquinoline-1-carboxylic acid 4-{2-[5-chloro-2-(5-methoxyquinoline-8-sulfonamido)phenyl]ethynyl}-isoquinoline-1-carboxylic acid 2-(methylamino)-4-{2-[2-(7-methylquinoline-8-sulfonamido)phenyl]ethynyl}-benzoic acid 4-methoxy-5-{2-[2-(4-methoxy-2,3-dimethylbenzenesulfonamido)phenyl]-ethynyl}pyridine-2-carboxylic acid methyl 5-{2-[2-(7-methylquinoline-8-sulfonamido)-5-nitrophenyl]ethynyl}-pyridine-2-carboxylate 5-{2-[5-methoxy-2-(7-methylquinoline-8-sulfonamido)phenyl]ethynyl}pyridine-2-carboxylic acid 5-[2-(4-Chloro-quinoline-8-sulfonylamino)-phenylethynyl]-pyridine-2-carboxylic acid 5-{2-[2-(4-ethoxynaphthalene-1-sulfonamido)phenyl]ethynyl}pyridine-2-carboxylic acid 5-[2-(2-{[1,1'-biphenyl]-4-sulfonamido}phenyl)ethynyl]pyridine-2-carboxylic acid 5-(2-{2-[4-(propan-2-yloxy)naphthalene-1-sulfonamido]phenyl}ethynyl)-pyridine-2-carboxylic acid 5-{2-[2-(3,4-dichloroquinoline-8-sulfonamido)phenyl]ethynyl}pyridine-2-carboxylic acid 5-{2-[2-(4,7-dichloroquinoline-8-sulfonamido)phenyl]ethynyl}pyridine-2-carboxylic acid 5-{2-[2-(5,6,7-trimethylquinoline-8-sulfonamido)phenyl]ethynyl}pyridine-2-carboxylic acid 5-{2-[2-(5,7-dichloroquinoline-8-sulfonamido)phenyl]ethynyl}pyridine-2-carboxylic acid 5-{2-[5-fluoro-2-(7-methylquinoline-8-sulfonamido)phenyl]ethynyl}-3-methylpyridine-2-carboxylic acid 5-{2-[2-(4,7-dimethylquinoline-8-sulfonamido)phenyl]ethynyl}pyridine-2-carboxylic acid 5-{2-[2-(7-bromo-2-chloroquinoline-8-sulfonamido)phenyl]ethynyl}pyridine-2-carboxylic acid 5-{2-[2-(7-bromo-4-chloroquinoline-8-sulfonamido)phenyl]ethynyl}pyridine-2-carboxylic acid 5-{2-[2-(4-chloro-7-fluoroquinoline-8-sulfonamido)phenyl]ethynyl}pyridine-2-carboxylic acid 5-{2-[2-(5-ethoxyquinoline-8-sulfonamido)phenyl]ethynyl}pyridine-2-carboxylic acid 3-Ethyl-5-[2-(quinoline-8-sulfonylamino)-phenylethynyl]-pyridine-2-carboxylic acid 5-{2-[5-bromo-4-fluoro-2-(7-methylquinoline-8-sulfonamido)phenyl]ethynyl}-4-methoxypyridine-2-carboxylic acid 4-methoxy-5-{2-[2-(quinoline-8-sulfonamido)phenyl]ethynyl}pyridine-2-carboxylic acid 3-Methyl-5-[2-(5-trifluoromethoxy-quinoline-8-sulfonylamino)-phenylethynyl]-pyridine-2-carboxylic acid 5-[2-(5-Trifluoromethoxy-quinoline-8-sulfonylamino)-phenylethynyl]-pyridine-2-carboxylic acid 5-[5-Chloro-2-(4-methoxy-2,3-dimethyl-benzenesulfonylamino)-phenylethynyl]-pyridine-2-carboxylic acid 5-[5-Chloro-2-(4-methoxy-benzenesulfonylamino)-phenylethynyl]-4-methoxy-pyridine-2-carboxylic acid 5-[5-Methoxy-2-(5-methoxy-quinoline-8-sulfonylamino)-phenylethynyl]-pyridine-2-carboxylic acid 4-{2-[5-bromo-2-(4-methoxy-2,3-dimethylbenzenesulfonamido)phenyl]ethynyl}isoquinoline-1-carboxylic acid 4-[5-Chloro-2-(4-methoxy-2,3-dimethyl-benzenesulfonylamino)-phenylethynyl]-isoquinoline-1-carboxylic acid 7-methyl-N-[2-(2-{7-oxo-5H,7H-furo[3,4-b]pyridin-3-yl}ethynyl)phenyl]-quinoline-8-sulfonamide 3-amino-5-{2-[2-(4-methoxy-2,3-dimethylbenzenesulfonamido)phenyl]-ethynyl}pyridine-2-carboxylic acid 5-{2-[5-chloro-2-(4-methoxy-2,3-dimethylbenzenesulfonamido)phenyl]-ethynyl}-3-(methylamino)pyridine-2-carboxylic acid (2,2-dimethyl-1,3-dioxolan-4-yl)methyl 4-methoxy-5-{2-[2-(7-methylquinoline-8-sulfonamido)phenyl]ethynyl}pyridine-2-carboxylate 2,3-dihydroxypropyl 4-methoxy-5-{2-[2-(7-methylquinoline-8-sulfonamido)-phenyl]ethynyl}pyridine-2-carboxylate 5-{2-[2-(4-methoxy-2,3-dimethylbenzenesulfonamido)-5-methylphenyl]-ethynyl}pyridine-2-carboxylic acid 5-{2-[2-(5-propylquinoline-8-sulfonamido)phenyl]ethynyl}pyridine-2-carboxylic acid;

5-(2-{2-[5-(propan-2-yloxy)quinoline-8-sulfonamido]phenyl}ethynyl)pyridine-2-carboxylic acid 5-{2-[5-bromo-2-(7-methylquinoline-8-sulfonamido)phenyl]ethynyl}pyridine-2-carboxylic acid 5-{2-[5-bromo-4-fluoro-2-(7-methylquinoline-8-sulfonamido)phenyl]ethynyl}-pyridine-2-carboxylic acid 5-{2-[2-(7-ethylquinoline-8-sulfonamido)phenyl]ethynyl}pyridine-2-carboxylic acid 5-{2-[2-(4-ethoxyquinoline-8-sulfonamido)phenyl]ethynyl}pyridine-2-carboxylic acid 5-{2-[5-bromo-2-(7-methylquinoline-8-sulfonamido)phenyl]ethynyl}-4-methoxypyridine-2-carboxylic acid 5-{2-[2-(5-ethoxyquinoline-8-sulfonamido)phenyl]ethynyl}-4-methoxypyridine-2-carboxylic acid 5-{2-[5-chloro-2-(7-methylquinoline-8-sulfonamido)phenyl]ethynyl}pyridine-2-carboxylic acid 3-Ethyl-5-[2-(7-ethyl-quinoline-8-sulfonylamino)-phenyl-ethynyl]-pyridine-2-carboxylic acid 3-(ethylamino)-5-{2-[2-(4-methoxy-2,3-dimethylbenzenesulfonamido)phenyl]-ethynyl}pyridine-2-carboxylic acid 5-{2-[2-(7-ethylquinoline-8-sulfonamido)phenyl]ethynyl}-3-(methylamino)-pyridine-2-carboxylic acid 5-{2-[2-(5,7-dimethylquinoline-8-sulfonamido)phenyl]ethynyl}pyridine-2-carboxylic acid 2-methoxyethyl 4-methoxy-5-{2-[2-(7-methylquinoline-8-sulfonamido)phenyl]-ethynyl}pyridine-2-carboxylate 4-Methoxy-5-[2-(4-methylamino-quinoline-8-sulfonylamino)-phenylethynyl]-pyridine-2-carboxylic acid 4-{2-[2-(5-ethoxyquinoline-8-sulfonamido)phenyl]ethynyl}isoquinoline-1-carboxylic acid 3-Ethyl-5-[2-(5-methoxy-quinoline-8-sulfonylamino)-phenylethynyl]-pyridine-2-carboxylic acid 3-Ethyl-5-[2-(2-methyl-quinoline-8-sulfonylamino)-phenylethynyl]-pyridine-2-carboxylic acid 5-[2-(5-Trifluoromethoxy-quinoline-8-sulfonylamino)-phenylethynyl]-pyridine-2-carboxylic acid 4-Methoxy-5-[2-(5-trifluoromethoxy-quinoline-8-sulfonylamino)-phenyl-ethynyl]-pyridine-2-carboxylic acid 5-{2-[5-(2,2,2-Trifluoro-ethoxy)-quinoline-8-sulfonylamino]-phenylethynyl}-pyridine-2-carboxylic acid 5-{5-Chloro-2-[5-(2,2,2-trifluoro-ethoxy)-quinoline-8-sulfonylamino]-phenyl-ethynyl}-pyridine-2-carboxylic acid 4-Methoxy-5-{2-[5-(2,2,2-trifluoro-ethoxy)-quinoline-8-sulfonylamino]-phenyl-ethynyl}-pyridine-2-carboxylic acid 5-{5-Chloro-2-[5-(2,2,2-trifluoro-ethoxy)-quinoline-8-sulfonylamino]-phenyl-ethynyl}-4-methoxy-pyridine-2-carboxylic acid 3-Ethyl-5-[2-(7-methyl-quinoline-8-sulfonylamino)-phenylethynyl]-pyridine-2-carboxylic acid.

As used herein, the following definitions shall apply unless otherwise indicated or defined specifically elsewhere in the description and/or the claims for specific substituents, radicals, residues, groups or moieties.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon or tricyclic hydrocarbon that is completely saturated or that contains one or more units of unsaturation, such as one or more C=C double bond(s) and/or C≡C triple bond(s), but which is not aromatic (also referred to herein as "carbocycle", "cycloaliphatic" or "cycloalkyl"), that has—in general and if not defined otherwise in this specification or the accompanied claims—a single point of attachment to the rest of the molecule. Unless otherwise specified, aliphatic groups contain 1-8 or 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" ("cycloalkyl") refers to a monocyclic $C_3$-$C_7$ hydrocarbon that is completely saturated or that contains one or more units of unsaturation, but which is not aromatic, that has a single point of attachment to the rest of the molecule. In another embodiment the term "carbocycle" refers to a monocyclic or bicyclic cycloaliphatic ring system which is fused to an aromatic, heteroaromatic or heterocyclic ring or ring system via 2 adjacent ring atoms of that aromatic, heteroaromatic or heterocyclic ring or ring system; in other words, such carbocycle shares two ring atoms with the ring or ring system to which it is fused thereby having two points of attachment to the rest of the molecule. Suitable aliphatic groups include, but are not limited to, linear or branched, substituted or unsubstituted alkyl, alkenyl, alkynyl groups and hybrids thereof as (cycloalkyl)alkyl, (cycloalkenyl)alkyl or (cycloalkyl)alkenyl.

The term "alkyl" usually refers to a saturated aliphatic and acyclic moiety, while the term "alkenyl" usually refers to an unsaturated aliphatic and acyclic moiety with one or more C=C double bonds and the term "alkynyl" usually refers to an aliphatic and acyclic moiety with one or more C≡C triple bonds. Exemplary aliphatic groups are linear or branched, substituted or unsubstituted $C_{1-8}$-alkyl, $C_{1-6}$-alkyl, $C_{1-4}$-alkyl, $C_{2-8}$-alkenyl, $C_{2-6}$-alkenyl, $C_{2-8}$-alkynyl, $C_{2-6}$-alkynyl groups and hybrids thereof such as (cycloalkyl)alkyl, (cycloalkenyl)alkyl or (cycloalkyl)alkenyl.

In particular, the term "$C_{1-3}$-alkyl" refers to alkyl groups, i.e. saturated acyclic aliphatic groups, having 1, 2 or 3 carbon atoms. Exemplary $C_{1-3}$-alkyl groups are methyl, ethyl, propyl and isopropyl. The term "$C_{1-4}$-alkyl" refers to alkyl groups having 1, 2, 3 or 4 carbon atoms. Exemplary $C_{1-4}$-alkyl groups are methyl, ethyl, propyl, isopropyl, butyl, isobutyl, and tert-butyl. The term "$C_{1-6}$-alkyl" refers to alkyl groups having 1, 2, 3, 4, 5 or 6 carbon atoms. Exemplary $C_{1-6}$-alkyl groups are methyl, ethyl, propyl, isopropyl, butyl, isobutyl, tert-butyl, n-pentyl, 2-pentyl, n-hexyl, and 2-hexyl. The term "$C_{1-8}$-alkyl" refers to alkyl groups having 1, 2, 3, 4, 5, 6, 7, or 8 carbon atoms. Exemplary $C_{1-8}$-alkyl groups are methyl, ethyl, propyl, isopropyl, butyl, isobutyl, tert-butyl, n-pentyl, 2-pentyl, n-hexyl, 2-hexyl n-heptyl, 2-heptyl, n-octyl, 2-octyl, and 2,2,4-trimethylpentyl. Each of these alkyl groups may be straight-chain or—except for $C_1$-alkyl and $C_2$-alkyl-branched and may be unsubstituted or substituted with 1, 2 or 3 substituents or even 4, 5 or 6 substituents that may be the same or different and are, if not specified differently elsewhere in this specification, selected from the group comprising halogen, hydroxy, alkoxy, unsubstituted or mono- or di-substituted amino.

In some instances the $C_{1-3}$-alkyl, $C_{1-4}$-alkyl, $C_{1-6}$-alkyl, $C_{1-8}$-alkyl groups may also comprise those residues in which 1 or 2 of non-terminal and non-adjacent —CH$_2$— (methylene) groups are replaced by —O—, —S— and/or 1 or 2 non-terminal and non-adjacent —CH$_2$— or —CH— groups are replaced by —NH— or —N—. These replacements yield, for instance, (modified) alkyl groups like —CH$_2$—CH$_2$—O—CH$_3$, —CH$_2$—CH$_2$—CH$_2$—S—CH$_3$, —CH$_2$—CH$_2$—NH—CH$_2$—CH$_3$, —CH$_2$—CH$_2$—O—CH$_2$—CH$_2$—O—CH$_3$, —CH$_2$—CH$_2$—N(CH$_3$)—CH$_2$—CH$_3$, and the like. Further and/or different replacements of —CH— and —CH$_2$— groups may be defined for specific alkyl substituents or radicals elsewhere in the description and/or the claims.

The term "$C_{3-7}$cycloalkyl" refers to a cycloaliphatic hydrocarbon, as defined above, with 3, 4, 5, 6 or 7 ring carbon atoms. $C_{3-7}$cycloalkyl groups may be unsubstituted or substituted with—unless specified differently elsewhere in this specification—1, 2 or 3 substituents that may be the same of different and are—unless specified differently elsewhere in this specification-selected from the group comprising $C_{1-6}$-alkyl, O—$C_{1-6}$-alkyl (alkoxy), halogen, hydroxy unsubstituted or mono- or di-substituted amino. Exemplary $C_{3-7}$-cycloalkyl groups are cyclopropyl, 2-methyl-cyclopropyl, cyclopropenyl, cyclobutyl, cyclobutenyl, cyclopentyl, cyclopentenyl, cyclohexyl, cyclohexenyl, cycloheptyl, cycloheptenyl.

The term "aliphatoxy" refers to saturated or unsaturated aliphatic groups or substituents as defined above that are connected to another structural moiety via an oxygen atom (—O—). The term "alkoxy" refers to a particular subgroup of saturated aliphatoxy, i.e. to alkyl substituents and residues that are connected to another structural moiety via an oxygen atom (—O—). Sometimes, it is also referred to as "O-alkyl" and more specifically as "O—$C_{1-4}$-alkyl", "O—$C_{1-6}$-alkyl", "O—$C_{1-8}$-alkyl". Like the similar alkyl groups, it may be straight-chain or—except for —O—$C_1$-alkyl and —O—$C_2$-alkyl-branched and may be unsubstituted or substituted with 1, 2 or 3 substituents or even 4, 5 or 6 substituents that may be the same or different and are, if not specified differently elsewhere in this specification, selected from the group comprising halogen, unsubstituted or mono- or di-substituted amino. Exemplary alkoxy groups are methoxy, trifluoromethoxy, ethoxy, 2,2,2-trifluoroethoxy, n-propoxy, iso-propoxy, n-butoxy, sec-butoxy, tert-butoxy, n-pentoxy.

The term "alkylene" refers to a divalent aliphatic group and in particular a divalent alkyl group. An "alkylene chain" is a polymethylene group, i.e., —$(CH_2)_x$—, wherein x is a positive integer, preferably 1, 2, 3, 4, 5 or 6. In the context of the present invention "$C_{1-3}$-alkylene" refers to an alkylene moiety with 1, 2 and 3, respectively, —$CH_2$— groups; the term "alkylene", however, not only comprises linear alkylene groups, i.e. "alkylene chains", but branched alkylene groups as well. The term "$C_{1-6}$-alkylene" refers to an alkylene moiety that is either linear, i.e. an alkylene chain, or branched and has 1, 2, 3, 4, 5 or 6 carbon atoms. A substituted alkylene chain is a polymethylene group in which one or more methylene hydrogen atoms are replaced by (or with) a substituent. Suitable substituents include those described herein for a substituted alkyl group. In some instances 1 or 2 methylene groups of the alkylene chain may be replaced by, for instance, O, S and/or NH or N—$CO_{14}$-alkyl. Exemplary alkylene groups are —$CH_2$—, —$CH_2$—$CH_2$—, —$CH_2$—$CH_2$—$CH_2$—$CH_2$—, —O—$CH_2$—O—, —O—$CH_2$—$CH_2$—O—, —O—$CH_2$—$CH_2$—$CH_2$—O—, —$CH_2$—NH—$CH_2$—$CH_2$—, —$CH_2$—$N(CH_3)$—$CH_2$—$CH_2$—.

The term "alkenylene" refers to a bivalent alkenyl group. A substituted alkenylene chain is a polymethylene group containing at least one double bond in which one or more hydrogen atoms are replaced with a substituent. Suitable substituents include those described herein for a substituted aliphatic group.

The term "alkynylene" refers to a bivalent alkynyl group. A substituted alkynylene chain is a polymethylene group containing at least one triple bond in which one or more hydrogen atoms are replaced with a substituent. Suitable substituents include those described herein for a substituted aliphatic group.

The term "halogen" means F, Cl, Br, or I.

The term "heteroatom" means one or more of oxygen (O), sulfur (S), or nitrogen (N), including, any oxidized form of nitrogen or sulfur, e.g. N-oxides, sulfoxides and sulfones; the quaternized form of any basic nitrogen or a substitutable nitrogen of a heterocyclic or heteroaromatic ring, for example N (as in 3,4-dihydro-2H-pyrrolyl), NH (as in pyrrolidinyl) or N-SUB with SUB being a suitable substituent (as in N-substituted pyrrolidinyl).

The term "aryl" used alone or as part of a larger moiety as in "aralkyl", "aralkoxy", or "aryloxyalkyl", refers to monocyclic, bicyclic and tricyclic ring systems having a total of five to fourteen ring members, that ring members being carbon atoms, wherein at least one ring in the system is aromatic, i.e., it has (4n+2) π (pi) electrons (with n being an integer selected from 0, 1, 2, 3), which electrons are delocalized over the system, and wherein each ring in the system contains three to seven ring members. Preferably, all rings in the aryl system or the entire ring system are aromatic. The term "aryl" is used interchangeably with the term "aryl ring". In certain embodiments of the present invention, "aryl" refers to an "aromatic ring system". More specifically, those aromatic ring systems may be mono-, bi- or tricyclic with 5, 6, 7, 8, 9, 10, 11, 12, 13, 14 ring carbon atoms. Even more specifically, those aromatic ring systems may be mono- or bicyclic with 6, 7, 8, 9, 10 ring carbon atoms. Exemplary aryl groups are phenyl, biphenyl, naphthyl, anthracyl and the like, which may be unsubstituted or substituted with one or more identical or different substituents. Also included within the scope of the terms "aryl" or "aromatic ring system", as they are used herein, is a group in which an aromatic ring is fused to one or more non-aromatic rings, such as indanyl, phthalimidyl, naphthimidyl, phenanthridinyl, or tetrahydronaphthyl, and the like. In the latter case the "aryl" group or substituent is attached to its pendant group via the aromatic part of the ring system.

The term "benzo" refers to a six-membered aromatic ring (with carbon ring atoms) that is fused via two adjacent carbon atoms to another ring, being it a cycloaliphatic, aromatic, heteroaromatic or heterocyclic (heteroaliphatic) ring; as a result a ring system with at least two rings is formed in which the benzo ring shares two common carbon atoms with the other ring to which it is fused. For example, if a benzo ring is fused to a phenyl ring, a napthaline ring system is formed, while fusing a benzo ring to a pyridine provides for either a quinoline or an isoquinoline.

The terms "heteroaryl" and "heteroar-", used alone or as part of a larger moiety, e.g., "heteroaralkyl", or "heteroaralkoxy", refer to groups having 3, 4, 5, 6, 7, 8, 9, 10, 11, 12, 13, 14 ring atoms (which atoms are carbon and hetero atoms), preferably 5, 6, 9 or 10 ring atoms; having 6, 10, or 14 π (pi) electrons shared in a cyclic array; and having, in addition to carbon atoms, 1, 2, 3, 4 or 5 heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, furazanyl, pyridyl (pyridinyl), pyridazinyl, pyrimidinyl, pyrazinyl, indolizinyl, purinyl, naphthyridinyl, pteridinyl, and pyrrolopyridinyl, in particular pyrrolo[2,3-b]pyridinyl. The terms "heteroaryl" and "heteroar-", as used herein, also include groups in which a heteroaromatic ring is fused to one or more aryl, cycloaliphatic, or heterocyclyl rings, where the radical or point of attachment is preferably on the heteroaromatic or, if present, the aryl ring. Nonlimiting examples include indolyl, isoindolyl, benzothienyl (benzothiophenyl), benzofuranyl, dibenzofuranyl, indazolyl, benzimidazolyl, benzothiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, 9H-carbazolyl, dibenzofuranyl and pyrido[2,3-b]-1,4-oxazin-3(4H)-one. For example, an indolyl ring may be attached via one of the ring atoms of the six-membered aryl ring or via one of the ring atoms of the five-membered heteroaryl ring. A heteroaryl group is optionally mono-, bi- or tricyclic. The term "heteroaryl" is used interchangeably with the terms "heteroaryl ring", "heteroaryl group", or "heteroaromatic", any of which terms include rings that are unsubstituted or substituted with one or more identical or different substituents. The term "heteroaralkyl" refers to an alkyl group substituted by a heteroaryl, wherein the alkyl and heteroaryl portions independently are optionally substituted.

A heteroaryl ring can be attached to its pendant group at any of its hetero or carbon ring atoms which attachment results in a stable structure or molecule: any of the ring atoms may be unsubstituted or substituted.
The structures of typical examples of "heteroaryl" substituents as used in the present invention are depicted below:
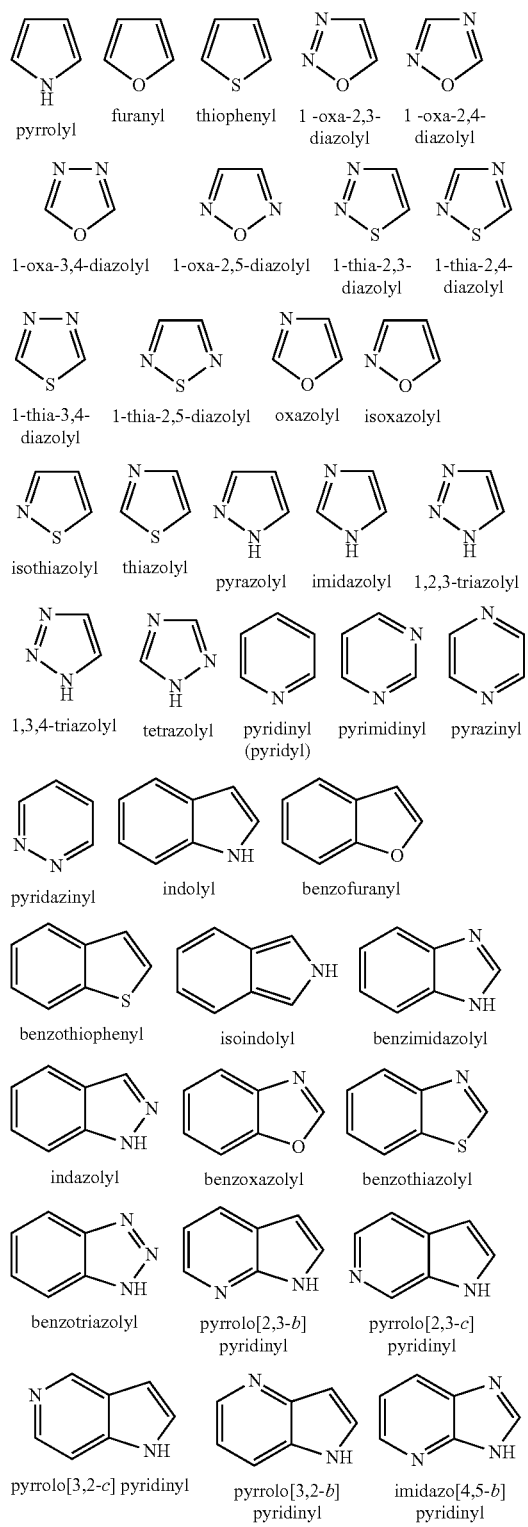
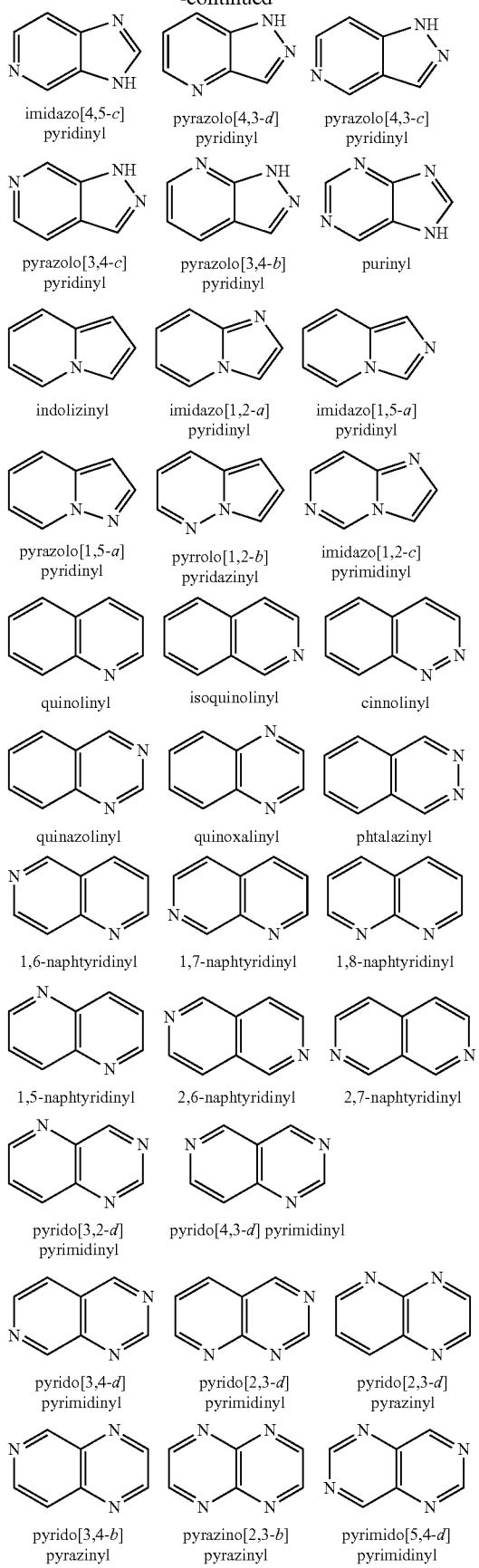

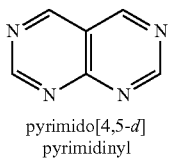

pyrimido[4,5-*d*]
pyrimidinyl

Those heteroaryl substituents can be attached to any pendant group via any of its ring atoms suitable for such an attachment.

As used herein, the terms "heterocycle", "heterocyclyl", "heterocyclic radical", and "heterocyclic ring" are used interchangeably and refer to a stable mono- bi- or tricyclic heterocyclic moiety with 5, 6, 7, 8, 9, 10, 11, 12, 13, 14 ring atoms wherein 1, 2, 3, 4, 5 of said ring atoms are hetero atoms and wherein that heterocyclic moiety is either saturated or partially unsaturated. Preferably, the heterocycle is a stable saturated or partially unsaturated 3-, 4-, 5-, 6-, or 7-membered monocyclic or 7-, 8-, 9-, 10-, or 11-membered bicyclic or 11-, 12-, 13-, or 14-membered tricyclic heterocyclic moiety.

When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen is N (as in 3,4-dihydro-2H-pyrrolyl), NH (as in pyrrolidinyl), or N-SUB with SUB being a suitable substituent (as in N-substituted pyrrolidinyl).

In the context of the term "heterocycle" the term "saturated" refers to a completely saturated heterocyclic system, like pyrrolidinyl, piperidinyl, morpholinyl, and piperidinonyl. With regard to the term "heterocycle" the term "partially unsaturated" refers to heterocyclic systems (i) that contain one or more units of unsaturation, e.g. a C=C or a C=Heteroatom bond, but that are not aromatic, for instance, tetrahydropyridinyl; or (ii) in which a (saturated or unsaturated but non-aromatic) heterocyclic ring is fused with an aromatic or heteroaromatic ring system, wherein, however, the "partially unsaturated heterocycle" is attached to the rest of the molecule (its pendant group) via one of the ring atoms of the "heterocyclic" part of the system and not via the aromatic or heteroaromatic part. This first class (i) of "partially unsaturated" heterocycles may also be referred to as "non-aromatic partially unsaturated" heterocycles. This second class (ii) of "partially unsaturated" heterocycles may also be referred to as (bicyclic or tricyclic) "partially aromatic" heterocycles indicating that at least one of the rings of that heterocycle is a saturated or unsaturated but non-aromatic heterocycle that is fused with at least one aromatic or heteroaromatic ring system. Typical examples of these "partially aromatic" heterocycles are 1,2,3,4-tetrahydroquinolinyl and 1,2,3,4-tetrahydroisoquinolinyl.

A heterocyclic ring can be attached to its pendant group at any heteroatom or carbon atom that results in a stable structure and any of the ring atoms may be unsubstituted or substituted. Examples of such saturated or partially unsaturated heterocyclic radicals include, without limitation, tetrahydrofuranyl, tetrahydropyranyl, tetrahydrothiophenyl pyrrolidinyl, piperidinyl, pyrrolinyl, morpholinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono-, bi- or tricyclic. The term "heterocyclylalkyl" refers to an alkyl group substituted by a heterocyclyl, wherein the alkyl and heterocyclyl portions independently are unsubstituted or substituted.

The term "unsaturated", as used herein, means that a moiety or group or substituent has one or more units of unsaturation.

As used herein with reference to any rings, ring systems, ring moieties, and the like, the term "partially unsaturated" refers to a ring moiety that includes at least one double or triple bond. The term "partially unsaturated" is intended to encompass rings having multiple sites of unsaturation. In particular, it encompasses (i) non-saturated (mono-, bi- or tricyclic) ring systems without any aromatic or heteroaromatic moiety or part; and (ii) bi- or tricyclic ring systems in which one of the rings of that system is an aromatic or heteroaromatic ring which is fused with another ring that is neither an aromatic nor a heteroaromatic ring, e.g. tetrahydronaphthyl or tetrahydroquinolinyl. The first class (i) of "partially unsaturated" rings, ring systems, ring moieties may also be referred to as "non-aromatic partially unsaturated" rings, ring systems, ring moieties, while the second class (ii) may be referred to as "partially aromatic" rings, ring systems, ring moieties.

As used herein, the term "bicyclic", "bicyclic ring" or "bicyclic ring system" refers to any bicyclic ring system, i.e. carbocyclic or heterocyclic, saturated or having one or more units of unsaturation, i.e. being partially unsaturated or aromatic, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. Likewise, the term "tricyclic", "tricyclic ring" or "tricyclic ring system" refers to any tricyclic ring system, i.e. carbocyclic or heterocyclic, saturated or having one or more units of unsaturation, i.e. being partially unsaturated or aromatic, in which a bicyclic ring system (as defined above) is fused with another, third ring. Thus, the term includes any permissible ring fusion. As used herein, the term "heterotricyclic" is a subset of "tricyclic" that requires that one or more heteroatoms are present in one or both rings of the tricycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a tricyclic group has 10-14 ring members and 0-5 heteroatoms independently selected from nitrogen, oxygen, or sulfur.

As described herein, certain compounds of the invention contain "substituted" or "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure. Unless otherwise indicated, a "substituted" or "optionally substituted" group has a suitable substituent at each substitutable position of the group, and when more than one position in any given structure is substituted with more than one substituent selected from a specified group, the substituent is either the same or different at every position. If a certain group, substituent, moiety or radical is "mono-substituted", it bears one (1) substituent. If it is "di-substituted", it bears two (2) substituents, being either the same or different; if it is "tri-substituted", it bears three (3) substituents, wherein all three are the same or two are the same and the third is different or all three are different from each other. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

If not specified otherwise elsewhere in the specification or the accompanying claims it is understood that each optional substituent on a substitutable carbon is a monovalent substituent independently selected from halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with one or more $R^\circ$; $-(CH_2)_{0-4}O(CH_2)_{0-1}Ph$ which may be substituted with one or more $R^\circ$; $-CH=CHPh$, which may be substituted with one or more $R^\circ$; $-(CH_2)_{0-4}O(CH_2)_{0-1}$-pyridyl which may be substituted with one or more $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-S(O)(NR^\circ)R^\circ$; $-S(O)_2N=C(NR^\circ_2)_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$. It is understood that "Ph" means phenyl; and that "$-(CH_2)_{0-4}$" means that there is either no alkylene group if the subscript is "0" (zero) or an alkylene group with 1, 2, 3 or 4 $CH_2$ units.

Each $R^\circ$ is independently hydrogen, halogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^\circ$ selected from $=O$ and $=S$; or each $R^\circ$ is optionally substituted with a monovalent substituent independently selected from halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$. It is understood that "Ph" means phenyl; "halo" means halogen; and "$-(CH_2)_{0-2}$" means that there is either no alkylene group if the subscript is "0" (zero) or an alkylene group with 1 or 2 $CH_2$ units.

Each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens; or wherein an optional substituent on a saturated carbon is a divalent substituent independently selected from $=O$, $=S$, $=NNR^\bullet_2$, $=NNHC(O)R^\bullet$, $=NNHC(O)OR^\bullet$, $=NNHS(O)_2R^\bullet$, $=NR^\bullet$, $=NOR^\bullet$, $-O(C(R^\bullet_2))_{2-3}O-$, or $-S(C(R^\bullet_2))_{2-3}S-$, or a divalent substituent bound to vicinal substitutable carbons of an "optionally substituted" group is $-O(CR^\bullet_2)_{2-3}O-$, wherein each independent occurrence of R is selected from hydrogen, $C_{1-6}$ aliphatic or an unsubstituted 5-6-membered saturated, partially unsaturated, or aryl ring having 0-4 heteroatoms independently selected from nitrogen, oxygen, or sulfur.

When R* is $C_{1-6}$ aliphatic, R* is optionally substituted with halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens.

An optional substituent on a substitutable nitrogen is independently $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic, unsubstituted $-OPh$, or an unsubstituted 5-6-membered saturated, partially unsaturated, or aryl ring having 0-4 heteroatoms independently selected from nitrogen, oxygen, or sulfur, or, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when $R^\dagger$ is $C_{1-6}$ aliphatic, $R^\dagger$ is optionally substituted with halogen, $-R^\bullet$, -(haloR$^\bullet$), $-OH$, $-OR^\bullet$, $-O(haloR^\bullet)$, $-CN$, $-C(O)OH$, $-C(O)OR^\dagger$, $-NH_2$, $-NHR^\dagger$, $-NR^\dagger_2$, or $-NO_2$, wherein each $R^\dagger$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens. It is understood that "Ph" means phenyl; and "halo" means halogen.

As described herein above and below in their most general meaning radicals $R^a$ and $R^b$ may be, inter alia, independently from each other unsubstituted or substituted, straight-chain or branched $C_{1-6}$-aliphatic. In other words, they may be, inter alia, $C_{1-6}$-alkyl, $C_{2-6}$-alkenyl or $C_{2-6}$- alkynyl, in each case either unsubstituted or substituted with one or more substituents, the substituents being the same or different. In some embodiments of the invention $R^a$ and/or $R^b$ are stable $C_{1-6}$-alkyl moieties bearing one or more substituents, the substituents being the same or different and being selected from halogen, OH, alkoxy. Examples of these substituents become apparent from the definitions of various radicals of the compound of formula (I) herein above and below and comprise, without being limited thereto, fluorine (1, 2 or 3 individual atoms on one or more of the carbon atoms of the aliphatic radical bearing substituents; or 1, 2, 3, 4 or 5 individual atoms on two or more of the carbon atoms of the aliphatic radical bearing substituents), chlorine (1, 2 or 3 individual atoms on one or more of the carbon atoms of the aliphatic radical bearing substituents; or 1, 2, 3, 4 or 5 individual atoms on two or more of the carbon atoms of the aliphatic radical bearing substituents), —OH (1, 2 or 3 individual hydroxy groups), methoxy (1 or 2 individual groups), ethoxy (1 or 2 individual groups), —O-ethylene-OH, —O-ethylene-O-methyl, and divalent —O—C((CH$_3$)$_2$)—O—.

In the context of the present invention the term "derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

The compounds of the present invention can be in the form of a prodrug compound. "Prodrugs" and "prodrug compound" mean a derivative that is converted into a biologically active compound according to the present invention under physiological conditions in the living body, e.g., by oxidation, reduction, hydrolysis or the like, each of which is carried out enzymatically, or without enzyme involvement. Examples of prodrugs are compounds, in which the amino group in a compound of the present invention is acylated, alkylated or phosphorylated, e.g., eicosanoylamino, alanylamino, pivaloyl-oxymethylamino or in which the hydroxyl group is acylated, alkylated, phosphorylated or converted into the borate, e.g. acetyloxy, palmitoyloxy, pivaloyloxy, succinyloxy, fumaryloxy, alanyloxy or in which the carboxyl group is esterified or amidated, or in which a sulfhydryl group forms a disulfide bridge with a carrier molecule, e.g. a peptide, that delivers the drug selectively to a target and/or to the cytosol of a cell. These compounds can be produced from compounds of the present invention according to well-known methods. Other examples of prodrugs are compounds, wherein the carboxylate in a compound of the present invention is for example converted into an alkyl-, aryl-, choline-, amino-, acyloxymethylester, linolenoyl-ester.

The term "solvates" means addition forms of the compounds of the present invention with solvents, preferably pharmaceutically acceptable solvents that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, e.g. a mono- or dihydrate. If the solvent is alcohol, the solvate formed is an alcoholate, e.g., a methanolate or ethanolate. If the solvent is an ether, the solvate formed is an etherate, e.g., diethyl etherate.

The term "N-oxides" means such compounds of the present invention that contain an amine oxide moiety, i.e. the oxide of a tertiary amine group.

The compounds of formula (I) may have one or more centres of chirality. They may accordingly occur in various enantiomeric and diastereomeric forms, as the case may be, and be in racemic or optically active form. The invention, therefore, also relates to the optically active forms, enantiomers, racemates, diastereomers, mixtures thereof in all ratios, collectively: "stereoisomers" for the purpose of the present invention, of these compounds. Since the pharmaceutical activity of the racemates or stereo-isomers of the compounds according to the invention may differ, it may be desirable to use a specific stereoisomer, e.g. one specific enantiomer or diastereomer. In these cases, a compound according to the present invention obtained as a racemate—or even intermediates thereof—may be separated into the stereoisomeric (enantiomeric, diastereoisomeric) compounds by chemical or physical measures known to the person skilled in the art. Another approach that may be applied to obtain one or more specific stereoisomers of a compound of the present invention in an enriched or pure form makes use of stereoselective synthetic procedures, e.g. applying starting material in a stereoisomerically enriched or pure form (for instance using the pure or enriched (R)- or (S)-enantiomer of a particular starting material bearing a chiral center) or utilizing chiral reagents or catalysts, in particular enzymes. In the context of the present invention the term "pure enantiomer" usually refers to a relative purity of one enantiomer over the other (its antipode) of equal to or greater than 95%, preferably 98%, more preferably 98.5%, still more preferably 99%.

Thus, for example, the compounds of the invention which have one or more centers of chirality and which occur as racemates or as mixtures of enantiomers or diastereoisomers can be fractionated or resolved by methods known per se into their optically pure or enriched isomers, i.e. enantiomers or diastereomers. The separation of the compounds of the invention can take place by chromatographic methods, e.g. column separation on chiral or nonchiral phases, or by recrystallization from an optionally optically active solvent or by use of an optically active acid or base or by derivatization with an optically active reagent such as, for example, an optically active alcohol, and subsequent elimination of the radical.

In the context of the present invention the term "tautomer" refers to compounds of the present invention that may exist in tautomeric forms and show tautomerism; for instance, carbonyl compounds may be present in their keto and/or their enol form and show keto-enol tautomerism. Those tautomers may occur in their individual forms, e.g., the keto or the enol form, or as mixtures thereof and are claimed separately and together as mixtures in any ratio. The same applies for cis/trans isomers, E/Z isomers, conformers and the like.

In one embodiment the compounds of the present invention are in the form of free base or acid—as the case may be —, i.e. in their non-salt (or salt-free) form. In another embodiment the compounds of the present invention are in the form of a pharmaceutically acceptable salt, a pharmaceutically acceptable solvate, or a pharmaceutically acceptable solvate of a pharmaceutically acceptable salt.

The term "pharmaceutically acceptable salts" refers to salts prepared from pharmaceutically acceptable bases or acids, including inorganic bases or acids and organic bases or acids. In cases where the compounds of the present invention contain one or more acidic or basic groups, the invention also comprises their corresponding pharmaceutically acceptable salts. Thus, the compounds of the present invention which contain acidic groups, such as carboxyl groups, can be present in salt form, and can be used according to the invention, for example, as alkali metal salts, alkaline earth metal salts, aluminium salts or as ammonium salts. More precise examples of such salts include lithium salts, sodium salts, potassium salts, calcium salts, magnesium salts, barium salts or salts with ammonia or organic amines such as, for example, ethylamine, ethanolamine, diethanolamine, triethanolamine, piperdine, N-methylglutamine or amino acids. These salts are readily available, for instance, by reacting the compound having an acidic group with a suitable base, e.g. lithium hydroxide, sodium hydroxide, sodium propoxide, potassium hydroxide, potassium ethoxide, magnesium hydroxide, calcium hydroxide or barium hydroxide. Other base salts of compounds of the present invention include but are not limited to copper(I), copper(II), iron(II), iron (Ill), manganese(II) and zinc salts. Compounds of the present invention which contain one or more basic groups, e.g. groups which can be protonated, can be present in salt form, and can be used according to the invention in the form of their addition salts with inorganic or organic acids. Examples of suitable acids include hydrogen chloride, hydrogen bromide, hydrogen iodide, phosphoric acid, sulfuric acid, nitric acid, methanesulfonic acid, p-toluenesulfonic acid, naphthalenedisulfonic acid, sulfoacetic acid, trifluoroacetic acid, oxalic acid, acetic acid, tartaric acid, lactic acid, salicylic acid, benzoic acid, carbonic acid, formic acid, propionic acid, pivalic acid, diethylacetic acid, malonic acid, succinic acid, pimelic acid, fumaric acid, malonic acid, maleic acid, malic acid, embonic acid, mandelic acid, sulfaminic acid, phenylpropionic acid, gluconic acid, ascorbic acid, isonicotinic acid, citric acid, adipic acid, taurocholic acid, glutaric acid, stearic acid, glutamic acid or aspartic acid, and other acids known to the person skilled in the art. The salts which are formed are, inter alia, hydrochlorides, chlorides, hydrobromides, bromides, iodides, sulfates, phosphates, methanesulfonates (mesylates), tosylates, carbonates, bicarbonates, formates, acetates, sulfoacetates, triflates, oxalates, malonates, maleates, succinates, tartrates, malates, embonates, mandelates, fumarates, lactates, citrates, glutarates, stearates, aspartates and glutamates. The stoichiometry of the salts formed from the compounds of the invention may moreover be an integral or non-integral multiple of one.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di($C_1$-$C_4$)alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

If the compounds of the present invention simultaneously contain acidic and basic groups in the molecule, the invention also includes, in addition to the salt forms mentioned, inner salts or betaines (zwitterions). The respective salts can be obtained by customary methods which are known to a person skilled in the art, for example by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Therefore, the following items are also in accordance with the invention:
(a) all stereoisomers or tautomers of the compounds, including mixtures thereof in all ratios;
(b) prodrugs of the compounds, or stereoisomers or tautomers of these prodrugs;
(c) pharmaceutically acceptable salts of the compounds and of the items mentioned under (a) and (b);
(d) pharmaceutically acceptable solvates of the compounds and of the items mentioned under (a), (b) and (c);
(e) N-oxides of the compounds and of the items mentioned under (a), (b), (c), and (d).

It should be understood that all references to compounds above and below are meant to include these items, in particular pharmaceutically acceptable solvates of the compounds, or pharmaceutically acceptable solvates of their pharmaceutically acceptable salts.

There is furthermore intended that a compound of the present invention includes isotope-labelled forms thereof. An isotope-labelled form of a compound of the formula (I) is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the present invention by well-known methods include isotopes of hydrogen, carbon, nitrogen, oxygen, phosphorus, sulfur, fluorine and chlorine, for example $^2H$, $^3H$, $^{13}C$, $^{14}C$, $^{15}N$, $^{18}O$, $^{17}O$, $^{31}P$, $^{32}P$, $^{33}S$, $^{34}S$, $^{35}S$, $^{36}S$, $^{18}F$ and $^{36}Cl$, respectively. A compound of formula (I) or a pharmaceutically acceptable salt thereof which contains one or more of the above-mentioned isotopes and/or other isotopes of other atoms is intended to be part of the present invention. An isotope-labelled compound of formula (I) can be used in a number of beneficial ways. For example, an isotope-labelled compound of the present invention into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of formula (I) has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of formula (I) can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$) can also be incorporated into a compound of formula (I) for the purpose of manipulating the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula Ia and Ib that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative meta-bolism. Significant improvements in the pharmacokinetic profiles of compounds of the formula I are thereby obtained, and can be expressed quantitatively in terms of increases in the in vivo half-life (t1/2), concentration at maximum therapeutic effect ($C_{max}$), area under the dose response curve (AUC), and F; and in terms of reduced clearance, dose and materials costs.

The following is intended to illustrate the above: a compound of formula (I) which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is deter-mined that the half-life of the parent compound can be extended by up to 100% as the result of deuterium-hydrogen exchange of this type.

Deuterium-hydrogen exchange in a compound of the present invention can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1995.

Furthermore, the present invention relates to pharmaceutical compositions comprising at least one compound of formula (I), or its derivatives, prodrugs, solvates, tautomers or stereoisomers thereof as well as the pharmaceutically acceptable salts of each of the foregoing, including mixtures thereof in all ratios, as active ingredient, together with a pharmaceutically acceptable carrier.

For the purpose of the present invention the term "pharmaceutical composition" (or "pharmaceutical formulation") refers to a composition or product comprising one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier. It may further comprise physiologically acceptable excipients, auxiliaries, adjuvants, diluents and/or additional pharmaceutically active substance other than the compounds of the invention.

The pharmaceutical compositions include compositions and pharmaceutical formulations suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

A pharmaceutical composition of the present invention may additionally comprise one or more other compounds as active ingredients (drugs), such as one or more additional compounds of the present invention. In a particular embodiment the pharmaceutical composition further comprises a second active ingredient or its derivatives, prodrugs, solvates, tautomers or stereoisomers thereof as well as the pharmaceutically acceptable salts of each of the foregoing, including mixtures thereof in all ratios, wherein that second active ingredient is other than a compound of formula (I); preferably, that second active ingredient is a compound that is useful in the treatment, prevention, suppression and/or amelioration of medicinal conditions or pathologies for which the compounds of the present invention are useful as well and which are listed elsewhere hereinbefore or hereinafter. Such combination of two or more active ingredients or drugs may be safer or more effective than either drug or active ingredient alone, or the combination is safer or more effective than it would be expected based on the additive properties of the individual drugs. Such other drug(s) may be administered, by a route and in an amount commonly used contemporaneously or sequentially with a compound of the invention. When a compound of the invention is used contemporaneously with one or more other drugs or active ingredients, a combination product containing such other drug(s) and the compound of the invention—also referred to as "fixed dose combination"—is preferred. However, combination therapy also includes therapies in which the compound of the present invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of the invention.

The compounds of the present invention—or derivatives, N-oxides, prodrugs, solvates, tautomers or stereoisomers thereof and/or the pharmaceutically acceptable salts of each of the foregoing, including mixtures thereof in all ratios—can be used as medicaments. They have been found to exhibit pharmacological activity by inhibiting monocarboxylate transporters (MCT). In one embodiment compounds of the present invention inhibit selectively monocarboxylate transporter isoform 4 (MCT4), i.e. their inhibitory activity on MCT4 is substantially higher than on any other MCT, in particular MCT1. Selectivity assessment is based on cellular activity, considering different cell lines with different MCT4/MCT1 expression levels. For MDA-MB231 cells this ratio is 120 based on mRNA levels (MCT4: 2750; MCT1: 23). Many compounds of the present invention show low IC50 values even down to single digit nanomolar level in this cell line when measuring lactate efflux inhibition. In SNU-398 cells on the other hand, the ratio is 0.02 (mRNA MCT4: 22; MCT1: 874) and the compounds of the present invention typically have IC50 values >25 µM if they are selective MCT4 inhibitors. These findings support the conclusion that most of the compounds of the present invention are highly MCT4 selective transporter inhibitors. While there is evidence that selective inhibition of MCT1, in particular in highly hypoxic cancer cells, are compensated by cellular upregulating MCT4 which compensation renders the treatment of diseases that are affected by MCT activity with an MCT1 inhibitor ineffective, it is believed that selective inhibition of MCT4 may not be compensated by cellular MCT1 upregulation; this makes selective MCT4 inhibitors useful for the treatment, prevention, suppression and/or amelioration of medicinal conditions or pathologies that are affected by MCT activity. In another embodiment some compounds of the present invention exhibit both MCT4 and MCT1 inhibitory activity, i.e. a dual inhibitory effect. Without wished to be bound to a particular theory it seems that in particular compounds of formula (I-a) (PE3a), especially those in which $R^1$ is —$NHR^a$ or —$NR^aR^b$ as well as compounds of formula (I-b) (PE3b) are prone to exhibit such dual mode of action. In still another embodiment, compounds of the present invention being MCT4 inhibitors may be combined with other compounds that exhibit MCT1 inhibition, in particular primarily or even selectively, in order to provide for a treatment, prevention, suppression and/or amelioration of medicinal conditions or pathologies that are affected by MCT activity that would benefit from the dual inhibition of both MCT4 and MCT1. Examples of MCT1 inhibitors to combine with the compounds of the present invention are those known as AZD3965 (5-((S)-4-Hydroxy-4-methyl-isoxazolidine-2-carbonyl)-1-isopropyl-3-methyl-6-(3-methyl-5-trifluoromethyl-1H-pyrazol-4-ylmethyl)-1H-thieno[2,3-d]pyrimidine-2,4-dione), BAY-8002 (2-(5-Benzenesulfonyl-2-chloro-benzoylamino)-benzoic acid) and those described in J. Med. Chem. 2014, 7317; and ACS Med. Chem. Lett. 2015, 558.

Thus, the compounds of the present invention being selective MCT4 or dual MCT4 and MCT1 inhibitors are useful in particular in the treatment, prevention, suppression and/or amelioration of hyperproliferative disorders and cancer, more particular adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, Wilms' tumor. However, since activity of MCT, in particular of MCT4 or MCT4 and MCT1, plays a role in the genesis and progress of other than hyperproliferative diseases, the compounds of the present invention are useful in the the treatment, prevention, suppression and/or amelioration of inflammatory disorders or diseases, in particular Crohn's disease, ulcerative colitis, idiopathic pulmonary fibrosis, muscular dystrophy, rheumatoid arthritis, and systemic sclerosis (scleroderma); or neurogenerative disorders or diseases, in particular Huntington's disease.

In a particular embodiment the compounds of the present invention are for use in the prevention and/or treatment, especially in the treatment of any of the disorders or diseases listed above, preferably of cancer, more preferably of a cancer selected from the group consisting of adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer and Wilms' tumor.

Another particular embodiment of the present invention is a method for preventing and/or treating, preferably treating a disorder or disease selected from the group consisting of hyperproliferative disorders and cancer, more particular adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, Wilms' tumor; of inflammatory disorders or diseases, in particular Crohn's disease, ulcerative colitis, idiopathic pulmonary fibrosis, muscular dystrophy, rheumatoid arthritis, and systemic sclerosis (scleroderma); or neurogenerative disorders or diseases, in particular Huntington's disease; wherein the method comprises administering to a patient in need thereof an effective amount of a compound of formula (I) or derivatives, N-oxides, prodrugs, solvates, tautomers or stereoisomers thereof and/or the pharmaceutically acceptable salts of each of the foregoing, including mixtures thereof in all ratios.

Still another particular embodiment of the invention is the use of a compound of the present invention—or derivatives, N-oxides, prodrugs, solvates, tautomers or stereoisomers thereof and/or the pharmaceutically acceptable salts of each of the foregoing, including mixtures thereof in all ratios— for the manufacturing of a medicament, in particular for preventing and/or treating, preferably treating a disorder or disease selected from the group consisting of hyperproliferative disorders and cancer, more particular adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, Wilms' tumor; of inflammatory disorders or diseases, in particular Crohn's disease, ulcerative colitis, idiopathic pulmonary fibrosis, muscular dystrophy, rheumatoid arthritis, and systemic sclerosis (scleroderma); or neurogenerative disorders or diseases, in particular Huntington's disease.

Preferably, the present invention relates to a compound of the present invention for use in the prevention and/or treatment of a disease—or, alternatively, a method for preventing and/or treating a disease by administering an effective amount of a compound of the present invention; or, in another alternative, a use of a compound of the present invention for the manufacturing of a medicament for the prevention and/or treatment of a disease—wherein that disease is a cancer; and more preferably, wherein administration of the compound is simultaneous, sequential or in alternation with administration of at least one other active drug agent. The disclosed compounds of formula (I) can be administered in combination with other known therapeutic agents, including anticancer agents. As used here, the term "anticancer agent" relates to any agent which is administered to a patient with cancer for the purposes of treating the cancer. The anti-cancer treatment defined above may be applied as a monotherapy or may involve, in addition to the herein disclosed compounds of formula (I), conventional surgery or radiotherapy or medicinal therapy. Such medicinal therapy, e.g. a chemotherapy or a targeted therapy, may include one or more, but preferably one, of the following anti-tumor agents:

Alkylating Agents
  such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds
  such as carboplatin, cisplatin, eptaplatin, miriplatine hydrate, oxaliplatin, lobaplatin, nedaplatin, picoplatin, satraplatin;
  lobaplatin, nedaplatin, picoplatin, satraplatin;
DNA Altering Agents
  such as amrubicin, bisantrene, decitabine, mitoxantrone, procarbazine, trabectedin, clofarabine;
  amsacrine, brostallicin, pixantrone, laromustine[1,3];
Topoisomerase Inhibitors
  such as etoposide, irinotecan, razoxane, sobuzoxane, teniposide, topotecan; amonafide, belotecan, elliptinium acetate, voreloxin;
Microtubule Modifiers
  such as cabazitaxel, docetaxel, eribulin, ixabepilone, paclitaxel, vinblastine, vincristine, vinorelbine, vindesine, vinflunine; fosbretabulin, tesetaxel;
Antimetabolites
  such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;
Anticancer Antibiotics
  such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin; aclarubicin, peplomycin, pirarubicin;
Hormones/Antagonists
  such as abarelix, abiraterone, bicalutamide, buserelin, calusterone, chlorotrianisene, degarelix, dexamethasone, estradiol, fluocortolone, fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];
Aromatase Inhibitors
  such as aminoglutethimide, anastrozole, exemestane, fadrozole, letrozole, testolactone; formestane;
Small Molecule Kinase Inhibitors
  such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tepotinib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];
Photosensitizers
  such as methoxsalen[3]; porfimer sodium, talaporfin, temoporfin;
Antibodies
  such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], atezolizumab, durvalumab, pembrolizumab, nivolumab[1,3];

Cytokines
such as aldesleukin, interferon alfa[2], interferon alfa2a[3], interferon alfa2b[2,3] celmoleukin, tasonermin, teceleukin, oprelvekin[1,3], recombinant interferon beta-1a[4];

Drug Conjugates
such as denileukin diftitox, ibritumomab tiuxetan, iobenguane 1123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines
such as sipuleucel[3]; vitespen[3], emepepimut-S[3], oncoVAX[4], rindopepimut[3], troVax[4], MGN-16014, MGN-1703[4];

Miscellaneous
alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];

PARP Inhibitors
Olaparib, Veliparib.

MCT1 Inhibitors
AZD3965[4], BAY-8002[4].

[1] Prop. INN (Proposed International Nonproprietary Name)
[2] Rec. INN (Recommended International Nonproprietary Names)
[3] USAN (United States Adopted Name)
[4] no INN.

A further embodiment of the present invention is a process for the manufacture of the pharmaceutical compositions of the present invention, characterized in that one or more compounds according to the invention and one or more compounds selected from the group consisting of solid, liquid or semiliquid excipients, auxiliaries, adjuvants, diluents, carriers and pharmaceutically active agents other than the compounds according to the invention, are converted in a suitable dosage form.

In another aspect of the invention, a set or kit is provided comprising a therapeutically effective amount of at least one compound of the invention and/or at least one pharmaceutical composition as described herein and a therapeutically effective amount of at least one further pharmacologically active substance other than the compounds of the invention. It is preferred that this set or kit comprises separate packs of a) an effective amount of a compound of formula (I), or its derivatives, prodrugs, solvates, tautomers or stereoisomers thereof as well as the physiologically acceptable salts of each of the foregoing, including mixtures thereof in all ratios, and b) an effective amount of a further active ingredient that further active ingredient not being a compound of formula (I).

The pharmaceutical compositions (formulations) of the present invention may be administered by any means that achieve their intended purpose. For example, administration may be via oral, parenteral, topical, enteral, intravenous, intramuscular, inhalant, nasal, intraarticular, intraspinal, transtracheal, transocular, subcutaneous, intraperitoneal, transdermal, or buccal routes. Alternatively, or concurrently, administration may be via the oral route. The dosage administered will be dependent upon the age, health, and weight of the recipient, kind of concurrent treatment, if any, frequency of treatment, and the nature of the effect desired. Parenteral administration is preferred. Oral administration is especially preferred.

Suitable dosage forms include, but are not limited to capsules, tablets, pellets, dragees, semi-solids, powders, granules, suppositories, ointments, creams, lotions, inhalants, injections, cataplasms, gels, tapes, eye drops, solution, syrups, aerosols, suspension, emulsion, which can be produced according to methods known in the art, for example as described below: Tablets: mixing of active ingredient/s and auxiliaries, compression of said mixture into tablets (direct compression), optionally granulation of part of mixture before compression.

Capsules: mixing of active ingredient/s and auxiliaries to obtain a flowable powder, optionally granulating powder, filling powders/granulate into opened capsules, capping of capsules.

Semi-solids (ointments, gels, creams): dissolving/dispersing active ingredient/s in an aqueous or fatty carrier; subsequent mixing of aqueous/fatty phase with complementary fatty/aqueous phase, homogenization (creams only).

Suppositories (rectal and vaginal): dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms.

Aerosols: dispersing/dissolving active agent/s in a propellant, bottling said mixture into an atomizer.

In general, non-chemical routes for the production of pharmaceutical compositions and/or pharmaceutical preparations comprise processing steps on suitable mechanical means known in the art that transfer one or more compounds of the invention into a dosage form suitable for administration to a patient in need of such a treatment. Usually, the transfer of one or more compounds of the invention into such a dosage form comprises the addition of one or more compounds, selected from the group consisting of carriers, excipients, auxiliaries and pharmaceutical active ingredients other than the compounds of the invention. Suitable processing steps include, but are not limited to combining, milling, mixing, granulating, dissolving, dispersing, homogenizing, casting and/or compressing the respective active and nonactive ingredients. Mechanical means for performing said processing steps are known in the art, for example from Ullmann's Encyclopedia of Industrial Chemistry, 5th Edition. In this respect, active ingredients are preferably at least one compound of the invention and optionally one or more additional compounds other than the compounds of the invention, which show valuable pharmaceutical properties, preferably those pharmaceutical active agents other than the compounds of the invention, which are disclosed herein.

Particularly suitable for oral use are tablets, pills, coated tablets, capsules, powders, granules, syrups, juices or drops, suitable for rectal use are suppositories, suitable for parenteral use are solutions, preferably oil-based or aqueous solutions, furthermore suspensions, emulsions or implants, and suitable for topical use are ointments, creams or powders. The compounds of the invention may also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

Suitable excipients are organic or inorganic substances, which are suitable for enteral (for example oral), parenteral or topical administration and do not react with the compounds of the invention, for example water, vegetable oils, benzyl alcohols, alkylene glycols, polyethylene glycols, glycerol triacetate, gelatine, carbohydrates, such as lactose, sucrose, mannitol, sorbitol or starch (maize starch, wheat starch, rice starch, potato starch), cellulose preparations and/or calcium phosphates, for example tricalcium phosphate or calcium hydrogen phosphate, magnesium stearate, talc, gelatine, tragacanth, methyl cellulose, hydroxypropylmethylcellulose, sodium carboxymethylcellulose, polyvinyl pyrrolidone and/or vaseline.

If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries include, without limitation, flow-regulating agents and lubricants, for example, silica, talc, stearic acid or salts thereof, such as magnesium stearate or calcium stearate, and/or polyethylene glycol. Dragee cores are provided with suitable coatings, which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices or to provide a dosage form affording the advantage of prolonged action, the tablet, dragee or pill can comprise an inner dosage and an outer dosage component the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, acetyl alcohol, solutions of suitable cellulose preparations such as acetyl-cellulose phthalate, cellulose acetate or hydroxypropylmethyl-cellulose phthalate, are used. Dye stuffs or pigments may be added to the tablets or dragee coatings, for example, for identification or in order to characterize combinations of active compound doses.

Suitable carrier substances are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc and petroleum jelly. In particular, tablets, coated tablets, capsules, syrups, suspensions, drops or suppositories are used for enteral administration, solutions, preferably oily or aqueous solutions, furthermore suspensions, emulsions or implants, are used for parenteral administration, and ointments, creams or powders are used for topical application. The compounds of the invention can also be lyophilized and the lyophilizates obtained can be used, for example, for the production of injection preparations.

Other pharmaceutical preparations, which can be used orally include push-fit capsules made of gelatine, as well as soft, sealed capsules made of gelatine and a plasticizer such as glycerol or sorbitol. The push-fit capsules can contain the active compounds in the form of granules, which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatine.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400).

Aqueous injection suspensions may contain substances, which increase the viscosity of the suspension, including, for example, sodium carboxymethyl cellulose, sorbitol, and/or dextran, optionally, the suspension may also contain stabilizers.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

Possible pharmaceutical preparations, which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatine rectal capsules, which consist of a combination of the active compounds with a base. Possible base materials include, for example, liquid triglycerides, polyethylene glycols, or paraffin hydrocarbons.

For use in medicine, the compounds of the present invention may be in the form of pharmaceutically acceptable salts. Other salts may, however, be useful in the preparation of the compounds of the invention or of their pharmaceutically acceptable salts. Suitable pharmaceutically acceptable salts of the compounds of this invention are those described hereinbefore and include acid addition salts which may, for example be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic bases, e.g. quaternary ammonium salts.

The pharmaceutical preparations can be employed as medicaments in human and veterinary medicine. As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. Said therapeutic effective amount of one or more of the compounds of the invention is known to the skilled artisan or can be easily determined by standard methods known in the art.

The compounds of the present invention and the optional additional active substances are generally administered analogously to commercial preparations. Usually, suitable doses that are therapeutically effective lie in the range between 0.0005 mg and 1000 mg, preferably between 0.005 mg and 500 mg and especially between 0.5 mg and 100 mg per dose unit. The daily dose is preferably between about 0.001 mg/kg and 10 mg/kg of body weight.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The specific dose for the individual patient, in particular for the individual human patient, depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician, which advises or attends the therapeutic treatment.

The compounds of the present invention can be prepared according to the procedures of the following Schemes and Examples, using appropriate materials, and as further exemplified by the following specific examples. They may also be prepared by methods known per se, as described in the literature (for example in standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions which are known and suitable for the said reactions. Use can also be made of variants which are known per se, but are not mentioned here in greater detail.

Likewise, the starting materials for the preparation of compounds of the present invention can be prepared by methods as described in the examples or by methods known per se, as described in the literature of synthetic organic chemistry and known to the skilled person, or can be obtained commercially. The starting materials for the processes claimed and/or utilized may, if desired, also be formed in situ by not isolating them from the reaction mixture, but instead immediately converting them further into the compounds of the invention or intermediate compounds. On the other hand, in general it is possible to carry out the reaction stepwise.

Preferably, the reaction of the compounds is carried out in the presence of a suitable solvent, which is preferably inert under the respective reaction conditions. Examples of suitable solvents comprise but are not limited to hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methyl pyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents or mixtures with water.

The reaction temperature is between about −100° C. and 300° C., depending on the reaction step and the conditions used.

Reaction times are generally in the range between a fraction of a minute and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 minutes and 48 hours.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The present invention also refers to a process for manufacturing a compound of formula (I) in its most general form as well as any of the particular embodiments, PE, described herein, or derivatives, N-oxides, prodrugs, solvates, tautomers or stereoisomers thereof as well as the pharmaceutically acceptable salts of each of the foregoing, the process being characterized in that either (A)
(a) a compound of formula (II)

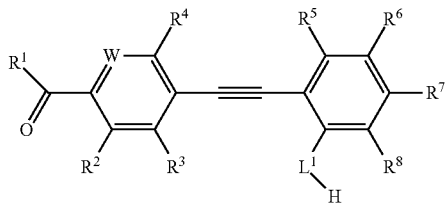

II wherein
$R^1$ is $—OR^a$;
$L^1$ is NH or $NR^a$; and
W, $R^2$, $R^3$, $R^4$, $R^5$, $R^6$, $R^7$, $R^8$ and $R^a$ are as defined for formula (I) or any of the particular embodiments, PE;
is reacted with a compound of formula (III)

$$Cl-L^2-(L^3)_n-A$$

III wherein
n is an integer selected from 0 and 1;
$L^2$ is a divalent $—SO_2—$ radical; and
$L^3$ is a divalent-CH=CH— radical;
to form a compound of formula (I)

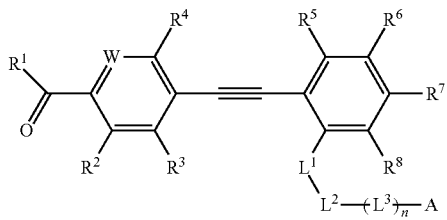

I wherein $R^1$ is $OR^a$;
(b) which compound of formula (I) optionally be converted into another compound of formula (I) wherein $R^1$ is $—OH$, $—NH_2$, $—NHR^a$, $—NR^aR^b$, $—N(H)OH$, $—N(H)O—R^a$, $—N(H)CN$, $—N(H)—C(=O)—R^a$, $—N(H)—SO_2—R^a$;
or
(B)
(a) a compound of formula (IV)

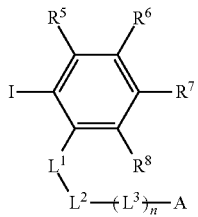

IV wherein
n is an integer selected from 0 and 1;
$L^1$ is $—N(CHO)—$, $—N(C(=O)R^a)—$, $N(C(=O)—NH_2)—$, $—N(C(=O)—NHR^a)—$ or $—N(C(=O)—NR^aR^b)—$;

$L^2$ is a divalent $—CH_2—$ radical;
$L^3$ is a divalent $—CH_2—$ radical; or
$L^1$ is a divalent $—CH_2—$ radical;
$L^2$ is $—N(CHO)—$, $—N(C(=O)R^a)—$, $—N(C(=O)—NH_2)—$, $—N(C(=O)—NHR^a)—$ or $—N(C(=O)—NR^aR^b)—$;
$L^3$ is a single bond; or
$L^1$ is a divalent-$SO_2—$ radical;
$L^2$ is a divalent $—N(R^a)—$ radical; and
$L^3$ is a single bond;
and
$R^5$, $R^6$, $R^7$, $R^8$ and A are as defined for formula (I) or any of the particular embodiments, PE;
is reacted under suitable C—C-coupling reaction conditions with a compound of formula (V)

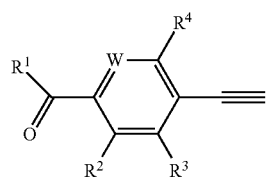

V wherein
$R^1$ is $OR^a$; and
W, $R^2$, $R^3$, $R^4$ and $R^a$ are as defined for formula (I) or any of the particular embodiments, PE;
to form a compound of formula (I) as defined above; and
(b) which optionally be converted into a compound of formula I wherein $R^1$ is $—OH$, $—NH_2$, $—NHR^a$, $—NR^aR^b$, $—N(H)OH$, $—N(H)O—R^a$, $—N(H)CN$, $—N(H)—C(=O)—R^a$, $—N(H)—SO_2—R^a$;
or
(C)
(a) a compound of formula (IV)

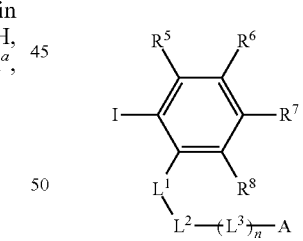

IV wherein
n is an integer selected from 0 and 1;
$L^1$ is a divalent-$SO_2—$ radical;
$L^2$ is a divalent $—N(PG)-$ radical with PG being a suitable protecting group, e.g., tert.-butyloxy carbonyl (BOC); and
$L^3$ is a single bond;
and
$R^5$, $R^6$, $R^7$, $R^8$ and A are as defined for formula (I) or any of the particular embodiments, PE;
is reacted under suitable C—C-coupling reaction conditions with a compound of formula (V)

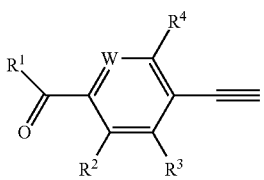

wherein
R¹ is OR$^a$; and
W, R², R³, R⁴ and R$^a$ are as defined for formula (I) or any of the particular embodiments, PE;
to form a compound of formula (VI)

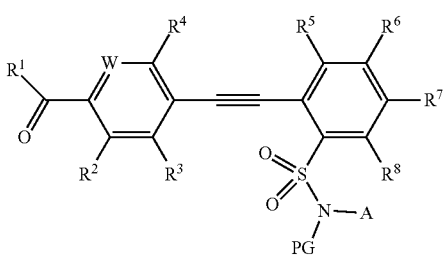

wherein
R¹ is OR$^a$;
PG is that suitable protecting group, e.g. BOC; and
A; W, R², R³, R⁴, R⁵, R⁶, R⁷, R⁸ and R$^a$ are as defined for formula (I) or any of the particular embodiments, PE;
and
(b) which is converted into a compound of formula (VII)

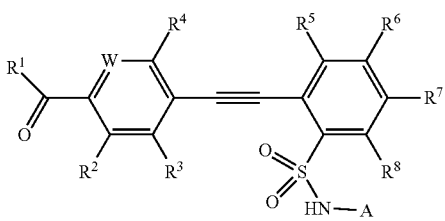

wherein
R¹ is OR$^a$; and
A; W, R², R³, R⁴, R⁵, R⁶, R¹, R⁸ and R$^a$ are as defined for formula (I) or any of the particular embodiments, PE;
and
(c) which optionally be converted into a compound of formula I wherein R¹ is —OH, —NH₂, —NHR$^a$, —NR$^a$R$^b$, —N(H)OH, —N(H)O—R$^a$, —N(H)CN, —N(H)—C(=O)—R$^a$, —N(H)—SO₂—R$^a$;

or
(D)
a compound of formula VIII

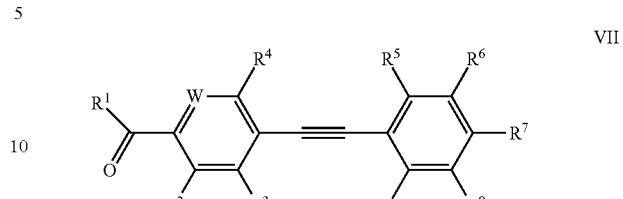

wherein
R¹ is —OR$^a$; and
W, R², R³, R⁴, R⁵, R⁶, R¹, R⁸ and R$^a$ are as defined for formula (I) or any of the particular embodiments, PE;
is reacted with a compound of formula (IX)

H-L¹-L²-A    IX wherein
L¹ is a divalent —N=radical; and
L² is a divalent =S(=O)(R$^a$)— radical;
A is as defined for formula (I) or any of the particular embodiments, PE; to form a compound of formula (I)

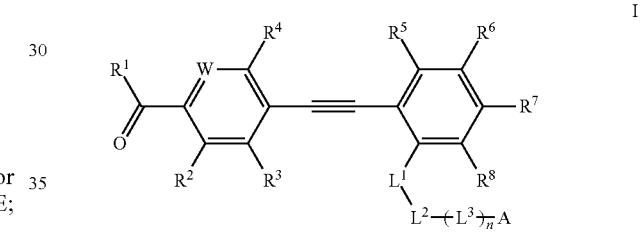

wherein R¹ is OR$^a$; and
n is 0;
(b) which compound of formula (I) optionally be converted into another compound of formula (I) wherein R¹ is —OH, —NH₂, —NHR$^a$, —NR$^a$R$^b$, —N(H)OH, —N(H)O—R$^a$, —N(H)CN, —N(H)—C(=O)—R$^a$, —N(H)—SO₂—R$^a$.

As will be understood by the person skilled in the art of organic synthesis compounds of the present invention, in particular compounds of formula (I), are readily accessible by various synthetic routes, some of which are exemplified in the accompanying Experimental Part. The skilled artisan will easily recognize which kind of reagents and reactions conditions are to be used and how they are to be applied and adapted in any particular instance—wherever necessary or useful—in order to obtain the compounds of the present invention. Furthermore, some of the compounds of the present invention can readily be synthesized by reacting other compounds of the present invention under suitable conditions, for instance, by converting one particular functional group being present in a compound of the present invention, or a suitable precursor molecule thereof, into another one by applying standard synthetic methods, like reduction, oxidation, addition or substitution reactions; those methods are well known to the skilled person.

Likewise, the skilled artisan will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

In the following general synthetic routes that may be utilized to prepare compounds of the present invention are described in more detail in Schemes A to J. If not specified otherwise all substituents, radicals, residues W, $R^1$, $R^2$, $R^3$, $R^4$, $R^5$, $R^6$, $R^7$, $R^8$, $R^a$, $R^b$ and A have the same meaning as defined throughout this specification and in the claims for formula (I).

Compounds of formula (I) in which $L^1$ is —NH— or —$NR^a$— and $L^2$ is —$SO_2$— are readily available by the general synthesis depicted in Scheme A below:

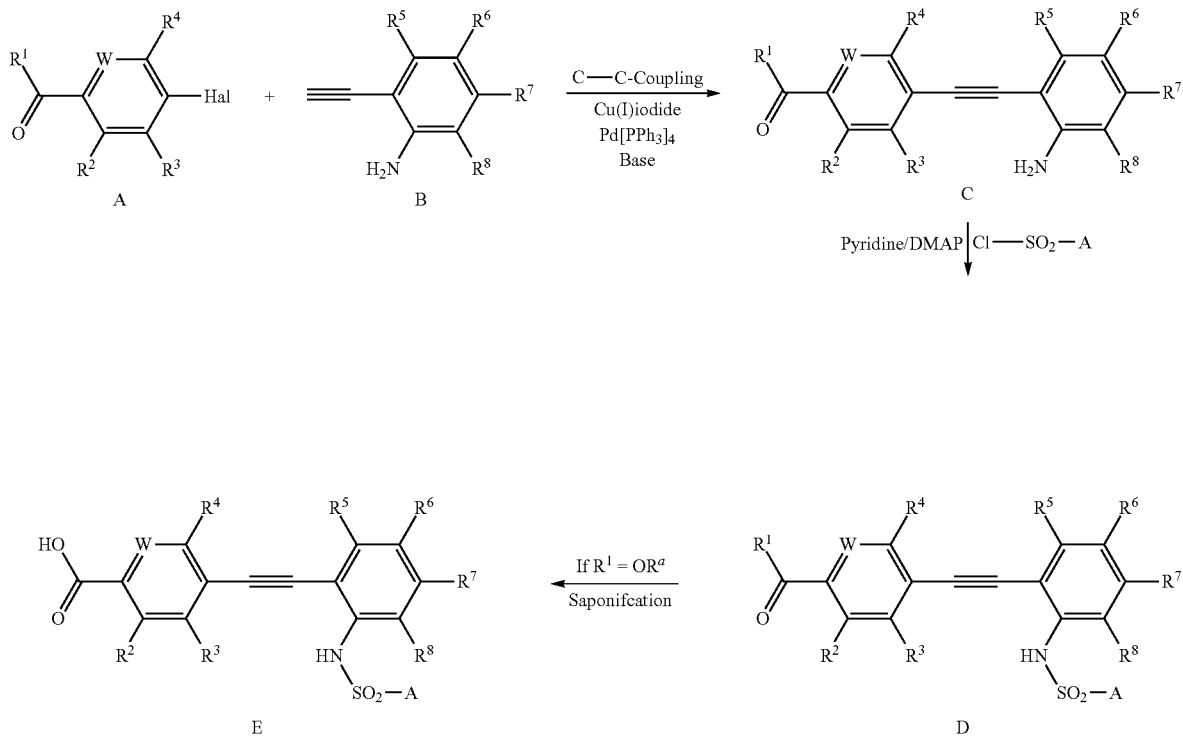

Scheme A

The halogenated aromatic (W=$CR^{W1}$) or heteroaromatic (W=N) derivative A—which is either commercially available or readily available by synthetic methods well know to the skilled person—may be reacted with the readily available ethynyl-substituted aniline derivative B under typical C—C cross-coupling reaction conditions of, for instance, the Sonogashira reaction, e.g. by subjecting the reaction mixture of A and B in a suitable solvent to Copper-(I)-iodide, a suitable Pd(0) complex, e.g. Pd(0)(bistriphenylphospan)-dichloride, in the presence of a nitrogen base, e.g. triethylamine (TEA) or di-isopropylamine (DIPA), to yield the alkyne C. The amino group of alkyne C may then be reacted with a suitable sulfonyl chloride Cl—$SO_2$-A in pyridine and in the presence of dimethylaminopyidine (DMAP) to yield sulfonamide D of the present invention. The carboxylic acid E is easily available via saponification of the ester D (with $R^1$ being an alkoxy group).

Alternatively, compounds of formula (I) in which $L^1$ is —NH— or —$NR^a$— and $L^2$ is —$SO_2$— may be prepared in accordance with the general synthesis depicted in Scheme B:

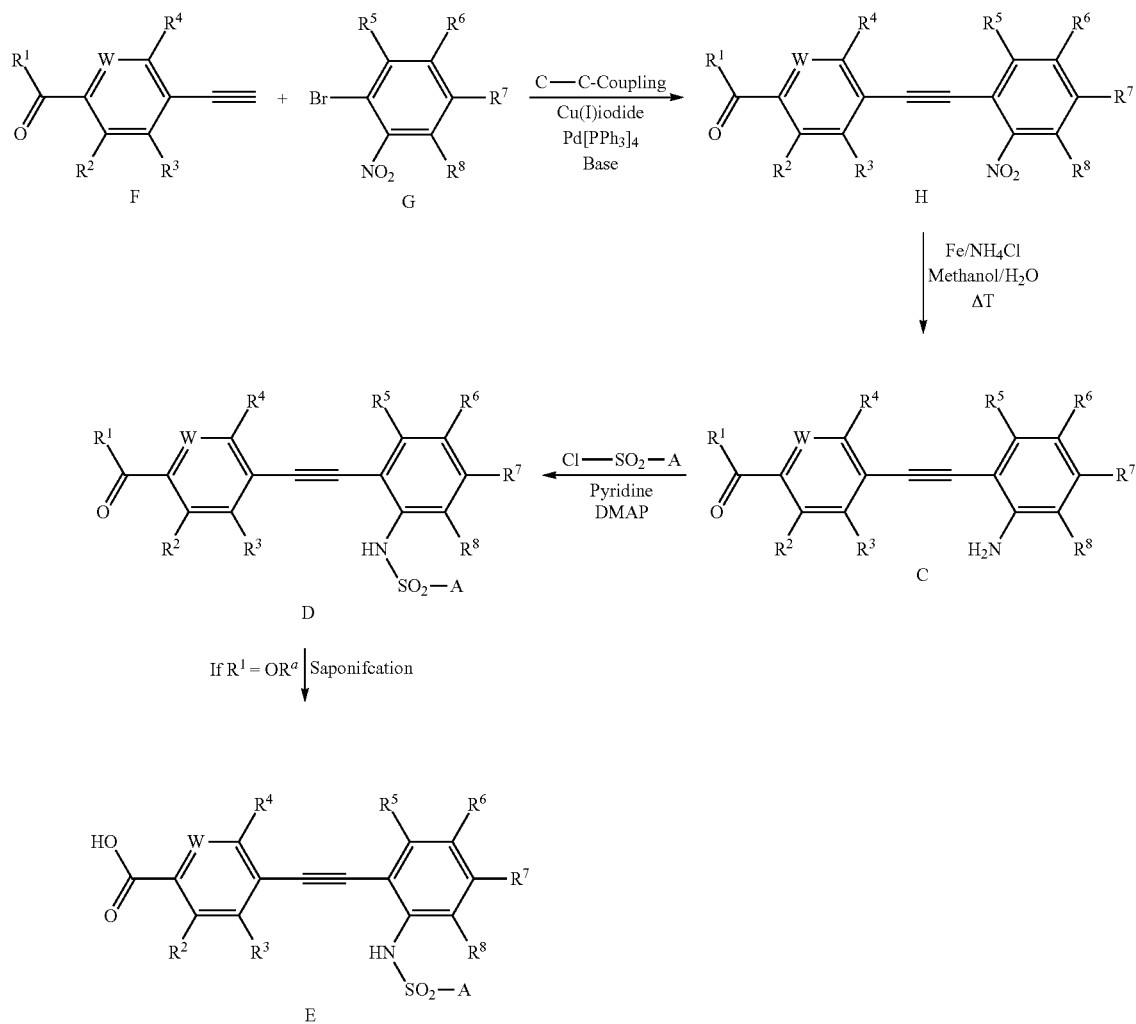

Alkyne derivative F is subjected to a C—C-cross coupling reaction with bromo-nitro-substituted phenyl G, for instance, under conditions typical for a Sonogashira reaction as described above for Scheme A, to yield the nitro-substituted compound H which in turn is subjected to a reduction reaction, e.g., with iron powder under heating, to yield the respective amino-substituted compound C. Further reaction as already described for Scheme A then provides the sulfonamide derivatives D and, after optional saponification (if $R^1$ is alkoxy), the carboxylic acid E.

As will be understood by the skilled person, sulfonamide derivatives of the present invention of formula (I) in which $L^1$ is —NH— or —NR$^a$—, $L^2$ is —SO$_2$— and $L^3$ is a divalent —CH=CH— radical can be obtained by applying the same general procedures depicted in both Schemes A and B but utilizing sulfonylchlorides of general formula Cl—SO$_2$—CH=CH-A instead of Cl—SO$_2$-A.

Compounds of formula (I) in which $L^1$ is —CH$_2$— and $L^2$ is —SO$_2$— can be prepared by the general synthesis shown in Scheme C below:

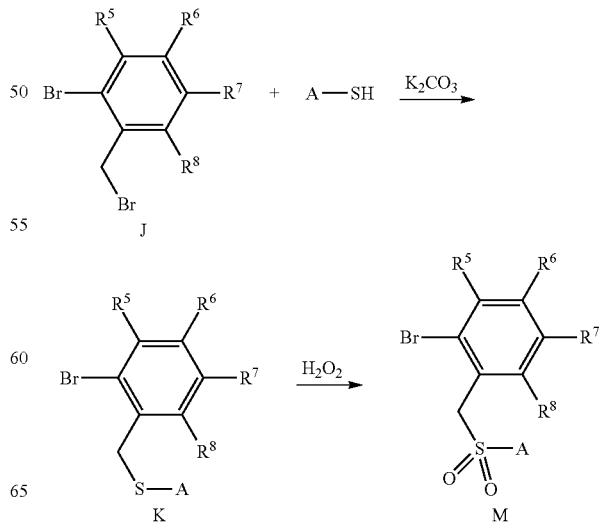

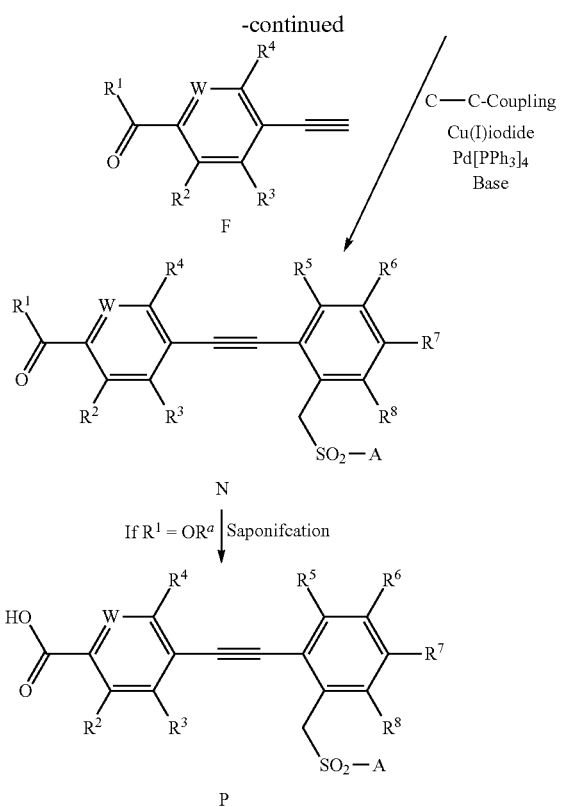

The bromomethyl-substituted bromo-phenyl derivative J is reacted in a nucleophilic substitution reaction with the thiol A-SH, for instance in the presence of potassium carbonate to form thioether K. Compound K is then oxidized my means of hydrogen peroxide to form the sulfone derivative M which is subsequently subjected to a C—C-cross coupling condition (e.g., Sonogashira reaction in a suitable solvent with Copper-(I)-iodide, a suitable Pd(0) complex, e.g. Pd(0)(bistriphenylphospan)-dichloride, and in the presence of a nitrogen base, e.g. triethylamine (TEA) or di-isopropylamine (DIPA)) with the alkyne derivative F to give the compound of the present invention N. If desired, carboxylic acid ester N may be saponified to give the respective carboxylic acid P. Again, if in the first reaction step compound J is reacted with the thiol derivative A-CH=CH—SH rather than A-SH, then this reaction procedure provides a compound of formula (I) in which $L^1$ is —$CH_2$, $L^2$ is —$SO_2$— and $L^3$ is —CH=CH—.

Compounds of formula (I) in which $L^1$ is a divalent —N(CHO)— or —N(C(=O)—$R^a$ radical and $L^2$ is a divalent —$CH_2$— radical can be prepared by the general synthesis shown in Scheme D below:

Scheme D

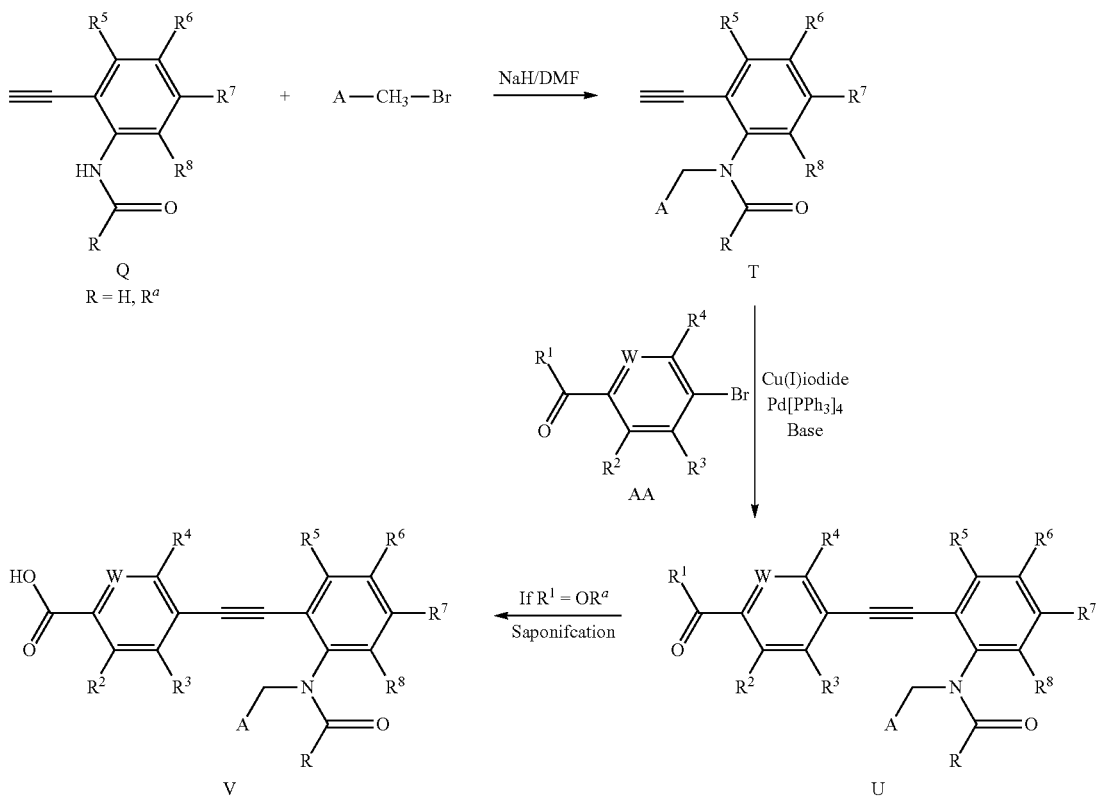

Compound Q—which is readily available from the respective alkynylated aniline derivative by formylation/acylation reaction well-known to the skilled person—is reacted with the bromide A-CH$_2$—Br in the presence of a strong base, e.g., sodium hydride, in a suitable solvent, e.g., DMF, to form compound T. This is subsequently reacted in a C—C-cross coupling reaction (e.g., Sonogashira reaction) with the phenyl-bromide AA to yield the compound of the present invention U. If desired and R$^1$ is alkoxy, saponification of U provides the carboxylic acid V.

Alternatively, compounds of formula (I) in which L$^1$ is a divalent —N(CHO)— radical and L$^2$ is a divalent —CH$_2$— radical can be prepared by the general synthesis shown in Scheme E below:

turn is available by formylation of the amino group of compound X utilizing formyl acetic acid anhydride.

It will be well understood by the skilled person that compounds of formula (I) in which L$^1$ is a divalent —N(CHO)— or —N(C(=O)—R$^a$ radical, L$^2$ is a divalent —CH$_2$— radical and L$^3$ is a —CH$_2$— radical too can be obtained by applying the syntheses described above in Schemes D and E by utilizing bromides A-CH$_2$—CH$_2$—Br or a compound X that bears a A-CH$_2$—CH$_2$— substituent on the amino functional group rather than a A-CH$_2$— substituent. Likewise, if in Scheme E X is reacted with a suitable acid anhydride other than formyl acetic acid anhydride, then compounds of formula 0 with L$^1$ being —N—(C(=O)—R$^a$) can be obtained.

Scheme E

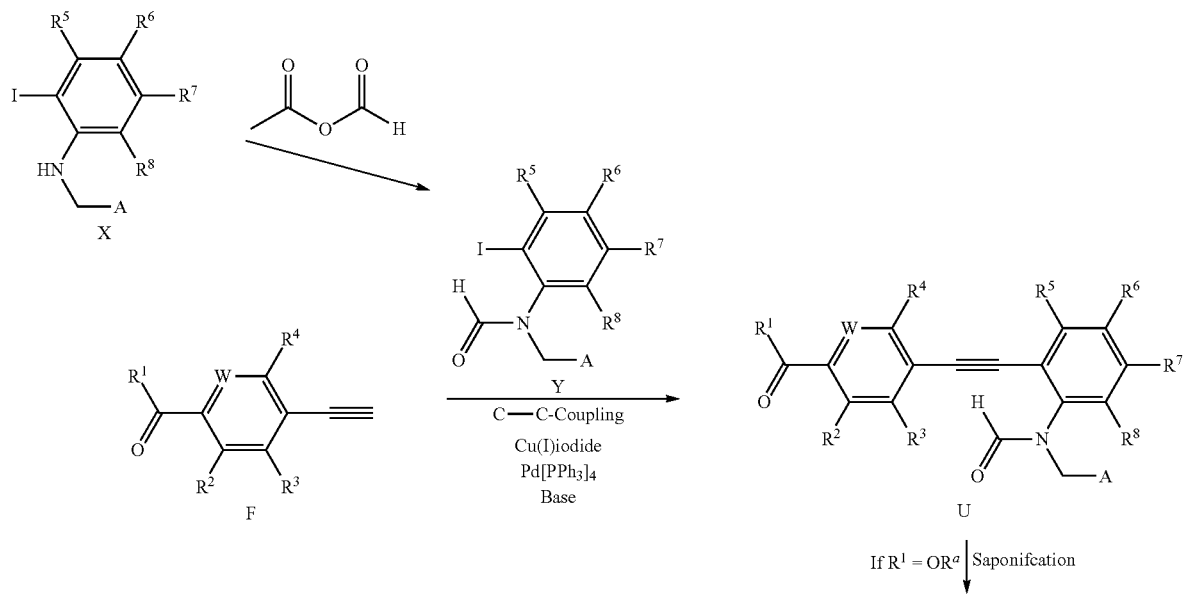

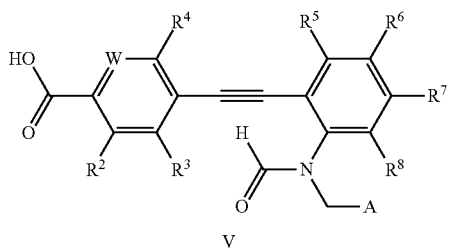

The alkyne derivative F may be reacted with phenyl derivative Y in a C—C-cross coupling reaction (e.g., Sonogashira reaction) to yield compound U, and after optional saponification, compound V of the present invention. Y in Compounds of formula (I) in which L$^1$ is —N(C(=O)—NH$_2$, —N(C(=O)—NHR$^a$ or —N(C(=O)—NR$^a$R$^b$ and L$^2$ is —CH$_2$— can be obtained by applying the synthetic procedure depicted in Scheme F:

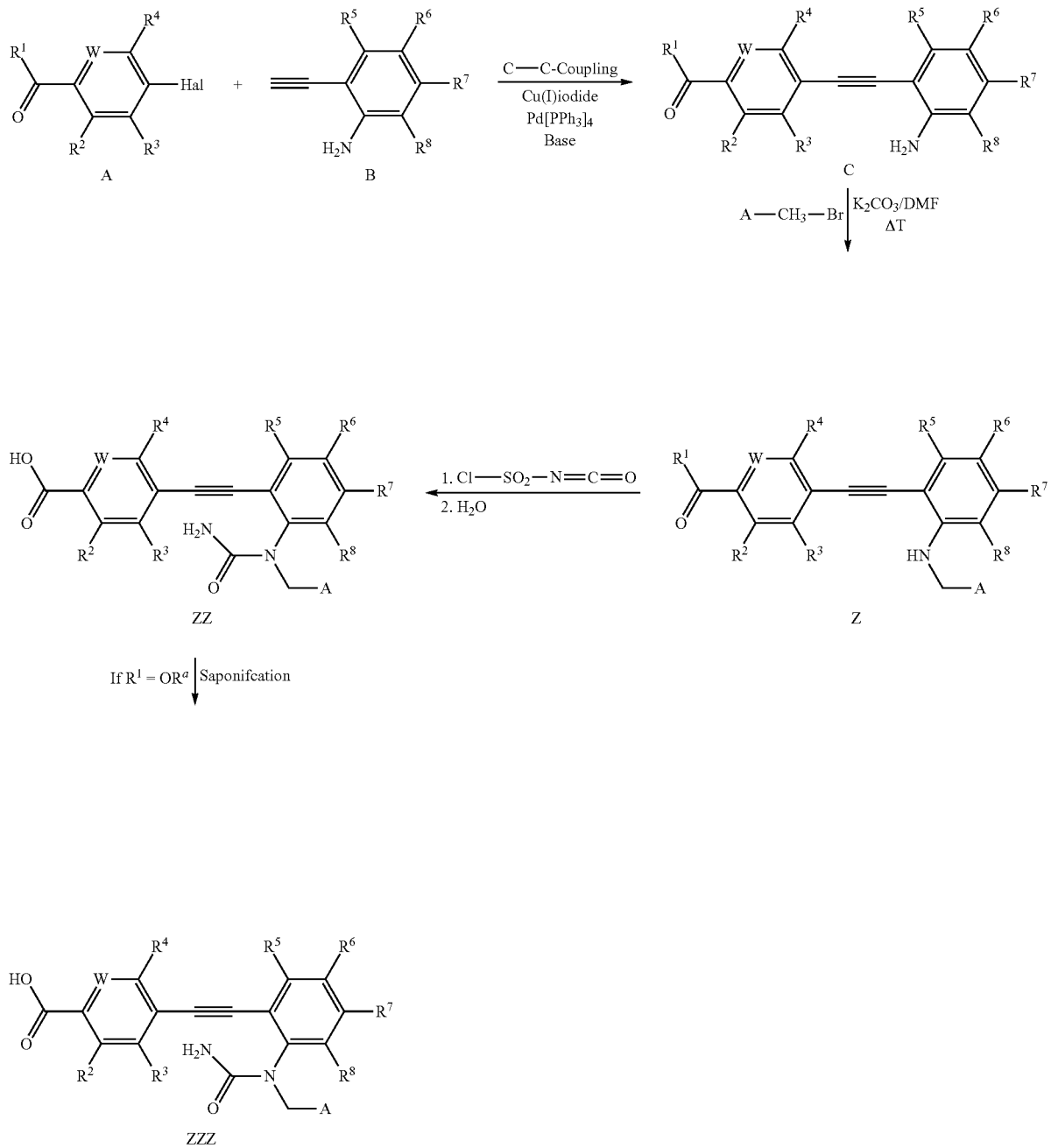

As described above for Scheme A by reacting the halogenated aromatic or heteroaromatic compound A with the alkynylated aniline derivative B under typical C—C-cross coupling reaction conditions alkyne derivative C is obtained. Compound C in turn is subjected to a nucleophilic substitution reaction with bromide A-CH$_2$—Br to give compound Z which is subsequently reacted with a suitable reagent, e.g. chlorosulfonylisocyanate, followed by hydrolysis, to introduce the H$_2$N—C(=O)— radical at the amino group of Z and yield the carbamoyl derivative ZZ. As the skilled person easily recognize by utilizing other suitable reagents than Cl—SO$_2$—N=C=O compounds ZZ with R$^a$HN—C (=O)— or R$^a$R$^b$N—C(=O)— radicals instead of the H$_2$N—C(=O)— radical can be prepared. If R$^1$ is alkoxy, then saponification of the carboxylic ester moiety provides the respective carboxylic acid ZZZ. Again, if C is reacted with bromide A-CH$_2$—CH$_2$—Br rather than A-CH$_2$—Br, compounds of formula (I) in which L$^1$ is —N(C(=O)— NH$_2$, —N(C(=O)—NHR$^a$)— or —N(C(=O)—NR$^a$R$^b$)—, L$^2$ is —CH$_2$— and L$^3$ is —CH$_2$— can be readily obtained.

Compounds of formula (I) in which L$^1$ is —CH$_2$— and L$^2$ is —N(CHO)—, —N(C(=O)R$^a$), —N(C(=O)—NH$_2$)—, —N(C(=O)—NHR$^a$)— or —N(C(=O)—NR$^a$R$^b$)— can be obtained by applying the synthetic procedure depicted in Scheme G below.

Scheme G

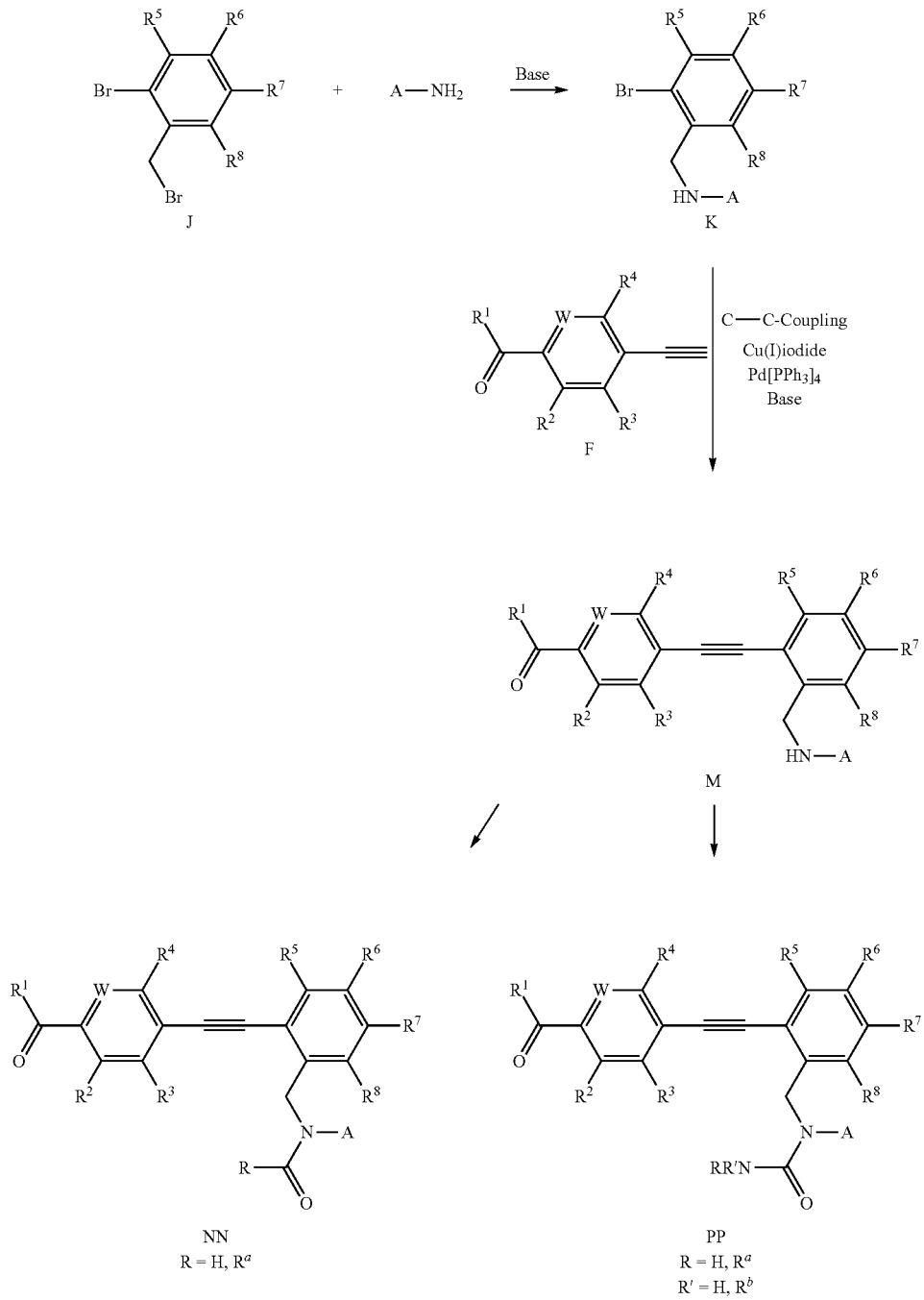

Similar to the reaction depicted in Scheme C above, the bromomethyl-substituted bromo-phenyl derivative J is reacted in a nucleophilic substitution reaction with the amine A-NH$_2$ under suitable conditions, e.g. in the presence of a suitable base, to yield bromo-phenyl derivative KK. Compound KK is in turn subjected to a C—C-cross coupling reaction with alkyne derivative F similar to the C—C-cross coupling reaction described in more detail for Scheme C thereby providing alkyne derivative MM. The secondary amino moiety of MM may then be converted in a formylated or acylated moiety yielding compound NN by utilizing suitable reaction conditions, e.g. using suitable acid anhydrides. If NN happens to be a carboxylic acid ester, this may then be converted into the respective carboxylic acid by saponification. Alternatively, compound MM may be converted into compound PP be applying reaction conditions described in more detail for Scheme F; again, saponification of the ester function, if present, provides the respective carboxylic acid.

Compounds of formula (I) in which $L^1$ is a divalent —N=radical, $L^2$ is a divalent =S(=O)(R$^a$)— radical and $L^3$ is a single bond can be obtained by applying the synthetic procedure depicted in Scheme H below.

Scheme H

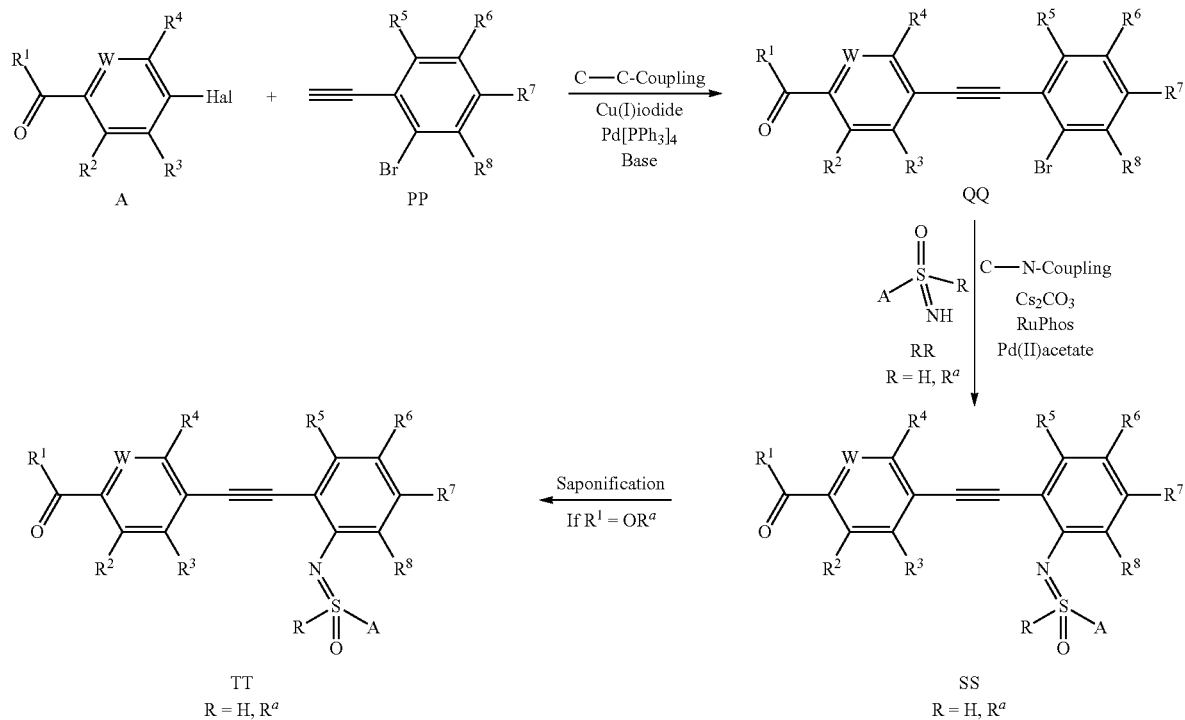

The halogenated aromatic or heteroaromatic compound A is reacted with alkyne derivative PP under typical C—C-coupling reaction conditions to yield alkyne derivative QQ. This is subjected to a C—N-Coupling reaction with the substituted imino-Aλ6-sulfanone derivative RR, e.g. in the presence of a base, for instance cesium carbonate, and a suitable catalyst like RuPhos (2-dicyclohexylphosphino-2', 6'-diisopropoxybiphenyl and palladium(II)acetate, to provide the oxo-Aλ6-sufanylidene-amino derivative SS of the present invention. If desired and SS is a carboxylic ester, then it can be converted into the corresponding carboxylic acid TT by means saponification.

Compounds of formula (I) in which $L^1$ is a divalent- $SO_2$— radical, $L^2$ is a divalent —NH— radical and $L^3$ is a single bond can be obtained by applying the synthetic procedure depicted in Scheme J below.

Scheme J

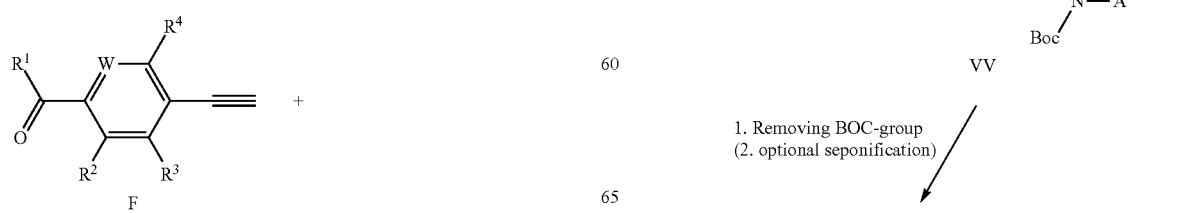

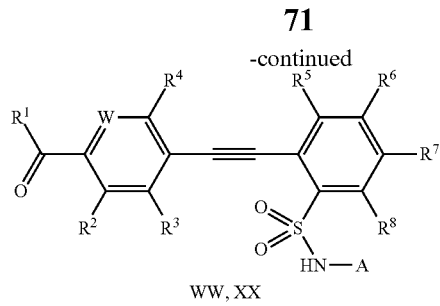

WW, XX

Alkyne derivative F and the iodo-phenyl derivative UU are subjected to a C—C-cross coupling reaction to yield alkyne derivative VV having a BOC protecting group at the N-atom bearing substituent A. This protecting is subsequently removed by reacting VV with an acid like hydrochloric acid to yield alkyne derivative WW of the present invention (with $R^1 \neq OH$) or alkyne derivative XX of the present invention (with $R^1$ being OH) if the carboxylic ester is already saponified under these conditions; otherwise saponification can be effected either before or after removing the BOC protecting group. Compounds of formula (I) in which $L^1$ is a divalent-$SO_2$— radical, $L^2$ is a —N($R^a$)— radical can be obtained by a synthesis similar to that of Scheme J by utilizing an iodo-phenyl derivative bearing a —S($O_2$)—N—($R^a$)-A group rather than a —S($O_2$)—NH-A group.

"Treating" or "treatment" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) refers to an amount (of a compound, drug, pharmaceutical compositions, etc.) capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

It is to be noted that—except for instances where it is specifically stated or the context provides for a different meaning—in general the number of a term, i.e. its singular and plural form, is used and can be read interchangeably. For example, the term "compound" in its singular form may also comprise or refer to a plurality of compounds, while the term "compounds" in its plural form may also comprise or refer to a singular compound.

EXPERIMENTAL PART

| Abbreviation | Meaning |
| --- | --- |
| ACN | acetonitrile |
| CDI | carbonyldiimidazole |
| DCM | dichloromethane |
| DIEA | di-iso-proyplethylamine |
| DIPEA | di-iso-propylethylamine |
| DMF | dimethylformamide |
| DMSO | dimethylsulfoxid |

-continued

| Abbreviation | Meaning |
| --- | --- |
| EDCI | 1-ethyl-3-(3-dimethylaminopropyl)carbodiimid |
| EtOAc, AcOEt, EA | ethyl acetate |
| HATU | O-(7-azabenzotriazol-1-yl)-N,N,N',N'-tetramethyluronium $PF_6$, 97% |
| MeOH | methanol |
| PE | petrol ether |
| RM | reaction mixture |
| RT | room temperature |
| TEA | trimethylamine |
| TFA | trifluoroacetic acid |
| THF | tetrahydrofuran |
| XPhos-PdCl-2nd G | chloro-(2-dicyclohexylphosphino-2',4',6'-triisopropyl-1,1'-biphenyl)[2-(2'-amino-1,1'-biphenyl)]palladium(II) |

The compounds of the present invention can be prepared according to the procedures of the following Schemes and Examples, using appropriate materials and are further exemplified by the following specific examples. The compounds are shown in Table 1. Analytical data of compounds made according to the following examples are shown in Table 2.

The invention will be illustrated, but not limited, by reference to the specific embodiments described in the following examples. Unless otherwise indicated in the schemes, the variables have the same meaning as described above and in the claims.

Unless otherwise specified, all starting materials are obtained from commercial suppliers and used without further purifications. Unless otherwise specified, all temperatures are expressed in ° C. and all reactions are conducted at RT. Compounds are purified by either silica chromatography or preparative HPLC.

$^1$H NMR:

$^1$H-NMR data is provided in Table 2 below. $^1$H NMR spectra were usually acquired on a Bruker Advance III 400 MHz, Bruker Fourier HD 300 MHz, Bruker DPX-300, DRX-400, AVII-400 or on a 500 MHz spectrometer, if not specified otherwise. Chemical shifts (δ) are reported in ppm relative to the residual solvent signal (δ=2.5 ppm for $^1$H NMR in DMSO-d6, δ=7.27 ppm for $^1$H NMR in $CDCl_3$; δ=3.31 ppm for Methanol-d4). $^1$H NMR data are reported as follows: chemical shift (multiplicity, coupling constants and number of hydrogens). Multiplicity is abbreviated as follows: s (singlet), d (doublet), t (triplet), q (quartet), m (multiplet), dd (doublet of doublets), tt (triplet of triplets), td (triplet of doublets) br (broad) and coupling constants (J) are reported in Hz.

LC-MS:

LC-MS data provided in Table 2 are given with retention time and mass in m/z. The results can be obtained by one of the methods described below. LC-MS analyses were usually performed on a Dionex Ultimate 3000 LC system (DAD I=254+280 nm) coupled with a Bruker Amazon SL MS detector (ESI positive and negative mode, scan range: 100-1000 m/z) at 25° C.

Method A: Kinetex-BCM

Column: Kinetex XB C18 (4.6×50 mm 2.6 μm); Solvent A: water+0.1% formic acid; Solvent B: ACN+0.1% formic acid; Flow: 0.5 ml/min; Gradient: 0 min: 20% B; 6.7 min: 80% B; 7.5 min: 80% B; 7.8 min: 95% B; 9.5 min: 95% B; 10.0 min: 20% B; 12.0 min: 20% B Method B: Kinetex-BCM-NP Column: Kinetex XB C18 (4.6×50 mm 2.6 μm); Solvent A: water+0.1% formic acid; Solvent B: ACN+0.1% formic acid; Flow: 0.5 ml/min; Gradient: 0 min: 20% B; 4.0 min: 80% B; 4.7 min: 80% B; 4.9 min: 95% B; 8.5 min: 95% B; 10.0 min: 20% B; 14.0 min: 20% B Method C: BCM-30

Column: Waters Symmetry C18 (3.9×150 mm 5 μm); Solvent A: water+0.1% formic acid; Solvent B: ACN+0.1% formic acid; Flow: 1.2 ml/min; Gradient: 0 min: 20% B; 20.0 min: 80% B; 22.0 min: 80% B; 22.5 min: 95% B; 25.0 min: 95% B; 25.3 min: 20% B; 30.0 min: 20% B Method D: Ascentis Express Column: Ascentis Express C18, 3.0*50 mm, 2.7 um; Mobile Phase A: Water/0.05% TFA, Mobile Phase B: ACN/0.05% TFA; Flow rate: 1.5 mL/min; Gradient: 5% B to 100% B in 1.2 min, hold 0.5 min; 254 nm Method E: CORTECS Column: CORTECS C18 100A,2.1*50 mm, 2.7 um; Mobile phase A: Water/0.1% FA, Mobile phase B: Acetonitrile/0.1% FA; Flow rate: 1.0 mL/min; Gradient: 10% B to 100% B in 2.0 min, hold 0.6 min; 254 nm Method F: Shim-pack Column: Shim-pack XR-ODS, 3.0*50 mm, 2.2 um; Mobile Phase A: water/0.05% TFA, Mobile Phase B: ACN/0.05% TFA; Flow rate: 1.2 mL/min; Gradient: 5% B to 100% B in 2.0 min, hold 0.7 min; 254 nm Method G: Poroshell Column: Poroshell HPH-C18, 3.0*50 mm, 2.7 um; Mobile Phase A: water/5 mM NH4HCO3, Mobile Phase B: Acetonitrile; Flow rate: 1.2 mL/min; Gradient: 10% B to 95% B in 2.1 min, hold 0.6 min; 254 nm.

Method H: Titank

Column: Titank C18, 3.0*50 mm, 3.0 um; Mobile Phase A: water/5 mM NH4HCO3, Mobile Phase B: Acetonitrile; Flow rate: 1.2 mL/min; Gradient: 10% B to 95% B in 2.1 min, hold 0.6 min; 254 nm Method J:

Column: HALO C18, 3.0*30 mm, 2.0 um; Mobile Phase A: Water/0.05% TFA, Mobile Phase B: ACN/0.05% TFA; Flow rate: 1.5 mL/min; Gradient: 5% B to 100% B in 1.2 min, hold 0.5 min; 254 nm Method K: YMC Column: YMC-Triart C18, 3.0 um, 50*3.0 mm; Mobile Phase A: 0.04% NH4OH, Mobile Phase B: ACN; Flow rate: 1.2 mL/min; Gradient: 10% B to 95% B in 2.1 min, hold 0.6 min; 254 nm Method L: Agilent 1200

Agilent 1200 Series; Chromolith RP-18e 50-4.6 mm; 3.3 ml/min; solvent A: Water+0.05% HCOOH; solvent B: Acetonitrile+0.04% HCOOH; 220 nm; 0 to 2.0 min: 0% B to 100% B; 2.0 to 2.5 min: 100% B Method M: Agilent Series Agilent Series; Kinetex EVO C18 5.0 um; 3.3 ml/min; solvent A: Water+0.05% HCOOH; solvent B: Acetonitrile+0.04% HCOOH; 220 nm; 0 to 0.8 min: 1% B to 990% B; 0.8 to 1.1 min: 99% B Example 1—General Procedure 1 (GP1)

Compounds of formula (I) with $L^1$ being a divalent —NH— or —N($R^a$)— radical and $L^2$ being a divalent —SO$_2$— radical (i.e. sulfonamide derivatives) may be prepared in accordance with the following scheme and synthetic procedure described below:

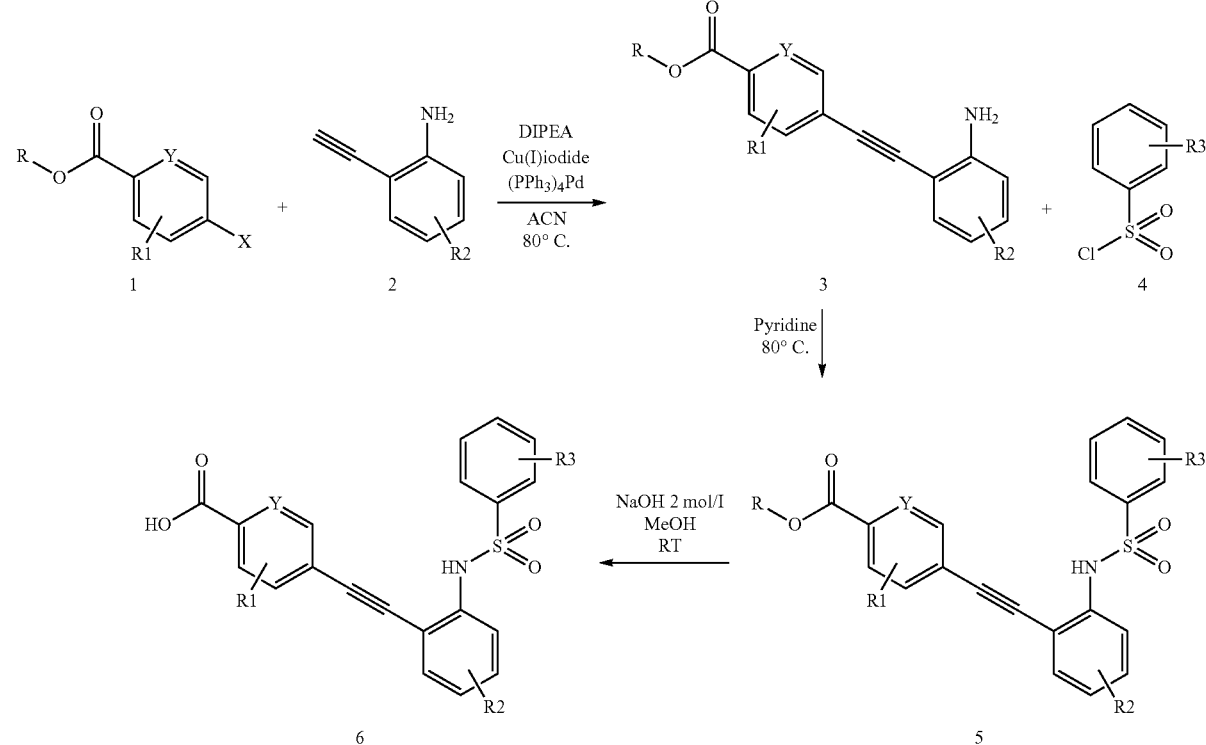

Commercially available 2-ethynylaniline 2 (R1=H) (1 eq) was dissolved in acetonitrile and 5-halo-picolinate 1 (Y=N; R2=H) (1.5 eq), diisopropylamine (1.5 eq), copper (I)iodide (0.1 eq) and tetrakis(triphenylphosphine)-palladium(0) (0.1 eq) were added. The mixture was stirred for 16 hrs at 80° C. After completion of the reaction and cooling down to room temperature the mixture was filtered and the residue was dried under vacuum. The product 3 was used in the next step without further purification.

Aniline 3 (1 eq) was dissolved in pyridine and phenylsulfonyl chloride 4 (R3 =H, 3 eq) was added. The mixture was stirred at 8000 for 2 hrs. After completion of the reaction and cooling to room temperature the reaction mixture was diluted with the hylacetate and water. After exhaustive extraction of the aqueous phase with ethylacetate the combined organic layers were washed with water and brine, dried over sodium sulphate, filtered and evaporated to dryness. The crude 5 was used in the next step without further purification. (Alternatively, ester 5 can be purified and isolated by standard working-up procedures known to the skilled person.)

Ester 5 (1 eq) was dissolved in THF and sodium hydroxide solution in water (2N, 1.1 eq) was added. The reaction mixture was stirred for 12 hrs at room temperature. After full conversion the mixture was acidified with 1N HCl and diluted with ethylacetate and water. The aqueous layer was extracted with ethylacetate and the combined organic layers were washed with brine and dried with sodium sulphate, filtered and evaporated to dryness. Either crystalisation from established solvent mixtures or purification via chromatography delivered the final products usually as solid.

In a similar manner 4-halo-benzoic acid ester 1 (Y=CH) can be reacted with a suitable ethynylaniline 2 to provide the respective anilines 3, esters 4 and carboxylic acids 5.

Alternatively or in case the ethynyl-aniline is not commercially available, it can be prepared by reaction of the corresponding halo-aniline with trimethylsilyl-ethyne under Sonogashira reaction conditions known to an expert in the field.

Alternatively, the carboxylate building block might be commercially available as ethynyl and not halogen analog (X=—C≡CH). In such a case the aniline component is applied as halogenated building block.

In case a desired substitution pattern on any building block 1, 2 or 4 was not commercially available a dedicated synthesis was performed. Explicit examples are described below:

Example 2

Synthesis of 5-ethylquinoline-8-sulfonyl chloride

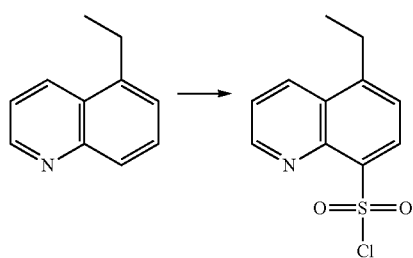 [SMILES: CCc1cccc2ncccc12 ; CCc1ccc(S(=O)(=O)Cl)c2ncccc12]

Chlorsulfonic acid (6.4 ml; 95.8 mmol; 20 eq.) was added to 5-ethylquinoline (753 mg; 4.8 mmol; 1 eq.) under ice-cooling. The mixture was stirred for 16 hrs at 120° C. After cooling to room temperature the reaction was added carefully dropwise to stirred ice-water and extracted 3× with ethylacetate. The combined organic layers were washed 2× with water, dried over Na₂SO₄ and evaporated to dryness. The product was used for sulfonamide formation without further purification.

Example 3

Synthesis of: 5-ethoxyquinoline-8-sulfonyl chloride

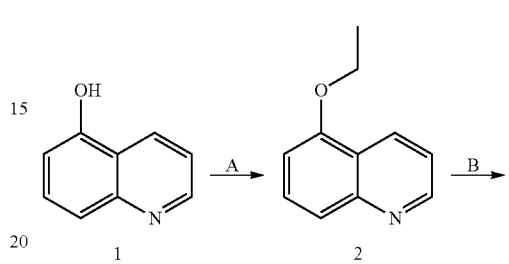

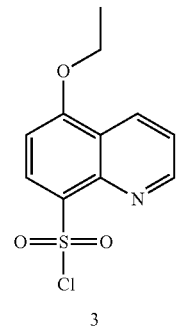

Step A

To a solution of 5-hydoxy-quinoline (15.0 g, 103 mmol) in acetone (300 mL) K₂CO₃ (21.0 g, 152 mmol) and ethyl iodide (23.4 g, 150 mmol) were added and the resulting mixture was refluxed for 8 h. After the reaction mass cooled to room temperature it was diluted with water (500 mL) and extracted with ethyl acetate (3×200 mL). The organic extract was washed with brine, dried over Na₂SO₄, and evaporated under reduced pressure to obtain 15.0 g (86.6 mmol, 87%) of 5-ethoxy-quinoline.

Step B 5-ethoxy-quinoline (15.0 g, 86.6 mmol) was mixed with pre-cooled chlorosulfonic acid (200 mL) and the temperature was kept below 10° C. The obtained mixture was stirred at 10° C. for 3 h and poured onto crushed ice (1500 g). The product was extracted with ethyl acetate (3×300 mL). The combined organic extract was washed with water (500 mL), saturated NaHCO₃ (2×500 mL), and brine (500 mL), dried over Na2SO4, and evaporated under reduced pressure to obtain 8.00 g (29.4 mmol, 34%) of 5-ethoxy-quinoline-8-sulfonylchloride.

Example 4

Synthesis of 5-methoxy-7-methylquinoline-8-sulfonyl chloride

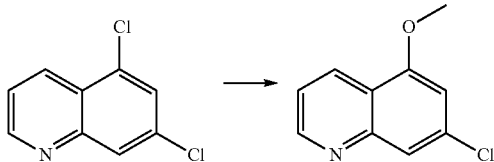

A solution of 5,7-dichloroquinoline (2 g, 9.59 mol, 1 eq, 95%) and MeONa (8 mL, 43.05 mmol, 4.49 eq, 30%) in THF (40 mL) was stirred at room temperature for 2 days at 75° C. under nitrogen atmosphere. The mixture was acidified to pH 6 with HCl (aq.). The reaction mixture was concentrated under vacuum. The aqueous layer was extracted with $CH_2Cl_2$ (3×50 mL). The combined organic layers were concentrated under vacuum. The residue was purified by reverse flash chromatography with the following conditions: column, C18 silica gel; mobile phase, MeOH in water, 10% to 50% gradient in 10 min; detector, UV 254 nm. This resulted in 7-chloro-5-methoxyquinoline (400 mg, 19%) as a yellow solid.

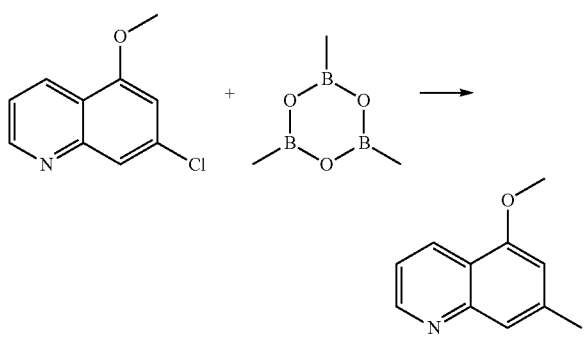

To a stirred mixture of 7-chloro-5-methoxyquinoline (500 mg, 2.32 mmol, 1 eq, 90%), $Na_2CO_3$ (1.2 g, 10.76 mmol, 4.63 eq, 95%) and XPhos-PdCl-2nd G (300 mg, 0.38 mmol, 0.16 eq, 95%) in dioxane (60 mL) were added $H_2O$ (15 mL) and trimethyl-1,3,5,2,4,6-trioxatriborinane (3 g, 11.95 mmol, 5.14 eq, 50%) dropwise at room temperature. The mixture was stirred overnight at 90° C. under nitrogen atmosphere and and then concentrated under vacuum. The aqueous layer was extracted with $CH_2Cl_2$ (3×20 mL). The combined organic layers were concentrated under vacuum. The residue was purified by reverse flash chromatography with the following conditions: column, C18 silica gel; mobile phase, MeOH in water, 10% to 50% gradient in 20 min; detector, UV 254 nm. This resulted in 5-methoxy-7-methylquinoline (200 mg, 45%) as a yellow oil.

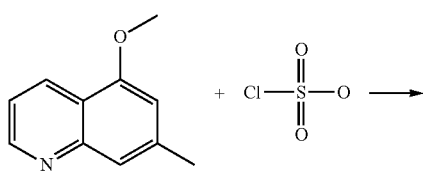

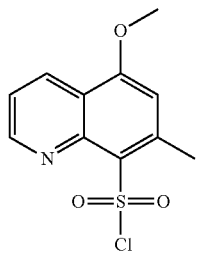

Into a 25-mL round-bottom flask, was placed 5-methoxy-7-methylquinoline (200 mg, 1.04 mmol, 1 eq, 90%) and sulfurochloridic acid (6 mL, 91.14 mmol, 87.71 eq, 100%) was added slowly under ice cooling. The resulting mixture was stirred for 3 h at −10° C. The reaction was quenched by the addition of 30 mL of water/ice. The resulting mixture was extracted with 3×30 mL of dichloromethane. The combined organic layers were concentrated under vacuum. This resulted in 340 mg (72%) of 5-methoxy-7-methylquinoline-8-sulfonyl chloride as a yellow solid.

Example 5

Synthesis of 5-{2-[4-ethoxy-2-(quinoline-8-sulfonamido)phenyl]ethynyl}-pyridine-2-carboxylic acid

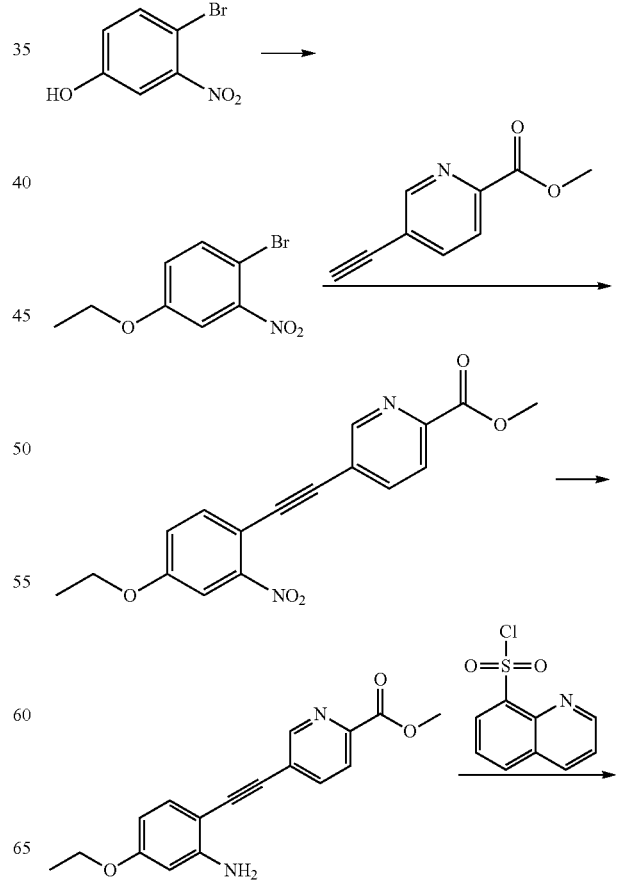

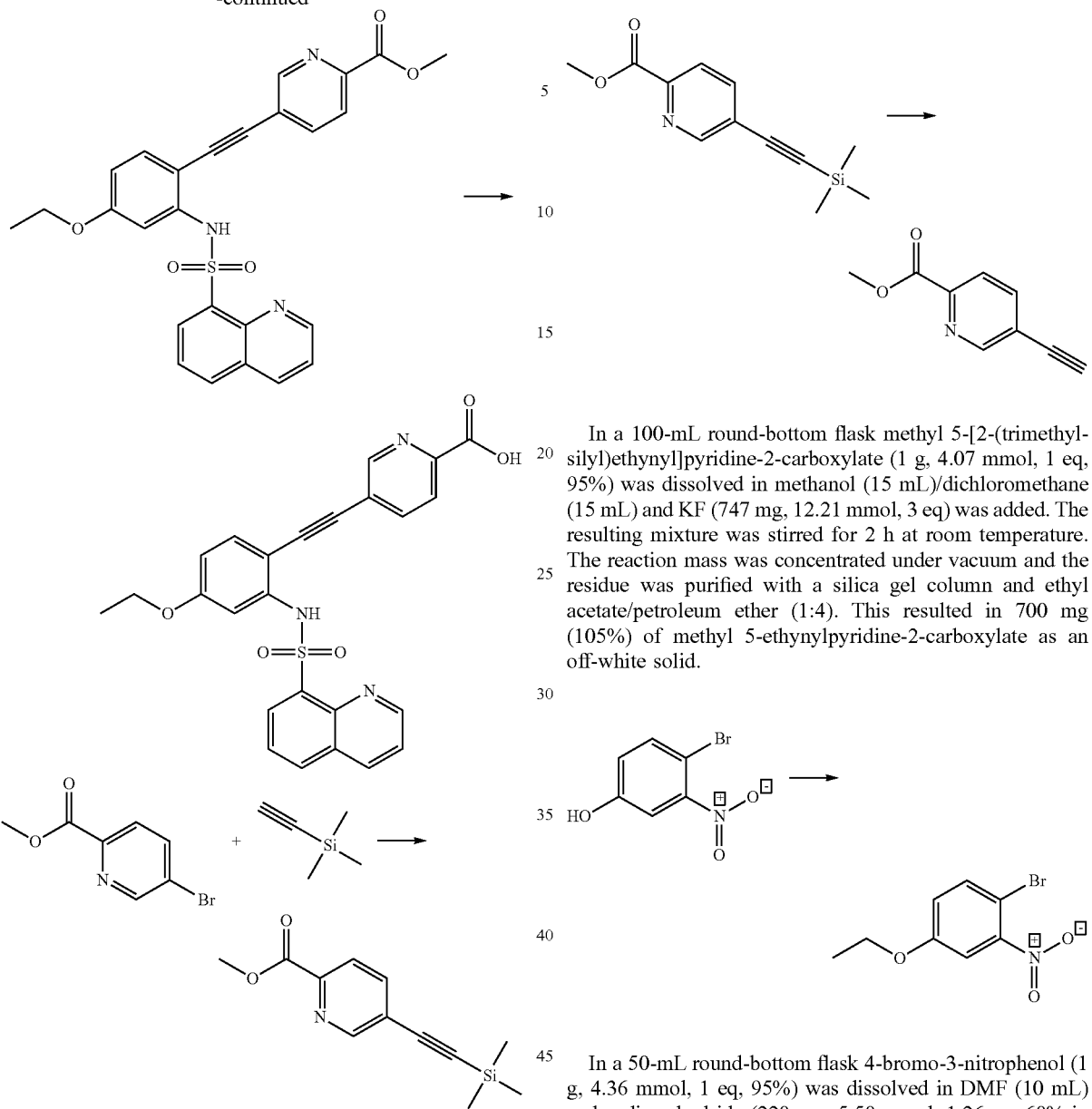

Into a 100-mL round-bottom flask, purged and maintained with an inert atmosphere of nitrogen, was placed methyl 5-bromopyridine-2-carboxylate (1.2 g, 5.28 mmol, 1 eq, 95%), THe (15 mL), TEA (15 mL, 102.52 mmol, 19.43 eq, 95%), CuI (28 mg, 0.14 mmol, 0.03 eq, 95%), Pd(PPh$_3$)$_2$Cl$_2$ (68 mg, 0.09 mmol, 0.02 eq, 90%) and ethynyltrimethylsilane (1.37 g, 13.25 mmol, 2.51 eq, 95%). The resulting mixture was stirred overnight at 50° C. and then diluted with 100 mL of H$_2$O. The resulting solution was extracted with 3×50 mL of ethyl acetate and the combined the organic layers were dried over sodium sulfate, filtered and concentrated under reduced pressure. The residue was purified by chromatography with a silica gel column with ethyl acetate/petroleum ether (1:5). This resulted in 1.2 g (96%) of methyl 5-[2-(trimethylsilyl)ethynyl]pyridine-2-carboxylate as a light yellow solid.

In a 100-mL round-bottom flask methyl 5-[2-(trimethylsilyl)ethynyl]pyridine-2-carboxylate (1 g, 4.07 mmol, 1 eq, 95%) was dissolved in methanol (15 mL)/dichloromethane (15 mL) and KF (747 mg, 12.21 mmol, 3 eq) was added. The resulting mixture was stirred for 2 h at room temperature. The reaction mass was concentrated under vacuum and the residue was purified with a silica gel column and ethyl acetate/petroleum ether (1:4). This resulted in 700 mg (105%) of methyl 5-ethynylpyridine-2-carboxylate as an off-white solid.

In a 50-mL round-bottom flask 4-bromo-3-nitrophenol (1 g, 4.36 mmol, 1 eq, 95%) was dissolved in DMF (10 mL) and sodium hydride (220 mg, 5.50 mmol, 1.26 eq, 60% in oil) was added at 0° C. The mixture was stirred for 0.5 h, and then iodoethane (860 mg, 5.24 mmol, 1.20 eq) was added. The resulting solution was stirred for 2 h at room temperature. The mixture was extracted with 3×50 mL of ethyl acetate and the combined organic layers were dried over anhydrous sodium sulfate and concentrated under reduced pressure. The residue was applied onto a silica gel column with ethyl acetate/hexane (1:100). This resulted in 0.975 g (98%) of 2-bromo-5-ethoxyaniline as an off-white solid.

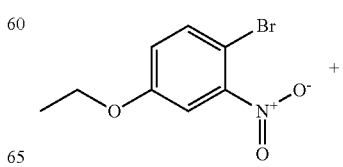

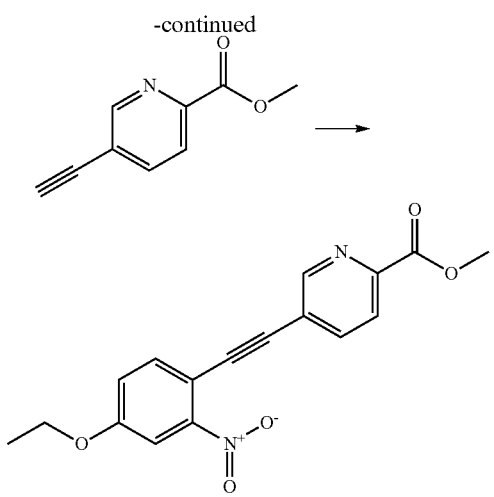

Into a 25-mL round-bottom flask, purged and maintained with an inert atmosphere of nitrogen, was placed 1-bromo-4-ethoxy-2-nitrobenzene (500 mg, 1.93 mmol, 1 eq, 95%), THF (8 mL), TEA (618 mg, 5.8 mmol, 3 eq, 95%), CuI (39 mg, 0.19 mmol, 0.1 eq, 95%), Pd(PPh$_3$)$_2$Cl$_2$ (143 mg, 0.18 mmol, 0.1 eq, 90%) and methyl 5-ethynylpyridine-2-carboxylate (394 mg, 2.4 mmol, 1.24 eq, 98%). The reaction mixture was stirred overnight at room temperature and then diluted with 50 ml of H$_2$O. The solids were filtered out and the resulting solution was extracted with 3×50 ml of ethyl acetate. The combined organic layers were dried over sodium sulfate and concentrated under vacuum after filtration. The residue was applied onto a silica gel column with petrolether:/ethylacetate (3:1). The collected fractions were combined and concentrated under vacuum. This resulted in 80 mg (13%) of methyl 5-[2-(4-ethoxy-2-nitrophenyl)ethynyl]pyridine-2-carboxylate as a yellow solid.

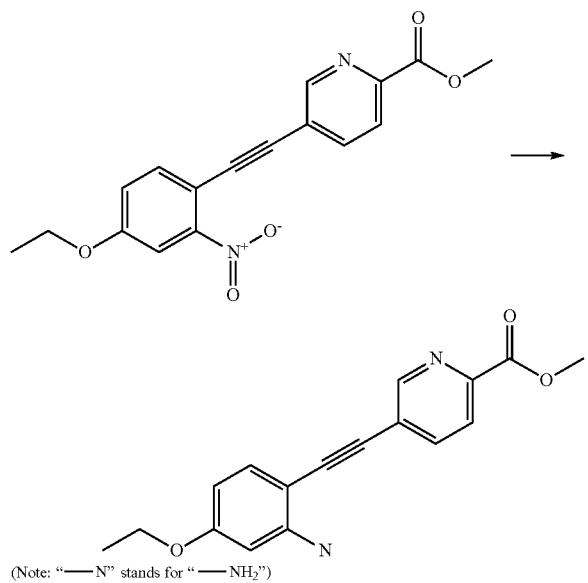

(Note: "——N" stands for "——NH$_2$")

In a 8-mL vial methyl 5-[2-(4-ethoxy-2-nitrophenyl)ethynyl]pyridine-2-carboxylate (60 mg, 0.18 mmol, 1 eq) was dissolved in methanol (1 mL) and water (0.5 mL). NH$_4$Cl (39 mg, 0.7 mmol, 3.8 eq, 95%) and Fe (51.5 mg, 0.9 mmol, 4.8 eq, 95%) were added. The resulting mixture was stirred overnight at 70° C. After cooling to room temperature the mixture was diluted with 30 mL of methanol. The solids were filtered out and the resulting solution was extracted with 3×50 mL of ethyl acetate. The organic layers were combined and dried over anhydrous sodium sulfate. After filtration and removal of all volatile components under reduced pressure the residue was applied onto a silica gel column with ethyl acetate/hexane (1:4). This resulted in 35 mg (61%) of methyl 5-[2-(2-amino-4-ethoxyphenyl)ethynyl]pyridine-2-carboxylate as a yellow solid.

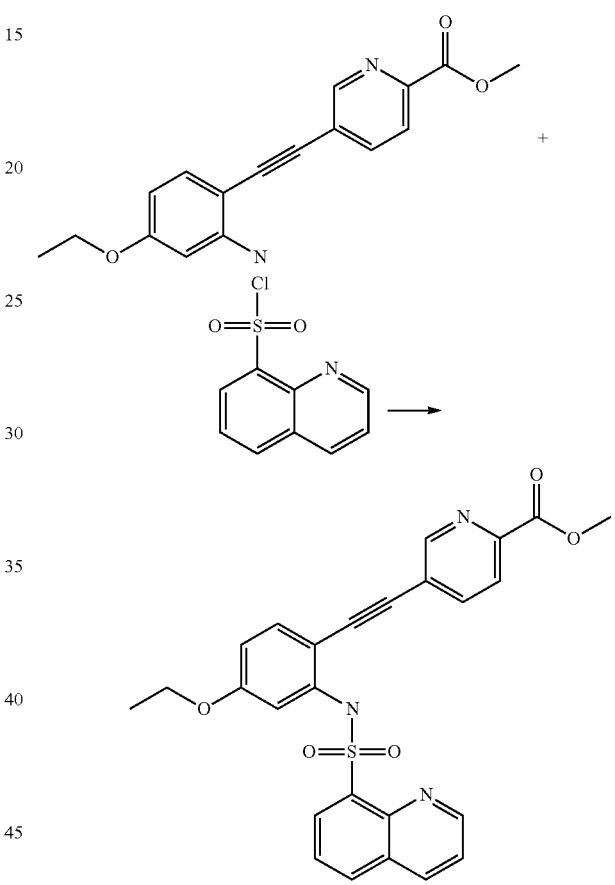

(Note: "——N" stands for "——NH$_2$"; "——N——" stands for "——NH——")

In a 8-mL vial methyl 5-[2-(2-amino-4-ethoxyphenyl)ethynyl]pyridine-2-carboxylate (35 mg, 0.11 mmol, 1 eq, 95%) was dissolved in pyridine (1 mL). 4-Dimethylaminopyridine (1.5 mg, 0.01 mmol, 0.1 eq) and quinoline-8-sulfonyl chloride (53.7 mg, 0.22 mmol, 2 eq, 95%) were added. The reaction mixture was stirred overnight at room temperature. The mixture was diluted with 30 mL of H$_2$O and extracted with 3×30 mL of ethyl acetate. The combined organic layers were dried over anhydrous sodium sulfate. After filtration and evaporation the residue was applied onto a silica gel column with ethyl acetate/hexane (1:4). The collected product fractions were combined and concentrated under vacuum. This resulted in 45 mg (75%) of methyl 5-[2-[4-ethoxy-2-(quinoline-8-sulfonamido)phenyl]ethynyl]pyridine-2-carboxylate as a light yellow solid.

83

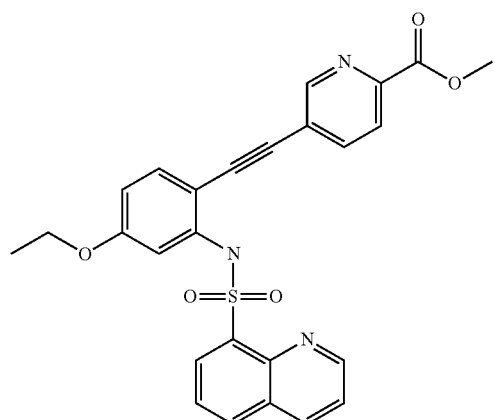

(Note: "—O" stands for "—OH"; "—N—" stands for "—NH—")

In a 8-mL vial methyl 5-[2-[4-ethoxy-2-(quinoline-8-sulfonamido)phenyl]-ethynyl]pyridine-2-carboxylate (40 mg, 0.07 mmol, 1 eq, 91%) was dissolved in THF (1 mL) and water (0.5 mL). Sodium hydroxide (33 mg, 0.8 mmol, 10 eq) was added. The mixture was stirred for 3 h at room temperature and concentrated under vacuum. The reminder was diluted with 50 mL of water and extracted with 3×50 mL of ethyl acetate. The combined organic layers were dried over anhydrous sodium sulfate and concentrated under vacuum. The crude product (50 mg) was purified by prep-HPLC with the following conditions: Column, XBridge Shield RP18 OBD, 5 μm, 19*150 mm; mobile phase: water (10 mmoL/L NH$_4$HCO$_3$+0.1% NH$_3$.H$_2$O) and ACN (24% ACN up to 45% in 8 min); Detector, UV 254/220 nm. This resulted in 23 mg (64%) of 5-[2-[4-ethoxy-2-(quinoline-8-sulfonamido)phenyl]ethynyl]pyridine-2-carboxylic acid as a white solid. The compound exhibited a melting point of 138-140° C.

84

Example 6

Synthesis of 3-ethyl-5-{2-[2-(quinoline-8-sulfonamido)phenyl]ethynyl}-pyridine-2-carboxylic acid

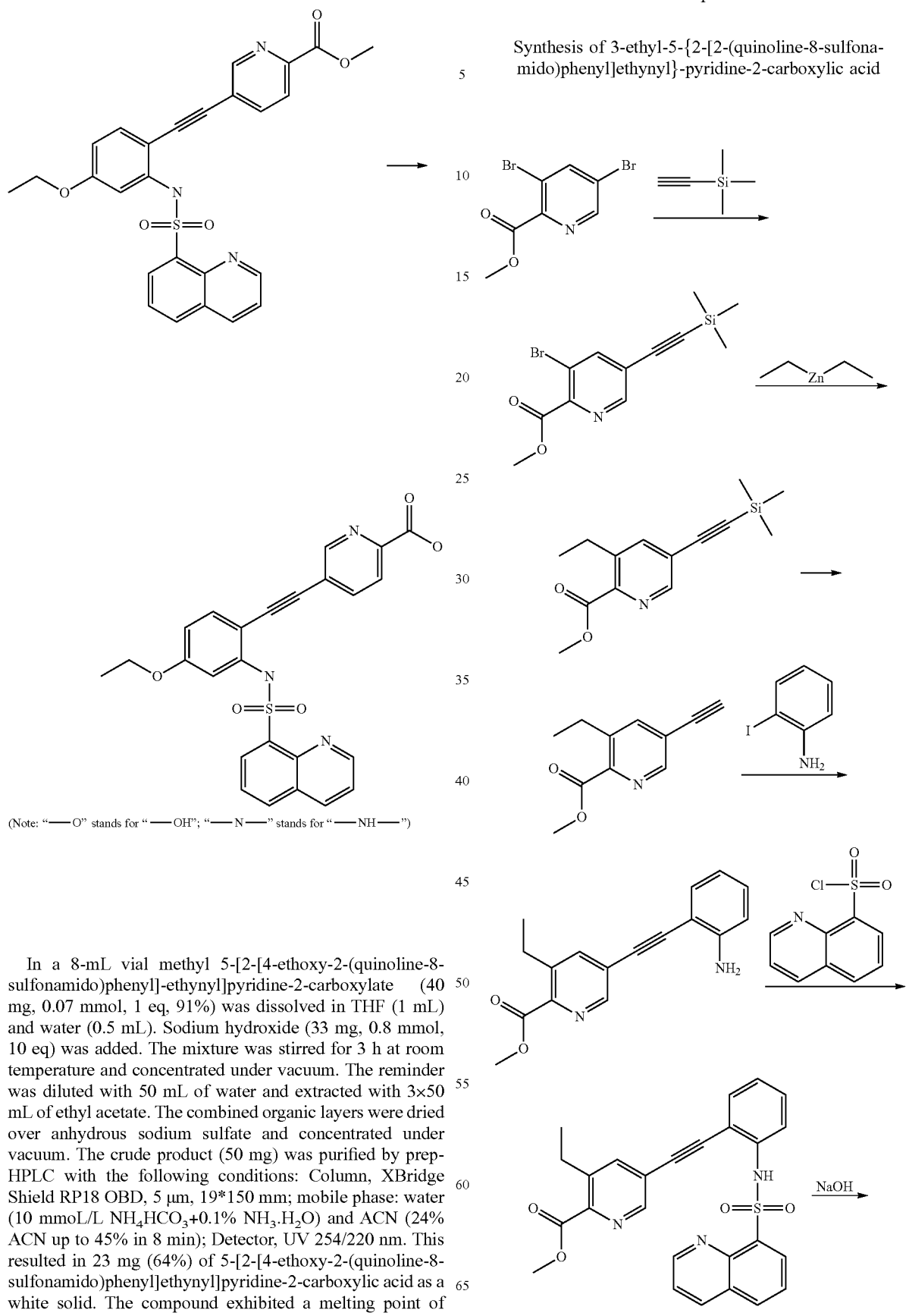

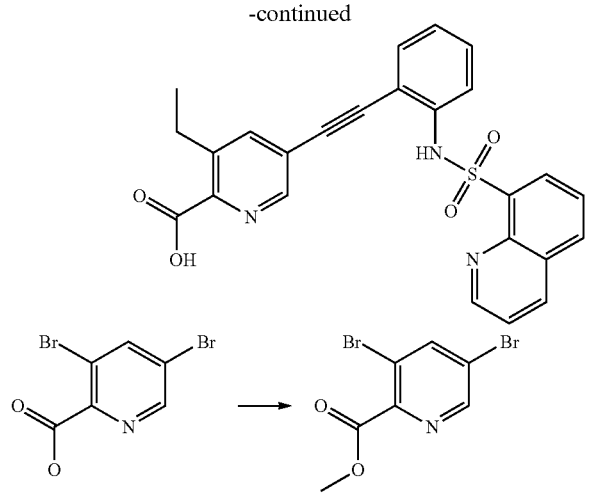

(Note: "–O)" stands for "–OH)"

To a stirred solution of 3,5-dibromopyridine-2-carboxylic acid (5 g, 16.91 mol, 1 eq) in MeOH (20 mL) was added SOCl$_2$ (3.2 g, 25.55 mmol, 1.51 eq) at room temperature. The resulting mixture was stirred overnight at 70° C. under nitrogen atmosphere. The resulting solution was diluted with 50 mL of H2O. The resulting solution was extracted with 3×50 mL of ethyl acetate and the organic layers combined. The mixture was dried over anhydrous sodium sulfate. The remainder after filtration was concentrated under vacuum. This resulted in methyl 3,5-dibromopyridine-2-carboxylate (5 g, 90%) as a white solid.

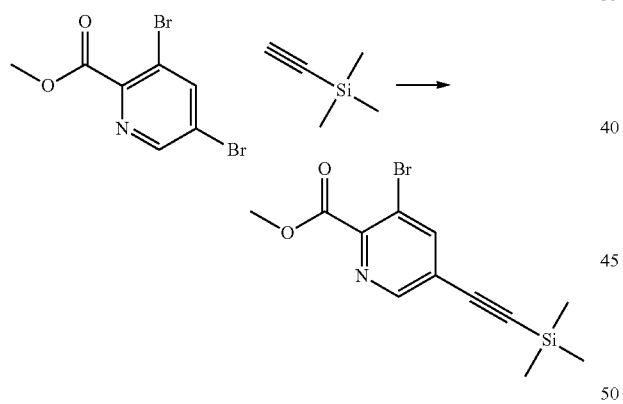

To a stirred solution of methyl 3,5-dibromopyridine-2-carboxylate (1 g, 3.05 mmol, 1 eq, 90%), Pd(PPh$_3$)$_2$Cl$_2$ (140 mg, 0.19 mmol, 0.06 eq, 95%) and CuI (100 mg, 0.50 mmol, 0.2 eq, 95%) in THF (30 mL) were added TEA (800 mg, 7.51 mmol, 2.5 eq, 95%) and ethynyltrimethylsilane (500 mg, 4.84 mol, 1.6 eq, 95%) dropwise at room temperature. The resulting mixture was stirred for 2 h at 50° C. under nitrogen atmosphere. After full conversion the reaction mixture was cooled to room temperature and concentrated under vacuum. The reminder was diluted with 50 mL of H$_2$O and extracted with 4×50 mL of ethyl acetate. The combined organic layers were dried over anhydrous sodium sulfate and concentrated under vacuum after filtration. The residue was purified by reverse flash chromatography with the following conditions: column, C18 silica gel; mobile phase, ACN in water, 10% to 80% gradient in 30 min; detector, UV 254 nm. This resulted in methyl 3-bromo-5-[2-(trimethylsilyl)ethynyl]pyridine-2-carboxylate (640 mg, 60%) as a yellow oil.

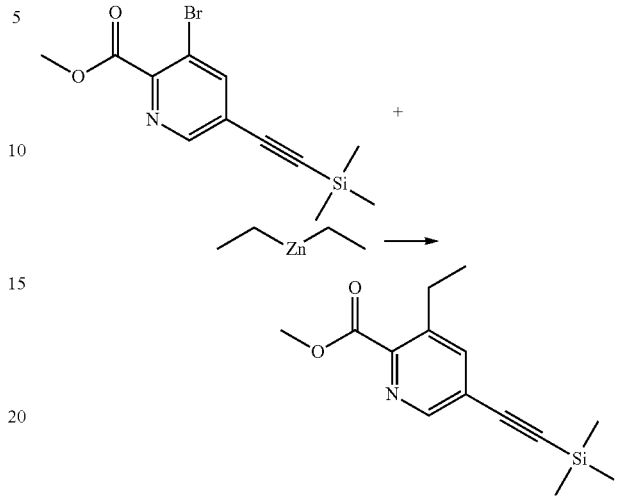

To a stirred solution of methyl 3-bromo-5-[2-(trimethylsilyl)ethynyl]pyridine-2-carboxylate (3.4 g, 9.80 mmol, 1 eq, 90%) and Pd(PPh$_3$)$_4$ (1 g, 0.82 mmol, 0.08 eq, 95%) in dioxane (100 mL) was added diethylzinc (20 mL, 19 mmol, 1.9 eq, 95%) dropwise at room temperature. The resulting mixture was stirred for 1 h at 100° C. under nitrogen atmosphere. The reaction was quenched with sat. NH$_4$Cl (aq.) at room temperature. The aqueous layer was extracted with CH$_2$Cl$_2$ (3×50 mL). The combined organic layers were concentrated under vacuum. The residue was purified by silica gel column chromatography, eluted with PE/EtOAc (10:1) to afford methyl 3-ethyl-5-[2-(trimethylsilyl)ethynyl]pyridine-2-carboxylate (2.1 g, 74%) as a yellow oil.

To a stirred solution of methyl 3-ethyl-5-[2-(trimethylsilyl)ethynyl]pyridine-2-carboxylate (2 g, 6.89 mmol, 1 eq, 90%) in MeOH (50 mL) was added KF (1.5 g, 24.53 mmol, 3.6 eq, 95%) at room temperature. The reaction mixture was stirred for 2 h at room temperature under nitrogen atmosphere. The mixture was concentrated under vacuum and the residue was purified by silica gel column chromatography, eluted with petrol ether/ethylacette (5:1) to afford methyl 3-ethyl-5-ethynylpyridine-2-carboxylate (1.3 g, 90%) as a yellow oil.

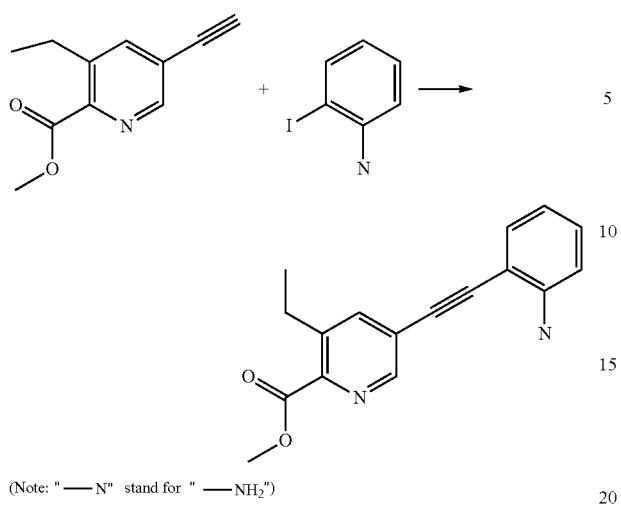

(Note: " —N" stand for " —NH₂")

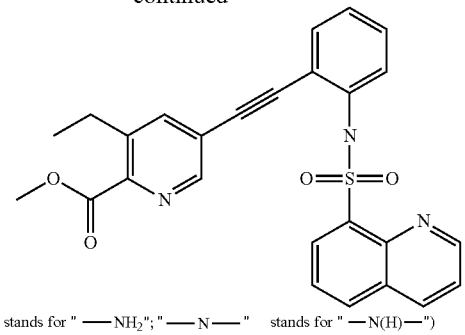

(Note: " —N" stands for " —NH₂"; " —N—" stands for " —N(H)—")

To a stirred solution of methyl 3-ethyl-5-ethynylpyridine-2-carboxylate (1.2 g, 5.71 mmol, 1 eq, 90%), CuI (200 mg, 1.00 mmol, 0.2 eq, 95%) and Pd(PPh₃)₂Cl₂ (300 mg, 0.41 mmol, 0.1 eq, 95%) in TEA (20 mL) was added 2-iodoaniline (2 g, 8.67 mmol, 1.52 eq, 95%) in portions at room temperature. The reaction mixture was stirred for 30 min at 80° C. under nitrogen atmosphere. After completion of the reaction the mixture was cooled to room temperature and concentrated under vacuum. The aqueous layer was extracted with CH₂Cl₂ (3×50 mL). The combined organic layers were concentrated under vacuum. The residue was purified by silica gel column chromatography, eluted with petro ether/ethyl acetate (5:1) to afford methyl 5-[2-(2-aminophenyl)ethynyl]-3-ethylpyridine-2-carboxylate (1.2 g, 68%) as a yellow solid.

To a stirred solution of methyl 5-[2-(2-aminophenyl)ethynyl]-3-ethylpyridine-2-carboxylate (300 mg, 1 mmol, 1 eq, 90%) and DMAP (130 mg, 1 mmol, 1 eq, 95%) in pyridine (10 mL) was added quinoline-8-sulfonyl chloride (450 mg, 1.9 mmol, 1.95 eq, 95%) in portions at room temperature. The reaction mixture was stirred for 3 h at 50° C. under nitrogen atmosphere. After full conversion the mixture was concentrated under vacuum after cooling to room temperature. The residue was purified by silica gel column chromatography, eluted with petro ether/ethyl acetate (1:3) to afford methyl 3-ethyl-5-[2-[2-(quinoline-8-sulfonamido)phenyl]ethynyl]pyridine-2-carboxylate (360 mg, 71%) as a yellow solid.

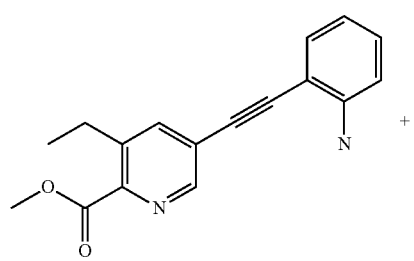

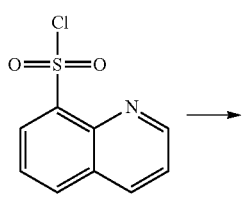

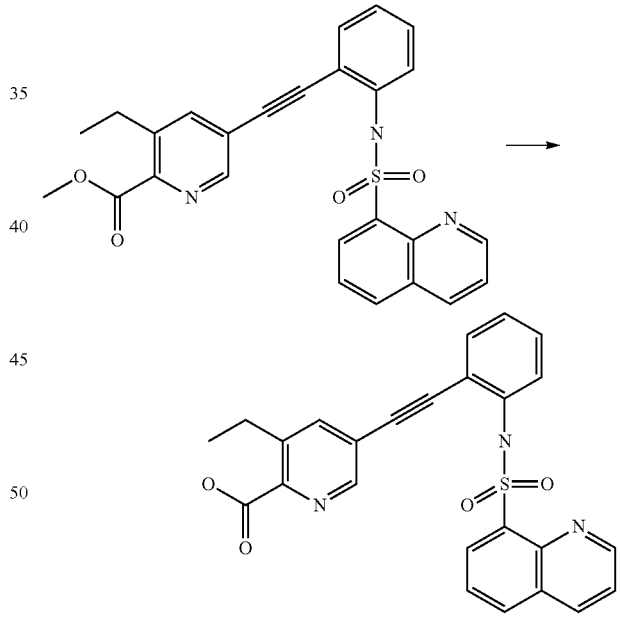

(Note: " —O" stands for " —OH"; " —N—" stands for " —N(H)—")

To a stirred solution of methyl 3-ethyl-5-[2-[2-(quinoline-8-sulfonamido)-phenyl]ethynyl]pyridine-2-carboxylate (200 mg, 380 mmol, 1 eq, 90%) and LiOH·H₂O (80 mg, 1.8 mmol, 4.7 eq, 95%) in THF (8 mL) was added H₂O (4 mL) dropwise at room temperature. The reaction mixture was stirred for 2 h at room temperature under nitrogen atmosphere. After complete saponification the mixture was acidified to pH 6 with HCl (aq.). The aqueous layer was extracted with CH₂Cl₂ (3×30 mL). The combined organic layers were concentrated under vacuum. The crude product (200 mg) was purified by prep-HPLC with the following conditions: Column, XBridge Shield RP18 OBD Column, 30*150 mm, 5 um; mobile phase, Water (10 mmoL/L $NH_4HCO_3$+0.1% $NH_3 \cdot H_2O$) and ACN (20% phase B up to 40% in 8 min). This resulted in 3-ethyl-5-[2-[2-(quinoline-8-sulfonamido) phenyl]ethynyl]-pyridine-2-carboxylic acid (40 mg, 23%) as a white solid. The compound exhibited a melting point of 205-210° C.

Example 7

Synthesis of N-methanesulfonyl-4-[2-[2-(4-methoxynaphthalene-1-sulfonamido)phenyl]ethynyl] benzamide

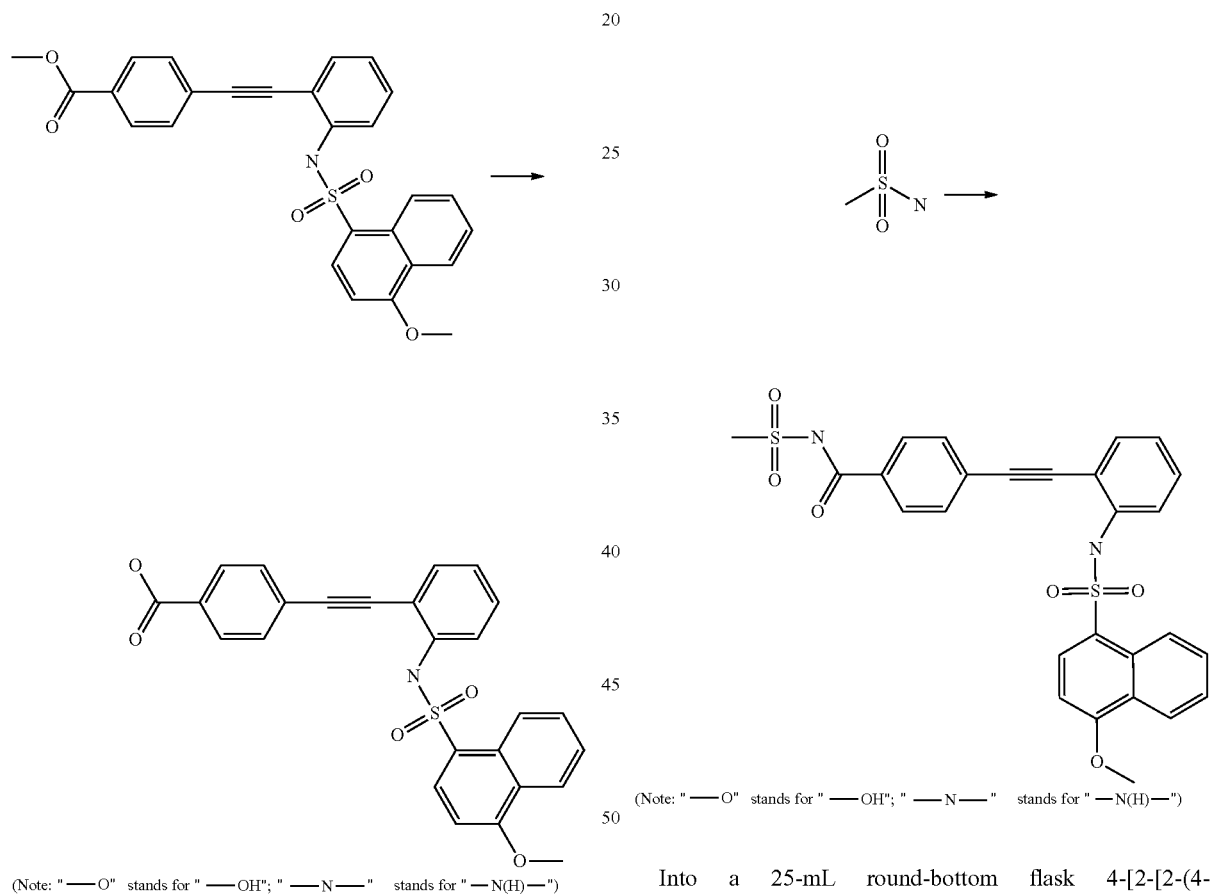

(Note: "—O" stands for "—OH"; "—N—" stands for "—N(H)—")

In a 50-mL round-bottom flask methyl 4-[2-[2-(4-methoxynaphthalene-1-sulfonamido)phenyl]ethynyl]benzoate (320 mg, 0.61 mmol, 1 eq, 90%) was dissolved in THF (10 mL). $LiOH \cdot H_2O$ (142 mg, 3.21 mmol, 5.26 eq, 95%) in water (2 mL) was added. The resulting mixture was stirred for 2 h at 60° C. The pH value of the solution was adjusted to 4 with aq. hydrogen chloride (1 M). The mixture was extracted with 30 mL of ethyl acetate, the combined organic layers were dried over anhydrous sodium sulfate and concentrated under vacuum. This resulted in 300 mg (97%) of 4-[2-[2-(4-methoxy-naphthalene-1-sulfonamido)phenyl] ethynyl]benzoic acid as a yellow solid.

Into a 25-mL round-bottom flask 4-[2-[2-(4-methoxynaphthalene-1-sulfonamido)phenyl]ethynyl]benzoic acid (70 mg, 0.14 mmol, 1 eq, 90%), methanesulfonamide (21.7 mg, 0.22 mmol, 1.6 eq, 95%), EDCI (35 mg, 0.17 mmol, 1.3 eq, 95%) and 4-dimethylaminopyridine (20.6 mg, 0.16 mmol, 1.2 eq, 95%) were dissolved in dichloromethane (3 mL). The resulting solution was stirred overnight at room temperature. The reaction mixture was concentrated under vacuum and the crude product (70 mg) was purified by prep-HPLC with the following conditions: Column, XBridge BEH130 Prep C18 OBD Column, 150 mm 5 um 13 nm; mobile phase, water (0.05% $NH_3H_2O$) and ACN (26% ACN up to 41% in 8 min). This resulted in 40 mg (52%) of N-methanesulfonyl-4-[2-[2-(4-methoxynaphthalene-1-sulfonamido)phenyl]ethynyl]benzamide as a white solid. The compound exhibited a melting point of 135-137° C.

Example 8

Synthesis of of N-cyano-4-[2-[2-(4-methoxynaphthalene-1-sulfonamido)-phenyl]ethynyl]benzamide

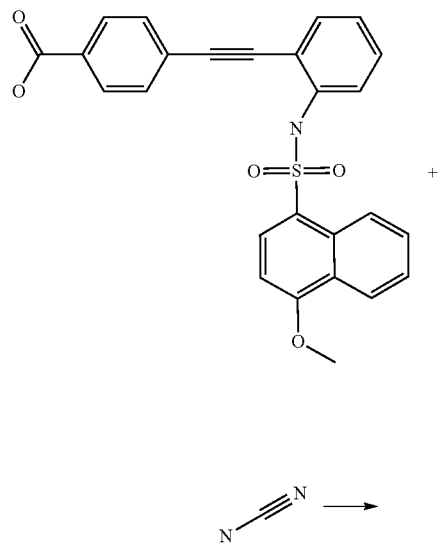

(Note: "—O" stands for "—OH"; "—N—" stands for "—N(H)—")

In a 25-mL round-bottom flask 4-[2-[2-(4-methoxynaphthalene-1-sulfon-amido)phenyl]ethynyl]benzoic acid (90 mg, 0.18 mmol, 1 eq, 90%) was dissolved in N,N-dimethylformamide (2 mL) and DIEA (76 mg, 0.56 mmol, 3.2 eq 95%). This was followed by the addition of HATU (90 mg, 0.22 mmol, 1.3 eq, 95%). The mixture was stirred for 10 min at 25° C. before adding aminoformonitrile (12.3 mg, 0.28 mmol, 1.57 eq, 95%). The reaction mixture was stirred overnight at room temperature and then concentrated under vacuum. The crude product (100 mg) was purified by prep-HPLC with the following conditions: Column, XBridge BEH130 Prep C18 OBD Column, 150 mm 5 um 13 nm; mobile phase: water (0.05% NH$_3$H$_2$O) and ACN (20% ACN up to 50% in 8 min. This resulted in 50 mg (56%) of N-cyano-4-[2-[2-(4-methoxynaphthalene-1-sulfonamido) phenyl]ethynyl]benzamide as a white solid. The compound exhibited a melting point of 150-152° C.

Example 9

Synthesis of 4-[2-[2-(2,3-dihydro-1,4-benzodioxine-5-sulfonamido)-phenyl]ethynyl]benzoic acid

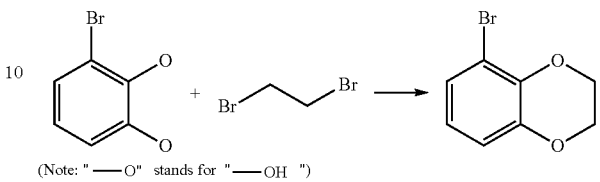

(Note: "—O" stands for "—OH")

In a 100-mL round-bottom flask, purged and maintained with an inert atmosphere of nitrogen, 3-bromobenzene-1,2-diol (3 g, 15.08 mmol, 1 eq, 95%) and 1,2-dibromoethane (4.5 g, 22.76 mmol, 1.5 eq, 95%) were dissolved in N,N-dimethylformamide (60 mL). Potassium carbonate (4.5 g, 30.93 mmol, 2.1 eq, 95%) and KF (462 mg, 7.55 mmol, 0.5 eq, 95%) were added. The resulting mixture was stirred for 2 h at 135° C. After completion of the reaction the mixture was cooled to room temperature and the solids were filtered out. The liquid phase was washed with 4×20 mL of H2O, dried over anhydrous sodium sulfate, filtered and concentrated under vacuum. The residue was applied onto a silica gel column with ethyl acetate/petroleum ether (1:50). This resulted in 1.81 g (47%) of 5-bromo-2,3-dihydro-1,4-benzodioxine as colorless oil.

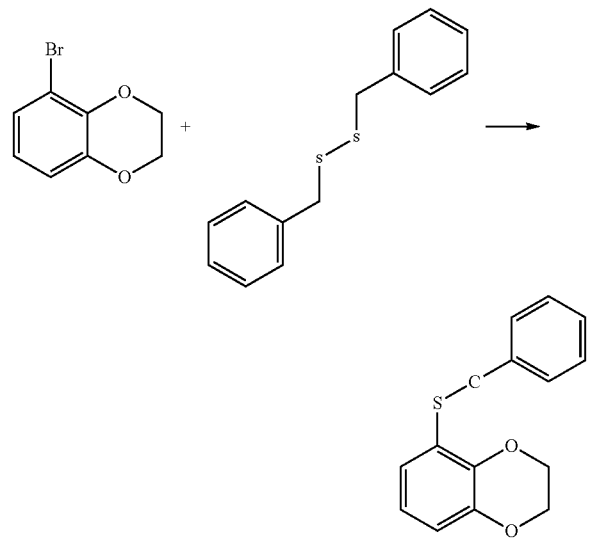

(Note: "—C—" stands for "—CH$_2$—")

In a 100-mL 3-necked round-bottom flask, purged and maintained with an inert atmosphere of nitrogen, 5-bromo-2,3-dihydro-1,4-benzodioxine (1.6 g, 6.70 mmol, 1 eq, 90%) was dissolved in THF (30 mL). This was followed by the addition of s-BuLi (12 mL, 1.87 mmol, 1.3M in THF) dropwise with stirring at −78° C. and stirring was continued for 30 min at the given temperature. Then [(benzyldisulfanyl)methyl]benzene (2.2 g, 8.48 mmol, 1.3 eq, 95%) was added. After complete addition the reaction was stirred for 1 h at room temperature. The reaction was quenched by the addition of water. The resulting solution was extracted with 100 mL of ethyl acetate and the organic layers were combined, dried over anhydrous sodium sulfate and concentrated under vacuum. This resulted in 1.5 g (78%) of 5-(benzylsulfanyl)-2,3-dihydro-1,4-benzodioxine as yellow oil.

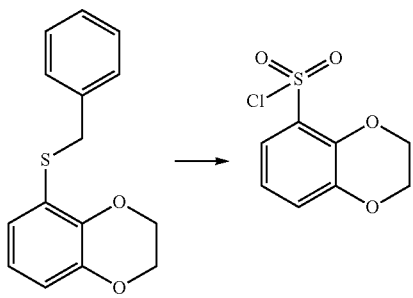 [SMILES: c1ccc(CSc2cccc3c2OCCO3)cc1 ; O=S(=O)(Cl)c1cccc2c1OCCO2]

In a 100-mL round-bottom flask 5-(benzylsulfanyl)-2,3-dihydro-1,4-benzodioxine (612 mg, 2.13 mmol, 1 eq, 90%) was dissolved in CH₃CN (50 mL), water (1.5 mL) and AcOH (1 mL). NCS (1.6 g, 11.38 mmol, 5.3 eq, 95%) was added and the reaction was stirred for 1.5 h at 10° C. in a water/ice bath. The mixture was diluted with 50 mL of ice cold H2O and extracted with 3×50 mL of ethyl acetate. The combined organic layers were dried over anhydrous sodium sulfate and concentrated under vacuum. The residue was applied onto a silica gel column with ethyl acetate/petroleum ether (1:3). This resulted in 443 mg (80%) of 2,3-dihydro-1,4-benzodioxine-5-sulfonyl chloride as yellow oil.

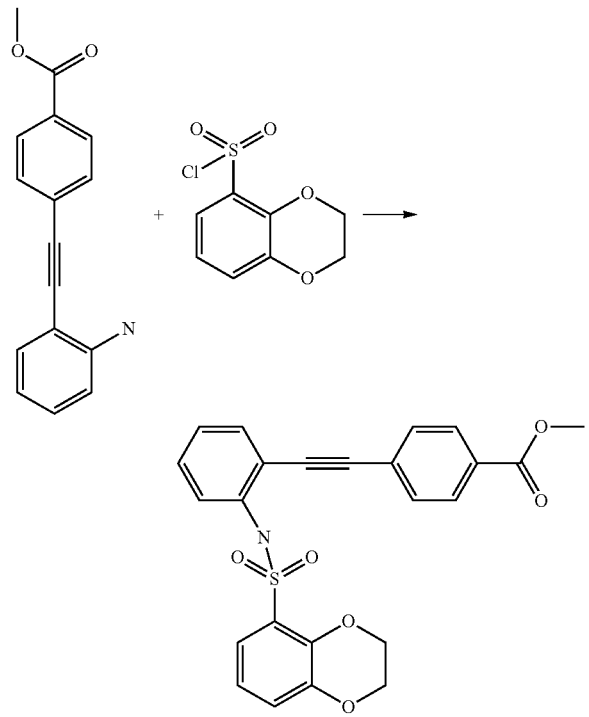

(Note: " —N" stands for " —NH₂"; " —N—" stands for " —N(H)—")

In a 25-mL round-bottom flask, purged and maintained with an inert atmosphere of nitrogen, 2,3-dihydro-1,4-benzodioxine-5-sulfonyl chloride (443 mg, 1.7 mmol, 6 equiv, 90%) was dissolved in pyridine (4 mL). Methyl 4-[2-(2-aminophenyl)ethynyl]benzoate (80 mg, 0.3 mmol, 1 eq, 90%) and 4-dimethylaminopyridine (9 mg, 0.07 mmol, 0.2 eq, 95%) were added. The reaction mixture was stirred for 2 h at 80° C. After cooling to room temperature the mixture was concentrated under vacuum. This resulted in 152 mg (83%) of methyl 4-[2-[2-(2,3-dihydro-1,4-benzodioxine-5-sulfon-amido)phenyl]ethynyl]benzoate as a yellow solid.

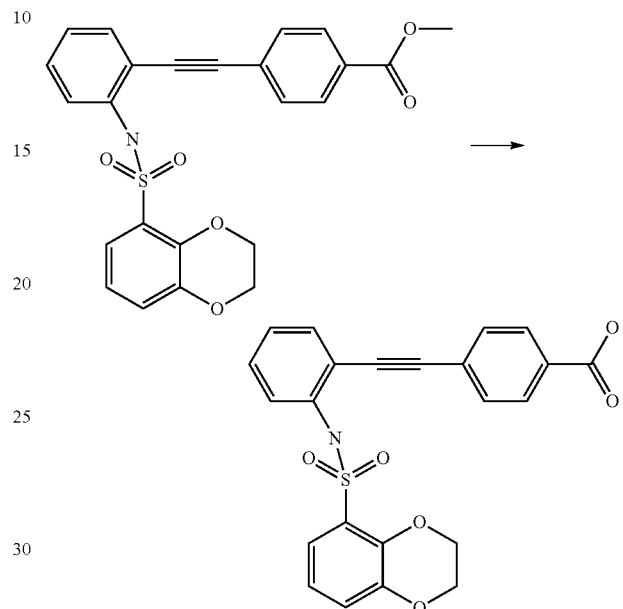

(Note: " —O" stands for " —OH"; " —N—" stands for " —N(H)—")

In a 50-mL round-bottom flask methyl 4-[2-[2-(2,3-dihydro-1,4-benzodioxine-5-sulfonamido)phenyl]ethynyl]benzoate (148 mg, 0.23 mmol, 1 eq, 70%) was dissolved in THF (3 mL) and water (2 mL). Sodium hydroxide (50 mg, 1.19 mmol, 5.2 eq, 95%) was added. The resulting solution was stirred for 2 h at room temperature. The pH value of the solution was adjusted to 6 with aq. hydrogen chloride (1 mol/L). The mixture was extracted with 2×15 mL of ethyl acetate and the combined organic layers were dried over sodium sulfate and concentrated under vacuum. The crude product (93 mg) was purified by prep-HPLC with the following conditions: Column, XBridge BEH130 Prep C18 OBD Column, 150 mm 5 um 13 nm; mobile phase: water (0.05% TFA) and ACN (46% ACN up to 57% in 9 min). This resulted in 35 mg (34%) of 4-[2-[2-(2,3-dihydro-1,4-benzodioxine-5-sulfonamido)phenyl]ethynyl]benzoic acid as a light yellow solid. The compound exhibited a melting point of 238-240° C.

Example 10

Synthesis of 3-ethyl-5-[2-[2-(7-ethylquinoline-8-sulfonamido)phenyl]-ethynyl]pyridine-2-carboxylic acid

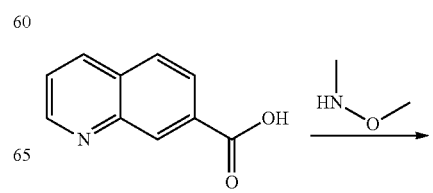

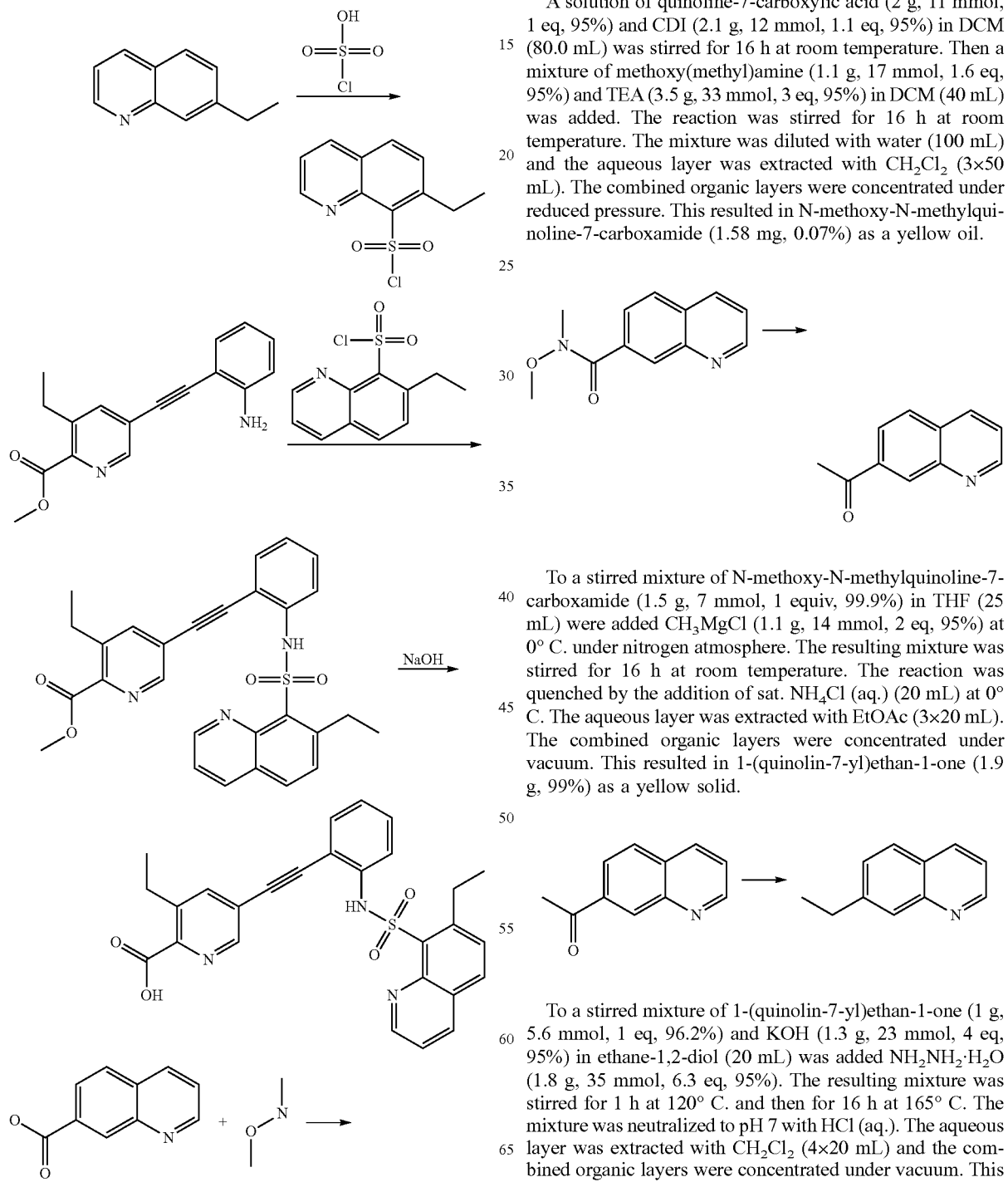

(Note: "—O" stands for "—OH"; "—N—" stands for "—N(H)—")

A solution of quinoline-7-carboxylic acid (2 g, 11 mmol, 1 eq, 95%) and CDI (2.1 g, 12 mmol, 1.1 eq, 95%) in DCM (80.0 mL) was stirred for 16 h at room temperature. Then a mixture of methoxy(methyl)amine (1.1 g, 17 mmol, 1.6 eq, 95%) and TEA (3.5 g, 33 mmol, 3 eq, 95%) in DCM (40 mL) was added. The reaction was stirred for 16 h at room temperature. The mixture was diluted with water (100 mL) and the aqueous layer was extracted with $CH_2Cl_2$ (3×50 mL). The combined organic layers were concentrated under reduced pressure. This resulted in N-methoxy-N-methylquinoline-7-carboxamide (1.58 mg, 0.07%) as a yellow oil.

To a stirred mixture of N-methoxy-N-methylquinoline-7-carboxamide (1.5 g, 7 mmol, 1 equiv, 99.9%) in THF (25 mL) were added $CH_3MgCl$ (1.1 g, 14 mmol, 2 eq, 95%) at 0° C. under nitrogen atmosphere. The resulting mixture was stirred for 16 h at room temperature. The reaction was quenched by the addition of sat. $NH_4Cl$ (aq.) (20 mL) at 0° C. The aqueous layer was extracted with EtOAc (3×20 mL). The combined organic layers were concentrated under vacuum. This resulted in 1-(quinolin-7-yl)ethan-1-one (1.9 g, 99%) as a yellow solid.

To a stirred mixture of 1-(quinolin-7-yl)ethan-1-one (1 g, 5.6 mmol, 1 eq, 96.2%) and KOH (1.3 g, 23 mmol, 4 eq, 95%) in ethane-1,2-diol (20 mL) was added $NH_2NH_2·H_2O$ (1.8 g, 35 mmol, 6.3 eq, 95%). The resulting mixture was stirred for 1 h at 120° C. and then for 16 h at 165° C. The mixture was neutralized to pH 7 with HCl (aq.). The aqueous layer was extracted with $CH_2Cl_2$ (4×20 mL) and the combined organic layers were concentrated under vacuum. This resulted in 7-ethylquinoline (900 mg, 97%) as a red oil.

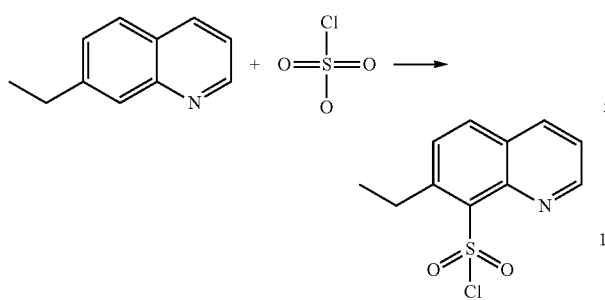

To a stirred mixture of sulfurochloridic acid (10 mL, 82 mmol, 20 eq, 95%) was added 7-ethylquinoline (600 mg, 3.5 mmol, 1 eq, 92.3%) dropwise at 0° C. The resulting mixture was stirred for 16 h at 120° C. The reaction was quenched by the addition of water/ice (200 mL) at 0° C. The aqueous layer was extracted with CH$_2$Cl$_2$ (5×20 mL). The combined organic layers were concentrated under reduced pressure and the resulting solid was dried under vacuum to afford 7-ethylquinoline-8-sulfonyl chloride (750 mg, 70%) as a brown solid.

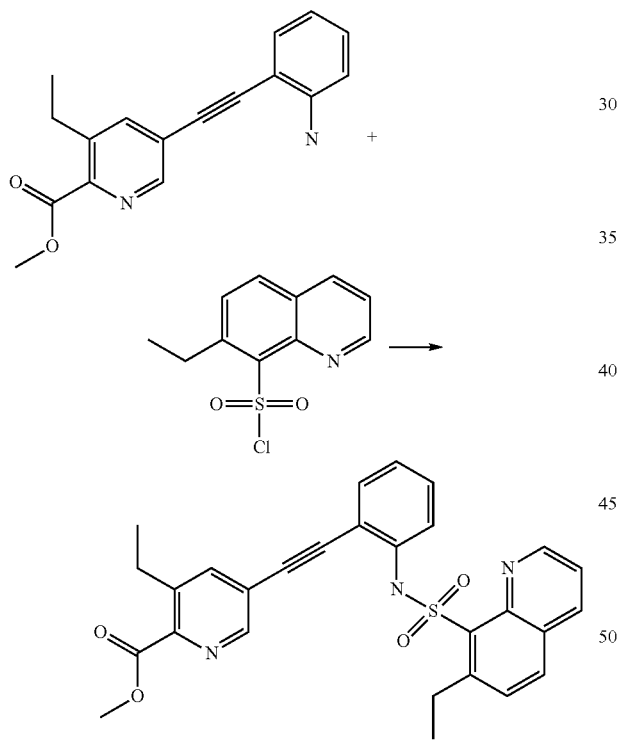

(Note: " —N" stands for " —NH$_2$ "; " —N— " stands for "—N(H)—")

To a stirred mixture of methyl 5-[2-(2-aminophenyl) ethynyl]-3-ethylpyridine-2-carboxylate (100 mg, 0.34 mmol, 1 eq, 95%) and 7-ethylquinoline-8-sulfonyl chloride (206 mg, 0.7 mmol, 2 eq, 84%) in pyridine (4.0 mL) was added DMAP (44 mg, 0.34 mmol, 1 eq, 95%). The resulting mixture was stirred for 16 h at 50° C. After cooling to room temperature the reaction mixture was concentrated under reduced pressure. The residue was purified by silica gel column chromatography, eluted with CH$_2$Cl$_2$/MeOH (10:1). The combined fractions were concentrated under reduced pressure to afford methyl 3-ethyl-5-[2-[2-(7-ethylquinoline-8-sulfonamido)phenyl]ethynyl]pyridine-2-carboxylate (150 mg, 46%) as a red oil.

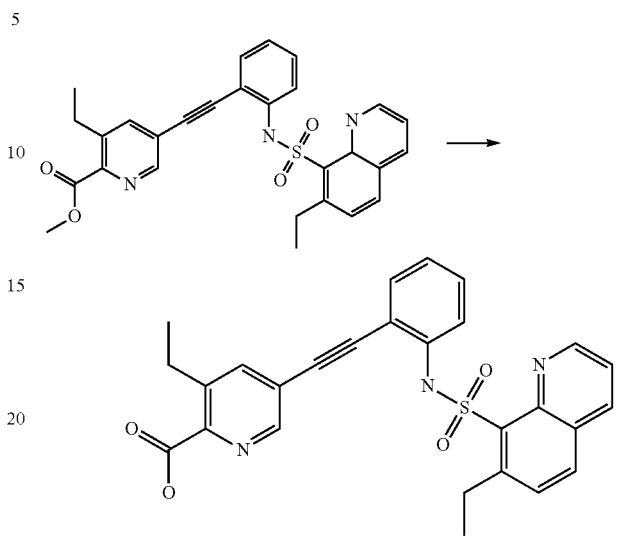

(Note: " —O" stands for " —OH"; " —N— " stands for "—N(H)— ")

Methyl 3-ethyl-5-[2-[2-(7-ethylquinoline-8-sulfonamido) phenyl]ethynyl]-pyridine-2-carboxylate (130 mg, 0.19 mmol, 1 eq, 75%) and LiOH (14.7 mg, 0.58 mmol, 3 eq, 95%) were dissolved in THF (4 mL) and H$_2$O (2.0 mL). The resulting mixture was stirred for 4 h at room temperature and then concentrated under reduced pressure. The crude product (120 mg) was purified by prep-HPLC with the following conditions: Column, XBridge Shield RP18 OBD Column, 30*150 mm, 5 um; mobile phase: water (10 mmoL/L NH$_4$HCO$_3$+0.1% NH$_3$.H$_2$O) and ACN (28% up to 40% in 8 min). The product fractions were combined and concentrated under reduced pressure to afford 3-ethyl-5-[2-[2-(7-ethylquinoline-8-sulfonamido)phenyl]ethynyl]pyridine-2-carboxylic acid (12 mg, 12%) as a white solid.

Example 11

Synthesis of 5-[2-(2-{4-[2-(2-methoxyethoxy) ethoxy]quinoline-8-sulfon-amido}phenyl)ethynyl] pyridine-2-carboxylic acid

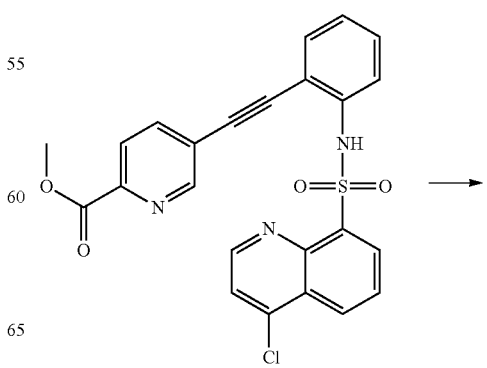

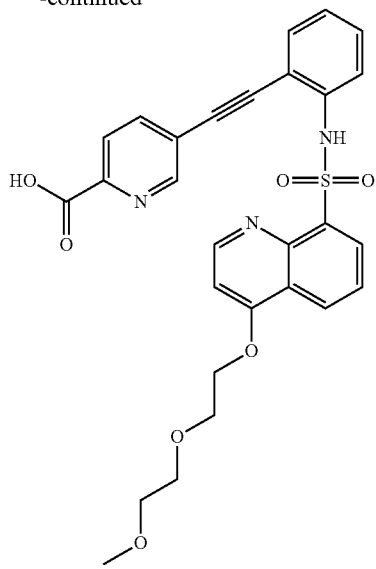

To a solution of 5-[2-(4-Chloro-quinoline-8-sulfonylamino)-phenylethynyl]-pyridine-2-carboxylic acid methyl ester (57 mg; 0.1 mmol; 1.0 eq.) in N,N-Dimethylformamide (3 ml) was added diethylene glycol monomethyl ether (0.1 ml; 1 mmol; 10 eq.) and potassium tert-butylate (69 mg; 0.6 mmol; 6 eq.). The reaction was stirred for 16 hrs at RT. The reaction was evaporated to dryness and purified by prep. HPLC giving 19 mg (32%) of the product.

Example 12

Synthesis of intermediate
2-(2-Ethynyl-4-fluoro-phenylamine

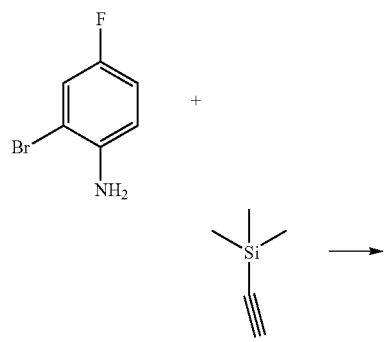

To 2-Bromo-4-fluoroaniline (8.79 mmol; 1.00 ml) in Acetonitrile dried (max. 0.005% H$_2$O) SeccoSolv® (15.00 ml) was added under nitrogen in a microwave vial Ethynyltrimethylsilane (14.06 mmol; 1.98 ml), N-Ethyl-diisopropylamine (9.67 mmol; 1.64 ml), copper (1) iodide (0.44 mmol; 83.69 mg) and tetrakis(triphenylphosphin)-palldium (0) (0.44 mmol; 507.80 mg). The reaction was stirred for 16 hrs at 100° C. HPLC-MS showed complete formation of the required product. The reactions were diluted with ethylacetate and extracted 3× with water, dried over Na2SO4 and evaporated to dryness. The residue was purified by flashchromatography yielding 950 mg of the product as brown oil.

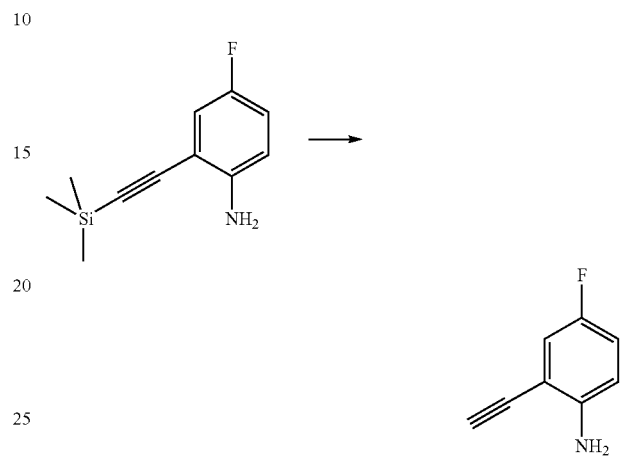

To a solution of 4-Fluoro-2-trimethylsilanylethynyl-phenylamine (3.62 mmol; 950.20 mg) in Methanol (3.00 ml) was added Potassium carbonate (0.36 mmol; 50 mg) and stirred for 2 days at RT. HPLC-MS showed the complete formation of the required product. The reactions were diluted with EA and extracted 3× with water, dried over Na$_2$SO$_4$ and evaporated to dryness. The reaction mixture was dissolved in EA and water. The layers were separated and the water layer was extracted with EA, the organic layer was washed with water and brine, dried over sodiumsulphate, filtered and evaporated to dryness giving 378 mg of the product as a brown oil.

Example 13

Synthesis of 5-(2-{2-[4-(prop-2-yn-1-yloxy)quinoline-8-sulfonamido]phenyl}ethynyl)pyridine-2-carboxylic acid

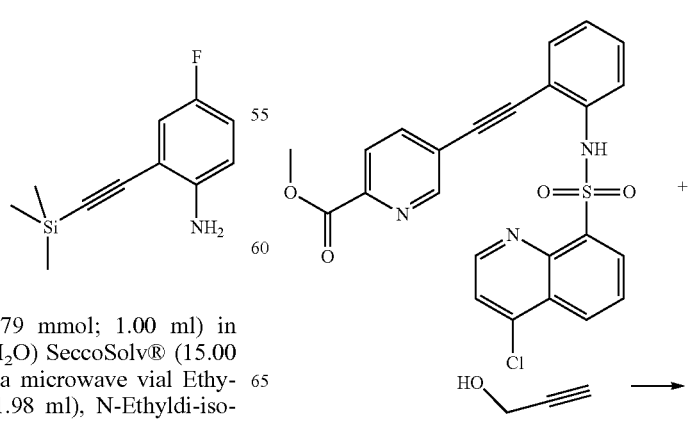

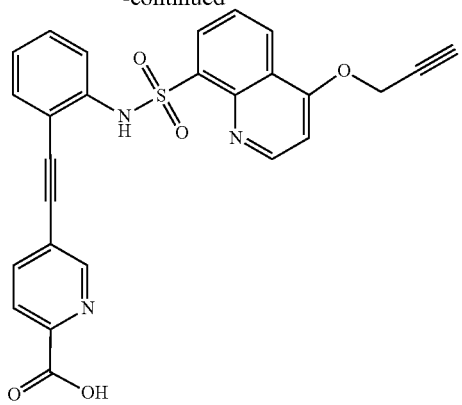

To a solution of 5-[2-(4-chloro-quinoline-8-sulfonylamino)-phenylethynyl]-pyridine-2-carboxylic acid methyl ester (200.0 mg; 0.35 mmol) in N,N-dimethylformamide (5.0 ml) was added 2-propyn-1-ol for synthesis (0.2 ml; 3.45 mmol) and potassium tert-butylate for synthesis (232.4 mg; 2.07 mmol) in a microwave vial. The reaction was stirred for 16 hrs at rt. HPLC-MS showed the formation of the required product. The reaction was evaporated to dryness and the residue was purified by HPLC giving 7 mg of the product as light yellow solid.

Example 13a

Synthesis of 5-[5-Ethoxy-2-(quinoline-8-sulfonylamino)-phenylethynyl]-pyridine-2-carboxylic acid

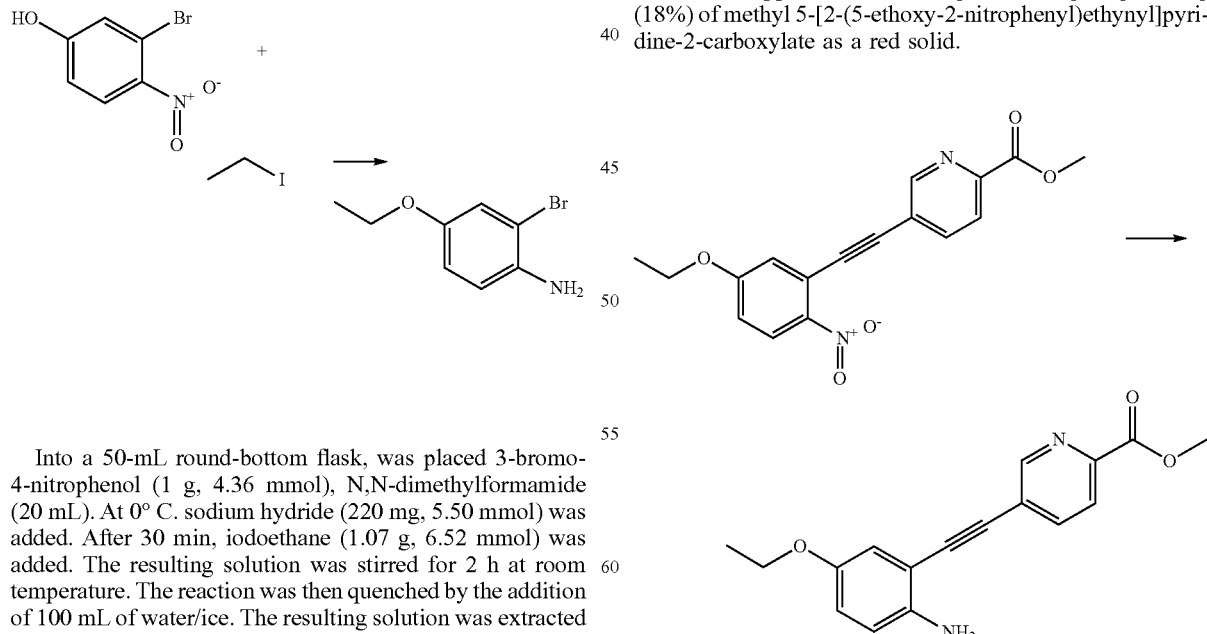

Into a 50-mL round-bottom flask, was placed 3-bromo-4-nitrophenol (1 g, 4.36 mmol), N,N-dimethylformamide (20 mL). At 0° C. sodium hydride (220 mg, 5.50 mmol) was added. After 30 min, iodoethane (1.07 g, 6.52 mmol) was added. The resulting solution was stirred for 2 h at room temperature. The reaction was then quenched by the addition of 100 mL of water/ice. The resulting solution was extracted with 3×50 mL of ethyl acetate and the organic layers were combined. The organic phase was dried over anhydrous sodium sulfate and concentrated under vacuum. The residue was applied onto a silica gel column giving 917 mg (95%) of 2-bromo-4-ethoxyaniline as a yellow solid.

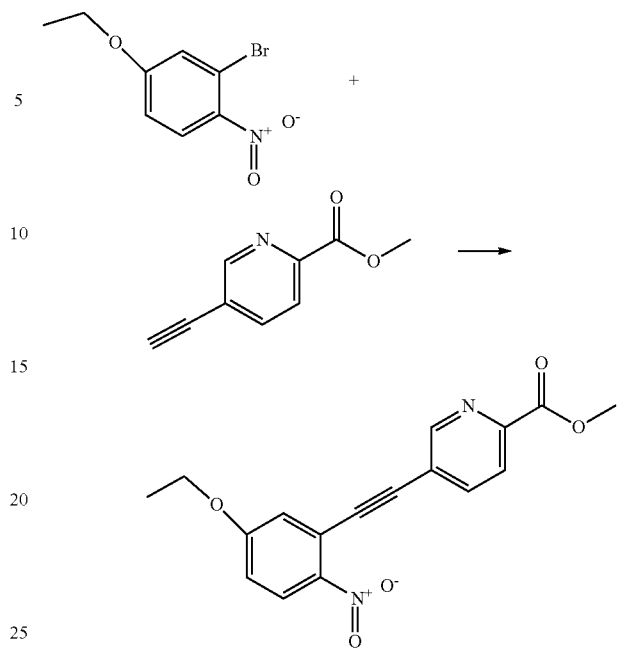

Into a 25-mL round-bottom flask, was placed 2-bromo-4-ethoxy-1-nitrobenzene (566.6 mg, 2.24 mmol), methyl 5-ethynylpyridine-2-carboxylate (445 mg, 2.71 mmol), Pd(PPh$_3$)$_2$Cl$_2$ (161.5 mg, 0.22 mmol), CuI (43.8 mg, 0.22 mmol), TEA (6.55 mmol) and tetrahydrofuran (10 mL). The resulting solution was stirred overnight at room temperature. The reaction mixture was diluted with 50 mL of H$_2$O, extracted with 3×50 mL of ethyl acetate and the organic layers were combined. The mixture was dried over anhydrous sodium sulfate and concentrated under vacuum. The residue was applied onto a silica gel column giving 140 mg (18%) of methyl 5-[2-(5-ethoxy-2-nitrophenyl)ethynyl]pyridine-2-carboxylate as a red solid.

Into a 8-mL vial, was placed methyl 5-[2-(5-ethoxy-2-nitrophenyl)ethynyl]-pyridine-2-carboxylate (140 mg, 0.41 mmol), Fe (119.9 mg, 2.04 mmol), NH4Cl (92.5 mg, 1.64 mmol), methanol (2 mL) and water (1 mL). The resulting solution was stirred for 5 h at 70° C. The solids were filtered out. The resulting solution was diluted with 10 mL of H2O. The pH value of the solution was adjusted to 7-8 with sodium bicarbonate (sat. aqueous solution). The resulting solution was extracted with 3×10 mL of ethyl acetate and the organic layers were combined. The mixture was dried over anhydrous sodium sulfate. This resulted in 80 mg (62%) of methyl 5-[2-(2-amino-5-ethoxyphenyl)ethynyl]pyridine-2-carboxylate as a yellow solid.

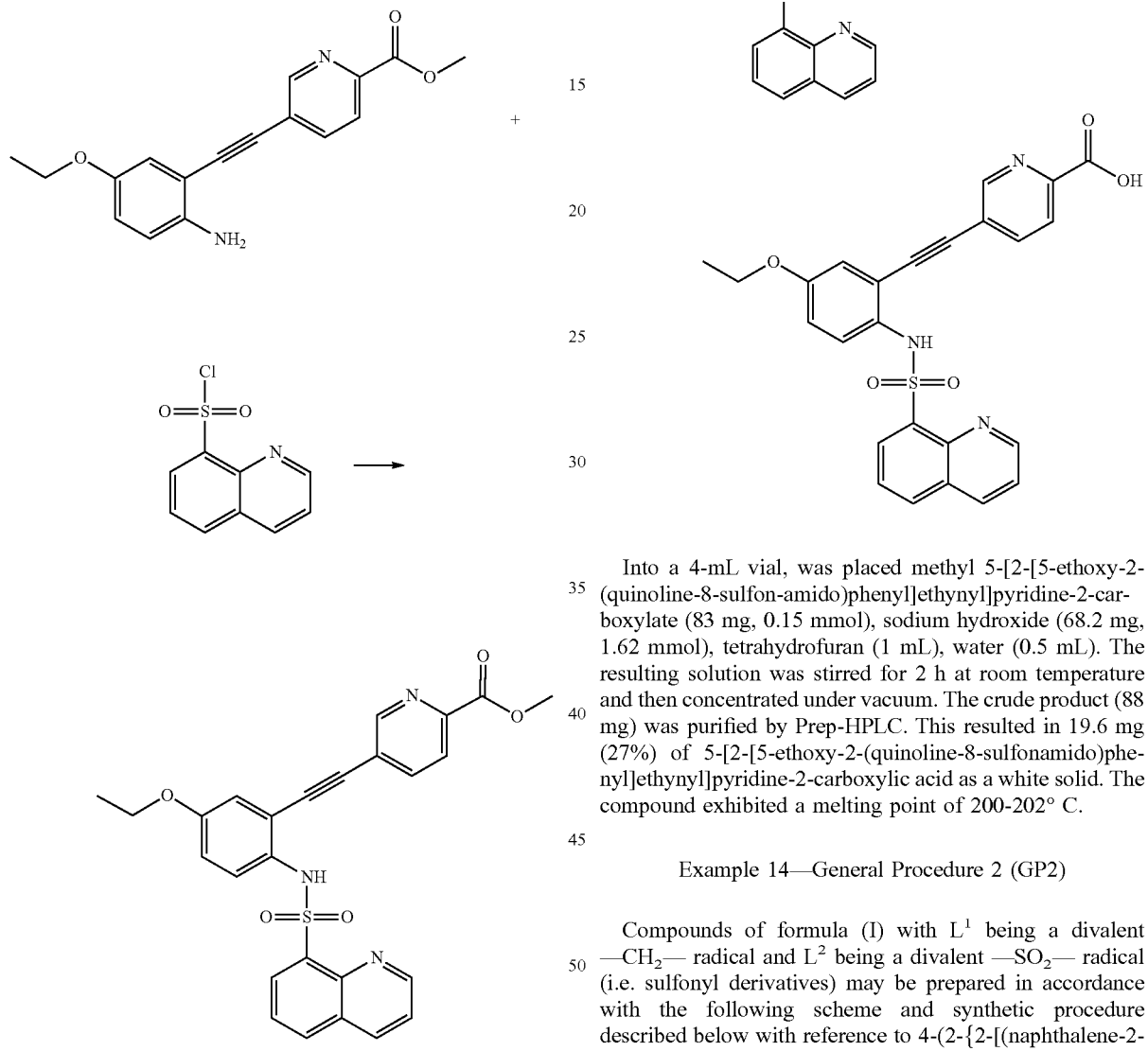

Into a 8-mL vial, was placed methyl 5-[2-(2-amino-5-ethoxyphenyl)-ethynyl]pyridine-2-carboxylate (62.5 mg, 0.20 mmol), quinoline-8-sulfonyl chloride (95.9 mg, 0.40 mmol), 4-dimethylaminopyridine (0.7 mg, 0.01 mmol), pyridine (2 mL). The resulting solution was stirred overnight at room temperature. The reaction mixture was diluted with 20 mL of H₂O, extracted with 3×20 mL of ethyl acetate and the organic layers were combined. The organic phase was dried over anhydrous sodium sulfate and concentrated under vacuum. The residue was applied onto a silica gel column. This resulted in 88.2 mg (82%) of methyl 5-[2-[5-ethoxy-2-(quinoline-8-sulfonamido)phenyl]ethynyl]pyridine-2-carboxylate as a yellow solid.

Into a 4-mL vial, was placed methyl 5-[2-[5-ethoxy-2-(quinoline-8-sulfon-amido)phenyl]ethynyl]pyridine-2-carboxylate (83 mg, 0.15 mmol), sodium hydroxide (68.2 mg, 1.62 mmol), tetrahydrofuran (1 mL), water (0.5 mL). The resulting solution was stirred for 2 h at room temperature and then concentrated under vacuum. The crude product (88 mg) was purified by Prep-HPLC. This resulted in 19.6 mg (27%) of 5-[2-[5-ethoxy-2-(quinoline-8-sulfonamido)phenyl]ethynyl]pyridine-2-carboxylic acid as a white solid. The compound exhibited a melting point of 200-202° C.

Example 14—General Procedure 2 (GP2)

Compounds of formula (I) with $L^1$ being a divalent —CH₂— radical and $L^2$ being a divalent —SO₂— radical (i.e. sulfonyl derivatives) may be prepared in accordance with the following scheme and synthetic procedure described below with reference to 4-(2-{2-[(naphthalene-2-sulfonyl)methyl]phenyl}-ethynyl)benzoic acid utilizing suitable starting material:

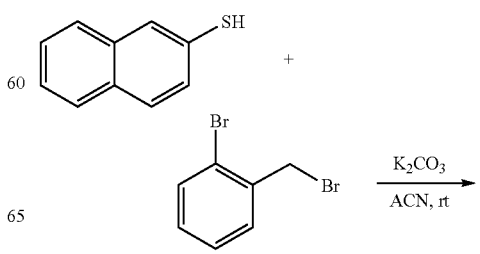

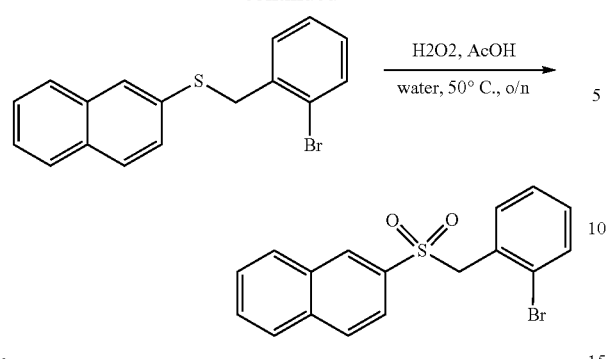

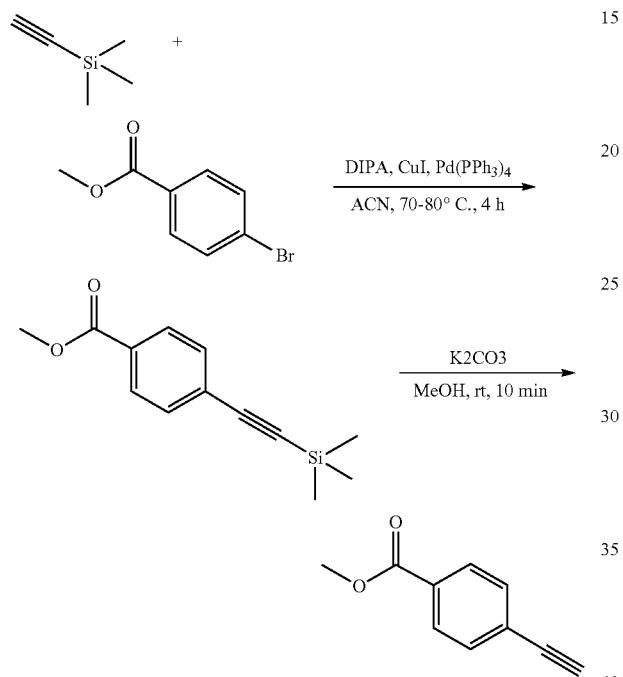

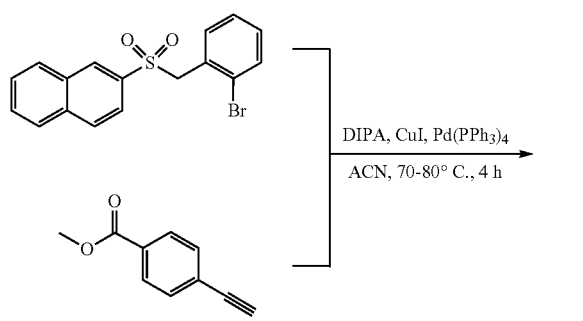

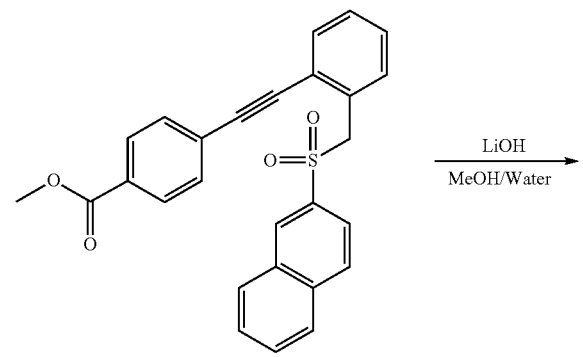

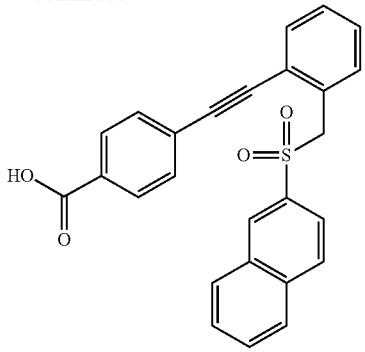

2-(2-Bromobenzylsulfanyl)naphthalene

Naphthalene-2-thiol (200 mg; 1.25 mmol; 1 eq.) and potassium carbonate (86 mg; 0.62 mmol; 0.5 eq.) were placed in a reaction vessel. Then a solution of 2-bromobenzylbromide (350 mg; 1.4 mmol; 1.12 eq.) in anhydrous acetonitrile (5 ml) was added and sealed. Resulting mixture was stirred at RT for 48 h. After that time RM was poured into the water. Resulted slurry was basified with 1 M NaOH and extracted with AcOEt. The organic layer was washed with aq. solution of NaOH, water and brine. Then it was dried over anhydrous sodium sulfate and filtered. The filtrate was evaporated under reduced pressure to give 2-(2-bromobenzylsulfanyl)naphthalene (382 mg; 1.1 mmol; yield 85% as a bright beige waxy solid. 2-(2-Bromophenylmethanesulfonyl)naphthalene A mixture of 2-(2-Bromobenzylsulfanyl)naphthalene (380 mg; 1.1 mmol; 1 eq.) and acetic acid (6 ml) was placed in 25 mL round bottom flask immersed in an ice bath. Then 30% hydrogen peroxide (1 ml; 10 mmol; 9.5 eq.) and water (0.5 ml) were added dropwise and the resulting mixture was stirred overnight at 50° C. The reaction mixture was poured onto ice-water followed by ethyl acetate addition. The organic layer was taken up and washed with water, diluted aq. solution of NaOH, water, brine and dried over anhydrous sodium sulfate. The solvent was evaporated in vacuo to give 2-(2-bromo-phenylmethanesulfonyl) naphthalene (307 mg; 0.8 mmol; yield 75%) as a beige solid which was used without further purification.

Methyl 3-(2-trimethylsillylethynyl)benzoate

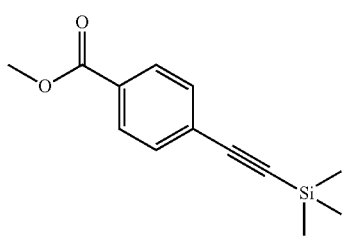

Methyl 3-(2-trimethylsillylethynyl)benzoate was obtained as follows: methyl 4-bromobenzoate (2.5 g; 11.6 mmol; 1 eq.), ethynyltrimethylsilane (1.8 ml; 12.8 mmol; 1.1 eq.), copper (1) iodide (40 mg; 0.23 mmol; 0.02 eq.), diisopropyl-amine (1.85 ml; 12.8 mmol; 1.1 eq.) in acetonitrile (15 ml) were placed in a screw capped glass reacting tube. The resulted mixture was purged with argon for 10 min, then tetrakis(triphenylphosphine)palladium(0) (0.05 eq.) was added under Ar and the reacting tube was screwed. The RM was heated to 60-65° C. and stirred overnight. After cooling to RT the RM was diluted with diethyl ether and filtered by celite. Evaporation of the filtrate yielded methyl 3-(2-trimethylsilylethynyl)benzoate (1.33 g; 5.5 mmol, yield 47%) as a brown oil.

Methyl 3-ethynylbenzoate

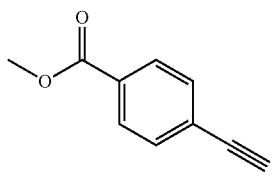

Methyl-3-ethynylbenzoate was obtained as follows: methyl 3-(2-trimethylsilyl-ethynyl)benzoate (4.1 g; 12.3 mmol; 1 eq.) was dissolved in methanol (61 mL) and potassium carbonate (2.6 g; 18.4 mmol; 1.5 eq.) was added. RM was stirred for 20 min, then diluted with diethyl ether and subsequently washed with water and brine. The organic layer was dried over $Na_2SO_4$ and evaporated. The resulted oily crude product was purified by FCC (silica gel, hexane/EtOAc, gradient) yielding methyl 3-ethynylbenzoate (2.24 g; 10.9 mmol; yield 89%) as a yellow powder.

Methyl 4-(2-{2-[(naphthalene-2-sulfonyl)methyl]phenyl}ethynyl)benzoate

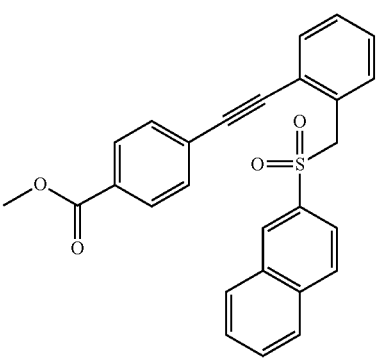 [SMILES: COC(=O)c1ccc(C#Cc2ccccc2CS(=O)(=O)c2ccc3ccccc3c2)cc1]

Sonogashira coupling was conducted as follows: 2-(2-bromophenylmethane-sulfonyl)naphthalene (67 mg; 0.18 mmol; 1 eq.), 4-methyl ethynylbenzoate (45.4 mg; 0.22 mmol; 1.2 eq.), copper (1) iodide (3 mg; 0.02 mmol; 0.1 eq.) were placed in a sealed tube. The air from the tube was evacuated in vacuo and and the tube backfilled with argon (cycle was repeated 3 times), then diisopropylamine (0.028 ml; 0.2 mmol; 1.1 eq.) and anhydrous acetonitrile (2 ml) was added dropwise by syringe. The RM was stirred and heated to 65-70° C. for 18 h, cooled to RT and diluted with EtOAc and filtered by celite. The filtrate was evaporated, the resulting residue purified by FCC (silica, hexane/EtOAc, gradient) yielding methyl 4-(2-{2-[(naphthalene-2-sulfonyl)-methyl]phenyl}ethynyl)benzoate (20 mg; 0.04 mmol; 21%) as colorless solid.

4-(2-{2-[(naphthalene-2-sulfonyl)methyl]phenyl}ethynyl)benzoic acid

Ester saponification step was conducted as follows: Methyl 4-(2-{2-[(naphthalene-2-sulfonyl)methyl]phenyl}ethynyl)benzoate (20 mg; 0.04 mmol) was dissolved in a mixture of 4 mL of methanol and 2 mL water, then lithium hydroxide (110 mg; 2.62 mmol, 14 eq.) was added. The resulting RM was stirred at RT for 3 h, diluted with water and acidified to pH 3 with 2M HCl. The resulting solution was taken up by extraction with EtOAc. The organic layer was washed with water and brine, dried over $Na_2SO_4$ and evaporated. The crude product was purified by prep. HPLC yielding 4-(2-{2-[(naphthalene-2-sulfonyl)methyl]phenyl}ethynyl)benzoic acid (14.7 mg; 0.03 mmol; 19%) as a white solid.

Example 15—General Procedure 3 (GP3)

Compounds of formula (I) with L¹ being a divalent —N(C(=O)—Rᵃ radical and L² being a divalent —CH₂— radical may be prepared in accordance with the following scheme and synthetic procedure described below with reference to 5-[2-(2-{N-[(naphthalen-2-yl)methyl]acetamido}phenyl)ethynyl]pyridine-2-carboxylic acid utilizing suitable starting material:

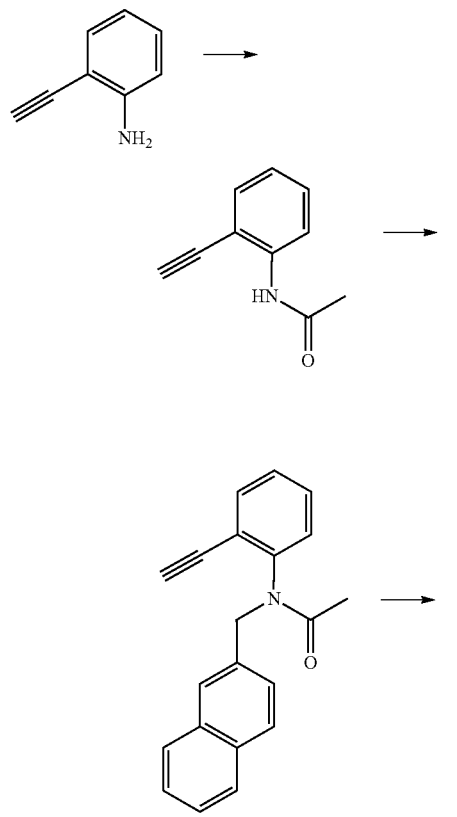

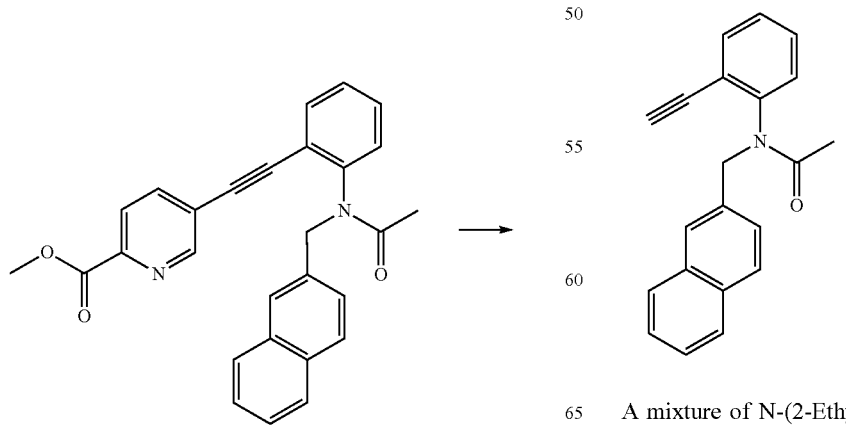

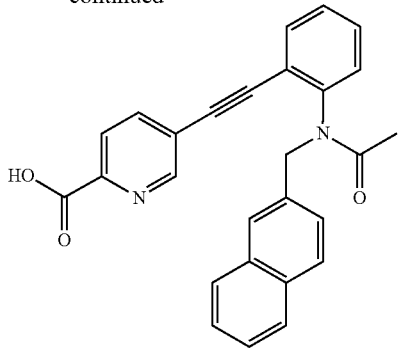

N-(2-ethynylphenyl)-acetamide

To a mixture of 2-Ethynylphenylamine (0.1 ml; 0.9 mmol; 1 eq.), triethylamine (0.14 ml; 1 mmol; 1.13 eq.) and anhydrous THF (1 ml) placed in 5 mL round bottom flask, cooled in an water-ice bath, the acetyl chloride (0.07 ml; 0.98 mmol; 1.12 eq.) was added, and the resulting mixture was allowed to warm up to RT. RM was stirred overnight and then partitioned between water and ethyl acetate. The organic layer was subsequently washed with water, brine and dried over anhydrous sodium sulfate. Solvent was removed under reduced pressure and the residue was purified by FCC (silica, hexane, hexane/ethyl acetate 20%, gradient) to give N-(2-Ethynylphenyl)acetamide (171 mg; 0.85 mmol; yield 96%) as a beige solid.

N-(2-ethynylphenyl)-N-(naphthalen-2-ylmethyl)-acetamide

A mixture of N-(2-Ethynyl-phenyl)-acetamide (120 mg; 0.6 mmol; 1 eq.), sodium hydride (60% in mineral oil, 26 mg; 0.65 mmol; 1.1 eq.) and anhydrous DMF (2 ml) was placed in 10 mL round bottom flask was stirred for 5 min. in an ice bath. Then 2-bromomethylnaphthalene (150 mg; 0.65 mmol; 1.1 eq.) was added and the resulting mixture was left to warm up to RT and stirred for 48 h at RT. Then the reaction mixture was partitioned between water and ethyl acetate. The organic layer was subsequently washed with water, brine, dried over anhydrous sodium sulfate and filtered. The filtrate was evaporated under reduced pressure and the residue was purified by FCC(silica, hexane, DCM, DCM/ethyl acetate 5%, gradient) to give N-(2-Ethynylphenyl)-N-(naphthalen-2-ylmethyl)acetamide (161 mg; 0.44 mmol; yield 74%) as yellow gel.

5-[2-(2-{N-[(naphthalen-2-yl)methyl] acetamido}phenyl)ethynyl]pyridine-2-carboxylic acid methyl ester

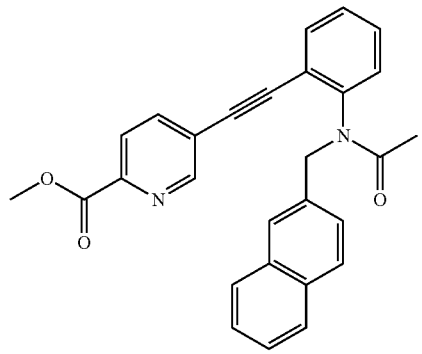 [SMILES: COC(=O)c1ccc(C#Cc2ccccc2N(Cc2ccc3ccccc3c2)C(C)=O)cn1]

Sonogashira coupling was conducted according to the procedure described above in Example 14: Starting from N-(2-Ethynylphenyl)-N-(naphthalen-2-ylmethyl)acetamide (154 mg; 0.42 mmol; 1 eq.) and 5-Bromopyridine-2-carboxylic acid methyl ester (122 mg; 0.57 mmol; 1.3 eq.) the 5-[2-(2-{N-[(naphthalen-2-yl)methyl]acetamido}phenyl) ethynyl]pyridine-2-carboxylic acid methyl ester (117 mg; 0.27 mmol; yield 63%) was obtained as colorless film.

5-[2-(2-{N-[(naphthalen-2-yl)methyl] acetamido}phenyl)ethynyl]pyridine-2-carboxylic acid

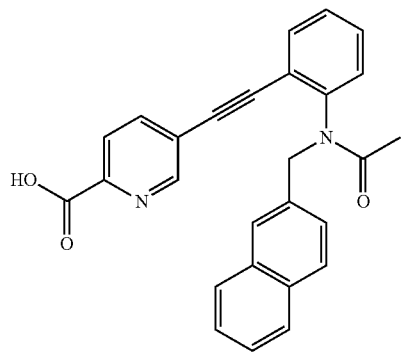 [SMILES: CC(=O)N(Cc1ccc2ccccc2c1)c1ccccc1C#Cc1ccc(C(=O)O)nc1]

Ester saponification step was conducted as outlined above in Example 14. Starting from 5-[2-(2-{N-[(naphthalen-2-yl) methyl]acetamido}phenyl)ethynyl]-pyridine-2-carboxylic acid methyl ester (117 mg; 0.27 mmol; 1 eq) and lithium hydroxide (56 mg; 1.33 mmol; 5 eq.) the 5-[2-(2-{N-[(naphthalen-2-yl)methyl]-acetamido}phenyl)ethynyl]pyridine-2-carboxylic acid (81 mg; 0.2 mmol; yield 72%) as a light yellow slid.

Example 16—General Procedure 4 (GP4)

Compounds of formula (I) with $L^1$ being a divalent —N(C(=O)—NH$_2$)—, —N(C(=O)—NHR$^a$)— or —N(C(=O)—NR$^a$R$^b$)— radical and $L^2$ being a divalent —CH$_2$— radical may be prepared in accordance with the following scheme and synthetic procedure described below with reference to Methyl 5-[2-(2-{carbamoyl[(naphthalen-2-yl) methyl]amino}phenyl)ethynyl]pyridine-2-carboxylate utilizing suitable starting material:

Methyl 5-[2-(2-{carbamoyl[(naphthalen-2-yl) methyl]amino}phenyl)ethynyl]-pyridine-2-carboxylate

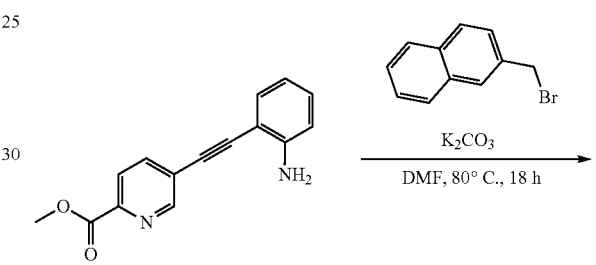

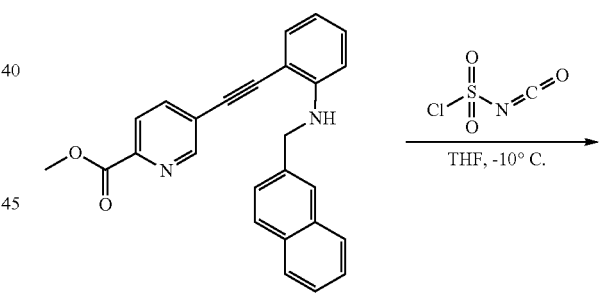

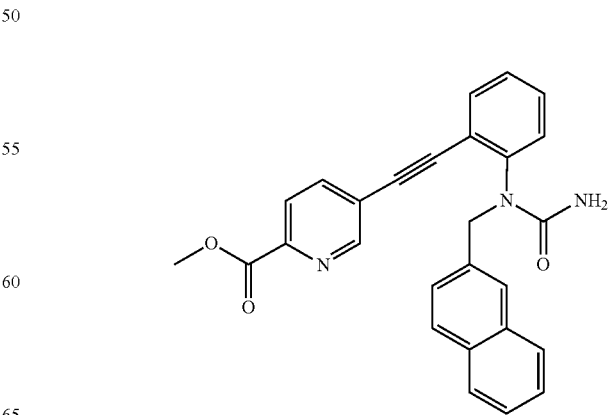

5-{2-[(Naphthalen-2-ylmethyl)amino]phenylethynyl}pyridine-2-carboxylic acid methyl ester

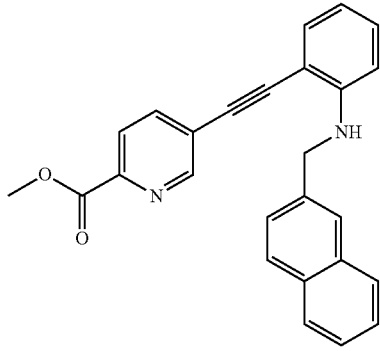 [SMILES: COC(=O)c1ccc(C#Cc2ccccc2NCc2ccc3ccccc3c2)cn1]

A mixture of 5-(2-aminophenylethynyl)pyridine-2-carboxylic acid methyl ester (75 mg; 0.3 mmol; 1 eq.), 2-bromomethylnaphthalene (82 mg; 0.36 mmol; 1.2 eq.) and potassium carbonate (49 mg; 0.36 mmol; 1.2 eq.), placed in a reacting vessel, was dissolved in DMF (0.6 ml) and bubbled under argon. The vessel was capped and the RM was heated at 80° C. overnight. Then RM was concentrated in vacuo and portioned between water and EtOAc. The organic layer was separated washed with water, dried over $Na_2SO_4$ and concentrated in vacuo to give an oil which was purified by FCC (hexane-EtOAc 4:1 isocratic) to afford 5-{2-[(Naphthalen-2-ylmethyl)amino]phenylethynyl}pyridine-2-carboxylic acid methyl ester (66 mg; 0.2 mmol; yield 5%).

Methyl 5-[2-(2-{carbamoyl[(naphthalen-2-yl)methyl]amino}phenyl)ethynyl]-pyridine-2-carboxylate

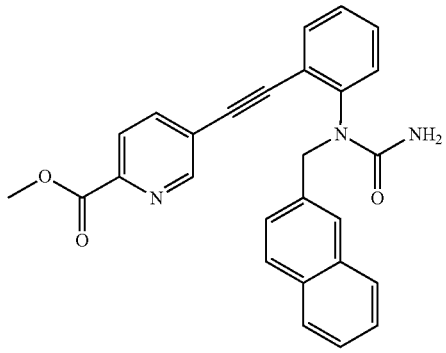 [SMILES: COC(=O)c1ccc(C#Cc2ccccc2N(Cc2ccc3ccccc3c2)C(N)=O)cn1]

To a stirred solution of chlorosulfonyl isocyanate (0.02 ml; 0.19 mmol; 1.20 eq.) in anhydrous THF (1.00 ml), the 5-{2-[(Naphthalen-2-ylmethyl)-amino]-phenylethynyl}-pyridine-2-carboxylic acid methyl ester (65 mg; 0.16 mmol; 1 eq.) dissolved in anhydrous THF (1 ml), was slowly added at −10° C. RM was stirred at −10° C. for 1 h and then was quenched with water (1 mL), stirred for 30 min at room temperature. The 2N NaOH was added until pH 10, and resulting mixture was extracted with AcOEt, dried over $Na_2SO_4$ and evaporated. The crude product was dissolved in DCM and $Et_2O$ was added, solid was filtered off and washed with $Et_2O$ to obtain methyl 5-[2-(2-{carbamoyl[(naphthalen-2-yl)methyl]amino}phenyl)ethynyl]pyridine-2-carboxylate (55 mg; 0.12 mmol; yield 74%) as yellow solid.

Example 17

Synthesis of 5-[2-(2-oxooxazolidine-3-sulfonylamino) phenylethynyl]pyridine-2-carboxylic acid methyl esters

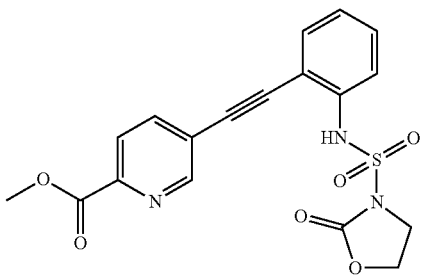 [SMILES: COC(=O)c1ccc(C#Cc2ccccc2NS(=O)(=O)N2CCOC2=O)cn1]

A solution of chlorosulfonyl isocyanate (0.1 ml; 1.16 mmol; 1 eq.) dissolved in anhydrous DCM (4 ml) was cooled to 0° C. Then 2-chloroethanol (0.08 ml; 1.16 mmol; 1 eq.) was added slowly and resulted mixture was stirred for 2 h at 0° C. Then the solution of 5-(2-aminophenylethynyl)pyridine-2-carboxylic acid methyl ester (300 mg; 1.16 mmol; 1 eq.) and triethylamine (0.45 ml; 3.5 mmol; 3 eq.) in anhydrous DCM (4 ml) was added slowly into the RM. Resulted solution warmed RT and stirred overnight. Then RM was quenched with 2M HCl and saturated NaCl. Organic layer was separated and water phase was additionally washed twice with DCM. Organic layers were combined and dried over $Na_2SO_4$, concentrated in vacuo. Crude product was purified by FCC (hexane 100% to EtOAc 100%1:2 gradient) yielding 5-[2-(2-Oxooxazolidine-3-sulfonylamino) phenylethynyl]pyridine-2-carboxylic acid methyl ester (198 mg; 0.41 mmol; yield 35%) as a white fine powder.

Example 18

Synthesis of rac-5-[2-(2-{[(4aR,8aS)-decahydroquinoline-1-sulfonyl]-amino}phenyl)ethynyl]pyridine-2-carboxylic acid methyl ester

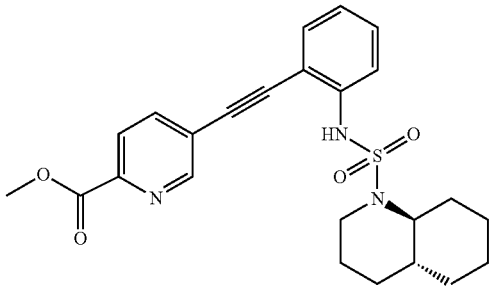 [SMILES: COC(=O)c1ccc(C#Cc2ccccc2NS(=O)(=O)N2CCC[C@H]3CCCC[C@@H]32)cn1]

5-[2-(2-oxooxazolidine-3-sulfonylamino)-phenylethynyl]pyridine-2-carboxylic acid methyl ester (67 mg; 0.15 mmol; 1 eq.) of Example 17 above was added to trans-decahydroquinoline (61 mg; 0.44 mmol; 2.9 eq.) dissolved in toluene (0.5 ml) placed in a reaction vessel. RM was flushed with argon and capped. Resulted mixture was stirred for 6 h at 80° C. Then RM was evaporated to give yellow oily residue. Crude product was purified by FCC (hexane-EtOAc 2:1 isocratic) to afford rac-5-{2-[(4aS,8aR)-(octahydro-quinolin-1-yl)sulfonylamino]phenylethynyl}pyridine-2-carboxylic acid methyl ester (35 mg; 0.07 mmol; yield 46%) as yellow solid.

Example 19

Synthesis of rac-5-[2-(2-{[(4aR,8aS)-decahydroquinoline-1-sulfonyl]-amino}phenyl)ethynyl]pyridine-2-carboxylic acid

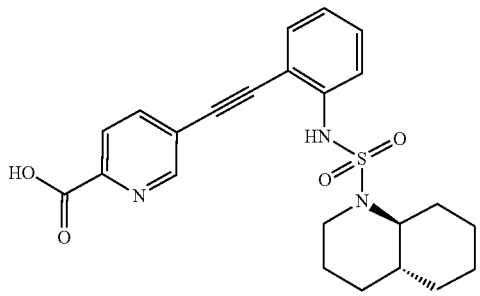 [SMILES: O=C(O)c1ccc(C#Cc2ccccc2NS(=O)(=O)N2CCC[C@H]3CCCC[C@@H]32)cn1]

To a stirred solution of rac-5-{2-[(4aS,8aR)-(decahydroquinolin-1-yl)sulfonyl-amino]phenylethynyl}-pyridine-2-carboxylic acid methyl ester (30 mg; 0.06 mmol; 1 eq.) of Example 18 in water (0.5 ml) and THF (0.5 ml) was added lithium hydroxide (28 mg; 1.2 mmol; 20 eq.). RM was stirred at room temperature overnight. RM was concentrated and neutralized with 1N HCl, then aqueous layer was extracted with EtOAc, dried over Na₂SO₄, and evaporated. The crude product was purified by HPLC preparative (ACN gradient in 0.1% TFA) to afford 5-{2-[(4aS,8aR)-(decahydroquinolin-1-yl)-sulfonylamino]phenylethynyl}pyridine-2-carboxylic acid (25 mg; 0.06 mmol; yield 99%) as a pale yellow solid.

Example 20

Synthesis of 5-{2-[2-({1H,2H,3H-pyrrolo[2,3-b]pyridine-1-sulfonyl}-amino)phenyl]ethynyl}pyridine-2-carboxylic acid methyl ester

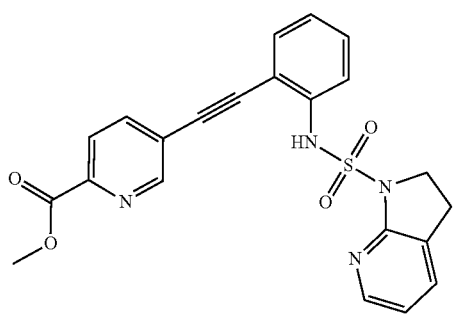 [SMILES: COC(=O)c1ccc(C#Cc2ccccc2NS(=O)(=O)N2CCc3cccnc32)cn1]

5-[2-(2-Oxooxazolidine-3-sulfonylamino)-henylethynyl]-yridine-2-carboxylic acid methyl ester (70 mg; 0.14 mmol; 1 eq.) (Example 17) was added to the 2,3-dihydro-7-azaindole (49 mg; 0.41 mmol; 2.9 eq.) dissolved in anhydrous acetonitrile (1 ml) placed in reacting vessel. RM was flushed with argon and capped. Resulted yellow mixture was stirred for 6 h at 1000. Then content was evaporated to give yellow oily residue. Resulting oil was purified by FCC (SiHP column, hexane-EtOAc 2:1 isocratic) to give 5-[2-(2, 3-dihydropyrrolo[2,3-b]pyridine-1-sulfonylamin)phenylethynyl]pyridine-2-carboxylic acid methyl ester (35 mg; 0.08 mmol; yield 56%) as a white solid.

Example 21

5-{2-[2-({1H,2H,3H-pyrrolo[2,3-b]pyridine-1-sulfonyl}amino)phenyl]-ethynyl}pyridine-2-carboxylic acid

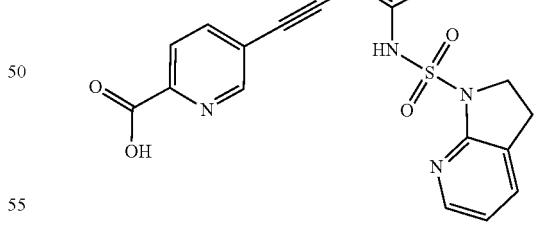

Saponification of 5-{2-[2-({1H,2H,3H-pyrrolo[2,3-b]pyridine-1-sulfonyl}amino)-phenyl]ethynyl}pyridine-2-carboxylic acid methyl ester was conducted in accordance to procedure described above in Example 19: Starting from 5-[2-(2,3-dihydropyrrolo[2,3-b]pyridine-1-sulfonylamino)phenylethynyl]pyridine-2-carboxylic acid methyl ester (15 mg; 0.03 mmol; 1 eq.) the 5-[2-(2,3-dihydropyrrolo[2,3-b]pyridine-1-sulfonylamino)phenylethynyl]pyridine-2-carboxylic acid (10 mg; 0.02 mmol; yield 68%) was obtained as a white solid.

Example 22

Synthesis of 5-{2-[2-(7-methylquinoline-8-sulfonamido)phenyl]ethynyl}-4-(prop-1-en-2-yl)pyridine-2-carboxylic acid

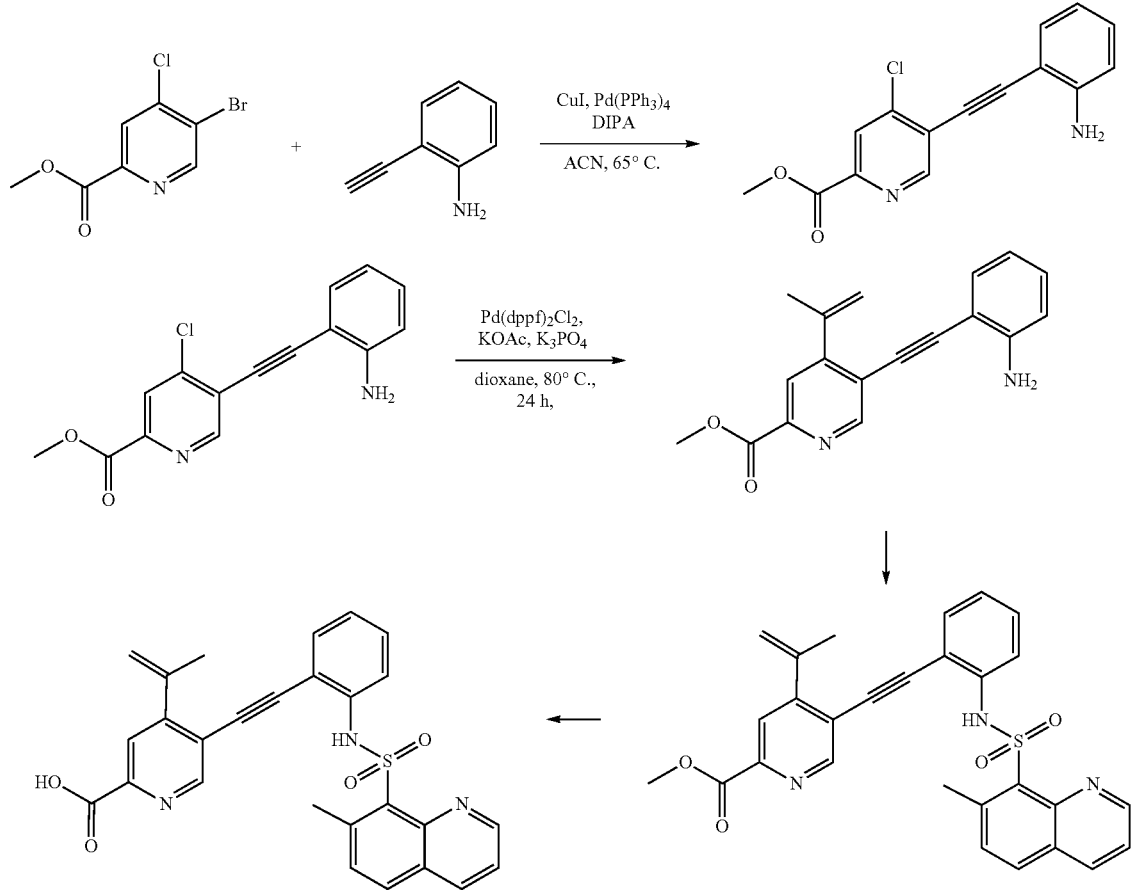

Methyl 5-(2-aminophenylethynyl)-4-chloropyridine-2-carboxylate

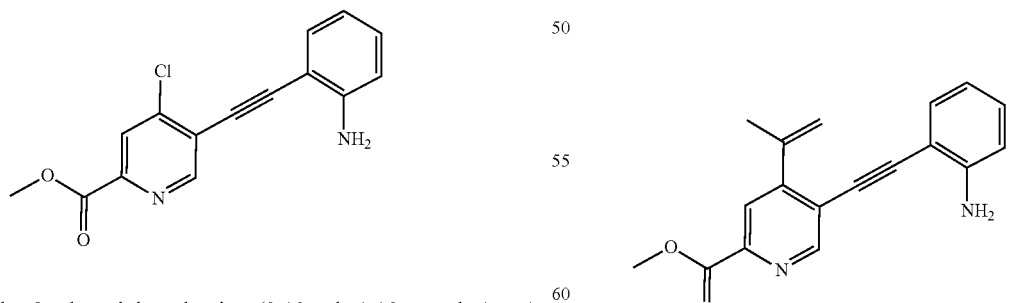

The 2-ethynylphenylamine (0.13 ml; 1.19 mmol; 1 eq.) and methyl 5-bromo-4-chloropyridine-2-carboxylate (300 mg; 1.19 mmol; 1 eq.), were added to the reaction vessel containing mixture of acetonitrile (5 ml), and diisopropylamine (0.26 ml; 1.78 mmol; 1.5 eq.). The resulting mixture was was bubbled with argon for 10 min, then the copper (1) iodide (6.77 mg; 0.04 mmol; 0.03 eq.) and tetrakis(triphenylphosphine)palladium(0) (41.11 mg; 0.04 mmol; 0.03 eq.) were added under Ar atm and vessel was capped. RM was stirred at 65° C. for 3 h. RM was cooled down to RT, diluted with AcOEt and filtered through a pad of Celite®. Filtrate was evaporated and residue was purified by FCC (SiHP, DCM-DCM:MeOH 20%) to give methyl 5-(2-aminophenylethynyl)-4-chloropyridine-2-carboxylate (306 mg; 1.06 mmol; yield 89%) as yellow solid.

Methyl 5-(2-aminophenylethynyl)-4-isopropenylpyridine-2-carboxylate

Microwave vial was charged with 5-(2-aminophenylethynyl)-4-chloropyridine-2-carboxylic acid methyl ester (100 mg; 0.35 mmol; 1 eq.), $K_3HOPH_24$ (220 mg; 1 mmol; 3 eq.), potassium acetate (8.5 mg; 0.09 mmol; 0.25 eq.) and [1,1'-bis(diphenylphosphino)ferrocene]dichloropalladium(II)

(PdCl2(dppf)2) (25 mg; 0.03 mmol; 0.1 eq.). The tube was sealed with a septum, air evacuated under vacuum, and back filled with argon (the cycle was repeated three times) and mixture of [1,4]-dioxane (2 ml) and 2-isopropenyl-4,4,5,5-tetramethyl-[1,3,2]-dioxaborolane (0.1 ml; 0.52 mmol; 1.5 eq.) was added by syringe. The reaction was stirred at 80° C. for 24 h, cooled to room temperature and filtrated through a pad of Celite®. Solvent was evaporated and residue was purified by FCC (SiHP, DCM-DCM:MeOH 20%) to yield 5-(2-aminophenylethynyl)-4-isopropenylpyridine-2-carboxylic acid methyl ester (69 mg; 0.23 mmol; yield 68%) as yellow solid.

4-Isopropenyl-5-[2-(7-methylquinoline-8-sulfonylamino)-phenylethynyl]-pyridine-2-carboxylic acid methyl ester

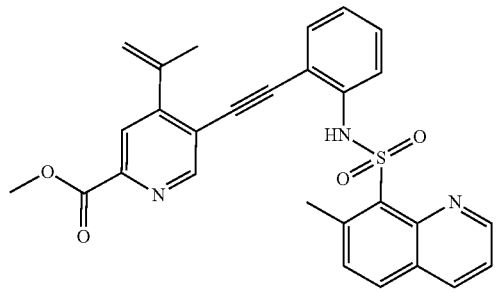 [SMILES: C=C(C)c1cc(C(=O)OC)ncc1C#Cc1ccccc1NS(=O)(=O)c1c(C)ccc2cccnc12]

7-Methylquinoline-8-sulfonyl chloride (67.77 mg; 0.28 mmol; 1.20 eq.) was added to the solution of 5-(2-aminophenylethynyl)-4-isopropenylpyridine-2-carboxylic acid methyl ester (0.07 ml; 0.23 mmol; 1 eq.) in pyridine (2 ml). Reaction was carried out in overnight. Then pyridine was evaporated with toluene and residue was purified by FCC (SiHP, hexane→hexane:EtOAc 50% v/v) to yield 4-Isopropenyl-5-[2-(7-methylquinoline-8-sulfonylamino)-phenylethynyl]-pyridine-2-carboxylic acid methyl ester (60 mg; 0.12 mmol; yield 51%) as a light yellow solid.

5-{2-[2-(7-methylquinoline-8-sulfonamido)phenyl]ethynyl}-4-(prop-1-en-2-yl)pyridine-2-carboxylic acid

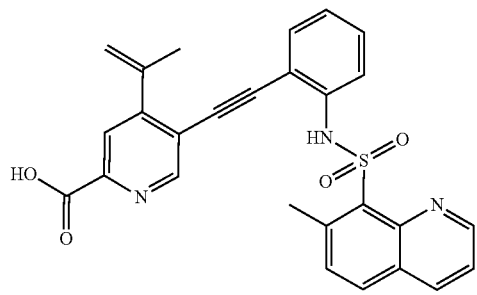 [SMILES: C=C(C)c1cc(C(=O)O)ncc1C#Cc1ccccc1NS(=O)(=O)c1c(C)ccc2cccnc12]

4-Isopropenyl-5-[2-(7-methylquinoline-8-sulfonylamino)-phenylethynyl]-pyridine-2-carboxylic acid methyl ester (60 mg; 0.12 mmol; 1 eq.) was dissolved in mixture of THF (2 ml), Methanol (5 ml). The solution of water (2 ml) and lithium hydroxide hydrate (125 mg; 3 mmol; 25 eq.) was added. RM was stirred overnight at RT. Then RM was diluted with AcOEt, washed with water in the presence of 2M HCl and extracted with AcOEt. Combined organic layers was dried over Na₂SO₄ and evaporated to give 4-Isopropenyl-5-[2-(7-methylquinoline-8-sulfonylamino)-phenylethynyl]-pyridine-2-carboxylic acid (55 mg; 0.11 mmol; yield 94%) as a light yellow solid.

5-{2-[2-(5-Methoxy-8-sulfonamido)phenyl]ethynyl}-4-(prop-1-en-2-yl)pyridine-2-carboxylic acid

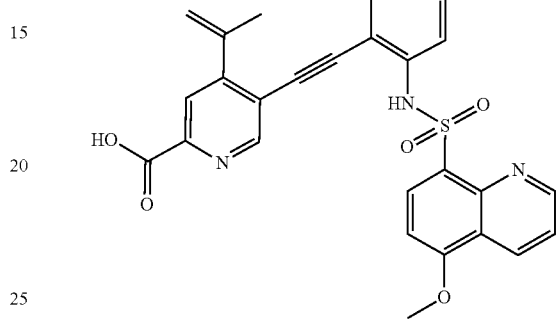

5-{2-[2-(5-Methoxy-8-sulfonamido)phenyl]ethynyl}-4-(prop-1-en-2-yl)pyridine-2-carboxylic acid was obtained in accordance with the procedure described above in Example 21.

Example 23

5-{2-[2-(7-Methyl-8-sulfonamido)phenyl]ethynyl}-4-(prop-1-en-2-yl)pyridine-2-carboxylic acid

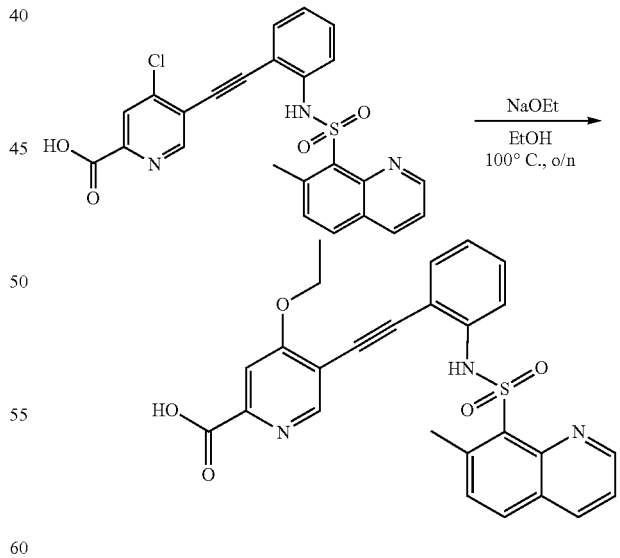

Sodium ethoxide 1M solution in EtOH (0.23 ml; 0.62 mmol; 10 eq.) was added to the solution of 4-chloro-5-[2-(7-methyl-quinoline-8-sulfonylamino)-phenylethynyl]-pyridine-2-carboxylic acid (30 mg; 0.06 mmol; 1 eq.) in ethanol (0.5 ml). Reaction was carried out overnight at 100° C. Solvent was evaporated and crude product was purified by preparative HPLC (ACN/0.1% TFA) to give 4-ethoxy-5-[2-

(7-methyl-quinoline-8-sulfonylamino)-phenylethynyl]-pyridine-2-carboxylic acid (18 mg; 0.04 mmol; yield 60%) as white solid.

Example 24

4-hydroxy-5-{2-[2-(7-methylquinoline-8-sulfonamido)phenyl]ethynyl}-pyridine-2-carboxylic acid

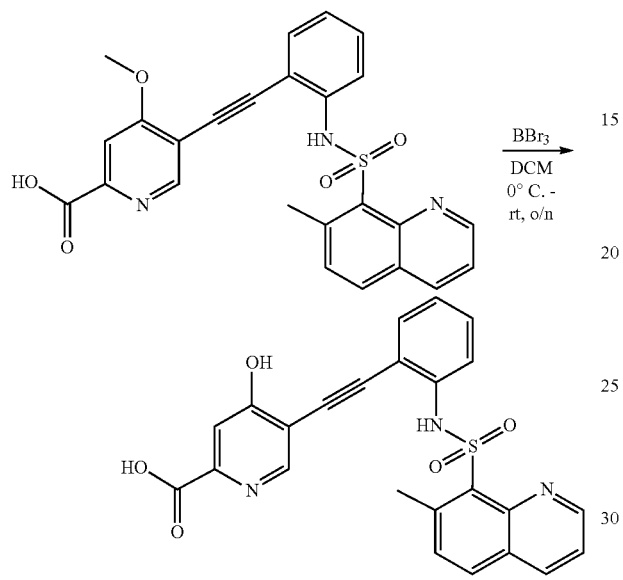

4-Methoxy-5-[2-(7-methyl-quinoline-8-sulfonylamino)-phenylethynyl]-pyridine-2-carboxylic acid (41 mg; 0.08 mmol; 1 eq.) was dissolved in anhydrous dichloromethane (4 ml) and cooled to 0° C. Then boron tribromide 1 M solution in DCM (0.24 ml; 0.24 mmol; 3 eq.) was added slowly at 0° under stirring. RM 10 was allowed to warm to RT and stirred overnight. After 16 h RM was cooled once again to 0° C. and water was added slowly. After quenching product was extracted with n-butanol, organic layers were collected and evaporated. The residue was washed with small amount of water to remove inorganic salts. Crude product was purified by preparative HPLC (ACN/0.1% TFA)) to give 4-hydroxy-5-[2-(7-methylquinoline-8-sulfonylamino)-phenylethynyl]-pyridine-2-carboxylic acid (6 mg; 0.01 mmol; yield 16%) as a beige solid.

Example 25

7-Methyl-N-[2-(2-{7-oxo-5H,7H-furo[3,4-b]pyridin-3-yl}ethynyl)phenyl]-quinoline-8-sulfonamide

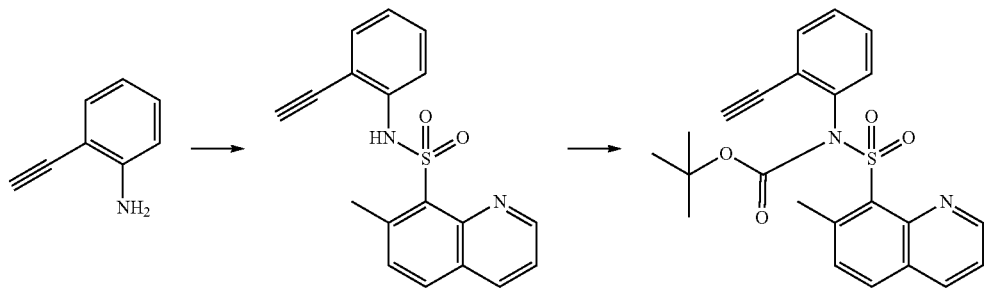

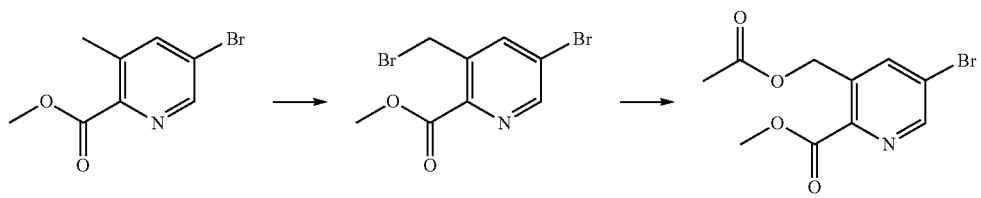

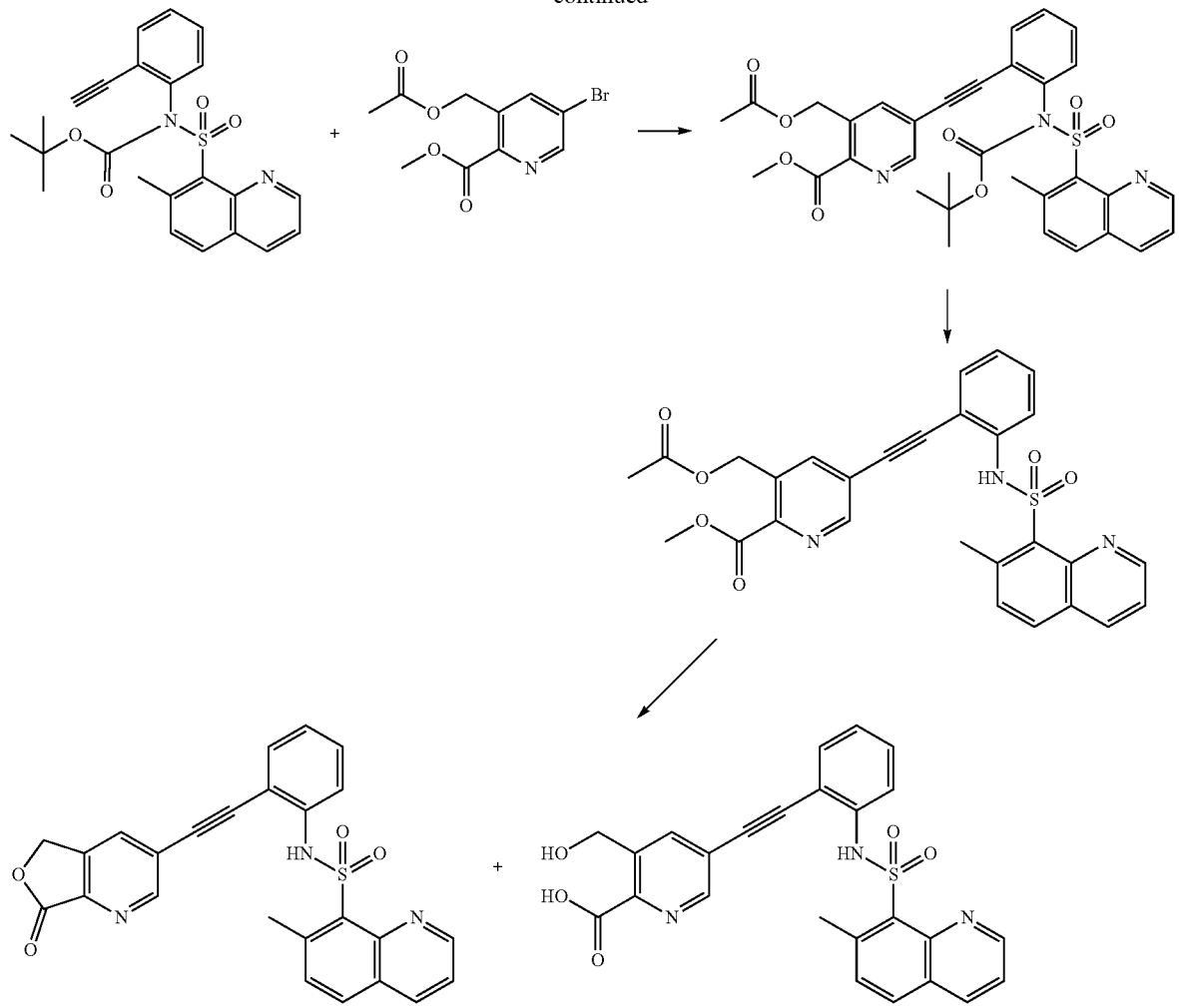

N-(2-Ethynylphenyl)-7-methylquinolin-8-ylsulfonamide

The following synthesis can serve as an alternative to GP1 for preparing N-(2-ethynylphenyl)-sulfonamides of the invention.

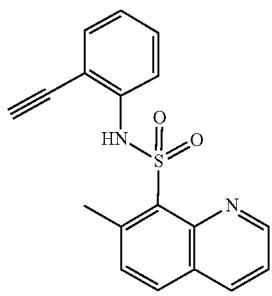 [SMILES: C#Cc1ccccc1NS(=O)(=O)c1c(C)ccc2cccnc12]

A mixture of 2-ethynylphenylamine (136 μl; 1.2 mmol; 1 eq.), 7-methyl-quinoline-8-sulfonyl chloride (390 mg; 1.6 mmol; 1.35 eq.) and pyridine (3 ml) was left stirring at room temperature until 2-ethynylphenylamine decayed. Then the reaction mixture was co-evaporated with toluene under reduced pressure and the residue was purified by FCC (SiHP, hexane, DCM, gradient) to give N-(2-ethynylphenyl)-7-methylquinolin-8-ylsulfonamide (374 mg; 1.14 mmol; yield 96%) as light beige solid.

tert-Butyl N-(2-ethynylphenyl)-N-[(7-methylquinolin-8-yl)sulfonyl]carbamate

N-(2-Ethynylphenyl)-7-methylquinolin-8-ylsulfonamide (374 mg; 1.14 mmol; 1 eq.), DMAP (28 mg; 0.23 mmol; 0.2 eq.) and anhydrous acetonitrile (5 ml) was stirred at RT for 5 min. Then, the mixture was heated to 80° C. The solution of tert-butoxycarbonyl tert-butyl carbonate (BOC₂O) (1 g;

4.6 mmol; 4 eq.) in acetonitrile (anhydrous) (2 ml) was added to the reaction mixture in four portions during 1 hour. The heating was continued for additional 0.5 h and left for overnight stirring at room temperature. The reaction mixture was portioned between ethyl acetate and water. The organic layer was subsequently washed with saturated NH$_4$Cl water solution, water, brine, dried over anhydrous sodium sulfate and filtered. The filtrate was evaporated under reduced pressure and the residue was purified by FCC (SiHP, hexane/ethyl acetate, gradient) to give tert-butyl N-(2-ethynylphenyl)-N-[(7-methylquinolin-8-yl)sulfonyl]carbamate (385 mg; 0.72 mmol; yield 63%) as light beige solid.

Methyl 5-bromo-3-(bromomethyl)pyridine-2-carboxylate

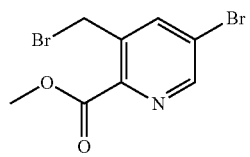

To a solution of methyl 5-bromo-3-methylpyridine-2-carboxylate (200 mg; 0.9 mmol; 1 eq.) in CCl$_4$ (5 ml) the N-Bromosuccinimide (162 mg; 0.9 mmol; 1 eq.) and 2,2'-Azobis(2-methylpropionitrile) (2.9 mg; 0.02 mmol; 0.02 eq.) were added under inert atmosphere. Resulted reaction mixture was refluxed for 5 h under argon stream. Than the RM was cooled to RT and evaporated in vacuo to give crude methyl 5-bromo-3-(bromomethyl)pyridine-2-carboxylate (439 mg; 0.78 mmol; 90%) as yellowish semisolid which was used to next step without further purification.

Methyl 3-[(acetyloxy)methyl]-5-bromopyridine-2-carboxylate

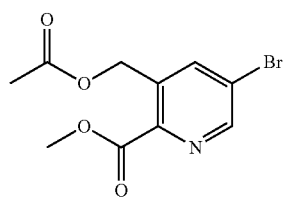 [SMILES: COC(=O)c1ncc(Br)cc1COC(C)=O]

Methyl 5-bromo-3-(bromomethyl)pyridine-2-carboxylate (439 mg; 0.8 mmol; 1 eq.), anhydrous sodium acetate (982 mg; 12 mmol; 15 eq.) and glacial acetic acid (3 ml) were placed into flame dried reacting vessel. The vessel content was purged with argon, capped and placed in preheated to 120° C. an oil bath. RM was stirred for 30 min at 120° C. and cooled down to RT. RM was cooled down and neutralized with saturated sodium bicarbonate, diluted with water and extracted with AcOEt. Combined organic extracts were subsequently washed with water, brine and dried over anhydrous Na$_2$SO$_4$ and evaporated. Residue was purified by FCC (SiHP, hexane/EtOAc, gradient) to give Methyl 3-[(acetyloxy)methyl]-5-bromopyridine-2-carboxylate (84 mg; 0.3 mmol; yield 37%) as orange solid.

Methyl 3-[(acetyloxy)methyl]-5-[2-(2-{N-[(tert-butoxy)carbonyl]7-methyl-quinoline-8-sulfonamido}phenyl)ethynyl]pyridine-2-carboxylate

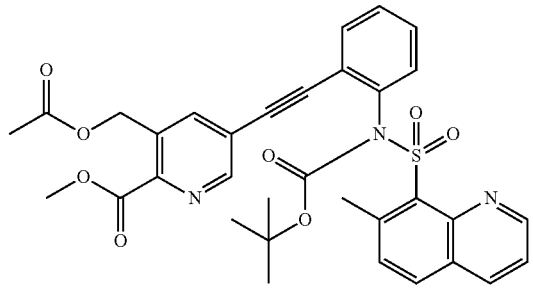 [SMILES: COC(=O)c1ncc(C#Cc2ccccc2N(CC(=O)OC(C)(C)C)S(=O)(=O)c2c(C)ccc3cccnc23)cc1COC(C)=O]

Sonogashira coupling was conducted accordingly to general procedure for Sonogashira coupling described above giving methyl 3-[(acetyloxy)methyl]-5-[2-(2-{N-[(tert-butoxy)carbonyl]7-methylquinoline-8-sulfonamido}phenyl)-ethynyl]pyridine-2-carboxylate (110 mg; 0.17 mmol; yield 99%) as beige solid.

Methyl 3-[(acetyloxy)methyl]-5-{2-[2-(7-methylquinoline-8-sulfonamido)-phenyl]ethynyl}pyridine-2-carboxylate

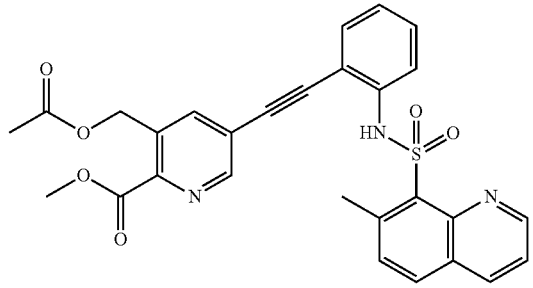 [SMILES: COC(=O)c1ncc(C#Cc2ccccc2NS(=O)(=O)c2c(C)ccc3cccnc23)cc1COC(C)=O]

Methyl 3-[(acetyloxy)methyl]-5-[2-(2-{N-[(tert-butoxy)carbonyl]7-methyl-quinoline-8-sulfonamido}phenyl)ethynyl]pyridine-2-carboxylate (111 mg; 0.17 mmol; 1 eq.) was dissolved in anhydrous dichloromethane (3 ml) and cooled to 0° C. The trifluoroacetic acid (1 ml; 13 mmol; 76 eq.) was added dropwise while stirring and ice bath was removed. Stirring continued for 18 hours at RT to complete reaction. The RM was quenched by slow dropwise addition of saturated sodium bicarbonate and extracted with DCM. Combined organic extracts were subsequently washed with water and brine, dried over anhydrous Na$_2$SO$_4$ and evaporated to give crude methyl 3-[(acetyloxy)methyl]-5-{2-[2-(7-methylquinoline-8-sulfonamido)phenyl]ethynyl}pyridine-2-carboxylate (86 mg; 0.16 mmol; yield 94%) as brown solid.

3-(Hydroxymethyl)-5-{2-[2-(7-methylquinoline-8-sulfonamido)phenyl]ethynyl}-pyridine-2-carboxylic acid and 7-methyl-N-[2-(2-{7-oxo-5H,7H-furo[3,4-b]pyridin-3-yl}ethynyl)phenyl]quinoline-8-sulfonamide

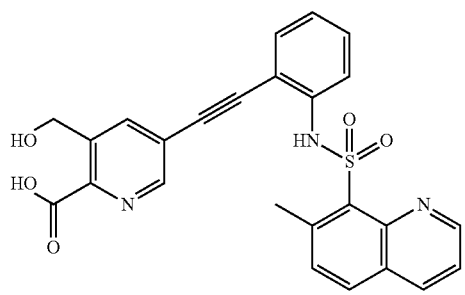

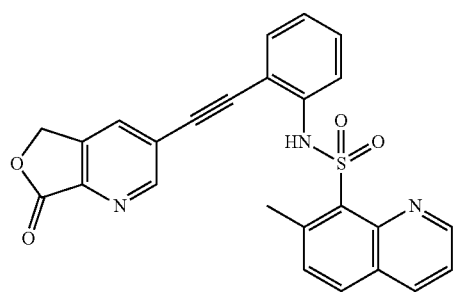

Methyl 3-[(acetyloxy)methyl]-5-{2-[2-(7-methylquinoline-8-sulfonamido)-phenyl]ethynyl}pyridine-2-carboxylate (86 mg; 0.16 mmol; 1 eq.) was dissolved in THF (5 ml). Water (2 ml) was added to resulted mixture followed by lithium hydroxide hydrate (34 mg; 0.8 mmol; 5 eq.) addition. The resulting mixture was stirred for 5 hours at RT. Then RM was concentrated under reduced pressure, acidified using 1 M hydrochloric acid 6 pH and extracted with AcOEt. The organic layer was subsequently washed with water, brine, dried over anhydrous Na₂SO₄, filtered and evaporated under reduced pressure. The residue was purified by preparative HPLC chromatography (0.1% FA with MeCN gradient) to give mixture of the compounds, 84% and 15% respectively.

Both compounds were separated using FCC (SiHP column, hexane/EtOAc 100%, gradient) to give:

3-(hydroxymethyl)-5-{2-[2-(7-methylquinoline-8-sulfonamido)phenyl]ethynyl}-pyridine-2-carboxylic acid (20 mg; 0.04 mmol; yield 26%) as yellowish solid; and 7-methyl-N-[2-(2-{7-oxo-5H,7H-furo[3,4-b]pyridin-3-yl}ethynyl)phenyl]-quinoline-8-sulfonamide (6 mg; 0.01 mmol; yield 8%) as white solid.

Example 26—General Procedure 5 (GP5)

Compounds of formula (I) L1 being a divalent —N(CHO)— radical; and L2 being a divalent —CH2— radical may be prepared in accordance with the following scheme and synthetic procedure described below for -[2-(2-{N-[(6-phenylpyridin-3-yl)methyl]formamido}phenyl) ethynyl]pyridine-2-carboxylic acid:

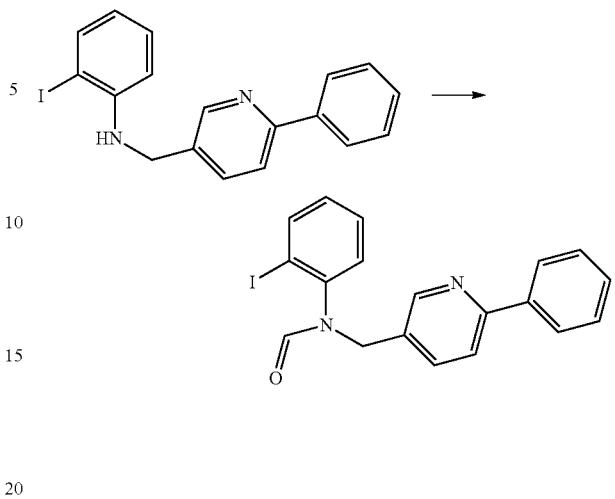

To a round-bottom flask acetic formic anhydride was generated by the dropwise addition of formic acid (0.27 ml; 7.16 mmol) to acetic anhydride (0.81 ml; 8.59 mmol) at 0° C. The mixture was added to a solution of (2-iodo-phenyl)-(6-phenyl-pyridin-3-ylmethyl)-amine (189.00 mg; 0.48 mmol) in tetrahydro-furan (3.00 ml). The mixture was stirred at 70° C. overnight. UPLC analysis showed conversion of starting material to desire product. Work-up: Solvents were removed in vacuo and residue was purified by FCC (SiHP column, 0-50% ethyl acetate gradient in hexane) provide to: N-(2-iodo-phenyl)-N-(6-phenyl-pyridin-3-ylmethyl)-formamide (196.00 mg; 0.47 mmol; 99.2%; yellow oil).

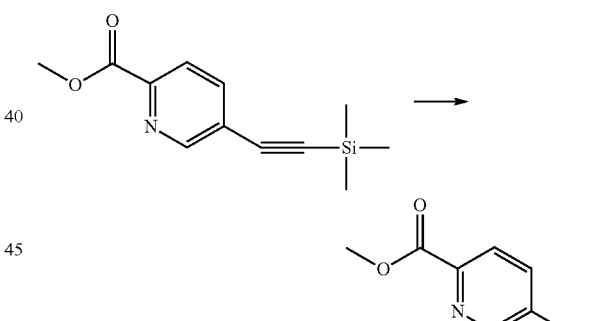

5-Trimethylsilanylethynyl-pyridine-2-carboxylic acid methyl ester (2.04 g; 8.49 mmol) was dissolved in anhydrous methanol (20.00 ml) at room temperature. Then potassium carbonate (23.46 mg; 0.17 mmol) was added. The mixture is stirred for 15 min under argon at RT. UPLC analysis showed that SM material was still present in RM. Then the RM was left stirring o/w. Full conversion of SM was confirmed by TLC (ethyl acetate/hexane 1/4). Work-up: The reaction mixture was evaporated under reduced pressure (bath temperature below 30° C.). Crude product was purified by FCC (SiHP column, 0-30% ethyl acetate gradient in hexane) provide to: 5-Ethynyl-pyridine-2-carboxylic acid methyl ester (1.17 g; 7.26 mmol; 85.5%; light yellow solid).

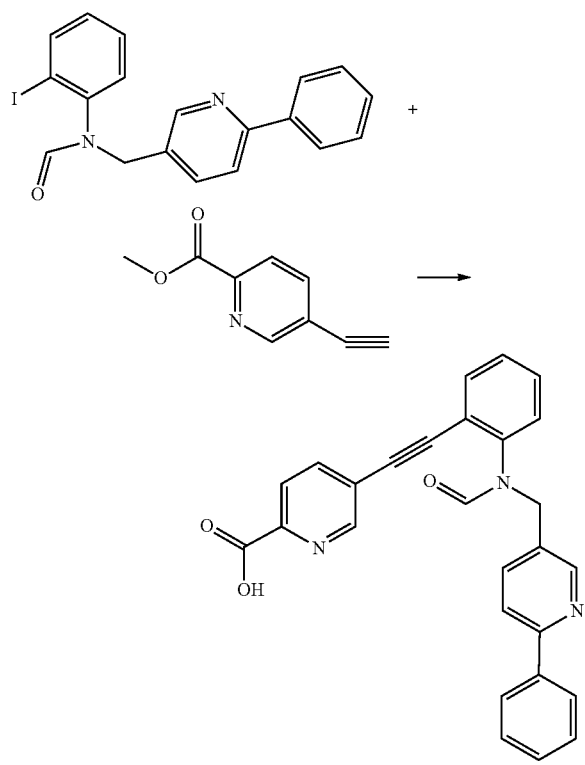

Step A:

A pressure vessel was charged with N-(2-iodo-phenyl)-N-(6-phenyl-pyridin-3-ylmethyl)-formamide (190.00 mg; 0.46 mmol), 5-ethynyl-pyridine-2-carboxylic acid methyl ester (147.84 mg; 0.92 mmol), triethylamine (anhydrous) (0.26 ml; 1.83 mmol) and N,N-dimethylformamide anhydrous, 99.8% (4.00 ml). The resulting mixture was purged with argon for 10 min. Then Copper(I) iodide, 98% (13.98 mg; 0.07 mmol) and Bis(triphenylphosphine)palladium(II) dichloride (12.88 mg; 0.02 mmol) were added. The reaction mixture was heated with stirring at 85° C. overnight. Conversion of starting material was confirmed by UPLC. The reaction mixture was cooled down, quenched with saturated aqueous solution of $NH_4Cl$ and extracted to ethyl acetate. The organic layer were washed with brine and dried over $Na_2SO_4$. The solvent were removed under reduced pressure and crude product was purified by FCC (SiHP column, 0-80% ethyl acetate gradient in hexane) providing 5-{2-[formyl-(6-phenyl-pyridin-3-ylmethyl)-amino]-phenylethynyl}-pyridine-2-carboxylic acid methyl ester (183.00 mg; 0.41 mmol; 89.2%; yellow solid).

Step B:

The ester from step A was dissolved in THF (6.00 ml) and water (2.00 ml). Then lithium hydroxide monohydrate (57.74 mg; 1.38 mmol) was added and reaction mixture was stirred at RT overnight. Conversion of starting material was confirmed by TLC. The reaction mixture was partially evaporated to remove THF, then diluted with additional portion of water and neutralized with 1 M HCl. Precipitated product was extracted to ethyl acetate. The organic layer was washed with brine and dried over $Na_2SO_4$. The crude product was purified by preparative HPLC (TFA) and gave after freeze-drying 5-{2-[formyl-(6-phenyl-pyridin-3-ylmethyl)-amino]-phenylethynyl}-pyridine-2-carboxylic acid (120.00 mg; 0.28 mmol; 60.1%; yellow solid).

Example 27—General Procedure 6 (GP6)

Compounds of formula (I) $R^2$ being either an alkoxy or amino substituent may be prepared in accordance with the following scheme and synthetic procedure described below:

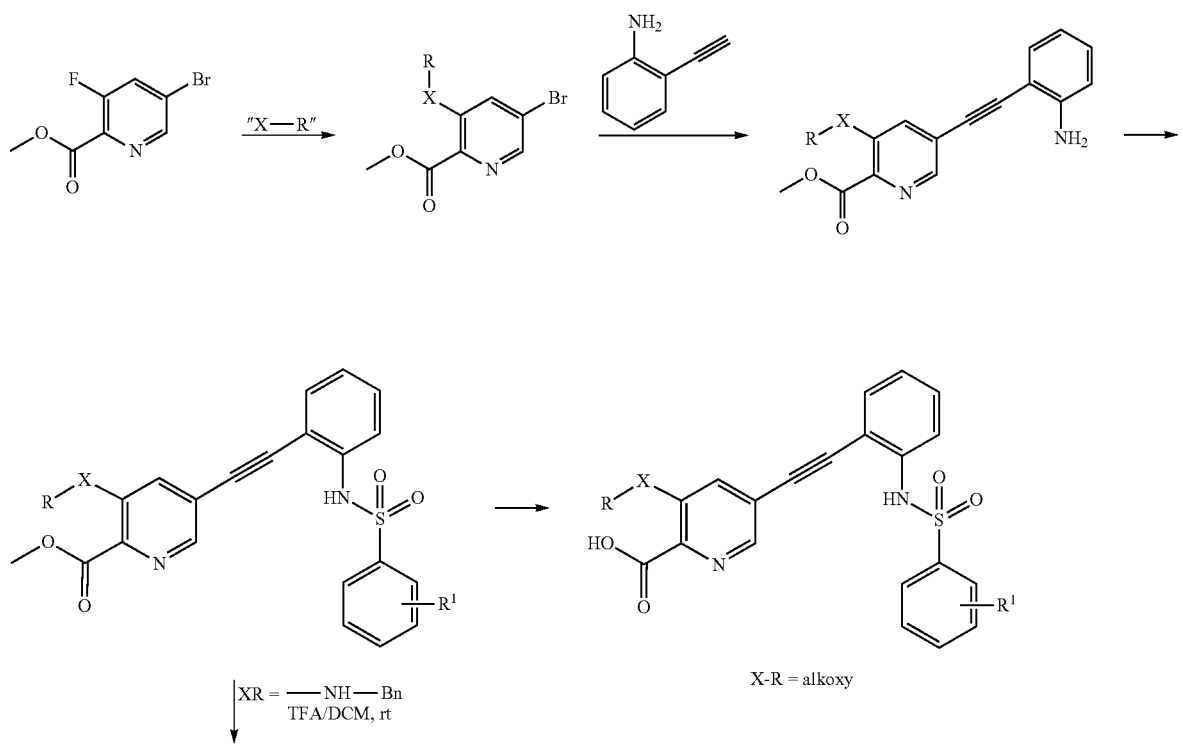

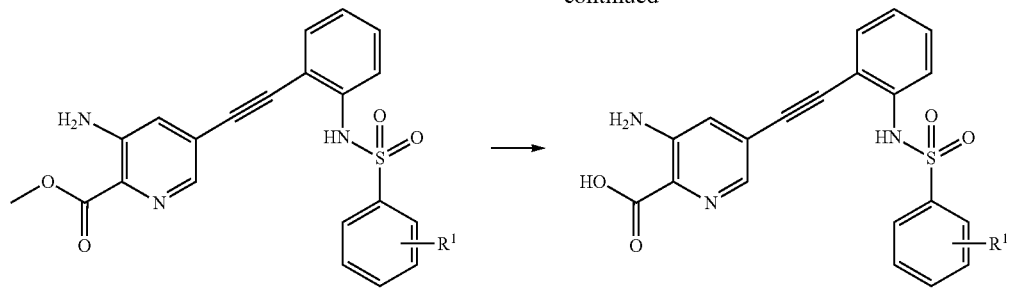

X-R = e.g. Me₂N, MeNH, EtNH, BnNH, MeO, EtO

3-{[(4-methoxyphenyl)methyl]amino}-5-{2-[2-(7-methylquinoline-8-sulfon-amido)phenyl]ethynyl}pyridine-2-carboxylic acid Methyl 3-(benzylamino)-5-bromopyridine-2-carboxylate

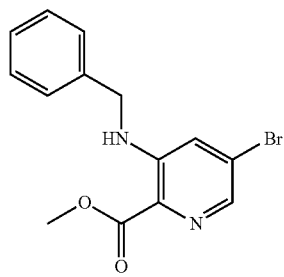 [SMILES: COC(=O)c1ncc(Br)cc1NCc1ccccc1]

A mixture of methyl 5-bromo-3-fluoro-pyridine-2-carboxylate (390 mg; 1.7 mmol; 1 eq.) and 4-methoxy-benzylamine (0.34 ml; 2.5 mmol; 1.5 eq.) in 4-methylmorpholine (4 ml) was heated at 110° C. for 2 h. The reaction mixture was concentrated and crude product was purified by FCC (SiHP, hexane/EtOAc, gradient) to give methyl 3-(benzylamino)-5-bromopyridine-2-carboxylate ester (471 mg; 1.33 mmol; yield 80%) as light yellow solid.

Methyl 3-(methylamino)-5-bromopyridine-2-carboxylate

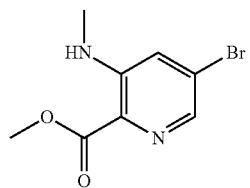

A pressure reactor vessel was charged with methyl 5-bromo-3-fluoro-pyridine-2-carboxylate (150 mg; 0.64 mmol; 1 eq.), methenamine hydrochloride (173 mg; 2.56 mmol; 4 eq.), Cesium carbonate (835 mg; 2.56 mmol; 4 eq.), then the vessel was capped and filled with argon. Then anhydrous toluene (3 ml) was added via syringe. The reaction mixture was stirred at 105° C. for 16 hours with stirring. The reaction mixture was diluted with ethyl acetate and subsequently washed with water and brine, dried over Na₂SO₄, evaporated under reduced pressure to provide: methyl 3-(methylamino)-5-bromopyridine-2-carboxylate (159 mg; 0.61 mmol; yield 95%) as yellow solid which was used in next step without further purification.

Methyl 3-(ethoxy)-5-bromopyridine-2-carboxylate

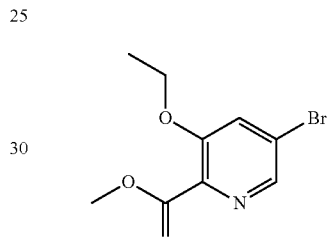

Step 1

In oven dried glass reacting vessel with septum methyl 5-bromo-3-fluoro-pyridine-2-carboxylate (130 mg; 0.56 mmol; 1 eq.) was dissolved in anhydrous ethanol (2 ml), 21% wt sodium ethanolate solution in ethanol (1 ml; 2.8 mmol; 5 eq.) was added and vessel was capped. The RM was stirred at 65° C. for 2 hours and than left for overnight stirring at RT. After that time RM was evaporated to dryness. Remaining solid was portioned by ethyl acetate and water, acidified to pH 4 with 1 M hydrochloric acid. The organic layer was collected, and water layer was extracted with EtOAC. The combined organic extracts washed with water and dried over anhydrous Na₂SO₄. EtOAc was evaporated in vacuo to give crude product which was purified by FCC (SiHP column, DCM→DCM/MeOH=9:1, v/v) to give 5-bromo-3-ethoxypyridine-2-carboxylic acid (107 mg; 0.4 mmol; yield 72%) as light beige solid.

Step 2

Thionyl chloride (51 µl; 0.84 mmol; 2.1 eq.) was dropped in to the mixture of 5-bromo-3-ethoxy-pyridine-2-carboxylic acid (107 mg; 0.4 mmol; 1 eq.) in anhydrous methanol (3 ml; 74 mmol) over 10 min at 0° C. RM was stirred at 0° C. for 30 min, then ice bath was removed and was stirred at RT for 2 hours. RM was refluxed for 2 hours. The RM was cooled down and methanol was evaporated in vacuo. The remaining residue were portioned by EtOAC and water. The organic layer was collected and water layer was extracted with EtOAc. Combined organic layers were subsequently washed with saturated sodium bicarbonate, water brine, dried over Na₂SO₄ and evaporated. Residue was purified by by FCC (SiHP column, hexane/EtOAc, gradient) to give methyl 5-bromo-3-ethoxypyridine-2-carboxylate (102 mg; 0.36 mmol; yield 91%) as beige solid.

Methyl 5-[2-(2-aminophenyl)ethynyl]-3-(benzylamino)pyridine-2-carboxylate

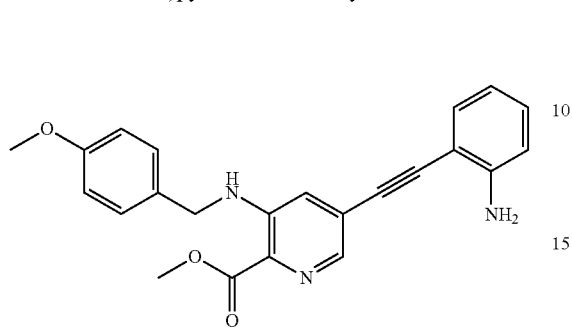

Sonogashira coupling was conducted according to the general procedure for Sonogashira coupling described above. Starting from methyl 3-(methylamino)-5-bromopyridine-2-carboxylate (270 mg; 0.76 mmol; 1.1 eq.) and 2-ethynylphenylamine (0.08 ml; 0.69 mmol; 1 eq.) the methyl 5-[2-(2-aminophenyl)ethynyl]-3-(benzylamino)pyridine-2-carboxylate (170 mg; 0.43 mmol; yield 62%) was obtained as orange solid.

Methyl 3-(benzylamino)-5-{2-[2-(7-methylquinoline-8-sulfonamido)phenyl]-ethynyl}pyridine-2-carboxylate

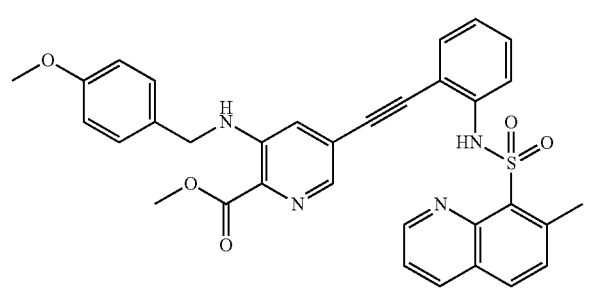

Sulfonamide synthesis was conducted accordingly to procedure described above: Starting from methyl 5-[2-(2-aminophenyl)ethynyl]-3-(benzylamino)-pyridine-2-carboxylate (38 mg; 0.09 mmol; 1 eq) and 7-Methyl-quinoline-8-sulfonylchloride (28 mg; 0.11 mmol; 1.2 eq.) the methyl 3-(benzylamino)-5-{2-[2-(7-methylquinoline-8-sulfonamido)phenyl]ethynyl}pyridine-2-carboxylate (55 mg; 0.09 mmol; yield 94%) was obtained as yellow solid.

Methyl 3-amino-5-{2-[2-(7-methylquinoline-8-sulfonamido)phenyl]ethynyl}-pyridine-2-carboxylate

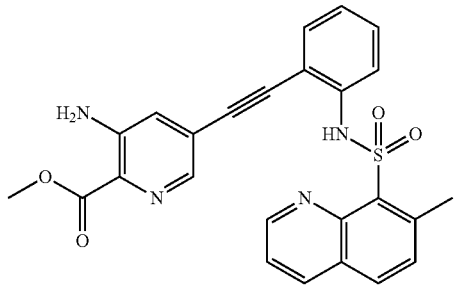

To a solution of methyl 3-(benzylamino)-5-{2-[2-(7-methylquinoline-8-sulfon-amido)phenyl]ethynyl}pyridine-2-carboxylate (40 mg; 0.06 mmol; 1 eq.) in anhydrous dichloromethane (1 ml) trifluoroacetic acid (0.5 ml; 6.48 mmol; 100 eq.) was added and RM was stirred at RT for 18 h. Then the solvent was evaporated in vacuo and crude product was purified by FCC (silica, hexane/EtOAc, gradient) to give methyl 3-amino-5-{2-[2-(7-methylquinoline-8-sulfonamido)phenyl]ethynyl}pyridine-2-carboxylate (25 mg; 0.05 mmol; yield 80%) as yellow solid.

3-{[(4-Methoxyphenyl)methyl]amino}-5-{2-[2-(7-methylquinoline-8-sulfon-amido)phenyl]ethynyl}pyridine-2-carboxylic acid

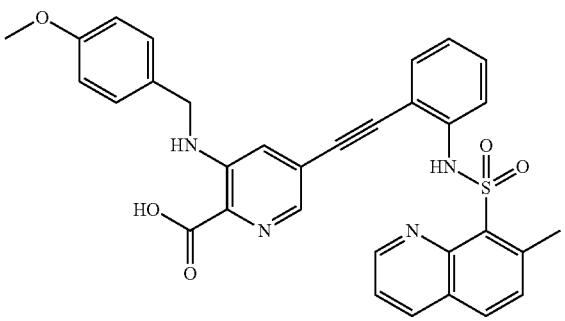

Saponification step was conducted according to the procedure described above: Starting from methyl 3-(benzylamino)-5-{2-[2-(7-methylquinoline-8-sulfonamido)phenyl]ethynyl}pyridine-2-carboxylate (10 mg; 0.02 mmol; 1 eq.), 3-{[(4-methoxyphenyl)methyl]amino}-5-{2-[2-(7-methylquinoline-8-sulfonamido)phenyl]ethynyl}pyridine-2-carboxylic acid (8 mg; 0.01 mmol; yield 82%) was obtained as yellow solid.

135

3-Amino-5-{2-[2-(7-methylquinoline-8-sulfonamido)phenyl]ethynyl}pyridine-2-carboxylic acid

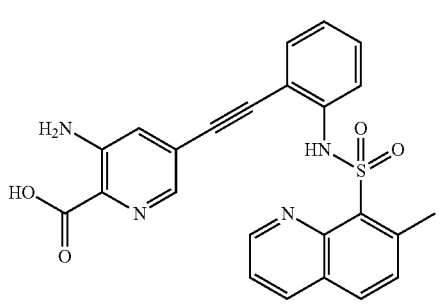 [SMILES: Cc1ccc2cccnc2c1S(=O)(=O)Nc1ccccc1C#Cc1cnc(C(=O)O)c(N)c1]

Saponification step was conducted accordingly to the procedure described above: Starting from methyl 3-amino-5-{2-[2-(7-methylquinoline-8-sulfon-amido)phenyl]ethynyl}pyridine-2-carboxylate (25 mg; 0.05 mmol; 1 eq.), the 3-amino-5-{2-[2-(7-methylquinoline-8-sulfonamido)phenyl]ethynyl}pyridine-2-carboxylic acid (11 mg; 0.02 mmol; yield 46%) was obtained as light yellow solid.

Example 28

8-{2-[2-(7-Methylquinoline-8-sulfonamido)phenyl]ethynyl}-1H,2H,3H,4H-pyrido[3,4-b]pyrazine-5-carboxylic acid

136

5,8-Dibromopyrido[3,4-b]pyrazine

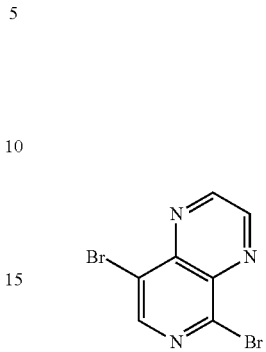

To a mixture of 3,4-diamino-2,5-dibromopyridine (300 mg; 1.12 mmol; 1 eq.) in anhydrous ethanol (2 ml) glyoxal 40 wt. % in water (0.45 ml; 4 mmol; 3.5 eq.) was added and reaction mixture was heated at 70° C. o/n. Ethanol was evaporated and the residue was purified by FCC (silica, hexane/EtOAc gradient) to afford 5,8-dibromo-pyrido[3,4-b]pyrazine (238 mg; 08 mmol; yield 70%) as light yellow solid.

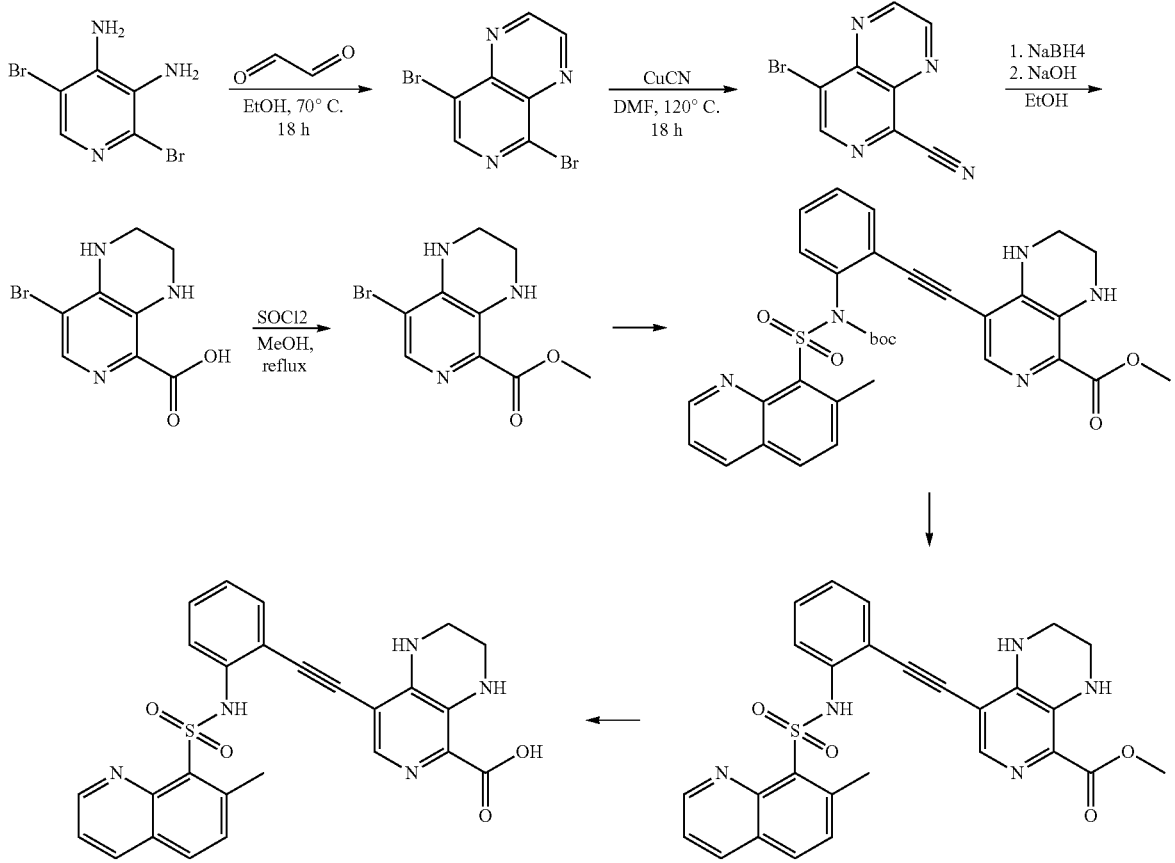

8-Bromopyrido[3,4-b]pyrazine-5-carbonitrile

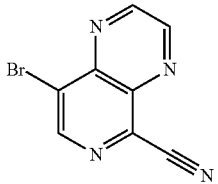 [SMILES: N#Cc1ncc(Br)c2nccnc12]

To a mixture of 5,8-dibromopyrido[3,4-b]pyrazine (238 mg; 0.79 mmol; 1 eq.) in anhydrous DMF 3 ml) placed in glass reacting vessel copper(I) cyanide (78 mg; 0.87 mmol; 1.1 eq.) was added and vessel was capped. The reaction mixture was heated at 120° C. overnight. Then reaction was quenched with water and resulted mixture was extracted with EtOAc. Organic layers were combined and washed with brine, dried over Na$_2$SO$_4$ and evaporated to give 8-bromopyrido[3,4-b]pyrazine-5-carbonitrile (190 mg; 0.47 mmol; yield 60%) as yellow solid. Crude product was used in without further purification.

8-Bromo-1H,2H,3H,4H-pyrido[3,4-b]pyrazine-5-carboxylic acid

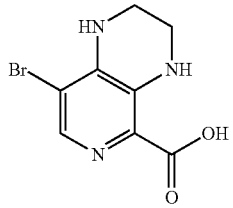 [SMILES: O=C(O)c1ncc(Br)c2c1NCCN2]

To a mixture of 8-bromopyrido[3,4-b]pyrazine-5-carbonitrile (190 mg; 0.47 mmol; 1 eq.) in anhydrous ethanol (4 ml), the sodium borohydride (63 mg; 1.66 mmol; 3.5 eq.) was added and RM was stirred at 40° C. overnight to complete reduction. The RM was cooled down to RT and 5M NaOH (1.2 ml; 5.68 mmol; 12 eq.) was added and RM was heated at 50° C. for 1 h. Then solvent was evaporated and the residue was portioned EtOAc and saturated sodium bicarbonate. Organic layers were combined and washed with brine, dried over Na$_2$SO$_4$ and evaporated to give 8-bromo-1H,2H,3H,4H-pyrido[3,4-b]pyrazine-5-carboxylic acid (124 mg; 0.35 mmol; yield 75%) as a colorless solid.

Methyl 8-bromo-1H,2H,3H,4H-pyrido[3,4-b]pyrazine-5-carboxylate

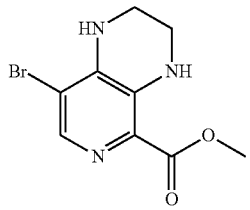

Thionyl chloride (0.3 ml; 4.07 mmol; 3 eq.) was dropped in to the mixture of 8-bromo-1H,2H,3H,4H-pyrido[3,4-b]pyrazine-5-carboxylic acid (110 mg; 0.14 mmol; 1 eq.) in anhydrous methanol (3 ml) placed in glass reacting vessel. The vessel was capped and RM was heated to reflux overnight. Then methanol was evaporated, and the residue was extracted with water and EtOAc. Organic layers were combined and subsequently washed with water, saturated sodium bicarbonate and brine. Organic layer was dried over Na$_2$SO$_4$ and evaporated to give methyl 8-bromo-1H,2H,3H,4H-pyrido[3,4-b]pyrazine-5-carboxylate (72. mg; 0.26 mmol; yield 72%) as an orange solid.

Methyl 8-[2-(2-{N-[(tert-butoxy)carbonyl]7-methylquinoline-8-sulfonamido}-phenyl)ethynyl]-1H,2H,3H,4H-pyrido[3,4-b]pyrazine-5-carboxylate

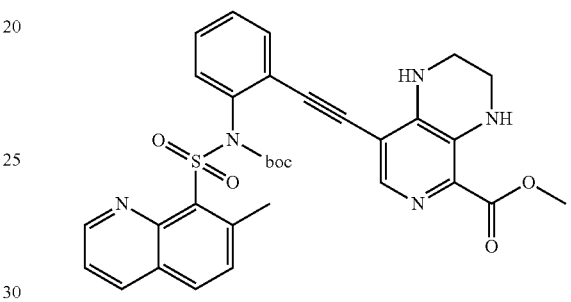

The Sonogashira coupling step was conducted according to the procedure for BOC protected sulfonamides as described above in Example 25: Starting from tert-butyl N-(2-ethynylphenyl)-N-[(7-methyl-8-quinolyl)sulfonyl]carbamate (85 mg; 0.19 mmol; 1 eq.) and methyl 8-bromo-1H,2H,3H,4H-pyrido[3,4-b]pyrazine-5-carboxylate (70 mg; 0.25 mmol; 1.3 eq.), the methyl 8-[2-(2-{N-[(tert-butoxy)carbonyl]7-methylquinoline-8-sulfonamido}phenyl)ethynyl]-1H,2H,3H,4H-pyrido[3,4-b]pyrazine-5-carboxylate (30 mg; 0.05 mmol; yield 25%) was obtained as orange solid.

Methyl 8-{2-[2-(7-methylquinoline-8-sulfonamido)phenyl]ethynyl}-1H,2H,3H,4H-pyrido[3,4-b]pyrazine-5-carboxylate

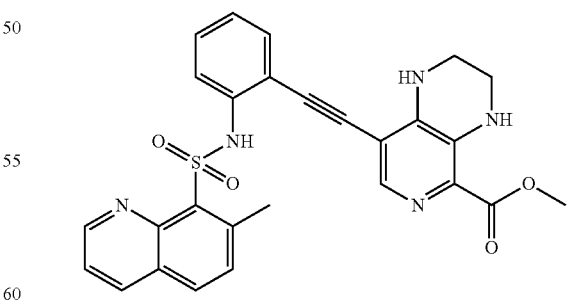

The boc deprotection step was conducted according to the procedure described above in Example 25: Starting from methyl 8-[2-(2-{N-[(tert-butoxy)carbonyl]7-methylquinoline-8-sulfonamido}phenyl)ethynyl]-1H,2H,3H,4H-pyrido[3,4-b]pyrazine-5-carboxylate (30 mg; 0.05 mmol; 1 eq.) methyl 8-{2-[2-(7-methylquinoline-8-sulfonamido)phenyl]

ethynyl}-1H,2H,3H,4H-pyrido[3,4-b]pyrazine-5-carboxylate (40 mg; 0.08 mmol) was obtained as brown solid.

8-{2-[2-(7-Methylquinoline-8-sulfonamido)phenyl]ethynyl}-1H,2H,3H,4H-pyrido[3,4-b]pyrazine-5-carboxylic acid

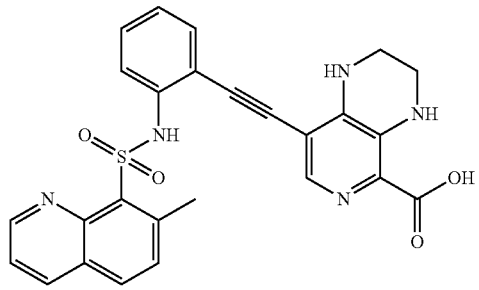 [SMILES: Cc1ccc2cccnc2c1S(=O)(=O)Nc1ccccc1C#Cc1cnc(C(=O)O)c2c1NCCN2]

The saponification step was conducted according to the procedure described above in Example 25: Starting from methyl 8-{2-[2-(7-methylquinoline-8-sulfonamido)phenyl]ethynyl}-1H,2H,3H,4H-pyrido[3,4-b]pyrazine-5-carboxylate (40 mg; 0.08 mmol; 1 eq.), the 8-{2-[2-(7-methylquinoline-8-sulfonamido)phenyl]ethynyl}-1H,2H,3H,4H-pyrido[3,4-b]pyrazine-5-carboxylic acid (22 mg; 0.04 mmol; yield 58%) was obtained as green solid.

Example 29

Synthesis of 5-[2-(9-Methyl-9H-carbazole-3-sulfonylamino)-phenyl-ethynyl]-pyridine-2-carboxylic acid

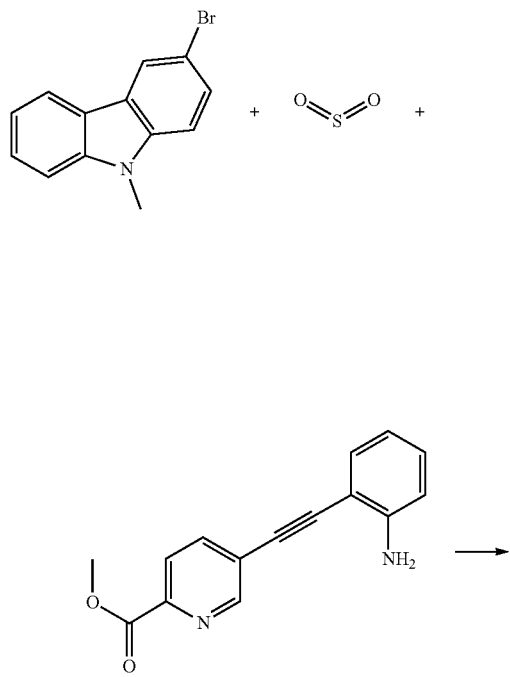

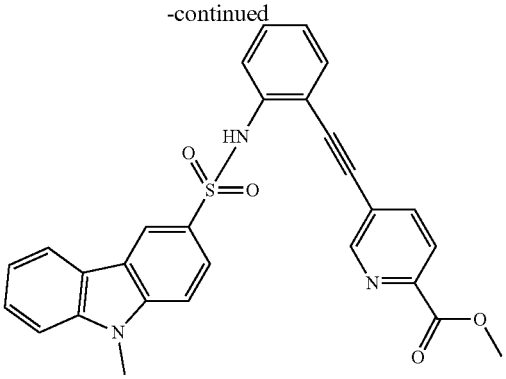

n-BuLi (2.5M in hexanes, 0.42 ml; 1.04 mmol) was added dropwise to a solution of 3-bromo-9-methyl-9H-carbazole (270.00 mg; 1.04 mmol) in dry Tetrahydrofuran (6.00 ml) at −78° C. and the reaction mixture was stirred at that temperature for 30 minutes. Then sulfur dioxide was conducted over the surface of the solution for 10 min. The reaction was allowed to warm to RT during ca. 1 h. After removal of the solvent, the residual crude lithium arylsulfinate was taken up in Dichloromethane (6.00 ml) and N-chlorosuccinimide (152.46 mg; 1.14 mmol) was added. The reaction was carried out in RT for 1 h. Then the solution was filtered and the filtrate was concentrated. The residue was dissolved in Pyridine (2.00 ml) and 5-(2-amino-phenylethynyl)-pyridine-2-carboxylic acid methyl ester (78.55 mg; 0.31 mmol) was added. Reaction was carried on in RT overnight. Then pyridine was co-evaporated with toluene and the residue was purified by FCC (SiHP 25 g, DCM-DCM:EtOAc 10% v/v) to yield 5-[2-(9-methyl-9H-carbazole-3-sulfonylamino)-phenylethynyl]-pyridine-2-carboxylic acid methyl ester (90.00 mg; 0.17 mmol; 16.1%; light yellow solid).

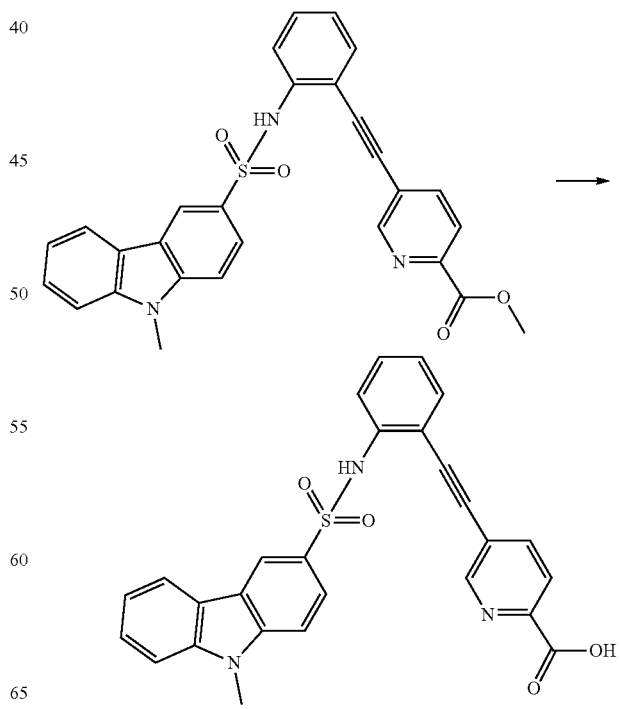

5-[2-(9-Methyl-9H-carbazole-3-sulfonylamino)-phenyl-ethynyl]-pyridine-2-carboxylic acid methyl ester (90.00 mg; 0.17 mmol) was dissolved in THF (2.00 ml) and methanol (5.00 ml). Water (2.00 ml) and lithium hydroxide hydrate (105.17 mg; 2.51 mmol; 15.00 eq.) was added. RM was stirred overnight in RT. Then RM was diluted with AcOEt, washed with water in the presence of 2M HCl and extracted with AcOEt. Combined organic layers were washed with brine, dried over $Na_2SO4$ and evaporated. Crude product was purified by preparative HPLC (ACN/0.1% TFA) to give 5-[2-(9-Methyl-9H-carbazole-3-sulfonylamino)-phenyl-ethynyl]-pyridine-2-carboxylic acid (77.00 mg; 0.16 mmol; 95.7%; yellow solid; purified product).

Example 30

Synthesis of 5-{2-[5-chloro-2-(5-methoxyquinoline-8-sulfonamido)-phenyl]ethynyl}-4-methoxy-N,N-dimethylpyridine-2-carboxamide

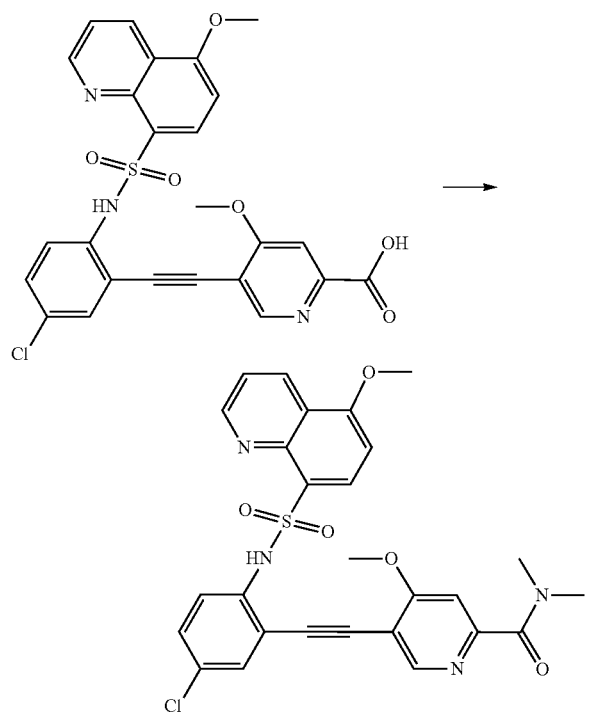

To a solution of 5-[5-chloro-2-(5-methoxy-quinoline-8-sulfonylamino)-phenyl-ethynyl]-4-methoxy-pyridine-2-carboxylic acid (30.0 mg; 0.06 mmol) in N,N-dimethylformamide (3.0 ml) was added dimethylamine (2.0 M in THF, 0.03 ml; 0.07 mmol), O-(7-azabenzotriazol-1-yl)-N,N,N',N'-tetramethyluronium $PF_6$, 97% (HATU) (32.7 mg; 0.09 mmol) and N-ethyldiisopropylamine (0.03 ml; 0.17 mmol). The reaction was stirred for 3 days at RT. HPLC-MS showed the complete formation of the required product. The reaction mixture was evaporated to dryness and the residue was purified by prep. HPLC giving 16 mg of the desired product as yellow solid.

Example 31

Synthesis of 2-methoxy-4-{2-[2-(5-methoxyquinoline-8-sulfonamido)-phenyl]ethynyl}-5-methylbenzoic acid

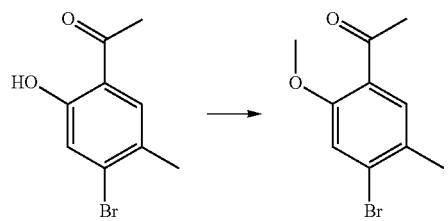

To a solution of 2-acetyl-4-methyl-5-bromophenol 97% (3.0 g; 13.10 mmol) in N,N-dimethylformamide (50.0 ml) was added iodomethane (0.9 ml; 14.41 mmol) and potassium carbonate (3.6 g; 26.19 mmol). The reaction was stirred for 16 h at RT. HPLC-MS showed the complete formation of the required product. The reaction was diluted with ethylacetate and extracted 3× with water, dried over $Na_2SO_4$ and evaporated to dryness.

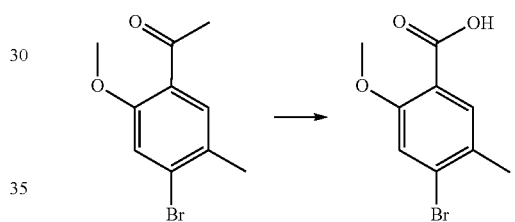

To a solution of 1-(4-bromo-2-methoxy-5-methyl-phenyl)-ethanone (3.6 g; 11.30 mmol) in 1,4-dioxane (50.0 ml) was added sodium hydroxide (4.5 g; 112.99 mmol) in water (50.0 ml). The solution was cooled to 0° C. and bromine (1.7 ml; 33.90 mmol) was added and stirred for 16 h at RT. HPLC-MS showed a not complete formation of the required product but as no progression after additional 8 h was observed it was worked up. The dioxane was removed under reduced pressure and the residue was acidified to pH 2 using 2N HCl.

The mixture was extracted 2× with EA and the combined organic layers were washed 3× with water, dried over $Na_2SO_4$ and evaporated to dryness.

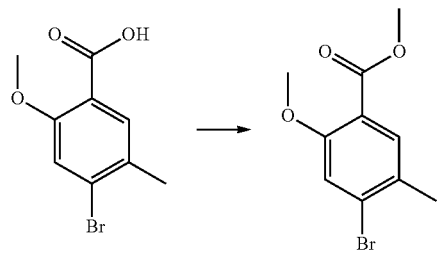

To a solution of 4-bromo-2-methoxy-5-methyl-benzoic acid (3.1 g; 7.70 mmol) in methanol (50.0 ml) was added in a flask sulfuric acid (95-98%) (0.6 ml; 0.01 mol) and stirred for 16 h at 65° C. HPLC-MS showed the complete formation of the required product. The reaction was evaporated to dryness. The residue was diluted with ethylacetate and extracted 3× with water, dried over Na$_2$SO$_4$ and evaporated to dryness. The residue was purified by flashchromatography giving 2 g of the product as yellow oil.

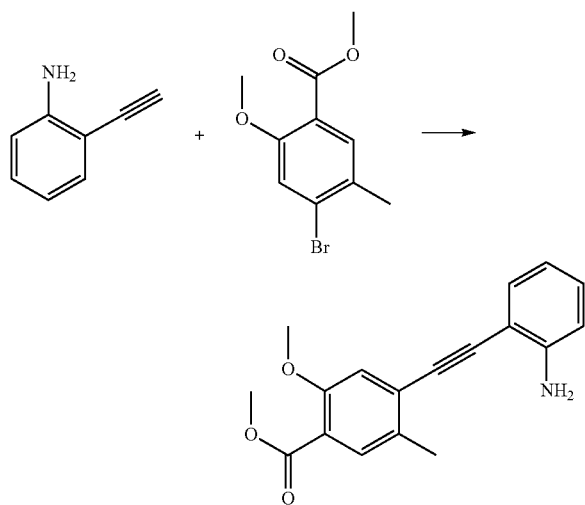

To a solution of 2-ethynylaniline (0.3 ml; 2.64 mmol) in acetonitrile (10.0 ml) was added in a microwave vial under nitrogen 4-bromo-2-methoxy-5-methyl-benzoic acid methyl ester (1.0 g; 3.96 mmol), copper (1) iodide (25.1 mg; 0.13 mmol), diisopropyl-amine (0.6 ml; 3.96 mmol) and tetrakis (triphenyl-phosphine)-palladium(0) (152.4 mg; 0.13 mmol). The reaction was stirred for 16 h at 80° C. HPLC-MS showed the complete formation of the required product. The reaction was cooled to RT and the precipitate was filtered off. The mother liquor was diluted with EA and extracted 3× with water, dried with Na$_2$SO$_4$ and evaporated to dryness. The residue was purified by flash chromatography giving 780 mg of the desired product as yellow solid.

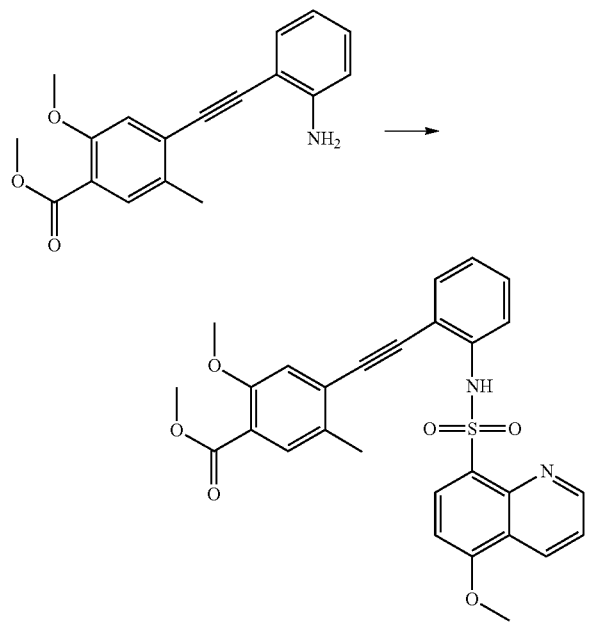

To a solution of 4-(2-amino-phenylethynyl)-2-methoxy-5-methyl-benzoic acid methyl ester (60.0 mg; 0.20 mmol) in pyridine (3.0 ml) was added 5-methoxyquinoline-8-sulfonyl chloride (153.4 mg; 0.60 mmol) in a microwave vial and stirred for 16 h at RT. HPLC-MS showed the formation of the required product. The reaction was diluted with EA and extracted 3× with water, dried over Na$_2$SO$_4$ and evaporated to dryness. The crude was used in next step without further purification.

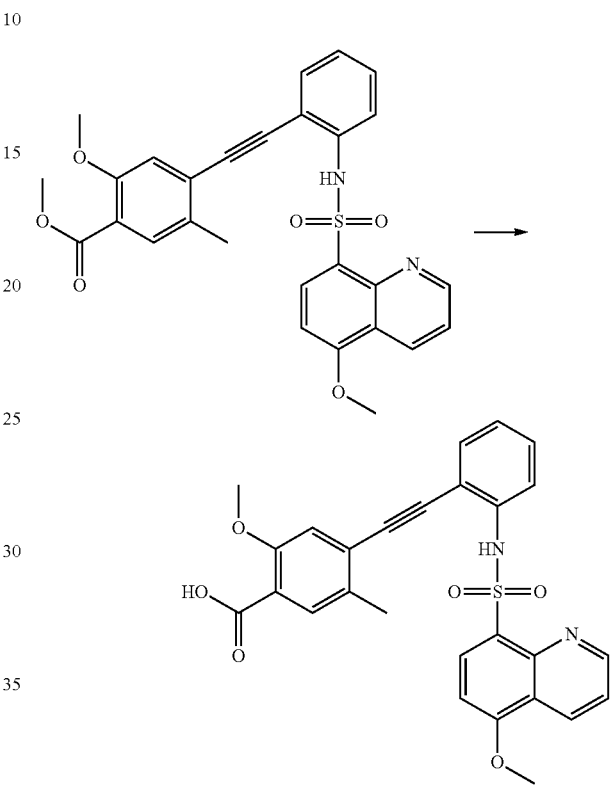

To a solution of 2-methoxy-4-[2-(5-methoxy-quinoline-8-sulfonylamino)-phenylethynyl]-5-methyl-benzoic acid methyl ester (118.0 mg; 0.21 mmol) in methanol (10.0 ml) was added sodium hydroxide solution (c(NaOH)=2 mol/l (2 N)) (2.1 ml; 4.11 mmol) and stirred for 16 h at RT. HPLC-MS showed an incomplete formation of the required product and the reaction was stirred for further 16 h at RT. HPLC-MS showed still some starting material but also some by product. The reaction was lyophilized and the residue was purified by prep. HPLC giving 16 mg of the desired product as yellow solid.

Example 32

Synthesis of 5-{2-[5-chloro-2-(5-ethoxyquinoline-8-sulfonamido)phenyl]-ethynyl}-4-methoxypyridine-2-carboxylic acid

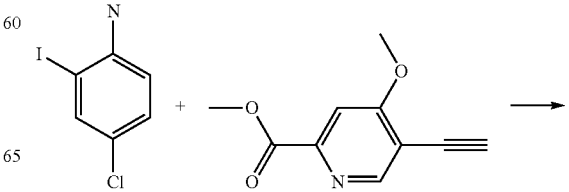

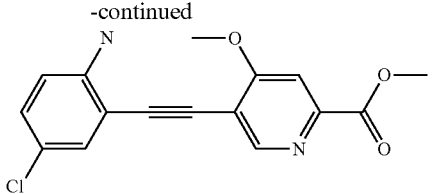

(Note: "—N" stands for "—NH₂")

To 4-Chloro-2-iodoaniline (3.0 g; 11.36 mmol) in acetonitrile (100 ml) was added in a flask under argon 5-ethynyl-4-methoxy-pyridine-2-carboxylic acid methyl ester (3.6 g; 17.04 mmol), Diisopropylamine (2.4 ml; 17.04 mmol), copper(I) iodide (216 mg; 1.14 mmol) and Tetrakis(triphenylphosphine)-palladium(0) (1.3 g; 1.14 mmol). The reaction was stirred for 16 hrs at 80° C. After cooling to room temperature the resulting precipitate was sucked off, washed with acetonitrile and dried in vacuum.

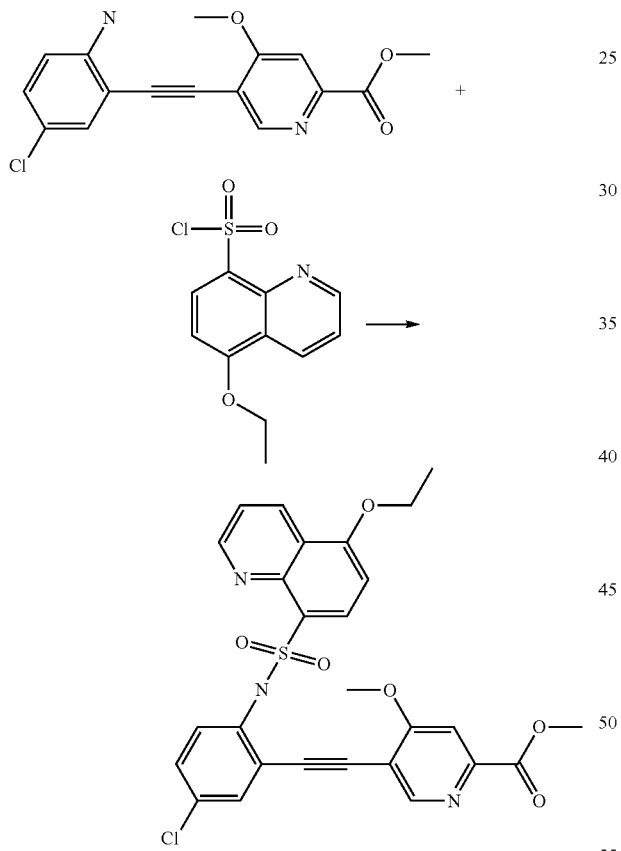

(Note: "—N" stands for "—NH₂"; "—N—" stands for "—N(H)—")

To a solution of 5-(2-Amino-5-chloro-phenylethynyl)-4-methoxy-pyridine-2-carboxylic acid methyl ester (1.5 g; 4.50 mmol) in pyridine (30 ml) was added 5-Ethoxyquionline-8-sulfonylchloride (3.7 g; 13.50 mmol) in a microwave vial and stirred for 3 days at RT. For work-up the reactions was diluted with ethylacetate and extracted 3× with water, dried over Na₂SO₄ and evaporated to dryness. The residue was purified by crystallization with methanol and dried in vacuum.

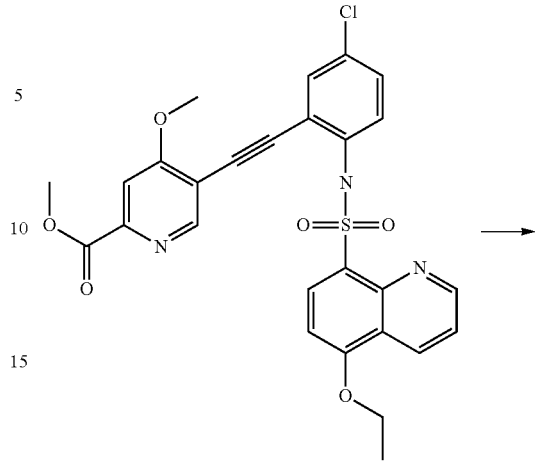

(Note: "—N—" stands for "—N(H)—"; "—O" stands for "—OH")

Methyl 5-{2-[5-chloro-2-(5-ethoxyquinoline-8-sulfonamido)phenyl]ethynyl}-4-methoxypyridine-2-carboxylate (2.2 g; 3.94 mmol) was dissolved in tetrahydrofuran (100 ml), sodium hydroxide solution c(NaOH)=2 mol/l (2 N) (3.9 ml; 7.88 mmol) was added and the reaction mixture was stirred for 16 hrs at RT. After that time more sodium hydroxide solution c(NaOH)=2 mol/l (2 N) (3.9 ml; 7.88 mmol) was added and stirring was continued for additional 3 hrs at RT. For work-up the suspension was acidified with HCl-37%, the resulting solution was diluted with ethylacetate and extracted 3× with a small amount of water. The organic layer was dried with Na₂SO₄, evaporated to dryness and the residue was triturated with ethylacetate/heptane and the precipitate was sucked off, washed with ethylacetate and dried in vacuum.

Example 33

Synthesis of 5-[2-(4-Dimethylamino-quinoline-8-sulfonylamino)-phenyl-ethynyl]-4-methyl-pyridine-2-carboxylic acid

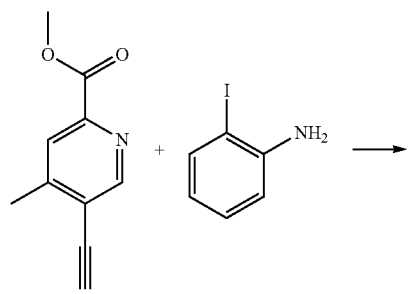

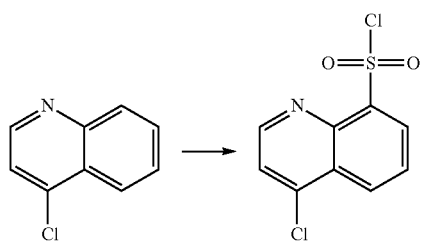 [SMILES: Clc1ccnc2ccccc12 ; O=S(=O)(Cl)c1cccc2c(Cl)ccnc12]

Into a 8-mL vial was placed methyl 5-ethynyl-4-methylpyridine-2-carboxylate (1.00 g, 5.480 mmol), 2-iodoaniline (1.90 g, 8.241 mmol), Pd(PPh₃)₂Cl₂ (0.61 g, 0.826 mmol), CuI (0.15 g, 0.748 mmol), ethyl acetate (20 mL). The resulting solution was stirred for 1 hr at 80° C. in an oil bath. The resulting mixture was concentrated. The residue was purified by silica gel column chromatography, eluted with PE/EtOAc (1:1) to afford methyl 5-[2-(2-aminophenyl)ethynyl]-4-methylpyridine-2-carboxylate (8 mg, 6%) as a yellow solid.

To a stirred solution of 4-chloroquinoline (1.00 g, 5.807 mmol) was added HSO₃Cl (4.00 mL, 57.722 mmol) dropwise at 0° C. The resulting mixture was stirred over night at 120° C. The reaction was quenched with ice at room temperature. The resulting mixture was extracted with CH₂Cl₂ (3×50 mL). The combined organic layers were washed with water (3×50 mL), dried over anhydrous Na₂SO₄. After filtration, the filtrate was concentrated under reduced pressure. This resulted in 4-chloroquinoline-8-sulfonyl chloride (207 mg, 14%) as a yellow solid.

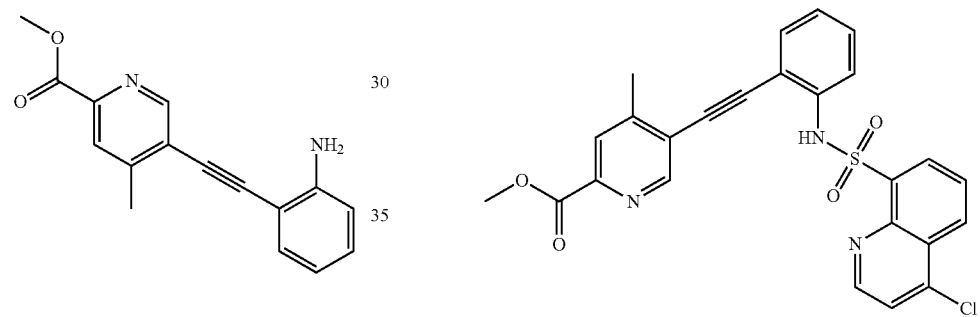

To a stirred solution of methyl 5-[2-(2-aminophenyl)ethynyl]-4-methylpyridine-2-carboxylate (200.00 mg, 0.750 mmol) and 4-chloroquinoline-8-sulfonyl chloride (621.00 mg, 2.251 mmol) in pyridine was added DMAP (289.45 mg, 2.251 mmol) dropwise at room temperature. The resulting mixture was stirred overnight at 50° C. The resulting mixture was concentrated under reduced pressure. The residue was purified by silica gel column chromatography, eluted with PE/EtOAc (1:1) to afford methyl 5-[2-[2-(4-chloroquinoline-8-sulfonamido)phenyl]ethynyl]-4-methylpyridine-2-carboxylate (125 mg, 30%) as a yellow solid.

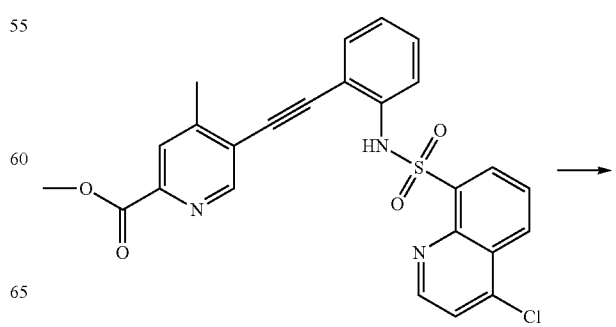

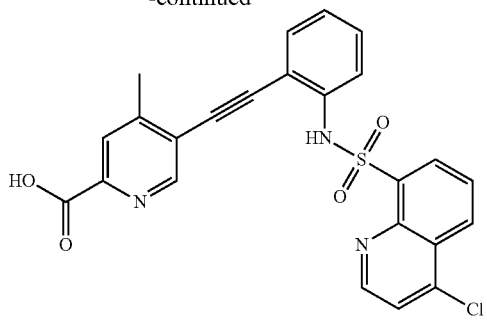

To a stirred solution of methyl 5-[2-[2-(4-chloroquinoline-8-sulfonamido)-phenyl]ethynyl]-4-methylpyridine-2-carboxylate (100.00 mg, 0.179 mmol) and LiOH (4.80 mg, 0.19 mmol) in THF was added H$_2$O (5 ml) dropwise at room temperature. The resulting mixture was stirred overnight at room temperature. The resulting mixture was concentrated under reduced pressure the residue was extracted with CH$_2$Cl$_2$ (3×20 mL). The combined organic layers were washed with water (3×20 mL), dried over anhydrous Na$_2$SO$_4$. After filtration, the filtrate was concentrated under reduced pressure. This resulted in 5-[2-[2-(4-chloroquinoline-8-sulfonamido)phenyl]ethynyl]-4-methylpyridine-2-carboxylic acid (85 mg, 99%) as a yellow solid.

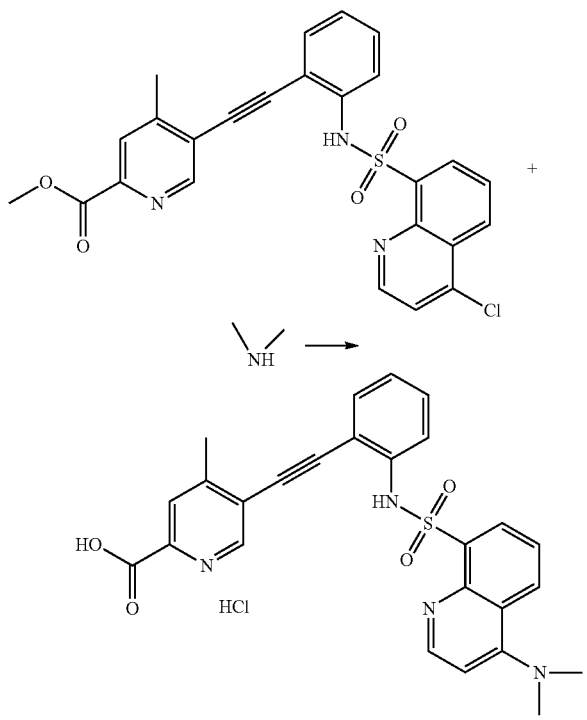

To a stirred solution of methyl 5-[2-[2-(4-chloroquinoline-8-sulfonamido)-phenyl]ethynyl]-4-methylpyridine-2-carboxylate (80.00 mg, 0.161 mmol) in MeOH was added dimethylamine (22.92 mg, 0.483 mmol) dropwise at room temperature. The resulting mixture was stirred overnight at room temperature. The resulting mixture was concentrated under reduced pressure. The crude product (80 mg) was purified by Prep-HPLC with the following conditions (2#SHIMADZU (HPLC-01)): Column, XBridge Shield RP18 OBD Column, 19*250 mm, 10 um; mobile phase, Water (0.05% HCl) and ACN (27% Phase B up to 45% in 8 min); Detector, UV. This resulted in 5-(2-[2-[4-(dimethylamino)quinoline-8-sulfonamido]phenyl]ethynyl)-4-methylpyridine-2-carboxylic acid hydrochloride (34.5 mg, 41%) as a white solid.

Example 34

Synthesis of 5-[2-(4-Dimethylamino-quinoline-8-sulfonylamino)-phenyl-ethynyl]-pyridine-2-carboxylic acid

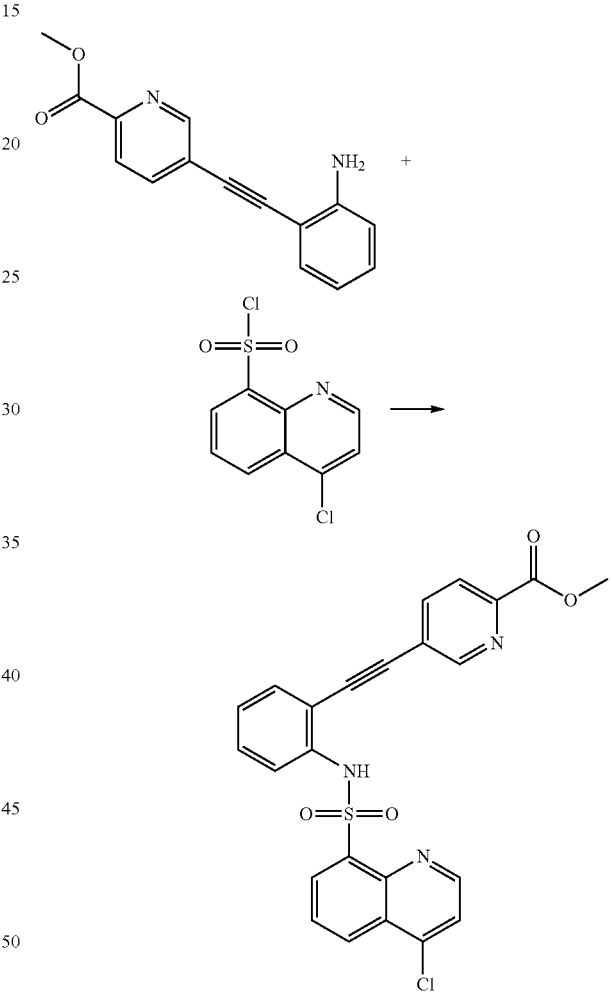

Into a 30-mL sealed tube, was placed methyl 5-[2-(2-aminophenyl)-ethynyl]pyridine-2-carboxylate (100 mg, 0.357 mmol), DMAP (225 mg, 1.750 mmol), pyridine (5 mL) and 4-chloroquinoline-8-sulfonyl chloride (810.53 mg, 2.647 mmol) (which can be prepared as described in Example 33). The resulting mixture was stirred over night at 54° C. The aqueous layer was extracted with ethyl acetate (3×50 mL). The combined organic layers were dried over Na$_2$SO$_4$. After filtration, the filtrate was concentrated under reduced pressure. The residue was purified by silica gel column chromatography, eluted with ethyl acetate/petroleum ether (4:1) to afford the crude product (100 mg). The crude product was purified by reverse phase flash chromatography with CH$_3$CN/H$_2$O (4:1) to afford methyl 5-[2-[2-

(4-chloroquinoline-8-sulfonamido)phenyl]ethynyl]pyridine-2-carboxylate (28 mg, 14%) as off-white solid.

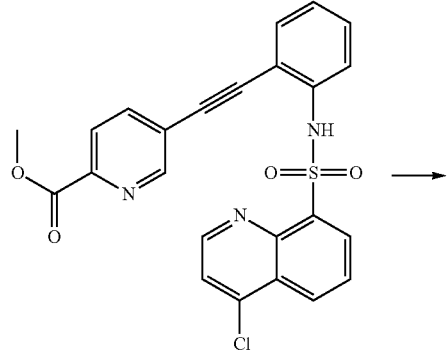

Into a 50-mL round-bottom flask were added methyl 5-[2-[2-(4-chloroquinoline-8-sulfonamido)phenyl]ethynyl]pyridine-2-carboxylate (28.00 mg, 0.035 mmol), THF (3 mL), LiOH (72.00 mg, 2.976 mmol) and H₂O (1.50 mL) at 25° C. The resulting mixture was stirred for 3 hr at that temperature. The mixture was neutralized to pH 5-6 with HCl (1 mol/L). The resulting mixture was extracted with ethyl acetate (3×50 mL). The combined organic layers were dried over anhydrous Na₂SO₄. After filtration, the filtrate was concentrated under reduced pressure. This resulted in 5-[2-[2-(4-chloroquinoline-8-sulfonamido)phenyl]ethynyl]pyridine-2-carboxylic acid (23 mg, 35%) as a yellow solid.

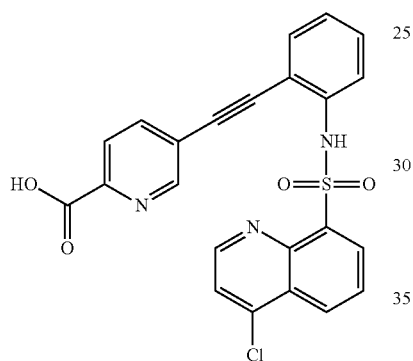

-continued

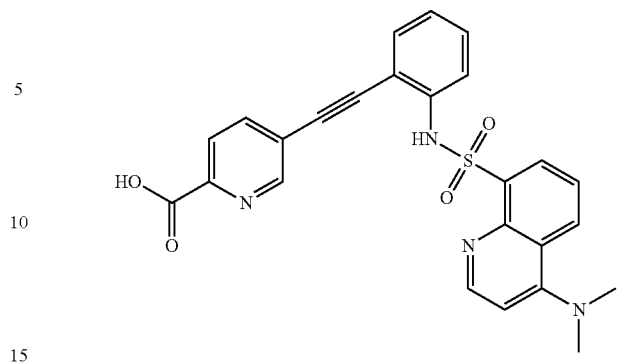

Into a 50-mL round-bottom flask were added 5-[2-[2-(4-chloroquinoline-8-sulfonamido)phenyl]ethynyl]pyridine-2-carboxylic acid (20.00 mg, 0.039 mmol) and Methylamine, 2M in methanol (6 mL) at 25° C. The resulting mixture was stirred for 18 hr at 25° C. The resulting mixture was concentrated under vacuum. The crude product (18 mg) was purified by Prep-HPLC with the following conditions (Column: XBridge Prep OBD C18 Column, 30×150 mm 5 um; Mobile Phase A: Water (10 mmoL/L NH₄HCO₃+0.1% NH₃.H₂O, Mobile Phase B: ACN; Flow rate: 60 mL/min; Gradient: 30B to 60 B in 8 min; 254 nm; RT1:6.8) to afford 5-(2-[2-[4-(dimethylamino)quinoline-8-sulfonamido]phenyl]ethynyl)pyridine-2-carboxylic acid (3.3 mg, 26%) as a white solid.

Example 35

Synthesis of 5-[2-[2-(4-Morpholin-4-yl-quinoline-8-sulfonylamino)-phenyl-ethynyl]-pyridine-2-carboxylic acid

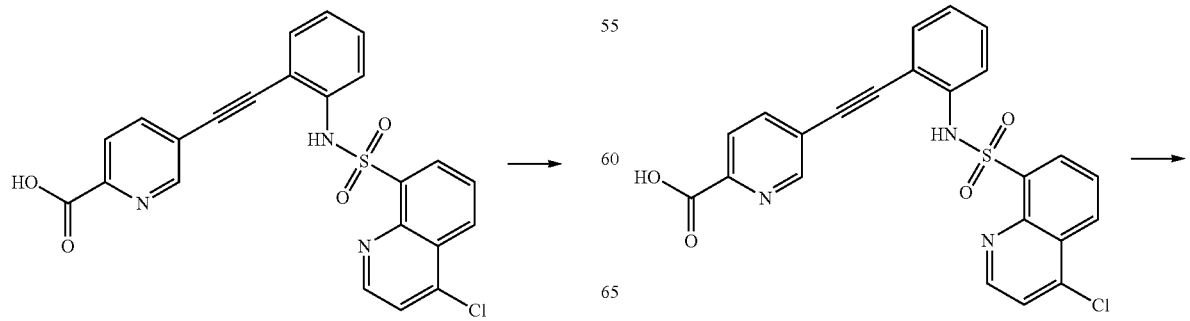

153

-continued

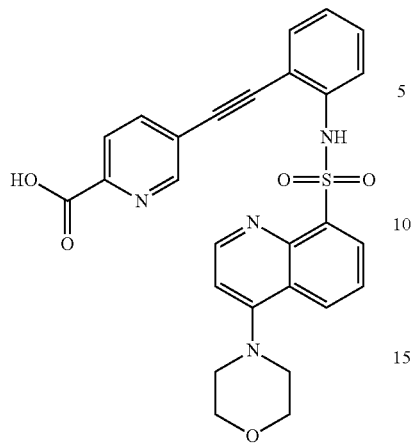

Into a 30-mL sealed tube were added 5-[2-[2-(4-chloro-quinoline-8-sulfon-amido)phenyl]ethynyl]pyridine-2-carboxylic acid (80.00 mg, 0.117 mmol), MeOH (5 mL) and morpholine (1 mL) at 25° C. The resulting mixture was stirred for 18 hr at 25° C. under N₂ atmosphere. The resulting mixture was concentrated under reduced pressure. The crude product was purified by Prep-HPLC with the following conditions (Column: XBridge Shield RP18 OBD Column 19×250 mm, 10 um; Mobile Phase A: Water (0.05% HCl), Mobile Phase B: ACN; Flow rate: 20 mL/min; Gradient: 35% B to 46% B in 9 min; 254 nm; Rt: 7.18 min) to afford 5-(2-[2-[4-(morpholin-4-yl)quinoline-8-sulfonamido]-phenyl]ethynyl)pyridine-2-carboxylic acid (20 mg, 33%) as a light yellow solid.

Example 36

Synthesis of 5-[2-(4-Methylamino-quinoline-8-sulfonylamino)-phenyl-ethynyl]-pyridine-2-carboxylic acid

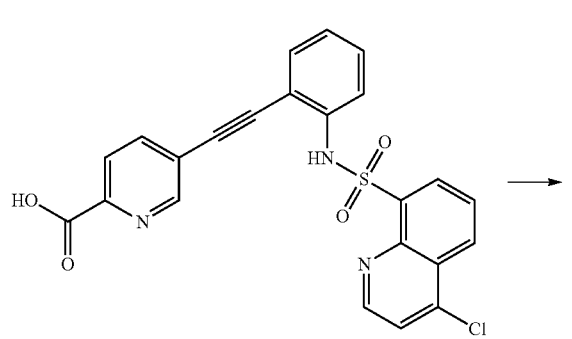

154

-continued

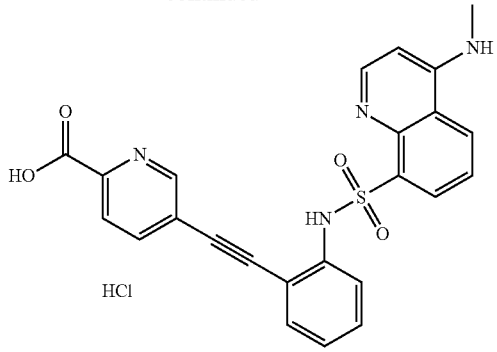

Into a 30-mL sealed tube were added 5-[2-[2-(4-chloro-quinoline-8-sulfon-amido)phenyl]ethynyl]pyridine-2-carboxylic acid (80.00 mg, 0.155 mmol) and methylamine (2M in methanol, 5 mL) at 25° C. The resulting mixture was stirred for 7 days at 25° C. under N₂ atmosphere. The resulting mixture was concentrated under reduced pressure. The crude product was purified by Prep-HPLC with the following conditions (Column: XBridge Prep OBD C18 Column, 30×150 mm 5 um; Mobile Phase A: Water (10 mmo/L NH₄HCO₃+0.1% NH3·H₂O), Mobile Phase B: ACN; Flow rate: 60 mL/min; Gradient: 30 B to 60 B in 8 min; 254 nm) to afford 5-(2-[2-[4-(methylamino)-quinoline-8-sulfonamido]phenyl]ethynyl)pyridine-2-carboxylic acid (3.5 mg, 5%) as a white solid.

Example 37

Synthesis of 4-Methyl-5-[2-(4-methylamino-quinoline-8-sulfonylamino)-phenylethynyl]-pyridine-2-carboxylic acid

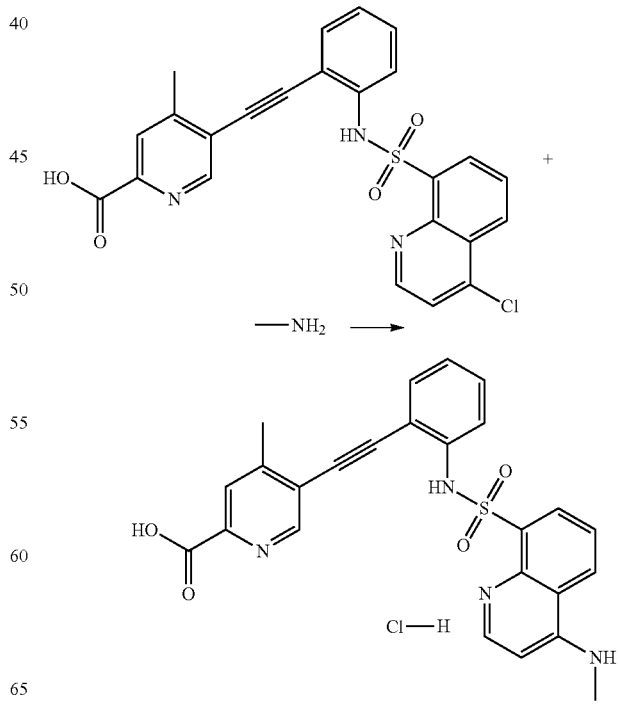

To a stirred solution of 5-[2-[2-(4-chloroquinoline-8-sulfonamido)phenyl]-ethynyl]-4-methylpyridine-2-carboxylic acid (80.00 mg, 0.167 mmol) in MeOH was added Methylamine (16.40 mg, 0.502 mmol) dropwise at room temperature. The resulting mixture was stirred overnight at room temperature. The resulting mixture was concentrated under reduced pressure. The crude product (100 mg) was purified by Prep-HPLC with the following conditions (2#SHIMADZU (HPLC-01)): Column, XBridge Prep OBD C18 Column, 30*150 mm 5 um; mobile phase, water (10 mmoL/L $NH_4HCO_3$+0.1% $NH_3.H_2O$) and ACN (20% PhaseB up to 50% in 8 min); Detector, UV.). This resulted in 4-methyl-5-(2-[2-[4-(methylamino)quinoline-8-sulfonamido]phenyl]ethynyl)pyridine-2-carboxylic acid hydrochloride (8.7 mg, 10%) as a white solid.

Into a 30-mL sealed tube were added 5-[2-[2-(4-chloroquinoline-8-sulfon-amido)phenyl]ethynyl]pyridine-2-carboxylic acid (80.00 mg, 0.155 mmol), Ethylamine solution 2.0 M in THF (160 μL, 0.444 mmol) and MeOH (5 mL) at 25° C. The resulting mixture was stirred for 7 days at 30° C. under $N_2$ atmosphere. The resulting mixture was concentrated under reduced pressure. The crude product was purified by Prep-HPLC with the following conditions (Column: XBridge Shield RP18 OBD Column, 30*150 mm, 5 um; Mobile Phase A: water (10 mmoL/L $NH_4HCO_3$+0.1% $NH_3.H_2O$), Mobile Phase B: ACN; Flow rate: 60 mL/min; Gradient: 15 B to 35 B in 8 min; 254 nm) to afford 5-(2-[2-[4-(ethylamino)quinoline-8-sulfonamido]phenyl]ethynyl)pyridine-2-carboxylic acid (3 mg, 4%) as a white solid.

Example 38

Synthesis of 5-[2-(4-Ethylamino-quinoline-8-sulfonylamino)-phenyl-ethynyl]-pyridine-2-carboxylic acid Example 39

Synthesis of 5-[2-(4-Isopropylamino-quinoline-8-sulfonylamino)-phenyl-ethynyl]-pyridine-2-carboxylic acid

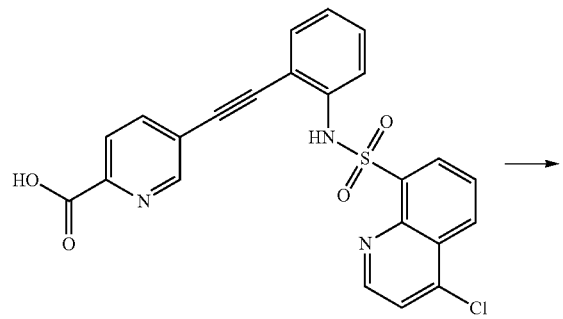

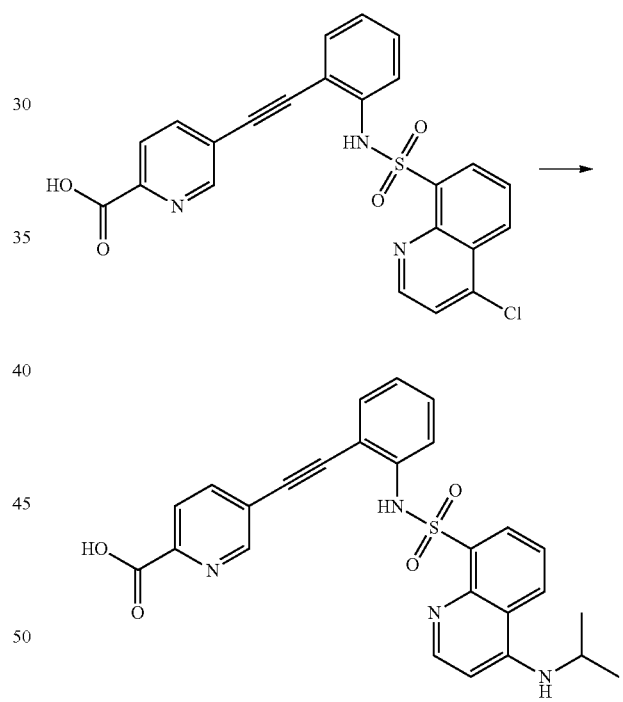

Into a 30 ml sealed tube were added 5-[2-[2-(4-chloroquinoline-8-sulfon-amido)phenyl]ethynyl]pyridine-2-carboxylic acid (190 mg, 0.279 mmol), propan-2-amine (173 uL, 2.785 mmol) and MeOH (5 mL) at 25° C. The resulting mixture was stirred for 14 days at 30° C. The resulting mixture was concentrated under reduced pressure. The crude product was purified by Prep-HPLC with the following conditions (Column: XBridge Shield RP18 OBD Column, 30*150 mm, 5 um; Mobile Phase A: Water (0.05% HCl), Mobile Phase B: ACN; Flow rate: 60 mL/min; Gradient: 15 B to 40 B in 8 min; 254 nm) to afford 5-(2-[2-[4-(isopropylamino)quinoline-8-sulfonamido]phenyl]ethynyl)pyridine-2-carboxylic acid (5 mg, 3%) as a white solid.

Example 40

Synthesis of 4-{2-[2-(4-chloroquinoline-8-sulfonamido)phenyl]ethynyl}-isoquinoline-1-carboxylic acid

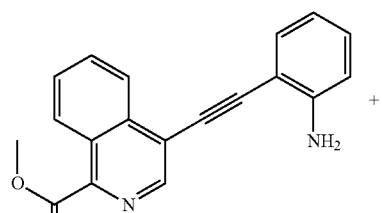

+

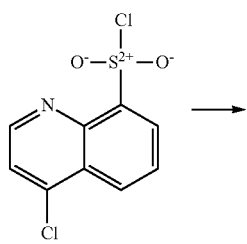

→

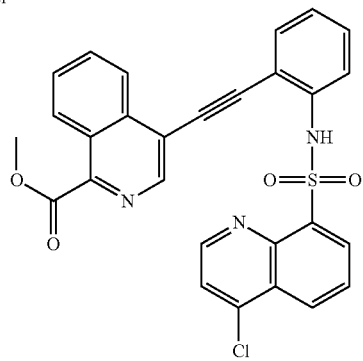

To a solution of methyl 4-[2-(2-aminophenyl)ethynyl]isoquinoline-1-carb-oxylate (50 mg; 0.17 mmol) in Pyridine (3 ml) was added 4-chloroquinoline-8-sulfonyl chloride (86.6 mg; 0.33 mmol) in a microwave vial and stirred for 3 days at RT. HPLC-MS showed the formation of the required product. The reaction was diluted with ethyl acetate and extracted 3× with water, dried over $Na_2SO_4$ and evaporated to dryness giving the crude as yellow solid in 48% yield (54 mg) which was used in the next step without further purification.

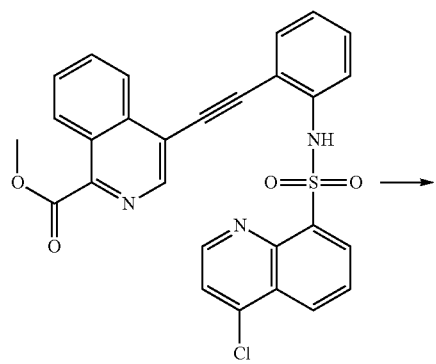

→

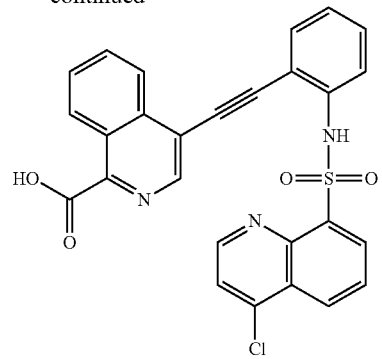

To a solution of methyl 4-{2-[2-(4-chloroquinoline-8-sulfonamido)phenyl]-ethynyl}isoquinoline-1-carboxylate (54 mg) in 1,4-Dioxane (3 ml) was added sodium hydroxide solution (c(NaOH)=2 mol/l (2 N)) (0.4 ml) and stirred for 16 hrs at RT. HPLC-MS showed the complete formation of the required product. The reaction was lyophilized. The residue was purified by prep. HPLC giving the product 4-{2-[2-(5-ethoxyquinoline-8-sulfonamido)phenyl]-ethynyl}isoquinoline-1-carboxylic acid as yellow solid in 37% yield (15 mg).

Example 41

Synthesis of 4-{2-[2-(5-ethoxyquinoline-8-sulfonamido)phenyl]ethynyl}-isoquinoline-1-carboxylic acid

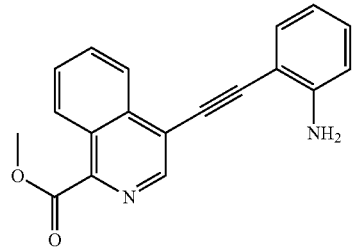

To a solution of methyl 4-bromoisoquinoline-1-carboxylate (650 mg; 2.44 mmol) in Acetonitrile (6 ml) was added 2-Ethynylaniline (0.4 ml; 3.66 mmol), copper (1) iodide (23.3 mg; 0.12 mmol), Diisopropyl-amine (0.5 ml; 3.66 mmol) and Tetrakis(triphenylphosphine)-palladium(0) (141.1 mg; 0.12 mmol) in a microwave vial under nitrogen. The reaction was stirred for 16 hrs at 100° C. HPLC-MS showed the complete formation of the required product. The reaction was cooled to RT and the yellow precipitate was filtered off, washed with ACN and dried in vacuum giving the product as brown solid, which was used in the next step without further purification.

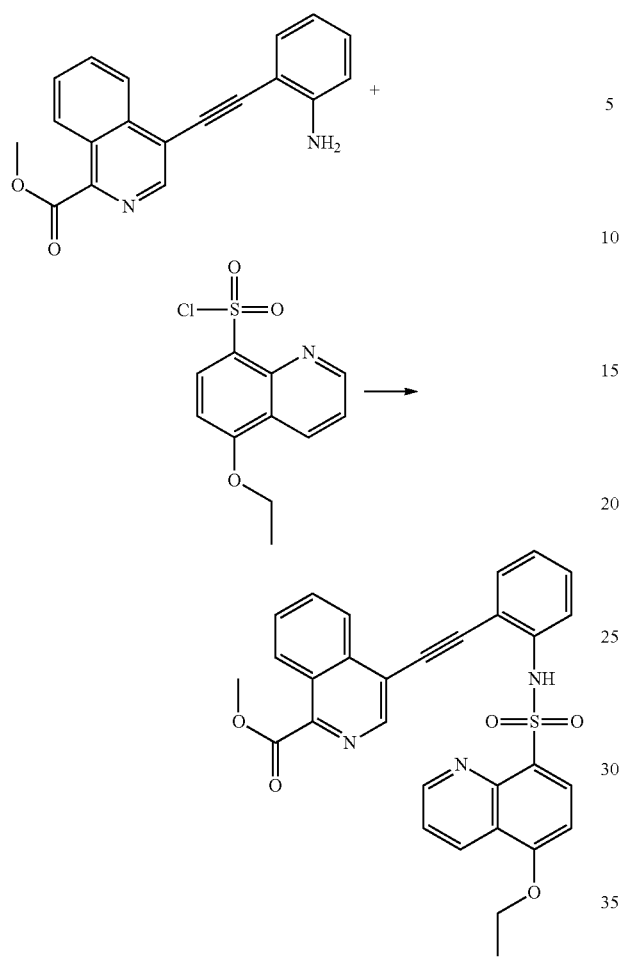

To a solution of methyl 4-[2-(2-aminophenyl)ethynyl]isoquinoline-1-carb-oxylate (80 mg; 0.26 mmol) in Pyridine (3 ml) was added 5-ethoxyquinoline-8-sulfonyl chloride (151.2 mg; 0.53 mmol) in a microwave vial and the mixture was stirred for 16 hrs at RT. HPLC-MS showed the complete formation of the required product. The reaction was diluted with ethyl acetate and extracted 3× with water, dried over Na₂SO₄ and evaporated to dryness giving the cure as beige solid in 62% yield (100 mg) which was used in the next step without further purification.

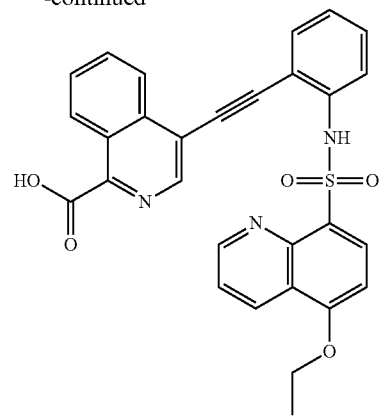

To a solution of methyl 4-{2-[2-(5-ethoxyquinoline-8-sulfonamido)phenyl]-ethynyl}isoquinoline-1-carboxylate (100 mg; 0.16 mmol) in 1,4-Dioxane (5 ml) was added Sodium hydroxide solution c(NaOH)=2 mol/l (2 N) (0.8 ml) and the mixture was stirred for 16 hrs at RT. HPLC-MS showed the complete formation of the required product. The reaction was lyophilized. The residue was purified by prep. HPLC giving the product 4-{2-[2-(5-ethoxyquinoline-8-sulfonamido)phenyl]ethynyl}isoquinoline-1-carboxylic acid as yellow solid in 47% yield (40 mg).

Example 42

Synthesis of 4-(2-{2-[4-(2-{2-[2-(2-aminoethoxy)ethoxy]ethoxy}ethoxy)-quinoline-8-sulfonamido]phenyl}ethynyl)isoquinoline-1-carboxylic acid

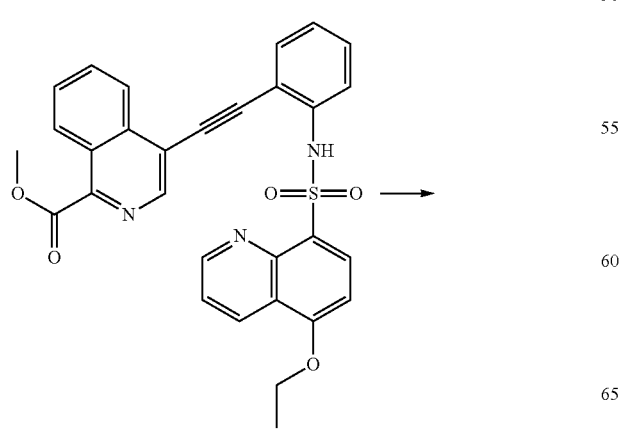

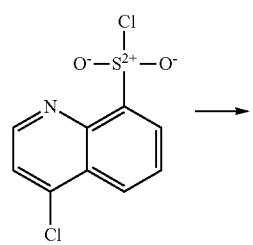

-continued

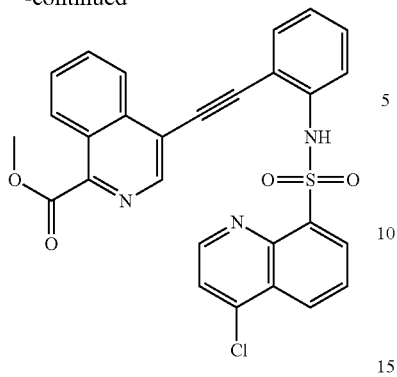

To a solution of methyl 4-[2-(2-aminophenyl)ethynyl]isoquinoline-1-carb-oxylate (200 mg; 0.66 mmol) in Pyridine (5 ml) was added 4-chloroquinoline-8-sulfonyl chloride (346.4 mg; 1.32 mmol) in a microwave vial and the mixture was stirred for 16 hrs at RT. HPLC-MS showed the formation of the required product. The reaction was diluted with ethyl acetate and extracted 3× with water, dried over $Na_2SO_4$ and evaporated to dryness. The product was obtained as brown oil in 77% yield (351 mg) and used in the next step without further purification.

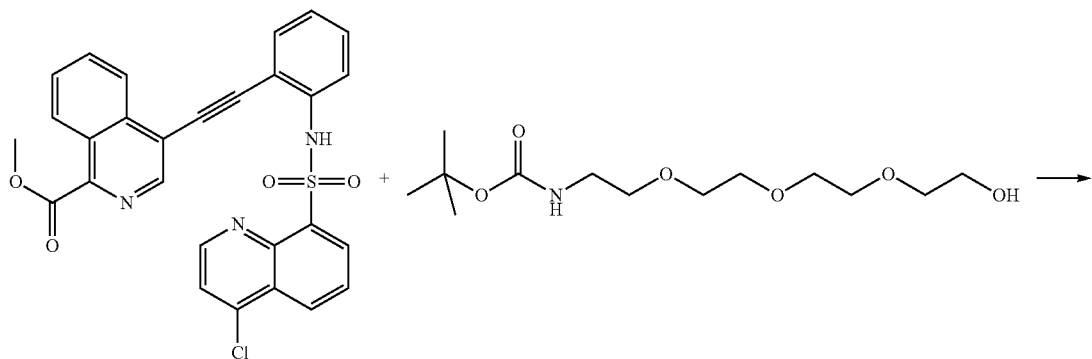

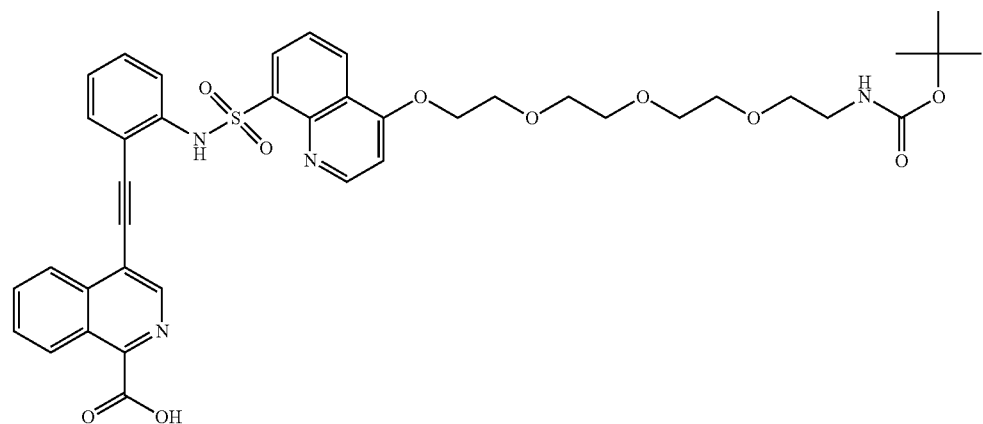

To a solution of methyl 4-{2-[2-(4-chloroquinoline-8-sulfonamido)phenyl]-ethynyl}isoquinoline-1-carboxylate in N,N-Dimethylformamide (4 ml) was added 1-Boc-Amino-3,6,9-trioxaundecanyl-11-ol (534.1 mg; 1.73 mmol) and Potassium tert-butylate (116.5 mg; 1.04 mmol) in a microwave vial. The reaction was stirred for 16 hrs at RT. HPLC-MS showed the complete formation of the required product. The reaction was acidified with HCl-1 N and extracted 3× with ethyl acetate. The combined organic layers were washed 3× with water, dried over $Na_2SO_4$ and evaporated to dryness giving the product as brown oil which was used in the next step without further purification.

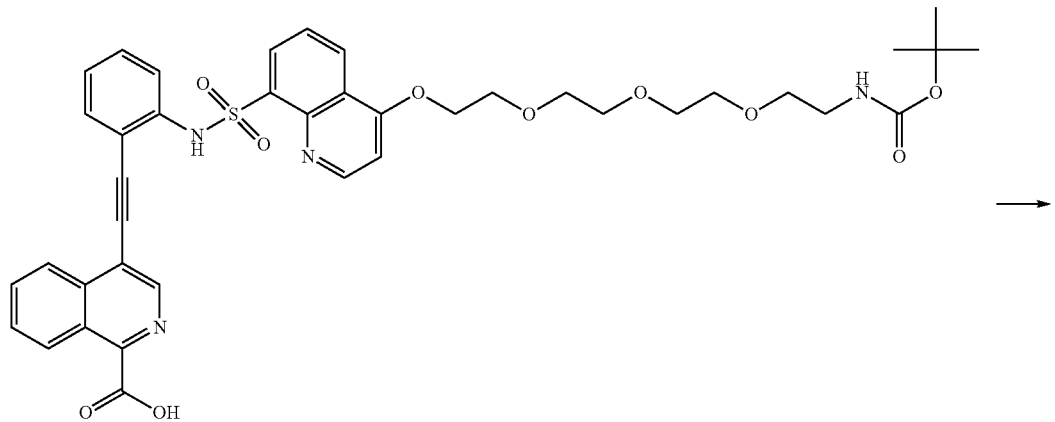

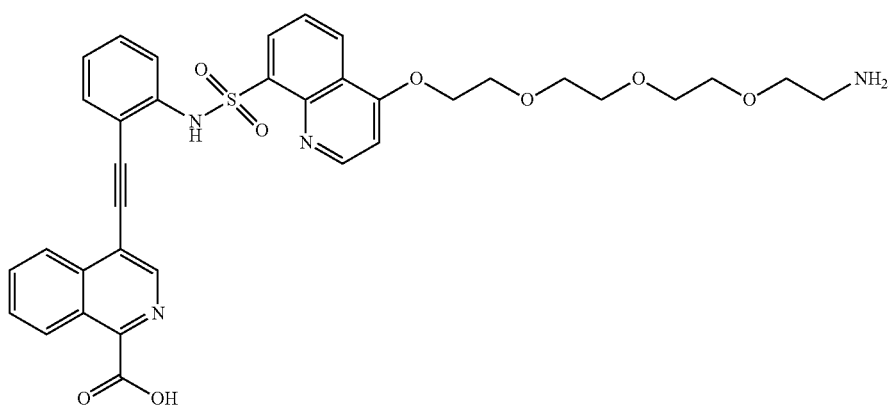

To a solution of 4-(2-{2-[4-(2-{2-[2-(2-{[(tert-butoxy)carbonyl]amino}ethoxy)-ethoxy]ethoxy}ethoxy)quinoline-8-sulfonamido]phenyl}ethynyl)isoquinoline-1-carboxylic acid (247 mg) in 1,4-Dioxane (200 ml) was added 4N HCl in dioxane (5 ml) and stirred for 16 hrs at RT. HPLC-MS showed the complete formation of the required product. The reactions were evaporated to dryness and the residue was purified by prep. HPLC giving the product 4-(2-{2-[4-(2-{2-[2-(2-aminoethoxy)ethoxy]ethoxy}ethoxy)quinoline-8-sulfonamido]phenyl}-ethynyl)isoquinoline-1-carboxylic acid as yellow solid in 47% yield (55 mg).

Example 43

Synthesis of 4-{2-[2-(2-methylquinoline-8-sulfonamido)phenyl]ethynyl}-isoquinoline-1-carboxylic acid

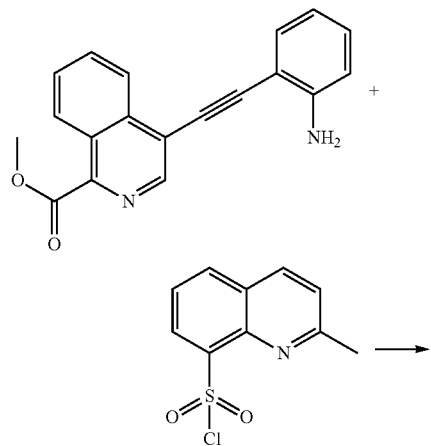

To a solution of methyl 4-[2-(2-aminophenyl)ethynyl]isoquinoline-1-carb-oxylate (80 mg; 0.26 mmol) in Pyridine (3 ml) was added 2-methylquinoline-8-sulfonyl chloride (134.5 mg; 0.53 mmol) in a microwave vial and the mixture was stirred for 16 hrs at RT. HPLC-MS showed the complete formation of the required product. The reaction was diluted with ethyl acetate and extracted 3× with water. dried over Na$_2$SO$_4$ and evaporated to dryness giving the product as brown solid in 36% yield (67 mg) which was used in the next step without further purification.

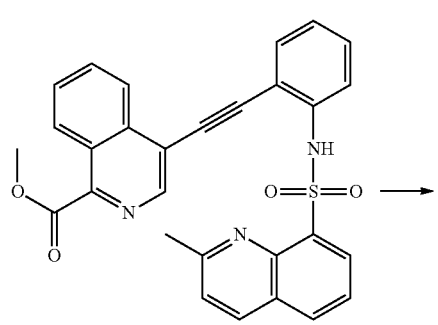

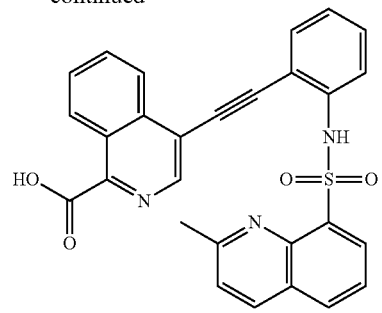

To a solution of methyl 4-{2-[2-(2-methylquinoline-8-sulfonamido)phenyl]-ethynyl}isoquinoline-1-carboxylate (67 mg; 0.09 mmol) in 1,4-Dioxane (3 ml) was added Sodium hydroxide solution c(NaOH)=2 mol/l (2 N) (0.5 ml) and the mixture was stirred for 16 hrs at RT. HPLC-MS showed the complete formation of the required product. The reaction was lyophilized. The residue was purified by prep. HPLC giving the product 4-{2-[2-(2-methylquinoline-8-sulfonamido)phenyl]ethynyl}isoquinoline-1-carboxylic acid in 98% yield (46 mg).

Example 44

Synthesis of 4-{2-[2-(7-ethylquinoline-8-sulfonamido)phenyl]ethynyl}-isoquinoline-1-carboxylic acid

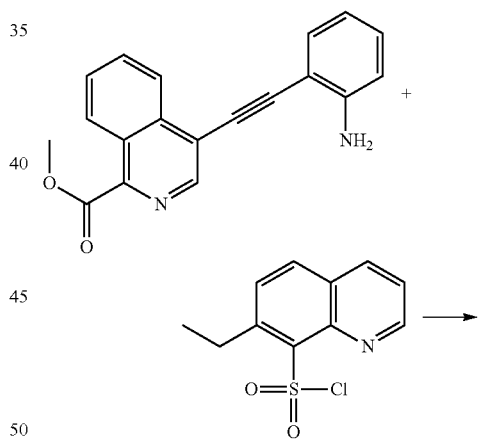

To a solution of methyl 4-[2-(2-aminophenyl)ethynyl]isoquinoline-1-carb-oxylate (60 mg; 0.20 mmol) in Pyridine (3 ml) was added 7-Ethylquinoline-8-sulfonylchloride (101.4 mg; 0.40 mmol) in a microwave vial and the mixture was stirred for 16 hrs at RT. HPLC-MS showed the complete formation of the required product. The reaction was diluted with ethyl acetate and extracted 3× with water, dried over Na$_2$SO$_4$ and evaporated to dryness giving the crude as yellow solid in 50% yield (54 mg) which was used in the next step without further purification.

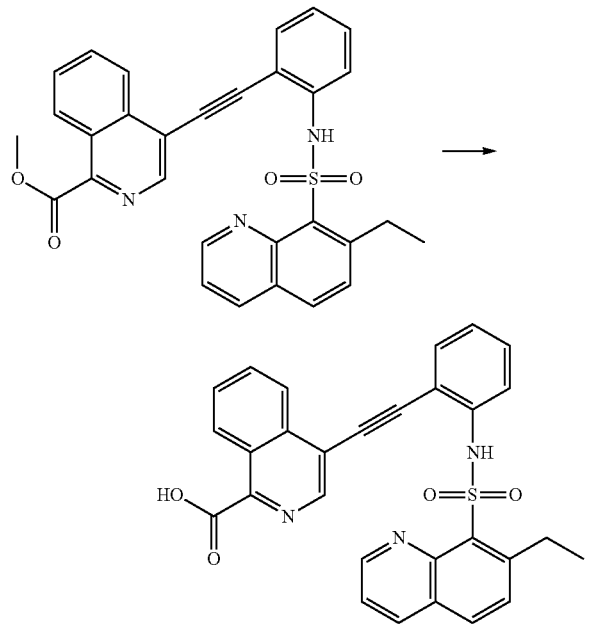

To a solution of methyl 4-{2-[2-(7-ethylquinoline-8-sulfonamido)phenyl]-ethynyl}isoquinoline-1-carboxylate (54 mg; 0.10 mmol) in 1,4-Dioxane (3 ml) was added Sodium hydroxide solution c(NaOH)=2 mol/l (2 N) (0.5 ml) and the mixture was stirred for 16 hrs at RT. HPLC-MS showed the complete formation of the required product. The reaction was lyophilized. The residue was purified by prep. HPLC giving the product 4-{2-[2-(7-ethylquinoline-8-sulfonamido)phenyl]ethynyl}isoquinoline-1-carboxylic acid a yellow solid in 46% yield (23 mg).

Example 45

Synthesis of 4-{2-[2-(5,7-dimethylquinoline-8-sulfonamido)phenyl]-ethynyl}isoquinoline-1-carboxylic acid

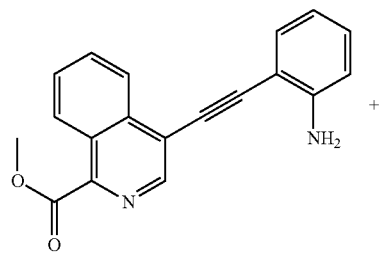

-continued

To a solution of methyl 4-[2-(2-aminophenyl)ethynyl]isoquinoline-1-carb-oxylate (60 mg; 0.20 mmol) in Pyridine (3 ml) was added 5,7-Dimethyl-quinoline-8-sulfonylchloride (101.4 mg; 0.40 mmol) in a microwave vial and the mixture was stirred for 16 hrs at RT. HPLC-MS showed a complete formation of the required product. The reaction was diluted with ethyl acetate and extracted 3× with water, dried over Na$_2$SO$_4$ and evaporated to dryness giving the product as orange oil in 40% yield (57 mg) which was used in the next step without further purification.

To a solution of methyl 4-{2-[2-(5,7-dimethylquinoline-8-sulfonamido)phenyl]-ethynyl}isoquinoline-1-carboxylate (57 mg; 0.08 mmol) in 1,4-Dioxane (3 ml) was added Sodium hydroxide solution c(NaOH)=2 mol/l (2 N) (0.4 ml) and the mixture was stirred for 16 hrs at RT. HPLC-MS showed the complete formation of the required product. The reaction was lyophilized. The residue was purified by prep. HPLC giving the product 4-{2-[2-(5,7-dimethylquinoline-8-sulfonamido)phenyl]ethynyl}isoquinoline-1-carboxylic acid as yellow solid in 15% yield (6 mg).

Example 46

Synthesis of 4-(2-{2-[5-(propan-2-yloxy)quinoline-8-sulfonamido]-phenyl}ethynyl)isoquinoline-1-carboxylic acid

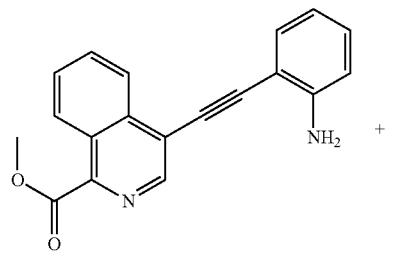

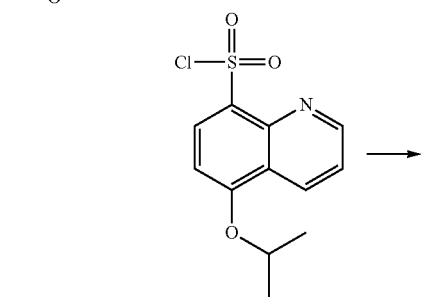

To a solution of methyl 4-[2-(2-aminophenyl)ethynyl]isoquinoline-1-carb-oxylate (60 mg; 0.20 mmol) in Pyridine (3 ml) was added 5-(Propan-2-yloxy)quinoline-8-sulfonylchloride (113.3 mg; 0.40 mmol) in a microwave vial and the mixture was stirred for 16 hrs at RT. HPLC-MS showed a complete formation of the required product. The reaction was diluted with ethyl acetate and extracted 3× with water, dried over Na$_2$SO$_4$ and evaporated to dryness giving the crude product as brown oil in 55% yield (70 mg) which was used in the next step without further purification.

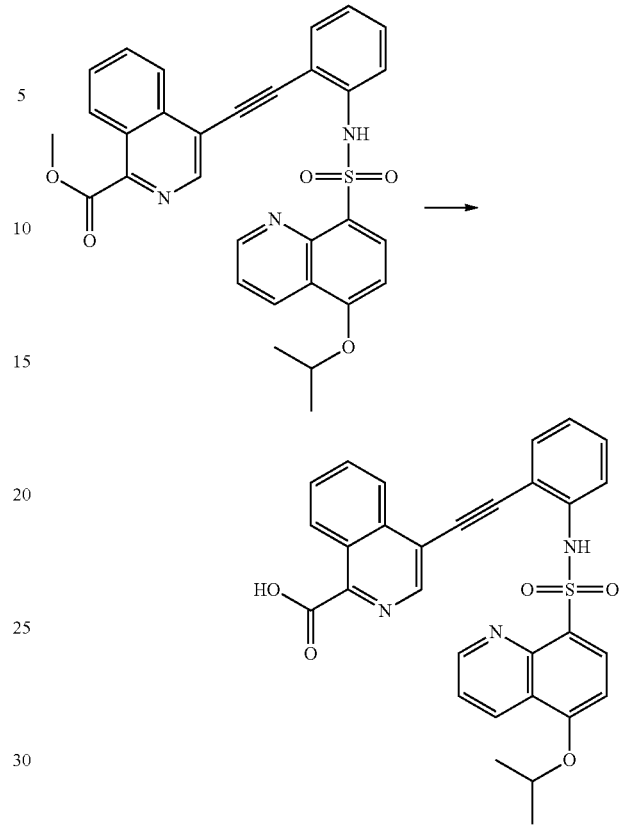

To a solution of methyl 4-(2-{2-[5-(propan-2-yloxy)quinoline-8-sulfonamido]-phenyl}ethynyl)isoquinoline-1-carboxylate (70.0 mg; 0.11 mmol) in 1,4-Dioxane (3 ml) was added Sodium hydroxide solution c(NaOH)=2 mol/l (2 N) (0.5 ml) and stirred for 16 hrs at RT. HPLC-MS showed the complete formation of the required product. The reaction was lyophilized. The residue was purified by prep. HPLC giving the product 4-(2-{2-[5-(propan-2-yloxy)quinoline-8-sulfonamido]phenyl}ethynyl)isoquinoline-1-carboxylic acid as yellow solid in 55% yield (32 mg).

Example 47

Synthesis of 3-Ethyl-5-[2-(5-methoxy-quinoline-8-sulfonylamino)-phenylethynyl]-pyridine-2-carboxylic acid

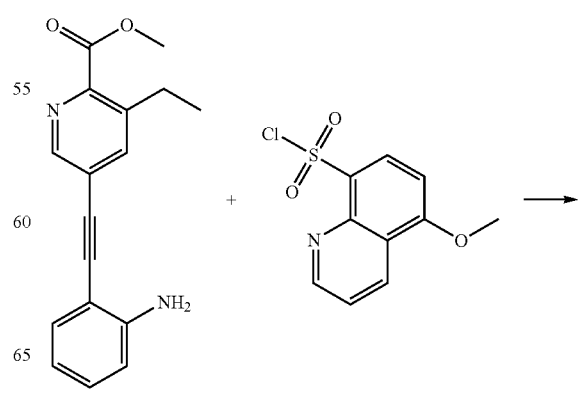

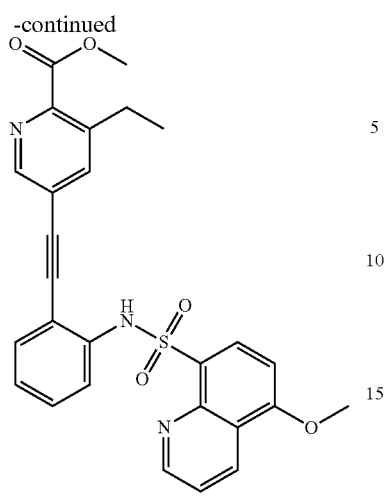

Into a 10 mL sealed tube were added methyl 5-[2-(2-aminophenyl)ethynyl]-3-ethylpyridine-2-carboxylate (20 mg, 0.070 mmol), Pyridine (1 mL), 5-methoxyquinoline-8-sulfonyl chloride (37 mg, 0.137 mmol) and DMAP (9.02 mg, 0.070 mmol) at room temperature. The resulting mixture was stirred for 3 h at 90° C. under nitrogen atmosphere. The crude was used in the next reaction without any further purification.

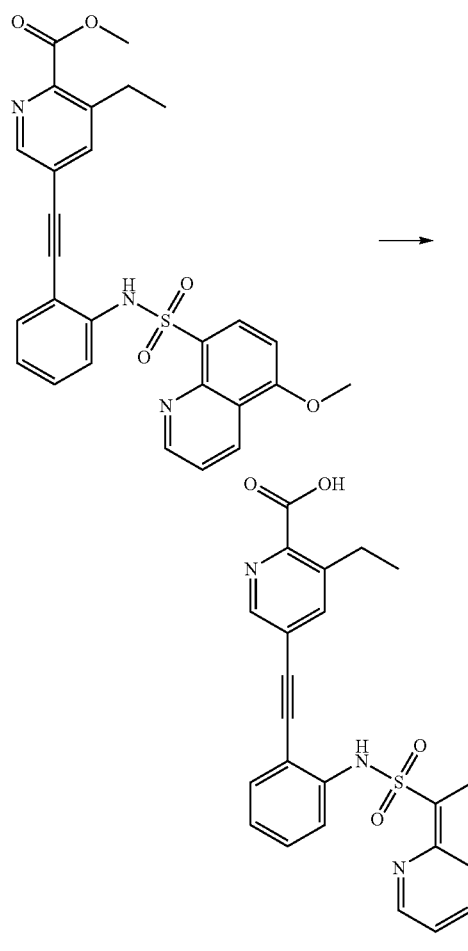

To a stirred solution of methyl 3-ethyl-5-[2-[2-(5-methoxyquinoline-8-sulfon-amido)phenyl]ethynyl]pyridine-2-carboxylate (100 mg, 0.195 mmol) and LiOH (80 mg, 3.174 mmol) in THF (8 mL) was added H2O (4 mL) dropwise at room temperature. The resulting mixture was stirred for 2 h at room temperature under nitrogen atmosphere. The mixture was acidified to pH 6 with HCl (aq.). The aqueous layer was extracted with CH2Cl2(3×30 mL). The resulting mixture was concentrated under vacuum. The crude product (100 mg) was purified by Prep-HPLC to afford 3-ethyl-5-[2-[2-(5-methoxyquinoline-8-sulfonamido)phenyl]ethynyl]pyridine-2-carboxylic acid (14.6 mg, 15%) as a white solid.

Example 48—General Procedure 7 (GP7)

Compounds of formula (I) with $L^1$ being divalent —N=radical, $L^2$ being a divalent —S(=O)($R^a$)— radical and $L^3$ being a single bond may be prepared in accordance to the following schemes and synthetic procedure described below with reference to 5-[2-(2-{[methyl(oxo)phenyl-A6-sulfanylidene]amino}-phenyl)ethynyl]pyridine-2-carboxylic acid:

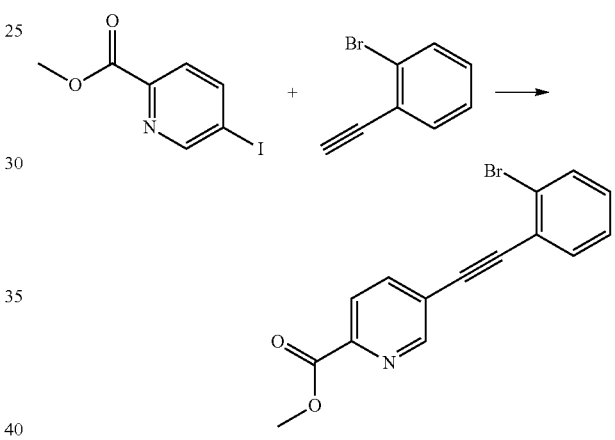

To a solution of Methyl 5-iodopicolinate (600.0 mg; 2.28 mmol) in Acetonitrile (10 ml) was added under argon in a microwave-vial 2-Bromophenylacetylene (619.4 mg; 3.42 mmol), Diisopropylamine (0.5 ml), Copper(I) iodide (43 mg; 0.23 mmol) and Tetrakis(triphenylphosphine)-palladium(0) for synthesis (263.6 mg; 0.23 mmol). The reaction was stirred for 16 hrs at 80° C. HPLC-MS showed the complete formation of the required product. The reaction was diluted with ethyl acetate and extracted 3× with water, dried over Na2SO4 and evaporated to dryness. The residue was purified by flash chromatography giving the product methyl 5-[2-(2-bromophenyl)ethynyl]pyridine-2-carboxylate in 73% yield (690 mg

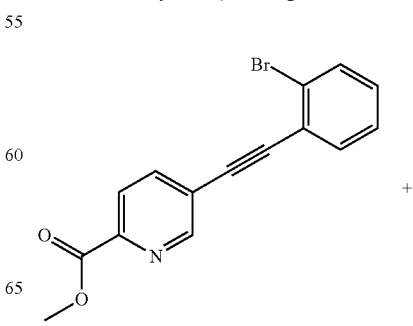

+

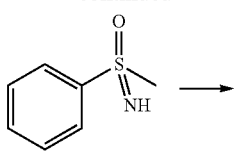

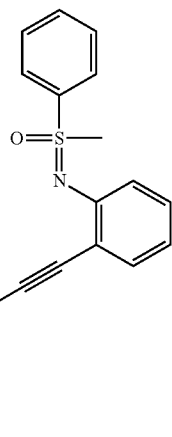

To a solution of methyl 5-[2-(2-bromophenyl)ethynyl]pyridine-2-carboxylate (50.0 mg; 0.12 mmol) in Toluene (3 ml) was added in a microwave vial under argon S-Methyl-S-phenylsulfoximine (22.5 mg; 0.14 mmol), Cesium carbonate (118 mg; 0.36 mmol), 2-Dicyclohexylphosphino-2',6'-diisopropoxybiphenyl (RuPhos) (11.9 mg; 0.02 mmol) and Palladium(II) acetate (47% Pd) for synthesis (2.7 mg; 0.01 mmol). The reaction was stirred for 16 hrs at 110° C. HPLC-MS showed the complete formation of the required product. The reaction was evaporated to dryness. The residue was diluted with ethyl acetate and extracted 3× with water, dried over Na2SO4 and evaporated to dryness. The residue was purified by flash chromatography giving the product methyl 5-[2-(2-{[methyl(oxo)phenyl-?6-sulfanylidene]amino}phenyl)ethynyl]pyridine-2-carboxylate as yellow oil in 38% yield (19 mg).

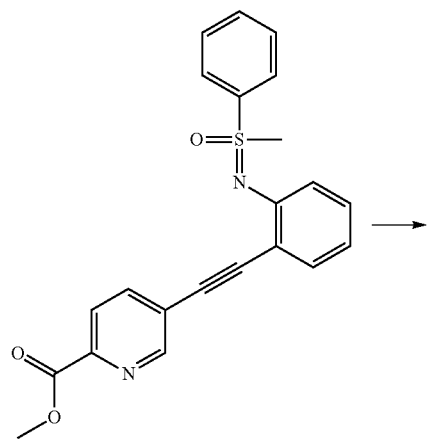

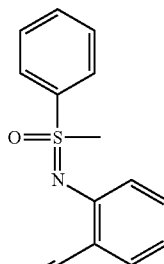

To a solution of methyl 5-[2-(2-{[methyl(oxo)phenyl-?6-sulfanylidene]amino}-phenyl)ethynyl]pyridine-2-carboxylate (19.0 mg; 0.05 mmol) in Methanol (5 ml) was added Sodium hydroxide solution c(NaOH)=2 mol/l (2 N) (0.5 ml) and stirred for 16 hrs at RT. HPLC-MS showed the complete formation of the required product. The reaction was evaporated to dryness. The residue was purified by prep. HPLC giving the product 5-[2-(2-{[methyl(oxo)phenyl-A6-sulfanylidene]amino}phenyl)ethynyl]pyridine-2-carboxylic acid as yellow solid in 84% yield (15 mg).

Example 49

Synthesis of 5-[2-(2-{[(4-methoxyphenyl)(methyl)oxo-A6-sulfanylidene]-amino}phenyl)ethynyl]pyridine-2-carboxylic acid

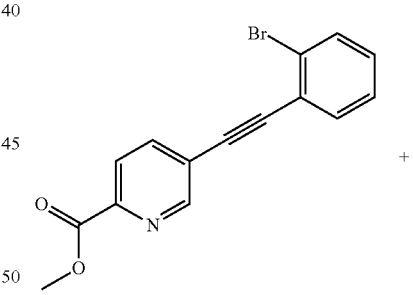

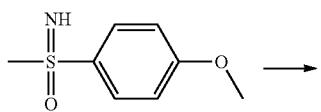

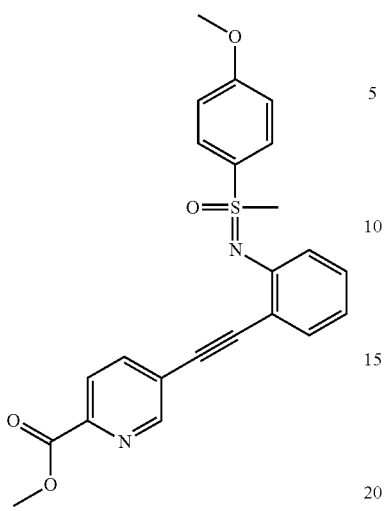

To a solution of methyl 5-[2-(2-bromophenyl)ethynyl]pyridine-2-carboxylate (70.0 mg; 0.17 mmol) in Toluene (3 ml) was added in a microwave vial under argon imino(4-methoxyphenyl)methyl-lambda6-sulfanone (37.6 mg; 0.20 mmol), Cesium carbonate (165 mg; 0.51 mmol), 2-Dicyclohexylphosphino-2',6'-diisopropoxybiphenyl (RuPhos) (16.6 mg; 0.03 mmol) and Palladium(II) acetate (47% Pd, 3.8 mg; 0.02 mmol). The reaction was stirred for 16 hrs at 110° C. HPLC-MS showed the complete formation of the required product. The reaction was diluted with ethyl acetate and extracted 3× with water, dried over $Na_2SO_4$ and evaporated to dryness. The residue was purified by flash chromatography giving the product as brown oil in 17% yield (16 mg).

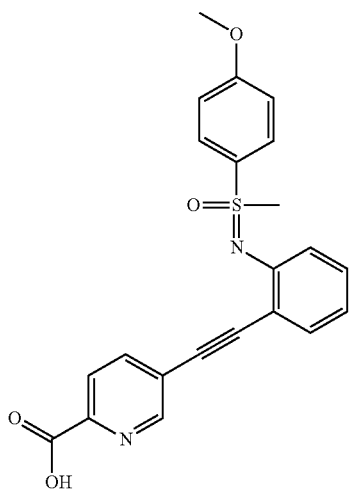

To a solution of methyl 5-[2-(2-{[(4-methoxyphenyl)(methyl)oxo-A6-sulfanylidene]amino}phenyl)ethynyl]pyridine-2-carboxylate (16 mg; 0.03 mmol) in Methanol (5 ml) was added Sodium hydroxide solution c(NaOH)=2 mol/l (2 N) (0.3 ml) and stirred for 16 hrs at RT. HPLC-MS showed the complete formation of the required product. The reaction was evaporated to dryness. The residue was purified by prep. HPLC giving the product 5-[2-(2-{[(4-methoxyphenyl)(methyl)oxo-A6-sulfanylidene]-amino}phenyl)ethynyl]pyridine-2-carboxylic acid as yellow solid in 52% yield (6 mg).

Example 50

Synthesis of 5-[2-(2-{[methyl(oxo)(quinolin-8-yl)-A6-sulfanylidene]-amino}phenyl)ethynyl]pyridine-2-carboxylic acid

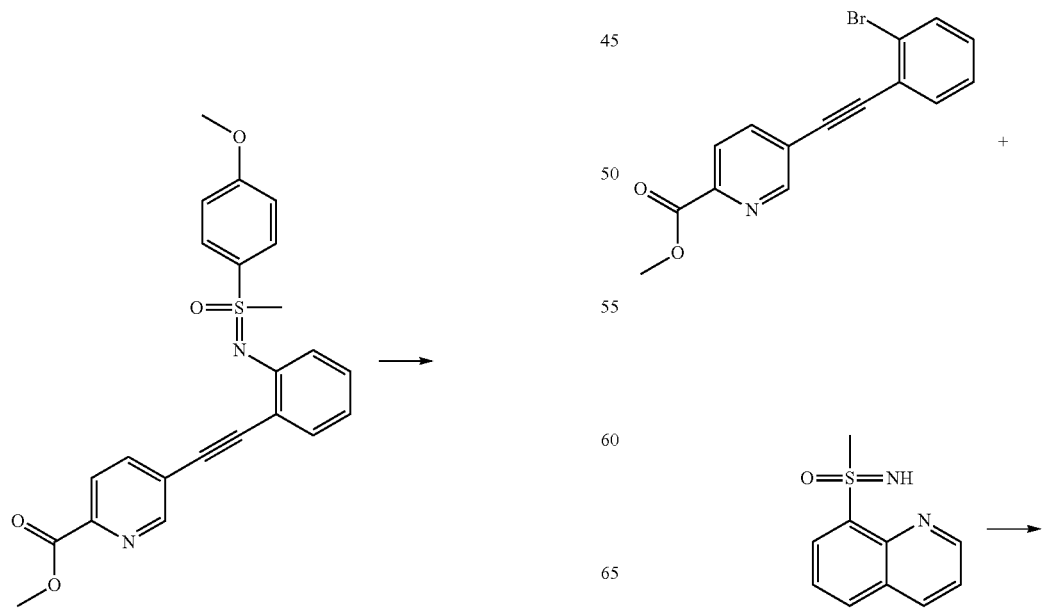

177
-continued

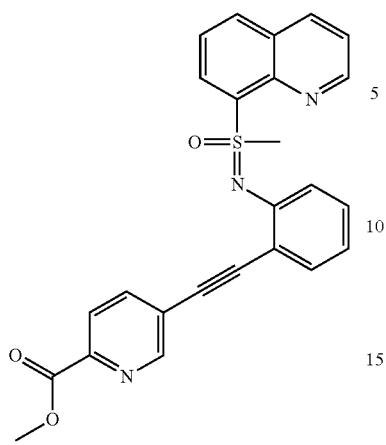

To a solution of methyl 5-[2-(2-bromophenyl)ethynyl]pyridine-2-carboxylate (133 mg; 0.32 mmol) in Toluene (5 ml) was added in a microwave vial under argon imino(methyl)(quinolin-8-yl)-lambda6-sulfanone Hydrochloride (93.5 mg; 0.39 mmol), Cesium carbonate (627 mg; 1.93 mmol), 2-Dicyclohexyl-phosphino-2',6'-diisopropoxybiphenyl (RuPhos) (31.5 mg; 0.06 mmol) and Palladium(II) acetate (47% Pd, 7.2 mg; 0.03 mmol). The reaction was stirred for 16 hrs at 110° C. HPLC-MS showed the required product. The reaction was diluted with ethyl acetate and extracted 3x with water, dried over $Na_2SO_4$ and evaporated to dryness. The residue was purified by flash chromatography giving the product as yellow solid in 10% yield (38 mg).

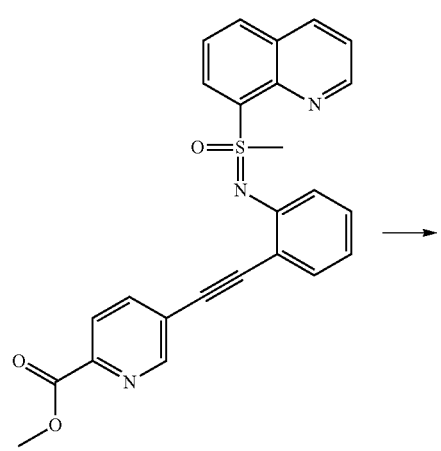

178
-continued

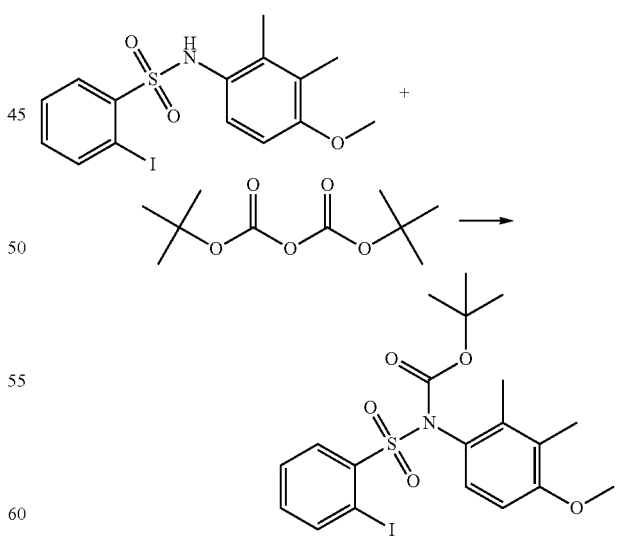

To a solution of methyl 5-[2-(2-{[methyl(oxo)(quinolin-8-yl)-?6-sulfanylidene]-amino}phenyl)ethynyl]pyridine-2-carboxylate (38 mg; 0.03 mmol) in Methanol (5 ml) was added Sodium hydroxide solution c(NaOH)=2 mol/l (2 N) (0.3 ml) and stirred for 16 hrs at RT. HPLC-MS showed the complete formation of the required product. The reaction was evaporated to dryness. The residue was purified by prep. HPLC giving the product 5-[2-(2-{[methyl(oxo)(208uinoline-8-yl)-A6-sulfanylidene]amino}phenyl)ethynyl]pyridine-2-carboxylic acid as yellow solid in 56% yield (8 mg).

Example 51—General Procedure 8 (GP8)

Compounds of formula (I) with $L^1$ being divalent —$SO_2$— radical, $L^2$ being a divalent —NH— or —N($R^a$)— radical and $L^3$ being a single bond may be prepared in accordance to the following schemes and synthetic procedure described below with reference to 5-(2-{2-[(4-methoxy-2,3-dimethylphenyl)sulfamoyl]-phenyl}ethynyl)pyridine-2-carboxylic acid:

To a solution of 2-iodo-N-(4-methoxy-2,3-dimethylphenyl)benzene-1-sulfon-amide (715 mg; 1.40 mmol) in Acetonitrile (50 ml) was added Di-tert-butyl dicarbonate (747.0 µl; 3.49 mmol) and 4-(Dimethylamino)pyridine (187.7 mg; 1.54 mmol). The reaction was stirred for 16 hrs at RT. HPLC-MS showed the complete formation of the required product. The reactions were diluted with ethyl acetate and extracted 3× with water, dried over Na₂SO₄ and evaporated to dryness. The crude product tert-butyl N-(2-iodobenzenesulfonyl)-N-(4-methoxy-2,3-dimethylphenyl) carbamate was used in the next step without further purification.

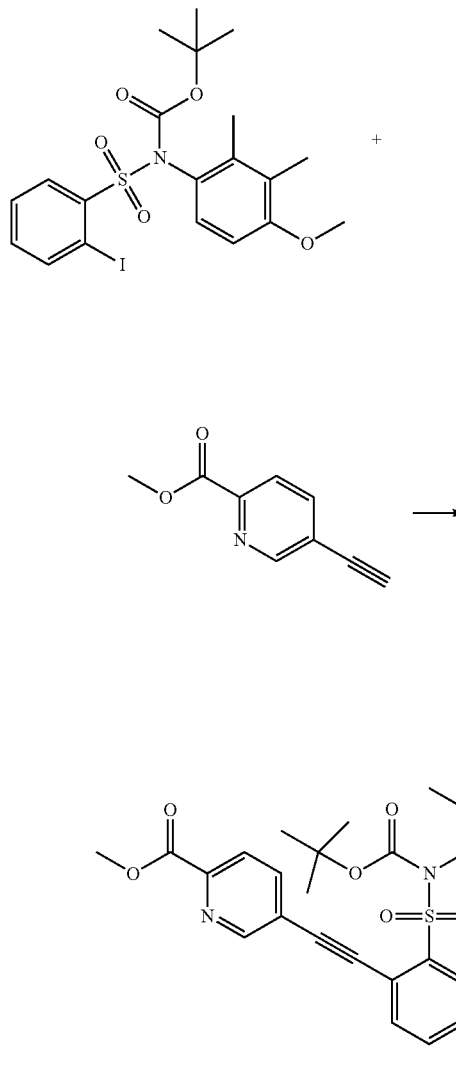

To a solution of tert-butyl N-(2-iodobenzenesulfonyl)-N-(4-methoxy-2,3-di-methylphenyl)carbamate (709 mg; 1.11 mmol) in Acetonitrile (10 ml) was added under argon in a microwave-vial Methyl 5-ethynylpyridine-2-carboxylate (281.8 mg; 1.66 mmol; 1.50 eq.), Diisopropylamine (0.2 ml; 1.66 mmol) Copper(I) iodide (21 mg; 0.11 mmol and Tetrakis(triphenylphosphine)-palladium(0) (128 mg; 0.11 mmol). The reaction was stirred for 1 hr at 80° C. in the microwave. HPLC-MS showed the complete formation of the required product. The reactions were diluted with ethyl acetate and extracted 3× with water, dried with Na2SO4 and evaporated to dryness. The residue was purified by flash chromatography giving the product methyl 5-{2-[2-({[(tert-butoxy)carbonyl](4-methoxy-2,3-dimethylphenyl) amino}sulfonyl)phenyl]ethyn-yl}pyridine-2-carboxylate as yellow solid in 71% yield (451 mg).

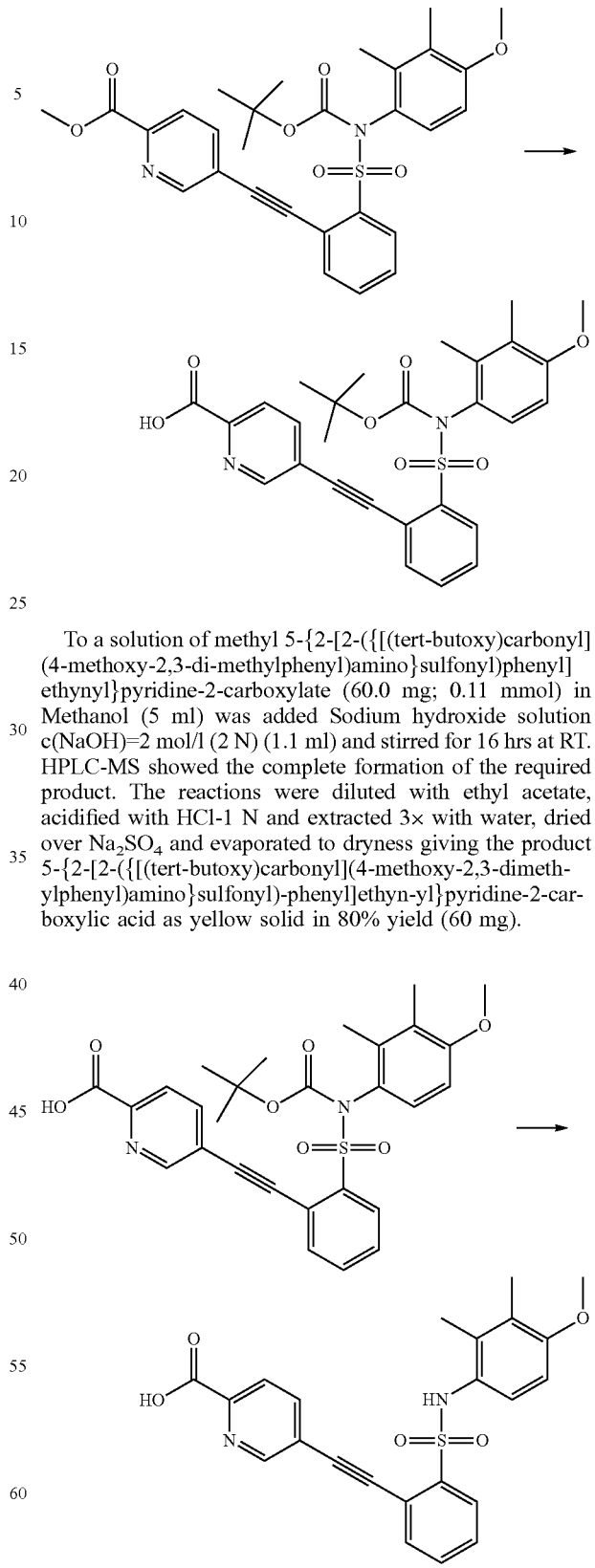

To a solution of methyl 5-{2-[2-({[(tert-butoxy)carbonyl](4-methoxy-2,3-di-methylphenyl)amino}sulfonyl)phenyl]ethynyl}pyridine-2-carboxylate (60.0 mg; 0.11 mmol) in Methanol (5 ml) was added Sodium hydroxide solution c(NaOH)=2 mol/l (2 N) (1.1 ml) and stirred for 16 hrs at RT. HPLC-MS showed the complete formation of the required product. The reactions were diluted with ethyl acetate, acidified with HCl-1 N and extracted 3× with water, dried over Na₂SO₄ and evaporated to dryness giving the product 5-{2-[2-({[(tert-butoxy)carbonyl](4-methoxy-2,3-dimethylphenyl)amino}sulfonyl)-phenyl]ethyn-yl}pyridine-2-carboxylic acid as yellow solid in 80% yield (60 mg).

To a solution of 5-{2-[2-({[(tert-butoxy)carbonyl](4-methoxy-2,3-dimethyl-phenyl)amino}sulfonyl)phenyl] ethynyl}pyridine-2-carboxylic acid (60.0 mg; 0.08 mmol) in 1,4-Dioxane (5 ml) was added HCl (4.0 M in dioxane, 1.0 ml) and stirred for 16 hrs at RT. HPLC-MS showed only starting material. More HCl (4.0 M in dioxane, 1.0 ml) was added and stirred for 16 hrs at RT. HPLC-MS showed a new peak with product mass. The reaction was diluted with water and lyophilized. The residue was purified by prep. HPLC giving the product 5-(2-{2-[(4-methoxy-2,3-dimethylphenyl)sulfamoyl]phenyl}ethynyl)pyridine-2-carboxylic acid as yellow solid in 17% yield (7 mg).

Example 52

Synthesis of 5-(2-{2-[(quinolin-8-yl)sulfamoyl]phenyl}ethynyl)pyridine-2-carboxylic acid

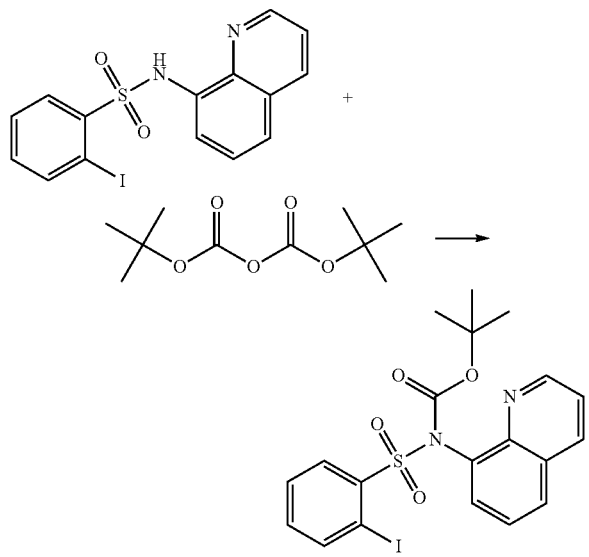

To a solution of 2-iodo-N-(quinolin-8-yl)benzene-1-sulfonamide (244.0 mg; 0.51 mmol) in Acetonitrile (20 ml) was added Di-tert-butyl dicarbonate (273.9 µl; 1.28 mmol) and 4-(Dimethylamino)pyridine (68.8 mg; 0.56 mmol). The reaction was stirred for 16 hrs at RT. HPLC-MS showed the complete formation of the required product. The reactions were diluted with ethyl acetate and extracted 3× with water, dried over Na₂SO₄ and evaporated to dryness giving the product as brown solid in quantitative yield (275 mg).

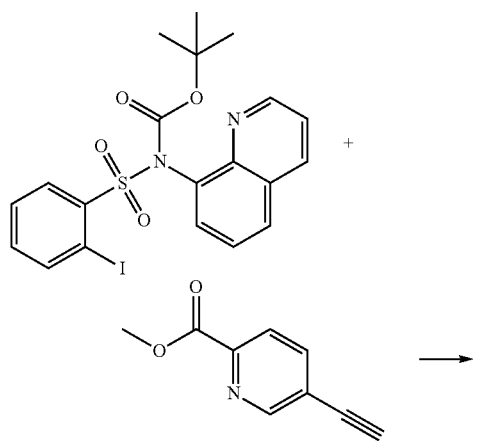

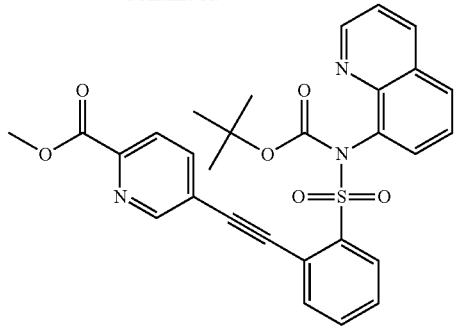

To a solution of tert-butyl N-(2-iodobenzenesulfonyl)-N-(quinolin-8-yl)-carbamate (275.0 mg; 0.52 mmol) was added under argon in a microwave-vial Methyl 5-ethynylpyridine-2-carboxylate (132.7 mg; 0.78 mmol), Copper (I) iodide for synthesis (10 mg; 0.05 mmol), Diisopropylamine (0.1 ml; 0.78 mmol) and Tetrakis(triphenylphosphine)-palladium(0) (60.3 mg; 0.05 mmol). The reaction was stirred for 16 hrs at 80° C. HPLC-MS showed a complete formation of the required product. The reactions were diluted with ethyl acetate and extracted 3× with water, dried over Na₂SO₄ and evaporated to dryness. The residue was purified by flash chromatography giving as yellow solid in 55% yield (170 mg).

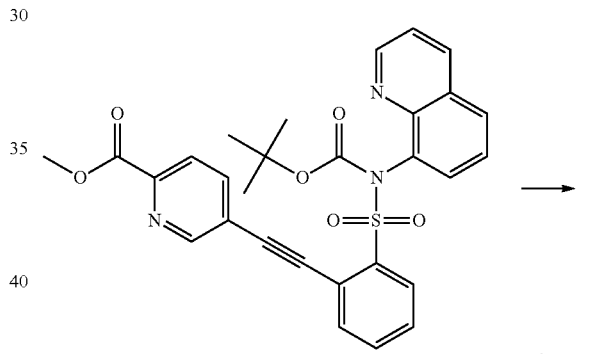

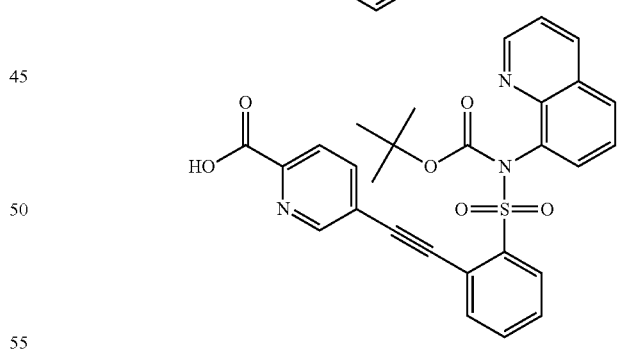

To a solution of methyl 5-{2-[2-({[(tert-butoxy)carbonyl](quinolin-8-yl)amino}-sulfonyl)phenyl]ethynyl}pyridine-2-carboxylate (170.0 mg; 0.29 mmol) in Methanol (10 ml) was added Sodium hydroxide solution c(NaOH)=2 mol/l (2 N) (2.9 ml) and stirred for 3 days at RT. HPLC-MS showed the complete formation of the required product. The reactions were diluted with ethyl acetate, acidified with HCl-1 N and extracted 3× with water, dried over Na₂SO₄ and evaporated to dryness giving the product 5-(2-{2-[(quinolin-8-yl)-sulfamoyl]phenyl}ethynyl)pyridine-2-carboxylic acid as yellow solid in 81% yield (154 mg).

Example 53

Synthesis of 5-[2-(2-{[(2-methoxyphenyl)(methyl)oxo-λ6-sulfanylidene]-amino}phenyl)ethynyl]pyridine-2-carboxylic acid

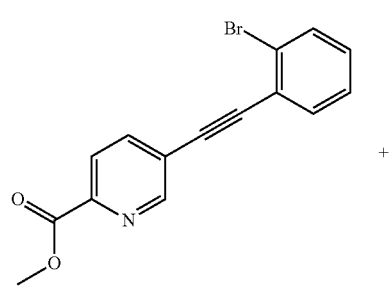

+

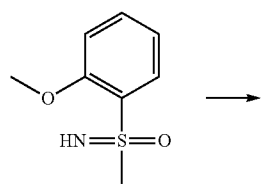

→

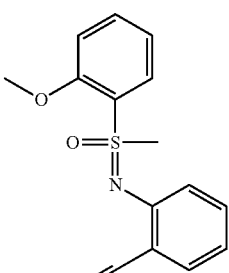

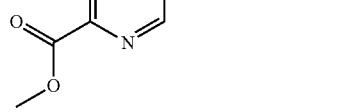

To a solution of methyl 5-[2-(2-bromophenyl)ethynyl]pyridine-2-carboxylate (80.0 mg; 0.21 mmol) in Toluene (4 ml) was added in a microwave vial under argon imino(2-methoxyphenyl)methyl-lambda6-sulfanone (46.5 mg; 0.25 mmol), Cesium carbonate (204 mg; 0.63 mmol), 2-Dicyclohexylphosphino-2',6'-diisopropoxybiphenyl (RuPhos) (20.6 mg; 0.04 mmol) and Palladium(II) acetate (47% Pd) (4.7 mg; 0.02 mmol). The reaction was stirred for 16 hrs at 110° C. HPLC-MS showed the complete formation of the required product. The reaction was diluted with ethyl acetate and extracted 3× with water, dried over Na₂SO₄ and evaporated to dryness. The residue was purified by flash chromatography giving the product as yellow oil in 18% yield (19 mg).

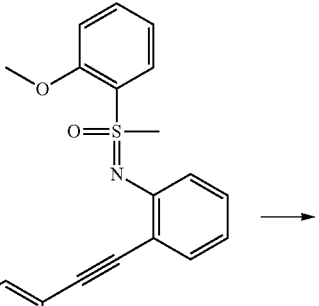

→

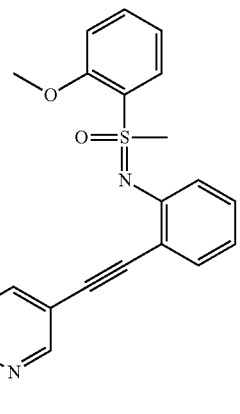

To a solution of methyl 5-[2-(2-{[(2-methoxyphenyl)(methyl)oxo-λ6-sulfanyl-idene]amino}phenyl)ethynyl]pyridine-2-carboxylate (19.0 mg; 0.04 mmol) in 1,4-Dioxane (3 ml) was added Sodium hydroxide solution c(NaOH)=2 mol/l (2 N) (0.4 ml) and stirred for 16 hrs at RT. HPLC-MS showed the complete formation of the required product. The reaction was evaporated to dryness. The residue was purified by prep. HPLC giving the product of 5-[2-(2-{[(2-methoxyphenyl)(methyl)oxo-λ6-sulfanylidene]amino}phenyl)ethynyl]pyridine-2-carboxylic acid as yellow solid in 95% yield (15 mg).

Example 54

Synthesis of 5-[2-(2-{[(3-methoxyphenyl)(methyl)oxo-λ6-sulfanylidene]-amino}phenyl)ethynyl]pyridine-2-carboxylic acid

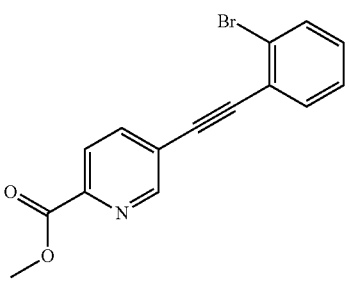

+

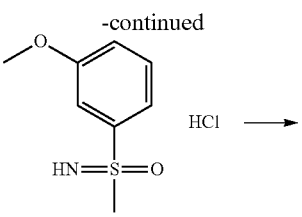 HCl →

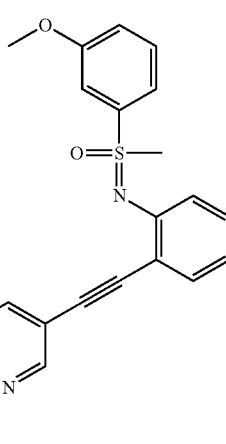

To a solution of methyl 5-[2-(2-bromophenyl)ethynyl]pyridine-2-carboxylate (128.0 mg; 0.33 mmol) in Toluene (5 ml) was added in a microwave vial under argon imino(3-methoxyphenyl)methyl-Λ6-sulfanone hydrochloride (89.1 mg; 0.40 mmol), Cesium carbonate (655 mg; 2.01 mmol), 2-Dicyclohexyl-phosphino-2',6'-diisopropoxybiphenyl (RuPhos) (32.9 mg; 0.07 mmol) and Palladium(II) acetate (47% Pd) (7.5 mg; 0.03 mmol). The reaction was stirred for 16 hrs at 110° C. HPLC-MS showed the complete formation of the required product. The reaction was diluted with ethyl acetate and extracted 3× with water, dried over Na$_2$SO$_4$ and evaporated to dryness. The residue was purified by flash chromatography giving the product as yellow solid in 19% yield (31 mg).

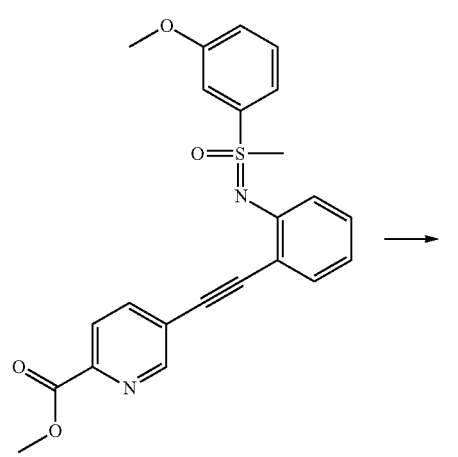

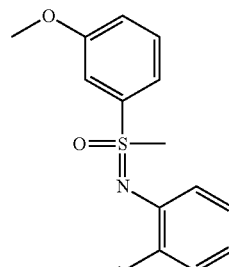

To a solution of methyl 5-[2-(2-{[(3-methoxyphenyl)(methyl)oxo-Λ6-sulfanyl-idene]amino}phenyl)ethynyl]pyridine-2-carboxylate (31.0 mg; 0.06 mmol) in 1,4-Dioxane (3 ml) was added Sodium hydroxide solution c(NaOH)=2 mol/l (2 N) (0.6 ml) and stirred for 16 hrs at RT. HPLC-MS showed the complete formation of the required product. The reaction was evaporated to dryness. The residue was purified by prep. HPLC giving the product 5-[2-(2-{[(3-methoxyphenyl)(methyl)oxo-Λ6-sulfanylidene]amino}phenyl)ethynyl]pyridine-2-carboxylic acid as yellow solid in 81% yield (21 mg).

Example 55

Synthesis of 5-[2-(2-{[methyl(3-methylphenyl)oxo-Λ6-sulfanylidene]-amino}phenyl)ethynyl]pyridine-2-carboxylic acid

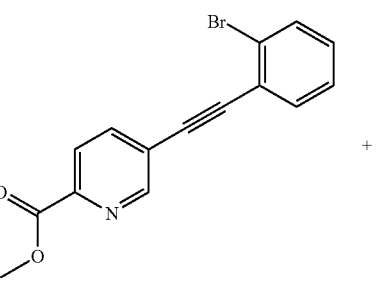

+

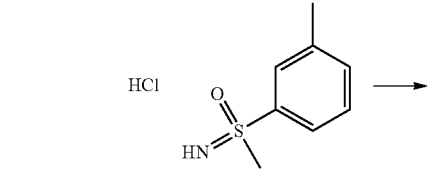

187
-continued

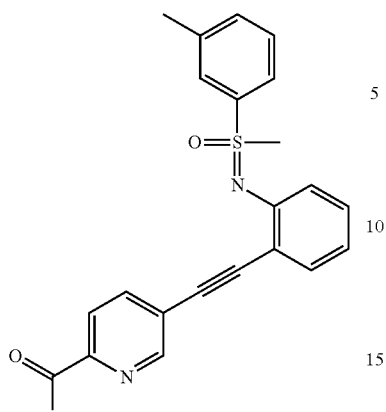

188
-continued

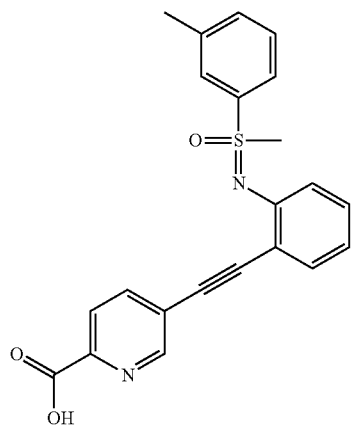

To a solution of methyl 5-[2-(2-bromophenyl)ethynyl]pyridine-2-carboxylate (100.0 mg; 0.29 mmol) in Toluene (5 ml) was added in a microwave vial under argon imino(methyl)(3-methylphenyl)-λ6-sulfanone (72.7 mg; 0.35 mmol), Cesium carbonate (576 mg; 1.77 mmol), 2-Dicyclohexylphosphino-2',6'-diisopropoxybiphenyl (RuPhos) (28.9 mg; 0.06 mmol) and Palladium(II) acetate (47% Pd) (6.6 mg; 0.03 mmol). The reaction was stirred for 16 hrs at 110° C. HPLC-MS showed the complete formation of the required product. The reaction was diluted with ethyl acetate and extracted 3× with water, dried over Na₂SO₄ and evaporated to dryness. The residue was purified by flash chromatography giving the product as yellow oil in 26% yield (36 mg).

To a solution of methyl 5-[2-(2-{[methyl(3-methylphenyl)oxo-λ6-sulfanylidene]amino}phenyl)ethynyl]pyridine-2-carboxylate (31.0 mg; 0.06 mmol) in 1,4-Dioxane (3 ml) was added Sodium hydroxide solution c(NaOH)=2 mol/l (2 N) (0.6 ml) and stirred for 16 hrs at RT. HPLC-MS showed the complete formation of the required product. The reaction was evaporated to dryness. The residue was purified by prep. HPLC giving the product 5-[2-(2-{[methyl(3-methylphenyl)oxo-λ6-sulfanylidene]amino}phenyl)ethynyl]pyridine-2-carboxylic acid as yellow solid in 70% yield (18 mg).

Example 56

Synthesis of 5-[2-(2-{[(3-fluorophenyl)(methyl)oxo-λ6-sulfanylidene]-amino}phenyl)ethynyl]pyridine-2-carboxylic acid

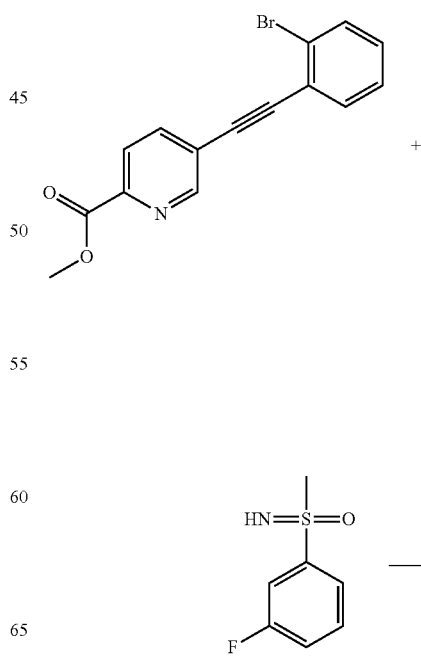

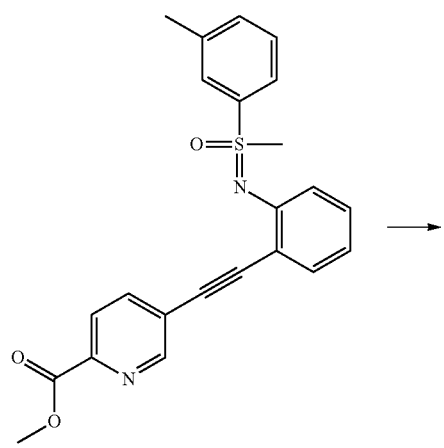

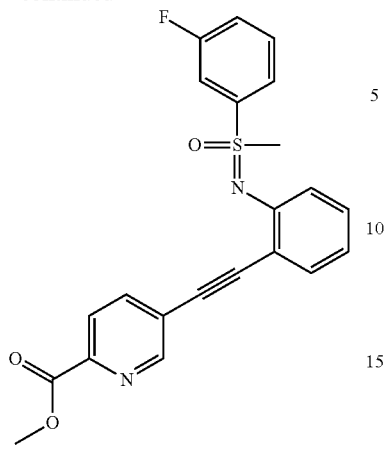

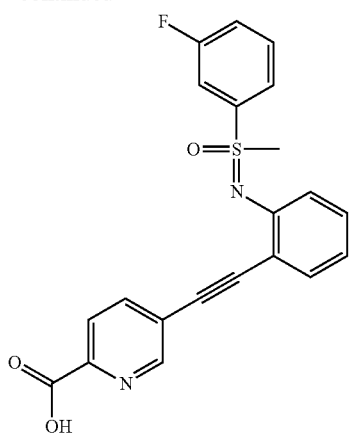

To a solution of methyl 5-[2-(2-bromophenyl)ethynyl]pyridine-2-carboxylate (100 mg; 0.29 mmol) in Toluene (5 ml) was added in a microwave vial under argon 3-fluorophenyl)(imino)methyl-A6-sulfanone (61.2 mg; 0.35 mmol), Cesium carbonate (288 mg; 0.88 mmol), 2-Dicyclohexylphosphino-2',6'-diiso-propoxybiphenyl (RuPhos) (28.9 mg; 0.06 mmol) and Palladium(II) acetate (47% Pd) (6.6 mg; 0.03 mmol). The reaction was stirred for 16 hrs at 110° C. HPLC-MS showed the complete formation of the required product. The reaction was diluted with ethyl acetate and extracted 3× with water, dried over Na₂SO₄ and evaporated to dryness. The residue was purified by flash chromatography giving the product as yellow oil in 21% yield (26 mg).

To a solution of methyl 5-[2-(2-{[(3-fluorophenyl)(methyl)oxo-A6-sulfanyl-idene]amino}phenyl)ethynyl]pyridine-2-carboxylate (26 mg; 0.06 mmol) in 1,4-Dioxane (3 ml) was added Sodium hydroxide solution c(NaOH)=2 mol/l (2 N) (0.6 ml) and stirred for 3 days at RT. HPLC-MS showed the complete formation of the required product. The reaction was evaporated to dryness. The residue was purified by prep. HPLC giving the product 5-[2-(2-{[(3-fluorophenyl)(methyl)oxo-A6-sulfanylidene]amino}phenyl)ethynyl]pyridine-2-carboxylic acid as yellow solid in 50% yield (12 mg).

Example 57

Synthesis of 5-[2-(2-{[(2-fluorophenyl)(methyl)oxo-A6-sulfanylidene]-amino}phenyl)ethynyl]pyridine-2-carboxylic acid

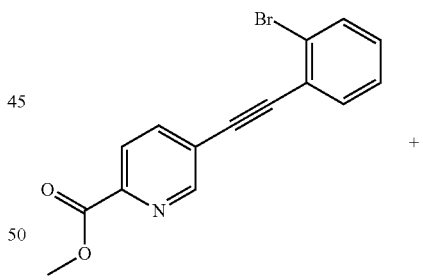

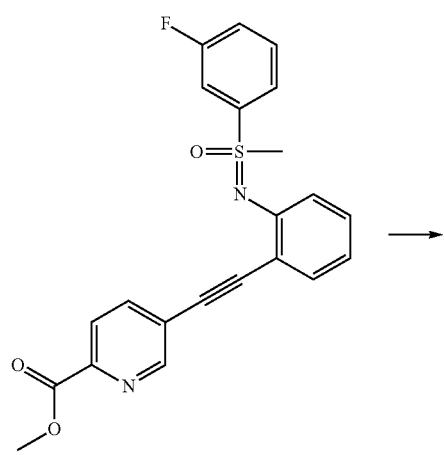

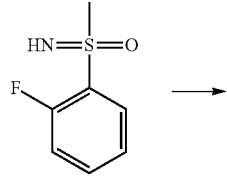

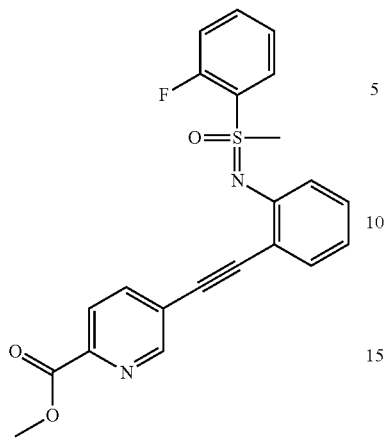

To a solution of methyl 5-[2-(2-bromophenyl)ethynyl]pyridine-2-carboxylate (100 mg; 0.29 mmol) in Toluene (5 ml) was added in a microwave vial under argon 2-fluorophenyl)(imino)methyl-A6-sulfanone (61.2 mg; 0.35 mmol), Cesium carbonate (288 mg; 0.88 mmol), 2-Dicyclohexylphosphino-2',6'-diiso-propoxybiphenyl (RuPhos) (28.9 mg; 0.06 mmol) and Palladium(II) acetate (47% Pd) (6.6 mg; 0.03 mmol). The reaction was stirred for 16 hrs at 110° C. HPLC-MS showed the complete formation of the required product. The reaction was diluted with ethyl acetate and extracted 3× with water, dried over Na$_2$SO$_4$ and evaporated to dryness. The residue was purified by flash chromatography giving the product as brown oil in 27% yield (35 mg).

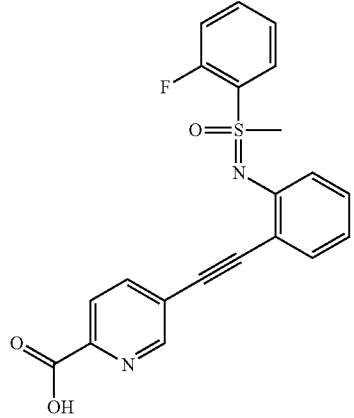

To a solution of methyl 5-[2-(2-{[(2-fluorophenyl)(methyl)oxo-A6-sulfanyl-idene]amino}phenyl)ethynyl]pyridine-2-carboxylate (35 mg; 0.08 mmol) in 1,4-Dioxane (3 ml) was added Sodium hydroxide solution c(NaOH)=2 mol/l (2 N) (0.8 ml) and stirred for 2 days at RT. HPLC-MS showed the complete formation of the required product. The reaction was evaporated to dryness. The residue was purified by prep. HPLC giving the product 5-[2-(2-{[(2-fluorophenyl)(methyl)oxo-A6-sulfanylidene]amino}phenyl)ethynyl]pyridine-2-carboxylic acid as orange solid in quantitative yield (32 mg).

Example 58

Synthesis of 5-[2-(2-{[methyl(2-methylphenyl)oxo-A6-sulfanylidene]-amino}phenyl)ethynyl]pyridine-2-carboxylic acid

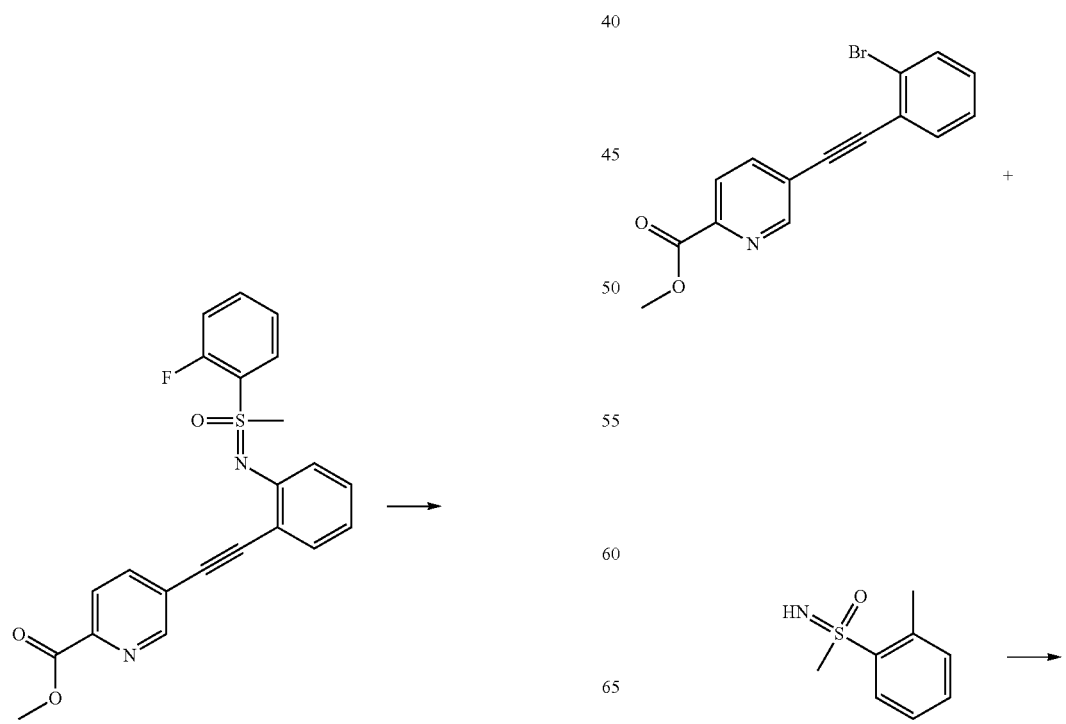

193

-continued

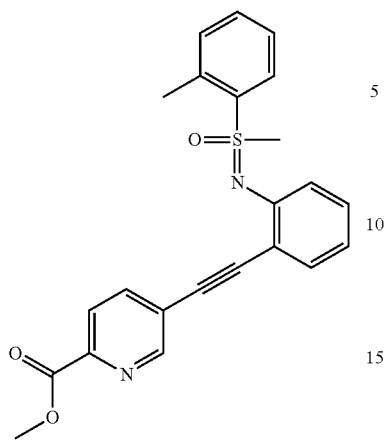

To a solution of methyl 5-[2-(2-bromophenyl)ethynyl]pyridine-2-carboxylate (100 mg; 0.29 mmol) in Toluene (5 ml) was added in a microwave vial under argon 3-fluorophenyl)(imino)methyl-A6-sulfanone (61.2 mg; 0.35 mmol), Cesium carbonate (288 mg; 0.88 mmol), 2-Dicyclohexylphosphino-2',6'-diiso-propoxybiphenyl (RuPhos) (28.9 mg; 0.06 mmol) and Palladium(II) acetate (47% Pd) (6.6 mg; 0.03 mmol). The reaction was stirred for 16 hrs at 110° C. HPLC-MS showed the complete formation of the required product. The reaction was diluted with ethyl acetate and extracted 3× with water, dried over $Na_2SO_4$ and evaporated to dryness. The residue was purified by flash chromatography giving the product as yellow oil in 37% yield (48 mg).

194

-continued

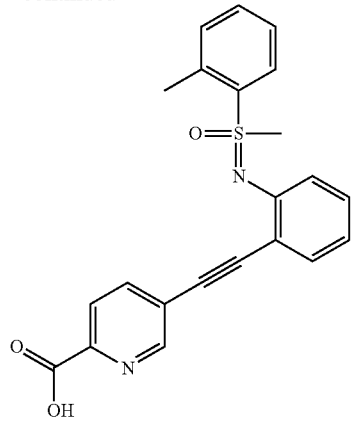

To a solution of methyl 5-[2-(2-{[(3-fluorophenyl)(methyl)oxo-A6-sulfanyl-idene]amino}phenyl)ethynyl]pyridine-2-carboxylate (26 mg; 0.06 mmol) in 1,4-Dioxane (3 ml) was added Sodium hydroxide solution c(NaOH)=2 mol/l (2 N) (0.6 ml) and stirred for 3 days at RT. HPLC-MS showed the complete formation of the required product. The reaction was evaporated to dryness. The residue was purified by prep. HPLC giving the product 5-[2-(2-{[methyl(2-methylphenyl)oxo-A6-sulfanylidene]amino}phenyl)ethynyl]pyridine-2-carboxylic acid as yellow solid in 71% yield (30 mg).

Example 59

Synthesis of 5-{2-[2-(phenylsulfamoyl)phenyl]ethynyl}pyridine-2-carb-oxylic acid

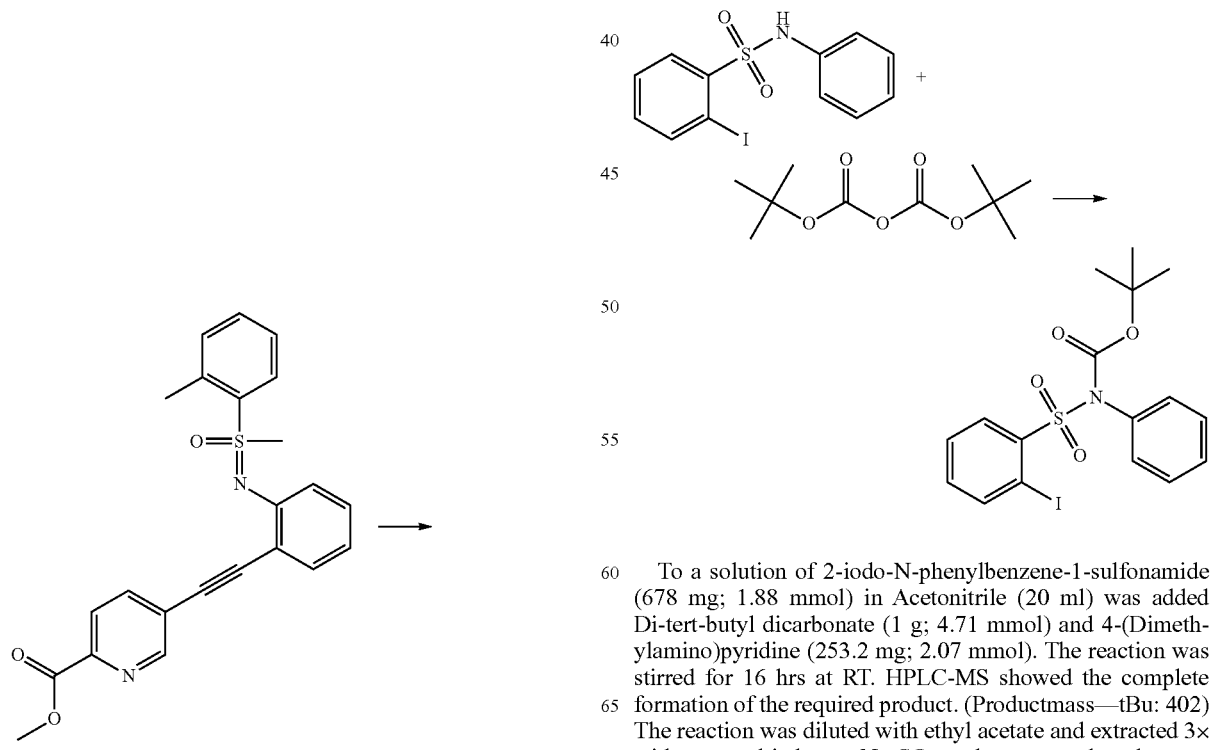

To a solution of 2-iodo-N-phenylbenzene-1-sulfonamide (678 mg; 1.88 mmol) in Acetonitrile (20 ml) was added Di-tert-butyl dicarbonate (1 g; 4.71 mmol) and 4-(Dimethylamino)pyridine (253.2 mg; 2.07 mmol). The reaction was stirred for 16 hrs at RT. HPLC-MS showed the complete formation of the required product. (Productmass—tBu: 402) The reaction was diluted with ethyl acetate and extracted 3× with water, dried over $Na_2SO_4$ and evaporated to dryness.

The crude product was obtained as orange oil in 93% yield (961 mg) and was used in the next step without further purification.

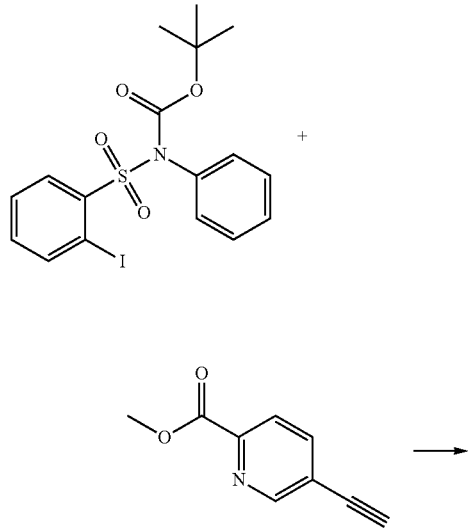

To a solution of tert-butyl N-(2-iodobenzenesulfonyl)-N-phenylcarbamate (961 mg; 1.75 mmol) was added under argon in a microwave-vial Methyl 5-ethynylpyridine-2-carboxylate (445.6 mg; 2.63 mmol), Copper(I) iodide for synthesis (33 mg; 0.18 mmol; 0.10 eq.), Diisopropylamine (0.4 ml; 2.63 mmol) and Tetrakis(triphenylphosphine)-palladium(0) (202.4 mg; 0.18 mmol). The reaction was stirred for 16 hrs at 80° C. HPLC-MS showed complete formation of the required product. The reactions were diluted with ethyl acetate and extracted 3× with water, dried over Na₂SO₄ and evaporated to dryness. The residue was purified by flash chromatography giving the product a yellow solid in 22% yield (200 mg).

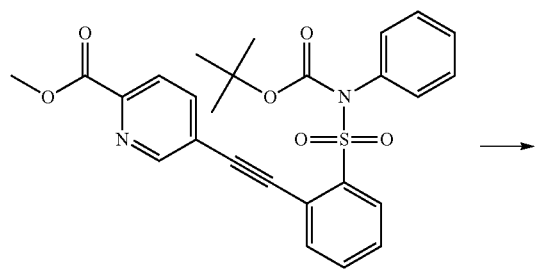

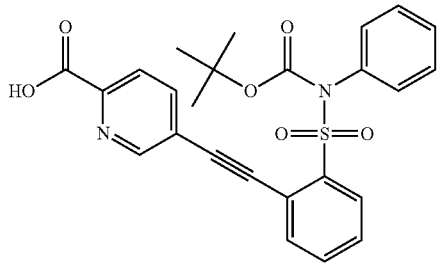

To a solution of methyl 5-{2-[2-({[(tert-butoxy)carbonyl](phenyl)amino}-sulfonyl)phenyl]ethynyl}pyridine-2-carboxylate (140 mg; 0.27 mmol) in Methanol (10 ml) was added Sodium hydroxide solution c(NaOH)=2 mol/l (2 N) (0.2 ml) and stirred for 16 hrs at RT. HPLC-MS showed the complete formation of the required product. The reactions were acidified with HCl-1 N, diluted with water, and extracted 2× with ethyl acetate. The combined organic layers were washed 3× with water, dried over Na₂SO₄ and evaporated to dryness giving the product 5-{2-[2-(phenylsulfamoyl)phenyl]ethynyl}pyridine-2-carboxylic acid a yellow solid in 87% yield (129 mg) which was used in the next step without further purification.

Example 60

Synthesis of 5-(2-{2-[methyl(phenyl)sulfamoyl]phenyl}ethynyl)pyridine-2-carboxylic acid

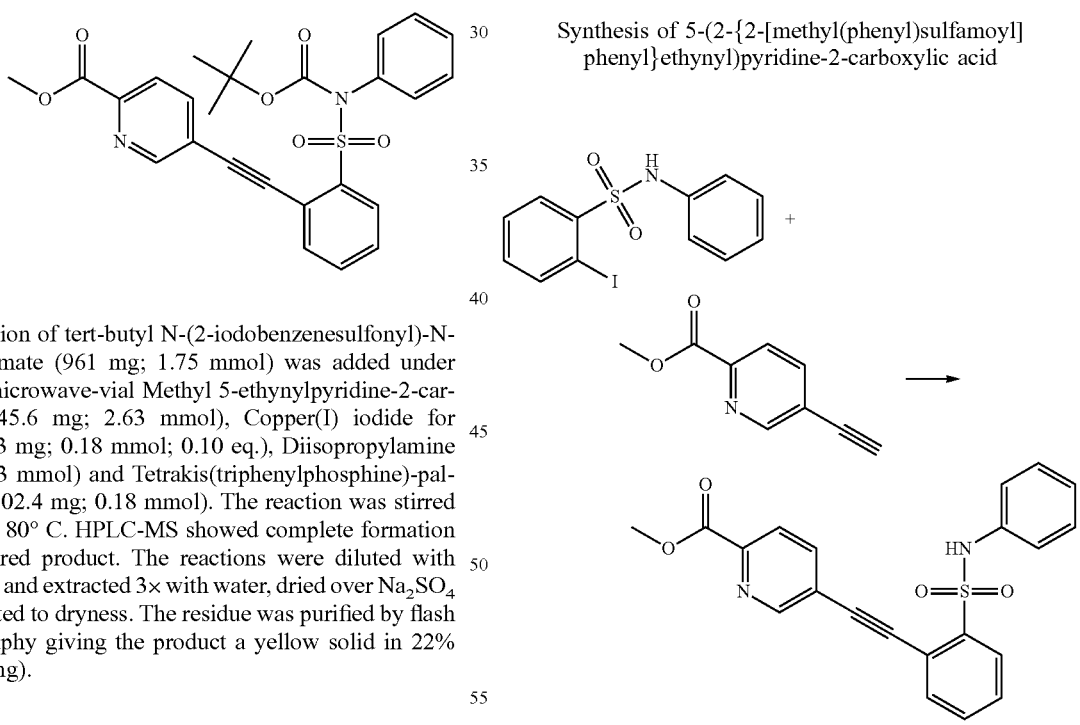

To a solution of 2-iodo-N-phenylbenzene-1-sulfonamide (1.5 g; 2 mmol; 2 eq.) in Tetrahydrofuran (10 ml) was added under argon in a microwave-vial Methyl 5-ethynylpyridine-2-carboxylate (528.7 mg; 3.12 mmol), Triethylamine (0.4 ml; 3.12 mmol), Copper(I) iodide (40 mg; 0.21 mmol) and Tetrakis-(triphenylphosphine)-palladium(0) (240.1 mg; 0.21 mmol). The reaction was stirred for 16 hrs at RT. HPLC-MS showed one peak with product mass. The reactions were diluted with ethyl acetate and extracted 3× with water, dried over Na₂SO₄ and evaporated to dryness. The residue was purified by flash chromatography giving the product as yellow solid in 36% yield (306 mg).

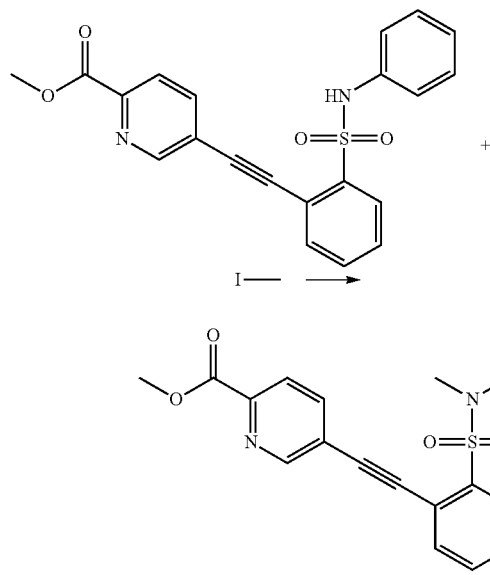

To a solution of methyl 5-{2-[2-(phenylsulfamoyl)phenyl]ethynyl}pyridine-2-carboxylate (156.0 mg; 0.38 mmol) in N,N-Dimethylformamide (10 ml) was added Iodomethane (0.1 ml; 0.96 mmol) and Potassium carbonate (106 mg; 0.76 mmol). The reaction was stirred for 16 hrs at RT. HPLC-MS showed the required product in a mixture. The reaction was diluted with ethyl acetate and extracted 3× with water, dried over Na$_2$SO$_4$ and evaporated to dryness. The residue was purified by flash chromatography giving the product in 63% yield (105 mg) as yellow solid.

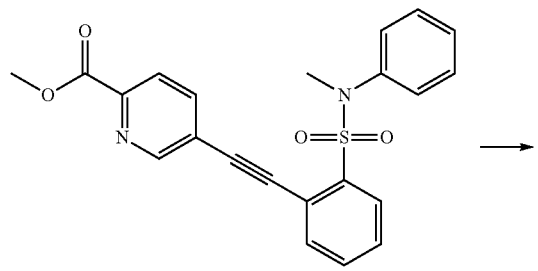

To a solution of methyl 5-(2-{2-[methyl(phenyl)sulfamoyl]phenyl}ethynyl)-pyridine-2-carboxylate (105 mg) in 1,4-Dioxane (5 ml) was added Sodium hydroxide solution c(NaOH)=2 mol/l (2 N) (1.2 ml) and stirred for 16 hrs at RT. HPLC-MS showed the complete formation of the required product. The resulting white precipitate was sucked off, washed with dioxane and dried in vacuum giving the product 5-(2-{2-[methyl(phenyl)sulfamoyl]phenyl}ethynyl)-pyridine-2-carboxylic acid as colorless solid in 86% yield (85 mg).

Example 61

Synthesis of 4-[2-(2-{[methyl(oxo)(quinolin-8-yl)-A6-sulfanylidene]-amino}phenyl)ethynyl]isoquinoline-1-carboxylic acid

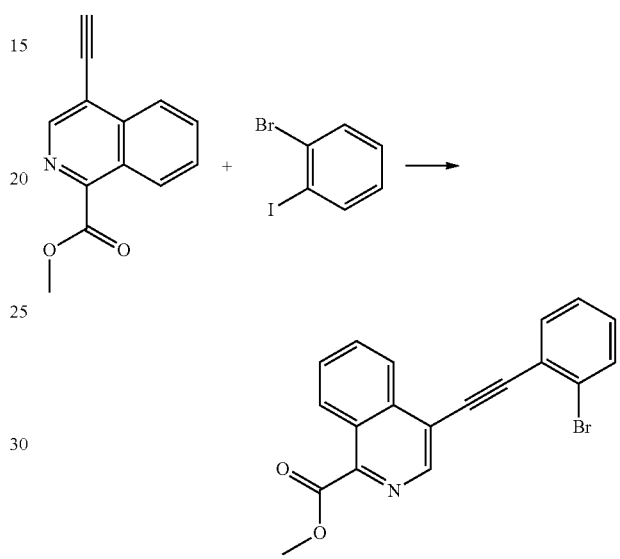

To a solution of methyl 4-ethynylisoquinoline-1-carboxylate (899 mg; 3.06 mmol) in Acetonitrile (15 ml) was added under argon in a microwave-vial 1-Bromo-2-iodobenzene, (1.3 g; 4.59 mmol), Diisopropylamine (0.6 ml; 4.59 mmol), Copper(I) iodide for synthesis (58 mg; 0.31 mmol) and Tetrakis-(triphenylphosphine)-palladium(0) (353.6 mg; 0.31 mmol). The reaction was stirred for 16 hrs at 100° C. HPLC-MS showed the formation of the required product. The reaction was diluted with ethyl acetate and extracted 3× with water, dried over Na$_2$SO$_4$ and evaporated to dryness. The residue was purified by flash chromatography giving the product as yellow solid in 14% yield (198 mg).

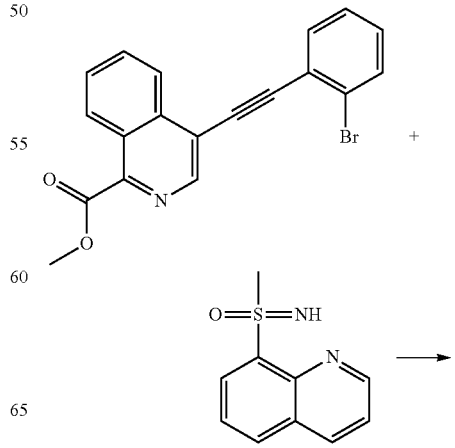

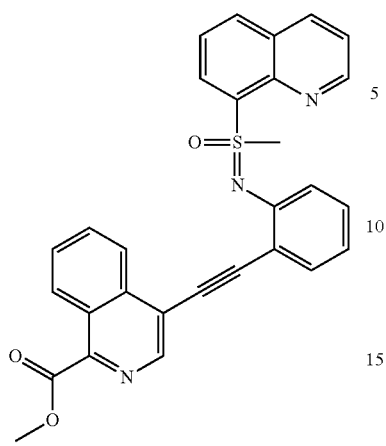

To a solution of methyl 4-[2-(2-bromophenyl)ethynyl]isoquinoline-1-carboxylate (100 mg; 0.21 mmol) in toluene was added in a microwave vial under argon imino(methyl)(quinolin-8-yl)-lambda6-sulfanone Hydrochloride (61.8 mg; 0.25 mmol), cesium carbonate (0.1 ml; 1.27 mmol), 2-Dicyclohexylphosphino-2',6'-diisopropoxybiphenyl (Ru-Phos) (20.8 mg; 0.04 mmol) and Palladium(II) acetate (47% Pd) for synthesis (4.8 mg; 0.02 mmol). The reaction was stirred for 16 hrs at 110° C. The reactions were diluted with Ethyl Acetate and extracted 3× with water, dried over Na₂SO₄ and evaporated to dryness. The residue was purified by flashchromatography giving the product in 45% (56 mg) yield as yellow solid.

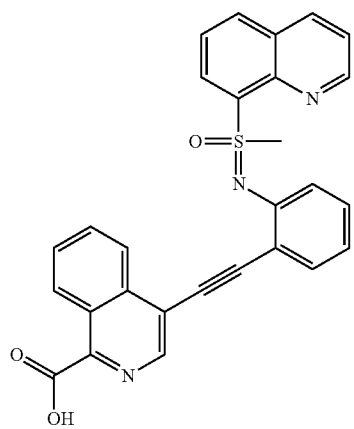

To a solution of methyl 4-[2-(2-{[methyl(oxo)(quinolin-8-yl)-A6-sulfanylidene]-amino}phenyl)ethynyl]isoquinoline-1-carboxylate (56 mg; 0.10 mmol) in Methanol (5 ml) was added Sodium hydroxide solution c(NaOH)=2 mol/l (2 N) (1 ml) and stirred for 16 hrs at RT. HPLC-MS showed the complete formation of the required product. The reaction was evaporated to dryness. The residue was purified by prep. HPLC giving the product 4-[2-(2-{[methyl(oxo)(quinolin-8-yl)-A6-sulfanylidene]amino}-phenyl)ethynyl]isoquinoline-1-carboxylic acid as yellow solid in 55% yield (25 mg).

Example 62

Synthesis of 4-[2-(2-{[(4-methoxyphenyl)(methyl)oxo-A6-sulfanylidene]-amino}phenyl)ethynyl]isoquinoline-1-carboxylic acid

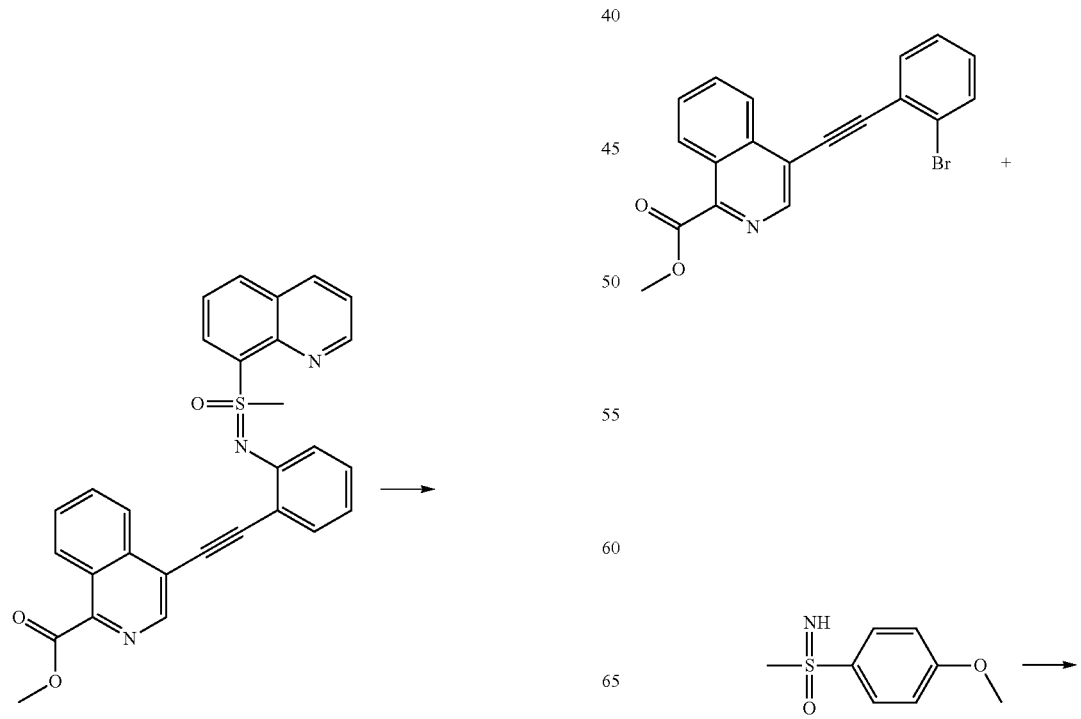

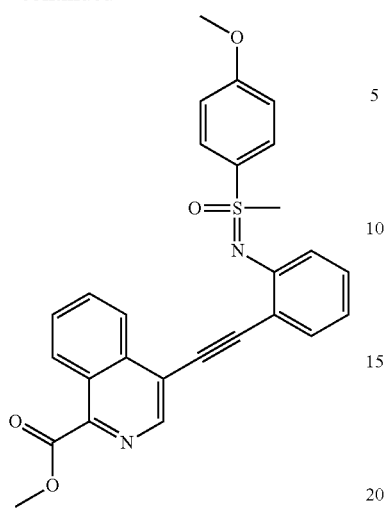

To a solution of methyl 4-[2-(2-bromophenyl)ethynyl] isoquinoline-1-carb-oxylate (98.0 mg; 0.21 mmol) in Toluene (5 ml) was added in a microwave vial under argon imino(4-methoxyphenyl)methyl-A6-sulfanone (46.2 mg; 0.25 mmol), Cesium carbonate (203 mg; 0.62 mmol), 2-Dicyclohexylphosphino-2',6'-diisopropoxybiphenyl (RuPhos) (20.4 mg; 0.04 mmol) and Palladium(II) acetate (47% Pd) (4.7 mg; 0.02 mmol). The reaction was stirred for 16 hrs at 110° C. HPLC-MS showed the required product. The reactions were diluted with ethyl acetate and extracted 3× with water, dried over $Na_2SO_4$ and evaporated to dryness. The residue was purified by flash chromatography giving the product as yellow solid in 20% yield (25 mg).

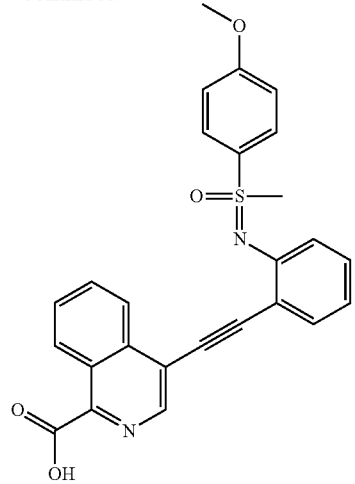

To a solution of methyl 4-[2-(2-{[(4-methoxyphenyl)(methyl)oxo-A6-sulfanyl-idene]amino}phenyl)ethynyl]isoquinoline-1-carboxylate (25 mg) in Methanol (4 ml) was added Sodium hydroxide solution c(NaOH)=2 mol/l (2 N) (0.4 ml) and stirred for 16 hrs at RT. HPLC-MS showed the complete formation of the required product. The reaction was evaporated to dryness. The residue was purified by prep. HPLC giving the sodium salt of the acid 4-[2-(2-{[(4-methoxyphenyl)(methyl)oxo-A6-sulfanylidene] amino}phenyl)ethynyl]iso-quinoline-1-carboxylic acid as orange solid in 99% yield (28 mg).

Example 63

Synthesis of 5-(2-{2-[(naphthalen-1-yl)sulfamoyl] phenyl}ethynyl)-pyridine-2-carboxylic acid

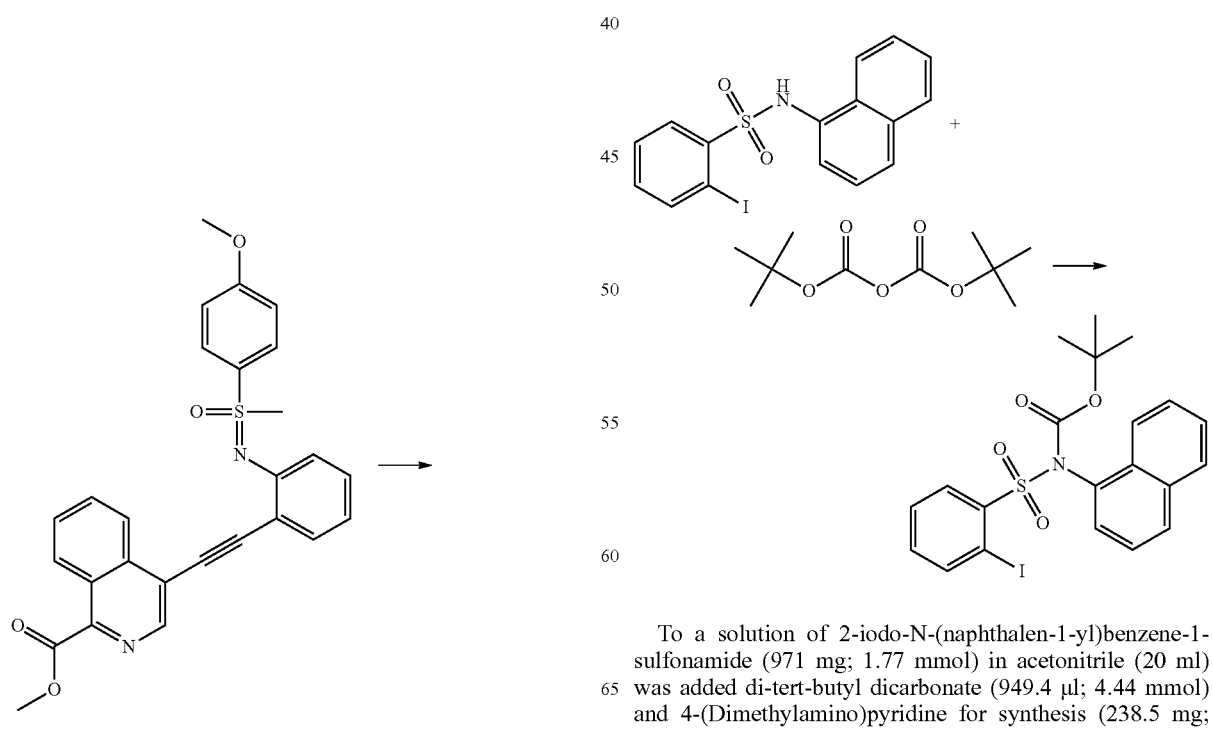

To a solution of 2-iodo-N-(naphthalen-1-yl)benzene-1-sulfonamide (971 mg; 1.77 mmol) in acetonitrile (20 ml) was added di-tert-butyl dicarbonate (949.4 µl; 4.44 mmol) and 4-(Dimethylamino)pyridine for synthesis (238.5 mg; 1.95 mmol). The reaction was stirred for 3 days at RT.

HPLC-MS showed the complete formation of the required product. The reaction was diluted with ethyl acetate and extracted 3× with water, dried over Na₂SO₄ and evaporated to dryness. The crude (760 mg; 50% yield) was used in the next step without further purification.

Tetrakis(triphenylphosphine)-palladium(0) for synthesis (94.7 mg; 0.08 mmol) was added and stirred for 16 hrs at 80° C. HPLC-MS showed as mainproduct, the required product without the boc-group and some product. The reaction was diluted with ethyl acetate and extracted 3× with water, dried over Na₂SO₄ and evaporated to dryness. The residue was purified by flash chromatography giving the product as yellow oil in 15% yield (70 mg).

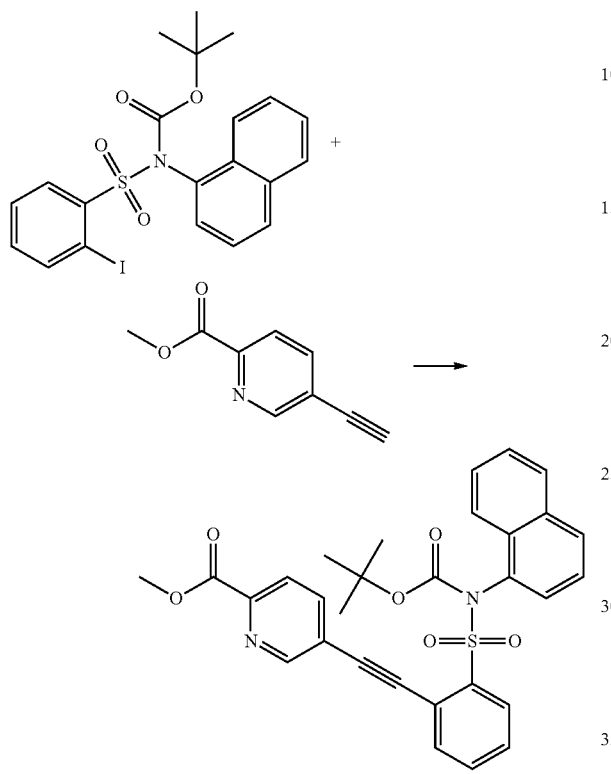

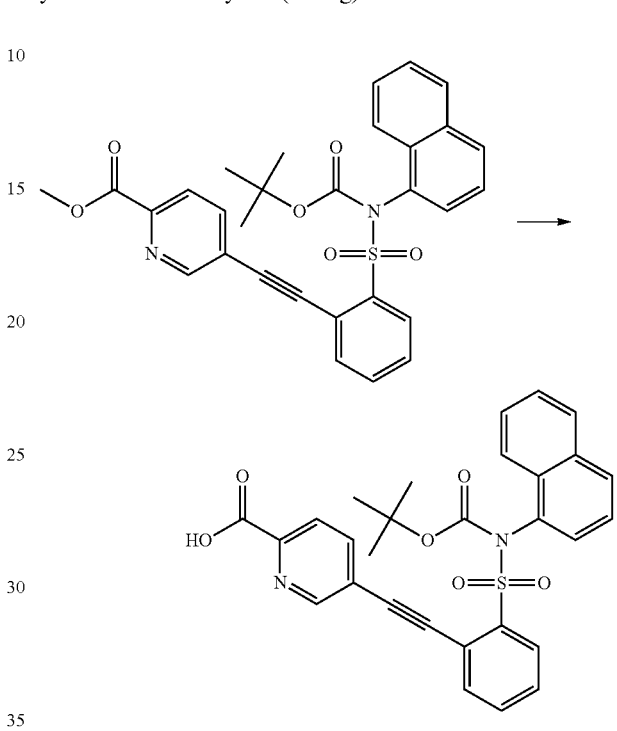

To a solution of tert-butyl N-(2-iodobenzenesulfonyl)-N-(naphthalen-1-yl)carbamate (710 mg; 0.82 mmol) was added under argon in a microwave-vial Methyl 5-ethynylpyridine-2-carboxylate (208.6 mg; 1.23 mmol), Copper (I) iodide for synthesis (15.6 mg; 0.08 mmol), Diisopropylamine (0.2 ml; 1.23 mmol) and Tetrakis(triphenylphosphine)-palladium(0) for synthesis (94.7 mg; 0.08 mmol). The reaction was stirred for 16 hrs at 80° C. HPLC-MS showed a not complete formation of the required product. More Methyl 5-ethynylpyridine-2-carboxylate (208.6 mg; 1.23 mmol), Copper(I) iodide for synthesis (15.6 mg; 0.08 mmol), Diisopropylamine (0.2 ml; 1.23 mmol) and To a solution of 5-{2-[2-({[(tert-butoxy)carbonyl](naphthalen-1-yl)amino}-sulfonyl)phenyl]ethynyl}pyridine-2-carboxylic acid (59 mg; 0.08 mmol;) in 1,4-Dioxane (5 ml) was added HCl (4.0 M in dioxane, 3 ml) and stirred for 16 hrs at RT. HPLC-MS showed a not complete formation of the required product. More HCl (4.0 M in dioxane, 2 ml) was added and stirred for 16 hrs at RT. HPLC-MS showed the complete formation of the required product. The reaction was diluted with water and lyophilized. The residue was purified by prep. HPLC giving the product 5-(2-{2-[(naphthalen-1-yl)sulfamoyl]phenyl}-ethynyl)pyridine-2-carboxylic acid as light yellow solid in 39% yield (10 mg).

Table 1 shows the compounds prepared in accordance with or similar to the synthetic procedures described above:

TABLE 1

| Compound Structure | IUPAC name | Cpd. No. |
|---|---|---|
| 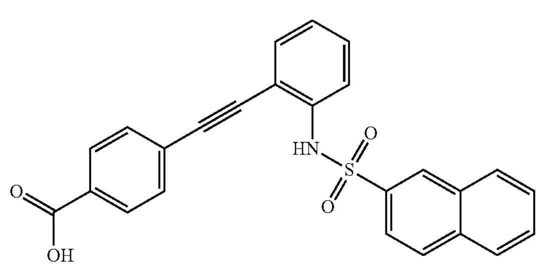 [SMILES: O=C(O)c1ccc(C#Cc2ccccc2NS(=O)(=O)c2ccc3ccccc3c2)cc1] | 4-{2-[2-(naphthalene-2-sulfonamido)phenyl]ethynyl}benzoic acid | 1 |

TABLE 1-continued

| Compound Structure | IUPAC name | Cpd. No. |
| --- | --- | --- |
| 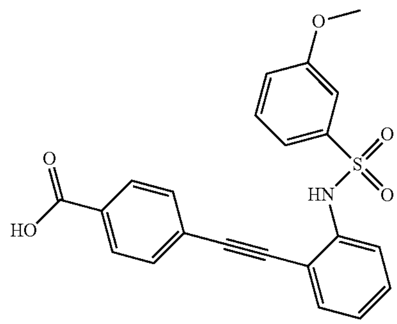 [SMILES: COc1cccc(S(=O)(=O)Nc2ccccc2C#Cc2ccc(C(=O)O)cc2)c1] | 4-{2-[2-(3-methoxybenzenesulfonamido)-phenyl]ethynyl}benzoic acid | 2 |
| 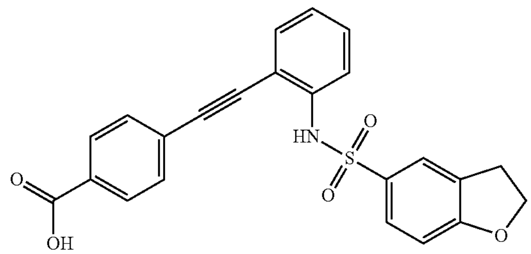 [SMILES: O=C(O)c1ccc(C#Cc2ccccc2NS(=O)(=O)c2ccc3c(c2)CCO3)cc1] | 4-{2-[2-(2,3-dihydro-1-benzofuran-5-sulfonamido)phenyl]ethynyl}benzoic acid | 3 |
| 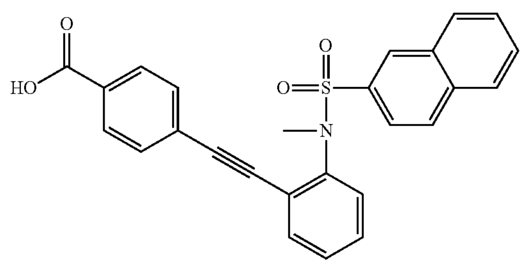 [SMILES: CN(c1ccccc1C#Cc1ccc(C(=O)O)cc1)S(=O)(=O)c1ccc2ccccc2c1] | 4-{2-[2-(N-methylnaphthalene-2-sulfonamido)phenyl]ethynyl}benzoic acid | 4 |
| 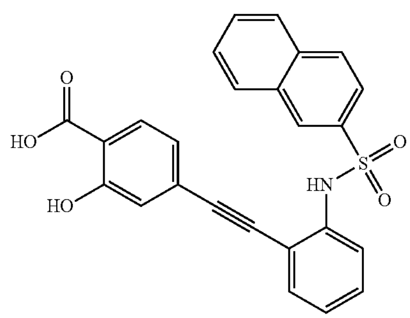 [SMILES: O=C(O)c1ccc(C#Cc2ccccc2NS(=O)(=O)c2ccc3ccccc3c2)cc1O] | 2-hydroxy-4-{2-[2-(naphthalene-2-sulfonamido)phenyl]ethynyl}benzoic acid | 5 |
| 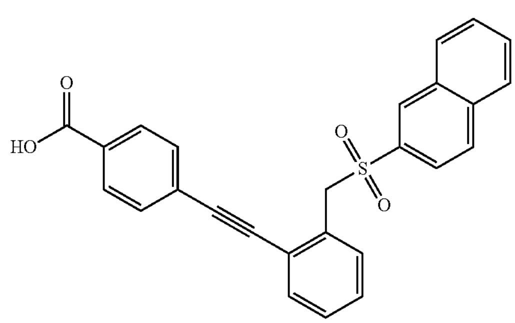 [SMILES: O=C(O)c1ccc(C#Cc2ccccc2CS(=O)(=O)c2ccc3ccccc3c2)cc1] | 4-(2-{2-[(naphthalene-2-sulfonyl)methyl]phenyl}ethynyl)benzoic acid | 6 |

TABLE 1-continued

| Compound Structure | IUPAC name | Cpd. No. |
|---|---|---|
| 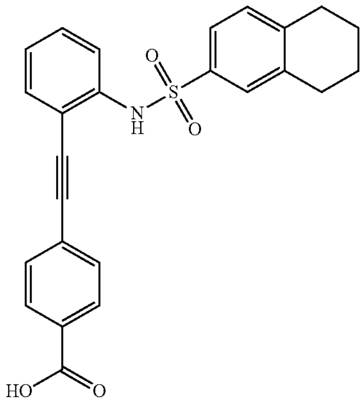 [SMILES: O=C(O)c1ccc(C#Cc2ccccc2NS(=O)(=O)c2ccc3c(c2)CCCC3)cc1] | 4-{2-[2-(5,6,7,8-tetrahydronaphthalene-2-sulfonamido)phenyl]ethynyl}benzoic acid | 7 |
| 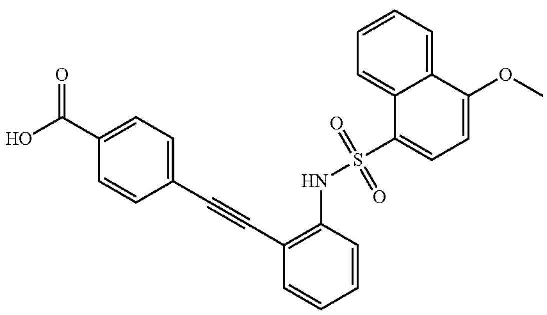 [SMILES: COc1ccc(S(=O)(=O)Nc2ccccc2C#Cc2ccc(C(=O)O)cc2)c2ccccc12] | 4-{2-[2-(4-methoxynaphthalene-1-sulfonamido)phenyl]ethynyl}benzoic acid | 8 |
| 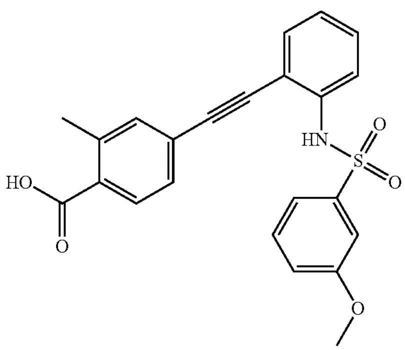 [SMILES: COc1cccc(S(=O)(=O)Nc2ccccc2C#Cc2ccc(C(=O)O)c(C)c2)c1] | 4-{2-[2-(3-methoxybenzenesulfonamido)phenyl]-ethynyl}-2-methylbenzoic acid | 9 |
| 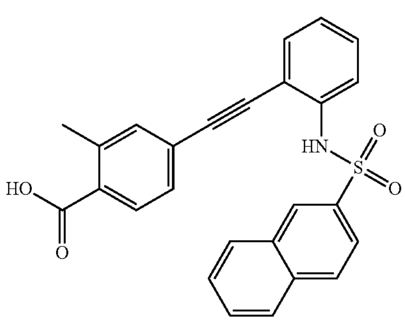 [SMILES: Cc1cc(C#Cc2ccccc2NS(=O)(=O)c2ccc3ccccc3c2)ccc1C(=O)O] | 2-methyl-4-{2-[2-(naphthalene-2-sulfonamido)phenyl]ethynyl}benzoic acid | 10 |

TABLE 1-continued

| Compound Structure | IUPAC name | Cpd. No. |
| --- | --- | --- |
| 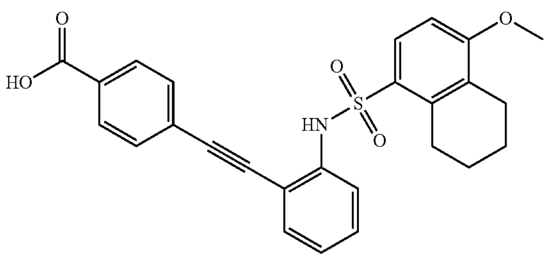 [SMILES: COc1ccc(S(=O)(=O)Nc2ccccc2C#Cc2ccc(C(=O)O)cc2)c2c1CCCC2] | 4-{2-[2-(4-methoxy-5,6,7,8-tetrahydronaphthalene-1-sulfonamido)phenyl]ethynyl}benzoic acid | 11 |
| 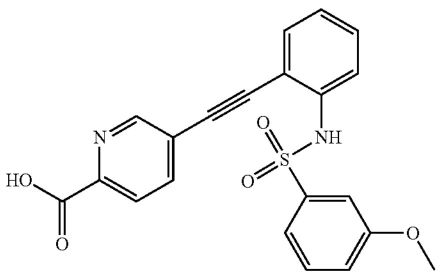 [SMILES: COc1cccc(S(=O)(=O)Nc2ccccc2C#Cc2ccc(C(=O)O)nc2)c1] | 5-{2-[2-(3-methoxybenzenesulfonamido)phenyl]-ethynyl}pyridine-2-carboxylic acid | 12 |
| 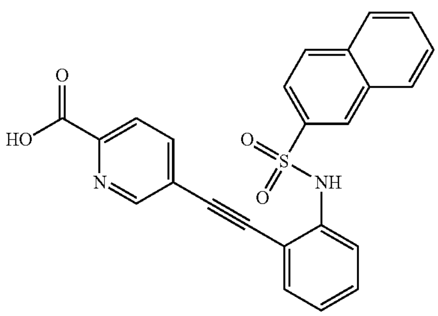 [SMILES: O=C(O)c1ccc(C#Cc2ccccc2NS(=O)(=O)c2ccc3ccccc3c2)cn1] | 5-{2-[2-(naphthalene-2-sulfonamido)phenyl]ethynyl}pyridine-2-carboxylic acid | 13 |
| 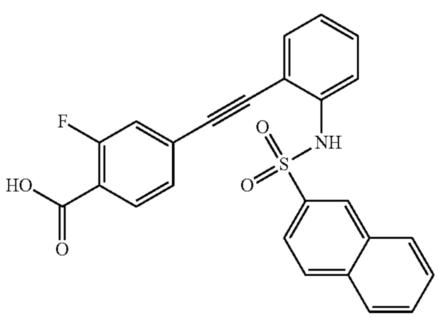 [SMILES: O=C(O)c1ccc(C#Cc2ccccc2NS(=O)(=O)c2ccc3ccccc3c2)cc1F] | 2-fluoro-4-{2-[2-(naphthalene-2-sulfonamido)phenyl]ethynyl}benzoic acid | 14 |
| 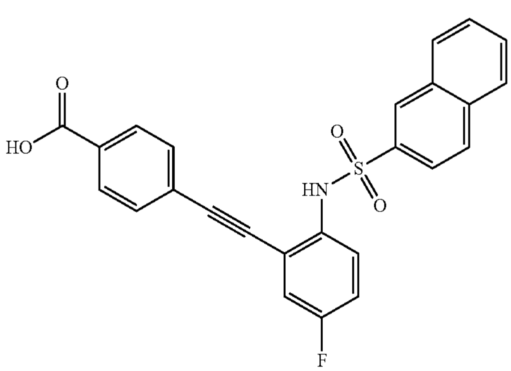 [SMILES: O=C(O)c1ccc(C#Cc2cc(F)ccc2NS(=O)(=O)c2ccc3ccccc3c2)cc1] | 4-{2-[5-fluoro-2-(naphthalene-2-sulfonamido)phenyl]ethynyl}benzoic acid | 15 |

TABLE 1-continued

| Compound Structure | IUPAC name | Cpd. No. |
|---|---|---|
| 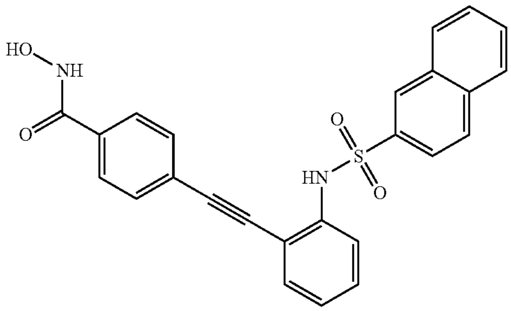 [SMILES: O=C(NO)c1ccc(C#Cc2ccccc2NS(=O)(=O)c2ccc3ccccc3c2)cc1] | N-hydroxy-4-{2-[2-(naphthalene-2-sulfonamido)phenyl]ethynyl}benzamide | 16 |
| 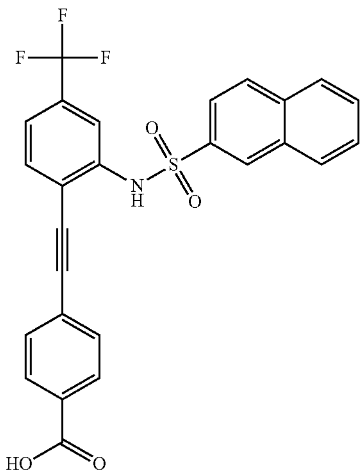 [SMILES: O=C(O)c1ccc(C#Cc2ccc(C(F)(F)F)cc2NS(=O)(=O)c2ccc3ccccc3c2)cc1] | 4-{2-[2-(naphthalene-2-sulfonamido)-4-(trifluoromethyl)phenyl]ethynyl}benzoic acid | 17 |
| 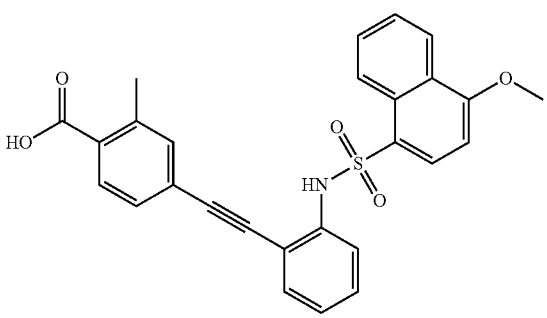 | 4-{2-[2-(4-methoxynaphthalene-1-sulfonamido)phenyl]ethynyl}-2-methylbenzoic acid | 18 |
| 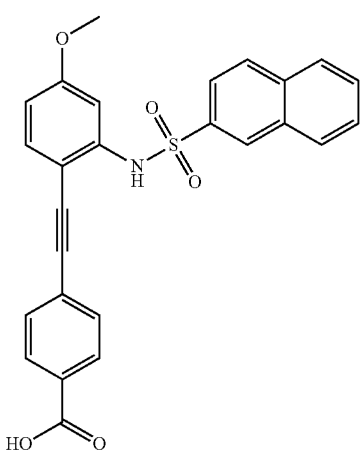 [SMILES: COc1ccc(C#Cc2ccc(C(=O)O)cc2)c(NS(=O)(=O)c2ccc3ccccc3c2)c1] | 4-{2-[4-methoxy-2-(naphthalene-2-sulfonamido)phenyl]ethynyl}benzoic acid | 19 |

TABLE 1-continued

| Compound Structure | IUPAC name | Cpd. No. |
| --- | --- | --- |
| 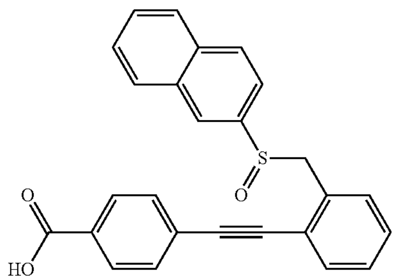 [SMILES: O=C(O)c1ccc(C#Cc2ccccc2CS(=O)c2ccc3ccccc3c2)cc1] | 4-(2-{2-[(naphthalene-2-sulfinyl)methyl]phenyl}ethynyl)benzoic acid | 20 |
| 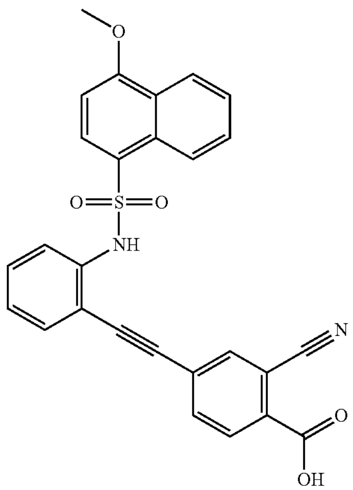 [SMILES: COc1ccc(S(=O)(=O)Nc2ccccc2C#Cc2ccc(C(=O)O)c(C#N)c2)c2ccccc12] | 2-cyano-4-{2-[2-(4-methoxynaphthalene-1-sulfonamido)phenyl]ethynyl}benzoic acid | 21 |
| 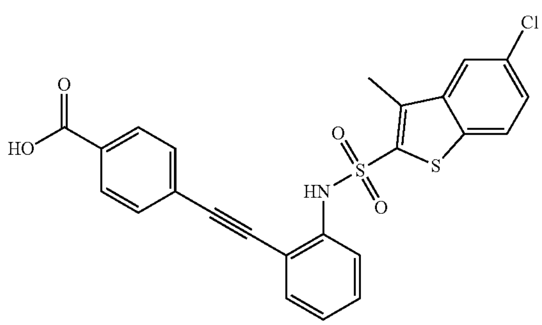 [SMILES: Cc1c(S(=O)(=O)Nc2ccccc2C#Cc2ccc(C(=O)O)cc2)sc2ccc(Cl)cc12] | 4-{2-[2-(5-chloro-3-methyl-1-benzothiophene-2-sulfonamido)phenyl]ethynyl}benzoic acid | 22 |
|  | 4-{2-[2-(2,3-dichloro-4-methoxybenzenesulfonamido)phenyl]ethynyl}benzoic acid | 23 |

TABLE 1-continued

| Compound Structure | IUPAC name | Cpd. No. |
|---|---|---|
| 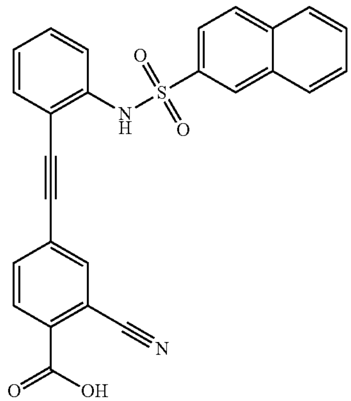 [SMILES: N#Cc1cc(C#Cc2ccccc2NS(=O)(=O)c2ccc3ccccc3c2)ccc1C(=O)O] | 2-cyano-4-{2-[2-(naphthalene-2-sulfonamido)phenyl]ethynyl}benzoic acid | 24 |
| 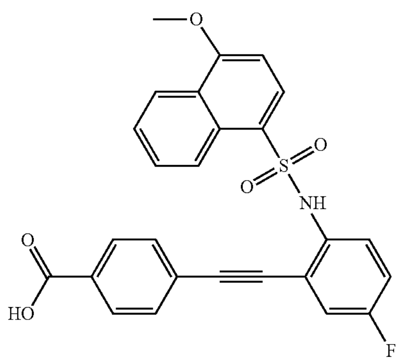 [SMILES: COc1ccc(S(=O)(=O)Nc2ccc(F)cc2C#Cc2ccc(C(=O)O)cc2)c2ccccc12] | 4-{2-[5-fluoro-2-(4-methoxynaphthalene-1-sulfonamido)phenyl]ethynyl}benzoic acid | 25 |
| 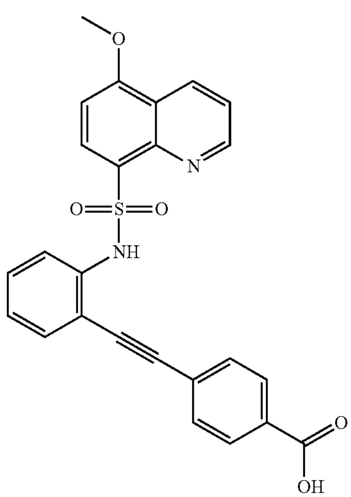 [SMILES: COc1ccc(S(=O)(=O)Nc2ccccc2C#Cc2ccc(C(=O)O)cc2)c2ncccc12] | 4-{2-[2-(5-methoxyquinoline-8-sulfonamido)phenyl]ethynyl}benzoic acid | 26 |

TABLE 1-continued

| Compound Structure | IUPAC name | Cpd. No. |
|---|---|---|
| 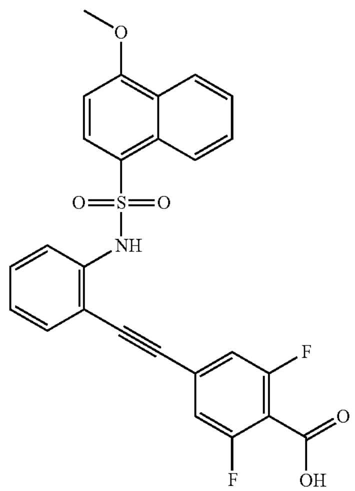 [SMILES: COc1ccc(S(=O)(=O)Nc2ccccc2C#Cc2cc(F)c(C(=O)O)c(F)c2)c2ccccc12] | 2,6-difluoro-4-{2-[2-(4-methoxynaphthalene-1-sulfonamido)phenyl]ethynyl}benzoic acid | 27 |
| 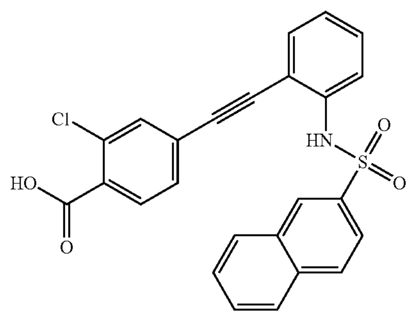 [SMILES: O=C(O)c1ccc(C#Cc2ccccc2NS(=O)(=O)c2ccc3ccccc3c2)cc1Cl] | 2-chloro-4-{2-[2-(naphthalene-2-sulfonamido)phenyl]ethynyl}benzoic acid | 28 |
| 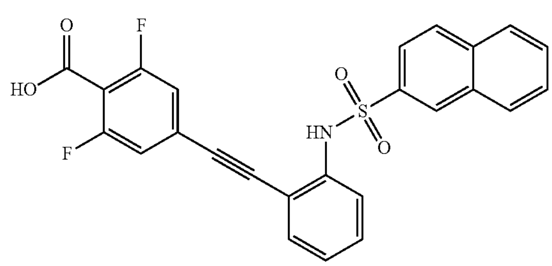 [SMILES: O=C(O)c1c(F)cc(C#Cc2ccccc2NS(=O)(=O)c2ccc3ccccc3c2)cc1F] | 2,6-difluoro-4-{2-[2-(naphthalene-2-sulfonamido)phenyl]ethynyl}benzoic acid | 29 |
| 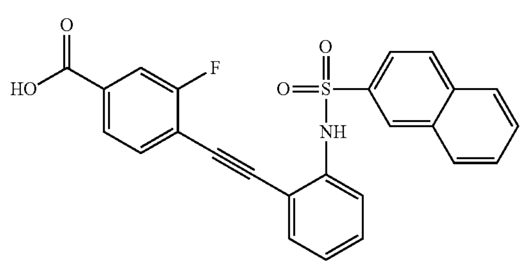 [SMILES: O=C(O)c1ccc(C#Cc2ccccc2NS(=O)(=O)c2ccc3ccccc3c2)c(F)c1] | 3-fluoro-4-{2-[2-(naphthalene-2-sulfonamido)phenyl]ethynyl}benzoic acid | 30 |
| 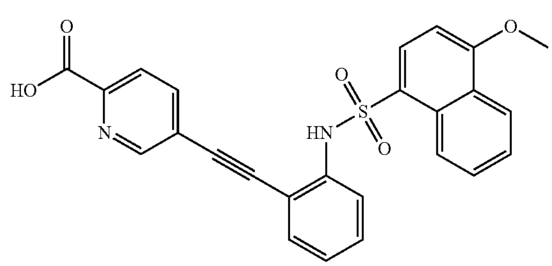 [SMILES: COc1ccc(S(=O)(=O)Nc2ccccc2C#Cc2ccc(C(=O)O)nc2)c2ccccc12] | 5-{2-[2-(4-methoxynaphthalene-1-sulfonamido)phenyl]ethynyl}pyridine-2-carboxylic acid | 31 |

TABLE 1-continued

| Compound Structure | IUPAC name | Cpd. No. |
|---|---|---|
| 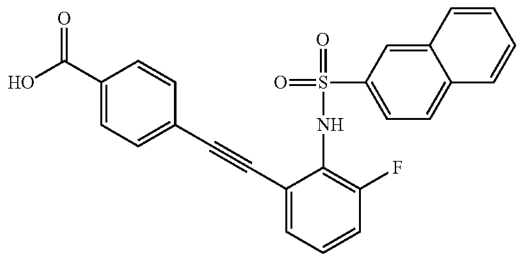 [SMILES: O=C(O)c1ccc(C#Cc2cccc(F)c2NS(=O)(=O)c2ccc3ccccc3c2)cc1] | 4-{2-[3-fluoro-2-(naphthalene-2-sulfonamido)phenyl]ethynyl}benzoic acid | 32 |
| 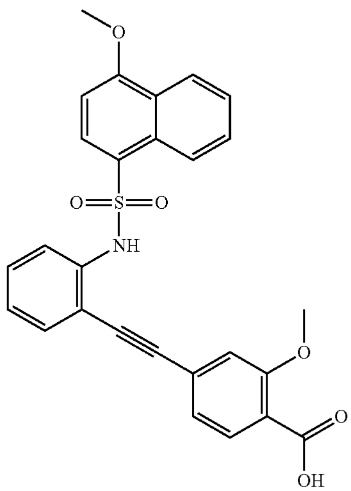 [SMILES: COc1cc(C#Cc2ccccc2NS(=O)(=O)c2ccc(OC)c3ccccc23)ccc1C(=O)O] | 2-methoxy-4-{2-[2-(4-methoxynaphthalene-1-sulfonamido)phenyl]ethynyl}benzoic acid | 33 |
| 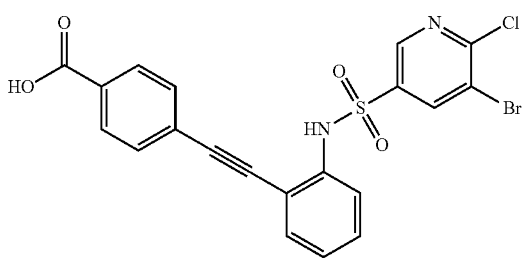 [SMILES: O=C(O)c1ccc(C#Cc2ccccc2NS(=O)(=O)c2cnc(Cl)c(Br)c2)cc1] | 4-{2-[2-(5-bromo-6-chloropyridine-3-sulfonamido)phenyl]ethynyl}benzoic acid | 34 |
| 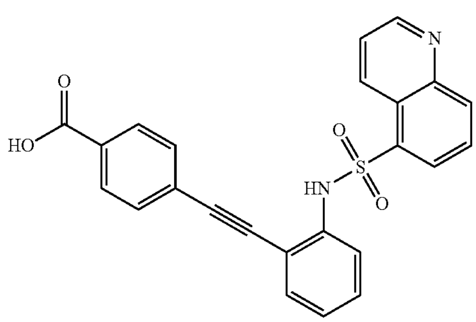 [SMILES: O=C(O)c1ccc(C#Cc2ccccc2NS(=O)(=O)c2cccc3ncccc23)cc1] | 4-{2-[2-(quinoline-5-sulfonamido)phenyl]ethynyl}benzoic acid | 35 |
| 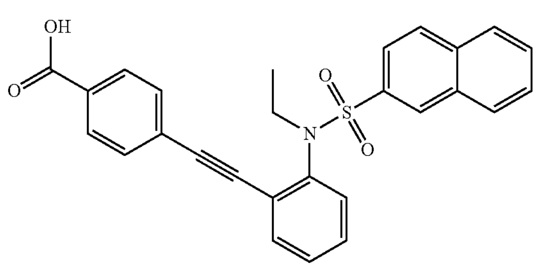 [SMILES: CCN(c1ccccc1C#Cc1ccc(C(=O)O)cc1)S(=O)(=O)c1ccc2ccccc2c1] | 4-{2-[2-(N-ethylnaphthalene-2-sulfonamido)phenyl]ethynyl}benzoic acid | 36 |

TABLE 1-continued

| Compound Structure | IUPAC name | Cpd. No. |
| --- | --- | --- |
| 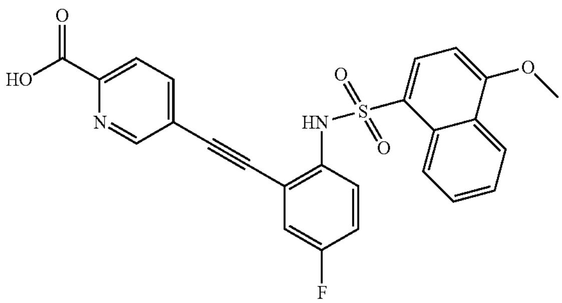 [SMILES: COc1ccc(S(=O)(=O)Nc2ccc(F)cc2C#Cc2ccc(C(=O)O)nc2)c2ccccc12] | 5-{2-[5-fluoro-2-(4-methoxynaphthalene-1-sulfonamido)phenyl]ethynyl}pyridine-2-carboxylic acid | 37 |
| 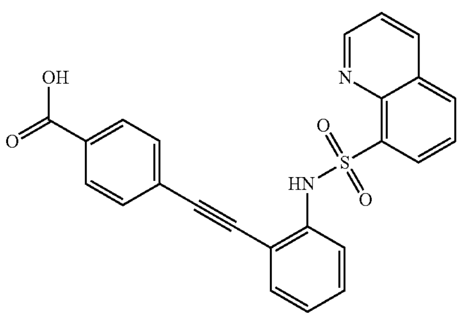 [SMILES: O=C(O)c1ccc(C#Cc2ccccc2NS(=O)(=O)c2cccc3cccnc23)cc1] | 4-{2-[2-(quinoline-8-sulfonamido)phenyl]ethynyl}benzoic acid | 38 |
| 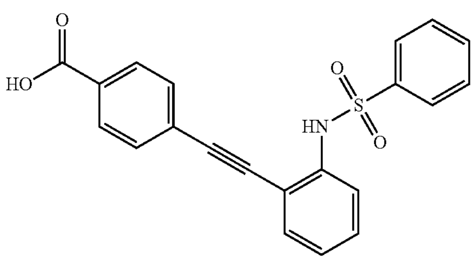 [SMILES: O=C(O)c1ccc(C#Cc2ccccc2NS(=O)(=O)c2ccccc2)cc1] | 4-[2-(2-benzenesulfonamidophenyl)ethynyl]-benzoic acid | 39 |
| 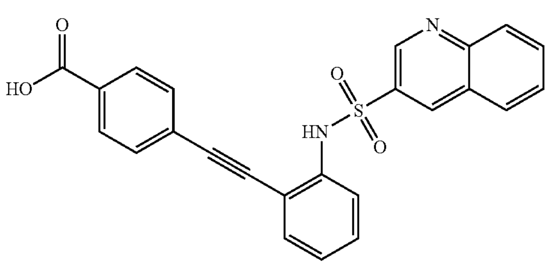 [SMILES: O=C(O)c1ccc(C#Cc2ccccc2NS(=O)(=O)c2cnc3ccccc3c2)cc1] | 4-{2-[2-(quinoline-3-sulfonamido)phenyl]ethynyl}benzoic acid | 40 |
| 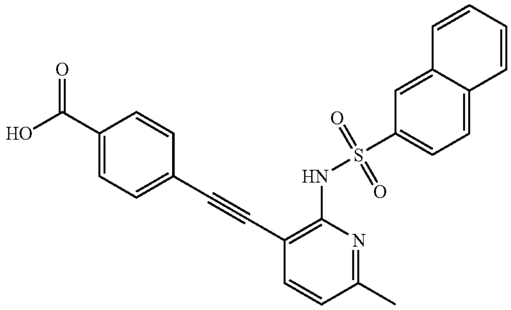 [SMILES: Cc1ccc(C#Cc2ccc(C(=O)O)cc2)c(NS(=O)(=O)c2ccc3ccccc3c2)n1] | 4-{2-[6-methyl-2-(naphthalene-2-sulfonamido)pyridin-3-yl]ethynyl}benzoic acid | 41 |

TABLE 1-continued

| Compound Structure | IUPAC name | Cpd. No. |
|---|---|---|
| 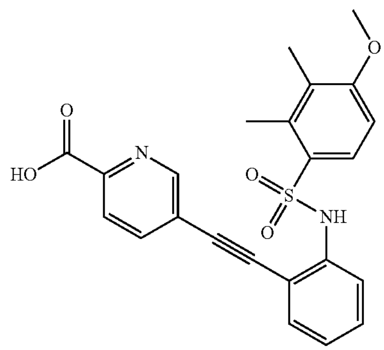 [SMILES: COc1ccc(S(=O)(=O)Nc2ccccc2C#Cc2ccc(C(=O)O)nc2)c(C)c1C] | 5-{2-[2-(4-methoxy-2,3-dimethylbenzenesulfonamido)phenyl]-ethynyl}pyridine-2-carboxylic acid | 42 |
| 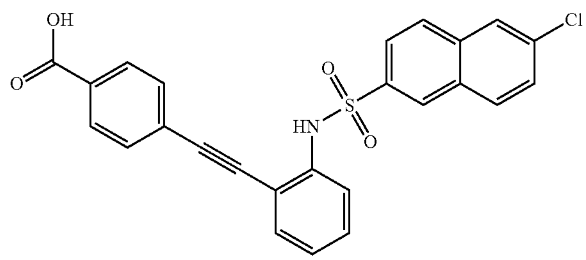 [SMILES: O=C(O)c1ccc(C#Cc2ccccc2NS(=O)(=O)c2ccc3cc(Cl)ccc3c2)cc1] | 4-{2-[2-(6-chloronaphthalene-2-sulfonamido)phenyl]ethynyl}benzoic acid | 43 |
| 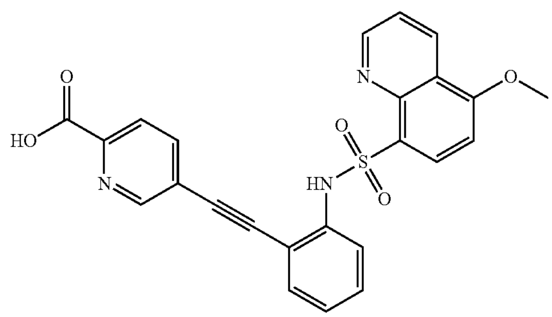 [SMILES: COc1ccc(S(=O)(=O)Nc2ccccc2C#Cc2ccc(C(=O)O)nc2)c2ncccc12] | 5-{2-[2-(5-methoxyquinoline-8-sulfonamido)phenyl]ethynyl}pyridine-2-carboxylic acid | 44 |
| 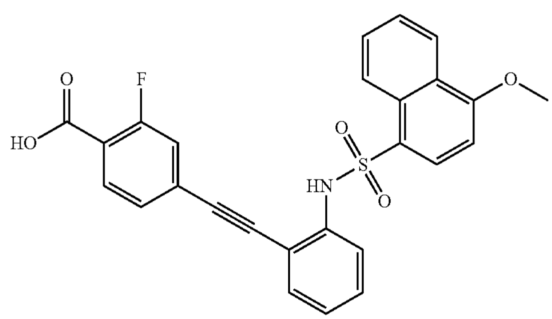 [SMILES: COc1ccc(S(=O)(=O)Nc2ccccc2C#Cc2ccc(C(=O)O)c(F)c2)c2ccccc12] | 2-fluoro-4-{2-[2-(4-methoxynaphthalene-1-sulfonamido)phenyl]ethynyl}benzoic acid | 45 |
| 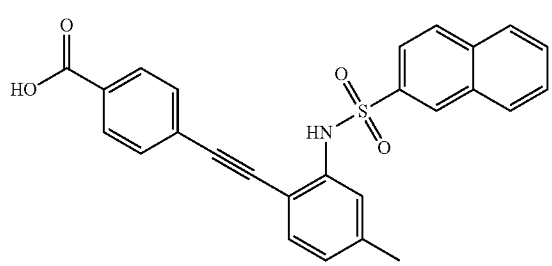 [SMILES: Cc1ccc(C#Cc2ccc(C(=O)O)cc2)c(NS(=O)(=O)c2ccc3ccccc3c2)c1] | 4-{2-[4-methyl-2-(naphthalene-2-sulfonamido)phenyl]ethynyl}benzoic acid | 46 |

TABLE 1-continued

| Compound Structure | IUPAC name | Cpd. No. |
|---|---|---|
| 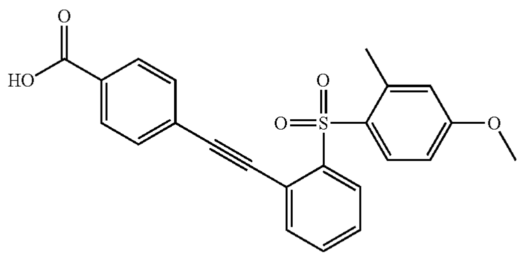 [SMILES: COc1ccc(S(=O)(=O)c2ccccc2C#Cc2ccc(C(=O)O)cc2)c(C)c1] | 4-{2-[2-(4-methoxy-2-methylbenzenesulfonamido)phenyl]ethynyl}benzoic acid | 47 |
| 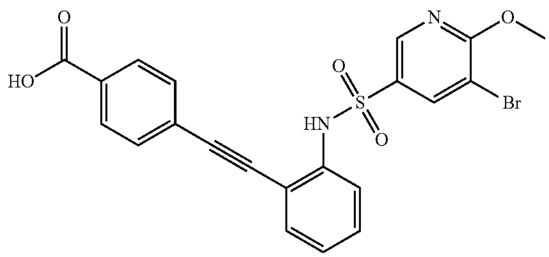 [SMILES: COc1ncc(S(=O)(=O)Nc2ccccc2C#Cc2ccc(C(=O)O)cc2)cc1Br] | 4-{2-[2-(5-bromo-6-methoxypyridine-3-sulfonamido)phenyl]ethynyl}benzoic acid | 48 |
| 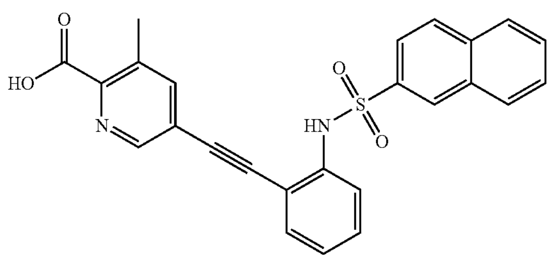 [SMILES: Cc1cc(C#Cc2ccccc2NS(=O)(=O)c2ccc3ccccc3c2)cnc1C(=O)O] | 3-methyl-5-{2-[2-(naphthalene-2-sulfonamido)phenyl]ethynyl}pyridine-2-carboxylic acid | 49 |
| 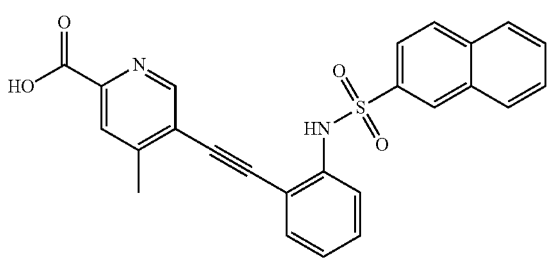 [SMILES: Cc1cc(C(=O)O)ncc1C#Cc1ccccc1NS(=O)(=O)c1ccc2ccccc2c1] | 4-methyl-5-{2-[2-(naphthalene-2-sulfonamido)phenyl]ethynyl}pyridine-2-carboxylic acid | 50 |
| 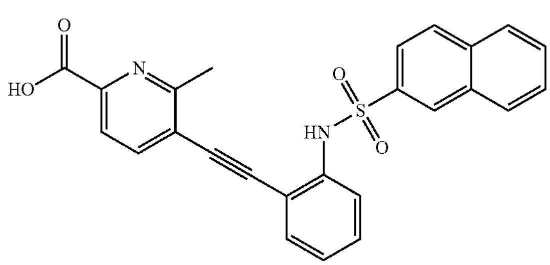 [SMILES: Cc1nc(C(=O)O)ccc1C#Cc1ccccc1NS(=O)(=O)c1ccc2ccccc2c1] | 6-methyl-5-{2-[2-(naphthalene-2-sulfonamido)phenyl]ethynyl}pyridine-2-carboxylic acid | 51 |
| 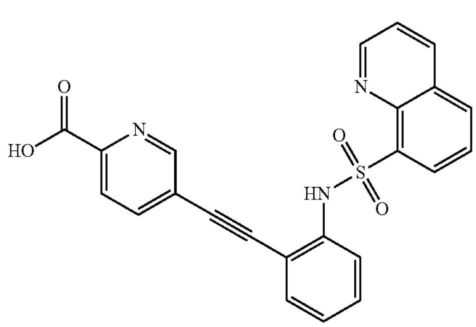 [SMILES: O=C(O)c1ccc(C#Cc2ccccc2NS(=O)(=O)c2cccc3cccnc23)cn1] | 5-{2-[2-(quinoline-8-sulfonamido)phenyl]ethynyl}pyridine-2-carboxylic acid | 52 |

TABLE 1-continued

| Compound Structure | IUPAC name | Cpd. No. |
|---|---|---|
| 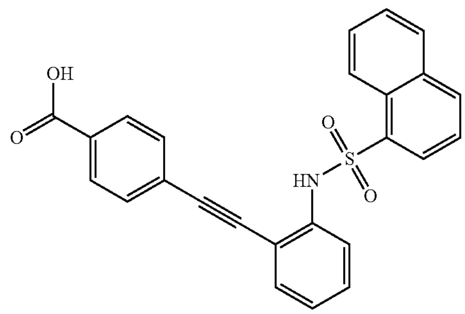 [SMILES: O=C(O)c1ccc(C#Cc2ccccc2NS(=O)(=O)c2cccc3ccccc23)cc1] | 4-{2-[2-(naphthalene-1-sulfonamido)phenyl]ethynyl}benzoic acid | 53 |
| 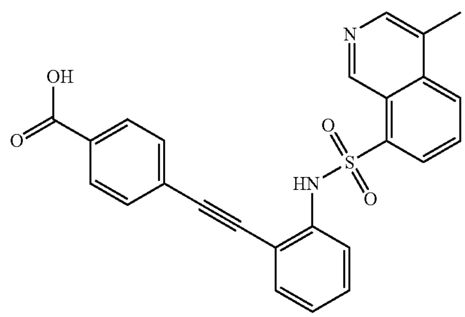 [SMILES: Cc1cncc2c(S(=O)(=O)Nc3ccccc3C#Cc3ccc(C(=O)O)cc3)cccc12] | 4-{2-[2-(4-methylisoquinoline-8-sulfonamido)phenyl]ethynyl}benzoic acid | 54 |
| 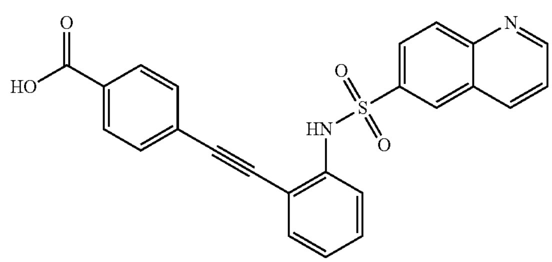 [SMILES: O=C(O)c1ccc(C#Cc2ccccc2NS(=O)(=O)c2ccc3ncccc3c2)cc1] | 4-{2-[2-(quinoline-6-sulfonamido)phenyl]ethynyl}benzoic acid | 55 |
| 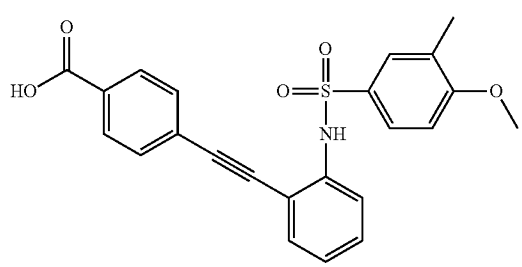 [SMILES: COc1ccc(S(=O)(=O)Nc2ccccc2C#Cc2ccc(C(=O)O)cc2)cc1C] | 4-{2-[2-(4-methoxy-3-methylbenzenesulfonamido)phenyl]-ethynyl}benzoic acid | 56 |
| 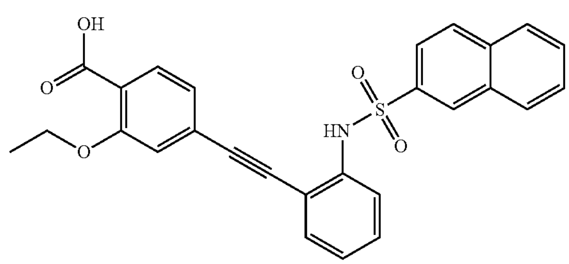 [SMILES: CCOc1cc(C#Cc2ccccc2NS(=O)(=O)c2ccc3ccccc3c2)ccc1C(=O)O] | 2-ethoxy-4-{2-[2-(naphthalene-2-sulfonamido)phenyl]ethynyl}benzoic acid | 57 |

TABLE 1-continued

| Compound Structure | IUPAC name | Cpd. No. |
|---|---|---|
| 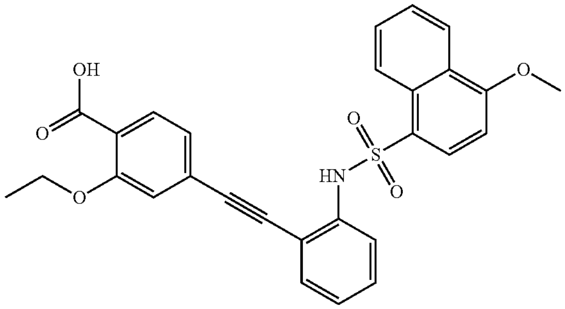 [SMILES: CCOc1cc(C#Cc2ccccc2NS(=O)(=O)c2ccc(OC)c3ccccc23)ccc1C(=O)O] | 2-ethoxy-4-{2-[2-(4-methoxynaphthalene-1-sulfonamido)phenyl]ethynyl}benzoic acid | 58 |
| 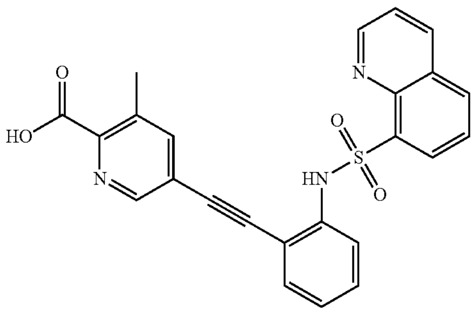 [SMILES: Cc1cc(C#Cc2ccccc2NS(=O)(=O)c2cccc3cccnc23)cnc1C(=O)O] | 3-methyl-5-{2-[2-(quinoline-8-sulfonamido)phenyl]ethynyl}pyridine-2-carboxylic acid | 59 |
| 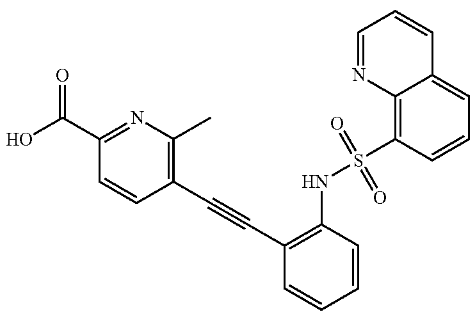 [SMILES: Cc1nc(C(=O)O)ccc1C#Cc1ccccc1NS(=O)(=O)c1cccc2cccnc12] | 6-methyl-5-{2-[2-(quinoline-8-sulfonamido)phenyl]ethynyl}pyridine-2-carboxylic acid | 60 |
| 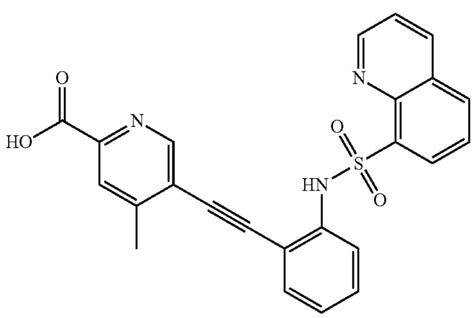 [SMILES: Cc1cc(C(=O)O)ncc1C#Cc1ccccc1NS(=O)(=O)c1cccc2cccnc12] | 4-methyl-5-{2-[2-(quinoline-8-sulfonamido)phenyl]ethynyl}pyridine-2-carboxylic acid | 61 |
| 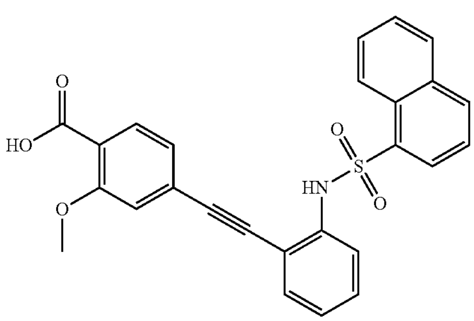 [SMILES: COc1cc(C#Cc2ccccc2NS(=O)(=O)c2cccc3ccccc23)ccc1C(=O)O] | 2-methoxy-4-{2-[2-(naphthalene-1-sulfonamido)phenyl]ethynyl}benzoic acid | 62 |

TABLE 1-continued

| Compound Structure | IUPAC name | Cpd. No. |
| --- | --- | --- |
| 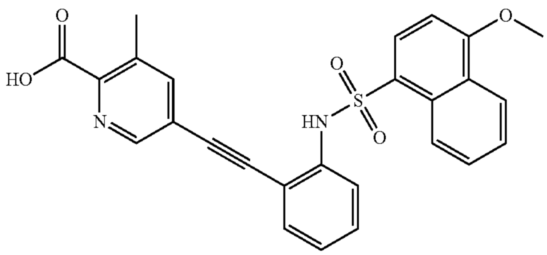 [SMILES: COc1ccc(S(=O)(=O)Nc2ccccc2C#Cc2cnc(C(=O)O)c(C)c2)c2ccccc12] | 5-{2-[2-(4-methoxynaphthalene-1-sulfonamido)phenyl]ethynyl}-3-methylpyridine-2-carboxylic acid | 63 |
| 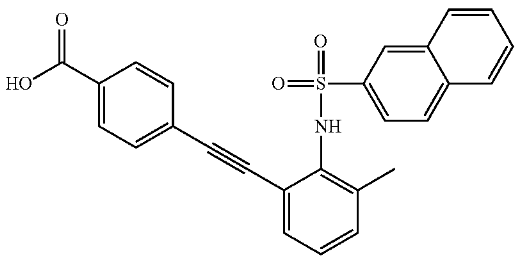 | 4-{2-[3-methyl-2-(naphthalene-2-sulfonamido)phenyl]ethynyl}benzoic acid | 64 |
| 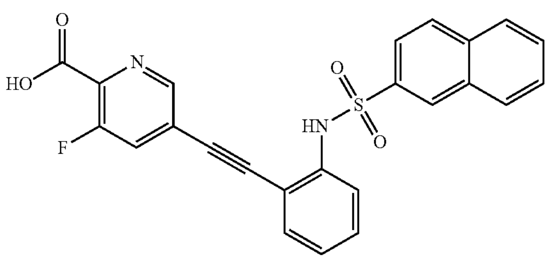 [SMILES: O=C(O)c1ncc(C#Cc2ccccc2NS(=O)(=O)c2ccc3ccccc3c2)cc1F] | 3-fluoro-5-{2-[2-(naphthalene-2-sulfonamido)phenyl]ethynyl}pyridine-2-carboxylic acid | 65 |
| 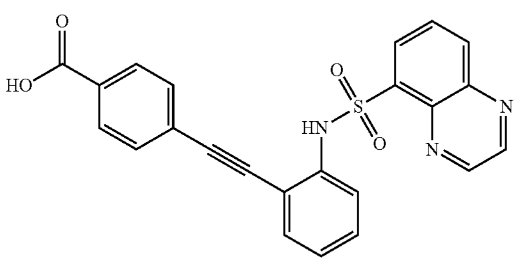 [SMILES: O=C(O)c1ccc(C#Cc2ccccc2NS(=O)(=O)c2cccc3nccnc23)cc1] | 4-{2-[2-(quinoxaline-5-sulfonamido)phenyl]ethynyl}benzoic acid | 66 |
| | 2-methoxy-4-{2-[2-(4-methoxy-2-methylbenzenesulfonamido)phenyl]ethynyl}benzoic acid | 67 |

TABLE 1-continued

| Compound Structure | IUPAC name | Cpd. No. |
|---|---|---|
| 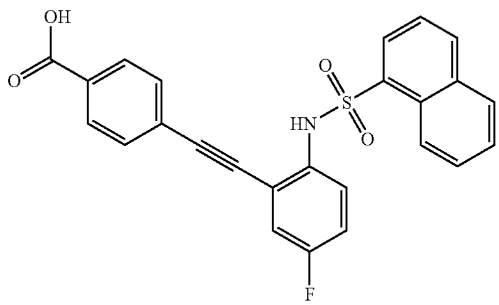 [SMILES: O=C(O)c1ccc(C#Cc2cc(F)ccc2NS(=O)(=O)c2cccc3ccccc23)cc1] | 4-{2-[5-fluoro-2-(naphthalene-1-sulfonamido)phenyl]ethynyl}benzoic acid | 68 |
| 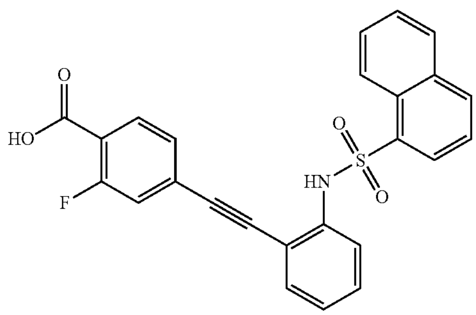 | 2-fluoro-4-{2-[2-(naphthalene-1-sulfonamido)phenyl]ethynyl}benzoic acid | 69 |
| 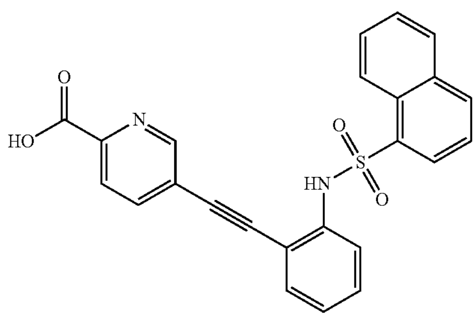 | 5-{2-[2-(naphthalene-1-sulfonamido)phenyl]ethynyl}pyridine-2-carboxylic acid | 70 |
| 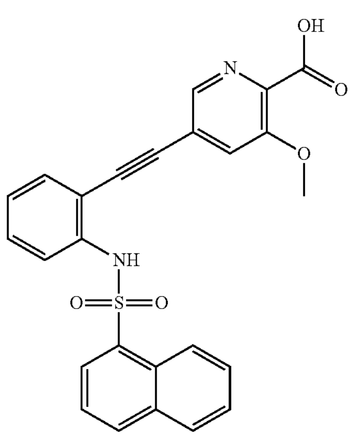 [SMILES: COc1cc(C#Cc2ccccc2NS(=O)(=O)c2cccc3ccccc23)cnc1C(=O)O] | 3-methoxy-5-{2-[2-(naphthalene-1-sulfonamido)phenyl]ethynyl}pyridine-2-carboxylic acid | 71 |

TABLE 1-continued

| Compound Structure | IUPAC name | Cpd. No. |
|---|---|---|
| 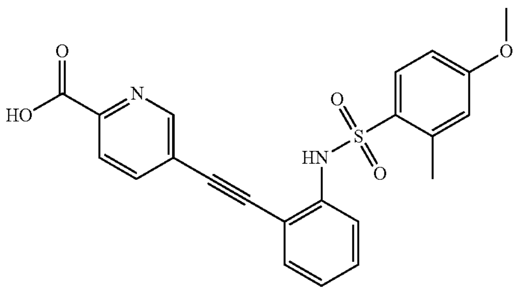 [SMILES: COc1ccc(S(=O)(=O)Nc2ccccc2C#Cc2ccc(C(=O)O)nc2)c(C)c1] | 5-{2-[2-(4-methoxy-2-methylbenzenesulfonamido)phenyl]-ethynyl}pyridine-2-carboxylic acid | 72 |
| 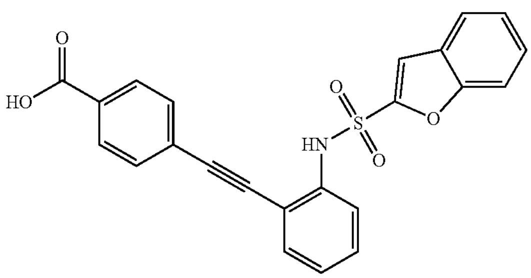 [SMILES: O=C(O)c1ccc(C#Cc2ccccc2NS(=O)(=O)c2cc3ccccc3o2)cc1] | 4-{2-[2-(1-benzofuran-2-sulfonamido)phenyl]ethynyl}benzoic acid | 73 |
| 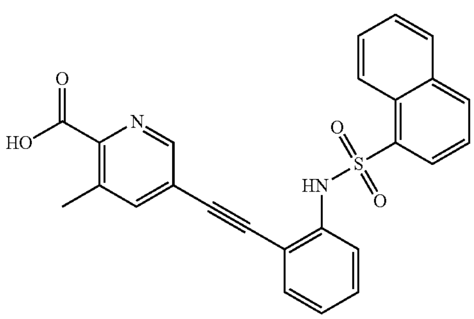 | 3-methyl-5-{2-[2-(naphthalene-1-sulfonamido)phenyl]ethynyl}pyridine-2-carboxylic acid | 74 |
| 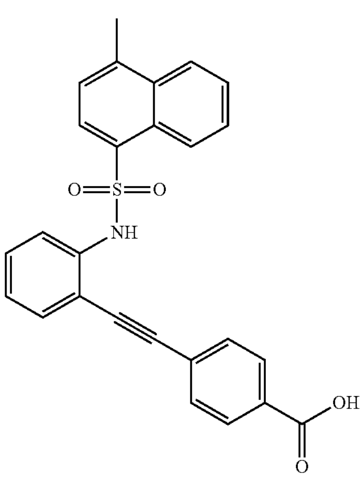 [SMILES: Cc1ccc(S(=O)(=O)Nc2ccccc2C#Cc2ccc(C(=O)O)cc2)c2ccccc12] | 4-{2-[2-(4-methylnaphthalene-1-sulfonamido)phenyl]ethynyl}benzoic acid | 75 |

TABLE 1-continued

| Compound Structure | IUPAC name | Cpd. No. |
|---|---|---|
| 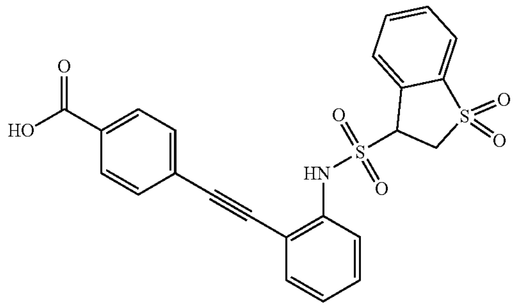 [SMILES: O=C(O)c1ccc(C#Cc2ccccc2NS(=O)(=O)C2CS(=O)(=O)c3ccccc32)cc1] | 4-{2-[2-(1,1-dioxo-2,3-dihydro-1lambda6-benzo[b]thiophene-3-sulfonamido)phenyl]ethynyl}benzoic acid | 76 |
| 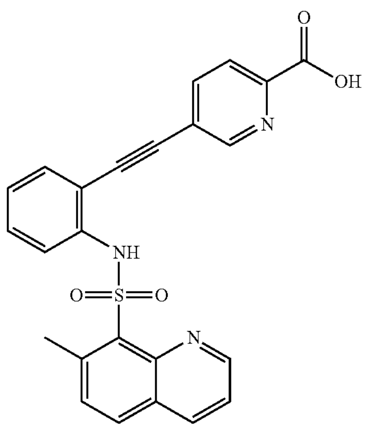 [SMILES: Cc1ccc2cccnc2c1S(=O)(=O)Nc1ccccc1C#Cc1ccc(C(=O)O)nc1] | 5-{2-[2-(7-methylquinoline-8-sulfonamido)phenyl]ethynyl}pyridine-2-carboxylic acid | 77 |
| 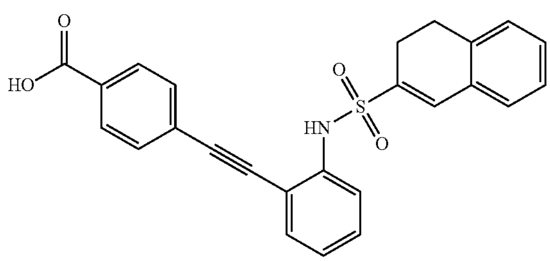 [SMILES: O=C(O)c1ccc(C#Cc2ccccc2NS(=O)(=O)C2=Cc3ccccc3CC2)cc1] | 4-{2-[2-(3,4-dihydronaphthalene-2-sulfonamido)phenyl]ethynyl}benzoic acid | 78 |
| 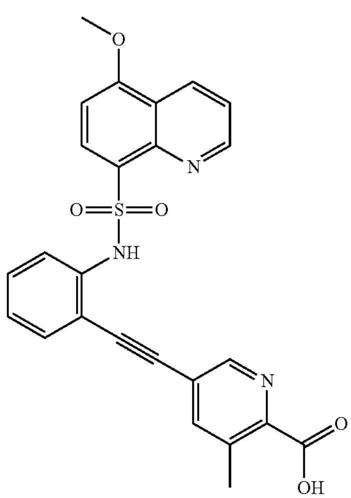 [SMILES: COc1ccc(S(=O)(=O)Nc2ccccc2C#Cc2cnc(C(=O)O)c(C)c2)c2ncccc12] | 5-{2-[2-(5-methoxyquinoline-8-sulfonamido)phenyl]ethynyl}-3-methylpyridine-2-carboxylic acid | 79 |

TABLE 1-continued

| Compound Structure | IUPAC name | Cpd. No. |
|---|---|---|
| 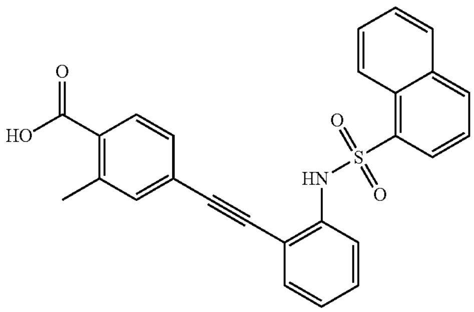 [SMILES: Cc1cc(C#Cc2ccccc2NS(=O)(=O)c2cccc3ccccc23)ccc1C(=O)O] | 2-methyl-4-{2-[2-(naphthalene-1-sulfonamido)phenyl]ethynyl}benzoic acid | 80 |
| 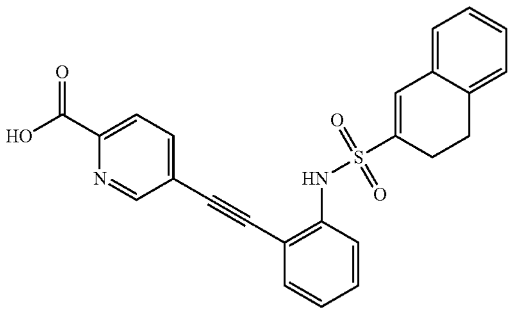 [SMILES: O=C(O)c1ccc(C#Cc2ccccc2NS(=O)(=O)C2=Cc3ccccc3CC2)cn1] | 5-{2-[2-(3,4-dihydronaphthalene-2-sulfonamido)phenyl]ethynyl}pyridine-2-carboxylic acid | 81 |
| 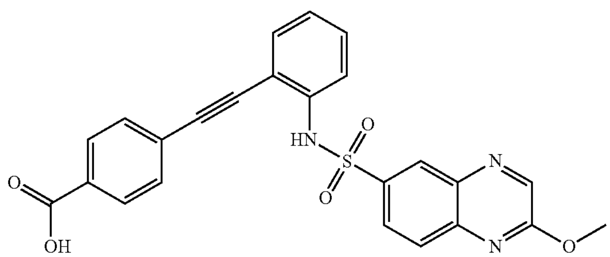 [SMILES: COc1cnc2cc(S(=O)(=O)Nc3ccccc3C#Cc3ccc(C(=O)O)cc3)ccc2n1] | 4-{2-[2-(2-methoxyquinoxaline-6-sulfonamido)phenyl]ethynyl}benzoic acid | 82 |
| 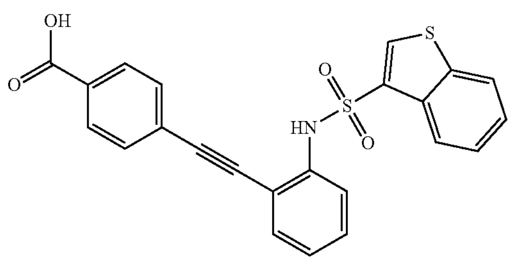 [SMILES: O=C(O)c1ccc(C#Cc2ccccc2NS(=O)(=O)c2csc3ccccc23)cc1] | 4-{2-[2-(1-benzothiophene-3-sulfonamido)pheny9 ethynyl}benzoic acid | 83 |
| 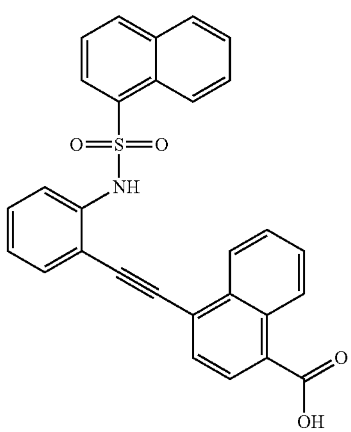 [SMILES: O=C(O)c1ccc(C#Cc2ccccc2NS(=O)(=O)c2cccc3ccccc23)c2ccccc12] | 4-{2-[2-(naphthalene-1-sulfonamido)phenyl]ethynyl}-naphthalene-1-carboxylic acid | 84 |

TABLE 1-continued

| Compound Structure | IUPAC name | Cpd. No. |
|---|---|---|
| 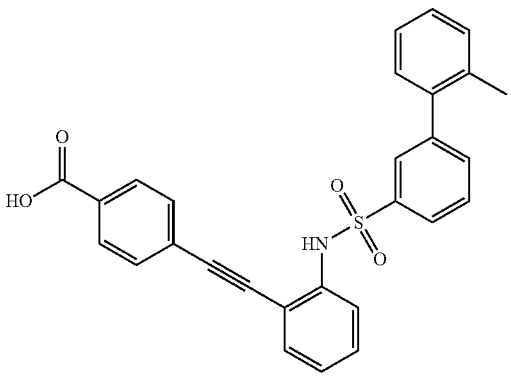 [SMILES: Cc1ccccc1-c1cccc(S(=O)(=O)Nc2ccccc2C#Cc2ccc(C(=O)O)cc2)c1] | 4-[2-(2-{2'-methyl-[1,1'-biphenyl]-3-sulfonamido}phenyl)ethynyl]benzoic acid | 86 |
| 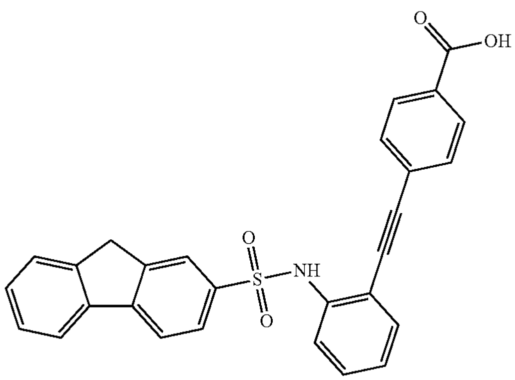 [SMILES: O=C(O)c1ccc(C#Cc2ccccc2NS(=O)(=O)c2ccc3c(c2)Cc2ccccc2-3)cc1] | 4-{2-[2-(9H-fluorene-2-sulfonamido)phenyl]ethynyl}benzoic acid | 87 |
| 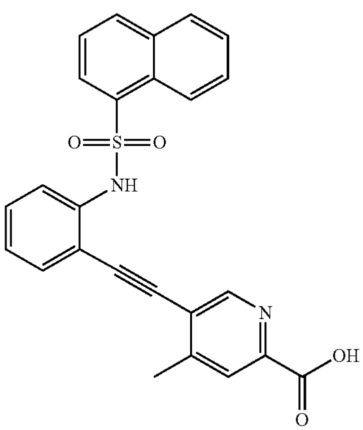 [SMILES: Cc1cc(C(=O)O)ncc1C#Cc1ccccc1NS(=O)(=O)c1cccc2ccccc12] | 4-methyl-5-{2-[2-(naphthalene-1-sulfonamido)phenyl]ethynyl}pyridine-2-carboxylic acid | 88 |
| 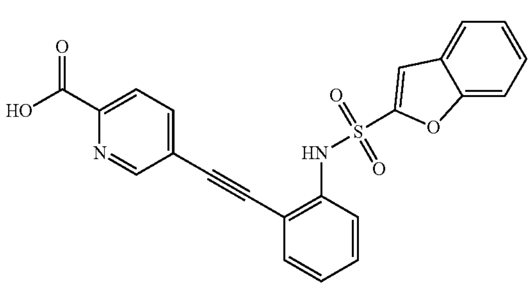 [SMILES: O=C(O)c1ccc(C#Cc2ccccc2NS(=O)(=O)c2cc3ccccc3o2)cn1] | 5-{2-[2-(1-benzofuran-2-sulfonamido)phenyl]ethynyl}pyridine-2-carboxylic acid | 89 |

TABLE 1-continued

| IUPAC name | Cpd. No. |
|---|---|
| 4-(2-{2-[(1,2,3,4-tetrahydroisoquinoline-2-sulfonyl)amino]phenyl}ethynyl)benzoic acid | 90 |
| 5-{2-[2-(2-methoxyquinoxaline-6-sulfonamido)phenyl]ethynyl}pyridine-2-carboxylic acid | 91 |
| 5-{2-[2-(9H-fluorene-2-sulfonamido)phenyl]ethynyl}pyridine-2-carboxylic acid | 92 |
| 4-{2-[2-(2,3-dihydro-1H-indene-2-sulfonamido)phenyl]ethynyl}benzoic acid | 93 |

TABLE 1-continued

| Compound Structure | IUPAC name | Cpd. No. |
|---|---|---|
| 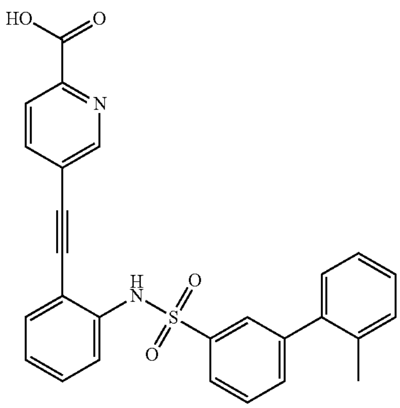 [SMILES: Cc1ccccc1-c1cccc(S(=O)(=O)Nc2ccccc2C#Cc2ccc(C(=O)O)nc2)c1] | 5-[2-(2-{2'-methyl-[1,1'-biphenyl]-3-sulfonamido}phenyl)ethynyl]pyridine-2-carboxylic acid | 94 |
| 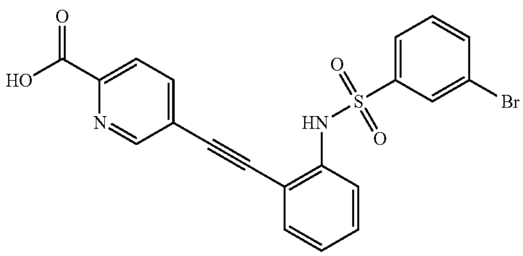 [SMILES: O=C(O)c1ccc(C#Cc2ccccc2NS(=O)(=O)c2cccc(Br)c2)cn1] | 5-{2-[2-(3-bromobenzenesulfonamido)phenyl]-ethynyl}pyridine-2-carboxylic acid | 95 |
| 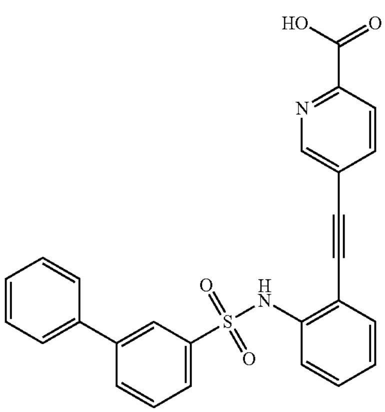 [SMILES: O=C(O)c1ccc(C#Cc2ccccc2NS(=O)(=O)c2cccc(-c3ccccc3)c2)cn1] | 5-[2-(2-{[1,1'-biphenyl]-3-sulfonamido}phenyl)ethynyl]pyridine-2-carboxylic acid | 96 |
| 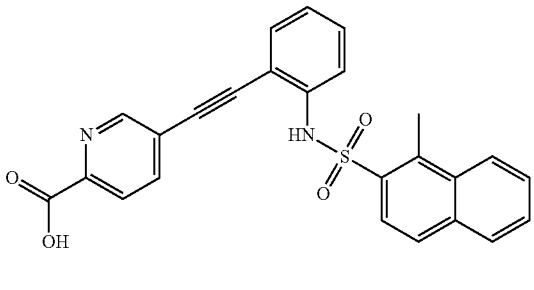 [SMILES: Cc1c(S(=O)(=O)Nc2ccccc2C#Cc2ccc(C(=O)O)nc2)ccc2ccccc12] | 5-{2-[2-(1-methylnaphthalene-2-sulfonamido)phenyl]ethynyl}pyridine-2-carboxylic acid | 97 |

TABLE 1-continued

| Compound Structure | IUPAC name | Cpd. No. |
| --- | --- | --- |
| 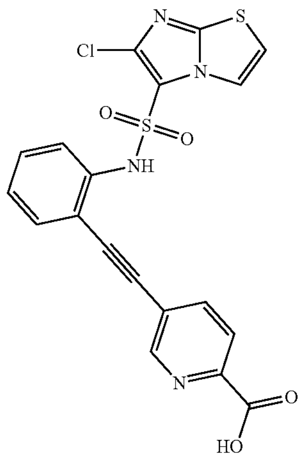 [SMILES: O=C(O)c1ccc(C#Cc2ccccc2NS(=O)(=O)c2c(Cl)nc3sccn23)cn1] | 5-[2-(2-{6-chloroimidazo[2,1-b][1,3]thiazole-5-sulfonamido}phenyl)-ethynyl]pyridine-2-carboxylic acid | 98 |
| 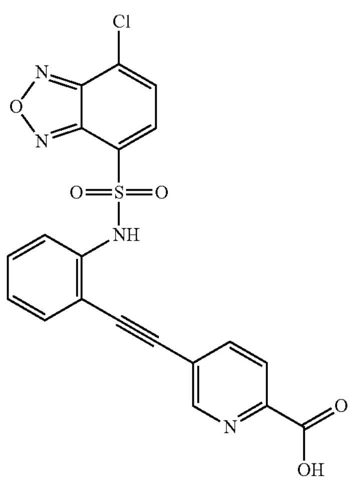 [SMILES: O=C(O)c1ccc(C#Cc2ccccc2NS(=O)(=O)c2ccc(Cl)c3nonc23)cn1] | 5-{2-[2-(7-chloro-2,1,3-benzoxadiazole-4-sulfonamido)phenyl]ethynyl}pyridine-2-carboxylic acid | 99 |
| 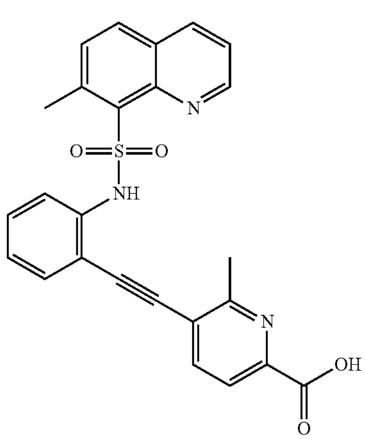 [SMILES: Cc1ccc2cccnc2c1S(=O)(=O)Nc1ccccc1C#Cc1ccc(C(=O)O)nc1C] | 6-methyl-5-{2-[2-(7-methylquinoline-8-sulfonamido)phenyl]ethynyl}pyridine-2-carboxylic acid | 100 |

| Compound Structure | IUPAC name | Cpd. No. |
|---|---|---|
| 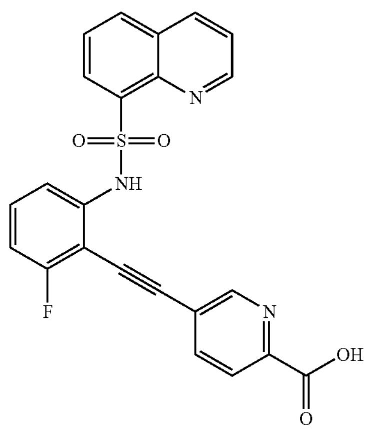 [SMILES: O=C(O)c1ccc(C#Cc2c(F)cccc2NS(=O)(=O)c2cccc3cccnc23)cn1] | 5-{2-[2-fluoro-6-(quinoline-8-sulfonamido)phenyl]ethynyl}pyridine-2-carboxylic acid | 101 |
| 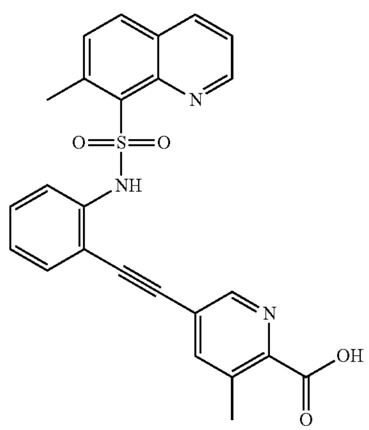 [SMILES: Cc1cc(C#Cc2ccccc2NS(=O)(=O)c2c(C)ccc3cccnc23)cnc1C(=O)O] | 3-methyl-5-{2-[2-(7-methylquinoline-8-sulfonamido)phenyl]ethynyl}pyridine-2-carboxylic acid | 102 |
| 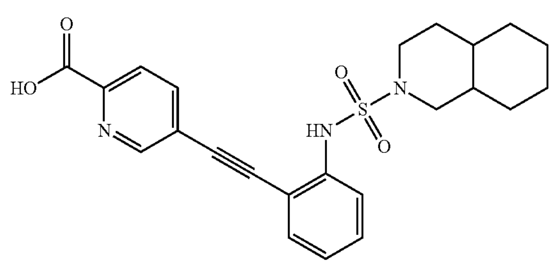 [SMILES: O=C(O)c1ccc(C#Cc2ccccc2NS(=O)(=O)N2CCC3CCCCC3C2)cn1] | 5-(2-{2-[(decahydroisoquinoline-2-sulfonyl)amino]phenyl}ethynyl)pyridine-2-carboxylic acid | 103 |
| 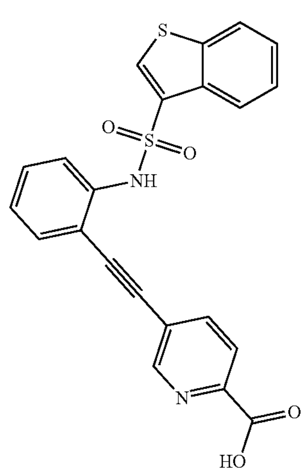 [SMILES: O=C(O)c1ccc(C#Cc2ccccc2NS(=O)(=O)c2csc3ccccc23)cn1] | 5-{2-[2-(1-benzothiophene-3-sulfonamido)phenyl]ethynyl}pyridine-2-carboxylic acid | 104 |

TABLE 1-continued

| Compound Structure | IUPAC name | Cpd. No. |
|---|---|---|
| 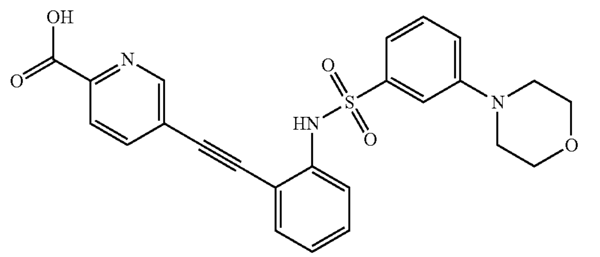 [SMILES: O=C(O)c1ccc(C#Cc2ccccc2NS(=O)(=O)c2cccc(N3CCOCC3)c2)cn1] | 5-(2-{2-[3-(morpholin-4-yl)benzenesulfonamido]phenyl}-ethynyl)pyridine-2-carboxylic acid | 105 |
| 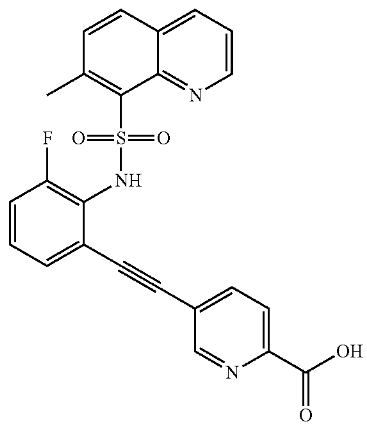 [SMILES: Cc1ccc2cccnc2c1S(=O)(=O)Nc1c(F)cccc1C#Cc1ccc(C(=O)O)nc1] | 5-{2-[3-fluoro-2-(7-methylquinoline-8-sulfonamido)phenyl]ethynyl}pyridine-2-carboxylic acid | 106 |
| 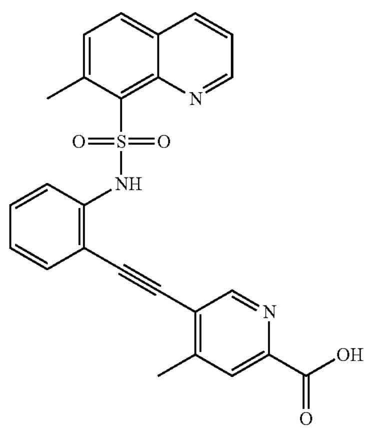 [SMILES: Cc1cc(C(=O)O)ncc1C#Cc1ccccc1NS(=O)(=O)c1c(C)ccc2cccnc12] | 4-methyl-5-{2-[2-(7-methylquinoline-8-sulfonamido)phenyl]ethynyl}pyridine-2-carboxylic acid | 107 |
| 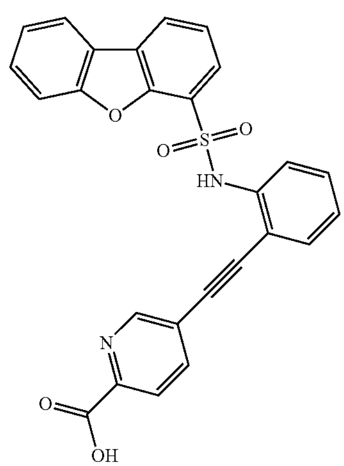 [SMILES: O=C(O)c1ccc(C#Cc2ccccc2NS(=O)(=O)c2cccc3c2oc2ccccc23)cn1] | 5-[2-(Dibenzofuran-4-sulfonylamino)-phenylethynyl]-pyridine-2-carboxylic acid (5-[2-(2-{8-oxatricyclo[7.4.0.0$^{2,7}$]trideca-1(9),2,4,6,10,12-hexaene-6-sulfonamido}phenyl)ethynyl]pyridine-2-carboxylic acid) | 108 |

TABLE 1-continued
| Compound Structure | IUPAC name | Cpd. No. |
|---|---|---|
| 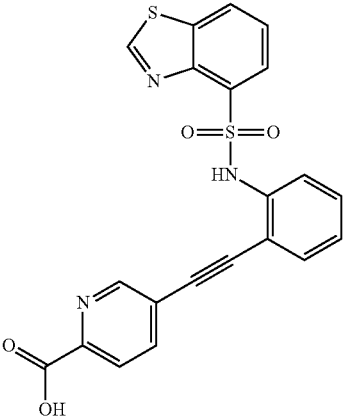 [SMILES: O=C(O)c1ccc(C#Cc2ccccc2NS(=O)(=O)c2cccc3scnc23)cn1] | 5-{2-[2-(1,3-benzothiazole-4-sulfonamido)phenyl]ethynyl}pyridine-2-carboxylic acid | 109 |
| 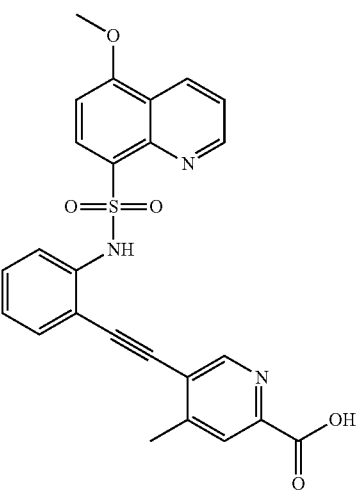 [SMILES: COc1ccc(S(=O)(=O)Nc2ccccc2C#Cc2cnc(C(=O)O)cc2C)c2ncccc12] | 5-{2-[2-(5-methoxyquinoline-8-sulfonamido)phenyl]ethynyl}-4-methylpyridine-2-carboxylic acid | 110 |
| 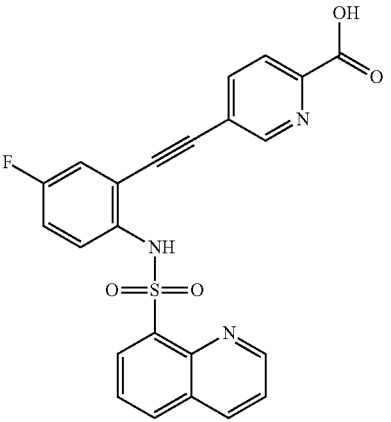 [SMILES: O=C(O)c1ccc(C#Cc2cc(F)ccc2NS(=O)(=O)c2cccc3cccnc23)cn1] | 5-{2-[5-fluoro-2-(quinoline-8-sulfonamido)phenyl]ethynyl}pyridine-2-carboxylic acid | 111 |

TABLE 1-continued

| Compound Structure | IUPAC name | Cpd. No. |
| --- | --- | --- |
| 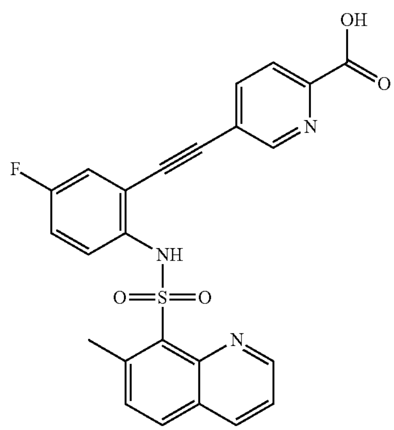 [SMILES: Cc1ccc2cccnc2c1S(=O)(=O)Nc1ccc(F)cc1C#Cc1ccc(C(=O)O)nc1] | 5-{2-[5-fluoro-2-(7-methylquinoline-8-sulfonamido)phenyl]ethynyl}pyridine-2-carboxylic acid | 112 |
| 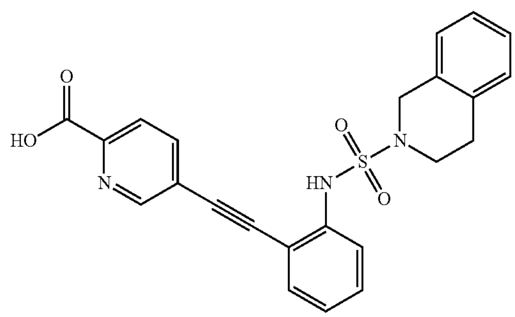 [SMILES: O=C(O)c1ccc(C#Cc2ccccc2NS(=O)(=O)N2CCc3ccccc3C2)cn1] | 5-(2-{2-[(1,2,3,4-tetrahydroisoquinoline-2-sulfonyl)amino]phenyl}ethynyl)pyridine-2-carboxylic acid | 113 |
| 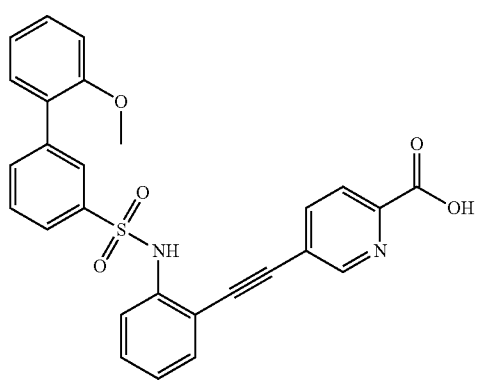 [SMILES: COc1ccccc1-c1cccc(S(=O)(=O)Nc2ccccc2C#Cc2ccc(C(=O)O)nc2)c1] | 5-[2-(2-{2'-methoxy-[1,1'-biphenyl]-3-sulfonamido}phenyl)ethynyl]pyridine-2-carboxylic acid | 114 |
| 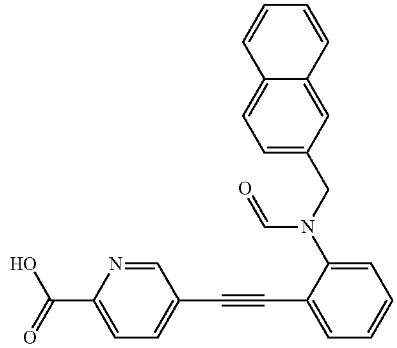 [SMILES: O=CN(Cc1ccc2ccccc2c1)c1ccccc1C#Cc1ccc(C(=O)O)nc1] | 5-[2-(2-{N-[(naphthalen-2-yl)methyl]formamido}phenyl)ethynyl]-pyridine-2-carboxylic acid | 115 |

TABLE 1-continued

| Compound Structure | IUPAC name | Cpd. No. |
|---|---|---|
| 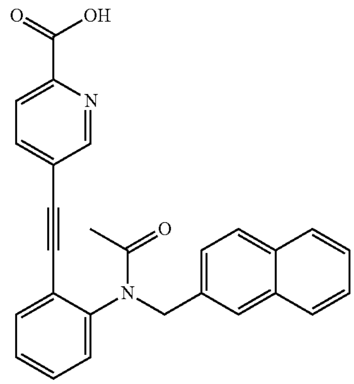 [SMILES: CC(=O)N(Cc1ccc2ccccc2c1)c1ccccc1C#Cc1ccc(C(=O)O)nc1] | 5-[2-(2-{N-[(naphthalen-2-yl)methyl]acetamido}phenyl)ethynyl]-pyridine-2-carboxylic acid | 116 |
| 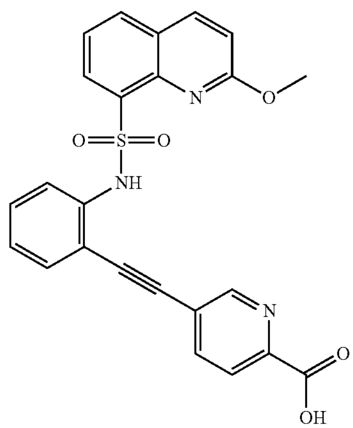 [SMILES: COc1ccc2cccc(S(=O)(=O)Nc3ccccc3C#Cc3ccc(C(=O)O)nc3)c2n1] | 5-{2-[2-(2-methoxyquinoline-8-sulfonamido)phenyl]ethynyl}pyridine-2-carboxylic acid | 117 |
| 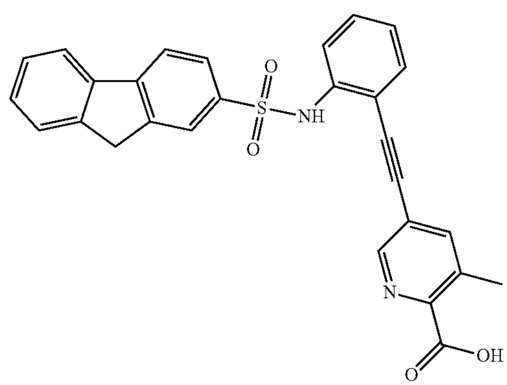 [SMILES: Cc1cc(C#Cc2ccccc2NS(=O)(=O)c2ccc3c(c2)Cc2ccccc2-3)cnc1C(=O)O] | 5-{2-[2-(9H-fluorene-2-sulfonamido)phenyl]ethynyl}-3-methylpyridine-2-carboxylic acid | 118 |
| 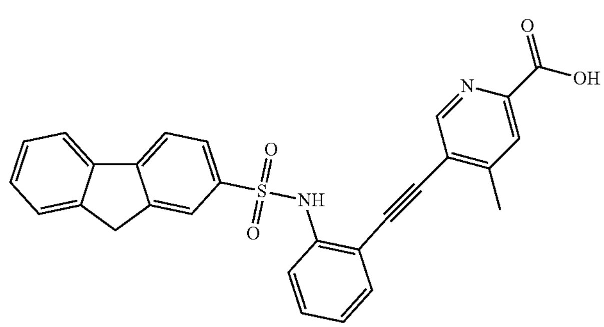 [SMILES: Cc1cc(C(=O)O)ncc1C#Cc1ccccc1NS(=O)(=O)c1ccc2c(c1)Cc1ccccc1-2] | 5-{2-[2-(9H-fluorene-2-sulfonamido)phenyl]ethynyl}-4-methylpyridine-2-carboxylic acid | 119 |

TABLE 1-continued

| Compound Structure | IUPAC name | Cpd. No. |
|---|---|---|
| 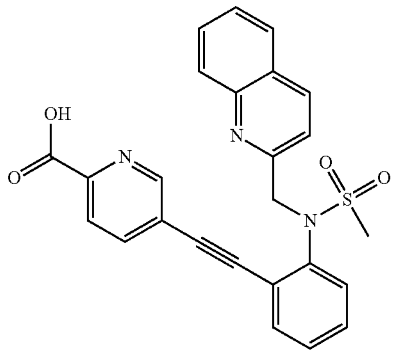 [SMILES: CS(=O)(=O)N(Cc1ccc2ccccc2n1)c1ccccc1C#Cc1ccc(C(=O)O)nc1] | 5-[2-(2-{N-[(quinolin-2-yl)methyl]methanesulfonamido}phenyl)ethynyl]pyridine-2-carboxylic acid | 120 |
| 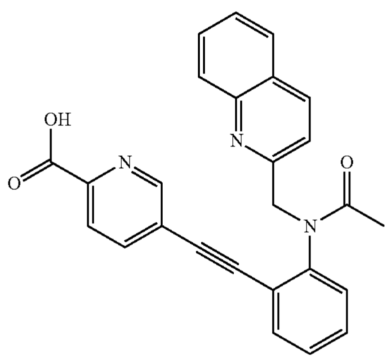 [SMILES: CC(=O)N(Cc1ccc2ccccc2n1)c1ccccc1C#Cc1ccc(C(=O)O)nc1] | 5-[2-(2-{N-[(quinolin-2-yl)methyl]acetamido}phenyl)ethynyl]-pyridine-2-carboxylic acid | 121 |
| 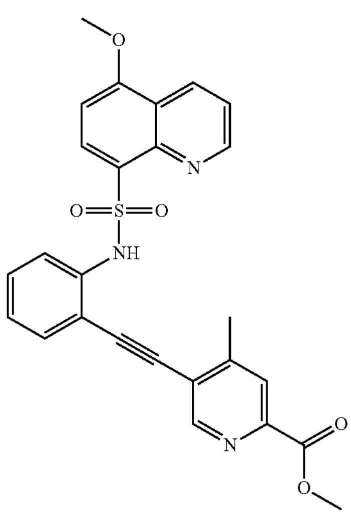 [SMILES: COC(=O)c1cc(C)c(C#Cc2ccccc2NS(=O)(=O)c2ccc(OC)c3cccnc23)cn1] | methyl 5-{2-[2-(5-methoxyquinoline-8-sulfonamido)phenyl]ethynyl}-4-methylpyridine-2-carboxylate | 122 |

TABLE 1-continued

| Compound Structure | IUPAC name | Cpd. No. |
|---|---|---|
| 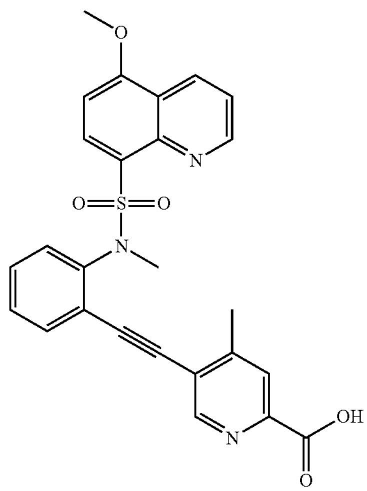 [SMILES: COc1ccc(S(=O)(=O)N(C)c2ccccc2C#Cc2cnc(C(=O)O)cc2C)c2ncccc12] | 4-methyl-5-{2-[2-(N-methyl5-methoxyquinoline-8-sulfonamido)phenyl]ethynyl}pyridine-2-carboxylic acid | 123 |
| 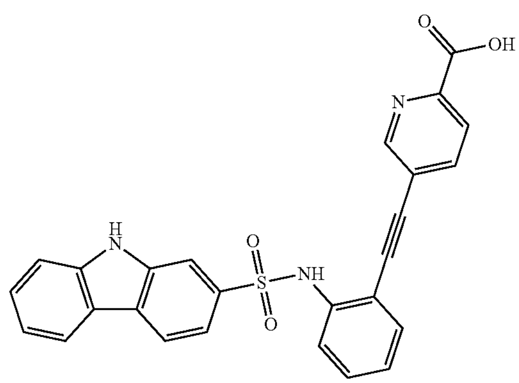 [SMILES: O=C(O)c1ccc(C#Cc2ccccc2NS(=O)(=O)c2ccc3c(c2)[nH]c2ccccc23)cn1] | 5-{2-[2-(9H-carbazole-2-sulfonamido)phenyl]ethynyl}pyridine-2-carboxylic acid | 124 |
| 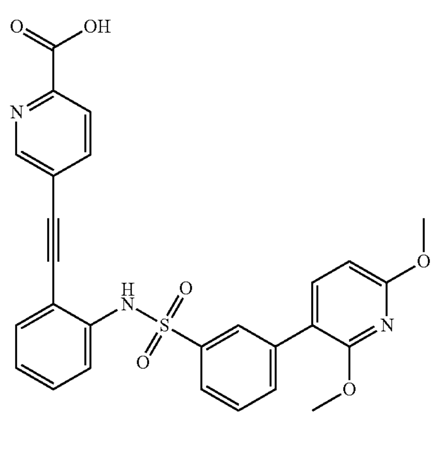 [SMILES: COc1ccc(-c2cccc(S(=O)(=O)Nc3ccccc3C#Cc3ccc(C(=O)O)nc3)c2)c(OC)n1] | 5-(2-{2-[3-(2,6-dimethoxypyridin-3-yl)benzenesulfonamido]phenyl}-ethynyl)pyridine-2-carboxylic acid | 125 |

TABLE 1-continued

| Compound Structure | IUPAC name | Cpd. No. |
|---|---|---|
| 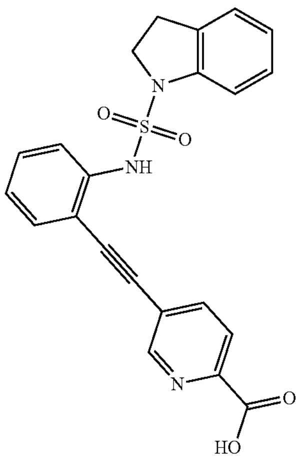 [SMILES: O=C(O)c1ccc(C#Cc2ccccc2NS(=O)(=O)N2CCc3ccccc32)cn1] | 5-(2-{2-[(2,3-dihydro-1H-indole-1-sulfonyl)amino]phenyl}ethynyl)pyridine-2-carboxylic acid | 126 |
| 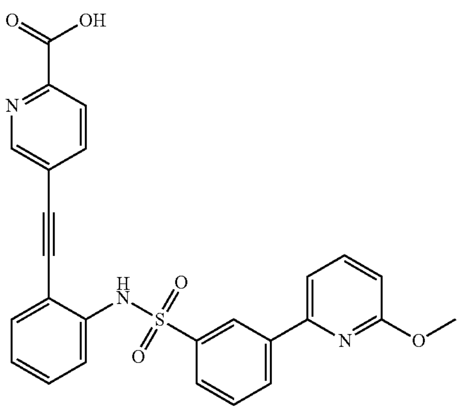 [SMILES: COc1cccc(-c2cccc(S(=O)(=O)Nc3ccccc3C#Cc3ccc(C(=O)O)nc3)c2)n1] | 5-(2-{2-[3-(6-methoxypyridin-2-yl)benzenesulfonamido]phenyl}-ethynyl)pyridine-2-carboxylic acid | 127 |
| 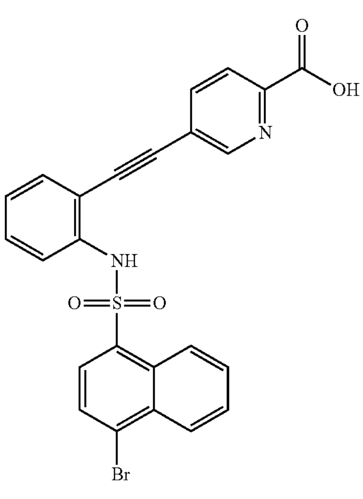 [SMILES: O=C(O)c1ccc(C#Cc2ccccc2NS(=O)(=O)c2ccc(Br)c3ccccc23)cn1] | 5-{2-[2-(4-bromonaphthalene-1-sulfonamido)phenyl]ethynyl}pyridine-2-carboxylic acid | 128 |

TABLE 1-continued
| Compound Structure | IUPAC name | Cpd. No. |
|---|---|---|
| 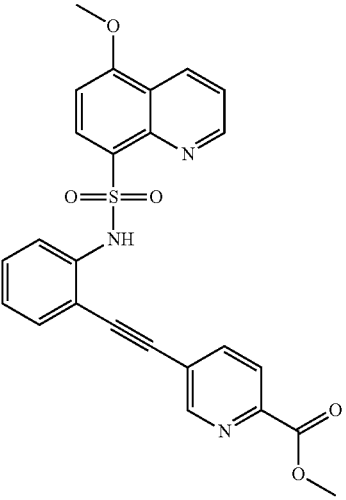 [SMILES: COC(=O)c1ccc(C#Cc2ccccc2NS(=O)(=O)c2ccc(OC)c3cccnc23)cn1] | methyl 5-{2-[2-(5-methoxyquinoline-8-sulfonamido)phenyl]ethynyl}pyridine-2-carboxylate | 129 |
| 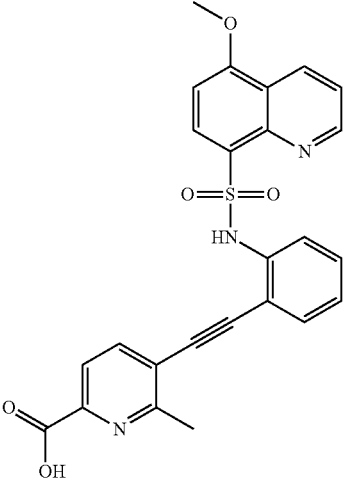 [SMILES: COc1ccc(S(=O)(=O)Nc2ccccc2C#Cc2ccc(C(=O)O)nc2C)c2ncccc12] | 5-{2-[2-(5-methoxyquinoline-8-sulfonamido)phenyl]ethynyl}-6-methylpyridine-2-carboxylic acid | 130 |
| 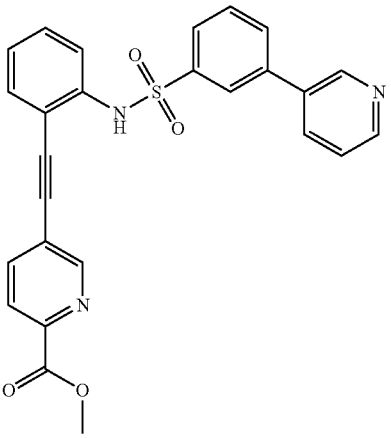 [SMILES: COC(=O)c1ccc(C#Cc2ccccc2NS(=O)(=O)c2cccc(-c3cccnc3)c2)cn1] | methyl 5-(2-{2-[3-(pyridin-3-yl)benzenesulfonamido]phenyl}-ethynyl)pyridine-2-carboxylate | 131 |

TABLE 1-continued

| Compound Structure | IUPAC name | Cpd. No. |
|---|---|---|
| 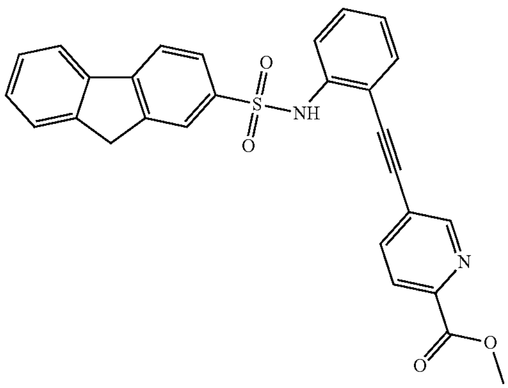 [SMILES: COC(=O)c1ccc(C#Cc2ccccc2NS(=O)(=O)c2ccc3c(c2)Cc2ccccc2-3)cn1] | methyl 5-{2-[2-(9H-fluorene-2-sulfonamido)phenyl]ethynyl}pyridine-2-carboxylate | 132 |
| 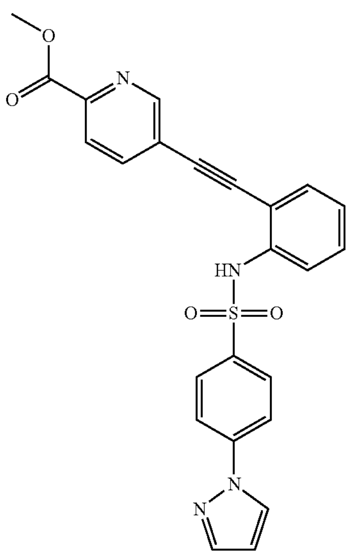 [SMILES: COC(=O)c1ccc(C#Cc2ccccc2NS(=O)(=O)c2ccc(-n3cccn3)cc2)cn1] | methyl 5-(2-{2-[4-(1H-pyrazol-1-yl)benzenesulfonamido]phenyl}-ethynyl)pyridine-2-carboxylate | 133 |
| 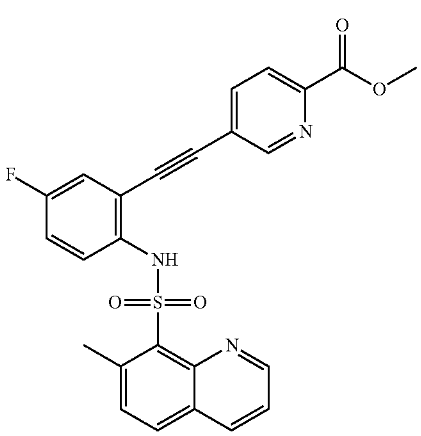 [SMILES: COC(=O)c1ccc(C#Cc2cc(F)ccc2NS(=O)(=O)c2c(C)ccc3cccnc23)cn1] | methyl 5-{2-[5-fluoro-2-(7-methylquinoline-8-sulfonamido)phenyl]ethynyl}pyridine-2-carboxylate | 134 |

| Compound Structure | IUPAC name | Cpd. No. |
|---|---|---|
| 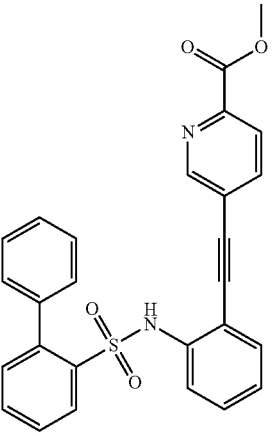 [SMILES: COC(=O)c1ccc(C#Cc2ccccc2NS(=O)(=O)c2ccccc2-c2ccccc2)cn1] | methyl 5-[2-(2-{[1,1'-biphenyl]-2-sulfonamido}phenyl)ethynyl]pyridine-2-carboxylate | 135 |
| 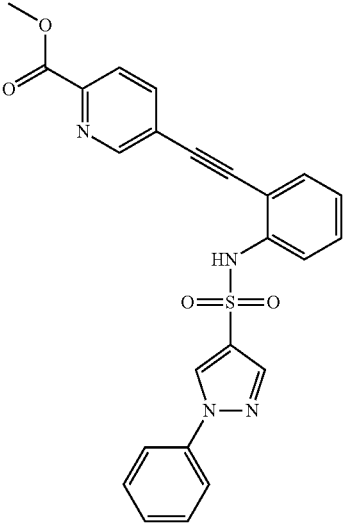 [SMILES: COC(=O)c1ccc(C#Cc2ccccc2NS(=O)(=O)c2cnn(-c3ccccc3)c2)cn1] | methyl 5-{2-[2-(1-phenyl-1H-pyrazole-4-sulfonamido)phenyl]ethynyl}pyridine-2-carboxylate | 136 |
| 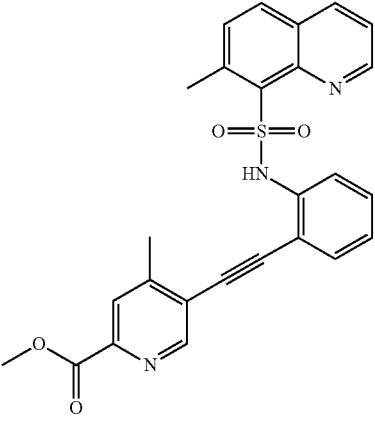 [SMILES: COC(=O)c1cc(C)c(C#Cc2ccccc2NS(=O)(=O)c2c(C)ccc3cccnc23)cn1] | methyl 4-methyl-5-{2-[2-(7-methylquinoline-8-sulfonamido)phenyl]ethynyl}pyridine-2-carboxylate | 137 |

TABLE 1-continued

| Compound Structure | IUPAC name | Cpd. No. |
|---|---|---|
| 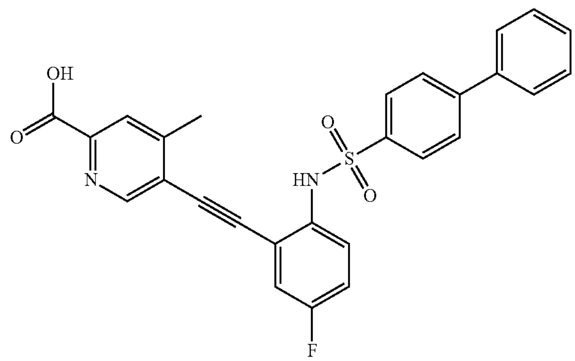 [SMILES: Cc1cc(C(=O)O)ncc1C#Cc1cc(F)ccc1NS(=O)(=O)c1ccc(-c2ccccc2)cc1] | 5-[2-(2-{[1,1'-biphenyl]-4-sulfonamido}-5-fluorophenyl)ethynyl]-4-methylpyridine-2-carboxylic acid | 138 |
| 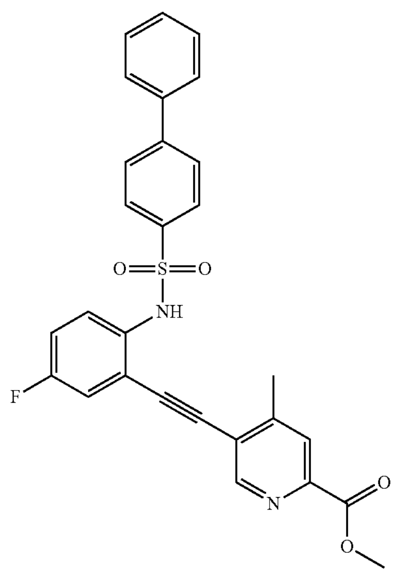 [SMILES: COC(=O)c1cc(C)c(C#Cc2cc(F)ccc2NS(=O)(=O)c2ccc(-c3ccccc3)cc2)cn1] | methyl 5-[2-(2-{[1,1'-biphenyl]-4-sulfonamido}-5-fluorophenyl)ethynyl]-4-methylpyridine-2-carboxylate | 139 |
| 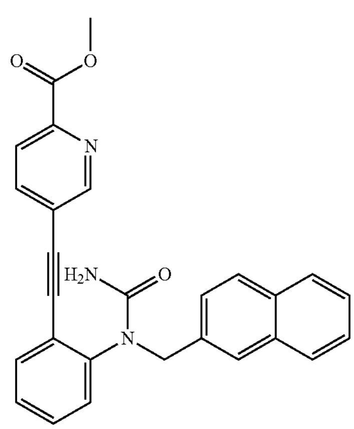 [SMILES: COC(=O)c1ccc(C#Cc2ccccc2N(Cc2ccc3ccccc3c2)C(N)=O)cn1] | methyl 5-[2-(2-{carbamoyl[(naphthalen-2-yl)methyl]amino}phenyl)ethynyl]pyridine-2-carboxylate | 140 |

TABLE 1-continued

| Compound Structure | IUPAC name | Cpd. No. |
|---|---|---|
| 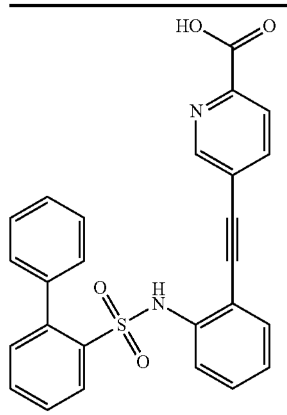 | 5-[2-(2-{[1,1'-biphenyl]-2-sulfonamido}phenyl)ethynyl]pyridine-2-carboxylic acid | 141 |
| 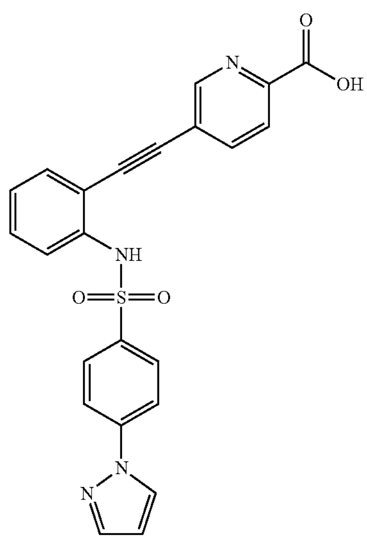 [SMILES: O=C(O)c1ccc(C#Cc2ccccc2NS(=O)(=O)c2ccc(-n3cccn3)cc2)cn1] | 5-(2-{2-[4-(1H-pyrazol-1-yl)benzenesulfonamido]phenyl}-ethynyl)pyridine-2-carboxylic acid | 142 |
| 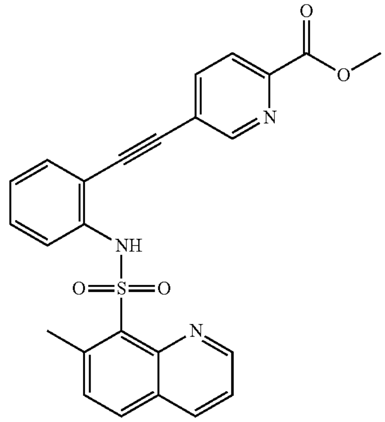 [SMILES: COC(=O)c1ccc(C#Cc2ccccc2NS(=O)(=O)c2c(C)ccc3cccnc23)cn1] | methyl 5-{2-[2-(7-methylquinoline-8-sulfonamido)phenyl]ethynyl}pyridine-2-carboxylate | 143 |

TABLE 1-continued

| Compound Structure | IUPAC name | Cpd. No. |
|---|---|---|
| 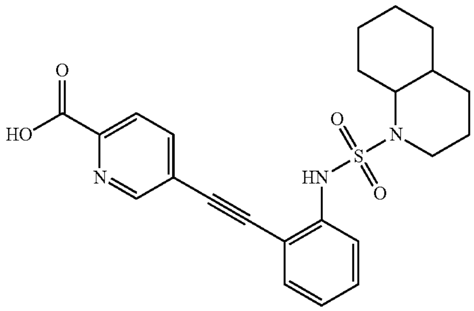 [SMILES: O=C(O)c1ccc(C#Cc2ccccc2NS(=O)(=O)N2CCCC3CCCCC32)cn1] | 5-(2-{2-[(decahydroquinoline-1-sulfonyl)amino]phenyl}ethynyl)pyridine-2-carboxylic acid | 144 |
| 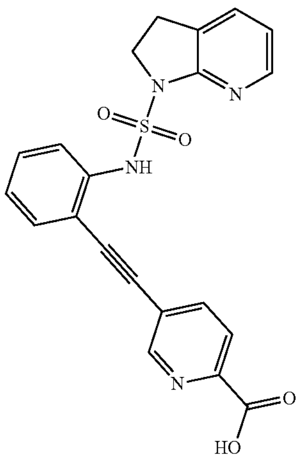 [SMILES: O=C(O)c1ccc(C#Cc2ccccc2NS(=O)(=O)N2CCc3cccnc32)cn1] | 5-{2-[2-({1H,2H,3H-pyrrolo[2,3-b]pyridine-1-sulfonyl}amino)phenyl]-ethynyl}pyridine-2-carboxylic acid | 145 |
| 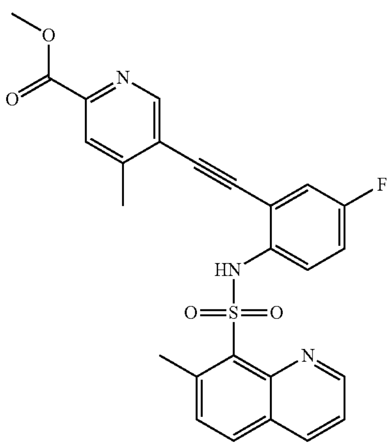 [SMILES: COC(=O)c1cc(C)c(C#Cc2cc(F)ccc2NS(=O)(=O)c2c(C)ccc3cccnc23)cn1] | methyl 5-{2-[5-fluoro-2-(7-methylquinoline-8-sulfonamido)phenyl]ethynyl}-4-methylpyridine-2-carboxylate | 146 |
| 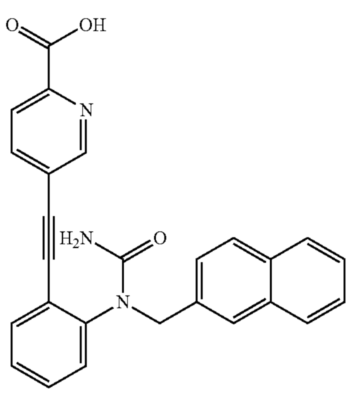 [SMILES: NC(=O)N(Cc1ccc2ccccc2c1)c1ccccc1C#Cc1ccc(C(=O)O)nc1] | 5-[2-(2-{carbamoyl[(naphthalen-2-yl)methyl]amino}phenyl)ethynyl]pyridine-2-carboxylic acid | 147 |

TABLE 1-continued

| Compound Structure | IUPAC name | Cpd. No. |
| --- | --- | --- |
| 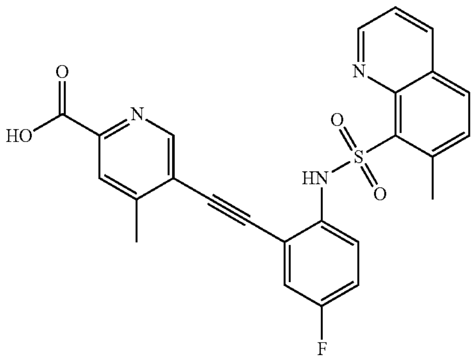 [SMILES: Cc1cc(C(=O)O)ncc1C#Cc1cc(F)ccc1NS(=O)(=O)c1c(C)ccc2cccnc12] | 5-{2-[5-fluoro-2-(7-methylquinoline-8-sulfonamido)phenyl]ethynyl}-4-methylpyridine-2-carboxylic acid | 148 |
| 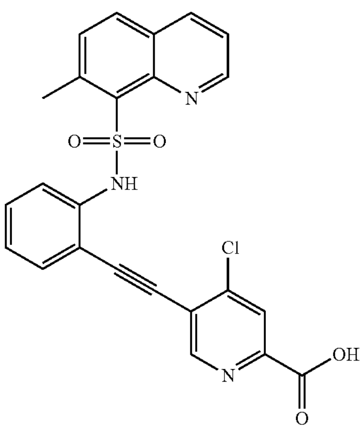 [SMILES: Cc1ccc2cccnc2c1S(=O)(=O)Nc1ccccc1C#Cc1cnc(C(=O)O)cc1Cl] | 4-chloro-5-{2-[2-(7-methylquinoline-8-sulfonamido)phenyl]ethynyl}pyridine-2-carboxylic acid | 149 |
| 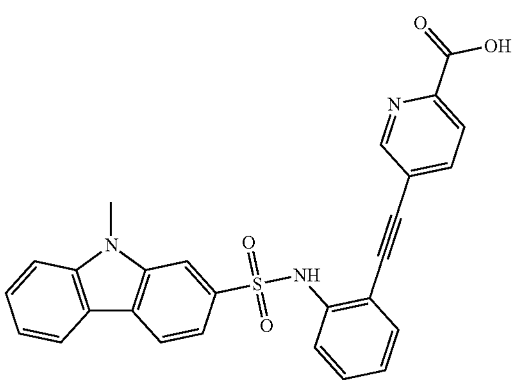 [SMILES: Cn1c2ccccc2c2ccc(S(=O)(=O)Nc3ccccc3C#Cc3ccc(C(=O)O)nc3)cc21] | 5-{2-[2-(9-methyl-9H-carbazole-2-sulfonamido)phenyl]ethynyl}pyridine-2-carboxylic acid | 150 |
| 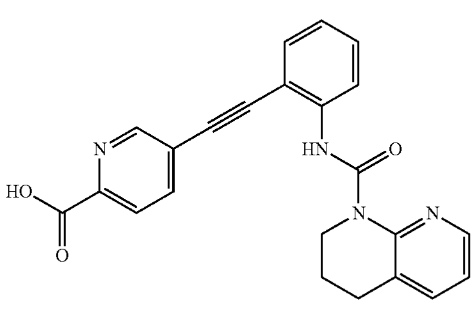 [SMILES: O=C(O)c1ccc(C#Cc2ccccc2NC(=O)N2CCCc3cccnc32)cn1] | 5-(2-{2-[(1,2,3,4-tetrahydro-1,8-naphthyridine-1-carbonyl)amino]phenyl}-ethynyl)pyridine-2-carboxylic acid<br>Not within the scope of this invention | 151 |

TABLE 1-continued

| Compound Structure | IUPAC name | Cpd. No. |
|---|---|---|
| 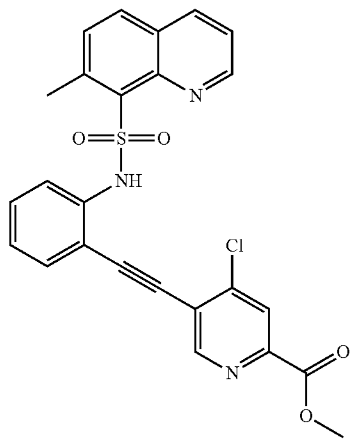 [SMILES: COC(=O)c1cc(Cl)c(C#Cc2ccccc2NS(=O)(=O)c2c(C)ccc3cccnc23)cn1] | methyl 4-chloro-5-{2-[2-(7-methylquinoline-8-sulfonamido)phenyl]-ethynyl}pyridine-2-carboxylate | 152 |
| 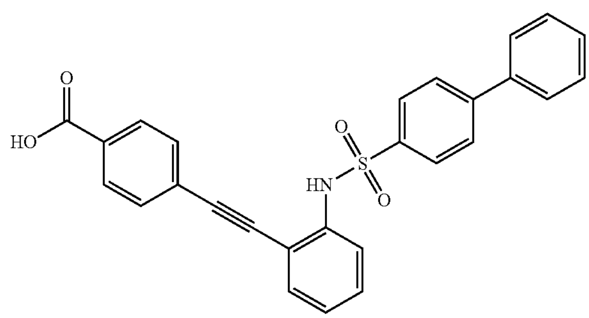 [SMILES: O=C(O)c1ccc(C#Cc2ccccc2NS(=O)(=O)c2ccc(-c3ccccc3)cc2)cc1] | 4-[2-(2-{[1,1'-biphenyl]-4-sulfonamido}phenyl)ethynyl]benzoic acid | 153 |
| 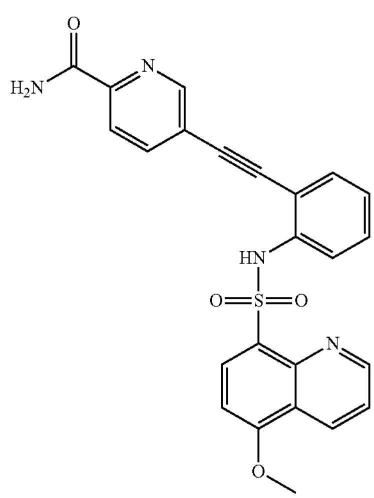 [SMILES: COc1ccc(S(=O)(=O)Nc2ccccc2C#Cc2ccc(C(N)=O)nc2)c2ncccc12] | 5-{2-[2-(5-methoxyquinoline-8-sulfonamido)phenyl]ethynyl}pyridine-2-carboxamide | 154 |

TABLE 1-continued

| Compound Structure | IUPAC name | Cpd. No. |
|---|---|---|
| 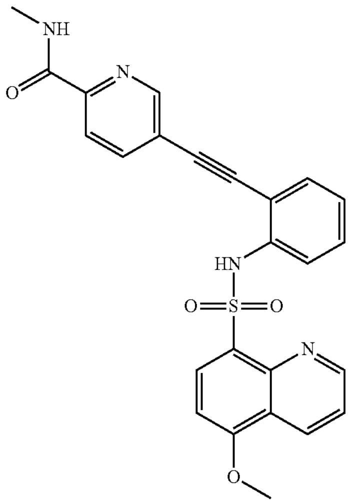 [SMILES: CNC(=O)c1ccc(C#Cc2ccccc2NS(=O)(=O)c2ccc(OC)c3cccnc23)cn1] | 5-{2-[2-(5-methoxyquinoline-8-sulfonamido)phenyl]ethynyl}-N-methylpyridine-2-carboxamide | 156 |
| 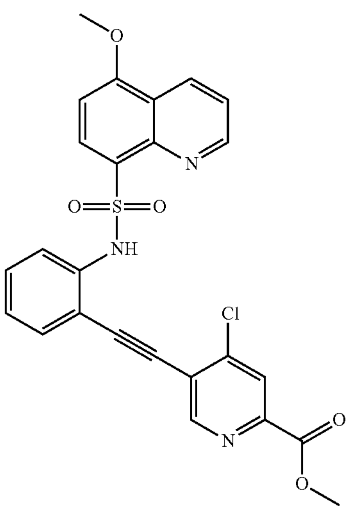 [SMILES: COC(=O)c1cc(Cl)c(C#Cc2ccccc2NS(=O)(=O)c2ccc(OC)c3cccnc23)cn1] | methyl 4-chloro-5-{2-[2-(5-methoxyquinoline-8-sulfonamido)phenyl]ethynyl}pyridine-2-carboxylate | 157 |
| 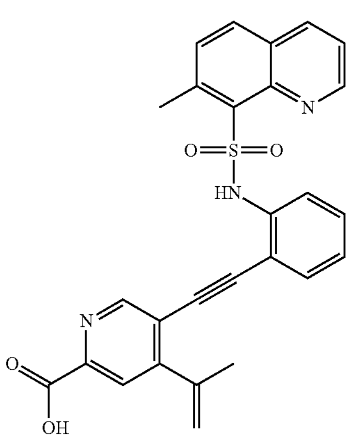 | 5-{2-[2-(7-methylquinoline-8-sulfonamido)phenyl]ethynyl}-4-(prop-1-en-2-yl)pyridine-2-carboxylic acid | 158 |

TABLE 1-continued

| Compound Structure | IUPAC name | Cpd. No. |
|---|---|---|
| 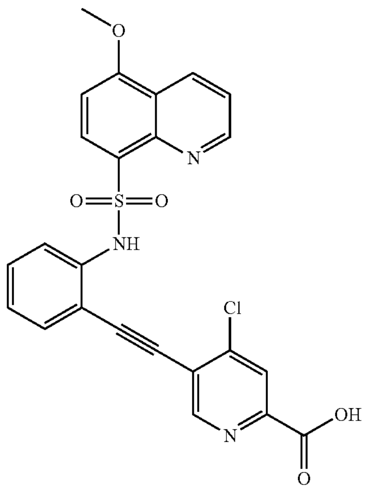 [SMILES: COc1ccc(S(=O)(=O)Nc2ccccc2C#Cc2cnc(C(=O)O)cc2Cl)c2ncccc12] | 4-chloro-5-{2-[2-(5-methoxyquinoline-8-sulfonamido)phenyl]ethynyl}pyridine-2-carboxylic acid | 159 |
| 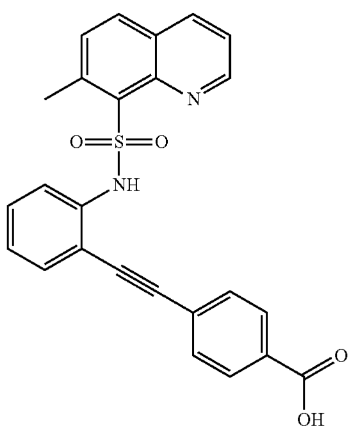 [SMILES: Cc1ccc2cccnc2c1S(=O)(=O)Nc1ccccc1C#Cc1ccc(C(=O)O)cc1] | 4-{2-[2-(7-methylquinoline-8-sulfonamido)phenyl]ethynyl}benzoic acid | 160 |
| 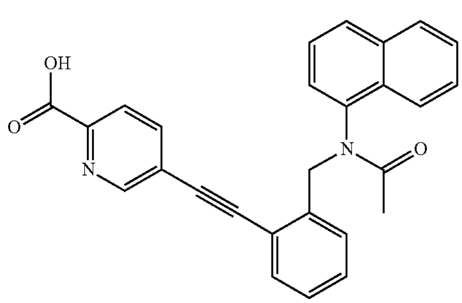 [SMILES: CC(=O)N(Cc1ccccc1C#Cc1ccc(C(=O)O)nc1)c1cccc2ccccc12] | 5-[2-(2-{[N-(naphthalen-1-yl)acetamido]-methyl}phenyl)ethynyl]pyridine-2-carboxylic acid | 161 |

TABLE 1-continued

| Compound Structure | IUPAC name | Cpd. No. |
|---|---|---|
| 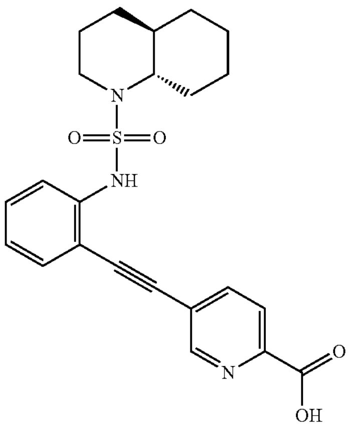 [SMILES: O=C(O)c1ccc(C#Cc2ccccc2NS(=O)(=O)N2CCC[C@H]3CCCC[C@@H]32)cn1] | 5-[2-(2-{[(4aR,8aS)-decahydroquinoline-1-sulfonyl]amino}phenyl)ethynyl]pyridine-2-carboxylic acid | 162 |
| 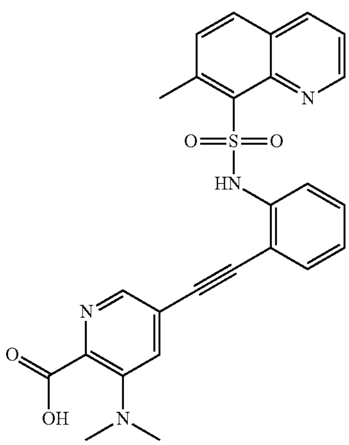 [SMILES: Cc1ccc2cccnc2c1S(=O)(=O)Nc1ccccc1C#Cc1cnc(C(=O)O)c(N(C)C)c1] | 3-(dimethylamino)-5-{2-[2-(7-methylquinoline-8-sulfonamido)-phenyl]ethynyl}pyridine-2-carboxylic acid | 163 |
| 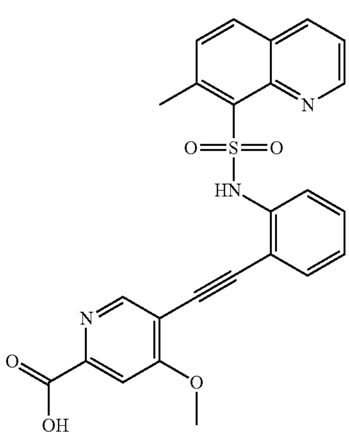 [SMILES: COc1cc(C(=O)O)ncc1C#Cc1ccccc1NS(=O)(=O)c1c(C)ccc2cccnc12] | 4-methoxy-5-{2-[2-(7-methylquinoline-8-sulfonamido)phenyl]ethynyl}pyridine-2-carboxylic acid | 164 |

TABLE 1-continued

| Compound Structure | IUPAC name | Cpd. No. |
|---|---|---|
| 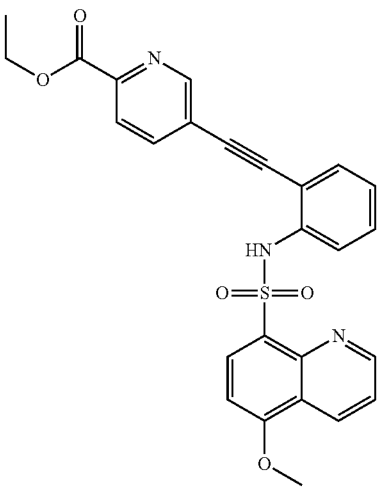 [SMILES: CCOC(=O)c1ccc(C#Cc2ccccc2NS(=O)(=O)c2ccc(OC)c3cccnc23)cn1] | ethyl 5-{2-[2-(5-methoxyquinoline-8-sulfonamido)phenyl]ethynyl}pyridine-2-carboxylate | 165 |
| 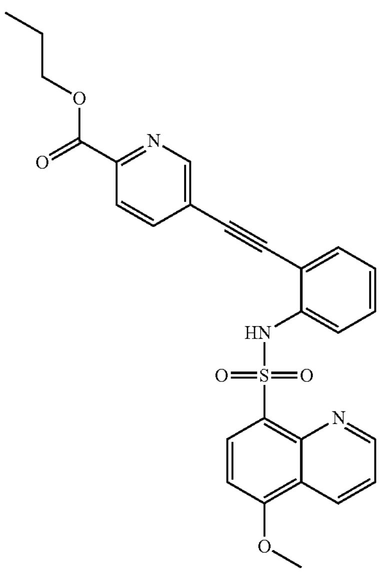 [SMILES: CCCOC(=O)c1ccc(C#Cc2ccccc2NS(=O)(=O)c2ccc(OC)c3cccnc23)cn1] | propyl 5-{2-[2-(5-methoxyquinoline-8-sulfonamido)phenyl]ethynyl}pyridine-2-carboxylate | 166 |
| 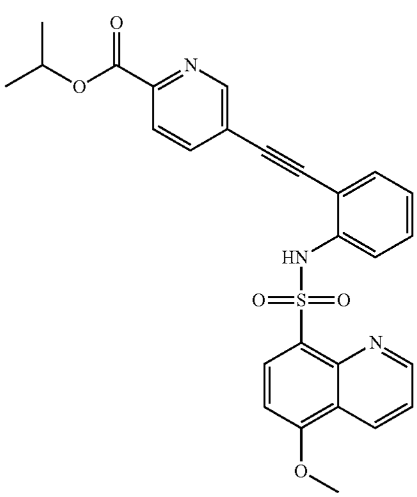 [SMILES: COc1ccc(S(=O)(=O)Nc2ccccc2C#Cc2ccc(C(=O)OC(C)C)nc2)c2ncccc12] | propan-2-yl 5-{2-[2-(5-methoxyquinoline-8-sulfonamido)phenyl]ethynyl}pyridine-2-carboxylate | 167 |

TABLE 1-continued

| Compound Structure | IUPAC name | Cpd. No. |
|---|---|---|
| 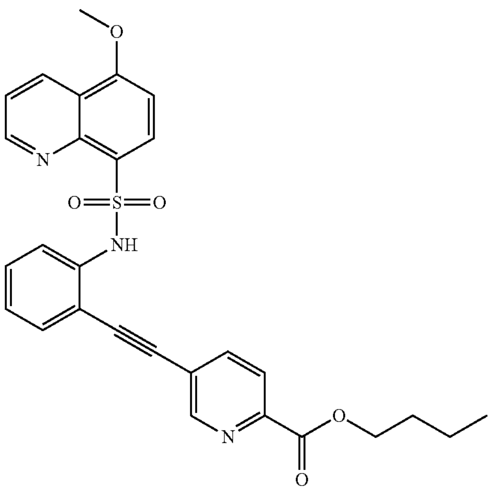 [SMILES: CCCCOC(=O)c1ccc(C#Cc2ccccc2NS(=O)(=O)c2ccc(OC)c3cccnc23)cn1] | butyl 5-{2-[2-(5-methoxyquinoline-8-sulfonamido)phenyl]ethynyl}pyridine-2-carboxylate | 168 |
| 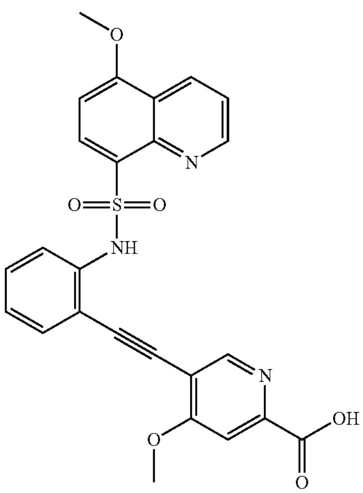 [SMILES: COc1cc(C(=O)O)ncc1C#Cc1ccccc1NS(=O)(=O)c1ccc(OC)c2cccnc12] | 4-methoxy-5-{2-[2-(5-methoxyquinoline-8-sulfonamido)phenyl]ethynyl}pyridine-2-carboxylic acid | 169 |
| 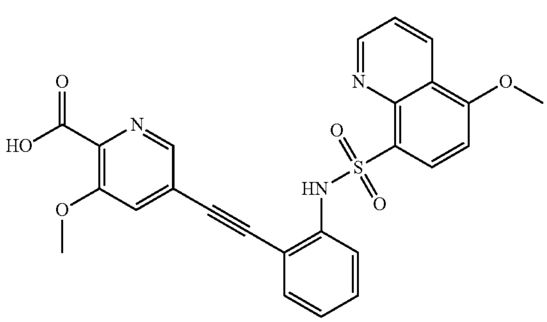 [SMILES: COc1cc(C#Cc2ccccc2NS(=O)(=O)c2ccc(OC)c3cccnc23)cnc1C(=O)O] | 3-methoxy-5-{2-[2-(5-methoxyquinoline-8-sulfonamido)phenyl]ethynyl}pyridine-2-carboxylic acid | 170 |

TABLE 1-continued

| Compound Structure | IUPAC name | Cpd. No. |
|---|---|---|
| 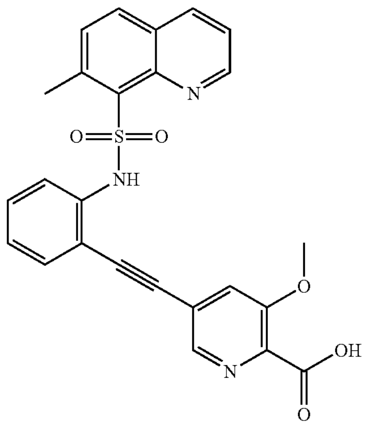 [SMILES: COc1cc(C#Cc2ccccc2NS(=O)(=O)c2c(C)ccc3cccnc23)cnc1C(=O)O] | 3-methoxy-5-{2-[2-(7-methylquinoline-8-sulfonamido)phenyl]ethynyl}pyridine-2-carboxylic acid | 171 |
| 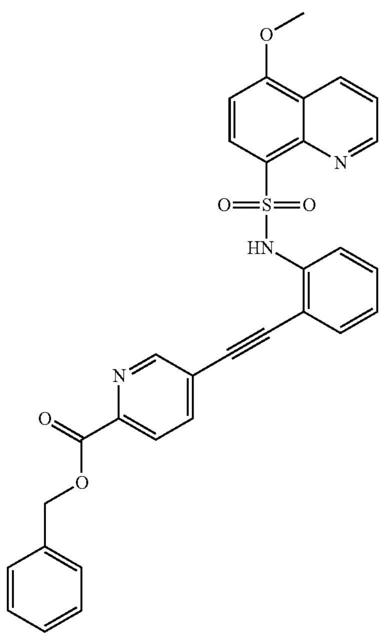 [SMILES: COc1ccc(S(=O)(=O)Nc2ccccc2C#Cc2ccc(C(=O)OCc3ccccc3)nc2)c2ncccc12] | benzyl 5-{2-[2-(5-methoxyquinoline-8-sulfonamido)phenyl]ethynyl}pyridine-2-carboxylate | 172 |
| 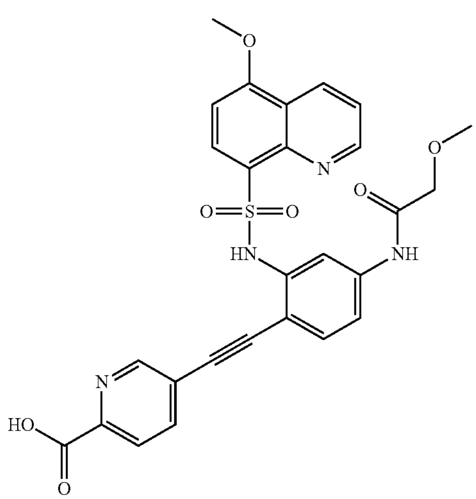 [SMILES: COCC(=O)Nc1ccc(C#Cc2ccc(C(=O)O)nc2)c(NS(=O)(=O)c2ccc(OC)c3cccnc23)c1] | 5-{2-[4-(2-methoxyacetamido)-2-(5-methoxyquinoline-8-sulfonamido)phenyl]ethynyl}pyridine-2-carboxylic acid | 173 |

TABLE 1-continued

| Compound Structure | IUPAC name | Cpd. No. |
| --- | --- | --- |
| 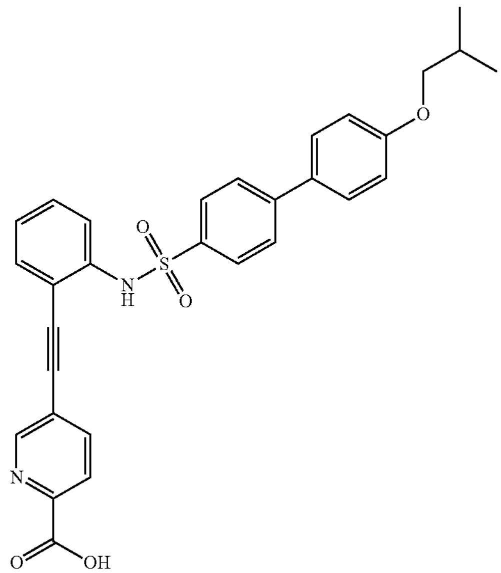 [SMILES: CC(C)COc1ccc(-c2ccc(S(=O)(=O)Nc3ccccc3C#Cc3ccc(C(=O)O)nc3)cc2)cc1] | 5-(2-{2-[4'-(2-methylpropoxy)-[1,1'-biphenyl]-4-sulfonamido]phenyl}-ethynyl)pyridine-2-carboxylic acid | 174 |
| 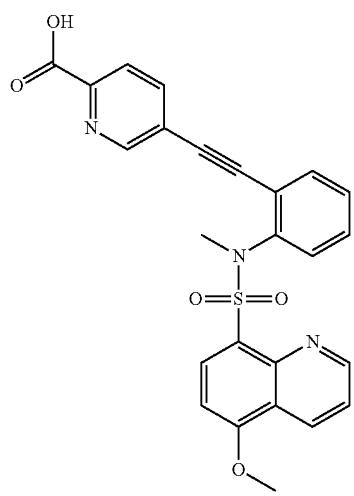 [SMILES: COc1ccc(S(=O)(=O)N(C)c2ccccc2C#Cc2ccc(C(=O)O)nc2)c2ncccc12] | 5-{2-[2-(N-methyl5-methoxyquinoline-8-sulfonamido)phenyl]ethynyl}pyridine-2-carboxylic acid | 175 |
| 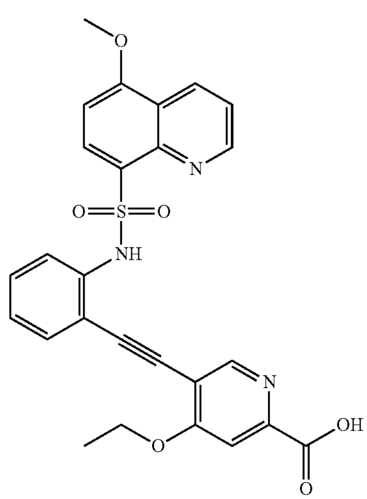 [SMILES: CCOc1cc(C(=O)O)ncc1C#Cc1ccccc1NS(=O)(=O)c1ccc(OC)c2cccnc12] | 4-ethoxy-5-{2-[2-(5-methoxyquinoline-8-sulfonamido)phenyl]ethynyl}pyridine-2-carboxylic acid | 176 |

TABLE 1-continued

| Compound Structure | IUPAC name | Cpd. No. |
|---|---|---|
| 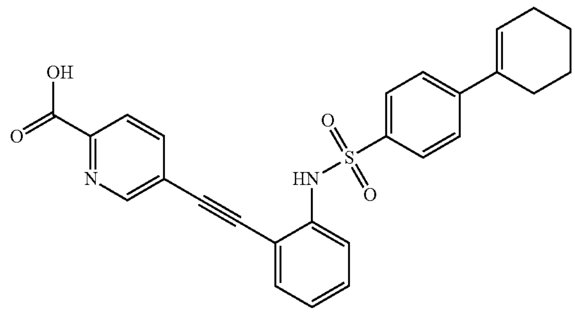 [SMILES: O=C(O)c1ccc(C#Cc2ccccc2NS(=O)(=O)c2ccc(C3=CCCCC3)cc2)cn1] | 5-(2-{2-[4-(cyclohex-1-en-1-yl)benzenesulfonamido]phenyl}-ethynyl)pyridine-2-carboxylic acid | 177 |
| 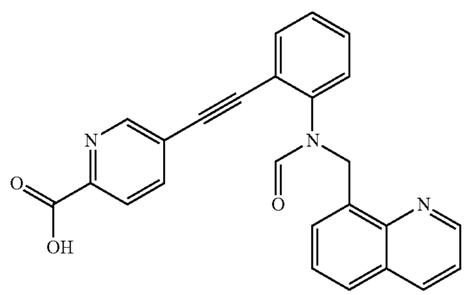 [SMILES: O=CN(Cc1cccc2cccnc12)c1ccccc1C#Cc1ccc(C(=O)O)nc1] | 5-[2-(2-{N-[(quinolin-8-yl)methyl]formamido}phenyl)ethynyl]pyridine-2-carboxylic acid | 178 |
| 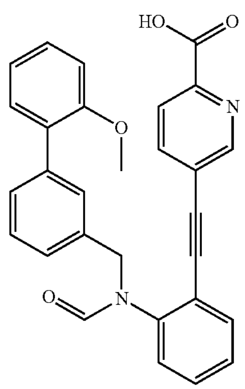 [SMILES: COc1ccccc1-c1cccc(CN(C=O)c2ccccc2C#Cc2ccc(C(=O)O)nc2)c1] | 5-(2-{2-[N-({2'-methoxy-[1,1'-biphenyl]-3-yl}methyl)formamido]phenyl}ethynyl)pyridine-2-carboxylic acid | 179 |
| 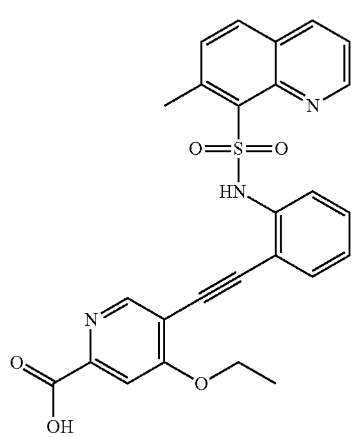 [SMILES: CCOc1cc(C(=O)O)ncc1C#Cc1ccccc1NS(=O)(=O)c1c(C)ccc2cccnc12] | 4-ethoxy-5-{2-[2-(7-methylquinoline-8-sulfonamido)phenyl]ethynyl}pyridine-2-carboxylic acid | 180 |

TABLE 1-continued

| Compound Structure | IUPAC name | Cpd. No. |
|---|---|---|
| 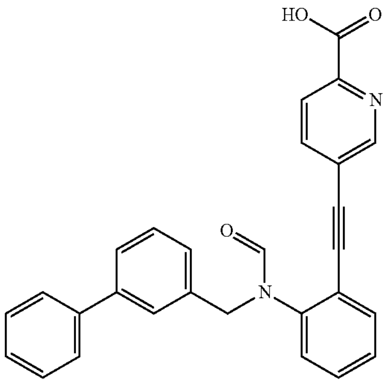 [SMILES: O=CN(Cc1cccc(-c2ccccc2)c1)c1ccccc1C#Cc1ccc(C(=O)O)nc1] | 5-(2-{2-[N-({[1,1'-biphenyl]-3-yl}methyl)formamido]phenyl}-ethynyl)pyridine-2-carboxylic acid | 181 |
| 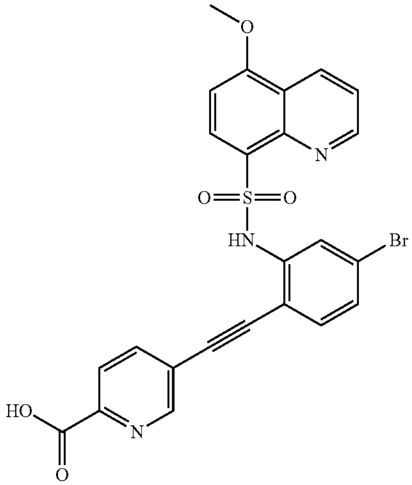 [SMILES: COc1ccc(S(=O)(=O)Nc2cc(Br)ccc2C#Cc2ccc(C(=O)O)nc2)c2ncccc12] | 5-{2-[4-bromo-2-(5-methoxyquinoline-8-sulfonamido)phenyl]ethynyl}pyridine-2-carboxylic acid | 182 |
| 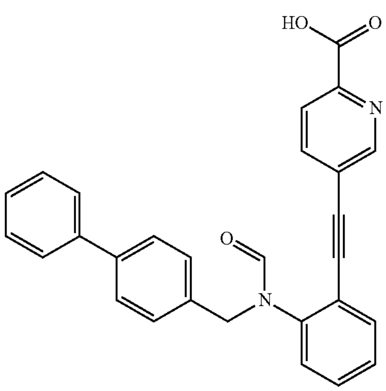 [SMILES: O=CN(Cc1ccc(-c2ccccc2)cc1)c1ccccc1C#Cc1ccc(C(=O)O)nc1] | 5-(2-{2-[N-({[1,1'-biphenyl]-4-yl}methyl)formamido]phenyl}-ethynyl)pyridine-2-carboxylic acid | 183 |
| 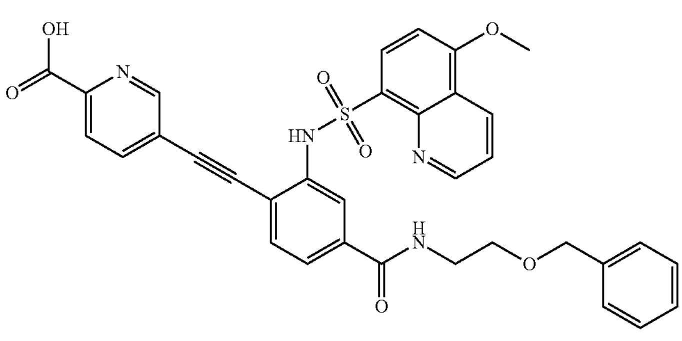 [SMILES: COc1ccc(S(=O)(=O)Nc2cc(C(=O)NCCOCc3ccccc3)ccc2C#Cc2ccc(C(=O)O)nc2)c2ncccc12] | 5-[2-(4-{[2-(benzyloxy)ethyl]carbamoyl}-2-(5-methoxyquinoline-8-sulfonamido)-phenyl)ethynyl]pyridine-2-carboxylic acid | 184 |

TABLE 1-continued

| Compound Structure | IUPAC name | Cpd. No. |
|---|---|---|
| 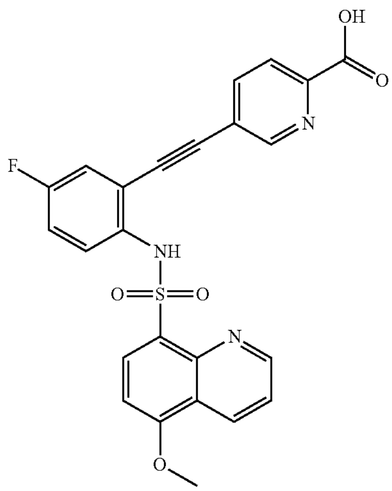 [SMILES: COc1ccc(S(=O)(=O)Nc2ccc(F)cc2C#Cc2ccc(C(=O)O)nc2)c2ncccc12] | 5-{2-[5-fluoro-2-(5-methoxyquinoline-8-sulfonamido)phenyl]ethynyl}pyridine-2-carboxylic acid | 185 |
| 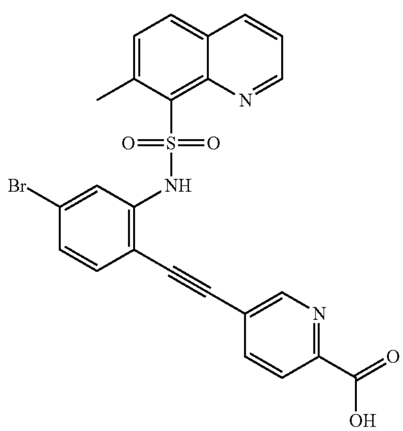 [SMILES: Cc1ccc2cccnc2c1S(=O)(=O)Nc1cc(Br)ccc1C#Cc1ccc(C(=O)O)nc1] | 5-{2-[4-bromo-2-(7-methylquinoline-8-sulfonamido)phenyl]ethynyl}pyridine-2-carboxylic acid | 186 |
|  | 4-(dimethylamino)-5-{2-[2-(7-methylquinoline-8-sulfonamido)phenyl]ethynyl}pyridine-2-carboxylic acid | 187 |

TABLE 1-continued

| Compound Structure | IUPAC name | Cpd. No. |
|---|---|---|
| 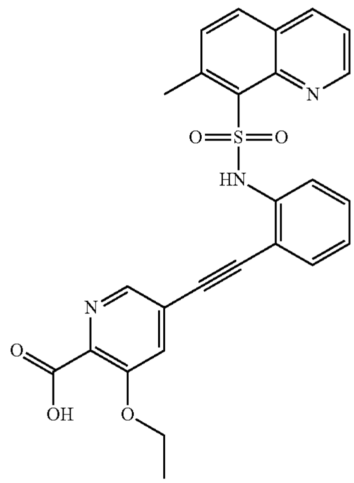 [SMILES: CCOc1cc(C#Cc2ccccc2NS(=O)(=O)c2c(C)ccc3cccnc23)cnc1C(=O)O] | 3-ethoxy-5-{2-[2-(7-methylquinoline-8-sulfonamido)phenyl]ethynyl}pyridine-2-carboxylic acid | 188 |
| 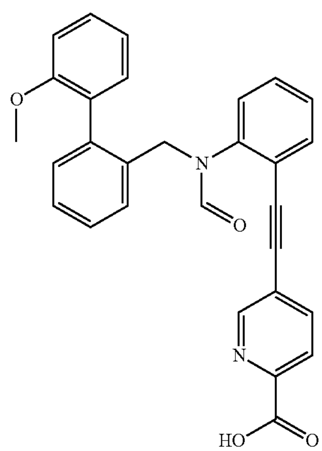 [SMILES: COc1ccccc1-c1ccccc1CN(C=O)c1ccccc1C#Cc1ccc(C(=O)O)nc1] | 5-(2-{2-[N-({2'-methoxy-[1,1'-biphenyl]-2-yl}methyl)formamido]phenyl}-ethynyl)pyridine-2-carboxylic acid | 189 |
| 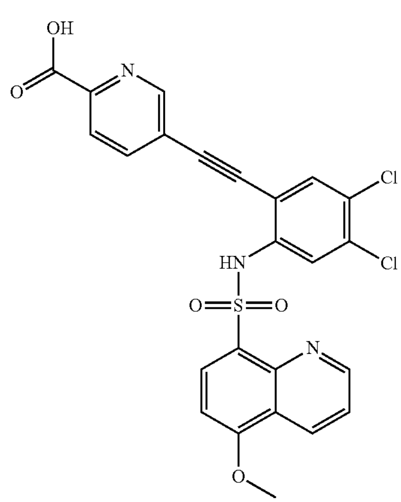 [SMILES: COc1ccc(S(=O)(=O)Nc2cc(Cl)c(Cl)cc2C#Cc2ccc(C(=O)O)nc2)c2ncccc12] | 5-{2-[4,5-dichloro-2-(5-methoxyquinoline-8-sulfonamido)phenyl]ethynyl}pyridine-2-carboxylic acid | 190 |

TABLE 1-continued

| Compound Structure | IUPAC name | Cpd. No. |
|---|---|---|
| 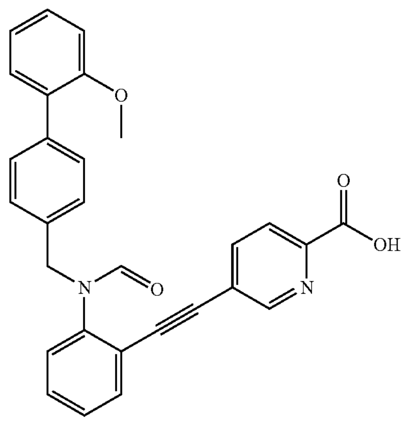 [SMILES: COc1ccccc1-c1ccc(CN(C=O)c2ccccc2C#Cc2ccc(C(=O)O)nc2)cc1] | 5-(2-{2-[N-({2'-methoxy-[1,1'-biphenyl]-4-yl}methyl)formamido]phenyl}ethynyl)-pyridine-2-carboxylic acid | 191 |
| 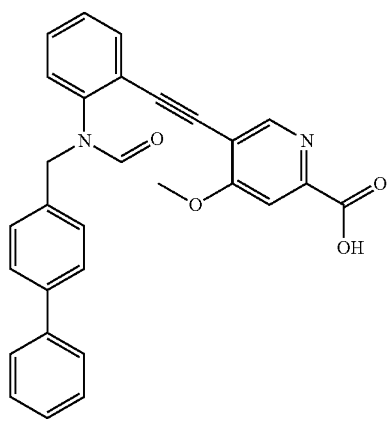 [SMILES: COc1cc(C(=O)O)ncc1C#Cc1ccccc1N(C=O)Cc1ccc(-c2ccccc2)cc1] | 5-(2-{2-[N-({[1,1'-biphenyl]-4-yl}methyl)formamido]phenyl}ethynyl)-4-methoxypyridine-2-carboxylic acid | 192 |
| 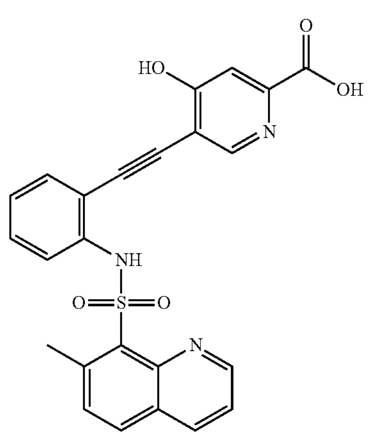 [SMILES: Cc1ccc2cccnc2c1S(=O)(=O)Nc1ccccc1C#Cc1cnc(C(=O)O)cc1O] | 4-hydroxy-5-{2-[2-(7-methylquinoline-8-sulfonamido)phenyl]ethynyl}pyridine-2-carboxylic acid | 193 |

TABLE 1-continued

| Compound Structure | IUPAC name | Cpd. No. |
|---|---|---|
| 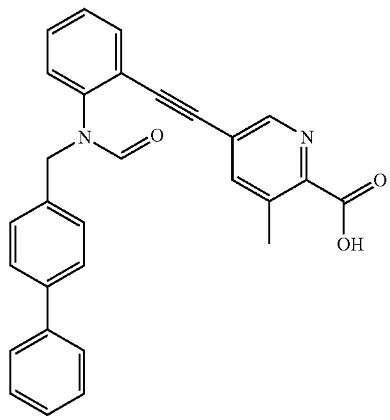 [SMILES: Cc1cc(C#Cc2ccccc2N(C=O)Cc2ccc(-c3ccccc3)cc2)cnc1C(=O)O] | 5-(2-{2-[N-({[1,1'-biphenyl]-4-yl}methyl)formamido]phenyl}ethynyl)-3-methylpyridine-2-carboxylic acid | 194 |
| 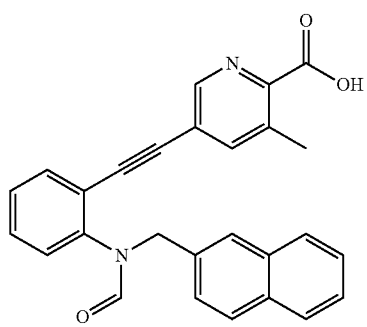 [SMILES: Cc1cc(C#Cc2ccccc2N(C=O)Cc2ccc3ccccc3c2)cnc1C(=O)O] | 3-methyl-5-[2-(2-{N-[(naphthalen-2-yl)methyl]formamido}phenyl)ethynyl]-pyridine-2-carboxylic acid | 195 |
| 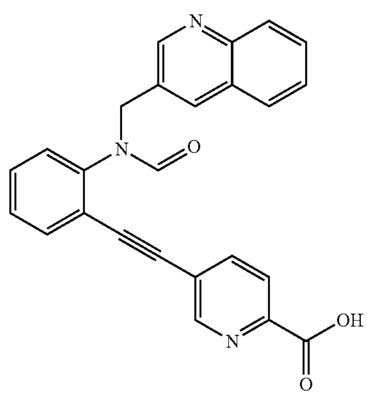 [SMILES: O=CN(Cc1cnc2ccccc2c1)c1ccccc1C#Cc1ccc(C(=O)O)nc1] | 5-[2-(2-{N-[(quinolin-3-yl)methyl]formamido}phenyl)ethynyl]-pyridine-2-carboxylic acid | 196 |
| 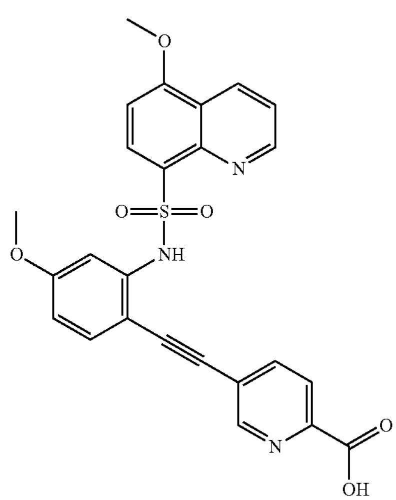 [SMILES: COc1ccc(C#Cc2ccc(C(=O)O)nc2)c(NS(=O)(=O)c2ccc(OC)c3cccnc23)c1] | 5-{2-[4-methoxy-2-(5-methoxyquinoline-8-sulfonamido)phenyl]ethynyl}pyridine-2-carboxylic acid | 197 |

TABLE 1-continued
| Compound Structure | IUPAC name | Cpd. No. |
|---|---|---|
| 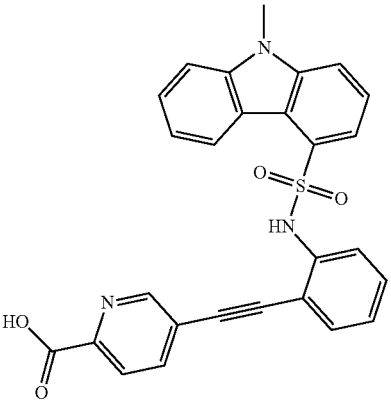 [SMILES: Cn1c2ccccc2c2c(S(=O)(=O)Nc3ccccc3C#Cc3ccc(C(=O)O)nc3)cccc21] | 5-{2-[2-(9-methyl-9H-carbazole-4-sulfonamido)phenyl]ethynyl}pyridine-2-carboxylic acid | 198 |
| 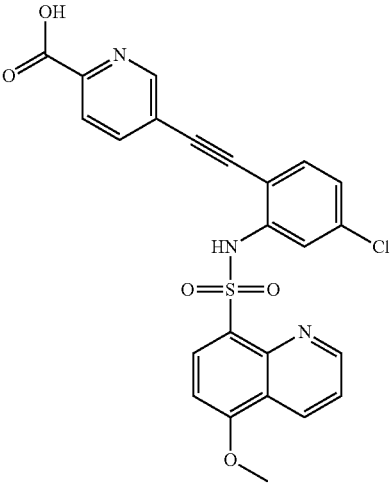 [SMILES: COc1ccc(S(=O)(=O)Nc2cc(Cl)ccc2C#Cc2ccc(C(=O)O)nc2)c2ncccc12] | 5-{2-[4-chloro-2-(5-methoxyquinoline-8-sulfonamido)phenyl]ethynyl}pyridine-2-carboxylic acid | 199 |
| 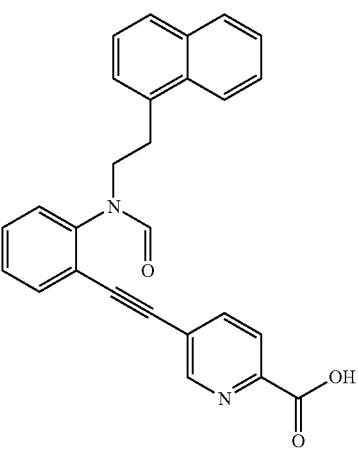 [SMILES: O=CN(CCc1cccc2ccccc12)c1ccccc1C#Cc1ccc(C(=O)O)nc1] | 5-[2-(2-{N-[2-(naphthalen-1-yl)ethyl]-formamido}phenyl)ethynyl]pyridine-2-carboxylic acid | 200 |

| Compound Structure | IUPAC name | Cpd. No. |
|---|---|---|
| 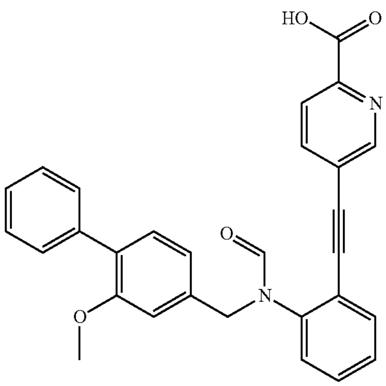 [SMILES: COc1cc(CN(C=O)c2ccccc2C#Cc2ccc(C(=O)O)nc2)ccc1-c1ccccc1] | 5-(2-{2-[N-({2-methoxy-[1,1'-biphenyl]-4-yl}methyl)formamido]phenyl}-ethynyl)pyridine-2-carboxylic acid | 201 |
| 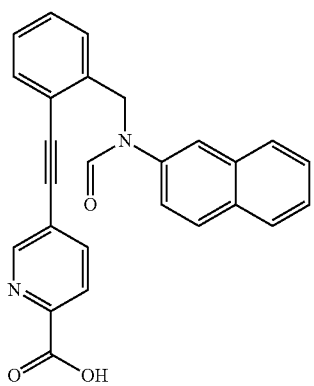 [SMILES: O=CN(Cc1ccccc1C#Cc1ccc(C(=O)O)nc1)c1ccc2ccccc2c1] | 5-[2-(2-{[N-(naphthalen-2-yl)formamido]methyl}phenyl)-ethynyl]pyridine-2-carboxylic acid | 202 |
| 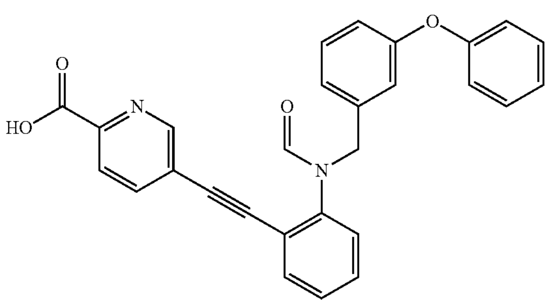 [SMILES: O=CN(Cc1cccc(Oc2ccccc2)c1)c1ccccc1C#Cc1ccc(C(=O)O)nc1] | 5-[2-(2-{N-[(3-phenoxyphenyl)methyl]-formamido}phenyl)ethynyl]pyridine-2-carboxylic acid | 203 |
| 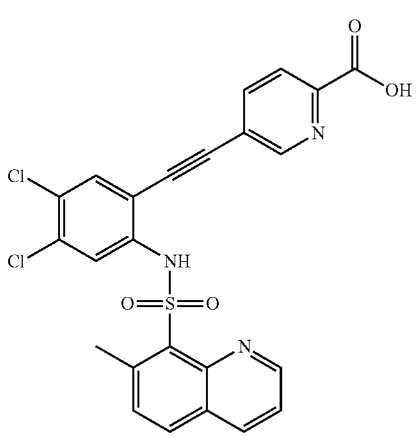 [SMILES: Cc1ccc2cccnc2c1S(=O)(=O)Nc1cc(Cl)c(Cl)cc1C#Cc1ccc(C(=O)O)nc1] | 5-{2-[4,5-dichloro-2-(7-methylquinoline-8-sulfonamido)phenyl]ethynyl}pyridine-2-carboxylic acid | 204 |

TABLE 1-continued
| Compound Structure | IUPAC name | Cpd. No. |
|---|---|---|
| 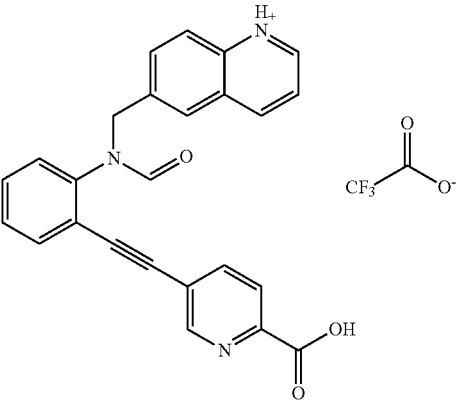 | 6-[({2-[2-(6-carboxypyridin-3-yl)ethynyl]phenyl}-(formyl)imino)methyl]quinolin-1-ium trifluoroacetate | 205 |
| 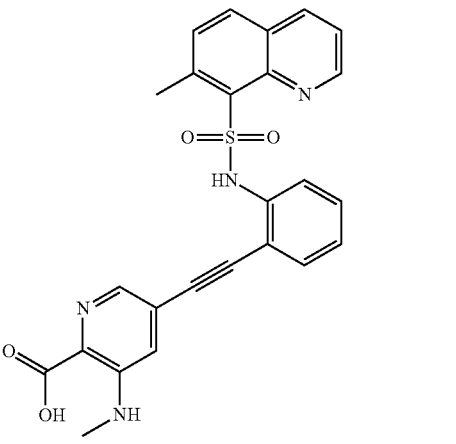 | 3-(methylamino)-5-{2-[2-(7-methylquinoline-8-sulfonamido)phenyl]-ethynyl}pyridine-2-carboxylic acid | 206 |
| 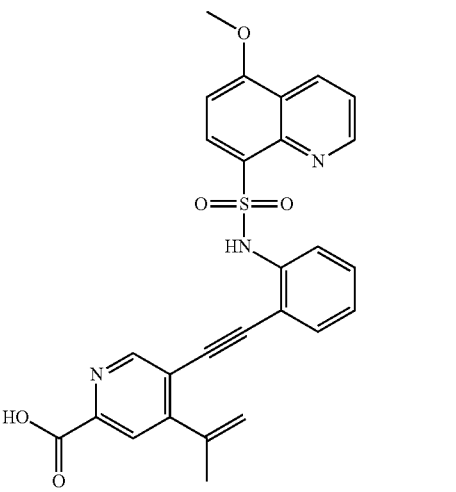 [SMILES: C=C(C)c1cc(C(=O)O)ncc1C#Cc1ccccc1NS(=O)(=O)c1ccc(OC)c2cccnc12] | 5-{2-[2-(5-methoxyquinoline-8-sulfonamido)phenyl]ethynyl}-3-(methylamino)pyridine-2-carboxylic acid | 207 |

TABLE 1-continued

| Compound Structure | IUPAC name | Cpd. No. |
|---|---|---|
| 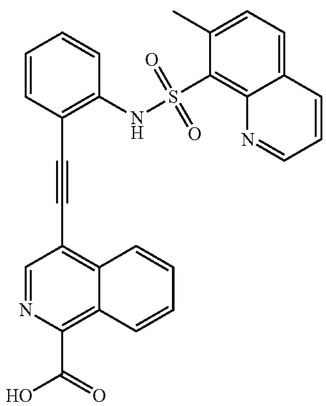 [SMILES: Cc1ccc2cccnc2c1S(=O)(=O)Nc1ccccc1C#Cc1cnc(C(=O)O)c2ccccc12] | 4-{2-[2-(7-methylquinoline-8-sulfonamido)phenyl]ethynyl}isoquinoline-1-carboxylic acid | 208 |
| 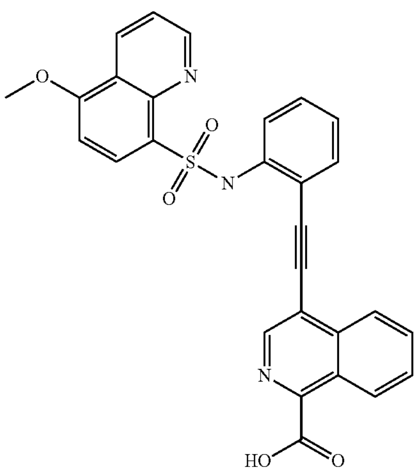 | 4-{2-[2-(5-methoxyquinoline-8-sulfonamido)phenyl]ethynyl}isoquinoline-1-carboxylic acid | 209 |
| 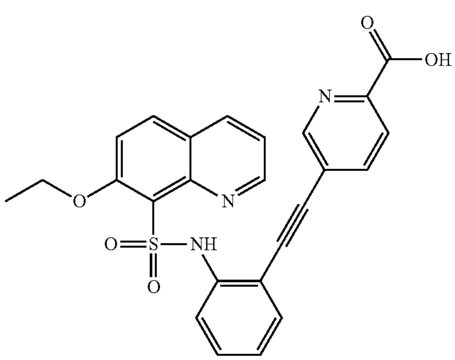 [SMILES: CCOc1ccc2cccnc2c1S(=O)(=O)Nc1ccccc1C#Cc1ccc(C(=O)O)nc1] | 5-{2-[2-(7-ethoxyquinoline-8-sulfonamido)phenyl]ethynyl}pyridine-2-carboxylic acid | 210 |
| 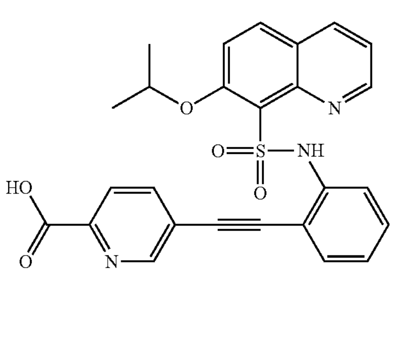 [SMILES: CC(C)Oc1ccc2cccnc2c1S(=O)(=O)Nc1ccccc1C#Cc1ccc(C(=O)O)nc1] | 5-(2-{2-[7-(propan-2-yloxy)quinoline-8-sulfonamido]phenyl}ethynyl)pyridine-2-carboxylic acid | 211 |

TABLE 1-continued

| Compound Structure | IUPAC name | Cpd. No. |
|---|---|---|
| 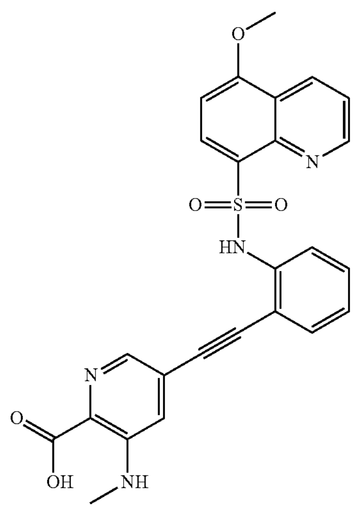 [SMILES: CNc1cc(C#Cc2ccccc2NS(=O)(=O)c2ccc(OC)c3cccnc23)cnc1C(=O)O] | 5-{2-[2-(5-methoxyquinoline-8-sulfonamido)phenyl]ethynyl}-3-(methylamino)pyridine-2-carboxylic acid | 212 |
| 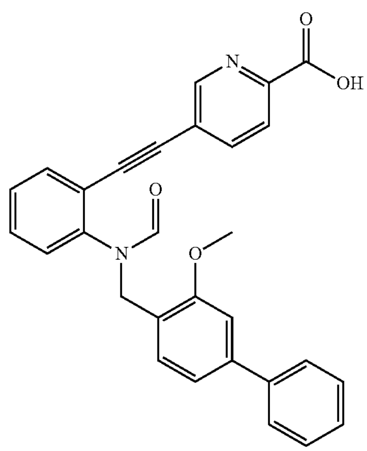 [SMILES: COc1cc(-c2ccccc2)ccc1CN(C=O)c1ccccc1C#Cc1ccc(C(=O)O)nc1] | 5-(2-{2-[N-({3-methoxy-[1,1'-biphenyl]-4-yl}methyl)formamido]phenyl}-ethynyl)pyridine-2-carboxylic acid | 213 |
| 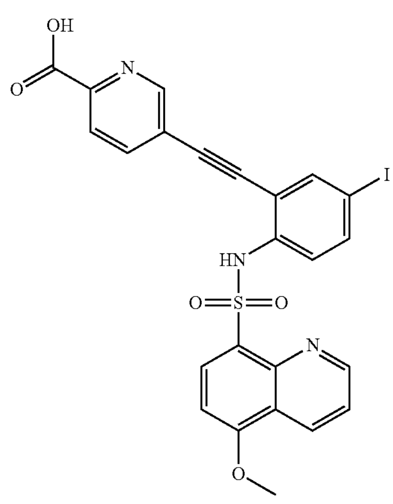 [SMILES: COc1ccc(S(=O)(=O)Nc2ccc(I)cc2C#Cc2ccc(C(=O)O)nc2)c2ncccc12] | 5-{2-[5-iodo-2-(5-methoxyquinoline-8-sulfonamido)phenyl]ethynyl}pyridine-2-carboxylic acid | 214 |

TABLE 1-continued

| Compound Structure | IUPAC name | Cpd. No. |
|---|---|---|
| 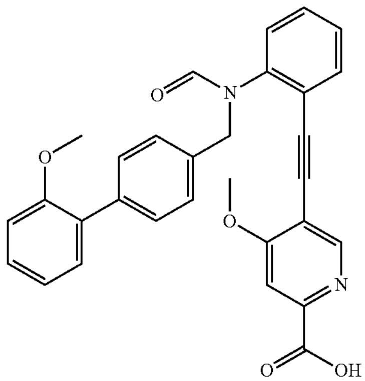 [SMILES: COc1cc(C(=O)O)ncc1C#Cc1ccccc1N(C=O)Cc1ccc(-c2ccccc2OC)cc1] | 4-methoxy-5-(2-{2-[N-({2'-methoxy-[1,1'-biphenyl]-4-yl}methyl)formamido]phenyl}-ethynyl)pyridine-2-carboxylic acid | 215 |
| 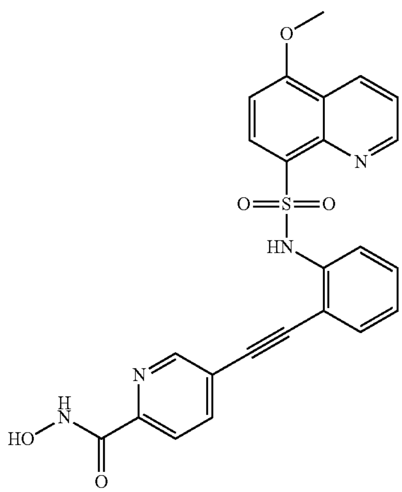 [SMILES: COc1ccc(S(=O)(=O)Nc2ccccc2C#Cc2ccc(C(=O)NO)nc2)c2ncccc12] | N-hydroxy-5-{2-[2-(5-methoxyquinoline-8-sulfonamido)phenyl]ethynyl}pyridine-2-carboxamide | 216 |
| 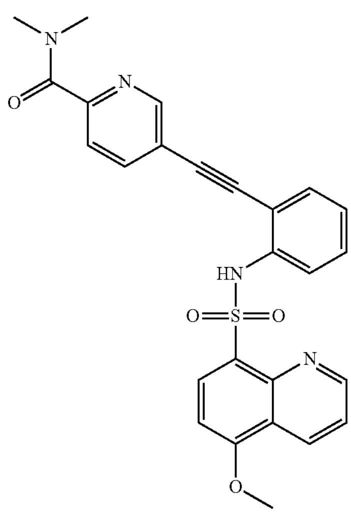 [SMILES: COc1ccc(S(=O)(=O)Nc2ccccc2C#Cc2ccc(C(=O)N(C)C)nc2)c2ncccc12] | 5-{2-[2-(5-methoxyquinoline-8-sulfonamido)phenyl[ethynyl}-N,N-dimethylpyridine-2-carboxamide | 217 |

TABLE 1-continued

| Compound Structure | IUPAC name | Cpd. No. |
|---|---|---|
| 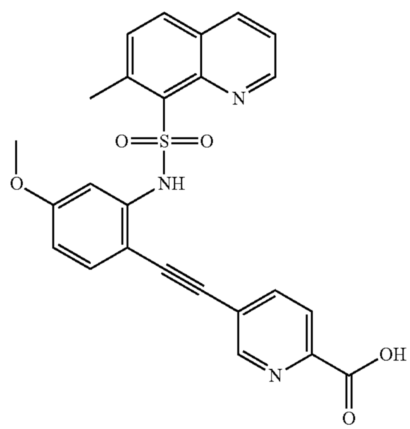 [SMILES: COc1ccc(C#Cc2ccc(C(=O)O)nc2)c(NS(=O)(=O)c2c(C)ccc3cccnc23)c1] | 5-{2-[4-methoxy-2-(7-methylquinoline-8-sulfonamido)phenyl]ethynyl}pyridine-2-carboxylic acid | 218 |
| 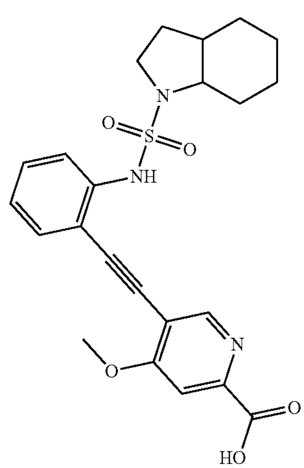 [SMILES: COc1cc(C(=O)O)ncc1C#Cc1ccccc1NS(=O)(=O)N1CCC2CCCCC21] | 4-methoxy-5-(2-{2-[(octahydro-1H-indole-1-sulfonyl)amino]phenyl}ethynyl)pyridine-2-carboxylic acid | 219 |
| 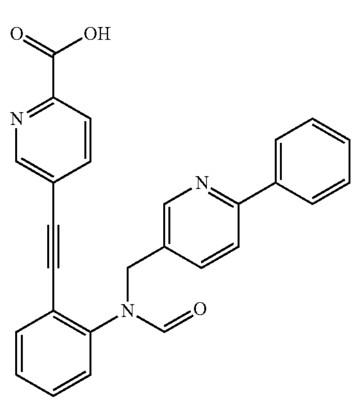 [SMILES: O=CN(Cc1ccc(-c2ccccc2)nc1)c1ccccc1C#Cc1ccc(C(=O)O)nc1] | 5-[2-(2-{N-[(6-phenylpyridin-3-yl)methyl]formamido}phenyl)-ethynyl]pyridine-2-carboxylic acid | 220 |

TABLE 1-continued
| Compound Structure | IUPAC name | Cpd. No. |
|---|---|---|
| 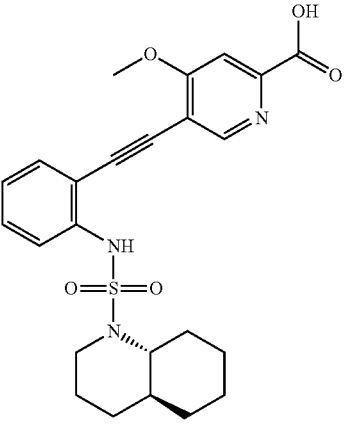 [SMILES: COc1cc(C(=O)O)ncc1C#Cc1ccccc1NS(=O)(=O)N1CCC[C@@H]2CCCC[C@H]21] | 5-[2-(2-{[(4a,8a-trans)-decahydro-quinoline-1-sulfonyl]amino}phenyl)-ethynyl]-4-methoxypyridine-2-carboxylic acid | 221 |
| 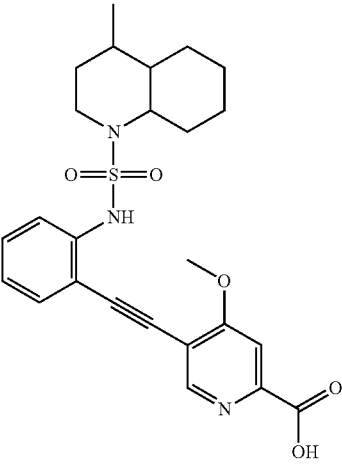 [SMILES: COc1cc(C(=O)O)ncc1C#Cc1ccccc1NS(=O)(=O)N1CCC(C)C2CCCCC21] | 4-methoxy-5-[2-(2-{[(4-methyl-deca-hydroquinolin-1-yl)sulfonyl]amino}-phenyl)ethynyl]pyridine-2-carboxylic acid | 222 |
| 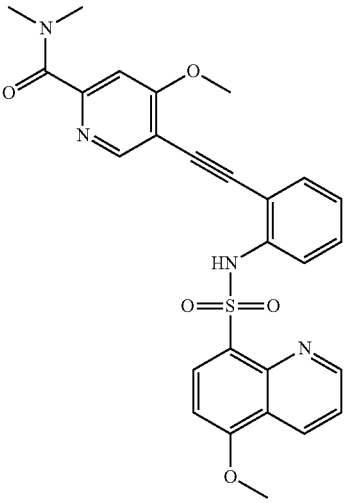 [SMILES: COc1cc(C(=O)N(C)C)ncc1C#Cc1ccccc1NS(=O)(=O)c1ccc(OC)c2cccnc12] | 4-methoxy-5-{2-[2-(5-methoxyquinoline-8-sulfonamido)phenyl]ethynyl}-N,N-dimethylpyridine-2-carboxamide | 223 |

TABLE 1-continued

| Compound Structure | IUPAC name | Cpd. No. |
|---|---|---|
| 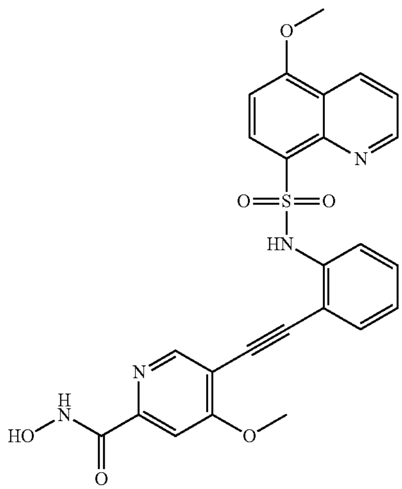 [SMILES: COc1cc(C(=O)NO)ncc1C#Cc1ccccc1NS(=O)(=O)c1ccc(OC)c2cccnc12] | N-hydroxy-4-methoxy-5-{2-[2-(5-methoxyquinoline-8-sulfonamido)phenyl-]ethynyl}pyridine-2-carboxamide | 224 |
| 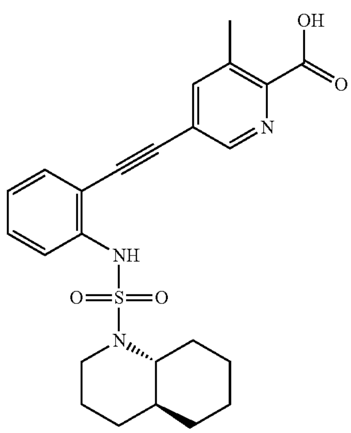 [SMILES: Cc1cc(C#Cc2ccccc2NS(=O)(=O)N2CCC[C@@H]3CCCC[C@H]32)cnc1C(=O)O] | 5-[2-(2-{[(4a,8a-trans)-decahydro-quinoline-1-sulfonyl]amino}phenyl)-ethynyl]-3-methylpyridine-2-carboxylic acid | 225 |
| 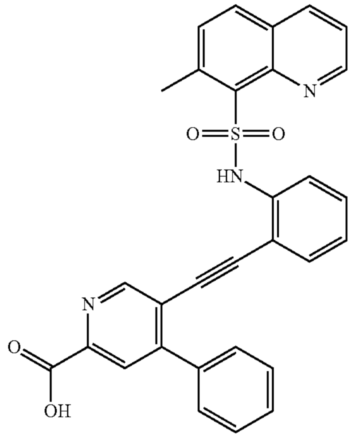 [SMILES: Cc1ccc2cccnc2c1S(=O)(=O)Nc1ccccc1C#Cc1cnc(C(=O)O)cc1-c1ccccc1] | 5-{2-[2-(7-methylquinoline-8-sulfonamido)phenyl]ethynyl}-4-phenylpyridine-2-carboxylic acid | 226 |

TABLE 1-continued

| Compound Structure | IUPAC name | Cpd. No. |
|---|---|---|
| 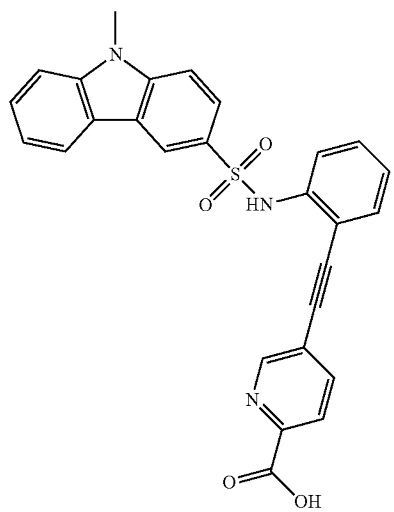 [SMILES: Cn1c2ccccc2c2cc(S(=O)(=O)Nc3ccccc3C#Cc3ccc(C(=O)O)nc3)ccc21] | 5-{2-[2-(9-methyl-9H-carbazole-3-sulfonamido)phenyl]ethynyl}pyridine-2-carboxylic acid | 227 |
| 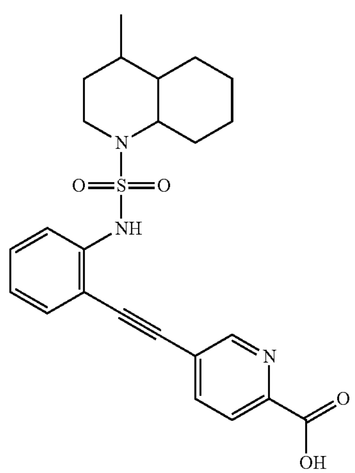 [SMILES: CC1CCN(S(=O)(=O)Nc2ccccc2C#Cc2ccc(C(=O)O)nc2)C2CCCCC12] | 5-[2-(2-{[(4-methyl-decahydroquinolin-1-yl)sulfonyl]amino}phenyl)ethynyl]pyridine-2-carboxylic acid | 228 |
| 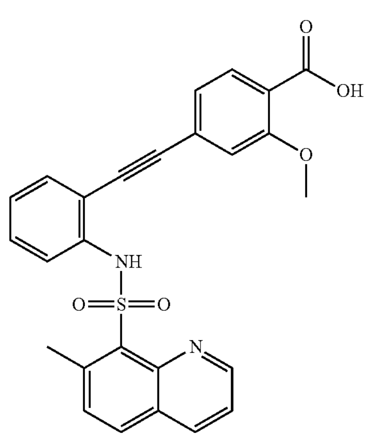 [SMILES: COc1cc(C#Cc2ccccc2NS(=O)(=O)c2c(C)ccc3cccnc23)ccc1C(=O)O] | 2-methoxy-4-{2-[2-(7-methylquinoline-8-sulfonamido)phenyl]ethynyl}benzoic acid | 229 |

TABLE 1-continued

| Compound Structure | IUPAC name | Cpd. No. |
|---|---|---|
| 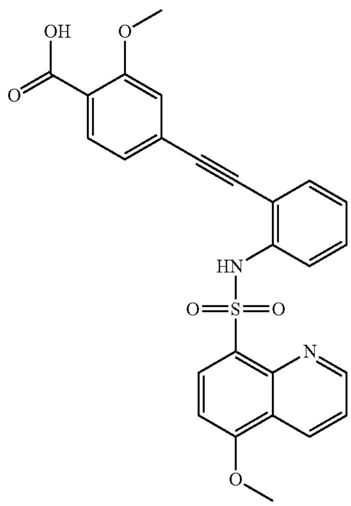 [SMILES: COc1cc(C#Cc2ccccc2NS(=O)(=O)c2ccc(OC)c3cccnc23)ccc1C(=O)O] | 2-methoxy-4-{2-[2-(5-methoxyquinoline-8-sulfonamido)phenyl]ethynyl}benzoic acid | 230 |
| 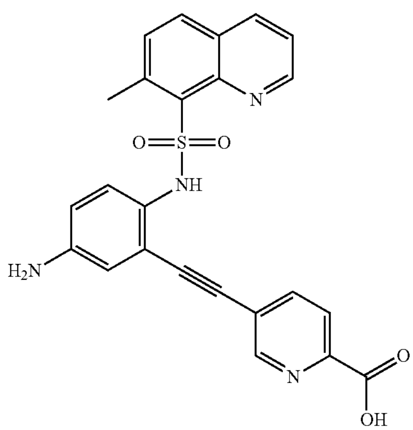 [SMILES: Cc1ccc2cccnc2c1S(=O)(=O)Nc1ccc(N)cc1C#Cc1ccc(C(=O)O)nc1] | 5-{2-[5-amino-2-(7-methylquinoline-8-sulfonamido)phenyl]ethynyl}pyridine-2-carboxylic acid | 231 |
| 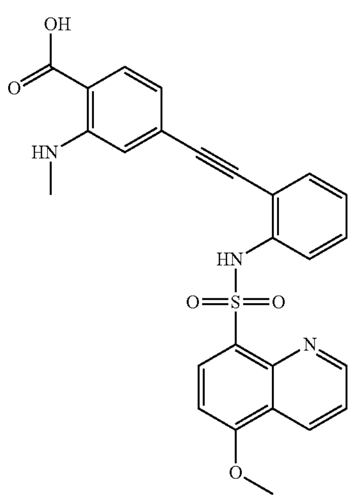 [SMILES: CNc1cc(C#Cc2ccccc2NS(=O)(=O)c2ccc(OC)c3cccnc23)ccc1C(=O)O] | 4-{2-[2-(5-methoxyquinoline-8-sulfonamido)phenyl]ethynyl}-2-(methylamino)benzoic acid | 232 |

TABLE 1-continued

| Compound Structure | IUPAC name | Cpd. No. |
|---|---|---|
| 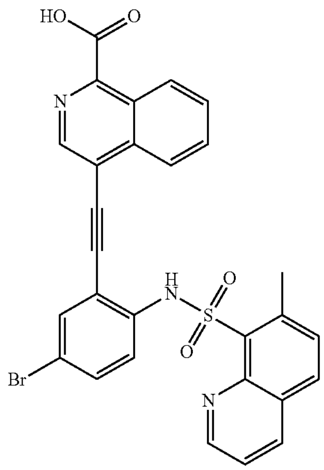 | 4-{2-[5-bromo-2-(7-methylquinoline-8-sulfonamido)phenyl]ethynyl}isoquinoline-1-carboxylic acid | 233 |
| 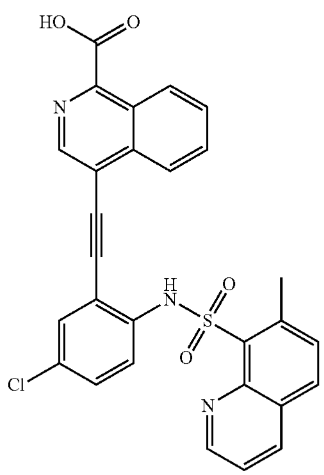 [SMILES: Cc1ccc2cccnc2c1S(=O)(=O)Nc1ccc(Cl)cc1C#Cc1cnc(C(=O)O)c2ccccc12] | 4-{2-[5-chloro-2-(7-methylquinoline-8-sulfonamido)phenyl]ethynyl}isoquinoline-1-carboxylic acid | 234 |
| 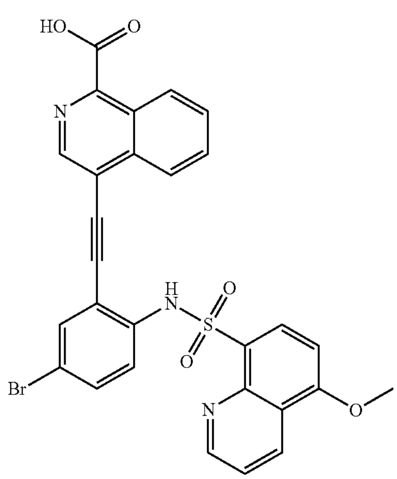 [SMILES: COc1ccc(S(=O)(=O)Nc2ccc(Br)cc2C#Cc2cnc(C(=O)O)c3ccccc23)c2ncccc12] | 4-{2-[5-bromo-2-(5-methoxyquinoline-8-sulfonamido)phenyl]ethynyl}isoquinoline-1-carboxylic acid | 235 |

TABLE 1-continued

| Compound Structure | IUPAC name | Cpd. No. |
|---|---|---|
| 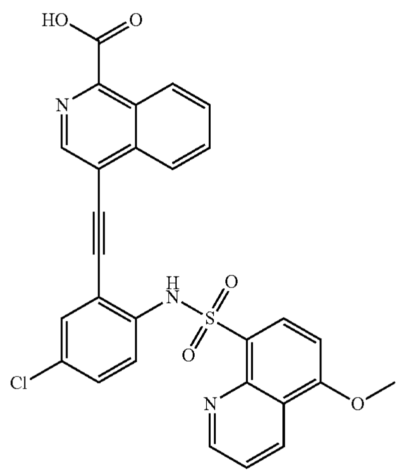 [SMILES: COc1ccc(S(=O)(=O)Nc2ccc(Cl)cc2C#Cc2cnc(C(=O)O)c3ccccc23)c2ncccc12] | 4-{2-[5-chloro-2-(5-methoxyquinoline-8-sulfonamido)phenyl]ethynyl}isoquinoline-1-carboxylic acid | 236 |
| 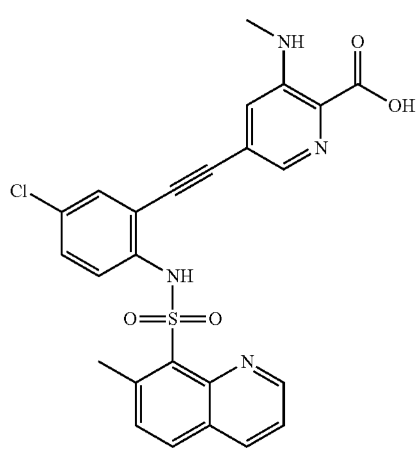 [SMILES: CNc1cc(C#Cc2cc(Cl)ccc2NS(=O)(=O)c2c(C)ccc3cccnc23)cnc1C(=O)O] | 5-{2-[5-chloro-2-(7-methylquinoline-8-sulfonamido)phenyl]ethynyl}-3-(methylamino)pyridine-2-carboxylic acid | 237 |
| 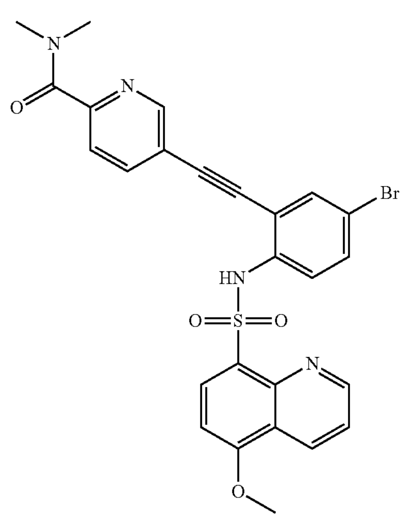 [SMILES: COc1ccc(S(=O)(=O)Nc2ccc(Br)cc2C#Cc2ccc(C(=O)N(C)C)nc2)c2ncccc12] | 5-{2-[5-bromo-2-(5-methoxyquinoline-8-sulfonamido)phenyl]ethynyl}-N,N-dimethylpyridine-2-carboxamide | 238 |

TABLE 1-continued

| Compound Structure | IUPAC name | Cpd. No. |
|---|---|---|
| 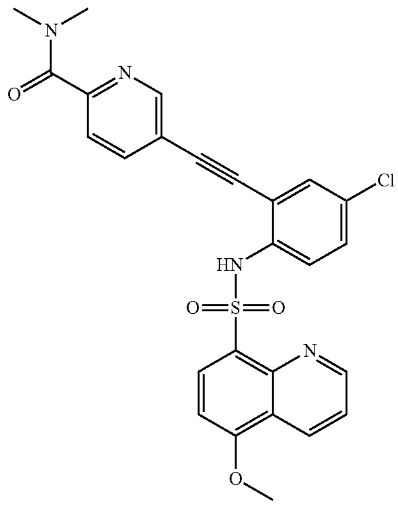 [SMILES: COc1ccc(S(=O)(=O)Nc2ccc(Cl)cc2C#Cc2ccc(C(=O)N(C)C)nc2)c2ncccc12] | 5-{2-[5-chloro-2-(5-methoxyquinoline-8-sulfonamido)phenyl]ethynyl}-N,N-dimethylpyridine-2-carboxamide | 239 |
| 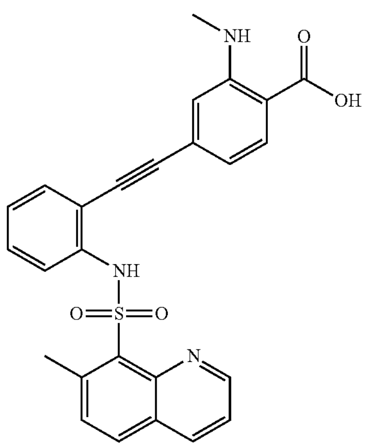 [SMILES: CNc1cc(C#Cc2ccccc2NS(=O)(=O)c2c(C)ccc3cccnc23)ccc1C(=O)O] | 2-(methylamino)-4-{2-[2-(7-methylquinoline-8-sulfonamido)-phenyl]ethynyl}benzoic acid | 240 |
| 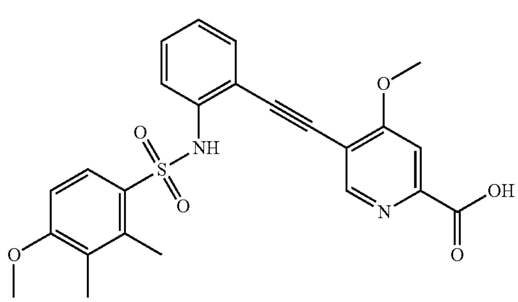 [SMILES: COc1cc(C(=O)O)ncc1C#Cc1ccccc1NS(=O)(=O)c1ccc(OC)c(C)c1C] | 4-methoxy-5-{2-[2-(4-methoxy-2,3-dimethylbenzenesulfonamido)-phenyl]ethynyl}pyridine-2-carboxylic acid | 241 |

TABLE 1-continued

| Compound Structure | IUPAC name | Cpd. No. |
|---|---|---|
| | 5-{2-[5-chloro-2-(5-methoxyquinoline-8-sulfonamido)phenyl]ethynyl}-3-(methyl-amino)pyridine-2-carboxylic acid | 242 |
| 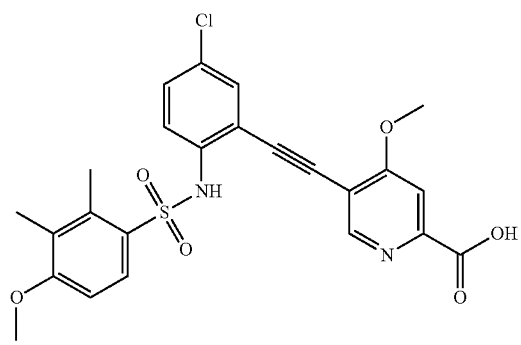 [SMILES: COc1cc(C(=O)O)ncc1C#Cc1cc(Cl)ccc1NS(=O)(=O)c1ccc(OC)c(C)c1C] | 5-{2-[5-chloro-2-(4-methoxy-2,3-dimethylbenzenesulfonamido)-phenyl]ethynyl}-4-methoxypyridine-2-carboxylic acid | 243 |
| 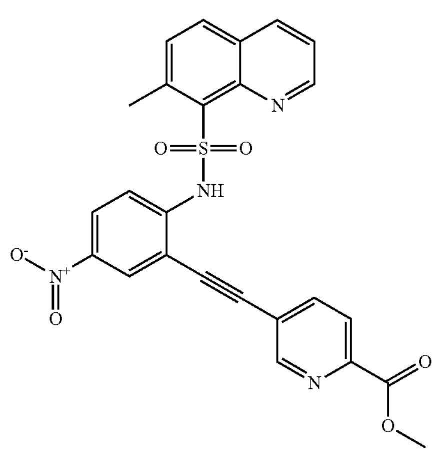 [SMILES: COC(=O)c1ccc(C#Cc2cc([N+](=O)[O-])ccc2NS(=O)(=O)c2c(C)ccc3cccnc23)cn1] | methyl 5-{2-[2-(7-methylquinoline-8-sulfonamido)-5-nitrophenyl]ethynyl}-pyridine-2-carboxylate | 244 |

TABLE 1-continued

| Compound Structure | IUPAC name | Cpd. No. |
|---|---|---|
| 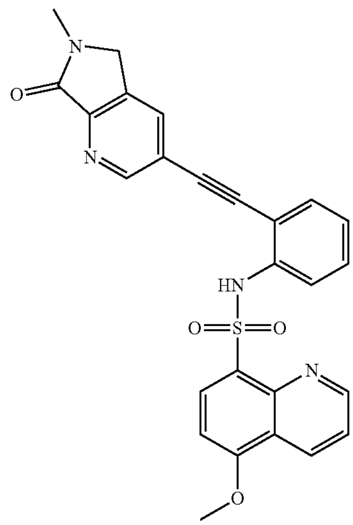 [SMILES: COc1ccc(S(=O)(=O)Nc2ccccc2C#Cc2cnc3c(c2)CN(C)C3=O)c2ncccc12] | 5-methoxy-N-[2-(2-{6-methyl-7-oxo-5H,6H,7H-pyrrolo[3,4-b]pyridin-3-yl}ethynyl)phenyl]quinoline-8-sulfonamide | 245 |
| 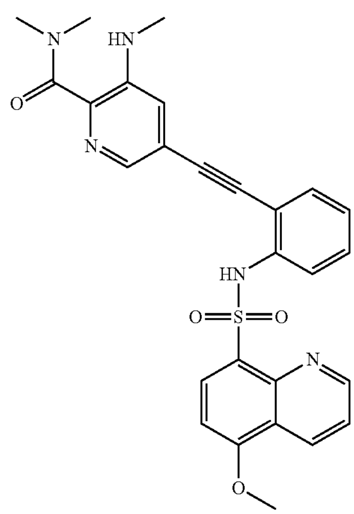 [SMILES: CNc1cc(C#Cc2ccccc2NS(=O)(=O)c2ccc(OC)c3cccnc23)cnc1C(=O)N(C)C] | 5-{2-[2-(5-methoxyquinoline-8-sulfonamido)phenyl]ethynyl}-N,N-dimethyl-3-(methylamino)pyridine-2-carboxamide | 246 |
| 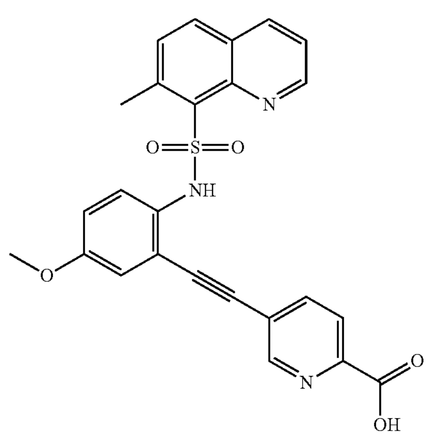 [SMILES: COc1ccc(NS(=O)(=O)c2c(C)ccc3cccnc23)c(C#Cc2ccc(C(=O)O)nc2)c1] | 5-{2-[5-methoxy-2-(7-methylquinoline-8-sulfonamido)phenyl]ethynyl}pyridine-2-carboxylic acid | 247 |

TABLE 1-continued

| Compound Structure | IUPAC name | Cpd. No. |
|---|---|---|
| 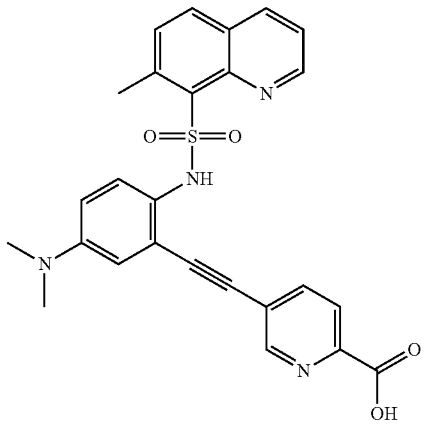 [SMILES: Cc1ccc2cccnc2c1S(=O)(=O)Nc1ccc(N(C)C)cc1C#Cc1ccc(C(=O)O)nc1] | 5-{2-[5-(dimethylamino)-2-(7-methylquinoline-8-sulfonamido)phenyl]ethynyl}pyridine-2-carboxylic acid | 248 |
| 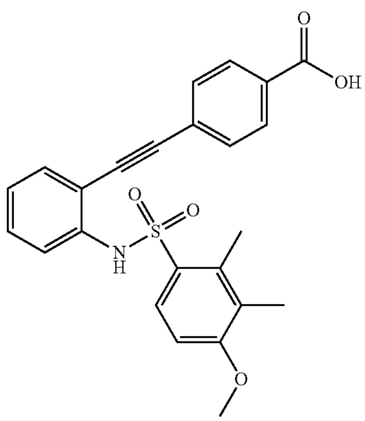 [SMILES: COc1ccc(S(=O)(=O)Nc2ccccc2C#Cc2ccc(C(=O)O)cc2)c(C)c1C] | 4-[2-(4-Methoxy-2,3-dimethyl-benzenesulfonylamino)-phenylethynyl]-benzoic acid | 249 |
| 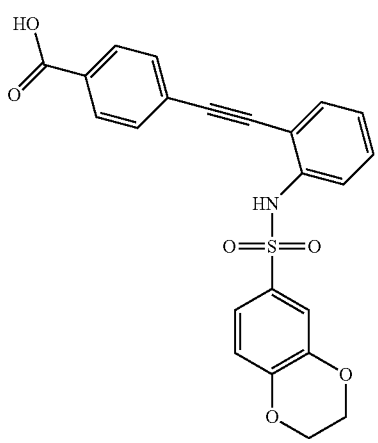 [SMILES: O=C(O)c1ccc(C#Cc2ccccc2NS(=O)(=O)c2ccc3c(c2)OCCO3)cc1] | 4-[2-(2,3-Dihydro-benzo[1,4]dioxine-6-sulfonylamino)-phenylethynyl]-benzoic acid | 250 |
| 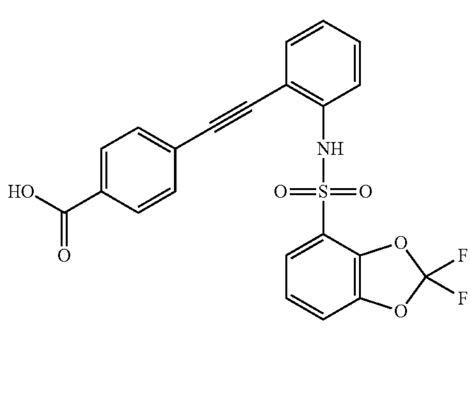 [SMILES: O=C(O)c1ccc(C#Cc2ccccc2NS(=O)(=O)c2cccc3c2OC(F)(F)O3)cc1] | 4-[2-(2,2-Difluoro-benzo[1,3]dioxole-4-sulfonylamino)-phenylethynyl]-benzoic acid | 251 |

| Compound Structure | IUPAC name | Cpd. No. |
|---|---|---|
| 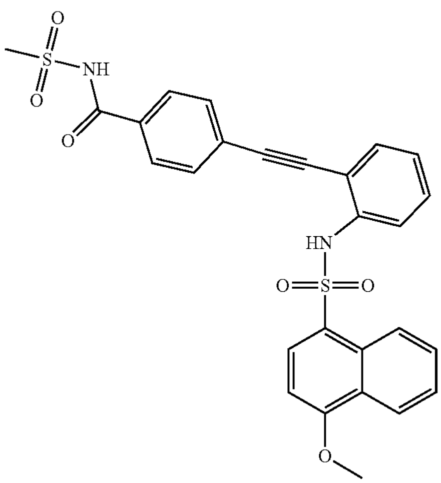 | 4-Methoxy-naphthalene-1-sulfonic acid [2-(4-methanesulfonylaminocarbonyl-phenylethynyl)-phenyl]-amide | 252 |
| 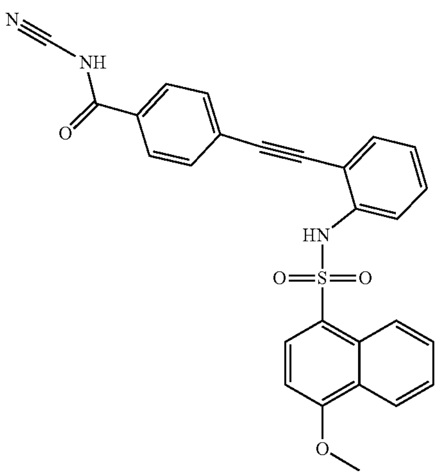 [SMILES: COc1ccc(S(=O)(=O)Nc2ccccc2C#Cc2ccc(C(=O)NC#N)cc2)c2ccccc12] | N-cyano-4-{2-[2-(4-methoxy-naphthalene-1-sulfonamido)phenyl]-ethynyl}benzamide | 253 |
| 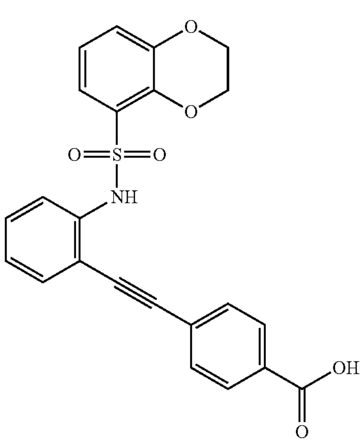 [SMILES: O=C(O)c1ccc(C#Cc2ccccc2NS(=O)(=O)c2cccc3c2OCCO3)cc1] | 4-[2-(2,3-Dihydro-benzo[1,4]dioxine-5-sulfonylamino)-phenylethynyl]-benzoic acid | 254 |

TABLE 1-continued

| Compound Structure | IUPAC name | Cpd. No. |
|---|---|---|
| 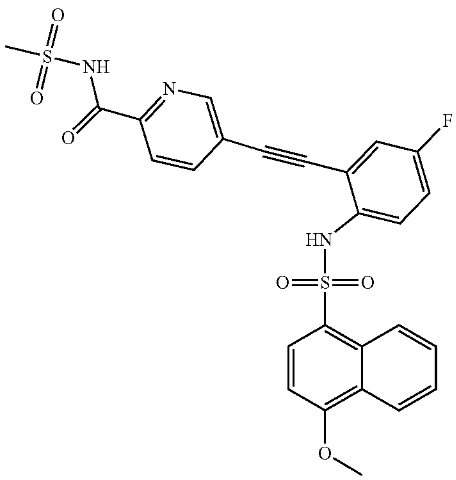 | 4-Methoxy-naphthalene-1-sulfonic acid [4-fluoro-2-(6-methanesulfonyl-aminocarbonyl-pyridin-3-ylethynyl)-phenyl]-amide | 255 |
| 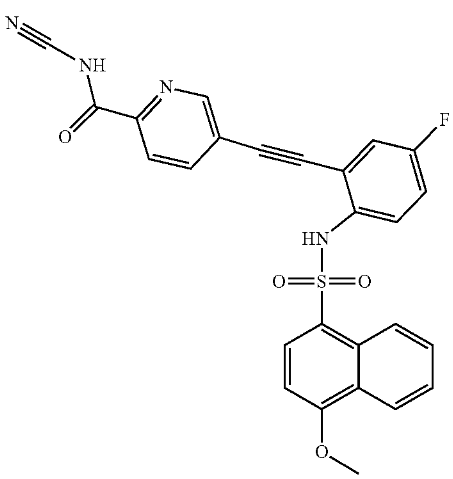 [SMILES: COc1ccc(S(=O)(=O)Nc2ccc(F)cc2C#Cc2ccc(C(=O)NC#N)nc2)c2ccccc12] | N-cyano-5-{2-[5-fluoro-2-(4-methoxynaphthalene-1-sulfonamido)-phenyl]ethynyl}pyridine-2-carboxamide | 256 |
| 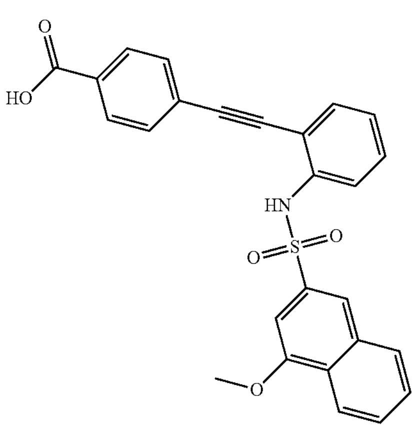 [SMILES: COc1cc(S(=O)(=O)Nc2ccccc2C#Cc2ccc(C(=O)O)cc2)cc2ccccc12] | 4-[2-(4-Methoxy-naphthalene-2-sulfonylamino)-phenylethynyl]-benzoic acid | 258 |

TABLE 1-continued

| Compound Structure | IUPAC name | Cpd. No. |
|---|---|---|
| 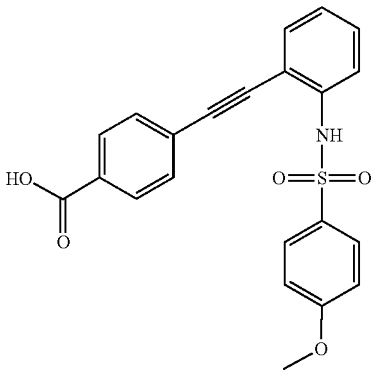 [SMILES: COc1ccc(S(=O)(=O)Nc2ccccc2C#Cc2ccc(C(=O)O)cc2)cc1] | 4-[2-(4-Methoxy-benzenesulfonylamino)-phenylethynyl]-benzoic acid | 259 |
| 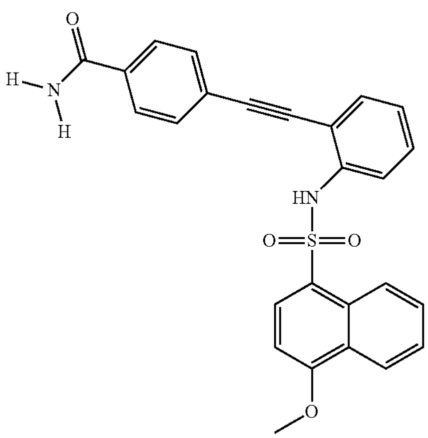 [SMILES: COc1ccc(S(=O)(=O)Nc2ccccc2C#Cc2ccc(C(N)=O)cc2)c2ccccc12] | 4-[2-(4-Methoxy-naphthalene-1-sulfonylamino)-phenylethynyl]-benzamide | 261 |
| 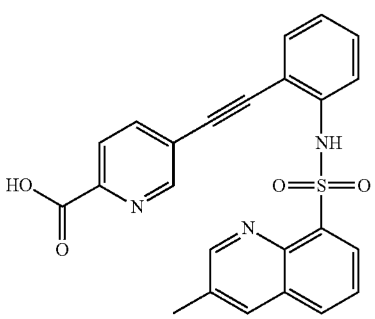 [SMILES: Cc1cnc2c(S(=O)(=O)Nc3ccccc3C#Cc3ccc(C(=O)O)nc3)cccc2c1] | 5-[2-(3-Methyl-quinoline-8-sulfonyl-amino)-phenylethynyl]-pyridine-2-carboxylic acid | 262 |
| 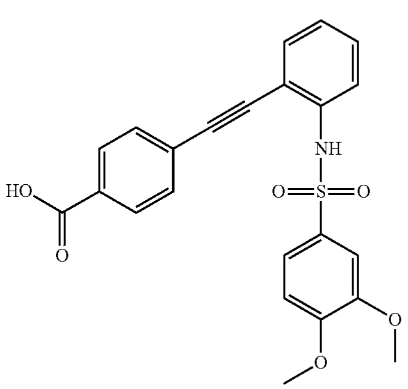 [SMILES: COc1ccc(S(=O)(=O)Nc2ccccc2C#Cc2ccc(C(=O)O)cc2)cc1OC] | 4-[2-(3,4-Dimethoxy-benzenesulfonyl-amino)-phenylethynyl]-benzoic acid | 263 |

TABLE 1-continued

| Compound Structure | IUPAC name | Cpd. No. |
| --- | --- | --- |
| 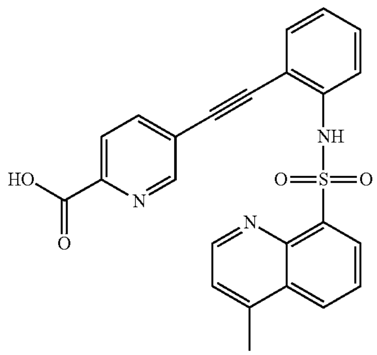 [SMILES: Cc1ccnc2c(S(=O)(=O)Nc3ccccc3C#Cc3ccc(C(=O)O)nc3)cccc12] | 5-[2-(4-Methyl-quinoline-8-sulfonyl-amino)-phenylethynyl]-pyridine-2-carboxylic acid | 264 |
| 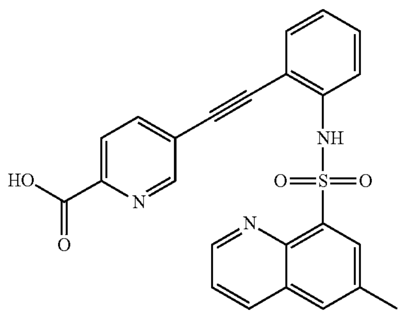 [SMILES: Cc1cc(S(=O)(=O)Nc2ccccc2C#Cc2ccc(C(=O)O)nc2)c2ncccc2c1] | 5-[2-(6-Methyl-quinoline-8-sulfonyl-amino)-phenylethynyl]-pyridine-2-carboxylic acid | 265 |
| 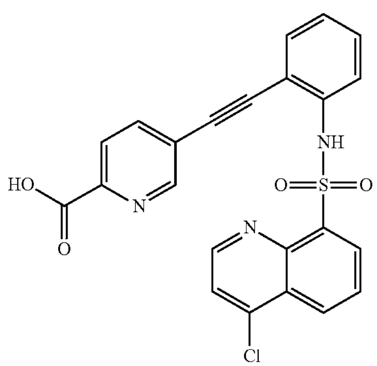 [SMILES: O=C(O)c1ccc(C#Cc2ccccc2NS(=O)(=O)c2cccc3c(Cl)ccnc23)cn1] | 5-[2-(4-Chloro-quinoline-8-sulfonylamino)-phenylethynyl]-pyridine-2-carboxylic acid | 266 |
| 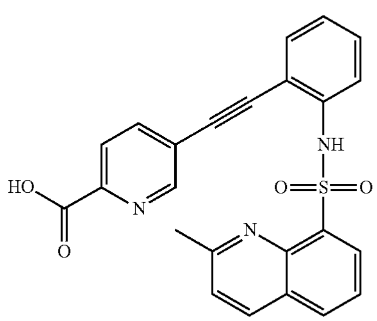 [SMILES: Cc1ccc2cccc(S(=O)(=O)Nc3ccccc3C#Cc3ccc(C(=O)O)nc3)c2n1] | 5-[2-(2-Methyl-quinoline-8-sulfonylamino)-phenylethynyl]-pyridine-2-carboxylic acid | 267 |

TABLE 1-continued

| Compound Structure | IUPAC name | Cpd. No. |
|---|---|---|
| 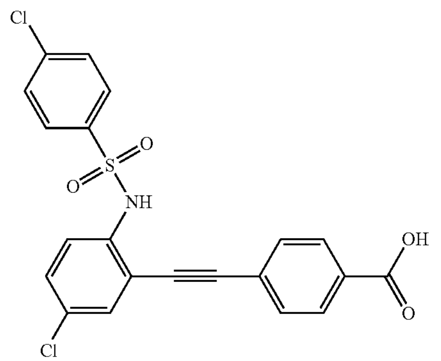 [SMILES: O=C(O)c1ccc(C#Cc2cc(Cl)ccc2NS(=O)(=O)c2ccc(Cl)cc2)cc1] | 4-[5-Chloro-2-(4-chloro-benzenesulfonylamino)-phenylethynyl]-benzoic acid (see EP 0 947 500 A1) | 269 |
| 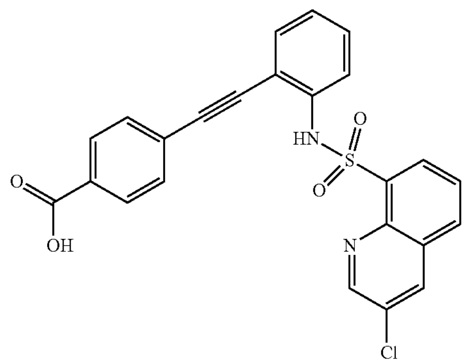 [SMILES: O=C(O)c1ccc(C#Cc2ccccc2NS(=O)(=O)c2cccc3cc(Cl)cnc23)cc1] | 4-[2-(3-Chloro-quinoline-8-sulfonyl-amino)-phenylethynyl]-benzoic acid | 270 |
| 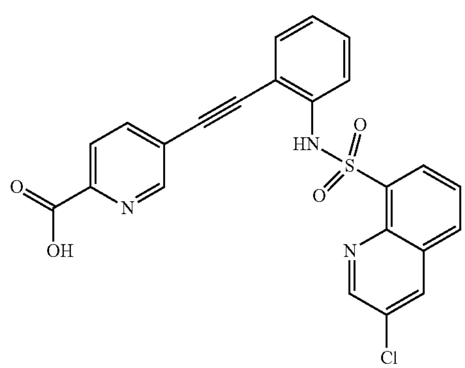 [SMILES: O=C(O)c1ccc(C#Cc2ccccc2NS(=O)(=O)c2cccc3cc(Cl)cnc23)cn1] | 5-[2-(3-Chloro-quinoline-8-sulfonyl-amino)-phenylethynyl]-pyridine-2-carboxylic acid | 271 |
| 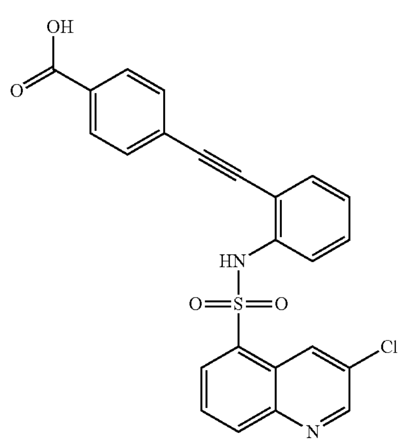 [SMILES: O=C(O)c1ccc(C#Cc2ccccc2NS(=O)(=O)c2cccc3ncc(Cl)cc23)cc1] | 4-[2-(3-Chloro-quinoline-5-sulfonyl-amino)-phenylethynyl]-benzoic acid | 272 |

TABLE 1-continued

| Compound Structure | IUPAC name | Cpd. No. |
|---|---|---|
| 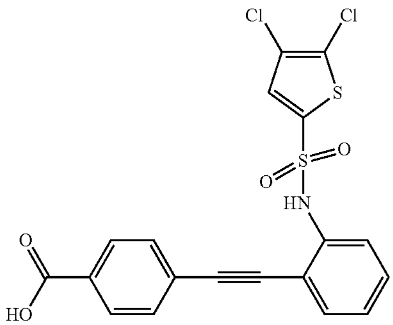 [SMILES: O=C(O)c1ccc(C#Cc2ccccc2NS(=O)(=O)c2cc(Cl)c(Cl)s2)cc1] | 4-{2-[2-(4,5-dichlorothiophene-2-sulfonamido)phenyl]ethynyl}benzoic acid | 275 |
| 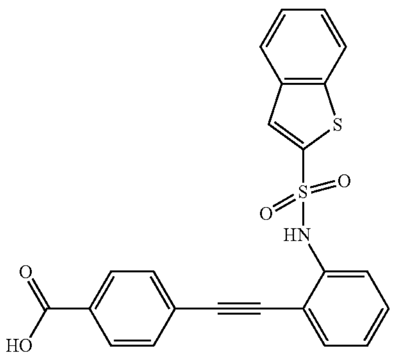 [SMILES: O=C(O)c1ccc(C#Cc2ccccc2NS(=O)(=O)c2cc3ccccc3s2)cc1] | 4-{2-[2-(1-benzothiophene-2-sulfonamido)phenyl]ethynyl}benzoic acid | 276 |
| 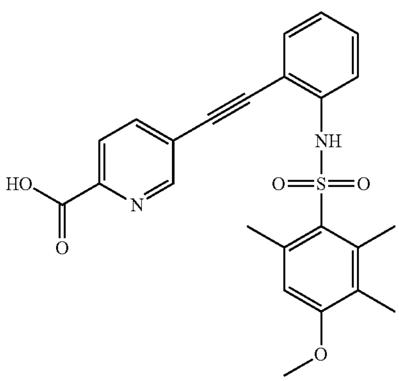 [SMILES: COc1cc(C)c(S(=O)(=O)Nc2ccccc2C#Cc2ccc(C(=O)O)nc2)c(C)c1C] | 5-{2-[2-(4-methoxy-2,3,6-trimethyl-benzenesulfonamido)phenyl]ethynyl}-pyridine-2-carboxylic acid | 277 |
| 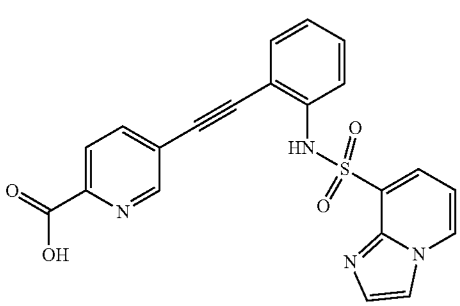 [SMILES: O=C(O)c1ccc(C#Cc2ccccc2NS(=O)(=O)c2cccn3ccnc23)cn1] | 5-[2-(Imidazo[1,2-a]pyridine-8-sulfonyl-amino)-phenylethynyl]-pyridine-2-carboxylic acid | 278 |

| Compound Structure | IUPAC name | Cpd. No. |
|---|---|---|
| 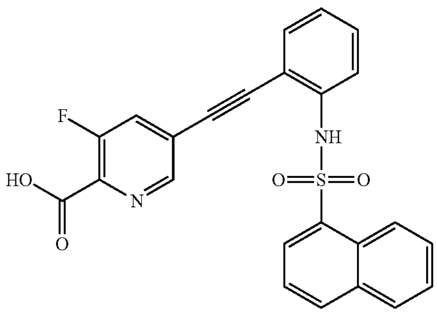 [SMILES: O=C(O)c1ncc(C#Cc2ccccc2NS(=O)(=O)c2cccc3ccccc23)cc1F] | 3-fluoro-5-{2-[2-(naphthalene-1-sulfon-amido)phenyl]ethynyl}pyridine-2-carboxylic acid | 279 |
| 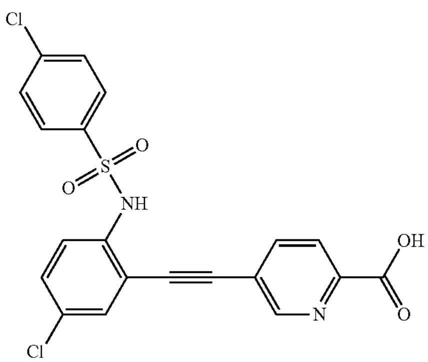 [SMILES: O=C(O)c1ccc(C#Cc2cc(Cl)ccc2NS(=O)(=O)c2ccc(Cl)cc2)cn1] | 5-{2-[5-chloro-2-(4-chlorobenzene-sulfonamido)phenyl]ethynyl}pyridine-2-carboxylic acid | 280 |
| 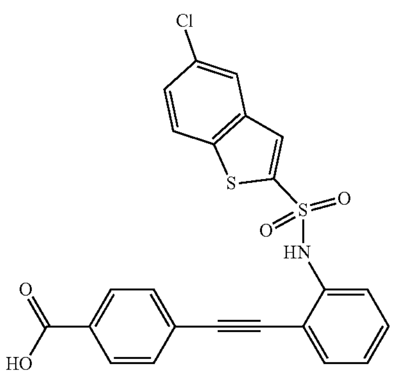 [SMILES: O=C(O)c1ccc(C#Cc2ccccc2NS(=O)(=O)c2cc3cc(Cl)ccc3s2)cc1] | 4-{2-[2-(5-chloro-1-benzothiophene-2-sulfonamido)phenyl]ethynyl}benzoic acid | 281 |
| 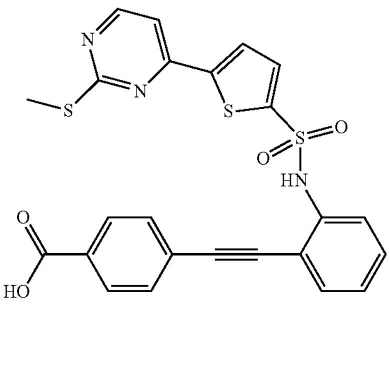 [SMILES: CSc1nccc(-c2ccc(S(=O)(=O)Nc3ccccc3C#Cc3ccc(C(=O)O)cc3)s2)n1] | 4-[2-(2-{5-[2-(methylsulfanyl)pyrimidin-4-yl]thiophene-2-sulfonamido}phenyl)-ethynyl]benzoic acid | 282 |

TABLE 1-continued

| Compound Structure | IUPAC name | Cpd. No. |
|---|---|---|
| 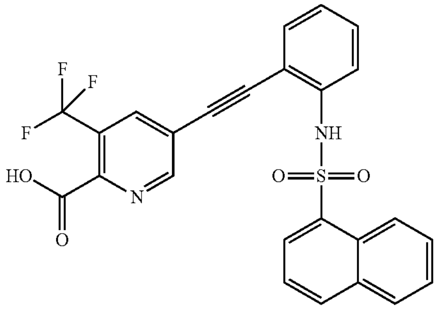 [SMILES: O=C(O)c1ncc(C#Cc2ccccc2NS(=O)(=O)c2cccc3ccccc23)cc1C(F)(F)F] | 5-{2-[2-(naphthalene-1-sulfonamido)phenyl]ethynyl}-3-(trifluoromethyl)pyridine-2-carboxylic acid | 283 |
| 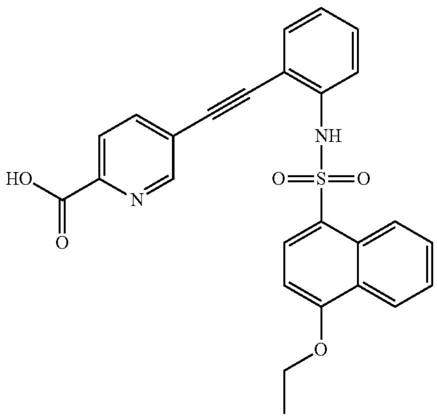 [SMILES: CCOc1ccc(S(=O)(=O)Nc2ccccc2C#Cc2ccc(C(=O)O)nc2)c2ccccc12] | 5-{2-[2-(4-ethoxynaphthalene-1-sulfonamido)phenyl]ethynyl}pyridine-2-carboxylic acid | 284 |
| 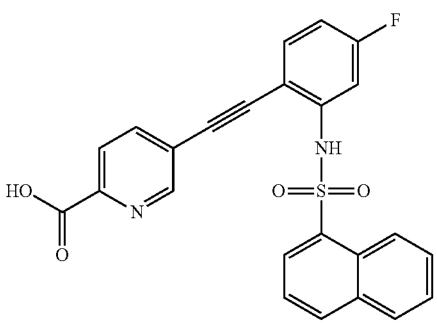 [SMILES: O=C(O)c1ccc(C#Cc2ccc(F)cc2NS(=O)(=O)c2cccc3ccccc23)cn1] | 5-{2-[4-fluoro-2-(naphthalene-1-sulfonamido)phenyl]ethynyl}pyridine-2-carboxylic acid | 285 |
| 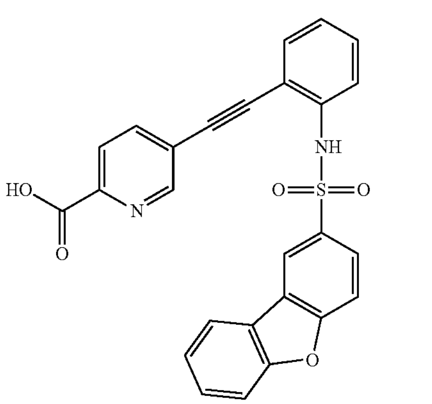 [SMILES: O=C(O)c1ccc(C#Cc2ccccc2NS(=O)(=O)c2ccc3oc4ccccc4c3c2)cn1] | 5-[2-(2-{8-oxatricyclo[7.4.0.0$^{2,7}$]trideca-1(9),2(7),3,5,10,12-hexaene-4-sulfonamido}phenyl)ethynyl]pyridine-2-carboxylic acid | 286 |

TABLE 1-continued

| Compound Structure | IUPAC name | Cpd. No. |
|---|---|---|
| 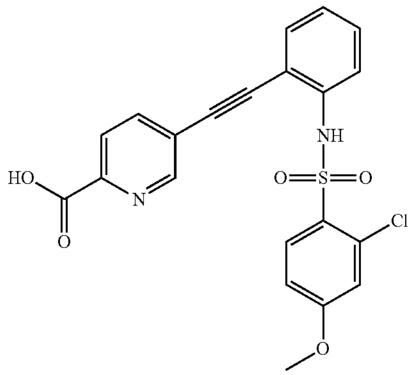 [SMILES: COc1ccc(S(=O)(=O)Nc2ccccc2C#Cc2ccc(C(=O)O)nc2)c(Cl)c1] | 5-{2-[2-(2-chloro-4-methoxybenzene-sulfonamido)phenyl]ethynyl}pyridine-2-carboxylic acid | 287 |
| 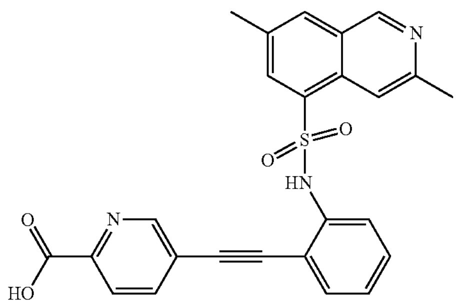 [SMILES: Cc1cc(S(=O)(=O)Nc2ccccc2C#Cc2ccc(C(=O)O)nc2)c2cc(C)ncc2c1] | 5-{2-[2-(3,7-dimethylisoquinoline-5-sulfonamido)phenyl]ethynyl}pyridine-2-carboxylic acid | 288 |
| 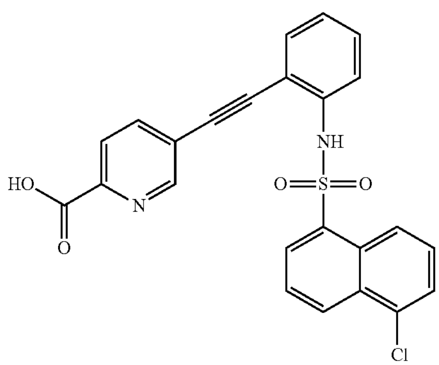 [SMILES: O=C(O)c1ccc(C#Cc2ccccc2NS(=O)(=O)c2cccc3c(Cl)cccc23)cn1] | 5-{2-[2-(5-chloronaphthalene-1-sulfonamido)phenyl]ethynyl}pyridine-2-carboxylic acid | 289 |
| 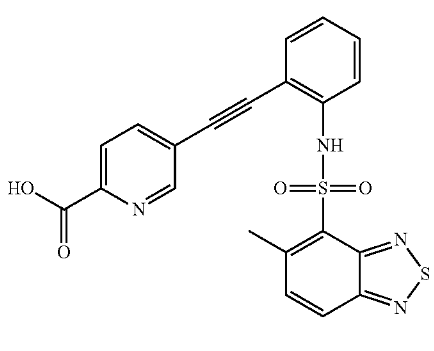 [SMILES: Cc1ccc2nsnc2c1S(=O)(=O)Nc1ccccc1C#Cc1ccc(C(=O)O)nc1] | 5-{2-[2-(5-methyl-2,1,3-benzothia-diazole-4-sulfonamido)phenyl]-ethynyl}pyridine-2-carboxylic acid | 290 |

TABLE 1-continued

| Compound Structure | IUPAC name | Cpd. No. |
|---|---|---|
| 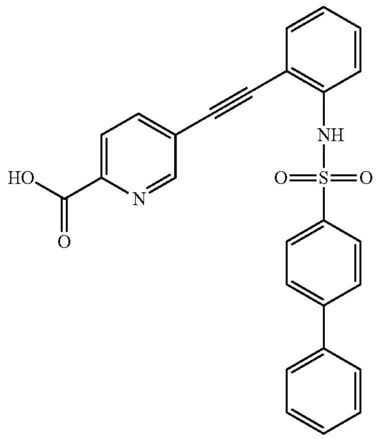 [SMILES: O=C(O)c1ccc(C#Cc2ccccc2NS(=O)(=O)c2ccc(-c3ccccc3)cc2)cn1] | 5-[2-(2-{[1,1'-biphenyl]-4-sulfonamido}phenyl)ethynyl]pyridine-2-carboxylic acid | 291 |
| 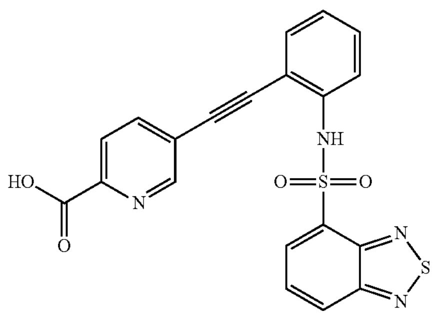 [SMILES: O=C(O)c1ccc(C#Cc2ccccc2NS(=O)(=O)c2cccc3nsnc23)cn1] | 5-{2-[2-(2,1,3-benzothiadiazole-4-sulfonamido)phenyl]ethynyl}pyridine-2-carboxylic acid | 292 |
| 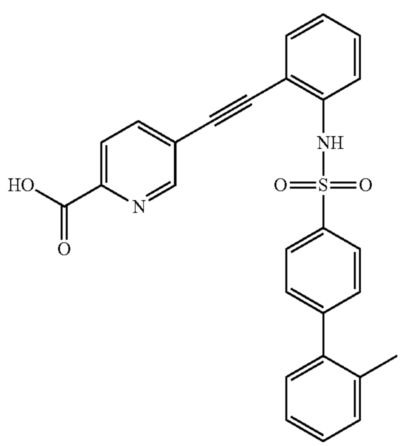 [SMILES: Cc1ccccc1-c1ccc(S(=O)(=O)Nc2ccccc2C#Cc2ccc(C(=O)O)nc2)cc1] | 5-[2-(2-{2'-methyl-[1,1'-biphenyl]-4-sulfonamido}phenyl)ethynyl]pyridine-2-carboxylic acid | 293 |
| 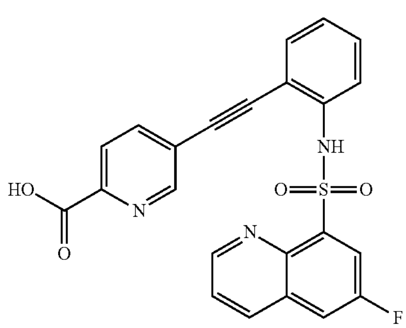 [SMILES: O=C(O)c1ccc(C#Cc2ccccc2NS(=O)(=O)c2cc(F)cc3cccnc23)cn1] | 5-{2-[2-(6-fluoroquinoline-8-sulfonamido)phenyl]ethynyl}pyridine-2-carboxylic acid | 294 |

TABLE 1-continued

| Compound Structure | IUPAC name | Cpd. No. |
|---|---|---|
| 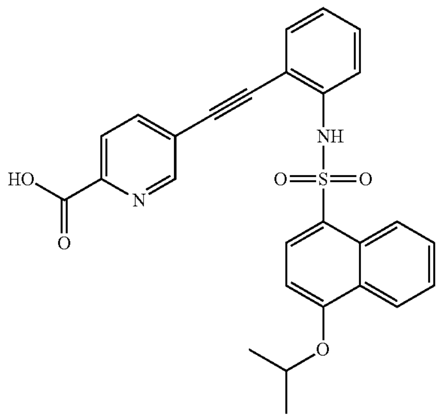 [SMILES: CC(C)Oc1ccc(S(=O)(=O)Nc2ccccc2C#Cc2ccc(C(=O)O)nc2)c2ccccc12] | 5-(2-{2-[4-(propan-2-yloxy)naphthalene-1-sulfonamido]phenyl}ethynyl)pyridine-2-carboxylic acid | 295 |
| 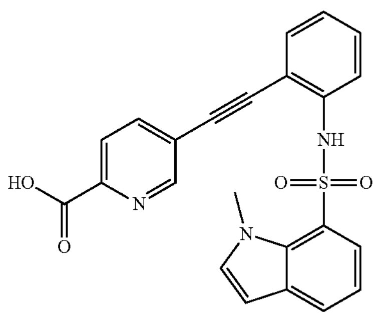 [SMILES: Cn1ccc2cccc(S(=O)(=O)Nc3ccccc3C#Cc3ccc(C(=O)O)nc3)c21] | 5-{2-[2-(1-methyl-1H-indole-7-sulfonamido)phenyl]ethynyl}pyridine-2-carboxylic acid | 296 |
| 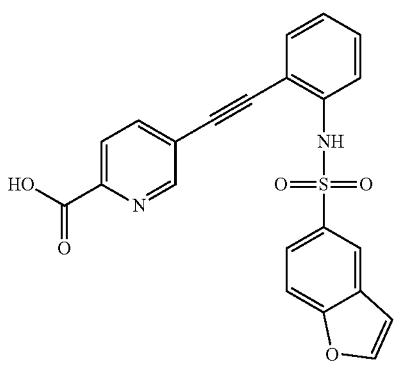 [SMILES: O=C(O)c1ccc(C#Cc2ccccc2NS(=O)(=O)c2ccc3occc3c2)cn1] | 5-{2-[2-(1-benzofuran-5-sulfonamido)phenyl]ethynyl}pyridine-2-carboxylic acid | 297 |
| 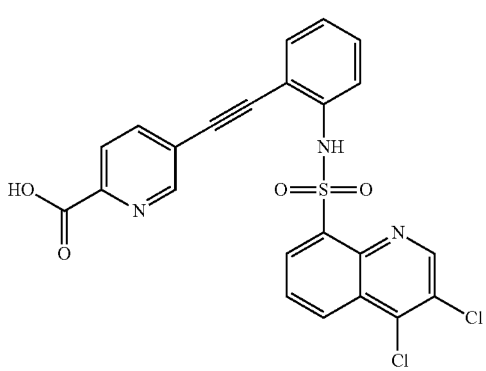 [SMILES: O=C(O)c1ccc(C#Cc2ccccc2NS(=O)(=O)c2cccc3c(Cl)c(Cl)cnc23)cn1] | 5-{2-[2-(3,4-dichloroquinoline-8-sulfonamido)phenyl]ethynyl}pyridine-2-carboxylic acid | 298 |

TABLE 1-continued

| Compound Structure | IUPAC name | Cpd. No. |
|---|---|---|
|  | 5-{2-[2-(2,4-dimethoxybenzenesulfon-amido)phenyl]ethynyl}pyridine-2-carboxylic acid | 299 |
| 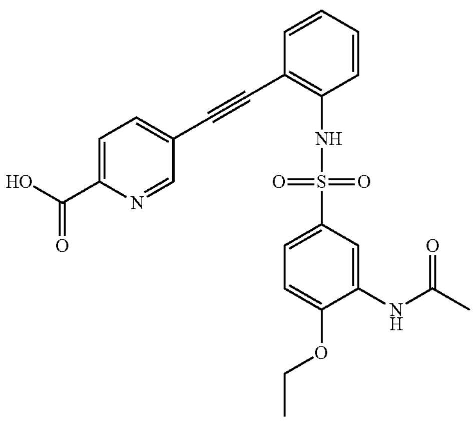 [SMILES: CCOc1ccc(S(=O)(=O)Nc2ccccc2C#Cc2ccc(C(=O)O)nc2)cc1NC(C)=O] | 5-{2-[2-(3-acetamido-4-ethoxy-benzenesulfonamido)phenyl]ethynyl}-pyridine-2-carboxylic acid | 300 |
| 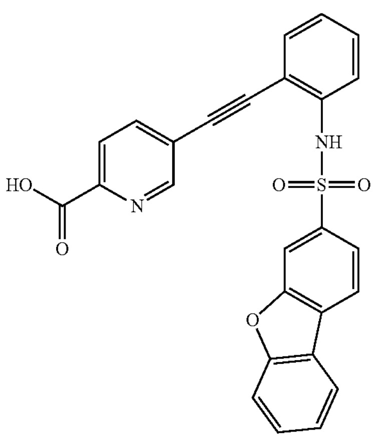 [SMILES: O=C(O)c1ccc(C#Cc2ccccc2NS(=O)(=O)c2ccc3c(c2)oc2ccccc23)cn1] | 5-[2-(2-{8-oxatricyclo[7.4.0.0$^{2,7}$]trideca-1(9),2(7),3,5,10,12-hexaene-5-sulfonamido}phenyl)ethynyl]pyridine-2-carboxylic acid | 301 |
| 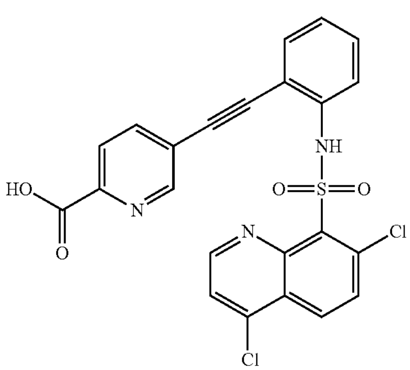 [SMILES: O=C(O)c1ccc(C#Cc2ccccc2NS(=O)(=O)c2c(Cl)ccc3c(Cl)ccnc23)cn1] | 5-{2-[2-(4,7-dichloroquinoline-8-sulfonamido)phenyl]ethynyl}pyridine-2-carboxylic acid | 302 |

TABLE 1-continued

| Compound Structure | IUPAC name | Cpd. No. |
|---|---|---|
| 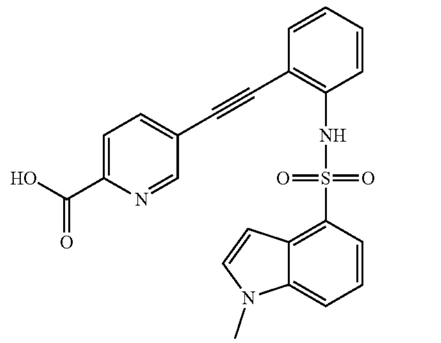 [SMILES: Cn1ccc2c(S(=O)(=O)Nc3ccccc3C#Cc3ccc(C(=O)O)nc3)cccc21] | 5-{2-[2-(1-methyl-1H-indole-4-sulfonamido)phenyl]ethynyl}pyridine-2-carboxylic acid | 303 |
| 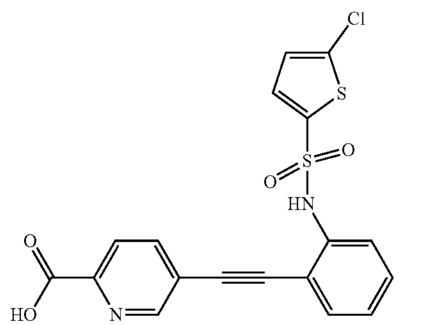 [SMILES: O=C(O)c1ccc(C#Cc2ccccc2NS(=O)(=O)c2ccc(Cl)s2)cn1] | 5-{2-[2-(5-chlorothiophene-2-sulfonamido)phenyl]ethynyl}pyridine-2-carboxylic acid | 304 |
| 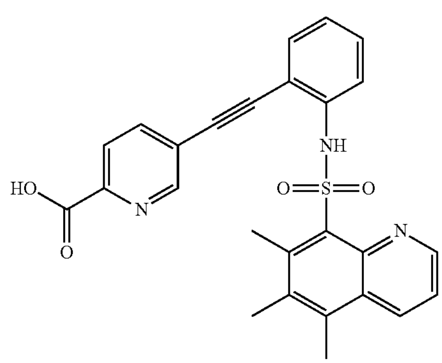 [SMILES: Cc1c(C)c(S(=O)(=O)Nc2ccccc2C#Cc2ccc(C(=O)O)nc2)c2ncccc2c1C] | 5-{2-[2-(5,6,7-trimethylquinoline-8-sulfonamido)phenyl]ethynyl}pyridine-2-carboxylic acid | 305 |
| 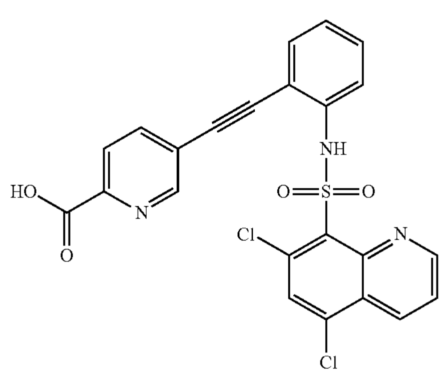 [SMILES: O=C(O)c1ccc(C#Cc2ccccc2NS(=O)(=O)c2c(Cl)cc(Cl)c3cccnc23)cn1] | 5-{2-[2-(5,7-dichloroquinoline-8-sulfonamido)phenyl]ethynyl}pyridine-2-carboxylic acid | 306 |

TABLE 1-continued

| Compound Structure | IUPAC name | Cpd. No. |
|---|---|---|
| 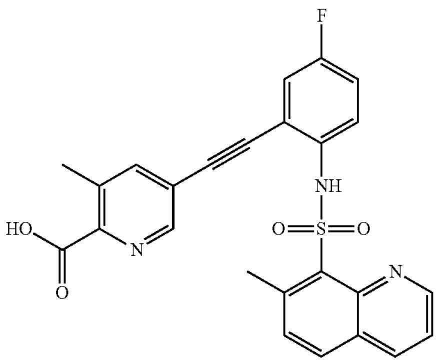 [SMILES: Cc1cc(C#Cc2cc(F)ccc2NS(=O)(=O)c2c(C)ccc3cccnc23)cnc1C(=O)O] | 5-{2-[5-fluoro-2-(7-methylquinoline-8-sulfonamido)phenyl]ethynyl}-3-methylpyridine-2-carboxylic acid | 307 |
| 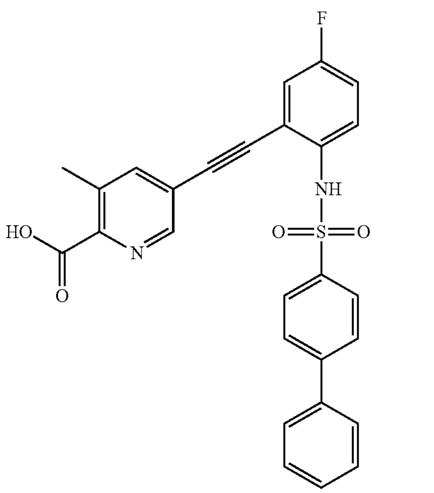 [SMILES: Cc1cc(C#Cc2cc(F)ccc2NS(=O)(=O)c2ccc(-c3ccccc3)cc2)cnc1C(=O)O] | 5-[2-(2-{[1,1'-biphenyl]-4-sulfonamido}-5-fluorophenyl)ethynyl]-3-methylpyridine-2-carboxylic acid | 308 |
| 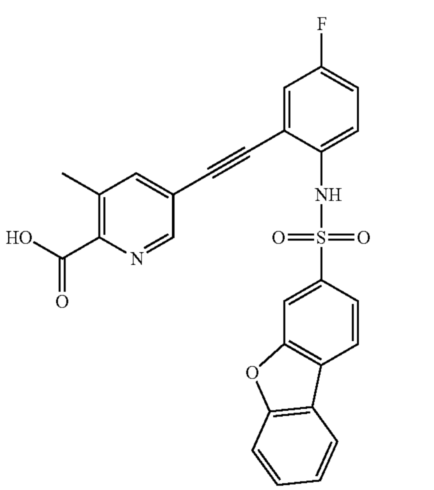 [SMILES: Cc1cc(C#Cc2cc(F)ccc2NS(=O)(=O)c2ccc3c(c2)oc2ccccc23)cnc1C(=O)O] | 5-[2-(5-fluoro-2-{8-oxatricyclo[7.4.0.0$^{2,7}$]trideca-1(9),2(7),3,5,10,12-hexaene-5-sulfonamido}phenyl)ethynyl]-3-methylpyridine-2-carboxylic acid | 309 |

| Compound Structure | IUPAC name | Cpd. No. |
|---|---|---|
| 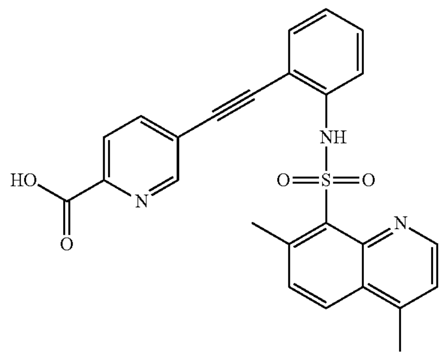 [SMILES: Cc1ccc2c(C)ccnc2c1S(=O)(=O)Nc1ccccc1C#Cc1ccc(C(=O)O)nc1] | 5-{2-[2-(4,7-dimethylquinoline-8-sulfonamido)phenyl]ethynyl}pyridine-2-carboxylic acid | 310 |
| 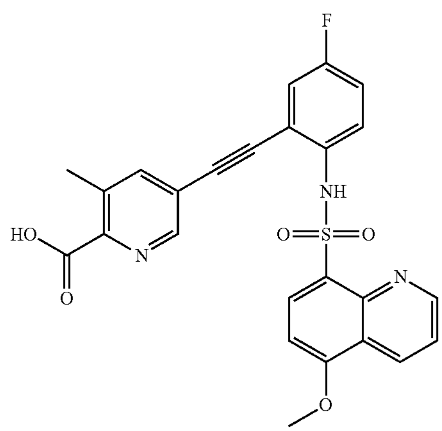 [SMILES: COc1ccc(S(=O)(=O)Nc2ccc(F)cc2C#Cc2cnc(C(=O)O)c(C)c2)c2ncccc12] | 5-{2-[5-fluoro-2-(5-methoxyquinoline-8-sulfonamido)phenyl]ethynyl}-3-methylpyridine-2-carboxylic acid | 311 |
| 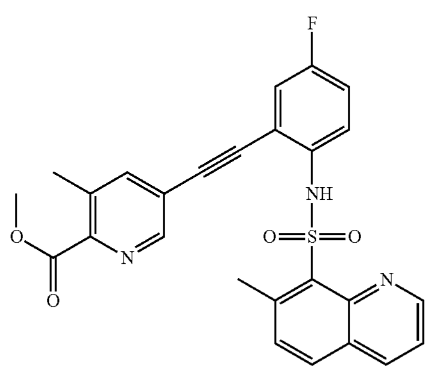 [SMILES: COC(=O)c1ncc(C#Cc2cc(F)ccc2NS(=O)(=O)c2c(C)ccc3cccnc23)cc1C] | methyl 5-{2-[5-fluoro-2-(7-methylquinoline-8-sulfonamido)phenyl]ethynyl}-3-methylpyridine-2-carboxylate | 312 |

| Compound Structure | IUPAC name | Cpd. No. |
|---|---|---|
| 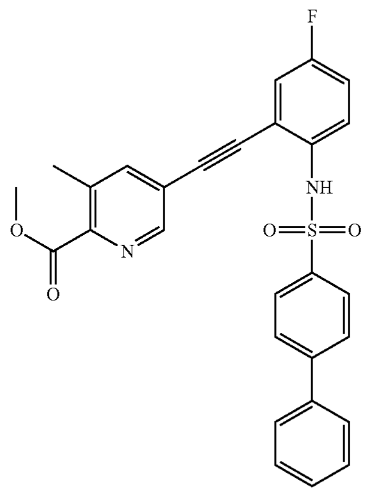 [SMILES: COC(=O)c1ncc(C#Cc2cc(F)ccc2NS(=O)(=O)c2ccc(-c3ccccc3)cc2)cc1C] | methyl 5-[2-(2-{[1,1'-biphenyl]-4-sulfonamido}-5-fluorophenyl)ethynyl]-3-methylpyridine-2-carboxylate | 313 |
| 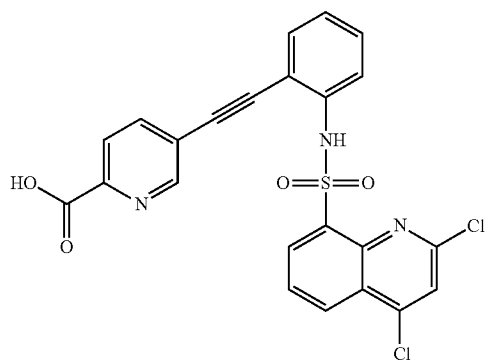 [SMILES: O=C(O)c1ccc(C#Cc2ccccc2NS(=O)(=O)c2cccc3c(Cl)cc(Cl)nc23)cn1] | 5-{2-[2-(2,4-dichloroquinoline-8-sulfonamido)phenyl]ethynyl}pyridine-2-carboxylic acid | 314 |
| 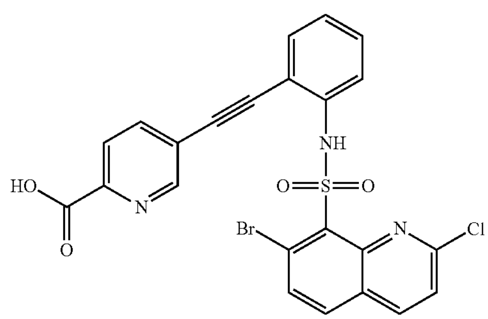 [SMILES: O=C(O)c1ccc(C#Cc2ccccc2NS(=O)(=O)c2c(Br)ccc3ccc(Cl)nc23)cn1] | 5-{2-[2-(7-bromo-2-chloroquinoline-8-sulfonamido)phenyl]ethynyl}pyridine-2-carboxylic acid | 315 |
| 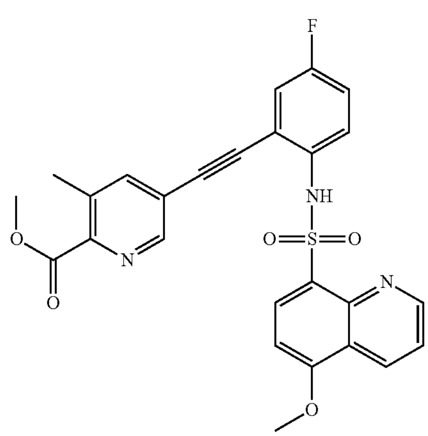 [SMILES: COC(=O)c1ncc(C#Cc2cc(F)ccc2NS(=O)(=O)c2ccc(OC)c3cccnc23)cc1C] | methyl 5-{2-[5-fluoro-2-(5-methoxyquinoline-8-sulfonamido)phenyl]ethynyl}-3-methylpyridine-2-carboxylate | 316 |

TABLE 1-continued

| Compound Structure | IUPAC name | Cpd. No. |
|---|---|---|
| 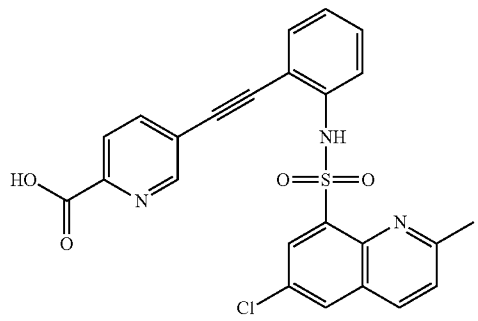 [SMILES: Cc1ccc2cc(Cl)cc(S(=O)(=O)Nc3ccccc3C#Cc3ccc(C(=O)O)nc3)c2n1] | 5-{2-[2-(6-chloro-2-methylquinoline-8-sulfonamido)phenyl]ethynyl}pyridine-2-carboxylic acid | 317 |
| 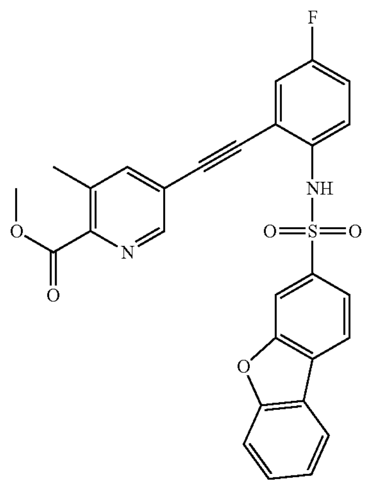 [SMILES: COC(=O)c1ncc(C#Cc2cc(F)ccc2NS(=O)(=O)c2ccc3c(c2)oc2ccccc23)cc1C] | methyl 5-[2-(5-fluoro-2-{8-oxatricyclo[7.4.0.0$^{2,7}$]trideca-1(9),2(7),3,5,10,12-hexaene-5-sulfonamido}phenyl)ethynyl]-3-methylpyridine-2-carboxylate | 318 |
| 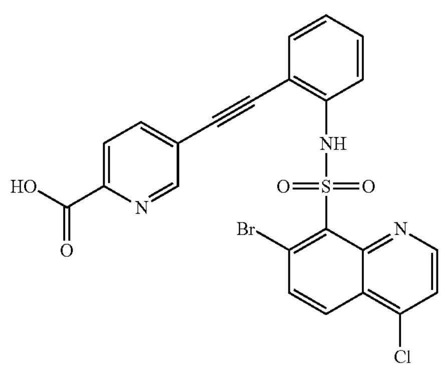 [SMILES: O=C(O)c1ccc(C#Cc2ccccc2NS(=O)(=O)c2c(Br)ccc3c(Cl)ccnc23)cn1] | 5-{2-[2-(7-bromo-4-chloroquinoline-8-sulfonamido)phenyl]ethynyl}pyridine-2-carboxylic acid | 319 |
| 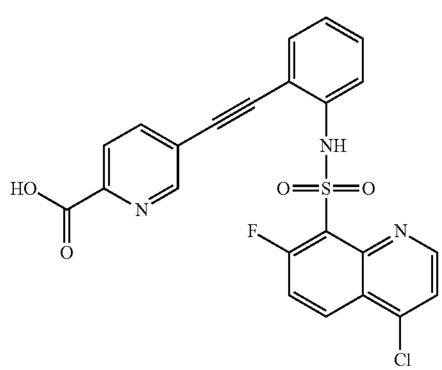 [SMILES: O=C(O)c1ccc(C#Cc2ccccc2NS(=O)(=O)c2c(F)ccc3c(Cl)ccnc23)cn1] | 5-{2-[2-(4-chloro-7-fluoroquinoline-8-sulfonamido)phenyl]ethynyl}pyridine-2-carboxylic acid | 320 |

TABLE 1-continued

| Compound Structure | IUPAC name | Cpd. No. |
|---|---|---|
| 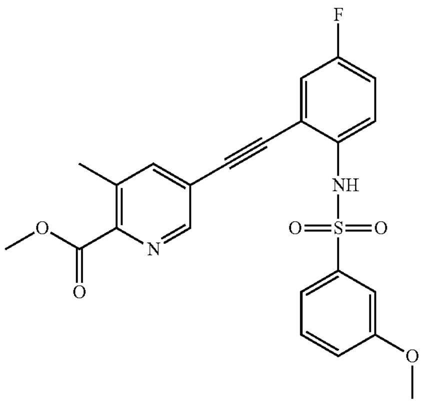 | methyl 5-{2-[5-fluoro-2-(3-methoxy-benzenesulfonamido)phenyl]ethynyl}-3-methylpyridine-2-carboxylate | 321 |
| 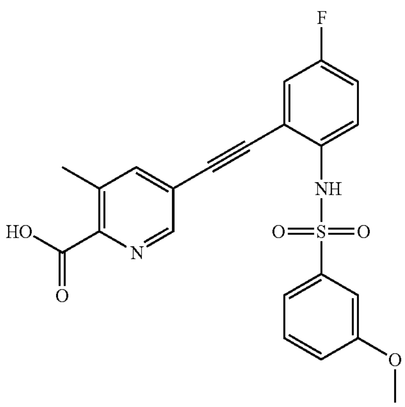 [SMILES: COc1cccc(S(=O)(=O)Nc2ccc(F)cc2C#Cc2cnc(C(=O)O)c(C)c2)c1] | 5-{2-[5-fluoro-2-(3-methoxybenzene-sulfonamido)phenyl]ethynyl}-3-methylpyridine-2-carboxylic acid | 322 |
| 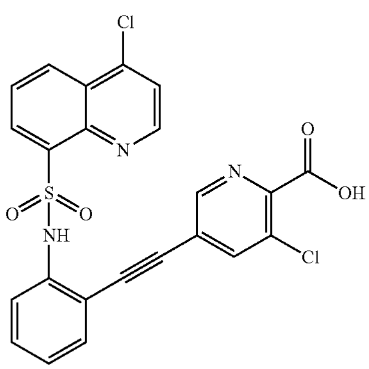 [SMILES: O=C(O)c1ncc(C#Cc2ccccc2NS(=O)(=O)c2cccc3c(Cl)ccnc23)cc1Cl] | 3-chloro-5-{2-[2-(4-chloroquinoline-8-sulfonamido)phenyl]ethynyl}pyridine-2-carboxylic acid | 323 |
| 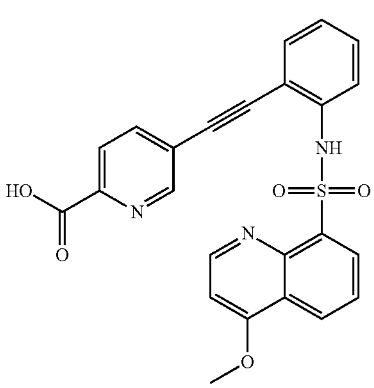 [SMILES: COc1ccnc2c(S(=O)(=O)Nc3ccccc3C#Cc3ccc(C(=O)O)nc3)cccc12] | 5-{2-[2-(4-methoxyquinoline-8-sulfonamido)phenyl]ethynyl}pyridine-2-carboxylic acid | 324 |

TABLE 1-continued

| Compound Structure | IUPAC name | Cpd. No. |
|---|---|---|
| 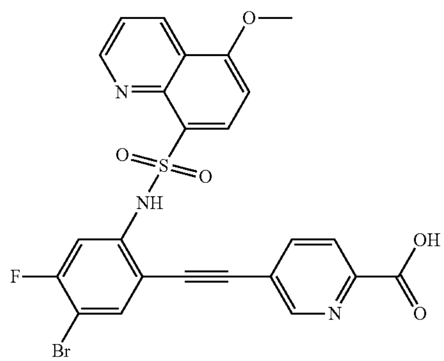 [SMILES: COc1ccc(S(=O)(=O)Nc2cc(F)c(Br)cc2C#Cc2ccc(C(=O)O)nc2)c2ncccc12] | 5-{2-[5-bromo-4-fluoro-2-(5-methoxy-quinoline-8-sulfonamido)phenyl]-ethynyl}pyridine-2-carboxylic acid | 325 |
| 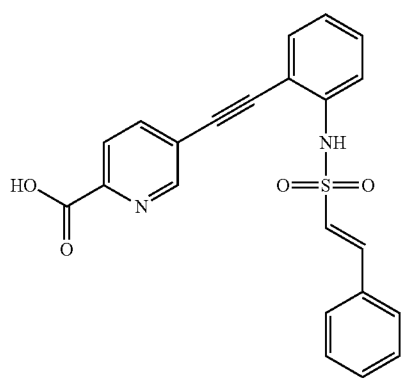 [SMILES: O=C(O)c1ccc(C#Cc2ccccc2NS(=O)(=O)/C=C/c2ccccc2)cn1] | 5-(2-{2-[(E)-2-phenylethenesulfon-amido]phenyl}ethynyl)pyridine-2-carboxylic acid | 326 |
| 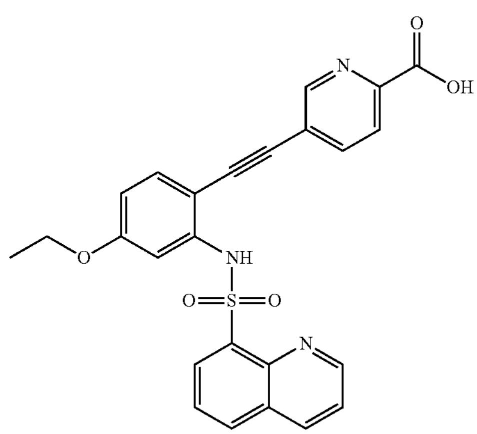 [SMILES: CCOc1ccc(C#Cc2ccc(C(=O)O)nc2)c(NS(=O)(=O)c2cccc3cccnc23)c1] | 5-[4-Ethoxy-2-(quinoline-8-sulfonylamino)-phenylethynyl]-pyridine-2-carboxylic acid | 327 |
| 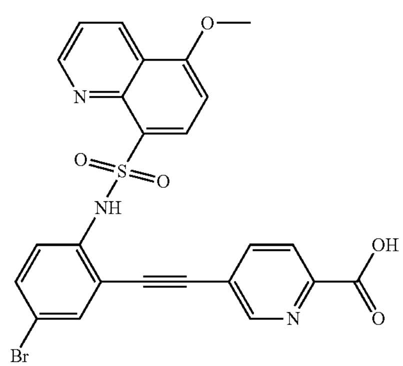 [SMILES: COc1ccc(S(=O)(=O)Nc2ccc(Br)cc2C#Cc2ccc(C(=O)O)nc2)c2ncccc12] | 5-{2-[5-bromo-2-(5-methoxyquinoline-8-sulfonamido)phenyl]ethynyl}pyridine-2-carboxylic acid | 328 |

TABLE 1-continued

| Compound Structure | IUPAC name | Cpd. No. |
|---|---|---|
| 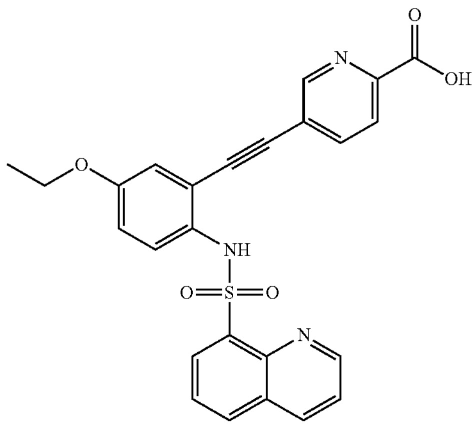 [SMILES: CCOc1ccc(NS(=O)(=O)c2cccc3cccnc23)c(C#Cc2ccc(C(=O)O)nc2)c1] | 5-[5-Ethoxy-2-(quinoline-8-sulfonylamino)-phenylethynyl]-pyridine-2-carboxylic acid | 329 |
| 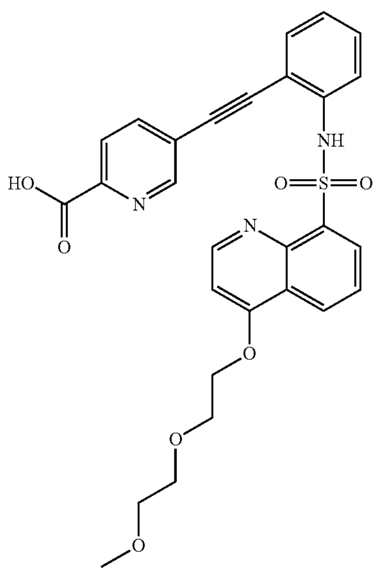 [SMILES: COCCOCCOc1ccnc2c(S(=O)(=O)Nc3ccccc3C#Cc3ccc(C(=O)O)nc3)cccc12] | 5-[2-(2-{4-[2-(2-methoxyethoxy)-ethoxy]quinoline-8-sulfonamido}-phenyl)ethynyl]pyridine-2-carboxylic acid | 330 |
| | 5-[5-{2-[2-(2-tert-Butoxycarbonylamino-ethoxy]-ethoxy}-2-(quinoline-8-sulfonylamino)-phenylethynyl]-pyridine-2-carboxylic acid | 331 |

TABLE 1-continued

| Compound Structure | IUPAC name | Cpd. No. |
| --- | --- | --- |
| 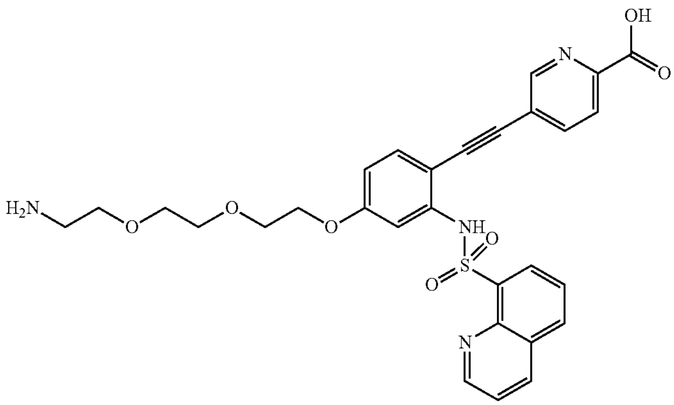 [SMILES: NCCOCCOCCOc1ccc(C#Cc2ccc(C(=O)O)nc2)c(NS(=O)(=O)c2cccc3cccnc23)c1] | 5-[4-{2-[2-(2-Amino-ethoxy)-ethoxy]-ethoxy}-2-(quinoline-8-sulfonylamino)-phenylethynyl]-pyridine-2-carboxylic acid | 332 |
| 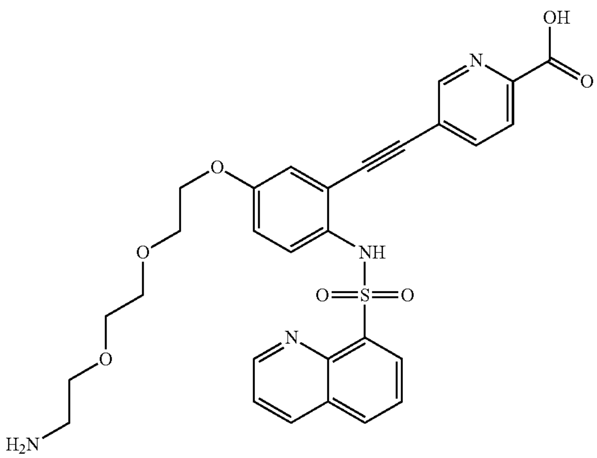 [SMILES: NCCOCCOCCOc1ccc(NS(=O)(=O)c2cccc3cccnc23)c(C#Cc2ccc(C(=O)O)nc2)c1] | 5-[5-{2-[2-(2-Amino-ethoxy)-ethoxy]-ethoxy}-2-(quinoline-8-sulfonylamino)-phenylethynyl]-pyridine-2-carboxylic acid | 333 |
| 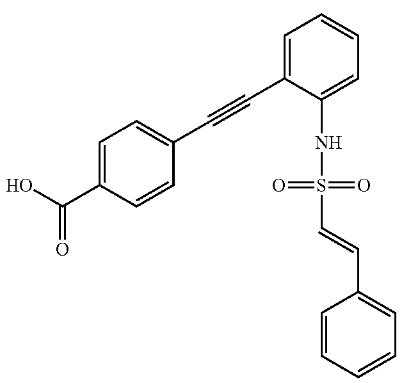 [SMILES: O=C(O)c1ccc(C#Cc2ccccc2NS(=O)(=O)/C=C/c2ccccc2)cc1] | 4-(2-{2-[(E)-2-phenylethenesulfonamido]-phenyl}ethynyl)benzoic acid | 334 |
| 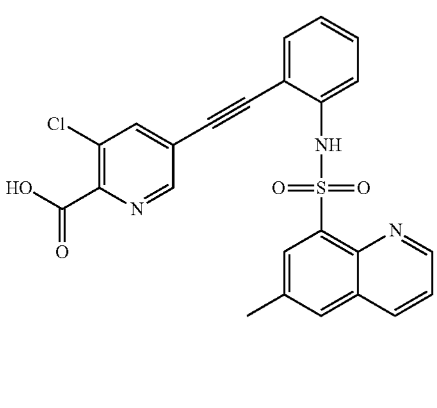 [SMILES: Cc1cc(S(=O)(=O)Nc2ccccc2C#Cc2cnc(C(=O)O)c(Cl)c2)c2ncccc2c1] | 3-chloro-5-{2-[2-(6-methylquinoline-8-sulfonamido)phenyl]ethynyl}pyridine-2-carboxylic acid | 335 |

TABLE 1-continued

| Compound Structure | IUPAC name | Cpd. No. |
|---|---|---|
| 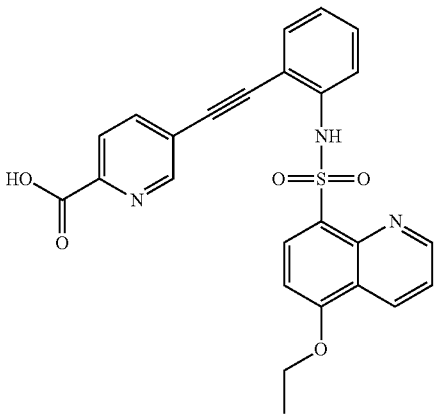 [SMILES: CCOc1ccc(S(=O)(=O)Nc2ccccc2C#Cc2ccc(C(=O)O)nc2)c2ncccc12] | 5-{2-[2-(5-ethoxyquinoline-8-sulfonamido)phenyl]ethynyl}pyridine-2-carboxylic acid | 336 |
| 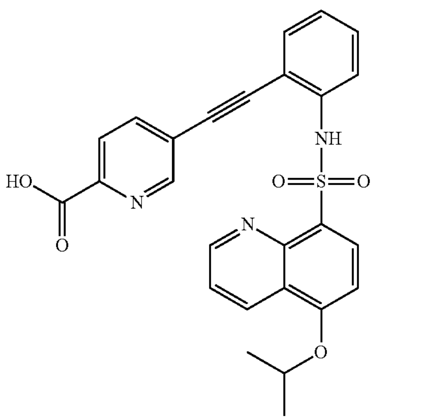 [SMILES: CC(C)Oc1ccc(S(=O)(=O)Nc2ccccc2C#Cc2ccc(C(=O)O)nc2)c2ncccc12] | 5-(2-{2-[5-(propan-2-yloxy)quinoline-8-sulfonamido]phenyl}ethynyl)pyridine-2-carboxylic acid | 339 |
| 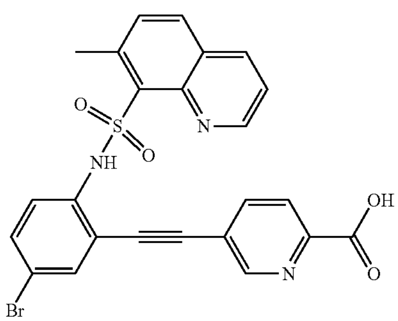 [SMILES: Cc1ccc2cccnc2c1S(=O)(=O)Nc1ccc(Br)cc1C#Cc1ccc(C(=O)O)nc1] | 5-{2-[5-bromo-2-(7-methylquinoline-8-sulfonamido)phenyl]ethynyl}pyridine-2-carboxylic acid | 340 |
|  | 5-{2-[5-bromo-4-fluoro-2-(7-methylquinoline-8-sulfonamido)phenyl]ethynyl}pyridine-2-carboxylic acid | 341 |

TABLE 1-continued

| Compound Structure | IUPAC name | Cpd. No. |
|---|---|---|
| 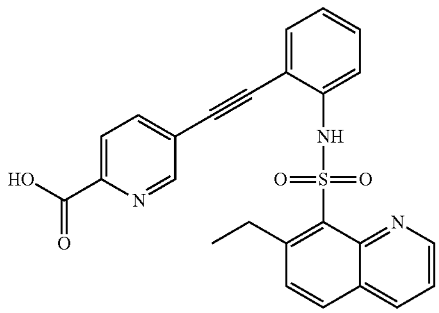 [SMILES: CCc1ccc2cccnc2c1S(=O)(=O)Nc1ccccc1C#Cc1ccc(C(=O)O)nc1] | 5-{2-[2-(7-ethylquinoline-8-sulfonamido)phenyl]ethynyl}pyridine-2-carboxylic acid | 342 |
| 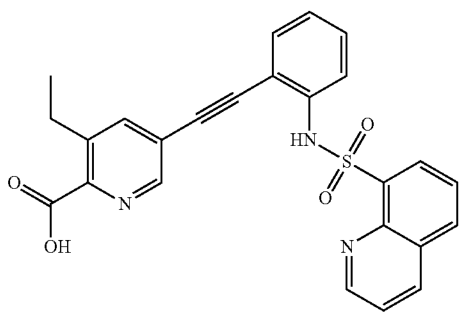 [SMILES: CCc1cc(C#Cc2ccccc2NS(=O)(=O)c2cccc3cccnc23)cnc1C(=O)O] | 3-Ethyl-5-[2-(quinoline-8-sulfonylamino)-phenylethynyl]-pyridine-2-carboxylic acid | 345 |
| 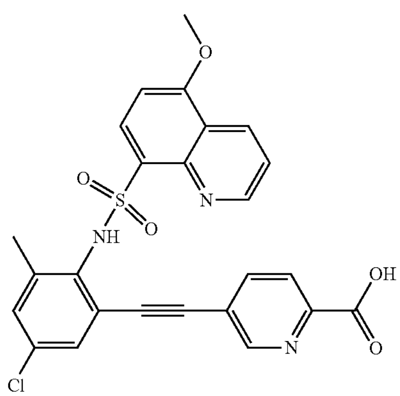 [SMILES: COc1ccc(S(=O)(=O)Nc2c(C)cc(Cl)cc2C#Cc2ccc(C(=O)O)nc2)c2ncccc12] | 5-{2-[5-chloro-2-(5-methoxyquinoline-8-sulfonamido)-3-methylphenyl]-ethynyl}pyridine-2-carboxylic acid | 346 |
| 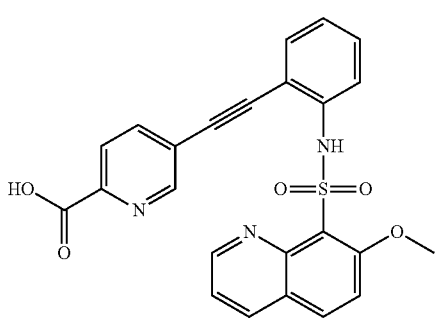 [SMILES: COc1ccc2cccnc2c1S(=O)(=O)Nc1ccccc1C#Cc1ccc(C(=O)O)nc1] | 5-{2-[2-(7-methoxyquinoline-8-sulfonamido)phenyl]ethynyl}pyridine-2-carboxylic acid | 347 |

TABLE 1-continued

| Compound Structure | IUPAC name | Cpd. No. |
|---|---|---|
| 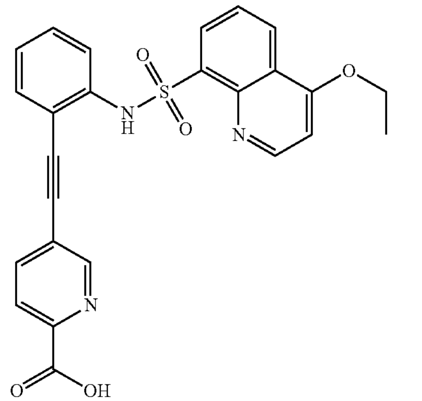 [SMILES: CCOc1ccnc2c(S(=O)(=O)Nc3ccccc3C#Cc3ccc(C(=O)O)nc3)cccc12] | 5-{2-[2-(4-ethoxyquinoline-8-sulfonamido)phenyl]ethynyl}pyridine-2-carboxylic acid | 348 |
| 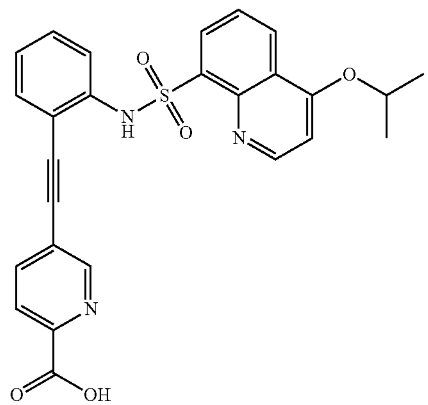 [SMILES: CC(C)Oc1ccnc2c(S(=O)(=O)Nc3ccccc3C#Cc3ccc(C(=O)O)nc3)cccc12] | 5-(2-{2-[4-(propan-2-yloxy)quinoline-8-sulfonamido]phenyl}ethynyl)pyridine-2-carboxylic acid | 349 |
| 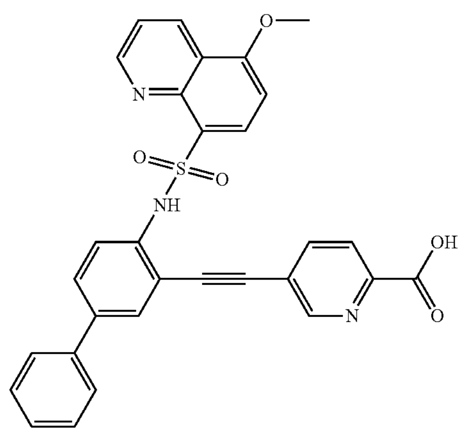 [SMILES: COc1ccc(S(=O)(=O)Nc2ccc(-c3ccccc3)cc2C#Cc2ccc(C(=O)O)nc2)c2ncccc12] | 5-{2-[4-(5-methoxyquinoline-8-sulfonamido)-[1,1'-biphenyl]-3-yl]ethynyl}pyridine-2-carboxylic acid | 350 |
| 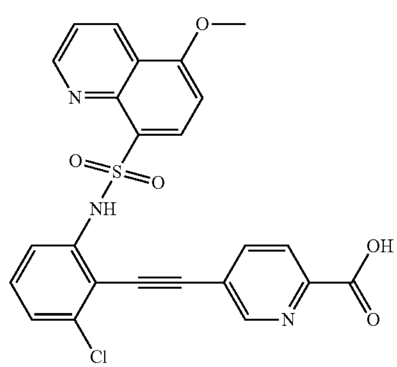 [SMILES: COc1ccc(S(=O)(=O)Nc2cccc(Cl)c2C#Cc2ccc(C(=O)O)nc2)c2ncccc12] | 5-{2-[2-chloro-6-(5-methoxyquinoline-8-sulfonamido)phenyl]ethynyl}pyridine-2-carboxylic acid | 351 |

TABLE 1-continued

| Compound Structure | IUPAC name | Cpd. No. |
|---|---|---|
| 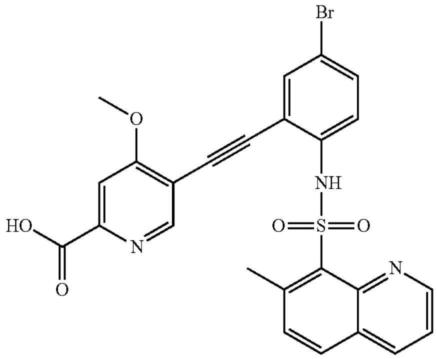 [SMILES: COc1cc(C(=O)O)ncc1C#Cc1cc(Br)ccc1NS(=O)(=O)c1c(C)ccc2cccnc12] | 5-{2-[5-bromo-2-(7-methylquinoline-8-sulfonamido)phenyl]ethynyl}-4-methoxypyridine-2-carboxylic acid | 352 |
| 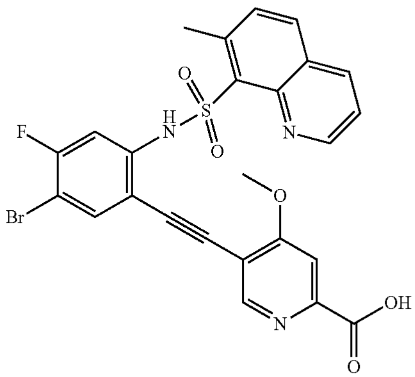 [SMILES: COc1cc(C(=O)O)ncc1C#Cc1cc(Br)c(F)cc1NS(=O)(=O)c1c(C)ccc2cccnc12] | 5-{2-[5-bromo-4-fluoro-2-(7-methylquinoline-8-sulfonamido)phenyl]ethynyl}-4-methoxypyridine-2-carboxylic acid | 353 |
| 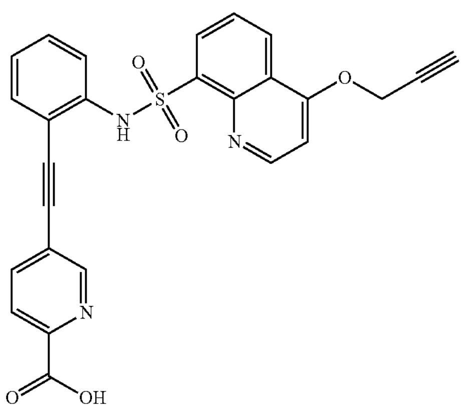 [SMILES: C#CCOc1ccnc2c(S(=O)(=O)Nc3ccccc3C#Cc3ccc(C(=O)O)nc3)cccc12] | 5-(2-{2-[4-(prop-2-yn-1-yloxy)quinoline-8-sulfonamido]phenyl}ethynyl)pyridine-2-carboxylic acid | 354 |
| 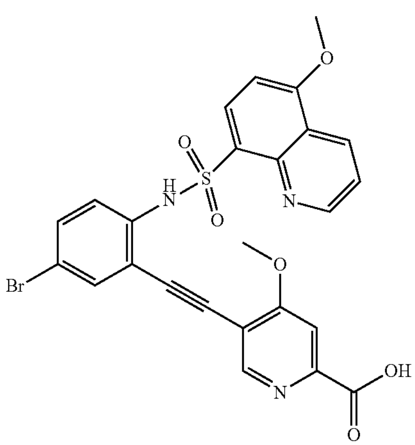 [SMILES: COc1cc(C(=O)O)ncc1C#Cc1cc(Br)ccc1NS(=O)(=O)c1ccc(OC)c2cccnc12] | 5-{2-[5-bromo-2-(5-methoxyquinoline-8-sulfonamido)phenyl]ethynyl}-4-methoxypyridine-2-carboxylic acid | 356 |

TABLE 1-continued

| Compound Structure | IUPAC name | Cpd. No. |
|---|---|---|
| 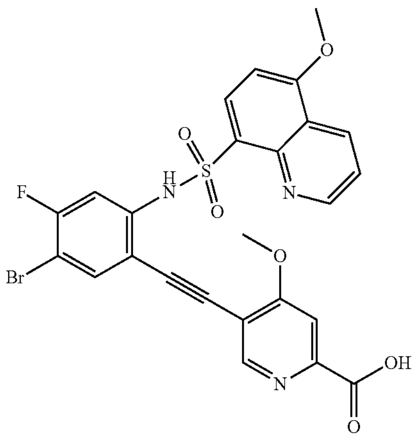 [SMILES: COc1cc(C(=O)O)ncc1C#Cc1cc(Br)c(F)cc1NS(=O)(=O)c1ccc(OC)c2cccnc12] | 5-{2-[5-bromo-4-fluoro-2-(5-methoxyquinoline-8-sulfonamido)phenyl]ethynyl}-4-methoxypyridine-2-carboxylic acid | 358 |
| 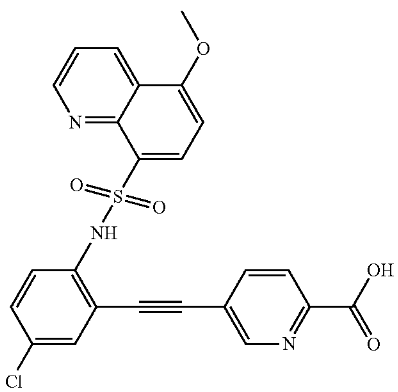 [SMILES: COc1ccc(S(=O)(=O)Nc2ccc(Cl)cc2C#Cc2ccc(C(=O)O)nc2)c2ncccc12] | 5-{2-[5-chloro-2-(5-methoxyquinoline-8-sulfonamido)phenyl]ethynyl}pyridine-2-carboxylic acid | 359 |
| 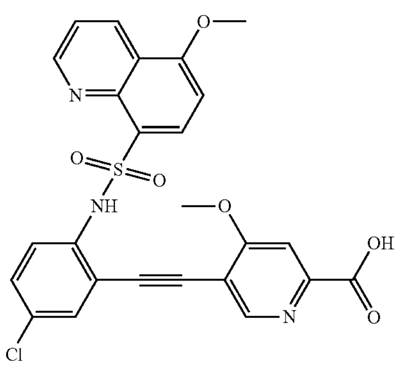 [SMILES: COc1cc(C(=O)O)ncc1C#Cc1cc(Cl)ccc1NS(=O)(=O)c1ccc(OC)c2cccnc12] | 5-{2-[5-chloro-2-(5-methoxyquinoline-8-sulfonamido)phenyl]ethynyl}-4-methoxypyridine-2-carboxylic acid | 360 |
| 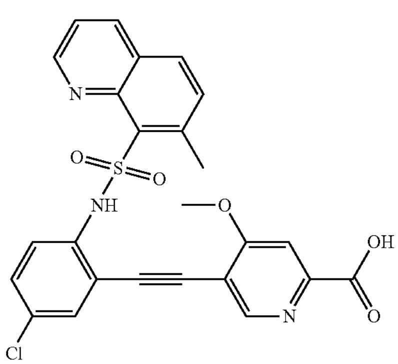 [SMILES: COc1cc(C(=O)O)ncc1C#Cc1cc(Cl)ccc1NS(=O)(=O)c1c(C)ccc2cccnc12] | 5-{2-[5-chloro-2-(7-methylquinoline-8-sulfonamido)phenyl]ethynyl}-4-methoxypyridine-2-carboxylic acid | 361 |

TABLE 1-continued

| Compound Structure | IUPAC name | Cpd. No. |
|---|---|---|
| 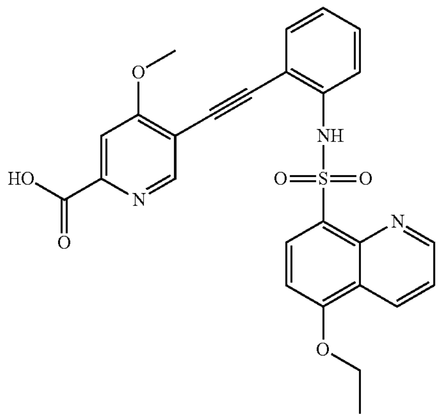 [SMILES: CCOc1ccc(S(=O)(=O)Nc2ccccc2C#Cc2cnc(C(=O)O)cc2OC)c2ncccc12] | 5-{2-[2-(5-ethoxyquinoline-8-sulfonamido)phenyl]ethynyl}-4-methoxypyridine-2-carboxylic acid | 362 |
| 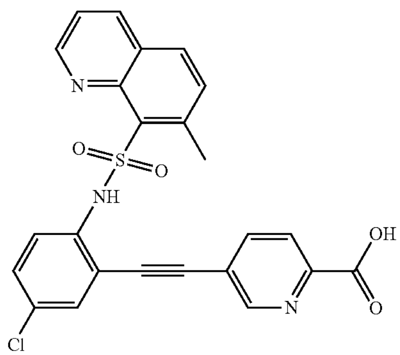 [SMILES: Cc1ccc2cccnc2c1S(=O)(=O)Nc1ccc(Cl)cc1C#Cc1ccc(C(=O)O)nc1] | 5-{2-[5-chloro-2-(7-methylquinoline-8-sulfonamido)phenyl]ethynyl}pyridine-2-carboxylic acid | 363 |
| 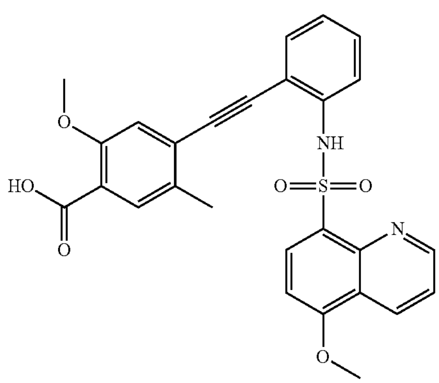 [SMILES: COc1cc(C#Cc2ccccc2NS(=O)(=O)c2ccc(OC)c3cccnc23)c(C)cc1C(=O)O] | 2-methoxy-4-{2-[2-(5-methoxyquinoline-8-sulfonamido)phenyl]ethynyl}-5-methylbenzoic acid | 364 |
| | 2-methoxy-5-methyl-4-{2-[2-(7-methylquinoline-8-sulfonamido)phenyl]ethynyl}benzoic acid | 365 |

TABLE 1-continued

| Compound Structure | IUPAC name | Cpd. No. |
|---|---|---|
| 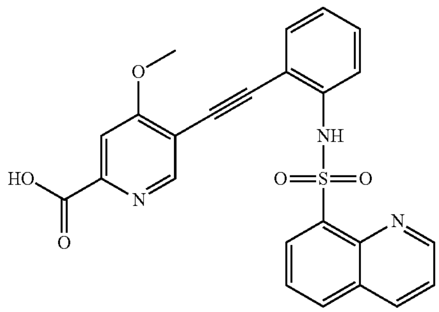 [SMILES: COc1cc(C(=O)O)ncc1C#Cc1ccccc1NS(=O)(=O)c1cccc2cccnc12] | 4-methoxy-5-{2-[2-(quinoline-8-sulfonamido)phenyl]ethynyl}pyridine-2-carboxylic acid | 366 |
| 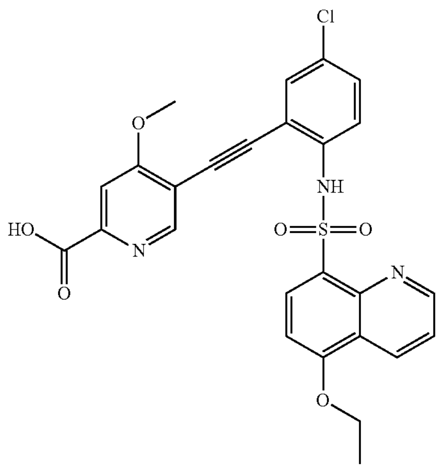 [SMILES: CCOc1ccc(S(=O)(=O)Nc2ccc(Cl)cc2C#Cc2cnc(C(=O)O)cc2OC)c2ncccc12] | 5-{2-[5-chloro-2-(5-ethoxyquinoline-8-sulfonamido)phenyl]ethynyl}-4-methoxypyridine-2-carboxylic acid | 367 |
| 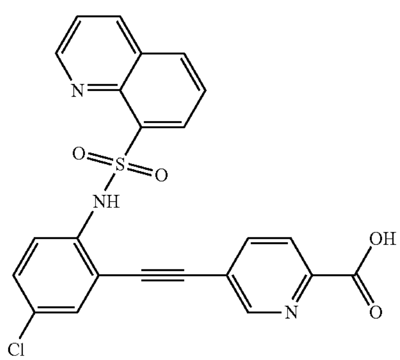 [SMILES: O=C(O)c1ccc(C#Cc2cc(Cl)ccc2NS(=O)(=O)c2cccc3cccnc23)cn1] | 5-{2-[5-chloro-2-(quinoline-8-sulfonamido)phenyl]ethynyl}pyridine-2-carboxylic acid | 368 |
| 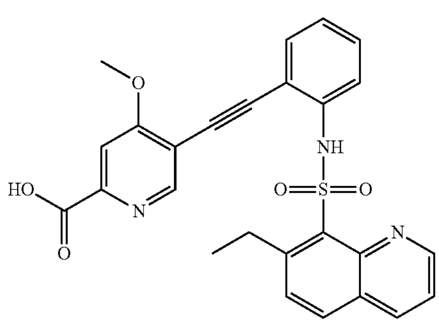 [SMILES: CCc1ccc2cccnc2c1S(=O)(=O)Nc1ccccc1C#Cc1cnc(C(=O)O)cc1OC] | 5-{2-[2-(7-ethylquinoline-8-sulfonamido)phenyl]ethynyl}-4-methoxypyridine-2-carboxylic acid | 369 |

TABLE 1-continued

| Compound Structure | IUPAC name | Cpd. No. |
|---|---|---|
| 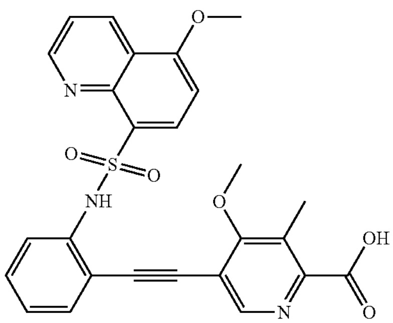 [SMILES: COc1c(C#Cc2ccccc2NS(=O)(=O)c2ccc(OC)c3cccnc23)cnc(C(=O)O)c1C] | 4-Methoxy-5-[2-(5-methoxy-quinoline-8-sulfonylamino)-phenylethynyl]-3-methyl-pyridine-2-carboxylic acid | 370 |
| 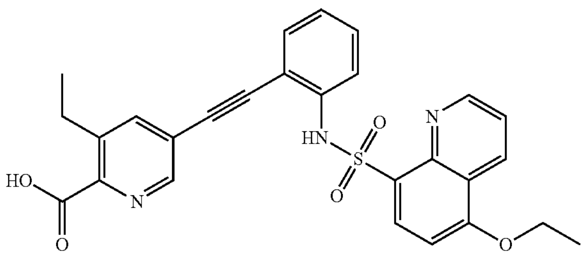 [SMILES: CCOc1ccc(S(=O)(=O)Nc2ccccc2C#Cc2cnc(C(=O)O)c(CC)c2)c2ncccc12] | 5-[2-(5-Ethoxy-quinoline-8-sulfonylamino)-phenylethynyl]-3-ethyl-pyridine-2-carboxylic acid | 371 |
| 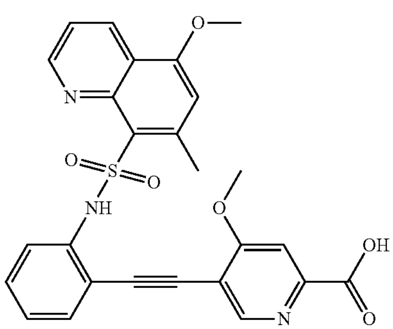 [SMILES: COc1cc(C(=O)O)ncc1C#Cc1ccccc1NS(=O)(=O)c1c(C)cc(OC)c2cccnc12] | 4-Methoxy-5-[2-(5-methoxy-7-methyl-quinoline-8-sulfonylamino)-phenylethynyl]-pyridine-2-carboxylic acid | 372 |
| 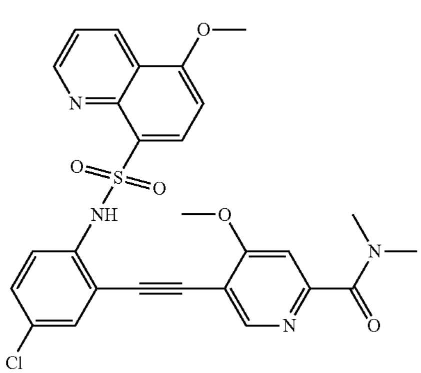 [SMILES: COc1cc(C(=O)N(C)C)ncc1C#Cc1cc(Cl)ccc1NS(=O)(=O)c1ccc(OC)c2cccnc12] | 5-{2-[5-chloro-2-(5-methoxyquinoline-8-sulfonamido)phenyl]ethynyl}-4-methoxy-N,N-dimethylpyridine-2-carboxamide | 373 |

TABLE 1-continued

| Compound Structure | IUPAC name | Cpd. No. |
|---|---|---|
| 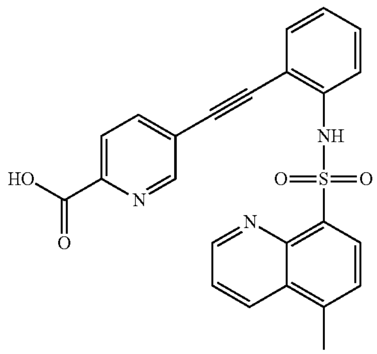 [SMILES: Cc1ccc(S(=O)(=O)Nc2ccccc2C#Cc2ccc(C(=O)O)nc2)c2ncccc12] | 5-{2-[2-(5-methylquinoline-8-sulfonamido)phenyl]ethynyl}pyridine-2-carboxylic acid | 374 |
| 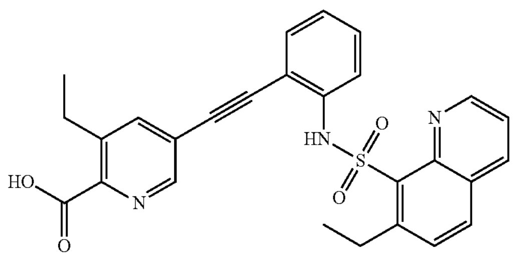 [SMILES: CCc1cc(C#Cc2ccccc2NS(=O)(=O)c2c(CC)ccc3cccnc23)cnc1C(=O)O] | 3-Ethyl-5-[2-(7-ethyl-quinoline-8-sulfonylamino)-phenylethynyl]-pyridine-2-carboxylic acid | 375 |
| 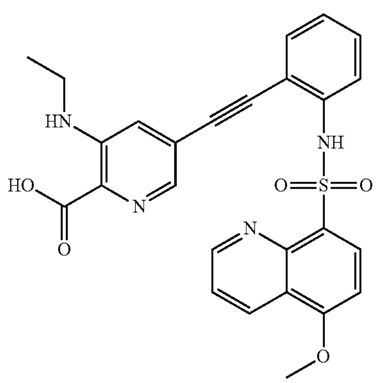 [SMILES: CCNc1cc(C#Cc2ccccc2NS(=O)(=O)c2ccc(OC)c3cccnc23)cnc1C(=O)O] | 3-(ethylamino)-5-{2-[2-(5-methoxyquinoline-8-sulfonamido)phenyl]ethynyl}pyridine-2-carboxylic acid | 376 |
| 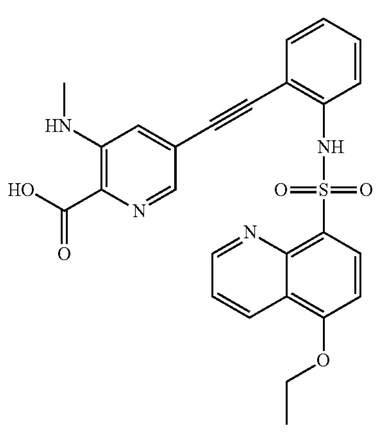 [SMILES: CCOc1ccc(S(=O)(=O)Nc2ccccc2C#Cc2cnc(C(=O)O)c(NC)c2)c2ncccc12] | 5-{2-[2-(5-ethoxyquinoline-8-sulfonamido)phenyl]ethynyl}-3-(methylamino)pyridine-2-carboxylic acid | 377 |

TABLE 1-continued

| Compound Structure | IUPAC name | Cpd. No. |
|---|---|---|
| 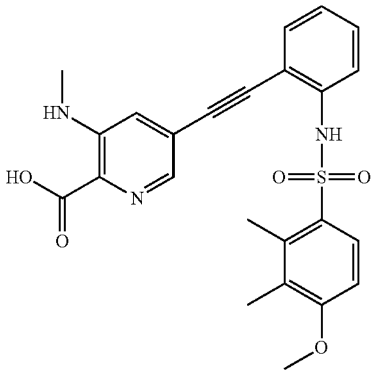 [SMILES: CNc1cc(C#Cc2ccccc2NS(=O)(=O)c2ccc(OC)c(C)c2C)cnc1C(=O)O] | 5-{2-[2-(4-methoxy-2,3-dimethyl-benzenesulfonamido)phenyl]ethynyl}-3-(methylamino)pyridine-2-carboxylic acid | 378 |
| 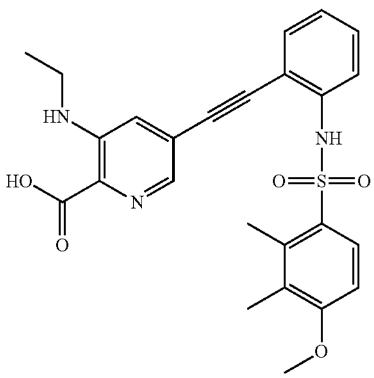 [SMILES: CCNc1cc(C#Cc2ccccc2NS(=O)(=O)c2ccc(OC)c(C)c2C)cnc1C(=O)O] | 3-(ethylamino)-5-{2-[2-(4-methoxy-2,3-dimethylbenzenesulfonamido)phenyl]ethynyl}pyridine-2-carboxylic acid | 379 |
| 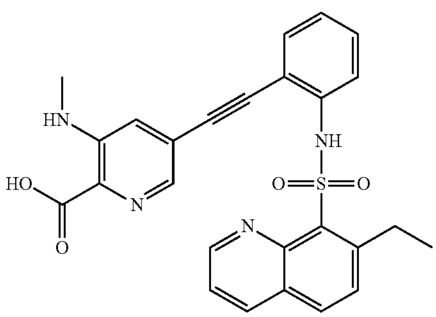 [SMILES: CCc1ccc2cccnc2c1S(=O)(=O)Nc1ccccc1C#Cc1cnc(C(=O)O)c(NC)c1] | 5-{2-[2-(7-ethylquinoline-8-sulfonamido)phenyl]ethynyl}-3-(methylamino)pyridine-2-carboxylic acid | 380 |
| 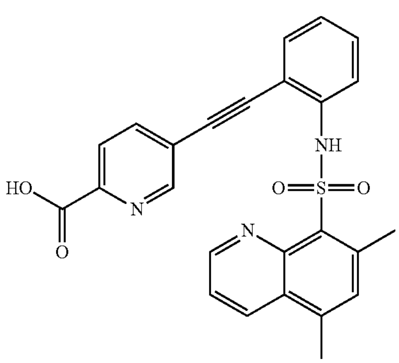 [SMILES: Cc1cc(C)c2cccnc2c1S(=O)(=O)Nc1ccccc1C#Cc1ccc(C(=O)O)nc1] | 5-{2-[2-(5,7-dimethylquinoline-8-sulfonamido)phenyl]ethynyl}pyridine-2-carboxylic acid | 381 |

| Compound Structure | IUPAC name | Cpd. No. |
|---|---|---|
| 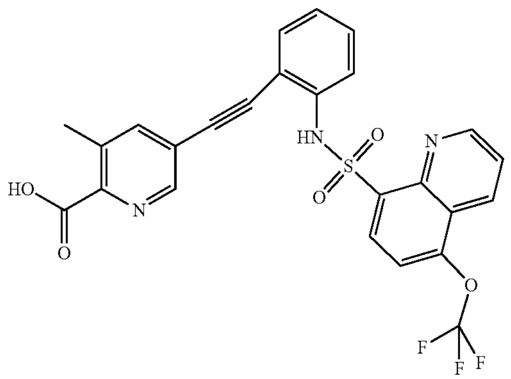 [SMILES: Cc1cc(C#Cc2ccccc2NS(=O)(=O)c2ccc(OC(F)(F)F)c3cccnc23)cnc1C(=O)O] | 3-Methyl-5-[2-(5-trifluoromethoxy-quinoline-8-sulfonylamino)-phenylethynyl]-pyridine-2-carboxylic acid | 382 |
| 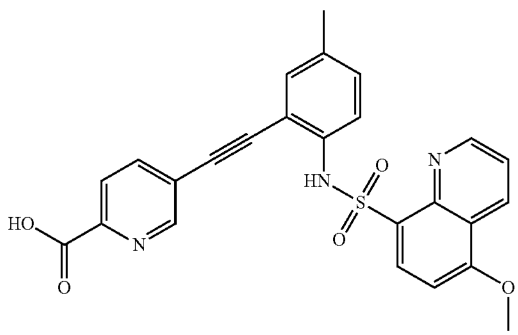 [SMILES: COc1ccc(S(=O)(=O)Nc2ccc(C)cc2C#Cc2ccc(C(=O)O)nc2)c2ncccc12] | 5-[2-(5-Methoxy-quinoline-8-sulfonylamino)-5-methyl-phenylethynyl]-pyridine-2-carboxylic acid | 383 |
| 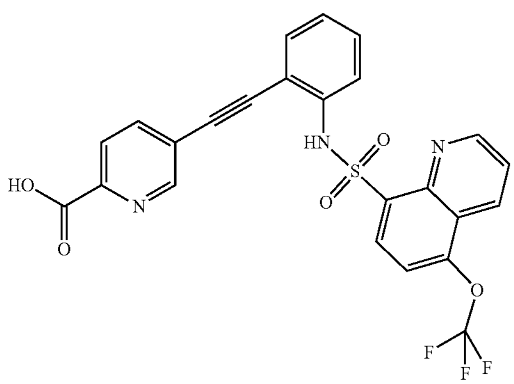 [SMILES: O=C(O)c1ccc(C#Cc2ccccc2NS(=O)(=O)c2ccc(OC(F)(F)F)c3cccnc23)cn1] | 5-[2-(5-Trifluoromethoxy-quinoline-8-sulfonylamino)-phenylethynyl]-pyridine-2-carboxylic acid | 384 |
| 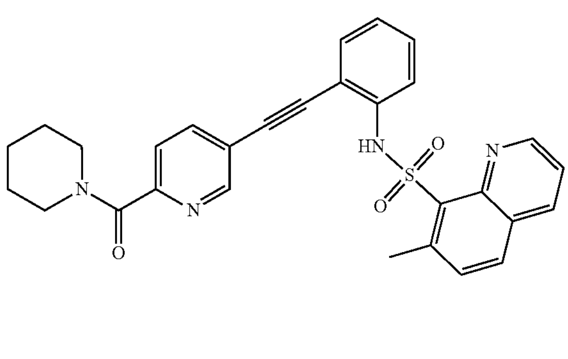 [SMILES: Cc1ccc2cccnc2c1S(=O)(=O)Nc1ccccc1C#Cc1ccc(C(=O)N2CCCCC2)nc1] | 7-Methyl-quinoline-8-sulfonic acid {2-[6-(piperidine-1-carbonyl)-pyridin-3-ylethynyl]-phenyl}-amide | 385 |

| Compound Structure | IUPAC name | Cpd. No. |
|---|---|---|
| 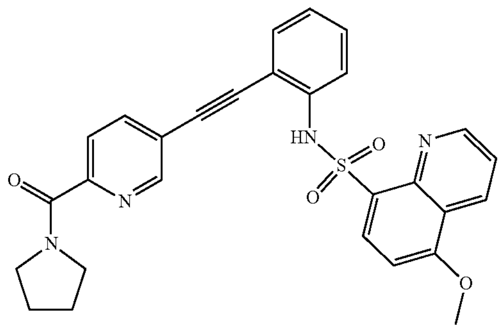 [SMILES: COc1ccc(S(=O)(=O)Nc2ccccc2C#Cc2ccc(C(=O)N3CCCC3)nc2)c2ncccc12] | 5-Methoxy-quinoline-8-sulfonic acid {2-[6-(pyrrolidine-1-carbonyl)-pyridin-3-ylethynyl]-phenyl}-amide | 386 |
| 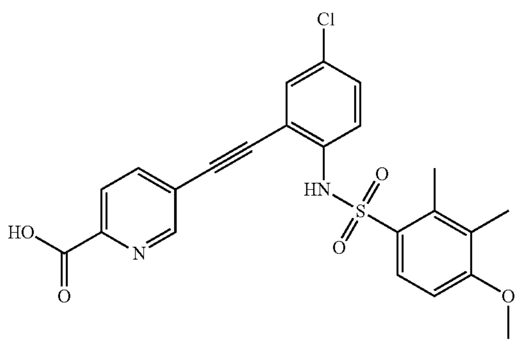 [SMILES: COc1ccc(S(=O)(=O)Nc2ccc(Cl)cc2C#Cc2ccc(C(=O)O)nc2)c(C)c1C] | 5-[5-Chloro-2-(4-methoxy-2,3-dimethyl-benzenesulfonylamino)-phenylethynyl]-pyridine-2-carboxylic acid | 387 |
| 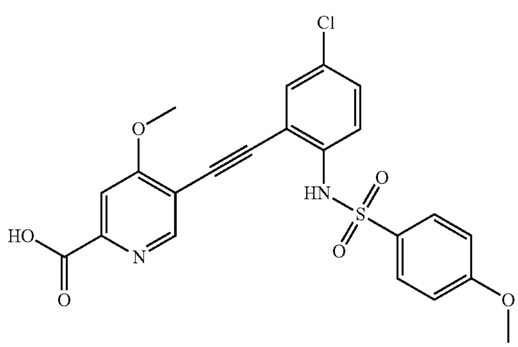 [SMILES: COc1ccc(S(=O)(=O)Nc2ccc(Cl)cc2C#Cc2cnc(C(=O)O)cc2OC)cc1] | 5-[5-Chloro-2-(4-methoxy-benzenesulfonylamino)-phenylethynyl]-4-methoxy-pyridine-2-carboxylic acid | 388 |
| 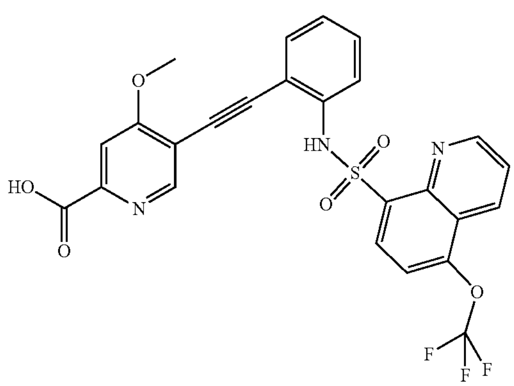 [SMILES: COc1cc(C(=O)O)ncc1C#Cc1ccccc1NS(=O)(=O)c1ccc(OC(F)(F)F)c2cccnc12] | 4-Methoxy-5-[2-(5-trifluoromethoxy-quinoline-8-sulfonylamino)-phenylethynyl]-pyridine-2-carboxylic acid | 389 |

TABLE 1-continued

| Compound Structure | IUPAC name | Cpd. No. |
|---|---|---|
| 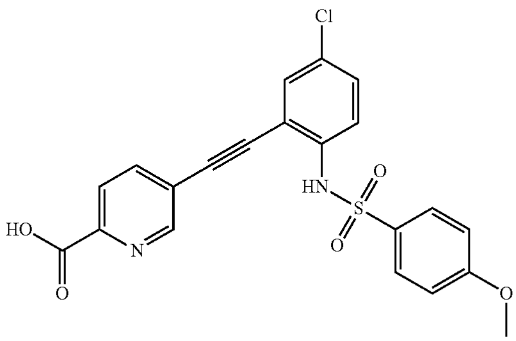 [SMILES: COc1ccc(S(=O)(=O)Nc2ccc(Cl)cc2C#Cc2ccc(C(=O)O)nc2)cc1] | 5-[5-Chloro-2-(4-methoxy-benzenesulfonylamino)-phenylethynyl]-pyridine-2-carboxylic acid | 390 |
| 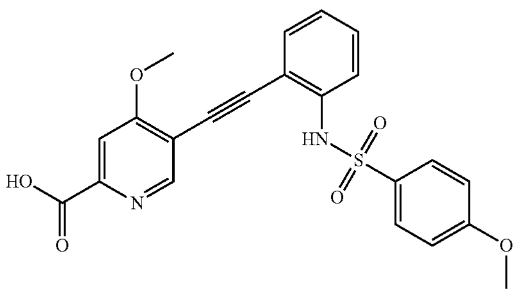 [SMILES: COc1ccc(S(=O)(=O)Nc2ccccc2C#Cc2cnc(C(=O)O)cc2OC)cc1] | 4-Methoxy-5-[2-(4-methoxy-benzenesulfonylamino)-phenylethynyl]-pyridine-2-carboxylic acid | 391 |
| 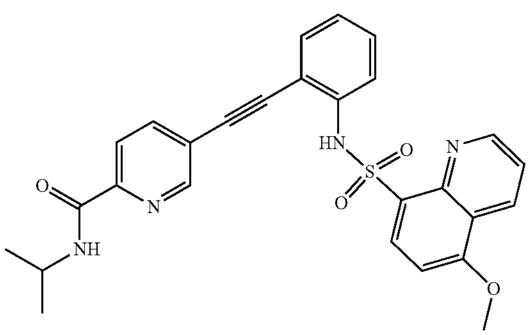 [SMILES: COc1ccc(S(=O)(=O)Nc2ccccc2C#Cc2ccc(C(=O)NC(C)C)nc2)c2ncccc12] | 5-[2-(5-Methoxy-quinoline-8-sulfonylamino)-phenylethynyl]-pyridine-2-carboxylic acid isopropylamide | 392 |
| 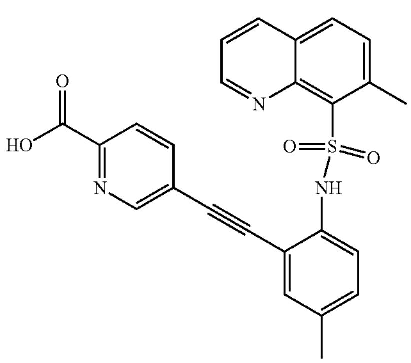 [SMILES: Cc1ccc(NS(=O)(=O)c2c(C)ccc3cccnc23)c(C#Cc2ccc(C(=O)O)nc2)c1] | 5-[5-Methyl-2-(7-methyl-quinoline-8-sulfonylamino)-phenylethynyl]-pyridine-2-carboxylic acid | 393 |

TABLE 1-continued

| Compound Structure | IUPAC name | Cpd. No. |
| --- | --- | --- |
| 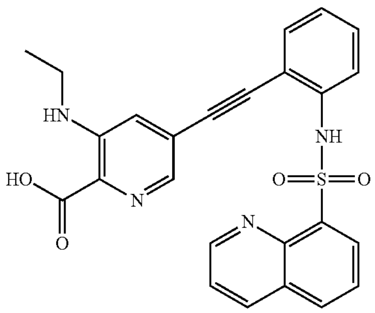 [SMILES: CCNc1cc(C#Cc2ccccc2NS(=O)(=O)c2cccc3cccnc23)cnc1C(=O)O] | 3-(ethylamino)-5-{2-[2-(quinoline-8-sulfonamido)phenyl]ethynyl}pyridine-2-carboxylic acid | 394 |
| 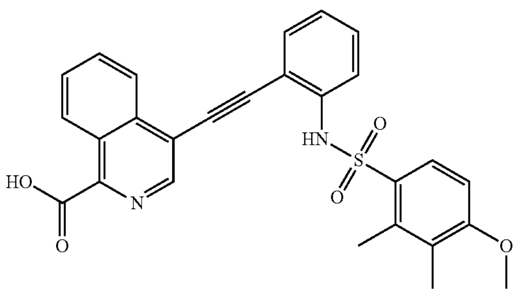 [SMILES: COc1ccc(S(=O)(=O)Nc2ccccc2C#Cc2cnc(C(=O)O)c3ccccc23)c(C)c1C] | 4-[2-(4-Methoxy-2,3-dimethyl-benzenesulfonylamino)-phenylethynyl]-isoquinoline-1-carboxylic acid | 395 |
| 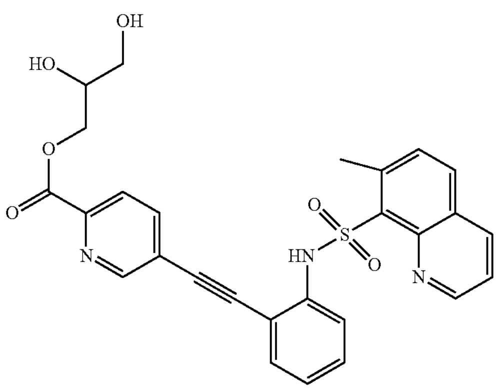 [SMILES: Cc1ccc2cccnc2c1S(=O)(=O)Nc1ccccc1C#Cc1ccc(C(=O)OCC(O)CO)nc1] | 2,3-dihydroxypropyl 5-{2-[2-(7-methylquinoline-8-sulfonamido)phenyl]ethynyl}pyridine-2-carboxylate | 396 |
| 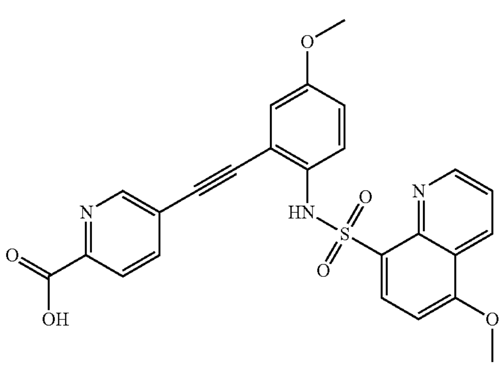 [SMILES: COc1ccc(NS(=O)(=O)c2ccc(OC)c3cccnc23)c(C#Cc2ccc(C(=O)O)nc2)c1] | 5-[5-Methoxy-2-(5-methoxy-quinoline-8-sulfonylamino)-phenylethynyl]-pyridine-2-carboxylic acid | 397 |

TABLE 1-continued

| Compound Structure | IUPAC name | Cpd. No. |
|---|---|---|
| 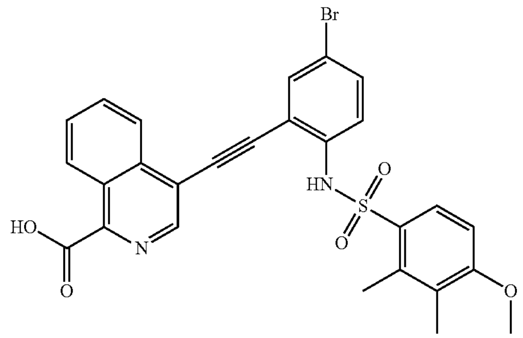 | 4-{2-[5-bromo-2-(4-methoxy-2,3-dimethylbenzenesulfonamido)phenyl]ethynyl}isoquinoline-1-carboxylic acid | 398 |
| 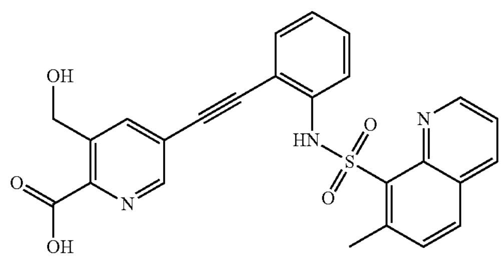 [SMILES: Cc1ccc2cccnc2c1S(=O)(=O)Nc1ccccc1C#Cc1cnc(C(=O)O)c(CO)c1] | 3-(hydroxymethyl)-5-{2-[2-(7-methylquinoline-8-sulfonamido)phenyl]ethynyl}pyridine-2-carboxylic acid | 399 |
| 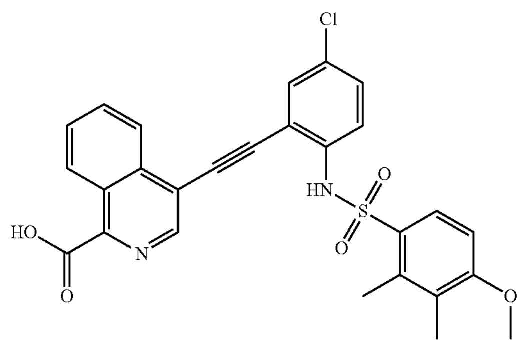 [SMILES: COc1ccc(S(=O)(=O)Nc2ccc(Cl)cc2C#Cc2cnc(C(=O)O)c3ccccc23)c(C)c1C] | 4-[5-Chloro-2-(4-methoxy-2,3-dimethyl-benzenesulfonylamino)-phenylethynyl]-isoquinoline-1-carboxylic acid | 400 |
| 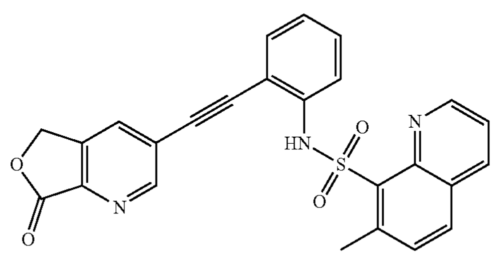 [SMILES: Cc1ccc2cccnc2c1S(=O)(=O)Nc1ccccc1C#Cc1cnc2c(c1)COC2=O] | 7-methyl-N-[2-(2-{7-oxo-5H,7H-furo[3,4-b]pyridin-3-yl}ethynyl)phenyl]quinoline-8-sulfonamide | 401 |
| 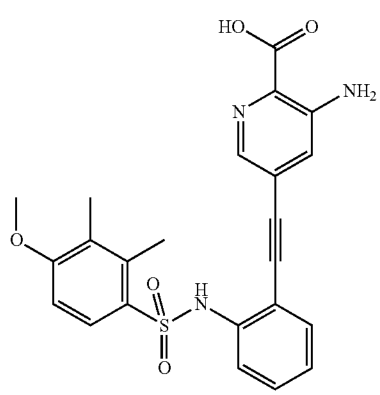 [SMILES: COc1ccc(S(=O)(=O)Nc2ccccc2C#Cc2cnc(C(=O)O)c(N)c2)c(C)c1C] | 3-amino-5-{2-[2-(4-methoxy-2,3-dimethylbenzenesulfonamido)phenyl]ethynyl}pyridine-2-carboxylic acid | 402 |

TABLE 1-continued

| Compound Structure | IUPAC name | Cpd. No. |
|---|---|---|
| 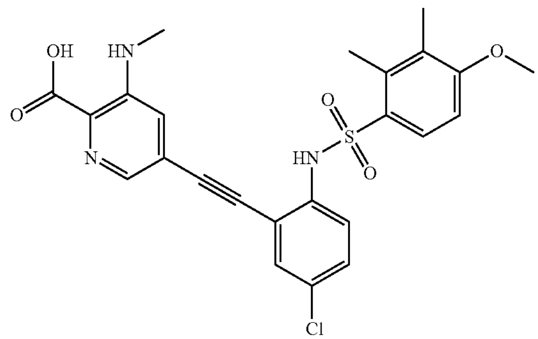 [SMILES: CNc1cc(C#Cc2cc(Cl)ccc2NS(=O)(=O)c2ccc(OC)c(C)c2C)cnc1C(=O)O] | 5-{2-[5-chloro-2-(4-methoxy-2,3-dimethylbenzenesulfonamido)phenyl]ethynyl}-3-(methylamino)pyridine-2-carboxylic acid | 403 |
| 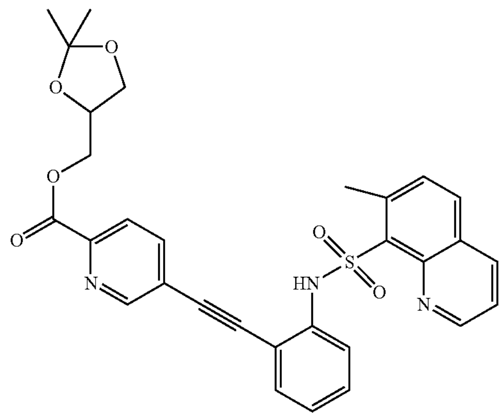 [SMILES: Cc1ccc2cccnc2c1S(=O)(=O)Nc1ccccc1C#Cc1ccc(C(=O)OCC2COC(C)(C)O2)nc1] | (2,2-dimethyl-1,3-dioxolan-4-yl)methyl 5-{2-[2-(7-methylquinoline-8-sulfonamido)phenyl]ethynyl}pyridine-2-carboxylate | 404 |
| 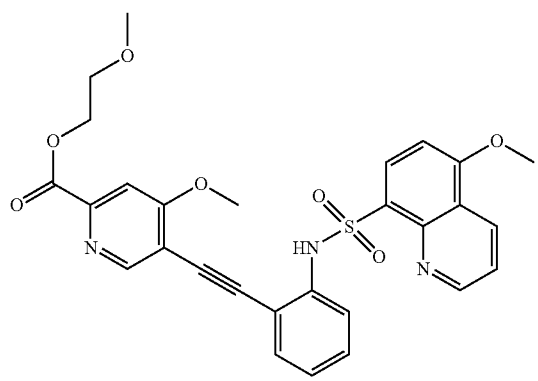 [SMILES: COCCOC(=O)c1cc(OC)c(C#Cc2ccccc2NS(=O)(=O)c2ccc(OC)c3cccnc23)cn1] | 2-methoxyethyl 4-methoxy-5-{2-[2-(5-methoxyquinoline-8-sulfonamido)phenyl]ethynyl}pyridine-2-carboxylate | 405 |
| 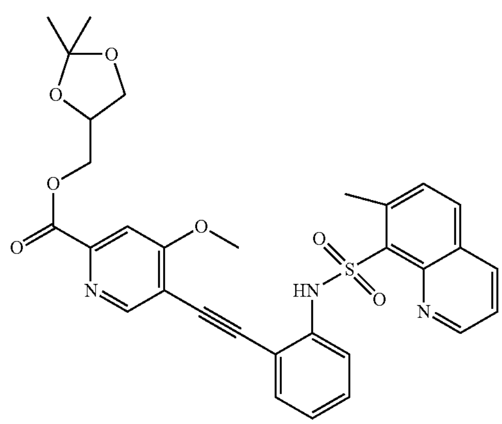 [SMILES: COc1cc(C(=O)OCC2COC(C)(C)O2)ncc1C#Cc1ccccc1NS(=O)(=O)c1c(C)ccc2cccnc12] | (2,2-dimethyl-1,3-dioxolan-4-yl)methyl 4-methoxy-5-{2-[2-(7-methylquinoline-8-sulfonamido)phenyl]ethynyl}pyridine-2-carboxylate | 406 |

TABLE 1-continued

| Compound Structure | IUPAC name | Cpd. No. |
| --- | --- | --- |
| 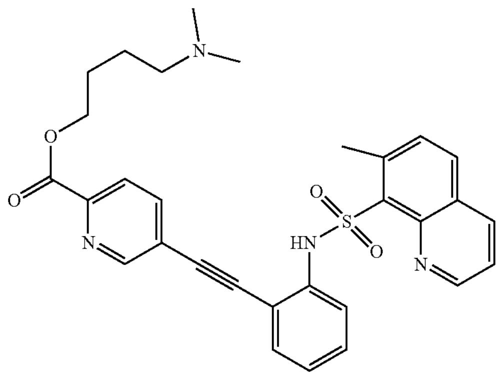 [SMILES: Cc1ccc2cccnc2c1S(=O)(=O)Nc1ccccc1C#Cc1ccc(C(=O)OCCCCN(C)C)nc1] | 4-(dimethylamino)butyl 5-{2-[2-(7-methylquinoline-8-sulfonamido)phenyl]ethyny}pyridine-2-carboxylate | 407 |
| 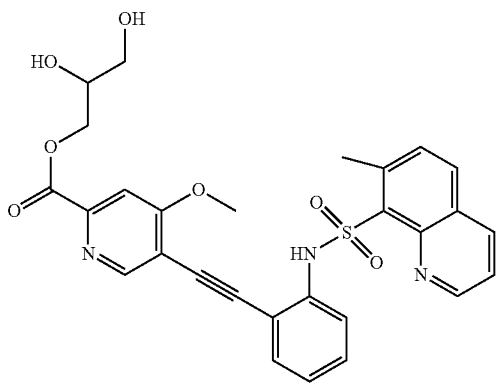 [SMILES: COc1cc(C(=O)OCC(O)CO)ncc1C#Cc1ccccc1NS(=O)(=O)c1c(C)ccc2cccnc12] | 2,3-dihydroxypropyl 4-methoxy-5-{2-[2-(7-methylquinoline-8-sulfonamido)phenyl]ethynyl}pyridine-2-carboxylate | 408 |
| 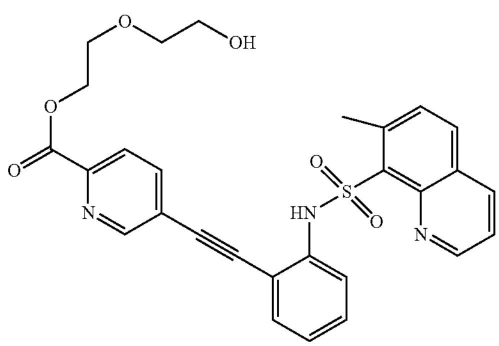 [SMILES: Cc1ccc2cccnc2c1S(=O)(=O)Nc1ccccc1C#Cc1ccc(C(=O)OCCOCCO)nc1] | 2-(2-hydroxyethoxy)ethyl 5-{2-[2-(7-methylquinoline-8-sulfonamido)phenyl]ethynyl}pyridine-2-carboxylate | 409 |
| 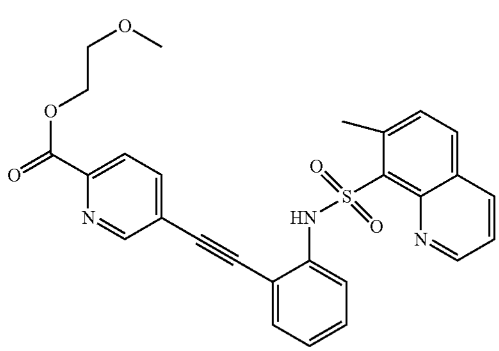 [SMILES: COCCOC(=O)c1ccc(C#Cc2ccccc2NS(=O)(=O)c2c(C)ccc3cccnc23)cn1] | 2-methoxyethyl 5-{2-[2-(7-methylquinoline-8-sulfonamido)phenyl]ethynyl}pyridine-2-carboxylate | 410 |

TABLE 1-continued

| Compound Structure | IUPAC name | Cpd. No. |
|---|---|---|
| 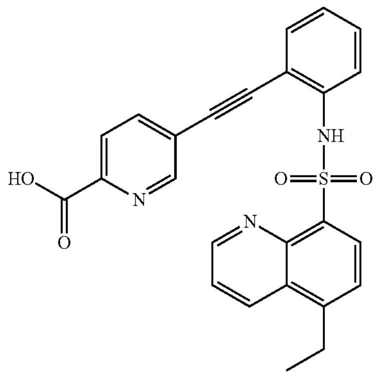 [SMILES: CCc1ccc(S(=O)(=O)Nc2ccccc2C#Cc2ccc(C(=O)O)nc2)c2ncccc12] | 5-{2-[2-(5-ethylquinoline-8-sulfonamido)phenyl]ethynyl}pyridine-2-carboxylic acid | 411 |
| 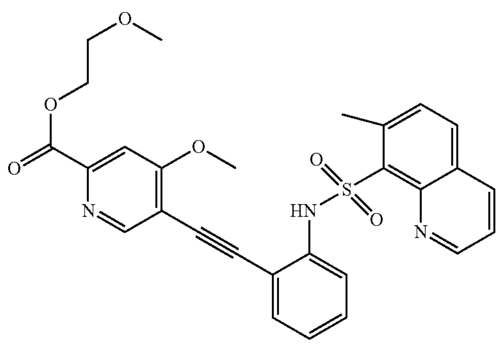 [SMILES: COCCOC(=O)c1cc(OC)c(C#Cc2ccccc2NS(=O)(=O)c2c(C)ccc3cccnc23)cn1] | 2-methoxyethyl 4-methoxy-5-{2-[2-(7-methylquinoline-8-sulfonamido)phenyl]ethynyl}pyridine-2-carboxylate | 412 |
| 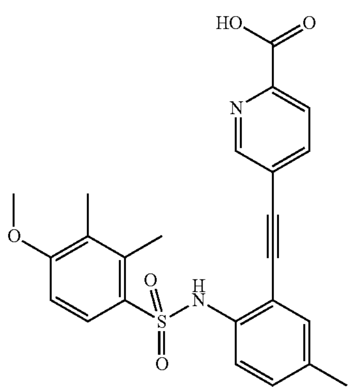 [SMILES: COc1ccc(S(=O)(=O)Nc2ccc(C)cc2C#Cc2ccc(C(=O)O)nc2)c(C)c1C] | 5-{2-[2-(4-methoxy-2,3-dimethylbenzenesulfonamido)-5-methylphenyl]ethynyl}pyridine-2-carboxylic acid | 413 |
| 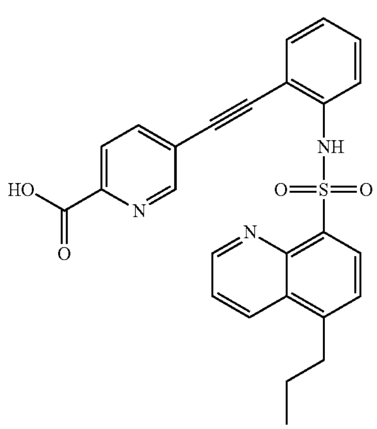 [SMILES: CCCc1ccc(S(=O)(=O)Nc2ccccc2C#Cc2ccc(C(=O)O)nc2)c2ncccc12] | 5-{2-[2-(5-propylquinoline-8-sulfonamido)phenyl]ethynyl}pyridine-2-carboxylic acid | 414 |

TABLE 1-continued

| Compound Structure | IUPAC name | Cpd. No. |
| --- | --- | --- |
| 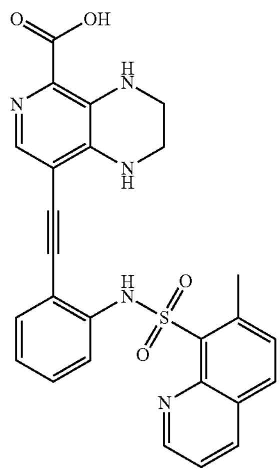 [SMILES: Cc1ccc2cccnc2c1S(=O)(=O)Nc1ccccc1C#Cc1cnc(C(=O)O)c2c1NCCN2] | 8-{2-[2-(7-methylquinoline-8-sulfonamido)phenyl]ethynyl}-1H,2H,3H,4H-pyrido[3,4-b]pyrazine-5-carboxylic acid | 415 |
| 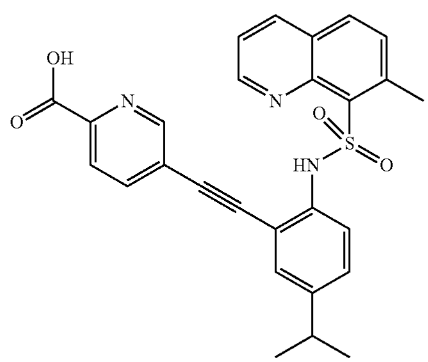 [SMILES: Cc1ccc2cccnc2c1S(=O)(=O)Nc1ccc(C(C)C)cc1C#Cc1ccc(C(=O)O)nc1] | 5-{2-[2-(7-methylquinoline-8-sulfonamido)-5-(propan-2-yl)phenyl]ethynyl}pyridine-2-carboxylic acid | 416 |
| 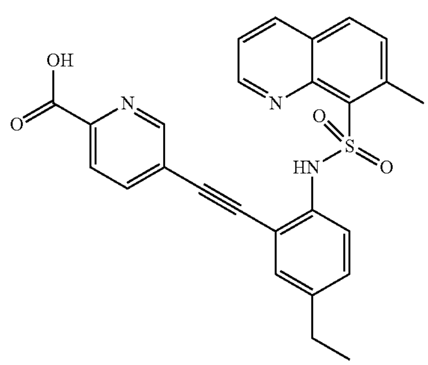 [SMILES: CCc1ccc(NS(=O)(=O)c2c(C)ccc3cccnc23)c(C#Cc2ccc(C(=O)O)nc2)c1] | 5-{2-[5-ethyl-2-(7-methylquinoline-8-sulfonamido)phenyl]ethynyl}pyridine-2-carboxylic acid | 417 |
| 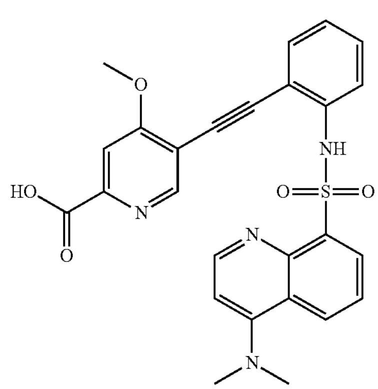 [SMILES: COc1cc(C(=O)O)ncc1C#Cc1ccccc1NS(=O)(=O)c1cccc2c(N(C)C)ccnc12] | 5-[2-(4-Dimethylamino-quinoline-8-sulfonylamino)-phenylethynyl]-4-methoxy-pyridine-2-carboxylic acid | 418 |

TABLE 1-continued

| Compound Structure | IUPAC name | Cpd. No. |
|---|---|---|
| 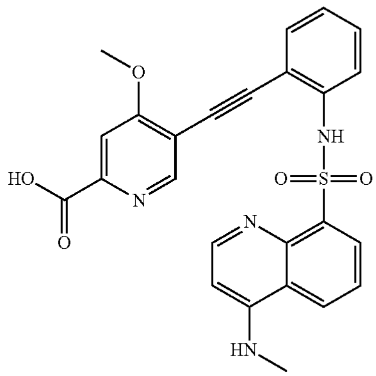 [SMILES: CNc1ccnc2c(S(=O)(=O)Nc3ccccc3C#Cc3cnc(C(=O)O)cc3OC)cccc12] | 4-Methoxy-5-[2-(4-methylamino-quinoline-8-sulfonylamino)-phenylethynyl]-pyridine-2-carboxylic acid | 419 |
| 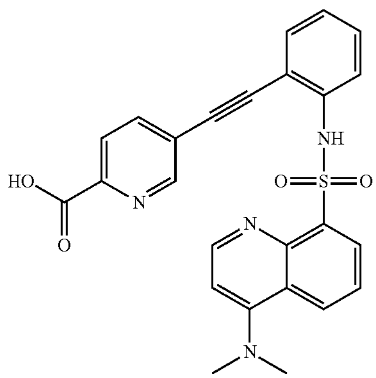 [SMILES: CN(C)c1ccnc2c(S(=O)(=O)Nc3ccccc3C#Cc3ccc(C(=O)O)nc3)cccc12] | 5-[2-(4-Dimethylamino-quinoline-8-sulfonylamino)-phenylethynyl]-pyridine-2-carboxylic acid | 420 |
| 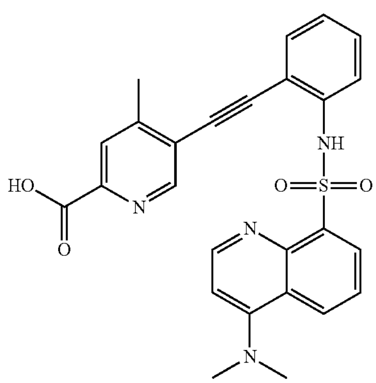 [SMILES: Cc1cc(C(=O)O)ncc1C#Cc1ccccc1NS(=O)(=O)c1cccc2c(N(C)C)ccnc12] | 5-[2-(4-Dimethylamino-quinoline-8-sulfonylamino)-phenylethynyl]-4-methyl-pyridine-2-carboxylic acid | 421 |
| 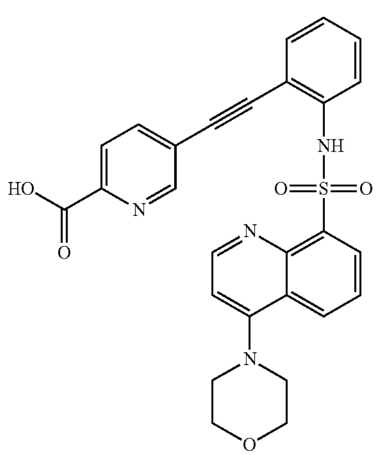 [SMILES: O=C(O)c1ccc(C#Cc2ccccc2NS(=O)(=O)c2cccc3c(N4CCOCC4)ccnc23)cn1] | 5-[2-(4-Morpholin-4-yl-quinoline-8-sulfonylamino)-phenylethynyl]-pyridine-2-carboxylic acid | 422 |

TABLE 1-continued

| Compound Structure | IUPAC name | Cpd. No. |
|---|---|---|
| 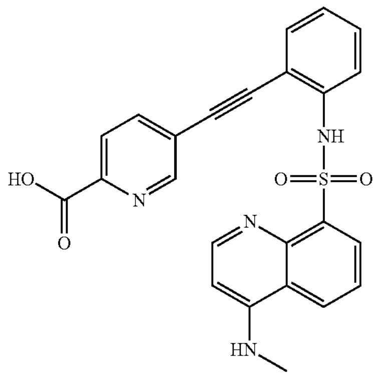 [SMILES: CNc1ccnc2c(S(=O)(=O)Nc3ccccc3C#Cc3ccc(C(=O)O)nc3)cccc12] | 5-[2-(4-Methylamino-quinoline-8-sulfonylamino)-phenylethynyl]-pyridine-2-carboxylic acid | 423 |
| 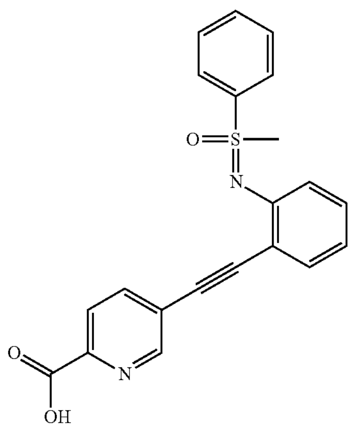 [SMILES: CS(=O)(=Nc1ccccc1C#Cc1ccc(C(=O)O)nc1)c1ccccc1] | 5-[2-(2-{[methyl(oxo)phenyl-λ6-sulfanylidene]amino}phenyl)ethynyl]pyridine-2-carboxylic acid | 424 |
| 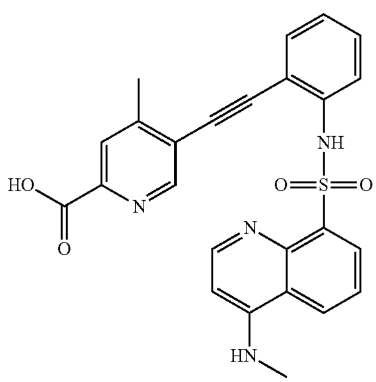 [SMILES: CNc1ccnc2c(S(=O)(=O)Nc3ccccc3C#Cc3cnc(C(=O)O)cc3C)cccc12] | 4-Methyl-5-[2-(4-methylamino-quinoline-8-sulfonylamino)-phenylethynyl]-pyridine-2-carboxylic acid | 425 |
| 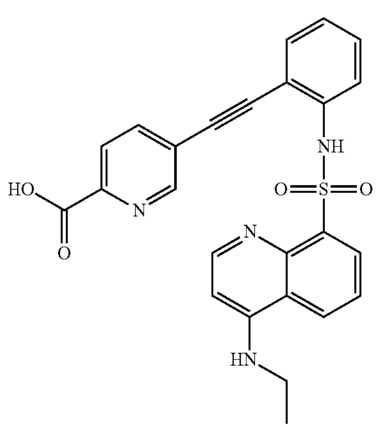 [SMILES: CCNc1ccnc2c(S(=O)(=O)Nc3ccccc3C#Cc3ccc(C(=O)O)nc3)cccc12] | 5-[2-(4-Ethylamino-quinoline-8-sulfonylamino)-phenylethynyl]-pyridine-2-carboxylic acid | 426 |

TABLE 1-continued

| Compound Structure | IUPAC name | Cpd. No. |
|---|---|---|
| 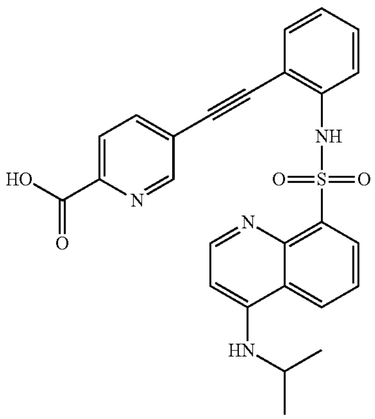 [SMILES: CC(C)Nc1ccnc2c(S(=O)(=O)Nc3ccccc3C#Cc3ccc(C(=O)O)nc3)cccc12] | 5-[2-(4-Isopropylamino-quinoline-8-sulfonylamino)-phenylethynyl]-pyridine-2-carboxylic acid | 427 |
| 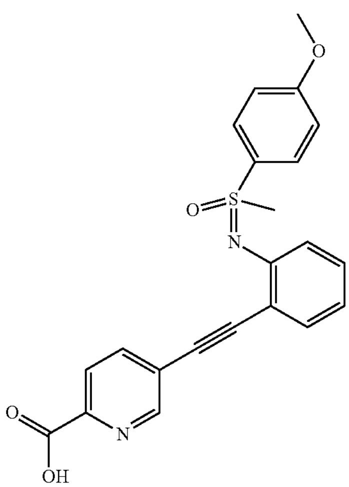 [SMILES: COc1ccc(S(C)(=O)=Nc2ccccc2C#Cc2ccc(C(=O)O)nc2)cc1] | 5-[2-(2-{[(4-methoxyphenyl)(methyl)oxo-λ6-sulfanylidene]amino}phenyl)ethynyl]pyridine-2-carboxylic acid | 428 |
| 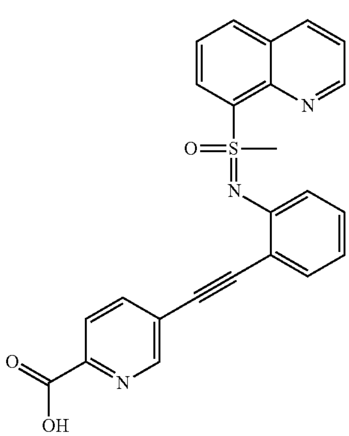 [SMILES: CS(=O)(=Nc1ccccc1C#Cc1ccc(C(=O)O)nc1)c1cccc2cccnc12] | 5-[2-(2-{[methyl(oxo)(quinolin-8-yl)-λ6-sulfanylidene]amino}phenyl)ethynyl]pyridine-2-carboxylic acid | 429 |

TABLE 1-continued

| Compound Structure | IUPAC name | Cpd. No. |
|---|---|---|
| 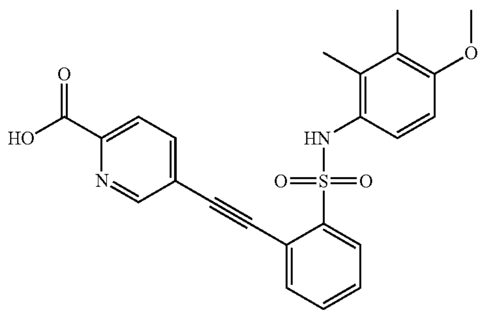 [SMILES: COc1ccc(NS(=O)(=O)c2ccccc2C#Cc2ccc(C(=O)O)nc2)c(C)c1C] | 5-(2-{2-[(4-methoxy-2,3-dimethylphenyl)sulfamoyl]phenyl}ethynyl)pyridine-2-carboxylic acid | 430 |
| 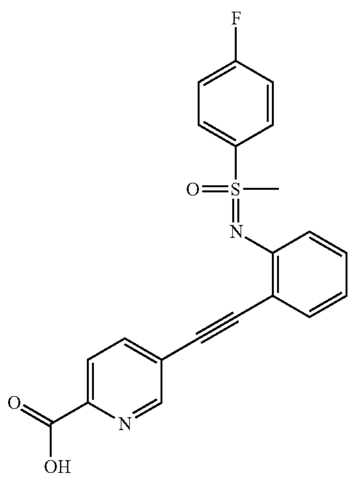 [SMILES: CS(=O)(=Nc1ccccc1C#Cc1ccc(C(=O)O)nc1)c1ccc(F)cc1] | 5-[2-(2-{[(4-fluorophenyl)(methyl)oxo-λ6-sulfanylidene]amino}phenyl)ethynyl]pyridine-2-carboxylic acid | 431 |
| 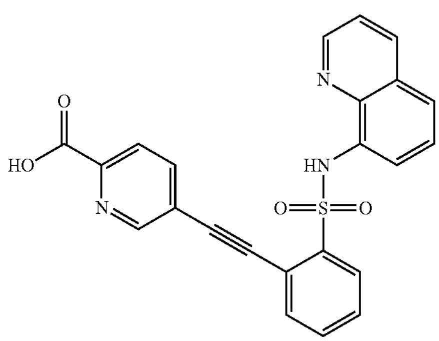 [SMILES: O=C(O)c1ccc(C#Cc2ccccc2S(=O)(=O)Nc2cccc3cccnc23)cn1] | 5-(2-{2-[(quinolin-8-yl)sulfamoyl]phenyl}ethynyl)pyridine-2-carboxylic acid | 432 |
| 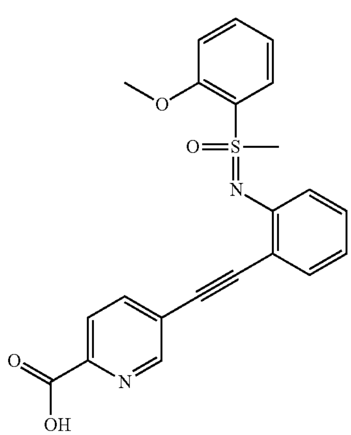 [SMILES: COc1ccccc1S(C)(=O)=Nc1ccccc1C#Cc1ccc(C(=O)O)nc1] | 5-[2-(2-{[(2-methoxyphenyl)(methyl)oxo-λ6-sulfanylidene]amino}phenyl)ethynyl]pyridine-2-carboxylic acid | 433 |

TABLE 1-continued
| Compound Structure | IUPAC name | Cpd. No. |
|---|---|---|
| 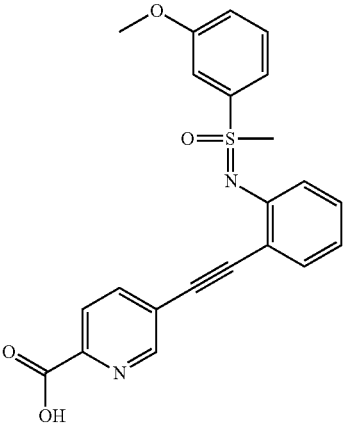 [SMILES: COc1cccc(S(C)(=O)=Nc2ccccc2C#Cc2ccc(C(=O)O)nc2)c1] | 5-[2-(2-{[(3-methoxyphenyl)(methyl)oxo-λ6-sulfanylidene]amino}phenyl)ethynyl]pyridine-2-carboxylic acid | 434 |
| 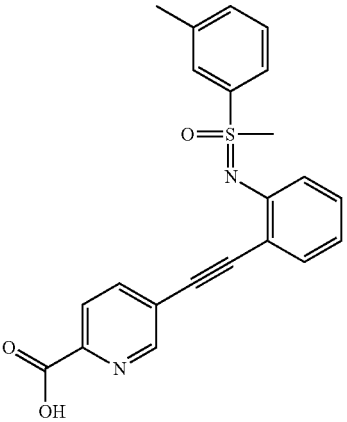 [SMILES: Cc1cccc(S(C)(=O)=Nc2ccccc2C#Cc2ccc(C(=O)O)nc2)c1] | 5-[2-(2-{[methyl(3-methylphenyl)oxo-λ6-sulfanylidene]amino}phenyl)ethynyl]pyridine-2-carboxylic acid | 435 |
| 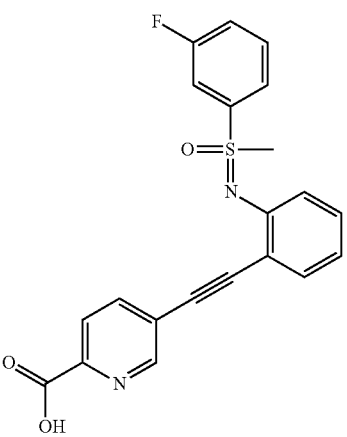 [SMILES: CS(=O)(=Nc1ccccc1C#Cc1ccc(C(=O)O)nc1)c1cccc(F)c1] | 5-[2-(2-{[(3-fluorophenyl)(methyl)oxo-λ6-sulfanylidene]amino}phenyl)ethynyl]pyridine-2-carboxylic acid | 436 |

TABLE 1-continued

| Compound Structure | IUPAC name | Cpd. No. |
|---|---|---|
| 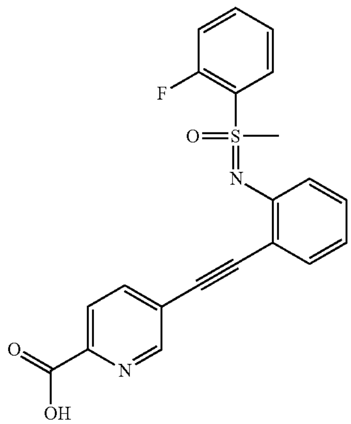 [SMILES: CS(=O)(=Nc1ccccc1C#Cc1ccc(C(=O)O)nc1)c1ccccc1F] | 5-[2-(2-{[(2-fluorophenyl)(methyl)oxo-λ6-sulfanylidene]amino}phenyl)ethynyl]pyridine-2-carboxylic acid | 437 |
| 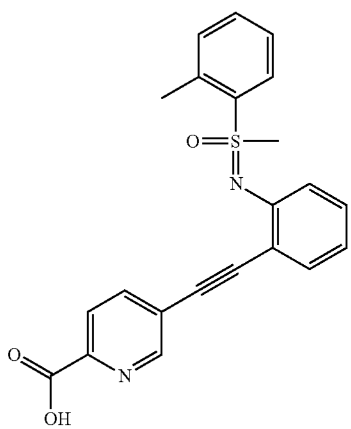 [SMILES: Cc1ccccc1S(C)(=O)=Nc1ccccc1C#Cc1ccc(C(=O)O)nc1] | 5-[2-(2-{[methyl(2-methylphenyl)oxo-λ6-sulfanylidene]amino}phenyl)ethynyl]pyridine-2-carboxylic acid | 438 |
| 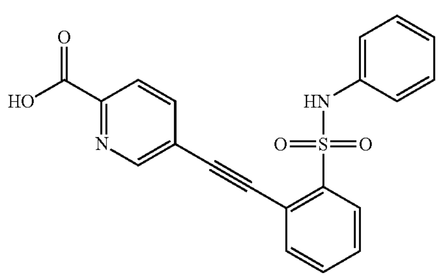 [SMILES: O=C(O)c1ccc(C#Cc2ccccc2S(=O)(=O)Nc2ccccc2)cn1] | 5-{2-[2-(phenylsulfamoyl)phenyl]ethynyl}pyridine-2-carboxylic acid | 439 |
| 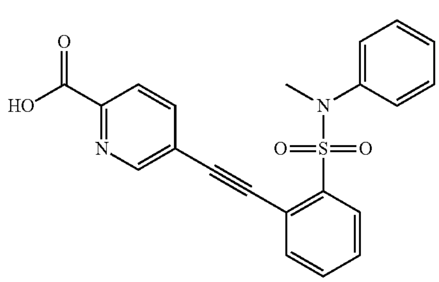 [SMILES: CN(c1ccccc1)S(=O)(=O)c1ccccc1C#Cc1ccc(C(=O)O)nc1] | 5-(2-{2-[methyl(phenyl)sulfamoyl]phenyl}-ethynyl)pyridine-2-carboxylic acid | 440 |

TABLE 1-continued

| Compound Structure | IUPAC name | Cpd. No. |
|---|---|---|
| | 4-{2-[2-(4-chloroquinoline-8-sulfonamido)phenyl]ethynyl}iso-quinoline-1-carboxylic acid | 441 |
| | 4-{2-[2-(5-ethoxyquinoline-8-sulfonamido)phenyl]ethynyl}iso-quinoline-1-carboxylic acid | 442 |
| | 4-(2-{2-[4-(2-{2-[2-(2-aminoethoxy)ethoxy]ethoxy}ethoxy)quinoline-8-sulfonamido]phenyl}-ethynyl)isoquinoline-1-carboxylic acid | 443 |
| | 4-{2-[2-(2-methylquinoline-8-sulfonamido)phenyl]ethynyl}iso-quinoline-1-carboxylic acid | 444 |

TABLE 1-continued

| Compound Structure | IUPAC name | Cpd. No. |
|---|---|---|
| 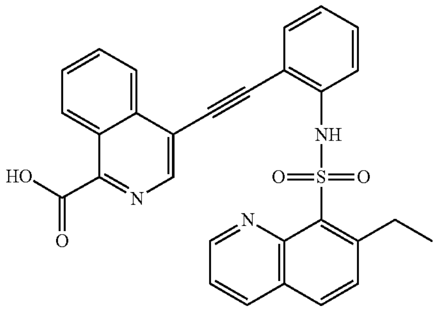 [SMILES: CCc1ccc2cccnc2c1S(=O)(=O)Nc1ccccc1C#Cc1cnc(C(=O)O)c2ccccc12] | 4-{2-[2-(7-ethylquinoline-8-sulfonamido)phenyl]ethynyl}isoquinoline-1-carboxylic acid | 445 |
| 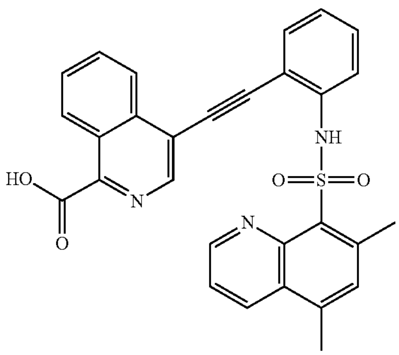 [SMILES: Cc1cc(C)c2cccnc2c1S(=O)(=O)Nc1ccccc1C#Cc1cnc(C(=O)O)c2ccccc12] | 4-{2-[2-(5,7-dimethylquinoline-8-sulfonamido)phenyl]ethynyl}isoquinoline-1-carboxylic acid | 446 |
| 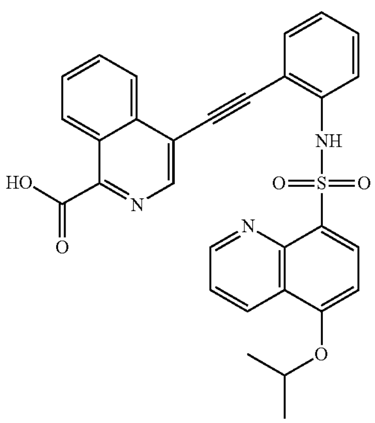 [SMILES: CC(C)Oc1ccc(S(=O)(=O)Nc2ccccc2C#Cc2cnc(C(=O)O)c3ccccc23)c2ncccc12] | 4-(2-{2-[5-(propan-2-yloxy)quinoline-8-sulfonamido]phenyl}ethynyl)isoquinoline-1-carboxylic acid | 447 |
| 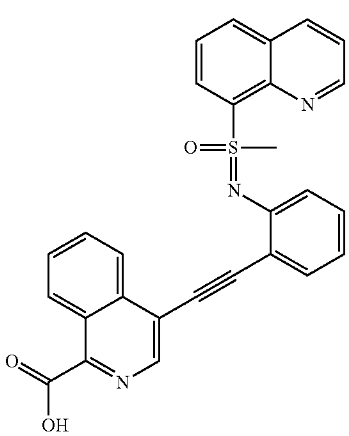 [SMILES: CS(=O)(=Nc1ccccc1C#Cc1cnc(C(=O)O)c2ccccc12)c1cccc2cccnc12] | 4-[2-(2-{[methyl(oxo)(quinolin-8-yl)-λ6-sulfanylidene]amino}phenyl)ethynyl]-isoquinoline-1-carboxylic acid | 448 |

TABLE 1-continued

| Compound Structure | IUPAC name | Cpd. No. |
|---|---|---|
| 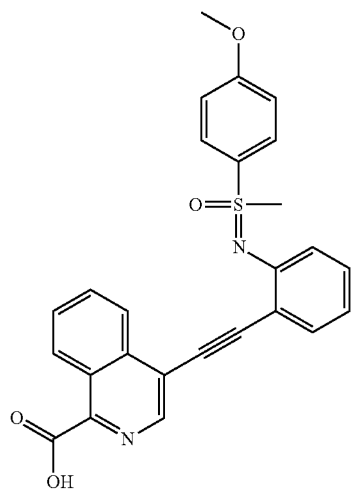 [SMILES: COc1ccc(S(C)(=O)=Nc2ccccc2C#Cc2cnc(C(=O)O)c3ccccc23)cc1] | 4-[2-(2-{[(4-methoxyphenyl)(methyl)oxo-λ6-sulfanylidene]amino}phenyl)ethynyl]-isoquinoline-1-carboxylic acid | 449 |
| 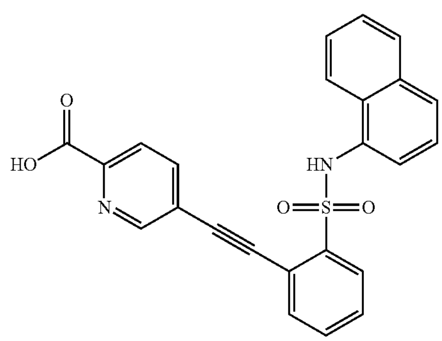 [SMILES: O=C(O)c1ccc(C#Cc2ccccc2S(=O)(=O)Nc2cccc3ccccc23)cn1] | 5-(2-{2-[(naphthalen-1-yl)sulfamoyl]phenyl}ethynyl)pyridine-2-carboxylic acid | 450 |
| 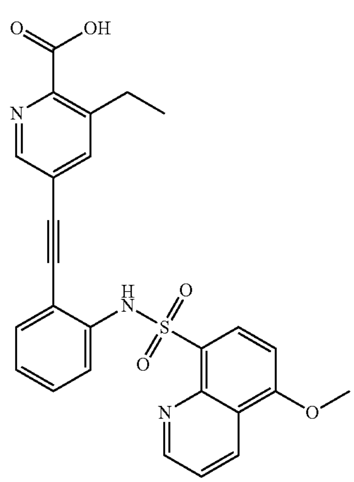 [SMILES: CCc1cc(C#Cc2ccccc2NS(=O)(=O)c2ccc(OC)c3cccnc23)cnc1C(=O)O] | 3-Ethyl-5-[2-(5-methoxy-quinoline-8-sulfonylamino)-phenylethynyl]-pyridine-2-carboxylic acid | 451 |

TABLE 1-continued

| Compound Structure | IUPAC name | Cpd. No. |
|---|---|---|
| 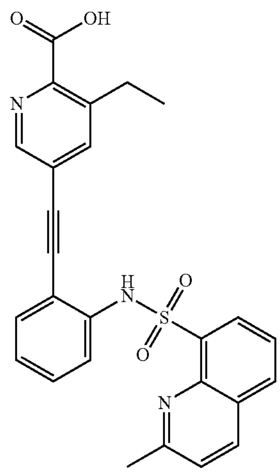 [SMILES: CCc1cc(C#Cc2ccccc2NS(=O)(=O)c2cccc3ccc(C)nc23)cnc1C(=O)O] | 3-Ethyl-5-[2-(2-methyl-quinoline-8-sulfonylamino)-phenylethynyl]-pyridine-2-carboxylic acid | 452 |
| 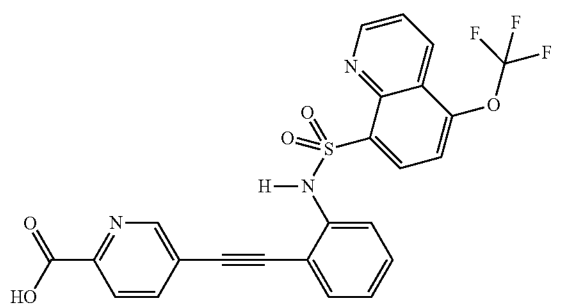 [SMILES: O=C(O)c1ccc(C#Cc2ccccc2NS(=O)(=O)c2ccc(OC(F)(F)F)c3cccnc23)cn1] | 5-[2-(5-Trifluoromethoxy-quinoline-8-sulfonylamino)-phenylethynyl]-pyridine-2-carboxylic acid | 453 |
| 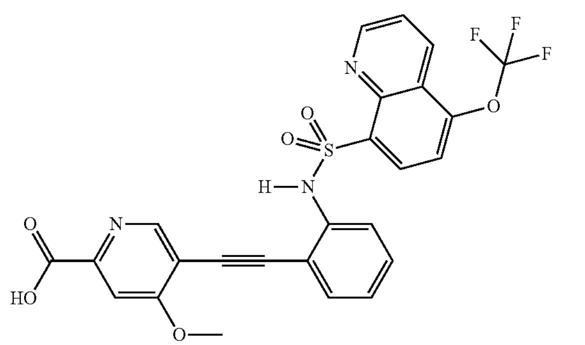 [SMILES: COc1cc(C(=O)O)ncc1C#Cc1ccccc1NS(=O)(=O)c1ccc(OC(F)(F)F)c2cccnc12] | 4-Methoxy-5-[2-(5-trifluoromethoxy-quinoline-8-sulfonylamino)-phenylethynyl]-pyridine-2-carboxylic acid | 454 |
| | 5-{2-[5-(2,2,2-Trifluoro-ethoxy)-quinoline-8-sulfonylamino]-phenylethynyl}-pyridine-2-carboxylic acid | 455 |

TABLE 1-continued

| Compound Structure | IUPAC name | Cpd. No. |
|---|---|---|
| 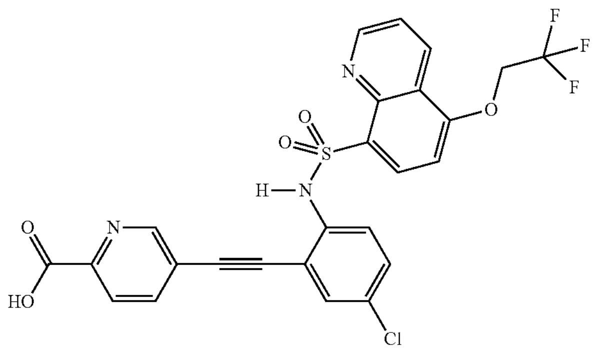 [SMILES: O=C(O)c1ccc(C#Cc2cc(Cl)ccc2NS(=O)(=O)c2ccc(OCC(F)(F)F)c3cccnc23)cn1] | 5-{5-Chloro-2-[5-(2,2,2-trifluoro-ethoxy)-quinoline-8-sulfonylamino]-phenylethynyl}-pyridine-2-carboxylic acid | 456 |
| 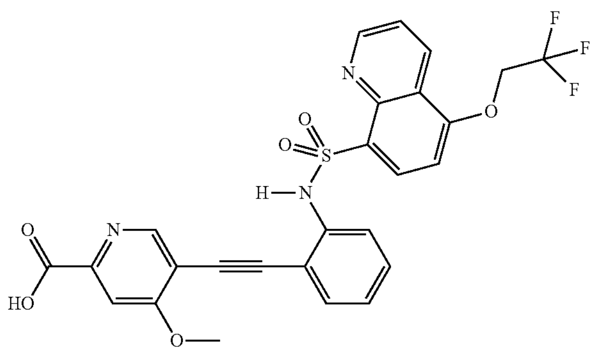 [SMILES: COc1cc(C(=O)O)ncc1C#Cc1ccccc1NS(=O)(=O)c1ccc(OCC(F)(F)F)c2cccnc12] | 4-Methoxy-5-{2-[5-(2,2,2-trifluoro-ethoxy)-quinoline-8-sulfonylamino]-phenylethynyl}-pyridine-2-carboxylic acid | 457 |
| 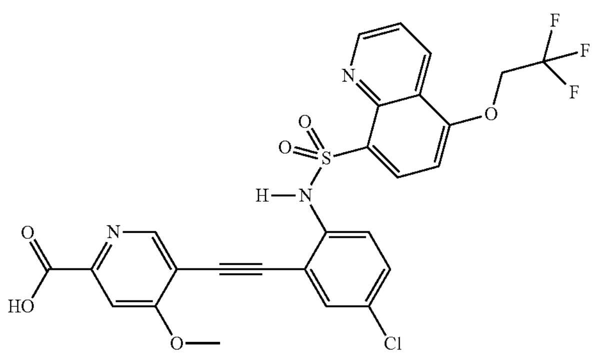 [SMILES: COc1cc(C(=O)O)ncc1C#Cc1cc(Cl)ccc1NS(=O)(=O)c1ccc(OCC(F)(F)F)c2cccnc12] | 5-{5-Chloro-2-[5-(2,2,2-trifluoro-ethoxy)-quinoline-8-sulfonylamino]-phenylethynyl}-4-methoxy-pyridine-2-carboxylic acid | 458 |
| 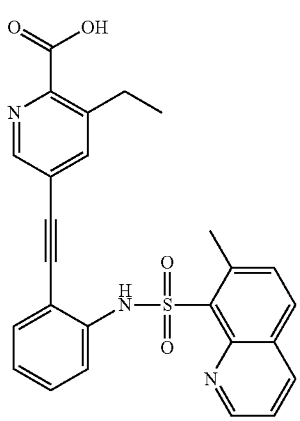 [SMILES: CCc1cc(C#Cc2ccccc2NS(=O)(=O)c2c(C)ccc3cccnc23)cnc1C(=O)O] | 3-Ethyl-5-[2-(7-methyl-quinoline-8-sulfonylamino)-phenylethynyl]-pyridine-2-carboxylic acid | 459 |

Table 2 shows analytical data of the compounds depicted in Table 1 above:

TABLE 2

| Cpd. No. | Formula | Mass | NMR | LCMS (M + H) |
|---|---|---|---|---|
| 1 | C25H17NO4S | 427.48 | 1H NMR (400 MHz, DMSO-d6): 13.15 (s, 1H), 10.20 (s, 1H), 8.36 (d, J = 1.8 Hz, 1H), 8.00--7.96 (m, 1H), 7.93 (d, J = 1.9 Hz, 1H), 7.91 (d, J = 1.6 Hz, 2H), 7.90 (d, J = 1.8 Hz, 1H), 7.71 (dd, J = 8.7, 1.9 Hz, 1H), 7.63 (ddd, J = 8.2, 6.8, 1.3 Hz, 1H), 7.55 (ddd, J = 8.1, 6.8, 1.2 Hz, 1H), 7.46--7.43 (m, 3H), 7.42--7.38 (m, 2H), 7.24 (ddd, J = 7.6, 6.4, 2.3 Hz, 1H). | 8.5 (428.0)+ |
| 2 | C22H17NO5S | 407.44 | 1H NMR (400 MHz, DMSO-d6): 13.16 (s, 1H), 10.06 (s, 1H), 8.01--7.95 (m, 2H), 7.63--7.57 (m, 2H), 7.49 (dd, J = 7.7, 1.5 Hz, 1H), 7.42 (ddd, J = 8.2, 7.3, 1.6 Hz, 1H), 7.38--7.32 (m, 2H), 7.29--7.20 (m, 2H), 7.18 (dd, J = 2.6, 1.7 Hz, 1H), 7.09 (ddd, J = 8.2, 2.6, 1.0 Hz, 1H), 3.60 (s, 3H). | 8.4 (408.0)+ |
| 3 | C23H17NO5S | 419.45 | 1H NMR (400 MHz, DMSO-d6): 13.21 (s, 1H, weak visible), 9.88 (s, 1H) 8.01 (d, J = 1.8 Hz, 1H), 7.99 (d, J = 1.8 Hz, 1H), 7.66 (d, J = 1.7 Hz, 1H), 7.64 (d, J = 1.7 Hz, 1H), 7.62 (t, J = 1.5 Hz, 1H), 7.47 (dd, J = 7.7, 1.5 Hz, 1H), 7.41 (ddd, J = 8.6, 7.1, 1.6 Hz, 1H), 7.34 (ddd, J = 12.9, 8.3, 1.8 Hz, 2H), 7.23 (td, J = 7.4, 1.6 Hz, 1H), 6.71 (d, J = 8.5 Hz, 1H), 4.44 (t, J = 8.8 Hz, 2H), 2.88 (t, J = 8.8 Hz, 2H). | 7.8 (420.0)+ |
| 4 | C26H19NO4S | 441.50 | 1H NMR (400 MHz, DMSO-d6): 13.14 (s, 1H), 8.46 (d, J = 1.9 Hz, 1H), 8.11 (d, J = 8.0 Hz, 1H), 8.01 (d, J = 8.7 Hz, 1H), 7.79--7.73 (m, 2H), 7.70-7.56 (m, 4H), 7.54--7.41 (m, 2H), 7.31 (dd, J = 7.5, 1.9 Hz, 1H), 7.22--7.17 (m, 2H), 3.34 (s, 3H). | 6.90 (442.30)+ |
| 5 | C25H17NO5S | 443.48 | 1H NMR (400 MHz, DMSO-d6): 10.17 (s, 1H), 8.35 (s, 1H), 7.96 (d, J = 8.1 Hz, 1H), 7.93 (s, 1H), 7.91 (s, 1H), 7.74 (d, J = 8.1 Hz, 1H), 7.70 (dd, J = 8.7, 1.9 Hz, 1H), 7.63 (t, J = 6.9 Hz, 1H), 7.54 (t, J = 6.9 Hz, 1H), 7.45-7.34 (m, 3H), 7.23 (td, J = 7.5, 1.7 Hz, 1H), 6.99 (d, J = 1.3 Hz, 1H), 6.87 (dd, J = 8.1, 1.5 Hz, 1H). | 9.2 (442.00)- |
| 6 | C26H18O4S | 426.49 | 1H NMR (400 MHz, DMSO-d6): 13.16 (s, 1H), 8.35 (d, J = 1.5 Hz, 1H), 8.01-7.94 (m, 3H), 7.94-7.88 (m, 2H), 7.72-7.65 (m, 1H), 7.59-7.51 (m, 2H), 7.49-7.38 (m, 6H), 4.95 (s, 2H). | 8.3 (427.3)+ |
| 7 | C25H21NO4S | 431.51 | 1H NMR (400 MHz, DMSO-d6): 13.15 (s, 1H), 9.92 (s, 1H), 7.97 (d, J = 8.5 Hz, 2H), 7.58 (d, J = 8.4 Hz, 2H), 7.47 (d, J = 7.8 Hz, 1H), 7.43 (s, 1H), 7.40-7.34 (m, 2H), 7.27 (dd, J = 8.0, 2.0 Hz, 1H), 7.22 (t, J = 6.9 Hz, 1H), 7.04 (d, J = 8.1 Hz, 1H), 2.61 (t, J = 6.2 Hz, 2H), 2.47 (t, J = 6.2 Hz, 2H), 1.59 (dt, J = 9.9, 4.6 Hz, 2H), 1.54-1.49 (m, 2H). | 9.0 (432.3)+ |
| 8 | C26H19NO5S | 457.50 | 1H NMR (400 MHz, DMSO-d6): 13.14 (s, 1H), 10.15 (s, 1H), 8.60 (d, J = 8.6 Hz, 1H), 8.18-8.13 (m, 1H), 8.06 (d, J = 8.4 Hz, 1H), 7.95 (d, J = 1.8 Hz, 1H), 7.94 (d, J = 1.8 Hz, 1H), 7.44 (dq, J = 9.1, 2.5, 1.8 Hz, 3H), 7.40 (dt, J = 6.8, 1.5 Hz, 1H), 7.38-7.31 (m, 3H), 7.19-7.12 (m, 1H), 6.96 (d, J = 8.5 Hz, 1H), 3.96 (s, 3H). | 6.8 (458.0)+ |
| 9 | C23H19NO5S | 421.47 | 1H NMR (400 MHz, DMSO-d6): 12.98 (s, 1H), 10.01 (s, 1H), 7.85 (d, J = 8.4 Hz, 1H), 7.47 (dd, J = 7.7, 1.6 Hz, 1H), 7.43-7.30 (m, 5H), 7.28-7.17 (m, 3H), 7.10 (ddd, J = 8.3, 2.5, 1.1 Hz, 1H), 3.60 (s, 3H), 2.55 (s, 3H) | 6.5 (420.10)- |
| 10 | C26H19NO4S | 441.50 | 1H NMR (400 MHz, DMSO-d6): 13.62-12.06 (s, 1H), 10.90-9.61 (s, 1H), 8.36 (d, J = 1.8 Hz, 1H), 7.94 (dd, J = 18.1, 8.6 Hz, 3H), 7.78 (d, J = 8.0 Hz, 1H), 7.72-7.58 (m, 2H), 7.54 (ddd, J = 8.1, 6.8, 1.2 Hz, 1H), 7.45-7.33 (m, 3H), 7.31-7.16 (m, 3H), 2.48 (s, 3H) | 6.9 (440.00)- |

TABLE 2-continued

| Cpd. No. | Formula | Mass | NMR | LCMS (M + H) |
|---|---|---|---|---|
| 11 | C26H23NO5S | 461.54 | 1H NMR (400 MHz, DMSO-d6): 13.14 (s, 1H), 9.91 (s, 1H), 7.99 (d, J = 1.8 Hz, 1H), 7.98 (d, J = 1.8 Hz, 1H), 7.69-7.64 (m, 3H), 7.48 (dd, J = 7.7, 1.5 Hz, 1H), 7.42 (dd, J = 8.3, 1.3 Hz, 1H), 7.35 (ddd, J = 8.3, 7.3, 1.6 Hz, 1H), 7.16 (td, J = 7.5, 1.3 Hz, 1H), 6.80 (d, J = 8.9 Hz, 1H), 3.76 (s, 3H), 3.12 (t, J = 5.8 Hz, 2H), 2.44 (t, J = 6.0 Hz, 2H), 1.51-1.43 (m, 4H). | 7.2 (460.00)− |
| 12 | C21H16N2O5S | 408.43 | 1H NMR (400 MHz, DMSO-d6): 10.12 (s, 1H), 8.75 (d, J = 1.9 Hz, 1H), 8.10 (d, J = 8.1 Hz, 1H), 8.04 (dd, J = 8.1, 2.0 Hz, 1H), 7.51 (dd, J = 7.7, 1.5 Hz, 1H), 7.45 (td, J = 7.7, 1.6 Hz, 1H), 7.40-7.25 (m, 3H), 7.19 (dd, J = 7.4, 1.5 Hz, 1H), 7.14 (t, J = 2.1 Hz, 1H), 7.07 (dd, J = 8.3, 2.6 Hz, 1H), 3.56 (s, 3H) | 5.7 (406.90)− |
| 13 | C24H16N2O4S | 428.47 | 1H NMR (400 MHz, DMSO-d6): 10.23 (s, 1H), 8.65 (s, 1H), 8.33 (d, J = 1.8 Hz, 1H), 8.00 (d, J = 8.1 Hz, 1H), 7.96-7.83 (m, 4H), 7.68 (dd, J = 8.7, 1.9 Hz, 1H), 7.60 (ddd, J = 8.2, 6.9, 1.2 Hz, 1H), 7.51 (ddd, J = 8.3, 6.9, 1.2 Hz, 1H), 7.43 (ddd, J = 9.2, 8.1, 6.8 Hz, 3H), 7.25 (td, J = 7.2, 2.0 Hz, 1H) | 6.2 (429.1)+ |
| 14 | C25H16FNO4S | 445.47 | 1H NMR (400 MHz, DMSO-d6): 10.17 (s, 1H), 8.34 (d, J = 1.8 Hz, 1H), 7.92 (dd, J = 15.2, 8.3 Hz, 3H), 7.81 (t, J = 7.9 Hz, 1H), 7.63 (ddd, J = 16.0, 8.4, 1.6 Hz, 2H), 7.52 (ddd, J = 8.1, 6.8, 1.2 Hz, 1H), 7.46-7.37 (m, 3H), 7.28-7.17 (m, 3H) | 6.7 (443.90)− |
| 15 | C25H16FNO4S | 445.47 | 1H NMR (400 MHz, DMSO-d6): 13.34-13.00 (m, 1H), 10.29 (s, 1H), 8.33 (d, J = 1.8 Hz, 1H), 7.97 (d, J = 8.2 Hz, 1H), 7.92 (s, 1H), 7.90 (d, J = 2.0 Hz, 2H), 7.88 (s, 1H), 7.69-7.64 (m, 1H), 7.64-7.60 (m, 1H), 7.54 (ddd, J = 8.1, 6.8, 1.2 Hz, 1H), 7.41 (d, J = 1.8 Hz, 1H), 7.39 (s, 1H), 7.38 (d, J = 5.4 Hz, 1H), 7.36-7.31 (m, 1H), 7.29 (dd, J = 8.6, 3.1 Hz, 1H). | 8.6 (444.00)− |
| 16 | C25H18N2O4S | 442.49 | 1H NMR (400 MHz, DMSO-d6): 11.31 (s, 1H), 10.14 (s, 1H), 9.10 (s, 1H), 8.36 (s, 1H), 7.97 (d, J = 8.1 Hz, 1H), 7.93 (d, J = 8.7 Hz, 2H), 7.73 (t, J = 7.9 Hz, 3H), 7.63 (d, J = 7.1 Hz, 1H), 7.56 (t, J = 7.5 Hz, 1H), 7.44-7.36 (m, 5H), 7.26-7.21 (m, 1H). | 5.9 (442.9)+ |
| 17 | C26H16F3NO4S | 495.47 | 1H NMR (400 MHz, DMSO-d6): 13.17 (s, 1H), 10.60 (s, 1H), 8.40-8.35 (m, 1H), 7.99 (d, J = 8.4 Hz, 1H), 7.96-7.86 (m, 4H), 7.73-7.51 (m, 6H), 7.46 (d, J = 8.1 Hz, 2H). | 7.2 (496.1)+ |
| 18 | C27H21NO5S | 471.53 | 1H NMR (400 MHz, DMSO-d6): 12.97 (s, 1H), 10.11 (s, 1H), 8.59-8.55 (m, 1H), 8.15 (dd, J = 8.2, 1.6 Hz, 1H), 8.05 (d, J = 8.4 Hz, 1H), 7.81 (d, J = 8.0 Hz, 1H), 7.49-7.30 (m, 5H), 7.26-7.11 (m, 3H), 6.95 (d, J = 8.5 Hz, 1H), 3.95 (s, 3H), 2.53 (s, 3H) | 7.0 (470.10)− |
| 19 | C26H19NO5S | 457.50 | 1H NMR (400 MHz, DMSO-d6): 13.09 (s, 1H), 10.17 (s, 1H), 8.41 (d, J = 1.8 Hz, 1H), 8.01 (d, J = 8.0 Hz, 1H), 7.97-7.90 (m, 3H), 7.89 (d, J = 1.8 Hz, 1H), 7.75 (dd, J = 8.7, 1.9 Hz, 1H), 7.64 (ddd, J = 8.2, 6.9, 1.3 Hz, 1H), 7.56 (ddd, J = 8.1, 6.9, 1.3 Hz, 1H), 7.45 (d, J = 8.3 Hz, 2H), 7.37 (d, J = 8.6 Hz, 1H), 6.91 (d, J = 2.6 Hz, 1H), 6.82 (dd, J = 8.6, 2.6 Hz, 1H), 3.75 (s, 3H). | 8.6 (458.0)+ |
| 20 | C26H18O3S | 410.49 | 1H NMR (400 MHz, DMSO-d6): 13.17 (s, 1H), 8.02 (d, J = 0.6 Hz, 1H), 8.00-7.93 (m, 4H), 7.88 (d, J = 8.1 Hz, 1H), 7.61 (ddd, J = 8.3, 7.0, 1.3 Hz, 1H), 7.58-7.53 (m, 3H), 7.54-7.48 (m, 2H), 7.41-7.36 (m, 2H), 7.33-7.29 (m, 1H), 4.57-4.48 (m, 2H). | 6.3 (410.9)+ |
| 21 | C27H18N2O5S | 482.51 | 1H NMR (400 MHz, DMSO-d6): 10.15 (s, 1H), 8.63-8.58 (m, 1H), 8.11 (dd, J = 8.1, 1.6 Hz, 1H), 8.02 (s, 1H), 8.00 (s, 1H), 7.78 (d, J = 1.7 Hz, 1H), 7.54 (dd, J = 8.1, 1.7 Hz, 1H), 7.47 (dd, J = 8.3, 1.2 Hz, 1H), 7.41 (ddt, J = 5.5, 2.7, 1.4 Hz, 1H), 7.38 (dd, J = 4.6, 1.6 Hz, 1H), 7.35 (d, J = 1.6 Hz, 1H), 7.33 (d, J = 1.5 Hz, 1H), 7.17 (t, J = 7.5 Hz, 1H), 6.93 (d, J = 8.5 Hz, 1H), 3.96 (s, 3H). Carboxylic proton not visible. | 8.5 (483.0)+ |

TABLE 2-continued

| Cpd. No. | Formula | Mass | NMR | LCMS (M + H) |
|---|---|---|---|---|
| 22 | C24H16ClNO4S2 | 481.98 | 1H NMR (400 MHz, DMSO-d6): 13.11 (s, 1H), 10.56 (s, 1H), 7.89-7.84 (m, 3H), 7.73 (d, J = 2.0 Hz, 1H), 7.51-7.41 (m, 4H), 7.37-7.27 (m, 3H). | 7.2 (480.00)− |
| 23 | C22H15Cl2NO5S | 476.33 | 1H NMR (400 MHz, DMSO-d6): 13.14 (s, 1H), 10.23 (s, 1H), 7.98-7.95 (m, 2H), 7.86 (d, J = 9.0 Hz, 1H), 7.58-7.55 (m, 2H), 7.52 (dd, J = 7.7, 1.3 Hz, 1H), 7.33 (dd, J = 8.0, 1.0 Hz, 2H), 7.26 (t, J = 7.4 Hz, 1H), 7.16 (d, J = 9.2 Hz, 1H), 3.86 (s, 3H). | 6.6 (473.7)− |
| 24 | C26H16N2O4S | 452.49 | 1H NMR (400 MHz, DMSO-d6): 10.19 (s, 1H), 8.33 (d, J = 1.9 Hz, 1H), 8.00 (d, J = 8.2 Hz, 1H), 7.93-7.88 (m, 2H), 7.86 (dd, J = 5.7, 2.4 Hz, 2H), 7.65-7.57 (m, 3H), 7.50 (ddd, J = 8.3, 6.8, 1.3 Hz, 1H), 7.46 (dd, J = 5.2, 1.7 Hz, 2H), 7.43 (d, J = 1.1 Hz, 1H), 7.27 (ddd, J = 8.4, 5.9, 2.8 Hz, 1H). Carboxylic proton not visible. | 8.4 (450.8)+ |
| 25 | C26H18FNO5S | 475.49 | 1H NMR (400 MHz, DMSO-d6): 13.15 (s, 1H), 10.16 (s, 1H), 8.54 (dd, J = 7.8, 2.0 Hz, 1H), 8.16-8.12 (m, 1H), 8.02 (d, J = 8.4 Hz, 1H), 7.94 (s, 1H), 7.92 (d, J = 1.7 Hz, 1H), 7.47-7.40 (m, 2H), 7.39-7.34 (m, 3H), 7.25 (td, J = 8.2, 2.4 Hz, 2H), 6.94 (d, J = 8.5 Hz, 1H), 3.94 (s, 3H). | 8.7 (474.00)− |
| 26 | C25H18N2O5S | 458.49 | 1H NMR (300 MHz, DMSO-d6): 13.23 (s, 1H), 9.05 (s, 1H), 8.76 (dd, J = 4.3, 1.8 Hz, 1H), 8.53 (dd, J = 8.5, 1.8 Hz, 1H), 8.36 (d, J = 8.4 Hz, 1H), 8.06-8.02 (m, 2H), 7.66-7.63 (m, 2H), 7.54-7.47 (m, 2H), 7.42-7.38 (m, 1H), 7.34-7.27 (m, 1H), 7.15 (d, J = 8.5 Hz, 1H), 7.05 (td, J = 7.5, 1.1 Hz, 1H), 4.04 (s, 3H).; 13C NMR (75 MHz, DMSO-d6): 167.18, 159.75, 151.93, 143.83, 138.96, 133.91, 132.96, 131.95, 131.78, 131.40, 130.67, 130.11, 126.86, 126.51, 124.72, 122.37, 120.77, 119.84, 113.99, 104.35, 94.68, 87.72, 57.15. | 6.8 (459.4)+ |
| 27 | C26H17F2NO5S | 493.48 | 1H NMR (400 MHz, DMSO-d6): 14.13 (s, 1H), 10.10 (s, 1H), 8.56 (d, J = 8.6 Hz, 1H), 8.12 (d, J = 8.2 Hz, 1H), 8.00 (d, J = 8.4 Hz, 1H), 7.47-7.31 (m, 5H), 7.19 (t, J = 7.4 Hz, 1H), 7.05 (d, J = 8.2 Hz, 2H), 6.94 (d, J = 8.5 Hz, 1H), 3.96 (s, 3H). | 6.9 (491.70)− |
| 28 | C25H16ClNO4S | 461.92 | 1H NMR (400 MHz, DMSO-d6): 13.53 (s, 1H), 10.17 (s, 1H), 8.33 (s, 1H), 7.91 (t, J = 9.2 Hz, 3H), 7.75 (d, J = 8.0 Hz, 1H), 7.66-7.59 (m, 2H), 7.54-7.49 (m, 2H), 7.45-7.41 (m, 3H), 7.33 (d, J = 8.0 Hz, 1H), 7.25 (t, 1H). | 6.9 (459.70)− |
| 29 | C25H15F2NO4S | 463.46 | 1H NMR (400 MHz, DMSO-d6): 14.10 (s, 1H), 10.12 (s, 1H), 8.35 (d, J = 1.7 Hz, 1H), 7.93-7.89 (m, 3H), 7.64-7.57 (m, 2H), 7.52 (t, J = 7.4 Hz, 1H), 7.48-7.41 (m, 3H), 7.29-7.24 (m, 1H), 7.09 (d, J = 8.4 Hz, 2H). | 6.8 (461.80)− |
| 30 | C25H16FNO4S | 445.47 | 1H NMR (400 MHz, DMSO-d6): 13.45 (s, 1H), 10.15 (s, 1H), 8.37 (d, J = 1.9 Hz, 1H), 7.97 (d, J = 8.2 Hz, 1H), 7.93 (t, J = 7.6 Hz, 2H), 7.78 (dd, J = 8.0, 1.6 Hz, 1H), 7.70 (dd, J = 8.7, 1.9 Hz, 1H), 7.68-7.64 (m, 1H), 7.63-7.58 (m, 2H), 7.54 (t, J = 7.5 Hz, 1H), 7.48-7.42 (m, 2H), 7.42-7.37 (m, 1H), 7.25 (td, J = 7.4, 1.5 Hz, 1H). | 8.8 (446.0)+ |
| 31 | C25H18N2O5S | 458.49 | 1H NMR (400 MHz, DMSO-d6): 13.35 (s, 1H), 10.20 (s, 1H), 8.58 (m, 2H), 8.14-8.08 (m, 1H), 8.08-7.99 (m, 2H), 7.85 (dd, J = 8.1, 2.1 Hz, 1H), 7.50-7.30 (m, 5H), 7.18 (td, J = 7.5, 1.4 Hz, 1H), 6.93 (d, J = 8.5 Hz, 1H), 3.94 (s, 3H) | 6.3 (458.8)+ |
| 32 | C25H16FNO4S | 445.47 | 1H NMR (400 MHz, DMSO-d6): 13.10 (s, 1H), 10.13 (s, 1H), 8.34 (s, 1H), 8.01 (d, J = 8.2 Hz, 1H), 7.89 (dd, J = 18.3, 8.4 Hz, 2H), 7.82-7.69 (m, 3H), 7.61 (t, J = 7.4 Hz, 1H), 7.54 (t, J = 7.5 Hz, 1H), 7.35 (m, 3H), 7.24 (d, J = 8.1 Hz, 2H) | 6.4 (443.70)− |
| 33 | C27H21NO6S | 487.53 | 1H NMR (400 MHz, DMSO-d6): 12.76 (s, 1H), 10.08 (s, 1H), 8.57 (d, J = 8.4 Hz, 1H), 8.15 (d, J = 8.4 Hz, 1H), 8.05 (d, J = 8.4 Hz, 1H), 7.64 (d, J = 7.9 Hz, 1H), 7.47-7.32 (m, 5H), 7.16 (td, J = 7.2, 2.1 Hz, 1H), 7.10 (d, J = 1.1 Hz, 1H), 6.96-6.93 (m, 2H), 3.95 (s, 3H), 3.85 (s, 3H). | 8.4 (485.80)− |

TABLE 2-continued

| Cpd. No. | Formula | Mass | NMR | LCMS (M + H) |
|---|---|---|---|---|
| 34 | C20H12BrClN2O4S | 491.75 | 1H NMR (400 MHz, DMSO-d6): 13.14 (s, 1H), 10.62 (s, 1H), 8.48 (d, J = 2.2 Hz, 1H), 8.29 (d, J = 2.2 Hz, 1H), 7.99-7.97 (m, 2H), 7.57-7.54 (m, 3H), 7.49 (td, J = 8.1, 1.6 Hz, 1H), 7.41-7.34 (m, 2H). | 8.3 (490.60)− |
| 35 | C24H16N2O4S | 428.47 | 1H NMR (400 MHz, DMSO-d6): 13.13 (s, 1H), 10.48 (s, 1H), 8.95 (d, J = 8.5 Hz, 1H), 8.79 (dd, J = 4.2, 1.6 Hz, 1H), 8.17 (d, J = 8.4 Hz, 1H), 8.09 (dd, J = 7.4, 1.1 Hz, 1H), 7.96-7.89 (m, 2H), 7.74 (dd, J = 8.3, 7.5 Hz, 1H), 7.45-7.30 (m, 6H), 7.26-7.19 (m, 1H). | 5.9 (428.8)+ |
| 36 | C27H21NO4S | 455.53 | 1H NMR (400 MHz, DMSO-d6): 13.11 (s, 1H), 8.44 (d, J = 1.8 Hz, 1H), 8.09 (d, J = 8.0 Hz, 1H), 7.99 (d, J = 8.7 Hz, 1H), 7.91 (d, J = 8.1 Hz, 1H), 7.81-7.74 (m, 2H), 7.71-7.54 (m, 4H), 7.48 (m, 2H), 7.30-7.19 (m, 3H), 3.78 (q, J = 7.1 Hz, 2H), 1.07 (t, J = 7.1 Hz, 3H) | 7.2 (453.70)− |
| 37 | C25H17FN2O5S | 476.48 | 1H NMR (400 MHz, DMSO-d6): 13.40 (s, 1H), 10.21 (s, 1H), 8.57-8.49 (m, 2H), 8.13-8.06 (m, 1H), 8.04 (d, J = 8.1 Hz, 1H), 7.97 (d, J = 8.4 Hz, 1H), 7.78 (dd, J = 8.1, 2.1 Hz, 1H), 7.44 (dd, J = 9.0, 5.3 Hz, 1H), 7.39-7.22 (m, 4H), 6.92 (d, J = 8.4 Hz, 1H), 3.93 (s, 3H) | 6.4 (474.70)− |
| 38 | C24H16N2O4S | 428.47 | 1H NMR (400 MHz, DMSO-d6): 13.21 (s, 1H), 9.26 (s, 1H), 8.79 (dd, J = 4.3, 1.8 Hz, 1H), 8.47 (dd, J = 8.4, 1.8 Hz, 1H), 8.39 (dd, J = 7.3, 1.5 Hz, 1H), 8.28 (dd, J = 8.3, 1.5 Hz, 1H), 8.02 (d, J = 8.3 Hz, 2H), 7.74 (dd, J = 8.3, 7.3 Hz, 1H), 7.64-7.58 (m, 2H), 7.55 (dd, J = 8.3, 4.3 Hz, 1H), 7.43 (ddd, J = 18.1, 8.0, 1.3 Hz, 2H), 7.30 (ddd, J = 8.5, 7.5, 1.6 Hz, 1H), 7.07 (td, J = 7.6, 1.2 Hz, 1H) | 6.6 (426.70)− |
| 39 | C21H15NO4S | 377.42 | 1H NMR (400 MHz, DMSO-d6): 13.13 (s, 1H), 10.08 (s, 1H), 8.00 (d, J = 8.4 Hz, 2H), 7.72-7.70 (m, 2H), 7.61 (d, J = 8.5 Hz, 2H), 7.56-7.52 (m, 1H), 7.48 (dd, J = 7.7, 1.3 Hz, 1H), 7.44-7.39 (m, 3H), 7.33 (dd, 1H), 7.25 (td, J = 7.6, 1.2 Hz, 1H). | 6.3 (376.50)− |
| 40 | C24H16N2O4S | 428.47 | 1H NMR (400 MHz, DMSO-d6): 13.11 (s, 1H), 10.46 (s, 1H), 8.96 (d, J = 2.3 Hz, 1H), 8.75 (d, J = 2.2 Hz, 1H), 8.02 (d, J = 7.4 Hz, 1H), 7.98 (d, J = 8.7 Hz, 1H), 7.87-7.83 (m, 3H), 7.60 (ddd, 1H), 7.48-7.41 (m, 3H), 7.38-7.36 (m, 2H), 7.30 (td, J = 7.4, 1.9 Hz, 1H). | 6.1 (428.8)+ |
| 41 | C25H18N2O4S | 442.49 | 1H NMR (400 MHz, DMSO-d6): 13.14 (s, 1H), 10.82 (s, 1H), 8.72 (s, 1H), 8.17 (d, J = 7.9 Hz, 1H), 8.14-7.96 (m, 5H), 7.85-7.61 (m, 5H), 6.90 (d, J = 7.4 Hz, 1H), 2.27 (s, 3H) | 6.7 (442.8)+ |
| 42 | C23H20N2O5S | 436.49 | 1H NMR (300 MHz, DMSO-d6): 13.20 (s, 1H, very weak visible), 10.02 (s, 1H), 8.78 (s, 1H), 8.09 (t, J = 6.7 Hz, 2H), 7.64 (d, J = 8.9 Hz, 1H), 7.50 (d, J = 7.7 Hz, 1H), 7.39 (d, J = 4.1 Hz, 2H), 7.21 (dq, J = 8.0, 4.3 Hz, 1H), 6.82 (d, J = 9.0 Hz, 1H), 3.74 (s, 3H), 2.41 (s, 3H), 1.90 (s, 3H). | 7.9 (437.4)+ |
| 43 | C25H16ClNO4S | 461.92 | 1H NMR (400 MHz, DMSO-d6): 13.12 (s, 1H), 10.22 (s, 1H), 8.40 (d, J = 1.8 Hz, 1H), 8.07-8.00 (m, 2H), 7.90 (dd, J = 8.5, 4.1 Hz, 3H), 7.72 (dd, J = 8.6, 1.9 Hz, 1H), 7.53 (dd, J = 8.8, 2.2 Hz, 1H), 7.46-7.42 (m, 2H), 7.42-7.36 (m, 3H), 7.25 (d, J = 7.6 Hz, 1H). | 7.1 (459.80)− |
| 44 | C24H17N3O5S | 459.48 | 1H NMR (400 MHz, DMSO-d6): 13.35 (s, 1H), 9.20 (s, 1H), 8.79-8.72 (m, 2H), 8.50 (dd, J = 8.5, 1.8 Hz, 1H), 8.32 (d, J = 8.4 Hz, 1H), 8.12 (dd, J = 8.1, 0.9 Hz, 1H), 8.04 (dd, J = 8.1, 2.1 Hz, 1H), 7.50-7.44 (m, 2H), 7.42 (dd, J = 7.7, 1.5 Hz, 1H), 7.34 (td, J = 8.4, 7.9, 1.6 Hz, 1H), 7.15-7.05 (m, 2H), 4.02 (s, 3H) | 6.1 (460.0)+ |
| 45 | C26H18FNO5S | 475.49 | 1H NMR (400 MHz, DMSO-d6): 13.41 (s, 1H), 10.14 (s, 1H), 8.57 (d, J = 8.3 Hz, 1H), 8.13 (dd, J = 8.2, 1.5 Hz, 1H), 8.03 (d, J = 8.4 Hz, 1H), 7.85 (t, J = 7.8 Hz, 1H), 7.49-7.31 (m, 5H), 7.25-7.11 (m, 3H), 6.95 (d, J = 8.4 Hz, 1H), 3.96 (s, 3H) | 6.8 (473.80)− |
| 46 | C26H19NO4S | 441.50 | 1H NMR (400 MHz, DMSO-d6): 13.11 (s, 1H), 10.10 (s, 1H), 8.37 (d, J = 1.8 Hz, 1H), 7.98 (d, J = 8.1 Hz, 1H), 7.89 (td, J = 8.3, 2.0 Hz, 4H), | 7.0 (439.80)− |

TABLE 2-continued

| Cpd. No. | Formula | Mass | NMR | LCMS (M + H) |
|---|---|---|---|---|
| | | | 7.70 (dd, J = 8.7, 1.9 Hz, 1H), 7.62 (ddd, J = 8.2, 6.8, 1.3 Hz, 1H), 7.54 (ddd, J = 8.1, 6.9, 1.2 Hz, 1H), 7.40 (d, J = 8.2 Hz, 2H), 7.32 (d, J = 7.8 Hz, 1H), 7.25 (d, J = 1.6 Hz, 1H), 7.11-7.02 (m, 1H), 2.31 (s, 3H). | |
| 47 | C23H19NO5S | 421.47 | 1H NMR (400 MHz, DMSO-d6): 13.15 (s, 1H), 9.91 (s, 1H), 8.00 (d, J = 1.8 Hz, 1H), 7.99 (d, J = 1.9 Hz, 1H), 7.69-7.64 (m, 2H), 7.62 (d, J = 1.9 Hz, 1H), 7.48 (dd, J = 7.6, 1.1 Hz, 1H), 7.40-7.35 (m, 2H), 7.24-7.16 (m, 1H), 6.82-6.73 (m, 2H), 3.71 (s, 3H), 2.49 (s, 3H). | 8.3 (420.00)− |
| 48 | C21H15BrN2O5S | 487.33 | 1H NMR (400 MHz, DMSO-d6): 13.14 (s, 1H), 10.32 (s, 1H), 8.35 (d, J = 2.2 Hz, 1H), 8.07 (d, J = 2.2 Hz, 1H), 7.98 (d, J = 8.3 Hz, 2H), 7.60 (d, J = 8.3 Hz, 2H), 7.53 (d, J = 7.6 Hz, 1H), 7.47 (t, J = 7.5 Hz, 1H), 7.39 (d, J = 7.5 Hz, 1H), 7.32 (t, J = 7.2 Hz, 1H), 3.83 (s, 3H). | 6.6 (448.8)+ |
| 49 | C25H18N2O4S | 442.49 | 1H NMR (400 MHz, DMSO-d6): 13.23 (s, 1H), 10.19 (s, 1H), 8.42 (d, J = 1.5 Hz, 1H), 8.34 (d, J = 1.1 Hz, 1H), 7.96-7.86 (m, 3H), 7.66-7.58 (m, 2H), 7.55-7.39 (m, 5H), 7.30-7.23 (m, 1H), 2.42 (s, 3H). | 8.0 (442.9)+ |
| 50 | C25H18N2O4S | 442.49 | 1H NMR (400 MHz, DMSO-d6): 13.25 (s, 1H), 10.19 (s, 1H), 8.69 (s, 1H), 8.31 (s, 1H), 7.92 (d, J = 9.4 Hz, 4H), 7.68 (d, J = 8.7 Hz, 1H), 7.61 (t, J = 7.4 Hz, 1H), 7.51 (t, J = 7.7 Hz, 2H), 7.43 (s, 1H), 7.34 (d, J = 8.3 Hz, 1H), 7.28 (t, J = 7.5 Hz, 1H), 2.24 (s, 3H). | 7.6 (443.0)+ |
| 51 | C25H18N2O4S | 442.49 | 1H NMR (400 MHz, DMSO-d6): 12.99 (s, 1H), 10.22 (s, 1H), 8.34 (s, 1H), 8.03-7.82 (m, 5H), 7.65 (dd, J = 24.0, 8.3 Hz, 2H), 7.58-7.46 (m, 2H), 7.41 (t, J = 7.8 Hz, 1H), 7.33 (d, J = 8.1 Hz, 1H), 7.26 (t, J = 7.6 Hz, 1H), 2.44 (s, 3H). | 7.7 (443.0)+ |
| 52 | C23H15N3O4S | 429.45 | 1H NMR (400 MHz, DMSO-d6): 13.41 (s, 1H), 9.43 (s, 1H), 8.81 (dd, J = 4.3, 1.8 Hz, 1H), 8.73 (d, J = 2.0 Hz, 1H), 8.45 (dd, J = 8.4, 1.8 Hz, 1H), 8.37 (dd, J = 7.3, 1.4 Hz, 1H), 8.27 (dd, J = 8.3, 1.5 Hz, 1H), 8.12 (d, J = 8.1 Hz, 1H), 8.01 (dd, J = 8.1, 2.1 Hz, 1H), 7.72 (t, J = 7.8 Hz, 1H), 7.52 (dd, J = 8.4, 4.2 Hz, 1H), 7.45 (ddd, J = 7.7, 3.6, 1.3 Hz, 2H), 7.35 (td, J = 8.3, 7.9, 1.6 Hz, 1H), 7.12 (td, J = 7.5, 1.2 Hz, 1H) | 5.9 (429.9)+ |
| 53 | C25H17NO4S | 427.48 | 1H NMR (400 MHz, DMSO-d6): 13.15 (s, 1H), 10.37 (s, 1H), 8.67 (d, J = 8.6 Hz, 1H), 8.15 (d, J = 8.2 Hz, 1H), 8.09 (dd, J = 7.4, 1.3 Hz, 1H), 7.98 (dd, J = 8.0, 1.5 Hz, 1H), 7.96-7.91 (m, 2H), 7.58-7.44 (m, 3H), 7.43-7.39 (m, 3H), 7.38-7.33 (m, 2H), 7.19 (dq, J = 8.2, 4.4 Hz, 1H). | 6.74 (428.0)+ |
| 54 | C25H18N2O4S | 442.49 | 1H NMR (400 MHz, DMSO-d6): 13.14 (s, 1H), 10.58 (s, 1H), 9.87 (s, 1H), 8.28 (d, J = 1.1 Hz, 1H), 8.23-8.15 (m, 1H), 8.08 (dd, J = 7.4, 1.0 Hz, 1H), 7.87 (d, J = 8.3 Hz, 2H), 7.78 (dd, J = 8.5, 7.4 Hz, 1H), 7.41 (ddd, J = 10.5, 7.2, 1.3 Hz, 3H), 7.30-7.17 (m, 3H), 2.48 (s, 3H). | 5.3 (442.9)+ |
| 55 | C24H16N2O4S | 428.47 | 1H NMR (400 MHz, DMSO-d6): 13.13 (s, 1H), 10.34 (s, 1H), 8.95 (dd, J = 4.2, 1.7 Hz, 1H), 8.42 (dd, J = 11.4, 2.0 Hz, 2H), 7.97 (d, J = 8.9 Hz, 1H), 7.92 (d, J = 2.1 Hz, 1H), 7.91-7.87 (m, 2H), 7.52 (dd, J = 8.3, 4.2 Hz, 1H), 7.47-7.37 (m, 5H), 7.26 (td, J = 7.2, 1.9 Hz, 1H). | 7.0 (426.70)− |
| 56 | C23H19NO5S | 421.47 | 1H NMR (400 MHz, DMSO-d6) = 13.15 (s, 1H), 9.83 (s, 1H), 8.06-7.94 (m, 2H), 7.69-7.59 (m, 2H), 7.55-7.32 (m, 5H), 7.23 (td, J = 7.4, 1.6 Hz, 1H), 6.90 (d, J = 8.7 Hz, 1H), 3.74 (s, 3H), 1.91 (s, 3H). | 6.5 (419.90)− |
| 57 | C27H21NO5S | 471.53 | 1H NMR (400 MHz, DMSO-d6): 12.73 (s, 1H), 10.16 (s, 1H), 8.34 (d, J = 1.4 Hz, 1H), 7.96-7.90 (m, 3H), 7.72 (dd, J = 8.7, 1.9 Hz, 1H), 7.64 (ddd, J = 8.2, 7.0, 1.2 Hz, 1H), 7.60 (d, J = 7.9 Hz, 1H), 7.55 (td, J = 7.6, 7.0, 1.1 Hz, 1H), 7.45-7.36 (m, 3H), 7.24 (ddd, J = 7.7, 6.7, 2.1 Hz, 1H), 7.08 (d, J = 1.1 Hz, 1H), 6.98 (dd, J = 7.9, 1.3 Hz, 1H), 4.07 (q, J = 6.9 Hz, 2H), 1.36 (t, J = 6.9 Hz, 3H). | 6.9 (472.2)+ |
| 58 | C28H23NO6S | 501.56 | 1H NMR (400 MHz, DMSO-d6): 12.72 (s, 1H), 10.09 (s, 1H), 8.57 (d, J = 8.5 Hz, 1H), 8.16 (dd, 1H), 8.06 (d, J = 8.4 Hz, 1H), 7.63 (d, J = 7.9 | 7.0 (502.00)− |

TABLE 2-continued

| Cpd. No. | Formula | Mass | NMR | LCMS (M + H) |
|---|---|---|---|---|
| | | | Hz, 1H), 7.45 (ddd, J = 8.3, 6.9, 1.2 Hz, 1H), 7.40-7.32 (m, 4H), 7.16 (td, J = 7.4, 2.0 Hz, 1H), 7.10 (d, J = 1.2 Hz, 1H), 6.96-6.93 (m, 2H), 4.11 (q, J = 6.9 Hz, 2H), 3.96 (s, 3H), 1.38 (t, J = 6.9 Hz, 3H). | |
| 59 | C24H17N3O4S | 443.48 | 1H NMR (400 MHz, DMSO-d6): 13.37 (s, 1H), 9.37 (s, 1H), 8.80 (d, J = 2.9 Hz, 1H), 8.50 (s, 1H), 8.44 (d, J = 7.8 Hz, 1H), 8.36 (d, J = 7.2 Hz, 1H), 8.27 (d, J = 8.1 Hz, 1H), 7.81-7.67 (m, 2H), 7.52 (dd, J = 8.2, 4.2 Hz, 1H), 7.48-7.38 (m, 2H), 7.38-7.28 (m, 1H), 7.10 (t, J = 7.4 Hz, 1H). Signal of methyl group covered by DMSO | 6.3 (444.0)+ |
| 60 | C24H17N3O4S | 443.48 | 1H NMR (400 MHz, DMSO-d6): 9.28 (s, 1H), 8.75 (s, 1H), 8.52-8.33 (m, 2H), 8.28 (d, J = 8.2 Hz, 1H), 7.94 (s, 2H), 7.73 (t, J = 7.8 Hz, 1H), 7.51 (s, 1H), 7.42 (dd, J = 22.5, 8.0 Hz, 2H), 7.31 (t, J = 7.9 Hz, 1H), 7.10 (t, J = 7.6 Hz, 1H), 2.67 (s, 3H). Carboxylic proton not visible. | 7.4 (444.0)+ |
| 61 | C24H17N3O4S | 443.48 | 1H NMR (300 MHz, DMSO-d6): 13.33 (s, 1H), 9.32 (s, 1H), 8.75 (dd, J = 4.3, 1.8 Hz, 1H), 8.65 (s, 1H), 8.43 (dd, J = 8.4, 1.8 Hz, 1H), 8.37 (dd, J = 7.3, 1.5 Hz, 1H), 8.27 (dd, J = 8.3, 1.5 Hz, 1H), 8.04 (s, 1H), 7.79-7.67 (m, 1H), 7.56-7.42 (m, 2H), 7.42-7.27 (m, 2H), 7.11 (td, J = 7.4, 1.5 Hz, 1H). Protons from methyl group are covered by peak from DMSO. | 7.2 (444.4)+ |
| 62 | C26H19NO5S | 457.50 | 1H NMR (400 MHz, DMSO-d6): 12.79 (s, 1H), 10.32 (s, 1H), 8.65 (dd, J = 8.5, 1.1 Hz, 1H), 8.15 (d, J = 8.2 Hz, 1H), 8.09 (dd, J = 7.4, 1.2 Hz, 1H), 7.97 (dd, J = 8.3, 1.4 Hz, 1H), 7.65 (d, J = 7.9 Hz, 1H), 7.56-7.33 (m, 6H), 7.19 (ddd, J = 7.6, 5.2, 3.5 Hz, 1H), 7.11 (d, J = 1.3 Hz, 1H), 6.93 (dd, J = 7.9, 1.4 Hz, 1H), 3.86 (s, 3H). | 8.3 (458.0)+ |
| 63 | C26H20N2O5S | 472.52 | 1H NMR (400 MHz, DMSO-d6): 13.27 (s, 1H), 10.15 (s, 1H), 8.61-8.53 (m, 1H), 8.34 (d, J = 1.7 Hz, 1H), 8.13-8.07 (m, 1H), 8.00 (d, J = 8.4 Hz, 1H), 7.55 (dd, J = 1.9, 0.8 Hz, 1H), 7.48-7.32 (m, 5H), 7.22-7.15 (m, 1H), 6.93 (d, J = 8.5 Hz, 1H), 3.94 (s, 3H), 2.48 (s, 3H). | 6.6 (473.1)+ |
| 64 | C26H19NO4S | 441.50 | 1H NMR (400 MHz, DMSO-d6): 13.04 (s, 1H), 9.85 (s, 1H), 8.30 (d, J = 1.5 Hz, 1H), 7.96 (d, J = 7.8 Hz, 1H), 7.86 (d, J = 8.8 Hz, 1H), 7.83 (d, J = 8.1 Hz, 1H), 7.76-7.71 (m, 2H), 7.67 (dd, J = 8.6, 1.9 Hz, 1H), 7.58 (ddd, J = 8.2, 6.9, 1.3 Hz, 1H), 7.50 (ddd, J = 8.1, 7.0, 1.2 Hz, 1H), 7.38-7.31 (m, 2H), 7.28-7.22 (m, 1H), 7.19-7.10 (m, 2H), 2.22 (s, 3H). | 6.7 (440.00)− |
| 65 | C24H15FN2O4S | 446.46 | 1H NMR (400 MHz, DMSO-d6): 13.75 (s, 1H), 10.19 (s, 1H), 8.43 (t, J = 1.5 Hz, 1H), 8.34 (d, J = 1.9 Hz, 1H), 7.90 (dt, J = 9.3, 4.8 Hz, 3H), 7.69 (dd, J = 10.9, 1.6 Hz, 1H), 7.63-7.58 (m, 2H), 7.51-7.43 (m, 4H), 7.28 (ddd, J = 8.1, 6.9, 1.6 Hz, 1H). | 6.3 (447.0)+ |
| 66 | C23H15N3O4S | 429.45 | 1H NMR (400 MHz, DMSO-d6): 13.20 (s, 1H), 9.58 (s, 1H), 8.86 (d, J = 1.8 Hz, 1H), 8.77 (d, J = 1.8 Hz, 1H), 8.38 (dd, J = 7.4, 1.3 Hz, 1H), 8.30 (dd, J = 8.4, 1.3 Hz, 1H), 7.99-7.95 (m, 2H), 7.92 (dd, J = 8.4, 7.5 Hz, 1H), 7.46-7.38 (m, 4H), 7.37-7.31 (m, 1H), 7.16 (td, J = 7.4, 1.5 Hz, 1H). | 6.2 (430.0)+ |
| 67 | C24H21NO6S | 451.50 | 1H NMR (400 MHz, DMSO-d6): 12.79 (s, 1H), 9.88 (s, 1H), 7.68 (d, J = 7.9 Hz, 1H), 7.63 (d, J = 8.8 Hz, 1H), 7.46 (d, J = 7.8 Hz, 1H), 7.41-7.34 (m, 2H), 7.25 (d, J = 1.3 Hz, 1H), 7.19 (ddd, J = 8.4, 6.5, 2.2 Hz, 1H), 7.14 (dd, J = 7.8, 1.4 Hz, 1H), 6.79 (d, J = 2.6 Hz, 1H), 6.74 (dd, J = 8.8, 2.7 Hz, 1H), 3.86 (s, 3H), 3.70 (s, 3H). | 6.4 (452.0)+ |
| 68 | C25H16FNO4S | 445.47 | 1H NMR (400 MHz, DMSO-d6): 13.15 (s, 1H), 10.41 (s, 1H), 8.64 (d, J = 8.3 Hz, 1H), 8.13 (d, J = 8.2 Hz, 1H), 8.05 (dd, J = 7.4, 1.2 Hz, 1H), 7.96 (dd, J = 7.7, 1.9 Hz, 1H), 7.93 (d, J = 1.8 Hz, 1H), 7.92 (d, J = 1.9 Hz, 1H), 7.55-7.51 (m, 1H), 7.51-7.48 (m, 1H), 7.47-7.42 (m, 1H), 7.40-7.31 (m, 3H), 7.25 (dq, J = 8.5, 5.1, 4.0 Hz, 2H). | 6.8 (444.00)− |
| 69 | C25H16FNO4S | 445.47 | 1H NMR (400 MHz, DMSO-d6): 13.48 (s, 1H), 10.48 (s, 1H), 8.71-8.64 (m, 1H), 8.17-8.10 (m, | 6.7 (444.00)− |

TABLE 2-continued

| Cpd. No. | Formula | Mass | NMR | LCMS (M + H) |
|---|---|---|---|---|
| | | | 1H), 8.04 (dd, J = 7.4, 1.2 Hz, 1H), 7.99-7.93 (m, 1H), 7.84 (t, J = 8.1 Hz, 1H), 7.54-7.33 (m, 6H), 7.22-7.13 (m, 3H) | |
| 70 | C24H16N2O4S | 428.47 | 1H NMR (400 MHz, DMSO-d6): 13.34 (s, 1H), 10.43 (s, 1H), 8.66 (dd, J = 8.2, 1.5 Hz, 1H), 8.56 (dd, J = 2.1, 0.8 Hz, 1H), 8.12 (d, J = 8.2 Hz, 1H), 8.04 (ddd, J = 7.4, 4.1, 1.1 Hz, 2H), 7.93 (dd, J = 7.5, 2.0 Hz, 1H), 7.82 (dd, J = 8.1, 2.1 Hz, 1H), 7.50 (dd, J = 8.2, 7.4 Hz, 1H), 7.47-7.35 (m, 5H), 7.20 (ddd, J = 8.0, 6.9, 1.8 Hz, 1H) | 6.2 (429.0)+ |
| 71 | C25H18N2O5S | 458.49 | 1H NMR (400 MHz, DMSO-d6): 13.31 (s, 1H), 10.33 (s, 1H), 8.64 (d, J = 8.7 Hz, 1H), 8.13 (d, J = 8.2 Hz, 1H), 8.05-8.02 (m, 2H), 7.93 (d, 1H), 7.51 (t, 1H), 7.48 (d, J = 1.5 Hz, 1H), 7.44-7.34 (m, 5H), 7.21 (ddd, J = 7.7, 6.3, 2.2 Hz, 1H), 3.88 (s, 3H). | 6.1 (459.0)+ |
| 72 | C22H18N2O5S | 422.46 | 1H NMR (400 MHz, Methanol-d4): 8.77 (s, 1H), 8.19 (s, 1H), 8.06 (s, 1H), 7.76 (d, J = 8.5 Hz, 1H), 7.55-7.44 (m, 2H), 7.41-7.33 (m, 1H), 7.19 (t, J = 7.5 Hz, 1H), 6.70 (s, 2H), 3.72 (s, 3H), 2.49 (s, 3H). Protons from carboxyl and sulfonamide group are invisible. | 7.4 (423.0)+ |
| 73 | C23H15NO5S | 417.44 | 1H NMR (400 MHz, DMSO-d6): 13.14 (s, 1H), 10.73 (s, 1H), 7.96-7.88 (m, 2H), 7.63 (d, J = 7.7 Hz, 1H), 7.51 (dd, J = 7.7, 1.5 Hz, 1H), 7.42 (m, 5H), 7.37-7.29 (m, 3H), 7.26 (ddd, J = 8.0, 6.3, 1.9 Hz, 1H) | 6.5 (415.95)− |
| 74 | C25H18N2O4S | 442.49 | 1H NMR (400 MHz, DMSO-d6): 13.27 (s, 1H), 10.35 (s, 1H), 8.65 (d, J = 8.3 Hz, 1H), 8.33 (d, J = 1.9 Hz, 1H), 8.13 (d, J = 8.2 Hz, 1H), 8.02 (dd, J = 7.4, 1.3 Hz, 1H), 7.92 (dd, J = 7.6, 1.8 Hz, 1H), 7.54-7.49 (m, 2H), 7.44-7.35 (m, 5H), 7.21 (ddd, J = 7.8, 6.3, 2.3 Hz, 1H), 2.47 (s, 3H). | 6.5 (443.0)+ |
| 75 | C26H19NO4S | 441.50 | 1H NMR (400 MHz, DMSO-d6): 13.15 (s, 1H), 10.30 (s, 1H), 8.70 (d, J = 8.6 Hz, 1H), 8.04 (d, J = 8.4 Hz, 1H), 7.99 (d, J = 7.6 Hz, 1H), 7.96-7.92 (m, 2H), 7.53 (ddd, J = 8.3, 6.8, 1.3 Hz, 1H), 7.46-7.32 (m, 8H), 7.16 (ddd, J = 8.4, 6.1, 2.7 Hz, 1H), 2.63 (s, 3H). | 8.9 (442.0)+ |
| 76 | C23H17NO6S2 | 467.52 | 1H NMR (400 MHz, DMSO-d6): 13.18 (s, 1H), 10.41 (s, 1H), 8.01 (d, J = 8.3 Hz, 1H), 7.86 (dd, J = 7.1, 1.7 Hz, 1H), 7.84-7.68 (m, 3H), 7.63 (dd, J = 7.5, 1.5 Hz, 1H), 7.47-7.41 (m, 1H), 7.38 (dd, J = 8.2, 1.4 Hz, 1H), 7.33 (t, J = 7.5 Hz, 1H), 5.55 (dd, J = 8.4, 4.2 Hz, 1H), 5.57-4.03 (m, 1H). | 7.2 (467.9)+ |
| 77 | C24H17N3O4S | 443.48 | 1H NMR (400 MHz, DMSO-d6): 13.48 (s, 1H), 9.72 (s, 1H), 8.93 (s, 1H), 8.86-8.79 (m, 1H), 8.43-8.36 (m, 1H), 8.17-8.07 (m, 3H), 7.61 (d, J = 8.5 Hz, 1H), 7.49 (dt, J = 13.0, 7.0 Hz, 3H), 7.37-7.31 (m, 1H), 7.07 (t, J = 7.6 Hz, 1H), 2.88 (s, 3H). | 7.8 (444.0)+ |
| 78 | C25H19NO4S | 429.49 | 1H NMR (400 MHz, DMSO-d6): 13.16 (s, 1H), 10.01 (s, 1H), 7.97 (d, J = 8.0 Hz, 2H), 7.68 (d, J = 8.0 Hz, 2H), 7.56 (d, J = 7.6 Hz, 1H), 7.46 (dd, J = 17.6, 7.8 Hz, 2H), 7.31-7.21 (m, 3H), 7.19 (d, J = 5.0 Hz, 2H), 7.13 (d, J = 7.4 Hz, 1H), 2.77 (t, J = 8.2 Hz, 2H), 2.64 (t, J = 8.2 Hz, 2H). | 6.9 (428.00)− |
| 79 | C25H19N3O5S | 473.51 | 1H NMR (300 MHz, DMSO-d6): 13.34 (s, 1H), 9.15 (s, 1H), 8.76 (dd, J = 4.3, 1.8 Hz, 1H), 8.52-8.48 (m, 2H), 8.31 (d, J = 8.4 Hz, 1H), 7.79-7.77 (m, 1H), 7.50-7.45 (m, 2H), 7.42-7.38 (m, 1H), 7.36-7.30 (m, 1H), 7.14-7.06 (m, 2H), 4.03 (s, 3H). | 6.5 (474.5)+ |
| 80 | C26H19NO4S | 441.50 | 1H NMR (400 MHz, DMSO-d6): 12.99 (s, 1H), 10.32 (s, 1H), 8.66 (d, J = 8.6 Hz, 1H), 8.14 (d, J = 8.2 Hz, 1H), 8.08 (dd, J = 7.4, 1.2 Hz, 1H), 7.97 (dd, J = 8.1, 1.4 Hz, 1H), 7.80 (d, J = 8.0 Hz, 1H), 7.58-7.39 (m, 3H), 7.39-7.31 (m, 3H), 7.19 (d, J = 7.7 Hz, 3H), 2.53 (s, 3H) | 6.9 (442.0)+ |
| 81 | C24H18N2O4S | 430.48 | 1H NMR (400 MHz, DMSO-d6): 10.09 (s, 1H), 9.00 (s, 1H), 8.08 (s, 2H), 7.60 (d, J = 7.7 Hz, 1H), 7.52-7.39 (m, 2H), 7.31-7.12 (m, 6H), 2.81 (t, J = 8.2 Hz, 2H), 2.67 (t, J = 8.1 Hz, 2H). Carboxylic proton not visible. | 8.0 (431.0)+ |
| 82 | C24H17N3O5S | 459.48 | 1H NMR (400 MHz, DMSO-d6): 13.14 (s, 1H), 10.29 (s, 1H), 8.52 (s, 1H), 8.24 (d, J = 2.1 Hz, | 7.9 (460.0)+ |

TABLE 2-continued

| Cpd. No. | Formula | Mass | NMR | LCMS (M + H) |
|---|---|---|---|---|
| | | | 1H), 7.89-7.83 (m, 3H), 7.78 (d, J = 8.7 Hz, 1H), 7.48-7.39 (m, 3H), 7.38-7.34 (m, 2H), 7.29 (td, J = 7.4, 1.6 Hz, 1H), 4.00 (s, 3H). | |
| 83 | C23H15NO4S2 | 433.50 | 1H NMR (400 MHz, DMSO-d6): 13.15 (s, 1H), 10.33 (s, 1H), 8.38 (s, 1H), 8.05 (d, J = 8.1 Hz, 1H), 7.98 (d, J = 8.1 Hz, 1H), 7.92 (d, J = 8.1 Hz, 2H), 7.45-7.38 (m, 5H), 7.33 (t, J = 7.6 Hz, 1H), 7.24 (t, J = 7.6 Hz, 2H). | 8.4 (432.00)− |
| 84 | C29H19NO4S | 477.54 | 1H NMR (400 MHz, DMSO-d6): 13.36 (s, 1H), 10.48 (s, 1H), 8.94-8.87 (m, 1H), 8.68 (d, J = 7.1 Hz, 1H), 8.35 (d, J = 4.7 Hz, 1H), 8.17-8.06 (m, 3H), 7.90-7.84 (m, 1H), 7.75-7.63 (m, 3H), 7.60 (d, J = 7.4 Hz, 1H), 7.55-7.48 (m, 1H), 7.38 (ddd, J = 13.9, 7.4, 4.5 Hz, 3H), 7.29-7.18 (m, 1H). | 7.2 (478.1)+ |
| 86 | C28H21NO4S | 467.54 | 1H NMR (400 MHz, DMSO-d6): 13.13 (s, 1H), 10.13 (s, 1H), 7.92-7.88 (m, 2H), 7.71 (dt, J = 7.4, 1.7 Hz, 1H), 7.53-7.39 (m, 8H), 7.29-7.19 (m, 3H), 7.14 (td, J = 7.2, 2.0 Hz, 1H), 6.97 (d, J = 7.1 Hz, 1H), 2.00 (s, 3H). | 9.3 (468.0)+ |
| 87 | C28H19NO4S | 465.53 | 1H NMR (400 MHz, DMSO-d6): 13.13 (s, 1H), 10.04 (s, 1H), 7.95 (s, 1H), 7.91 (d, J = 8.1 Hz, 2H), 7.86 (d, J = 8.4 Hz, 2H), 7.59 (dd, J = 8.0, 1.7 Hz, 1H), 7.52-7.34 (m, 8H), 7.25 (td, J = 7.4, 1.7 Hz, 1H), 3.67 (s, 2H). | 9.0 (466.1)+ |
| 88 | C25H18N2O4S | 442.49 | 1H NMR (400 MHz, DMSO-d6): 10.47 (s, 1H), 8.76 (s, 1H), 8.12 (s, 2H), 7.96 (s, 2H), 7.56 (d, J = 7.7 Hz, 1H), 7.46 (s, 3H), 7.22 (d, J = 35.5 Hz, 4H), 2.38 (s, 3H). Carboxylic proton not visible. | 7.6 (443.0)+ |
| 89 | C22H14N2O5S | 418.43 | 1H NMR (400 MHz, DMSO-d6): 13.33 (s, 1H), 10.80 (s, 1H), 8.63 (s, 1H), 8.03 (d, J = 8.1 Hz, 1H), 7.85 (dd, J = 8.1, 2.1 Hz, 1H), 7.60 (d, J = 7.7 Hz, 1H), 7.51 (d, J = 7.6 Hz, 1H), 7.48-7.36 (m, 3H), 7.35-7.19 (m, 4H) | 5.9 (419.0)+ |
| 90 | C24H20N2O4S | 432.50 | 1H NMR (400 MHz, DMSO-d6): 13.16 (s, 1H), 9.79 (s, 1H), 7.96 (d, J = 8.4 Hz, 2H), 7.67 (d, J = 8.3 Hz, 2H), 7.60-7.49 (m, 2H), 7.46-7.38 (m, 1H), 7.28-7.20 (m, 1H), 7.16-7.06 (m, 3H), 7.02-6.96 (m, 1H), 4.40 (s, 2H), 3.41 (t, J = 5.9 Hz, 2H), 2.77 (t, J = 6.0 Hz, 2H). | 6.9 (433.1)+ |
| 91 | C23H16N4O5S | 460.47 | 1H NMR (400 MHz, DMSO-d6): 10.48 (s, 1H) 8.56 (s, 1H), 8.51 (s, 1H), 8.24 (d, J = 2.0 Hz, 1H), 7.99 (d, J = 8.1 Hz, 1H), 7.91-7.81 (m, 2H), 7.78 (d, J = 8.7 Hz, 1H), 7.51-7.38 (m, 3H), 7.27 (t, J = 7.2 Hz, 1H), 4.01 (s, 3H). Carboxylic proton not visible. | 6.9 (461.0)+ |
| 92 | C27H18N2O4S | 466.51 | 1H NMR (400 MHz, DMSO-d6): 13.34 (s, 1H), 10.09 (s, 1H), 8.70 (s, 1H), 7.95-7.86 (m, 5H), 7.60 (d, J = 8.1 Hz, 1H), 7.51-7.33 (m, 6H), 7.27 (td, J = 7.4, 1.5 Hz, 1H), 3.70 (s, 2H). | 6.6 (467.4)+ |
| 93 | C24H19NO4S | 417.48 | 1H NMR (400 MHz, DMSO-d6): 12.99 (s, 1H), 9.93 (s, 1H), 7.99 (d, J = 8.4 Hz, 2H), 7.71 (d, J = 8.2 Hz, 2H), 7.60 (dd, J = 7.7, 1.6 Hz, 1H), 7.51 (dd, J = 8.2, 1.2 Hz, 1H), 7.44 (td, J = 8.2, 7.8, 1.6 Hz, 1H), 7.28 (td, J = 7.5, 1.4 Hz, 1H), 7.11 (s, 4H), 4.13 (tt, J = 9.0, 6.4 Hz, 1H), 3.34 (m, J = 16.9, 7.7 Hz, 4H) | 6.7 (416.10)− |
| 94 | C27H20N2O4S | 468.53 | 1H NMR (400 MHz, DMSO-d6): 13.36 (s, 1H), 10.20 (s, 1H), 8.71 (dd, J = 2.0, 1.0 Hz, 1H), 8.01-7.94 (m, 2H), 7.69 (dt, J = 7.5, 1.7 Hz, 1H), 7.53-7.44 (m, 6H), 7.29 (ddd, J = 7.7, 6.2, 2.6 Hz, 1H), 7.24-7.17 (m, 2H), 7.12 (td, J = 7.3, 2.2 Hz, 1H), 6.94 (dd, J = 7.4, 1.3 Hz, 1H), 2.00 (s, 3H). | 6.8 (469.3)+ |
| 95 | C20H13BrN2O4S | 457.31 | 1H NMR (400 MHz, DMSO-d6): 13.38 (s, 1H), 10.34-10.33 (m, 1H), 8.78-8.77 (m, 1H), 8.13-8.05 (m, 2H), 7.79 (t, J = 1.9 Hz, 1H), 7.73-7.70 (m, 1H), 7.59-7.56 (m, 1H), 7.54-7.46 (m, 2H), 7.41-7.29 (m, 3H). | 6.2 (457.2)+ |
| 96 | C26H18N2O4S | 454.50 | 1H NMR (400 MHz, DMSO-d6): 13.31 (s, 1H), 10.22 (s, 1H), 8.74 (s, 1H), 7.92 (d, J = 1.5 Hz, 2H), 7.88 (t, J = 1.8 Hz, 1H), 7.82 (d, J = 7.7 Hz, 1H), 7.62 (d, J = 7.7 Hz, 1H), 7.55-7.47 (m, 2H), 7.47-7.38 (m, 4H), 7.38-7.31 (m, 3H), 7.28 (td, J = 7.3, 1.7 Hz, 1H) | 6.5 (455.3)+ |
| 97 | C25H18N2O4S | 442.49 | 1H NMR (400 MHz, DMSO-d6): 13.38 (s, 1H), 10.33 (s, 1H), 8.68 (d, J = 8.4 Hz, 1H), 8.55 (dd, | 6.4 (443.4)+ |

TABLE 2-continued

| Cpd. No. | Formula | Mass | NMR | LCMS (M + H) |
|---|---|---|---|---|
| | | | J = 2.0, 0.8 Hz, 1H), 8.05 (dd, J = 8.0, 0.9 Hz, 1H), 7.98 (d, J = 8.7 Hz, 1H), 7.94 (d, J = 7.5 Hz, 1H), 7.82 (dd, J = 8.1, 2.1 Hz, 1H), 7.47-7.34 (m, 6H), 7.19 (td, J = 7.2, 1.7 Hz, 1H), 2.60 (s, 3H). | |
| 98 | C19H11ClN4O4S2 | 458.90 | 1H NMR (400 MHz, DMSO-d6): 13.36 (s, 1H), 10.66 (s, 1H), 8.67 (d, J = 2.0 Hz, 1H), 8.04 (d, J = 8.1 Hz, 1H), 7.94 (dd, J = 8.1, 2.1 Hz, 1H), 7.71 (d, J = 4.5 Hz, 1H), 7.57-7.46 (m, 3H), 7.42-7.35 (m, 1H), 7.23 (d, J = 4.4 Hz, 1H). | 5.4 (459.4)+ |
| 99 | C20H11ClN4O5S | 454.85 | 1H NMR (400 MHz, DMSO-d6): 13.43 (s, 1H), 10.85 (s, 1H), 8.50 (dd, J = 2.1, 0.9 Hz, 1H), 8.06 (dd, J = 8.1, 0.9 Hz, 1H), 7.86-7.75 (m, 2H), 7.68 (d, J = 7.4 Hz, 1H), 7.56-7.43 (m, 3H), 7.35 (t, J = 7.4 Hz, 1H). | 5.9 (455.4)+ |
| 100 | C25H19N3O4S | 457.51 | 1H NMR (400 MHz, DMSO-d6): 13.41 (s, 1H), 9.70 (s, 1H), 8.72 (s, 1H), 8.44-8.29 (m, 1H), 8.13 (d, J = 8.5 Hz, 1H), 8.00 (t, J = 11.1 Hz, 2H), 7.60 (d, J = 8.4 Hz, 1H), 7.45 (t, J = 7.4 Hz, 3H), 7.32 (t, J = 8.0 Hz, 1H), 7.07 (t, J = 7.5 Hz, 1H), 2.88 (s, 3H), 2.72 (s, 3H). | 7.9 (458.0)+ |
| 101 | C23H14FN3O4S | 447.44 | 1H NMR (400 MHz, DMSO-d6): 13.42 (s, 2H), 9.67 (s, 1H), 8.79 (d, J = 4.3 Hz, 1H), 8.72 (s, 1H), 8.50-8.22 (m, 3H), 8.16-7.94 (m, 2H), 7.72 (t, J = 7.8 Hz, 1H), 7.53 (dd, J = 8.4, 4.2 Hz, 1H), 7.41-7.22 (m, 2H), 7.05 (q, J = 10.8, 9.8 Hz, 1H) | 6.1 (448.3)+ |
| 102 | C25H19N3O4S | 457.51 | 1H NMR (400 MHz, DMSO-d6): 13.33 (s, 1H), 9.72 (s, 1H), 8.80 (dd, J = 4.3, 1.8 Hz, 1H), 8.57 (d, J = 1.9 Hz, 1H), 8.38 (dd, J = 8.3, 1.8 Hz, 1H), 8.12 (d, J = 8.4 Hz, 1H), 7.86 (d, J = 2.0 Hz, 1H), 7.59 (d, J = 8.5 Hz, 1H), 7.52-7.41 (m, 3H), 7.34 (ddd, J = 8.6, 7.5, 1.6 Hz, 1H), 7.07 (td, J = 7.6, 1.1 Hz, 1H), 2.87 (s, 3H), 2.52 (s, 3H). | 6.6 (458.4)+ |
| 103 | C23H25N3O4S | 439.53 | 1H NMR (400 MHz, DMSO-d6): 13.42 (s, 1H), 9.57 (s, 1H), 8.94 (s, 1H), 8.21 (dd, J = 8.2, 1.8 Hz, 1H), 8.12 (d, J = 8.1 Hz, 1H), 7.61 (d, J = 7.6 Hz, 1H), 7.56-7.52 (m, 1H), 7.46 (t, 1H), 7.28-7.22 (m, 1H), 3.62-3.43 (m, 1H), 3.26-3.19 (m, 1H), 3.02-2.80 (m, 2H), 1.67-0.59 (m, 12H). | 7.4 (440.4)+ |
| 104 | C22H14N2O4S2 | 434.49 | 1H NMR (400 MHz, DMSO-d6): 13.27 (s, 1H), 10.45 (s, 1H), 8.68 (s, 1H), 8.38 (s, 1H), 8.04 (t, J = 8.0 Hz, 2H), 7.95 (d, J = 8.0 Hz, 1H), 7.81 (dd, J = 8.0, 2.1 Hz, 1H), 7.43 (d, J = 7.8 Hz, 3H), 7.24 (dq, J = 15.1, 7.4 Hz, 3H). | 7.4 (435.0)+ |
| 105 | C24H21N3O5S | 463.51 | 1H NMR (400 MHz, DMSO-d6): 10.04 (s, 1H), 8.39-8.14 (m, 1H), 8.13-8.00 (m, 1H), 7.64-7.17 (m, 5H), 7.12 (s, 2H), 7.07-6.90 (m, 2H), 3.52 (s, 4H), 2.91 (d, J = 49.4 Hz, 4H). | 6.7 (464.0)+ |
| 106 | C24H16FN3O4S | 461.47 | 1H NMR (400 MHz, DMSO-d6): 13.42 (s, 1H), 10.12 (s, 1H), 9.03 (dd, J = 4.3, 1.7 Hz, 1H), 8.39 (d, J = 2.0 Hz, 1H), 8.30 (dd, J = 8.3, 1.8 Hz, 1H), 8.00 (dd, J = 11.8, 8.2 Hz, 2H), 7.60 (dd, J = 8.1, 2.1 Hz, 1H), 7.53 (dd, J = 8.3, 4.3 Hz, 1H), 7.49 (d, J = 8.5 Hz, 1H), 7.42 (dd, J = 7.7, 1.7 Hz, 1H), 7.38 (dd, J = 8.1, 5.1 Hz, 1H), 7.31 (td, J = 8.9, 8.2, 1.7 Hz, 1H), 2.70 (s, 3H). | 7.0 (462.3)+ |
| 107 | C25H19N3O4S | 457.51 | 1H NMR (400 MHz, DMSO-d6): 13.38 (s, 1H), 9.74 (s, 1H), 8.72 (d, J = 5.4 Hz, 2H), 8.38 (dd, J = 8.3, 1.9 Hz, 1H), 8.18-7.94 (m, 2H), 7.61 (d, J = 8.5 Hz, 1H), 7.54-7.38 (m, 3H), 7.33 (t, J = 7.5 Hz, 1H), 7.08 (t, J = 7.5 Hz, 1H), 2.89 (s, 3H), 2.56 (s, 3H). | 7.8 (458.4)+ |
| 108 | C26H16N2O5S | 468.49 | 1H NMR (400 MHz, DMSO-d6): 13.28 (s, 1H), 10.46 (s, 1H), 8.40 (s, 1H), 8.28 (d, J = 7.3 Hz, 1H), 8.01 (d, J = 7.5 Hz, 1H), 7.77 (d, J = 8.1 Hz, 1H), 7.64 (d, J = 7.6 Hz, 1H), 7.58 (dd, J = 8.1, 2.1 Hz, 1H), 7.52-7.46 (m, 2H), 7.43-7.25 (m, 6H). | 6.3 (469.4)+ |
| 109 | C21H13N3O4S2 | 435.48 | 1H NMR (400 MHz, DMSO-d6): 9.33 (s, 1H), 8.67 (d, J = 2.1 Hz, 1H), 8.41 (d, J = 8.0 Hz, 1H), 8.08 (d, J = 8.1 Hz, 1H), 7.95 (td, J = 6.0, 2.9 Hz, 2H), 7.55 (t, J = 7.8 Hz, 1H), 7.46-7.33 (m, 3H), 7.16 (t, J = 7.4 Hz, 1H), Carboxylic and sulfonamide protons are not visible. | 7.0 (436.4)+ |

TABLE 2-continued

| Cpd. No. | Formula | Mass | NMR | LCMS (M + H) |
|---|---|---|---|---|
| 110 | C25H19N3O5S | 473.51 | 1H NMR (400 MHz, DMSO-d6): 13.36 (s, 1H), 9.12 (s, 1H), 8.72 (dd, J = 4.3, 1.7 Hz, 1H), 8.69 (s, 1H), 8.50 (dd, J = 8.5, 1.8 Hz, 1H), 8.34 (d, J = 8.4 Hz, 1H), 8.06 (s, 1H), 7.53-7.39 (m, 3H), 7.37-7.28 (m, 1H), 7.14 (d, J = 8.5 Hz, 1H), 7.10 (t, J = 7.6 Hz, 1H), 4.04 (s, 3H). | 7.6 (474.4)+ |
| 111 | C23H14FN3O4S | 447.44 | 1H NMR (400 MHz, DMSO-d6): 13.33 (s, 1H), 9.59 (s, 1H), 8.80 (dd, J = 4.3, 1.8 Hz, 1H), 8.65-8.55 (m, 1H), 8.41 (dd, J = 8.4, 1.8 Hz, 1H), 8.27 (ddd, J = 24.2, 7.8, 1.5 Hz, 2H), 8.06 (d, J = 8.1 Hz, 1H), 7.86 (dd, J = 8.1, 2.2 Hz, 1H), 7.69 (t, J = 7.8 Hz, 1H), 7.48 (dd, J = 8.3, 4.2 Hz, 1H), 7.41-7.30 (m, 2H), 7.24 (td, J = 8.6, 3.1 Hz, 1H) | 6.0 (448.4)+ |
| 112 | C24H16FN3O4S | 461.47 | 1H NMR (400 MHz, DMSO-d6): 13.33 (s, 1H), 9.80 (s, 1H), 8.82 (dd, J = 4.3, 1.8 Hz, 1H), 8.68 (s, 1H), 8.36 (dd, J = 8.3, 1.8 Hz, 1H), 8.10 (dd, J = 10.4, 8.3 Hz, 2H), 7.96 (dd, J = 8.1, 2.1 Hz, 1H), 7.57 (d, J = 8.5 Hz, 1H), 7.51-7.32 (m, 3H), 7.23 (td, J = 8.7, 3.1 Hz, 1H), 2.81 (s, 3H). | 6.3 (462.3)+ |
| 113 | C23H19N3O4S | 433.49 | 1H NMR (400 MHz, DMSO-d6): 13.40 (s, 1H), 9.86 (s, 1H), 8.87 (s, 1H), 8.15-8.05 (m, 2H), 7.56 (t, J = 8.6 Hz, 2H), 7.45 (t, J = 7.8 Hz, 1H), 7.27-7.23 (m, 1H), 7.12-7.04 (m, 3H), 6.99-6.96 (m, 1H), 4.39 (s, 2H), 3.41 (t, J = 5.9 Hz, 2H), 2.75 (t, J = 5.4 Hz, 2H). | 6.4 (434.4)+ |
| 114 | C27H20N2O5S | 484.53 | 1H NMR (300 MHz, DMSO-d6): 13.36 (s, 1H), 10.20 (s, 1H), 8.70 (s, 1H), 7.94 (s, 2H), 7.83 (s, 1H), 7.66-7.39 (m, 6H), 7.28 (t, J = 7.6 Hz, 2H), 7.01 (d, J = 7.1 Hz, 2H), 6.87 (t, J = 7.5 Hz, 1H), 3.67 (s, 3H). | 6.5 (485.5)+ |
| 115 | C26H18N2O3 | 406.44 | 1H NMR (400 MHz, DMSO-d6): 13.41 (s, 1H), 8.78 (s, 1H), 8.55 (s, 1H), 8.12-7.96 (m, 2H), 7.82-7.34 (m, 11H), 5.22 (s, 2H) | 6.3 (407.5)+ |
| 116 | C27H20N2O3 | 420.47 | 1H NMR (300 MHz, DMSO-d6): 8.71 (s, 1H), 8.07 (d, J = 8.2 Hz, 1H), 7.94 (dd, J = 8.1, 2.1 Hz, 1H), 7.86-7.64 (m, 5H), 7.51-7.35 (m, 5H), 7.34-7.26 (m, 1H), 5.26 (d, J = 14.7 Hz, 1H), 4.89 (d, J = 14.6 Hz, 1H), 1.87 (s, 3H). Carboxylic proton not visible. | 6.4 (421.6)+ |
| 117 | C24H17N3O5S | 459.48 | 1H NMR (300 MHz, DMSO-d6): 13.35 (s, 1H), 9.18 (s, 1H), 8.51 (s, 1H), 8.21 (d, J = 8.5 Hz, 2H), 8.11 (d, J = 8.1 Hz, 1H), 8.04 (d, J = 8.1 Hz, 1H), 7.79 (d, J = 8.2 Hz, 1H), 7.44 (tt, J = 15.6, 7.7 Hz, 4H), 7.17 (s, 1H), 6.89 (d, J = 9.0 Hz, 1H), 3.81 (d, J = 23.5 Hz, 3H). Mixture of two conformers. | 7.7 (460.5)+ |
| 118 | C28H20N2O4S | 480.54 | 1H NMR (300 MHz, DMSO-d6): 13.22 (s, 1H), 10.02 (s, 1H), 8.50 (dd, J = 2.0, 0.7 Hz, 1H), 7.96-7.79 (m, 3H), 7.60-7.33 (m, 8H), 7.33-7.22 (m, 1H), 3.65 (s, 2H), 2.27 (s, 3H). | 6.9 (481.5)+ |
| 119 | C28H20N2O4S | 480.54 | 1H NMR (300 MHz, DMSO-d6): 8.68 (s, 1H), 7.95-7.86 (m, 3H), 7.73 (s, 1H), 7.59 (d, J = 8.3 Hz, 1H), 7.49 (t, J = 6.8 Hz, 2H), 7.43-7.29 (m, 4H), 7.19 (t, J = 6.8 Hz, 1H), 3.70 (s, 2H), 2.25 (s, 3H). Carboxylic proton not visible. | 6.6 (481.5)+ |
| 120 | C25H19N3O4S | 457.51 | 1H NMR (400 MHz, DMSO-d6) ? 8.77 (d, J = 2.0 Hz, 1H), 8.29 (d, J = 8.5 Hz, 1H), 8.06-7.97 (m, 2H), 7.91 (d, J = 8.6 Hz, 2H), 7.77 (d, J = 8.5 Hz, 1H), 7.70 (ddd, J = 8.5, 6.8, 1.5 Hz, 1H), 7.62 (dd, J = 7.5, 1.9 Hz, 1H), 7.60-7.51 (m, 2H), 7.38 (dtd, J = 19.2, 7.5, 1.7 Hz, 2H), 5.24 (s, 2H), 3.35 (s, 3H) | 5.4 (458.4)+ |
| 121 | C26H19N3O3 | 421.46 | 1H NMR (300 MHz, DMSO-d6): 8.64 (d, J = 2.0 Hz, 1H), 8.26 (d, J = 8.5 Hz, 1H), 8.00-7.82 (m, 4H), 7.76-7.61 (m, 3H), 7.60-7.35 (m, 4H), 5.48 (d, J = 15.4 Hz, 1H), 4.85 (d, J = 15.4 Hz, 1H), 1.90 (s, 3H) Carboxylic proton not visible. | 4.9 (422.4)+ |
| 122 | C26H21N3O5S | 487.53 | 1H NMR (300 MHz, CDCl3): 8.78 (s, 1H), 8.76 (s, 1H), 8.66 (dd, J = 4.3, 1.8 Hz, 1H), 8.54 (dd, J = 8.5, 1.8 Hz, 1H), 8.45 (d, J = 8.3 Hz, 1H), 8.13 (s, 1H), 7.72 (d, J = 8.4 Hz, 1H), 7.36 (dd, J = 7.7, 1.5 Hz, 1H), 7.33-7.29 (m, 1H), 7.27-7.20 (m, 1H), 6.96 (t, J = 7.6 Hz, 1H), 6.88 (d, J = 8.4 Hz, 1H), 4.08 (s, 3H), 4.07 (s, 3H), 2.71 (s, 3H). | 6.9 (488.5)+ |
| 123 | C26H21N3O5S | 487.53 | 1H NMR (300 MHz, DMSO-d6): 8.95 (dd, J = 4.2, 1.8 Hz, 1H), 8.36 (dd, J = 8.5, 1.8 Hz, 1H), 8.23 (s, 1H), 8.12 (d, J = 8.5 Hz, 1H), 7.82 (s, | 6.9 (488.5)+ |

TABLE 2-continued

| Cpd. No. | Formula | Mass | NMR | LCMS (M + H) |
|---|---|---|---|---|
| | | | 1H), 7.61-7.55 (m, 1H), 7.42 (dd, J = 8.5, 4.2 Hz, 1H), 7.17-7.01 (m, 1H), 4.02 (s, 3H), 3.62 (s, 3H), 2.26 (s, 3H). | |
| 124 | C26H17N3O4S | 467.50 | 1H NMR (400 MHz, DMSO-d6): 11.78 (s, 1H), 10.05 (s, 1H), 8.70 (s, 1H), 8.43 (d, J = 20.6 Hz, 1H), 8.16-7.86 (m, 6H), 7.73 (d, J = 6.4 Hz, 2H), 7.49-6.96 (m, 13H). | 6.1 (468.5)+ |
| 125 | C27H21N3O6S | 515.54 | 1H NMR (400 MHz, DMSO-d6): 13.23 (s, 1H), 10.23 (s, 1H), 8.66 (s, 1H), 7.97 (s, 1H), 7.93-7.84 (m, 2H), 7.65 (d, J = 7.5 Hz, 1H), 7.52-7.36 (m, 6H), 7.32-7.21 (m, 1H), 6.30 (d, J = 8.1 Hz, 1H), 3.82 (d, J = 28.1 Hz, 6H) | 6.6 (516.5)+ |
| 126 | C22H17N3O4S | 419.46 | 1H NMR (300 MHz, DMSO-d6): 13.35 (s, 1H), 10.15 (s, 1H), 8.78 (d, J = 1.9 Hz, 1H), 8.11-8.01 (m, 2H), 7.51-7.46 (m, 2H), 7.41 (td, J = 7.7, 1.6 Hz, 1H), 7.23 (t, J = 7.5 Hz, 1H), 7.10 (d, J = 7.9 Hz, 1H), 7.06 (d, J = 7.1 Hz, 1H), 6.85 (t, J = 7.4 Hz, 1H), 6.76 (t, J = 7.2 Hz, 1H), 3.88 (t, J = 8.5 Hz, 2H), 2.88 (t, J = 8.5 Hz, 2H). | 6.2 (420.4)+ |
| 127 | C26H19N3O5S | 485.52 | 1H NMR (300 MHz, DMSO-d6): 8.65 (s, 1H), 8.42 (s, 1H), 8.18 (d, J = 7.5 Hz, 1H), 7.91-7.78 (m, 2H), 7.77-7.31 (m, 8H), 7.30-7.16 (m, 1H), 6.73 (d, J = 8.2 Hz, 1H), 3.86 (s, 3H). Carboxylic proton not visible. | 6.4 (486.4)+ |
| 128 | C24H15BrN2O4S | 507.37 | 1H NMR (300 MHz, DMSO-d6): 13.34 (s, 1H), 10.59 (s, 1H), 8.71 (d, J = 8.4 Hz, 1H), 8.53 (s, 1H), 8.11 (d, J = 8.1 Hz, 1H), 8.03 (d, J = 8.1 Hz, 1H), 7.94-7.88 (m, 2H), 7.74 (dd, J = 8.1, 2.1 Hz, 1H), 7.59-7.35 (m, 5H), 7.21 (s, 1H). | 6.9 (507.7)+ |
| 129 | C25H19N3O5S | 473.51 | 1H NMR (400 MHz, DMSO-d6): 9.22 (s, 1H), 8.79-8.72 (m, 2H), 8.49 (dd, J = 8.6, 1.8 Hz, 1H), 8.31 (d, J = 8.4 Hz, 1H), 8.13 (d, J = 8.2 Hz, 1H), 8.06 (dd, J = 8.1, 2.1 Hz, 1H), 7.50-7.38 (m, 3H), 7.34 (td, J = 8.4, 7.9, 1.6 Hz, 1H), 7.15-7.04 (m, 2H), 4.02 (s, 3H), 3.93 (s, 3H) | 6.6 (474.4)+ |
| 130 | C25H19N3O5S | 473.51 | 1H NMR (300 MHz, DMSO-d6): 8.72 (dd, J = 4.3, 1.8 Hz, 1H), 8.51 (dd, J = 8.5, 1.8 Hz, 1H), 8.36 (d, J = 8.4 Hz, 1H), 7.96-7.85 (m, 2H), 7.54-7.39 (m, 3H), 7.35-7.25 (m, 1H), 7.15 (d, J = 8.5 Hz, 1H), 7.07 (td, J = 7.6, 1.2 Hz, 1H), 4.04 (s, 3H), 2.68 (s, 3H),. Carboxylic and sulfonamide protons not visible. | 7.7 (474.5)+ |
| 131 | C26H19N3O4S | 469.52 | 1H NMR (300 MHz, DMSO-d6): 10.23 (s, 1H), 8.65 (dd, J = 2.1, 0.9 Hz, 1H), 8.62 (d, J = 2.3 Hz, 1H), 8.52 (dd, J = 4.8, 1.6 Hz, 1H), 7.96 (d, J = 1.9 Hz, 1H), 7.93 (d, J = 2.0 Hz, 1H), 7.90 (dd, J = 3.1, 1.4 Hz, 1H), 7.88-7.82 (m, 2H), 7.61-7.55 (m, 1H), 7.54-7.44 (m, 4H), 7.41-7.28 (m, 2H), 3.92 (s, 3H). | 6.0 (470.5)+ |
| 132 | C28H20N2O4S | 480.54 | 1H NMR (300 MHz, DMSO-d6): 10.09 (s, 1H), 8.68 (t, J = 1.5 Hz, 1H), 7.94-7.83 (m, 5H), 7.59 (dd, J = 8.0, 1.7 Hz, 1H), 7.51-7.32 (m, 6H), 7.27 (td, J = 7.3, 1.8 Hz, 1H), 3.91 (s, 3H), 3.70 (s, 2H). | 9.0 (481.5)+ |
| 133 | C24H18N4O4S | 458.50 | 1H NMR (300 MHz, CDCl3): 8.78 (s, 1H), 8.14 (d, J = 8.1 Hz, 1H), 7.96-7.79 (m, 4H), 7.77-7.64 (m, 4H), 7.47-7.33 (m, 2H), 7.19-7.08 (m, 2H), 6.49 (s, 1H), 4.04 (s, 3H). | 6.2 (459.5)+ |
| 134 | C25H18FN3O4S | 475.50 | 1H NMR (400 MHz, DMSO-d6): 9.81 (s, 1H), 8.82 (dd, J = 4.3, 1.8 Hz, 1H), 8.70 (dd, J = 2.1, 0.9 Hz, 1H), 8.35 (dd, J = 8.3, 1.8 Hz, 1H), 8.16-8.07 (m, 2H), 7.99 (dd, J = 8.1, 2.1 Hz, 1H), 7.57 (d, J = 8.5 Hz, 1H), 7.41 (ddd, J = 18.4, 8.3, 3.6 Hz, 3H), 7.24 (td, J = 8.6, 3.0 Hz, 1H), 3.93 (s, 3H), 2.80 (s, 3H) | 6.9 (476.5)+ |
| 135 | C27H20N2O4S | 468.53 | 1H NMR (300 MHz, DMSO-d6): 9.62 (s, 1H), 8.80-8.79 (m, 1H), 8.16-8.05 (m, 3H), 7.62-7.54 (m, 2H), 7.47 (td, J = 7.7, 1.4 Hz, 1H), 7.37-7.30 (m, 1H), 7.28-7.18 (m, 5H), 7.16-7.10 (m, 3H), 3.91 (s, 3H). | 7.3 (469.6)+ |
| 136 | C24H18N4O4S | 458.50 | 1H NMR (300 MHz, DMSO-d6): 10.10 (s, 1H), 8.90 (s, 1H), 8.75-8.74 (m, 1H), 8.00 (dd, J = 8.1, 2.1 Hz, 1H), 7.92 (dd, J = 8.2, 0.9 Hz, 1H), 7.76 (s, 1H), 7.66-7.61 (m, 2H), 7.58-7.44 (m, 3H), 7.40-7.25 (m, 4H), 3.91 (s, 3H). | 6.3 (459.5)+ |
| 137 | C26H21N3O4S | 471.53 | 1H NMR (400 MHz, DMSO-d6): 9.73 (s, 1H), 8.75-8.68 (m, 2H), 8.37 (dd, J = 8.3, 1.8 Hz, | 7.0 (472.5)+ |

TABLE 2-continued

| Cpd. No. | Formula | Mass | NMR | LCMS (M + H) |
|---|---|---|---|---|
| | | | 1H), 8.16-8.07 (m, 2H), 7.60 (d, J = 8.5 Hz, 1H), 7.52-7.39 (m, 3H), 7.33 (td, J = 8.4, 7.9, 1.6 Hz, 1H), 7.08 (td, J = 7.6, 1.2 Hz, 1H), 3.93 (s, 3H), 2.87 (s, 3H), 2.56 (s, 3H) | |
| 138 | C27H19FN2O4S | 486.52 | 1H NMR (300 MHz, DMSO-d6): 8.69 (s, 1H), 7.91 (s, 1H), 7.79-7.65 (m, 4H), 7.58-7.48 (m, 2H), 7.51-7.36 (m, 4H), 7.35-7.25 (m, 2H), 2.39 (s, 3H). Carboxylic and sulfonamide protons not visible. | 6.8 (487.5)+ |
| 139 | C28H21FN2O4S | 500.55 | 1H NMR (300 MHz, DMSO-d6): 10.14 (s, 1H), 8.69 (s, 1H), 7.91 (s, 1H), 7.71 (d, J = 1.1 Hz, 4H), 7.55-7.39 (m, 6H), 7.37-7.31 (m, 2H), 3.91 (s, 3H), 2.37 (s, 3H). | 7.4 (501.5)+ |
| 140 | C27H21N3O3 | 435.48 | H NMR (300 MHz, DMSO-d6): 8.83 (dd, J = 2.0, 1.0 Hz, 1H), 8.23-8.00 (m, 2H), 7.91-7.69 (m, 3H), 7.62 (dd, J = 7.5, 1.8 Hz, 1H), 7.51-7.28 (m, 6H), 7.22 (dd, J = 7.8, 1.4 Hz, 1H), 5.92 (s, 2H), 5.03 (s, 2H), 3.93 (s, 3H). | 6.1 (436.6)+ |
| 141 | C26H18N2O4S | 454.50 | 1H NMR (300 MHz, DMSO-d6): 13.39 (s, 1H), 9.60 (s, 1H), 8.79 (s, 1H), 8.13-8.05 (m, 3H), 7.63-7.54 (m, 2H), 7.47 (td, J = 7.7, 1.4 Hz, 1H), 7.34 (td, J = 7.8, 1.7 Hz, 1H), 7.28-7.18 (m, 5H), 7.17-7.09 (m, 3H). | 6.8 (455.5)+ |
| 142 | C23H16N4O4S | 444.47 | 1H NMR (300 MHz, DMSO-d6): 13.35 (s, 1H), 10.16 (s, 1H), 8.74 (dd, J = 2.0, 1.0 Hz, 1H), 8.44 (d, J = 2.6 Hz, 1H), 8.04-7.94 (m, 2H), 7.90-7.82 (m, 2H), 7.80-7.70 (m, 3H), 7.56-7.34 (m, 3H), 7.29 (td, J = 7.5, 1.5 Hz, 1H), 6.55 (dd, J = 2.6, 1.7 Hz, 1H). | 5.6 (445.4)+ |
| 143 | C25H19N3O4S | 457.51 | 1H NMR (300 MHz, DMSO-d6): 9.75 (s, 1H), 8.84-8.77 (m, 2H), 8.39 (dd, J = 8.3, 1.8 Hz, 1H), 8.20-8.07 (m, 3H), 7.60 (d, J = 8.5 Hz, 1H), 7.54-7.43 (m, 3H), 7.35 (ddd, J = 8.5, 7.5, 1.6 Hz, 1H), 7.09 (td, J = 7.6, 1.2 Hz, 1H), 3.94 (s, 3H), 2.87 (s, 3H). | 8.5 (458.5)+ |
| 144 | C23H25N3O4S | 439.53 | 1H NMR (300 MHz, DMSO-d6): 9.48 (s, 1H), 8.93 (d, J = 2.0 Hz, 1H), 8.21 (dd, J = 8.1, 2.1 Hz, 1H), 8.12 (d, J = 8.1 Hz, 1H), 7.72-7.55 (m, 2H), 7.45 (td, J = 8.3, 7.9, 1.6 Hz, 1H), 7.21 (td, J = 7.6, 1.2 Hz, 1H), 3.82 (d, J = 13.0 Hz, 1H), 2.90-2.62 (m, 2H), 2.36-2.23 (m, 1H), 1.47 (dd, J = 27.9, 11.4 Hz, 8H), 1.09-0.73 (m, 3H). | 7.5 (440.5)+ |
| 145 | C21H16N4O4S | 420.45 | 1H NMR (300 MHz, DMSO-d6): 8.82 (d, J = 1.8 Hz, 1H), 8.21-7.97 (m, 2H), 7.83-7.67 (m, 1H), 7.58-7.36 (m, 5H), 7.23 (td, J = 7.4, 1.5 Hz, 1H), 6.77 (dd, J = 7.4, 5.1 Hz, 1H), 3.94 (t, J = 8.3 Hz, 2H), 2.95 (t, J = 8.4 Hz, 2H). | 6.5 (421.4)+ |
| 146 | C26H20FN3O4S | 489.52 | 1H NMR (300 MHz, DMSO-d6): 9.80 (s, 1H), 8.77 (dd, J = 4.3, 1.8 Hz, 1H), 8.63 (s, 1H), 8.35 (dd, J = 8.3, 1.8 Hz, 1H), 8.12 (d, J = 8.4 Hz, 1H), 8.06 (d, J = 0.8 Hz, 1H), 7.58 (d, J = 8.5 Hz, 1H), 7.47-7.38 (m, 2H), 7.31 (dd, J = 9.1, 5.2 Hz, 1H), 7.22 (td, J = 8.7, 3.0 Hz, 1H), 3.93 (s, 3H), 2.81 (s, 3H), 2.47 (s, 3H). | 7.1 (490.5)+ |
| 147 | C26H19N3O3 | 421.46 | 1H NMR (300 MHz, DMSO-d6): 8.82 (t, J = 1.5 Hz, 1H), 8.29-7.97 (m, 2H), 7.96-7.67 (m, 4H), 7.62 (dd, J = 7.5, 1.8 Hz, 1H), 7.53-7.29 (m, 5H), 7.21 (dd, J = 7.8, 1.4 Hz, 1H), 5.91 (s, 2H), 5.03 (s, 2H). | 6.8 (422.5)+ |
| 148 | C25H18FN3O4S | 475.50 | 1H NMR (400 MHz, DMSO-d6): 9.77 (s, 1H), 8.75 (dd, J = 4.3, 1.8 Hz, 1H), 8.52 (s, 1H), 8.35 (dd, J = 8.4, 1.8 Hz, 1H), 8.11 (d, J = 8.5 Hz, 1H), 7.96 (s, 1H), 7.57 (d, J = 8.5 Hz, 1H), 7.48-7.29 (m, 3H), 7.20 (td, J = 8.7, 3.0 Hz, 1H), 2.82 (s, 3H), 2.44 (s, 3H) | 6.5 (476.0)+ |
| 149 | C24H16ClN3O4S | 477.93 | 1H NMR (400 MHz, DMSO-d6): 13.78 (s, 1H), 9.73 (s, 1H), 8.91 (s, 1H), 8.76 (dd, J = 4.3, 1.8 Hz, 1H), 8.38 (dd, J = 8.3, 1.8 Hz, 1H), 8.26 (s, 1H), 8.13 (d, J = 8.4 Hz, 1H), 7.61 (d, J = 8.5 Hz, 1H), 7.53-7.42 (m, 3H), 7.35 (ddd, J = 8.5, 7.5, 1.6 Hz, 1H), 7.06 (td, J = 7.6, 1.2 Hz, 1H), 2.91 (s, 3H) | 7.1 (478.6)+ |

TABLE 2-continued

| Cpd. No. | Formula | Mass | NMR | LCMS (M + H) |
|---|---|---|---|---|
| 150 | C27H19N3O4S | 481.53 | 1H NMR (400 MHz, DMSO-d6): 13.31 (s, 1H), 10.00 (s, 1H), 8.58 (dd, J = 2.1, 0.8 Hz, 1H), 8.14 (t, J = 7.8 Hz, 2H), 7.90 (d, J = 1.5 Hz, 1H), 7.80 (dd, J = 8.1, 0.9 Hz, 1H), 7.68 (dd, J = 8.1, 2.1 Hz, 1H), 7.55-7.40 (m, 5H), 7.35 (dd, J = 8.2, 1.6 Hz, 1H), 7.33-7.17 (m, 2H), 3.70 (s, 3H) | 6.5 (482.4)+ |
| 151 | C23H18N4O3 | 398.42 | 1H NMR (300 MHz, DMSO-d6): 13.52 (s, 1H), 8.79 (t, J = 1.4 Hz, 1H), 8.23 (dd, J = 8.5, 1.0 Hz, 1H), 8.14-7.98 (m, 2H), 7.74 (dd, J = 5.0, 1.8 Hz, 1H), 7.63 (dt, J = 7.7, 1.8 Hz, 2H), 7.45 (ddd, J = 8.6, 7.4, 1.6 Hz, 1H), 7.12 (td, J = 7.6, 1.2 Hz, 1H), 6.88 (dd, J = 7.4, 4.9 Hz, 1H), 4.12-3.88 (m, 2H), 2.84 (t, J = 6.3 Hz, 2H), 2.01-1.82 (m, 2H). | 8.3 (399.3)+ |
| 152 | C25H18ClN3O4S | 491.95 | 1H NMR (400 MHz, DMSO-d6): 9.73 (s, 1H), 8.92 (d, J = 0.5 Hz, 1H), 8.76 (dd, J = 4.3, 1.8 Hz, 1H), 8.37 (dd, J = 8.3, 1.8 Hz, 1H), 8.29 (d, J = 0.5 Hz, 1H), 8.13 (d, J = 8.5 Hz, 1H), 7.61 (d, J = 8.5 Hz, 1H), 7.53-7.43 (m, 3H), 7.36 (ddd, J = 8.6, 7.5, 1.7 Hz, 1H), 7.06 (td, J = 7.5, 1.1 Hz, 1H), 3.95 (s, 3H), 2.90 (s, 3H) | 7.4 (492.5)+ |
| 153 | C27H19NO4S | 453.52 | 1H NMR (300 MHz, DMSO-d6): 13.13 (s, 1H), 10.13 (s, 1H), 7.98-7.93 (m, 2H), 7.79-7.74 (m, 2H), 7.71-7.66 (m, 2H), 7.61-7.55 (m, 2H), 7.52-7.36 (m, 8H), 7.27 (td, J = 7.4, 1.7 Hz, 1H). | 7.1 (454.6)+ |
| 154 | C24H18N4O4S | 458.50 | 1H NMR (300 MHz, DMSO-d6): 9.18 (s, 1H), 8.77 (dd, J = 4.3, 1.8 Hz, 1H), 8.70 (dd, J = 2.1, 0.9 Hz, 1H), 8.51 (dd, J = 8.5, 1.8 Hz, 1H), 8.33 (d, J = 8.4 Hz, 1H), 8.22 (s, 1H), 8.12 (dd, J = 8.2, 0.9 Hz, 1H), 8.05 (dd, J = 8.1, 2.0 Hz, 1H), 7.79 (s, 1H), 7.54-7.39 (m, 3H), 7.33 (ddd, J = 8.5, 7.4, 1.6 Hz, 1H), 7.17-7.04 (m, 2H), 4.03 (s, 3H). | 7.5 (459.4)+ |
| 156 | C25H20N4O4S | 472.52 | 1H NMR (300 MHz, DMSO-d6):: 9.18 (s, 1H), 8.88 (q, J = 4.7 Hz, 1H), 8.76 (dd, J = 4.3, 1.8 Hz, 1H), 8.70 (dd, J = 2.0, 0.9 Hz, 1H), 8.51 (dd, J = 8.5, 1.8 Hz, 1H), 8.32 (d, J = 8.4 Hz, 1H), 8.14-8.02 (m, 2H), 7.52-7.39 (m, 3H), 7.34 (td, J = 8.4, 7.9, 1.6 Hz, 1H), 7.17-7.04 (m, 2H), 4.03 (s, 3H), 2.87 (d, J = 4.8 Hz, 3H). | 8.0 (473.5)+ |
| 157 | C25H18ClN3O5S | 507.95 | 1H NMR (400 MHz, DMSO-d6): 9.17 (s, 1H), 8.87 (s, 1H), 8.75 (dd, J = 4.3, 1.8 Hz, 1H), 8.49 (dd, J = 8.5, 1.8 Hz, 1H), 8.36 (d, J = 8.4 Hz, 1H), 8.27 (s, 1H), 7.52-7.41 (m, 3H), 7.36 (ddd, J = 8.5, 7.5, 1.6 Hz, 1H), 7.17-7.04 (m, 2H), 4.03 (s, 3H), 3.95 (s, 3H) | 7.3 (508.5)+ |
| 158 | C27H21N3O4S | 483.55 | 1H NMR (400 MHz, DMSO-d6): 13.52 (s, 1H), 9.59 (s, 1H), 8.86 (s, 1H), 8.70 (dd, J = 4.3, 1.8 Hz, 1H), 8.38 (dd, J = 8.4, 1.8 Hz, 1H), 8.12 (d, J = 8.5 Hz, 1H), 8.00 (s, 1H), 7.61 (d, J = 8.5 Hz, 1H), 7.52-7.38 (m, 3H), 7.30 (ddd, J = 8.6, 7.5, 1.6 Hz, 1H), 7.03 (td, J = 7.6, 1.1 Hz, 1H), 5.57 (p, J = 1.3 Hz, 2H), 2.90 (s, 3H), 2.22 (t, J = 1.2 Hz, 3H) | 7.0 (484.5)+ |
| 159 | C24H16ClN3O5S | 493.92 | 1H NMR (400 MHz, DMSO-d6): 13.76 (s, 1H), 9.16 (s, 1H), 8.86 (s, 1H), 8.75 (dd, J = 4.3, 1.8 Hz, 1H), 8.49 (dd, J = 8.5, 1.8 Hz, 1H), 8.37 (d, J = 8.4 Hz, 1H), 8.23 (s, 1H), 7.51-7.41 (m, 3H), 7.36 (ddd, J = 8.5, 7.5, 1.6 Hz, 1H), 7.14 (d, J = 8.5 Hz, 1H), 7.08 (td, J = 7.6, 1.1 Hz, 1H), 4.03 (s, 3H) | 7.0 (494.6)+ |
| 160 | C25H18N2O4S | 442.49 | 1H NMR (300 MHz, DMSO-d6): 13.22 (s, 1H), 9.67 (s, 1H), 8.77 (dd, J = 4.3, 1.8 Hz, 1H), 8.41 (dd, J = 8.4, 1.8 Hz, 1H), 8.14 (d, J = 8.5 Hz, 1H), 8.07-8.02 (m, 2H), 7.69-7.65 (m, 2H), 7.61 (d, J = 8.5 Hz, 1H), 7.53-7.47 (m, 2H), 7.43 (dd, J = 7.7, 1.6 Hz, 1H), 7.33-7.27 (m, 1H), 7.03 (td, J = 7.6, 1.2 Hz, 1H), 2.90 (s, 3H). | 6.8 (443.4)+ |
| 161 | C27H20N2O3 | 420.47 | 1H NMR (300 MHz, DMSO-d6): 8.54 (s, 1H), 8.13-7.74 (m, 3H), 7.66 (d, J = 7.9 Hz, 1H), 7.62-7.19 (m, 8H), 7.12 (d, J = 7.0 Hz, 1H), 5.59 (dd, J = 29.0, 14.2 Hz, 1H), 4.81 (d, J = 14.0 Hz, 1H), 1.64 (d, J = 19.3 Hz, 3H). Carboxylic proton not visible. | 7.6 (421.5)+ |
| 162 | C23H25N3O4S | 439.53 | 1H NMR (300 MHz, DMSO-d6): 9.45 (s, 1H), 8.90 (s, 1H), 8.28-8.13 (m, 1H), 8.08 (d, J = 8.1 Hz, 1H), 7.74-7.53 (m, 2H), 7.44 (td, J = 8.3, | 9.2 (440.5)+ |

TABLE 2-continued

| Cpd. No. | Formula | Mass | NMR | LCMS (M + H) |
|---|---|---|---|---|
| | | | 7.9, 1.6 Hz, 1H), 7.20 (t, J = 7.5 Hz, 1H), 3.82 (d, J = 13.0 Hz, 1H), 2.84-2.60 (m, 3H), 2.38-2.24 (m, 1H), 1.68-1.21 (m, 8H), 1.18-0.70 (m, 3H). | |
| 163 | C26H22N4O4S | 486.55 | 1H NMR (300 MHz, DMSO-d6): 13.36 (s, 1H), 9.72 (s, 1H), 8.80 (dd, J = 4.3, 1.8 Hz, 1H), 8.38 (dd, J = 8.3, 1.8 Hz, 1H), 8.18-8.05 (m, 2H), 7.60 (d, J = 8.5 Hz, 1H), 7.54-7.39 (m, 4H), 7.32 (ddd, J = 8.5, 7.5, 1.6 Hz, 1H), 7.06 (td, J = 7.5, 1.2 Hz, 1H), 2.91 (s, 6H), 2.87 (s, 3H | 6.4 (487.1)+ |
| 164 | C25H19N3O5S | 473.51 | 1H NMR (400 MHz, DMSO-d6): 9.69 (s, 1H), 8.70-8.63 (m, 2H), 8.37 (dd, J = 8.3, 1.8 Hz, 1H), 8.13 (d, J = 8.5 Hz, 1H), 7.80 (s, 1H), 7.62 (d, J = 8.5 Hz, 1H), 7.53 (dd, J = 8.4, 1.0 Hz, 1H), 7.47 (dd, J = 8.3, 4.3 Hz, 1H), 7.38 (dd, J = 7.7, 1.5 Hz, 1H), 7.29 (ddd, J = 8.7, 7.5, 1.6 Hz, 1H), 6.98 (td, J = 7.6, 1.1 Hz, 1H), 4.14 (s, 3H), 2.95 (s, 3H) | 5.6 (474.4)+ |
| 165 | C26H21N3O5S | 487.53 | 1H NMR (300 MHz, CDCl3): 8.85 (dd, J = 2.1, 0.9 Hz, 1H), 8.70 (dd, J = 4.3, 1.8 Hz, 2H), 8.53 (dd, J = 8.5, 1.8 Hz, 1H), 8.42 (d, J = 8.3 Hz, 1H), 8.20 (dd, J = 8.1, 0.8 Hz, 1H), 8.02 (dd, J = 8.1, 2.1 Hz, 1H), 7.74 (dd, J = 8.5, 1.0 Hz, 1H), 7.35-7.32 (m, 1H), 7.31-7.27 (m, 1H), 7.25-7.18 (m, 1H), 6.93 (td, J = 7.6, 1.1 Hz, 1H), 6.85 (d, J = 8.4 Hz, 1H), 4.54 (q, J = 7.2 Hz, 2H), 4.04 (s, 3H), 1.48 (d, J = 7.2 Hz, 3H). | 7.1 (488.4)+ |
| 166 | C27H23N3O5S | 501.56 | 1H NMR (300 MHz, CDCl3): 8.88 (dd, J = 2.1, 0.9 Hz, 1H), 8.73 (dd, J = 4.3, 1.7 Hz, 2H), 8.56 (dd, J = 8.5, 1.8 Hz, 1H), 8.45 (d, J = 8.4 Hz, 1H), 8.21 (dd, J = 8.1, 0.9 Hz, 1H), 8.05 (dd, J = 8.1, 2.1 Hz, 1H), 7.76 (dd, J = 8.4, 1.0 Hz, 1H), 7.33 (ddd, J = 8.5, 5.1, 2.9 Hz, 2H), 7.27-7.21 (m, 1H), 6.96 (td, J = 7.6, 1.1 Hz, 1H), 6.87 (d, J = 8.4 Hz, 1H), 4.46 (t, J = 6.9 Hz, 2H), 4.07 (s, 3H), 1.91 (p, J = 7.2 Hz, 2H), 1.09 (t, J = 7.4 Hz, 3H). | 7.5 (502.5)+ |
| 167 | C27H23N3O5S | 501.56 | 1H NMR (300 MHz, CDCl3): 8.88 (dd, J = 2.1, 0.9 Hz, 1H), 8.77-8.68 (m, 2H), 8.56 (dd, J = 8.5, 1.8 Hz, 1H), 8.45 (d, J = 8.4 Hz, 1H), 8.20 (dd, J = 8.1, 0.9 Hz, 1H), 8.04 (dd, J = 8.1, 2.1 Hz, 1H), 7.76 (dd, J = 8.4, 1.0 Hz, 1H), 7.36-7.30 (m, 2H), 7.24 (dd, J = 8.4, 1.5 Hz, 1H), 7.01-6.91 (m, 2H), 6.87 (d, J = 8.4 Hz, 1H), 5.42 (hept, J = 6.3 Hz, 1H), 4.07 (s, 3H), 1.50 (d, J = 6.3 Hz, 6H). | 7.4 (502.5)+ |
| 168 | C28H25N3O5S | 515.59 | 1H NMR (300 MHz, CDCl3): 8.87 (dd, J = 2.1, 0.9 Hz, 1H), 8.73 (dd, J = 4.3, 1.8 Hz, 2H), 8.56 (dd, J = 8.5, 1.8 Hz, 1H), 8.45 (d, J = 8.4 Hz, 1H), 8.21 (dd, J = 8.1, 0.9 Hz, 1H), 8.05 (dd, J = 8.1, 2.1 Hz, 1H), 7.76 (dd, J = 8.5, 1.1 Hz, 1H), 7.33 (ddd, J = 8.5, 5.0, 3.0 Hz, 2H), 7.27-7.20 (m, 1H), 6.96 (td, J = 7.6, 1.1 Hz, 1H), 6.87 (d, J = 8.4 Hz, 1H), 4.50 (t, J = 6.8 Hz, 2H), 4.07 (s, 3H), 1.87 (dq, J = 8.5, 6.9 Hz, 2H), 1.57-1.47 (m, 2H), 1.03 (t, J = 7.4 Hz, 3H). | 8.0 (516.5)+ |
| 169 | C25H19N3O6S | 489.51 | 1H NMR (400 MHz, DMSO-d6): 9.07 (s, 1H), 8.71-8.63 (m, 2H), 8.51 (dd, J = 8.5, 1.8 Hz, 1H), 8.43 (d, J = 8.4 Hz, 1H), 7.80 (s, 1H), 7.57-7.46 (m, 2H), 7.36 (dd, J = 7.7, 1.5 Hz, 1H), 7.29 (ddd, J = 8.7, 7.5, 1.6 Hz, 1H), 7.17 (d, J = 8.5 Hz, 1H), 7.00 (td, J = 7.6, 1.1 Hz, 1H), 4.15 (s, 3H), 4.05 (s, 3H) | 5.7 (490.1)+ |
| 170 | C25H19N3O6S | 489.51 | 1H NMR (300 MHz, DMSO-d6): 13.36 (s, 1H), 9.14 (s, 1H), 8.78 (dd, J = 4.3, 1.8 Hz, 1H), 8.50 (dd, J = 8.5, 1.7 Hz, 1H), 8.31 (d, J = 8.4 Hz, 1H), 8.21 (d, J = 1.5 Hz, 1H), 7.65 (d, J = 1.6 Hz, 1H), 7.48 (ddd, J = 8.5, 2.8, 1.7 Hz, 2H), 7.40 (dd, J = 7.7, 1.5 Hz, 1H), 7.33 (ddd, J = 8.4, 7.5, 1.6 Hz, 1H), 7.16-7.03 (m, 2H), 4.03 (s, 3H), 3.91 (s, 3H). | 7.4 (490.1)+ |
| 171 | C25H19N3O5S | 473.51 | 1H NMR (300 MHz, DMSO-d6): 13.38 (s, 1H), 9.72 (s, 1H), 8.81 (dd, J = 4.2, 1.8 Hz, 1H), 8.39 (dd, J = 8.4, 1.8 Hz, 1H), 8.25 (d, J = 1.5 Hz, 1H), 8.13 (d, J = 8.4 Hz, 1H), 7.71 (d, J = 1.6 Hz, 1H), 7.59 (d, J = 8.4 Hz, 1H), 7.55-7.40 (m, 3H), 7.33 (td, J = 8.4, 8.0, 1.6 Hz, 1H), 7.13-7.01 (m, 1H), 3.92 (s, 3H), 2.87 (s, 3H). | 7.6 (474.1)+ |

TABLE 2-continued

| Cpd. No. | Formula | Mass | NMR | LCMS (M + H) |
|---|---|---|---|---|
| 172 | C31H23N3O5S | 549.60 | 1H NMR (300 MHz, CDCl3): 8.85 (s, 1H), 8.69 (d, J = 5.3 Hz, 2H), 8.58-8.48 (m, 1H), 8.42 (d, J = 8.3 Hz, 1H), 8.19 (d, J = 8.1 Hz, 1H), 8.01 (dd, J = 8.2, 2.1 Hz, 1H), 7.74 (d, J = 8.4 Hz, 1H), 7.53 (d, J = 7.1 Hz, 2H), 7.40 (q, J = 8.0, 7.2 Hz, 3H), 7.35-7.29 (m, 2H), 7.21 (d, J = 8.0 Hz, 1H), 6.93 (t, J = 7.5 Hz, 1H), 6.85 (d, J = 8.4 Hz, 1H), 5.51 (s, 2H), 4.04 (s, 3H). | 7.7 (550.1)+ |
| 173 | C27H22N4O7S | 546.56 | 1H NMR (300 MHz, DMSO-d6): 13.35 (s, 1H), 10.06 (s, 1H), 9.09 (s, 1H), 8.80-8.67 (m, 2H), 8.50 (dd, J = 8.5, 1.8 Hz, 1H), 8.33 (d, J = 8.4 Hz, 1H), 8.11 (d, J = 8.1 Hz, 1H), 8.02 (dd, J = 8.1, 2.1 Hz, 1H), 7.96 (d, J = 2.0 Hz, 1H), 7.55-7.39 (m, 2H), 7.33 (d, J = 8.5 Hz, 1H), 7.14 (d, J = 8.5 Hz, 1H), 4.01 (d, J = 10.8 Hz, 5H), 3.35 (s, 3H). | 5.4 (547.1)+ |
| 174 | C30H26N2O5S | 526.61 | 1H NMR (300 MHz, DMSO-d6): 13.37 (s, 1H), 10.12 (s, 1H), 8.73 (d, J = 1.9 Hz, 1H), 8.10-7.96 (m, 2H), 7.70 (d, J = 8.5 Hz, 2H), 7.62 (d, J = 8.5 Hz, 2H), 7.56-7.37 (m, 5H), 7.28 (td, J = 7.4, 1.6 Hz, 1H), 6.95 (d, J = 8.8 Hz, 2H), 3.77 (d, J = 6.5 Hz, 2H), 2.10-1.94 (m, 1H), 0.98 (d, J = 6.7 Hz, 6H). | 7.9 (527.2)+ |
| 175 | C25H19N3O5S | 473.51 | 1H NMR (400 MHz, DMSO-d6): 13.39 (s, 1H), 8.92 (dd, J = 4.2, 1.8 Hz, 1H), 8.41-8.32 (m, 2H), 8.17 (d, J = 8.4 Hz, 1H), 7.98 (dd, J = 8.1, 0.9 Hz, 1H), 7.63 (dd, J = 8.1, 2.1 Hz, 1H), 7.56 (dd, J = 7.4, 1.9 Hz, 1H), 7.48-7.35 (m, 3H), 7.21 (dd, J = 7.8, 1.5 Hz, 1H), 7.07 (d, J = 8.5 Hz, 1H), 4.01 (s, 3H), 3.56 (s, 3H) | 5.8 (474.1)+ |
| 176 | C26H21N3O6S | 503.53 | 1H NMR (400 MHz, DMSO-d6): 9.00 (s, 1H), 8.71-8.63 (m, 2H), 8.51 (dd, J = 8.5, 1.8 Hz, 1H), 8.39 (d, J = 8.4 Hz, 1H), 7.76 (s, 1H), 7.56 (dd, J = 8.4, 1.0 Hz, 1H), 7.49 (dd, J = 8.5, 4.3 Hz, 1H), 7.36 (dd, J = 7.7, 1.5 Hz, 1H), 7.29 (ddd, J = 8.7, 7.5, 1.6 Hz, 1H), 7.15 (d, J = 8.5 Hz, 1H), 7.01 (td, J = 7.6, 1.1 Hz, 1H), 4.43 (q, J = 7.0 Hz, 2H), 4.04 (s, 3H), 1.44 (t, J = 7.0 Hz, 3H) | 5.7 (504.1)+ |
| 177 | C26H22N2O4S | 458.54 | 1H NMR (300 MHz, DMSO-d6): 8.72 (s, 1H), 8.16 (s, 1H), 8.08-8.00 (m, 1H), 7.98-7.89 (m, 1H), 7.60 (d, J = 8.2 Hz, 2H), 7.47 (d, J = 8.1 Hz, 1H), 7.43-7.31 (m, 3H), 7.26-7.15 (m, 1H), 6.09 (s, 1H), 2.23-2.03 (m, 4H), 1.71-1.59 (m, 2H), 1.59-1.48 (m, 2H). Not visible signal of the acidic proton. | 7.2 (459.1)+ |
| 178 | C25H17N3O3 | 407.43 | 1H NMR (300 MHz, DMSO-d6): 8.94-8.84 (m, 1H), 8.84-8.73 (m, 2H), 8.60 (s, 1H), 8.52 (d, J = 2.0 Hz, 0H), 8.32 (dd, J = 8.3, 1.8 Hz, 1H), 8.25 (dd, J = 8.3, 1.8 Hz, 1H), 8.12 (d, J = 8.1 Hz, 1H), 8.04 (dt, J = 8.0, 1.8 Hz, 2H), 7.89-7.80 (m, 3H), 7.76 (dd, J = 8.1, 2.1 Hz, 0H), 7.64 (dd, J = 7.7, 1.6 Hz, 1H), 7.59-7.21 (m, 9H), 7.14 (d, J = 7.8 Hz, 1H), 5.73 (s, 3H), 5.57 (s, 1H).; Mixture of two conformers. | 6.0 (408.1)+ |
| 179 | C29H22N2O4 | 462.50 | 1H NMR (400 MHz, Chloroform-d): 8.66-8.50 (m, 1H), 8.44 (s, 1H), 8.07 (d, J = 7.9 Hz, 1H), 7.82 (d, J = 8.2 Hz, 1H), 7.60 (d, J = 7.8 Hz, 1H), 7.53-7.40 (m, 2H), 7.36 (d, J = 7.6 Hz, 2H), 7.28 (m, 1H) 7.22 (t, J = 7.6 Hz, 2H), 7.16-7.05 (m, 2H), 6.88 (t, J = 8.6 Hz, 2H), 5.06 (s, 2H), 3.71 (s, 3H). Carboxylic proton not visible.. | 8.1 (463.1)+ |
| 180 | C26H21N3O5S | 487.53 | 1H NMR (400 MHz, DMSO-d6): 13.46 (s, 1H), 9.66 (s, 1H), 8.75-8.62 (m, 2H), 8.37 (dd, J = 8.3, 1.8 Hz, 1H), 8.12 (d, J = 8.5 Hz, 1H), 7.76 (s, 1H), 7.59 (dd, J = 14.4, 8.4 Hz, 2H), 7.47 (dd, J = 8.3, 4.3 Hz, 1H), 7.39 (dd, J = 7.8, 1.6 Hz, 1H), 7.34-7.24 (m, 1H), 6.99 (t, J = 7.6 Hz, 1H), 4.44 (q, J = 7.0 Hz, 2H), 2.93 (s, 3H), 1.43 (t, J = 7.0 Hz, 3H) | 5.9 (488.1)+ |
| 181 | C28H20N2O3 | 432.48 | H NMR (300 MHz, DMSO-d6): 8.75-8.70 (m, 1H), 8.56 (s, 1H), 8.06-7.97 (m, 2H), 7.93 (dd, J = 8.1, 2.1 Hz, 1H), 7.67 (d, J = 1.5 Hz, 1H), 7.63-7.50 (m, 4H), 7.50-7.36 (m, 5H), 7.35-7.17 (m, 6H), 5.15 (s, 2H).; two conformers | 8.3 (433.1)+ |
| 182 | C24H16BrN3O5S | 538.38 | 1H NMR (300 MHz, DMSO-d6): 13.31 (s, 1H), 9.45 (s, 1H), 8.82-8.64 (m, 2H), 8.50 (dd, J = 8.5, 1.8 Hz, 1H), 8.36 (d, J = 8.4 Hz, 1H), 8.10 | 7.0 (537.80)− |

TABLE 2-continued

| Cpd. No. | Formula | Mass | NMR | LCMS (M + H) |
|---|---|---|---|---|
| | | | (d, J = 8.0 Hz, 1H), 8.00 (dd, J = 8.1, 2.1 Hz, 1H), 7.68 (d, J = 1.8 Hz, 1H), 7.47 (dd, J = 8.5, 4.3 Hz, 1H), 7.42-7.26 (m, 2H), 7.14 (d, J = 8.5 Hz, 1H), 4.03 (s, 3H). | |
| 183 | C28H20N2O3 | 432.48 | 1H NMR (300 MHz, DMSO-d6): 8.86-8.64 (m, 1H), 8.51 (s, 0H), 8.27-7.91 (m, 1H), 7.75-7.62 (m, 1H), 7.62-7.47 (m, 3H), 7.47-7.21 (m, 4H), 5.08 (s, 1H). Carboxylic proton not visible | 8.4 (433.1)+ |
| 184 | C34H28N4O7S | 636.68 | 1H NMR (300 MHz, DMSO-d6): 9.42 (s, 1H), 8.74 (dd, J = 4.3, 1.8 Hz, 1H), 8.70-8.64 (m, 2H), 8.47 (dd, J = 8.5, 1.8 Hz, 1H), 8.10 (d, J = 8.1 Hz, 1H), 8.03-7.94 (m, 2H), 7.58 (dd, J = 8.1, 1.7 Hz, 1H), 7.50 (d, J = 8.1 Hz, 1H), 7.44 (dd, J = 8.6, 4.3 Hz, 1H), 7.37-7.25 (m, 5H), 7.09 (d, J = 8.5 Hz, 1H), 4.51 (s, 2H), 4.00 (s, 3H), 3.56 (t, J = 5.6 Hz, 2H), 3.45 (dd, J = 11.5, 5.9 Hz, 2H). Carboxylic proton not visible. | 7.6 (635.9)+ |
| 185 | C24H16FN3O5S | 477.47 | 1H NMR (300 MHz, DMSO-d6): 9.37 (s, 1H), 8.77 (dd, J = 4.3, 1.8 Hz, 1H), 8.62 (dd, J = 2.1, 0.9 Hz, 1H), 8.47 (dd, J = 8.5, 1.8 Hz, 1H), 8.26 (d, J = 8.4 Hz, 1H), 8.15-8.00 (m, 1H), 7.92 (dd, J = 8.1, 2.1 Hz, 1H), 7.45 (dd, J = 8.5, 4.3 Hz, 1H), 7.39 (dd, J = 9.1, 5.3 Hz, 1H), 7.32 (dd, J = 8.9, 3.0 Hz, 1H), 7.24 (td, J = 8.6, 3.0 Hz, 1H), 7.09 (d, J = 8.5 Hz, 1H), 4.02 (s, 3H). | 6.2 (478.0)+ |
| 186 | C24H16BrN3O4S | 522.38 | 1H NMR (300 MHz, DMSO-d6): 13.46 (s, 1H), 9.90 (s, 1H), 8.84-8.73 (m, 2H), 8.40 (d, J = 8.3, 1.8 Hz, 1H), 8.19-8.03 (m, 3H), 7.69 (d, J = 1.9 Hz, 1H), 7.62 (d, J = 8.5 Hz, 1H), 7.47 (dd, J = 8.3, 4.3 Hz, 1H), 7.42 (d, J = 8.3 Hz, 1H), 7.30 (dd, J = 8.3, 1.9 Hz, 1H), 2.87 (s, 3H). | 7.3 (522.0)+ |
| 187 | C26H22N4O4S | 486.55 | 1H NMR (300 MHz, DMSO-d6): 9.63 (s, 1H), 8.82 (dd, J = 4.2, 1.7 Hz, 1H), 8.64 (s, 1H), 8.38 (dd, J = 8.3, 1.8 Hz, 1H), 8.13 (d, J = 8.4 Hz, 1H), 7.65-7.33 (m, 5H), 7.26 (t, J = 8.1 Hz, 1H), 7.01 (t, J = 7.5 Hz, 1H), 3.16 (d, J = 24.3 Hz, 6H), 2.88 (s, 3H) | 4.8 (487.1)+ |
| 188 | C26H21N3O5S | 487.53 | 1H NMR (300 MHz, DMSO-d6): 13.51 (s, 1H), 9.69 (s, 1H), 8.78 (s, 1H), 8.38 (s, 1H), 8.22 (s, 1H), 8.12 (d, J = 8.6 Hz, 1H), 7.59 (d, J = 11.4 Hz, 2H), 7.51 (d, J = 8.5 Hz, 2H), 7.42 (d, J = 7.4 Hz, 1H), 7.36-7.26 (m, 1H), 7.04 (t, J = 7.6 Hz, 1H), 4.16 (q, J = 6.9 Hz, 2H), 2.87 (s, 3H), 1.35 (t, J = 6.9 Hz, 3H). | 8.1 (488.0)+ |
| 189 | C29H22N2O4 | 462.50 | 1H NMR (300 MHz, DMSO-d6): 13.44 (s, 1H), 8.64 (s, 1H), 8.42 (s, 1H), 7.91 (s, 2H), 7.60 (dd, J = 7.2, 2.2 Hz, 1H), 7.49-7.41 (m, 1H), 7.34 (ddt, J = 12.8, 6.1, 2.6 Hz, 2H), 7.24 (qt, J = 7.8, 3.8 Hz, 3H), 7.12 (d, J = 7.3 Hz, 1H), 7.07-6.97 (m, 1H), 6.92 (d, J = 8.4 Hz, 1H), 6.85 (s, 1H), 6.77 (s, 1H), 5.11 (d, J = 15.6 Hz, 1H), 4.67 (t, J = 12.6 Hz, 1H), 3.60 (d, J = 3.3 Hz, 3H). | 8.2 (463.1)+ |
| 190 | C24H15Cl2N3O5S | 528.37 | 1H NMR (300 MHz, DMSO-d6): 13.45 (s, 1H), 9.67 (s, 1H), 8.72 (dd, J = 4.3, 1.8 Hz, 1H), 8.64 (d, J = 1.9 Hz, 1H), 8.48 (dd, J = 8.5, 1.8 Hz, 1H), 8.35 (d, J = 8.4 Hz, 1H), 8.09 (d, J = 8.1 Hz, 1H), 7.95 (dd, J = 8.1, 2.1 Hz, 1H), 7.73 (d, J = 11.7 Hz, 2H), 7.46 (dd, J = 8.5, 4.3 Hz, 1H), 7.12 (d, J = 8.5 Hz, 1H), 4.02 (s, 3H) | 7.7 (527.9)+ |
| 191 | C29H22N2O4 | 462.50 | 1H NMR (300 MHz, DMSO-d6): 13.38 (s, 1H), 8.75 (s, 1H), 8.51 (s, 1H), 8.07 (q, J = 7.7 Hz, 2H), 7.75-7.62 (m, 1H), 7.60-7.50 (m, 2H), 7.49-7.37 (m, 1H), 7.30 (q, J = 8.2 Hz, 5H), 7.13 (dd, J = 7.6, 1.9 Hz, 1H), 7.05 (d, J = 8.2 Hz, 1H), 7.00-6.91 (m, 1H), 5.04 (d, J = 15.1 Hz, 2H), 3.68 (d, J = 2.6 Hz, 3H). Mixture of two conformers. | 8.3 (463.1)+ |
| 192 | C29H22N2O4 | 462.50 | 1H NMR (300 MHz, DMSO-d6): 8.67 (s, 1H), 8.33 (d, J = 40.2 Hz, 2H), 7.76 (d, J = 26.8 Hz, 1H), 7.68-7.21 (m, 11H), 7.21-6.87 (m, 1H), 5.09 (d, J = 23.0 Hz, 2H), 4.26-3.78 (m, 3H). Carboxylic proton not visible.. | 7.6 (463.1)+ |

TABLE 2-continued

| Cpd. No. | Formula | Mass | NMR | LCMS (M + H) |
|---|---|---|---|---|
| 193 | C24H17N3O5S | 459.48 | 1H NMR (400 MHz, DMSO-d6): 12.35 (s, 1H), 9.68 (s, 1H), 8.90 (s, 1H), 8.38 (dd, J = 8.3, 1.8 Hz, 1H), 8.12 (m, 2H), 7.60 (d, J = 8.5 Hz, 1H), 7.53 (ddd, J = 12.6, 8.4, 2.7 Hz, 2H), 7.32 (dd, J = 7.7, 1.5 Hz, 1H), 7.24 (ddd, J = 8.7, 7.5, 1.6 Hz, 1H), 6.96 (m, 1.1 Hz, 2H), 2.92 (s, 3H) | 5.2 (460.0)+ |
| 194 | C29H22N2O3 | 446.51 | 1H NMR (300 MHz, DMSO-d6): 8.54 (d, J = 1.9 Hz, 1H), 8.50 (s, 1H), 7.82 (d, J = 1.9 Hz, 1H), 7.73-7.64 (m, 1H), 7.60-7.49 (m, 7H), 7.46-7.38 (m, 3H), 7.38-7.27 (m, 3H), 5.08 (s, 2H), 2.45 (s, 3H).; Mixture of two conformers. | 7.1 (447.2)+ |
| 195 | C27H20N2O3 | 420.47 | 1H NMR (300 MHz, DMSO-d6): 8.54 (d, J = 2.2 Hz, 1H), 8.53 (s, 1H), 7.87-7.79 (m, 2H), 7.78-7.73 (m, 3H), 7.74-7.62 (m, 2H), 7.57-7.48 (m, 2H), 7.47-7.37 (m, 4H), 5.22 (s, 2H), 2.46 (s, 3H).; Mixture of two conformers. | 6.7 (421.1)+ |
| 196 | C25H17N3O3 | 407.43 | 1H NMR (300 MHz, DMSO-d6): 8.83 (d, J = 2.2 Hz, 1H), 8.71 (d, J = 2.0 Hz, 1H), 8.52 (s, 1H), 8.30 (d, J = 2.1 Hz, 1H), 8.05 (d, J = 8.0 Hz, 1H), 7.95 (dd, J = 8.2, 1.8 Hz, 2H), 7.84 (d, J = 8.2 Hz, 1H), 7.78-7.61 (m, 2H), 7.60-7.52 (m, 2H), 7.48-7.39 (m, 1H), 5.27 (s, 2H). | 4.3 (408.1)+ |
| 197 | C25H19N3O6S | 489.51 | 1H NMR (400 MHz, DMSO-d6): 13.42 (br, 1H), 9.08 (s, 1H), 8.79 (dd, J = 2.1, 0.9 Hz, 1H), 8.76 (dd, J = 4.3, 1.8 Hz, 1H), 8.52 (dd, J = 8.5, 1.8 Hz, 1H), 8.38 (d, J = 8.4 Hz, 1H), 8.13 (dd, J = 8.1, 0.9 Hz, 1H), 8.07 (dd, J = 8.1, 2.1 Hz, 1H), 7.50 (dd, J = 8.5, 4.3 Hz, 1H), 7.35 (d, J = 8.6 Hz, 1H), 7.15 (d, J = 8.5 Hz, 1H), 7.06 (d, J = 2.5 Hz, 1H), 6.66 (dd, J = 8.6, 2.5 Hz, 1H), 4.04 (s, 3H), 3.71 (s, 3H). | 6.3 (490.0)+ |
| 198 | C27H19N3O4S | 481.53 | 1H NMR (400 MHz, DMSO-d6): 13.37 (s, 1H), 10.31 (s, 1H), 8.82 (d, J = 8.1 Hz, 1H), 8.41 (d, J = 2.0 Hz, 1H), 7.94 (dd, J = 8.1, 0.9 Hz, 1H), 7.88 (dd, J = 8.3, 1.0 Hz, 1H), 7.66 (dd, J = 7.7, 0.9 Hz, 1H), 7.59 (dd, J = 8.1, 2.1 Hz, 1H), 7.56-7.32 (m, 6H), 7.15 (td, J = 7.5, 1.3 Hz, 1H), 7.06 (ddd, J = 8.2, 7.0, 1.1 Hz, 1H), 3.83 (s, 3H) | 6.4 (482.1)+ |
| 199 | C24H16ClN3O5S | 493.92 | 1H NMR (300 MHz, DMSO-d6) 9.48 (s, 1H), 8.87-8.64 (m, 2H), 8.50 (d, J = 8.3 Hz, 1H), 8.36 (d, J = 8.3 Hz, 1H), 8.20-8.06 (m, 1H), 8.05-7.93 (m, 1H), 7.62-7.52 (m, 1H), 7.52-7.40 (m, 2H), 7.28-7.06 (m, 2H), 4.03 (s, 3H). Carboxylic proton not visible. | 6.9 (493.9)+ |
| 200 | C27H20N2O3 | 420.47 | 1H NMR (300 MHz, DMSO-d6): 8.77 (d, J = 1.9 Hz, 1H), 8.41 (s, 1H), 8.10 (dd, J = 6.6, 2.9 Hz, 2H), 8.06 (d, J = 1.1 Hz, 1H), 8.02 (dd, J = 8.1, 2.1 Hz, 1H), 7.96-7.88 (m, 1H), 7.85-7.70 (m, 3H), 7.62-7.45 (m, 6H), 7.39-7.32 (m, 2H), 4.20-4.05 (m, 3H), 3.34-3.25 (m, 3H).; Mixture of two conformers | 7.1 (421.1)+ |
| 201 | C29H22N2O4 | 462.50 | 1H NMR (400 MHz, DMSO-d6): 13.41 (s, 1H), 8.85-8.74 (m, 1H), 8.55 (s, 1H), 8.13-7.99 (m, 2H), 7.69 (dd, J = 20.6, 7.7 Hz, 1H), 7.61-7.47 (m, 2H), 7.42 (ddt, J = 11.3, 7.6, 4.0 Hz, 1H), 7.37-7.24 (m, 5H), 7.15 (dd, J = 9.6, 7.5 Hz, 1H), 7.01-6.89 (m, 2H), 5.06 (d, J = 24.6 Hz, 2H), 3.60 (d, J = 11.4 Hz, 3H) | 6.8 (463.1)+ |
| 202 | C26H18N2O3 | 406.44 | 1H NMR (300 MHz, DMSO-d6) 13.40 (s, 1H), 8.97 (s, 1H), 8.84-8.75 (m, 1H), 8.23-8.14 (m, 1H), 8.13-8.02 (m, 1H), 7.96-7.71 (m, 4H), 7.66-7.53 (m, 2H), 7.53-7.44 (m, 2H), 7.44-7.33 (m, 2H), 7.33-7.24 (m, 1H), 5.45-5.26 (m, 2H). Mixture of two conformers. | 8.1 (407.0)+ |
| 203 | C28H20N2O4 | 448.48 | 1H NMR (300 MHz, DMSO-d6): 13.14 (s, 1H), 8.78 (s, 1H), 8.49 (s, 1H), 8.08-8.04 (m, 1H), 7.99-7.94 (m, 1H), 7.71-7.67 (m, 1H), 7.57-7.38 (m, 3H), 7.35-7.21 (m, 3H), 7.14-7.04 (m, 2H), 6.88-6.77 (m, 4H), 5.05 (s, 2H). | 6.6 (449.2)+ |
| 204 | C24H15Cl2N3O4S | 512.37 | 1H NMR (300 MHz, DMSO-d6): 13.48 (s, 1H), 10.04 (s, 1H), 8.77 (dd, J = 4.3, 1.8 Hz, 1H), 8.72 (dd, J = 2.1, 0.9 Hz, 1H), 8.38 (dd, J = 8.3, 1.8 Hz, 1H), 8.18-8.08 (m, 2H), 8.02 (dd, J = 8.1, 2.1 Hz, 1H), 7.81 (s, 1H), 7.71 (s, 1H), 7.60 (d, J = 8.5 Hz, 1H), 7.45 (dd, J = 8.3, 4.3 Hz, 1H), 2.86 (s, 3H) | 7.9 (512.0)+ |

TABLE 2-continued

| Cpd. No. | Formula | Mass | NMR | LCMS (M + H) |
|---|---|---|---|---|
| 205 | C25H18N3O3 * C2F3O2 | 521.45 | 1H NMR (300 MHz, DMSO-d6): 8.92 (dd, J = 4.5, 1.7 Hz, 1H), 8.74 (d, J = 2.0 Hz, 1H), 8.55 (s, 1H), 8.37 (d, J = 8.3 Hz, 1H), 8.08 (d, J = 7.9 Hz, 1H), 8.00 (dd, J = 8.1, 2.1 Hz, 1H), 7.92 (dd, J = 5.3, 3.3 Hz, 2H), 7.73 (dd, J = 8.8, 1.9 Hz, 1H), 7.67 (dd, J = 7.7, 1.3 Hz, 1H), 7.60-7.52 (m, 3H), 7.42 (dd, J = 7.7, 1.9 Hz, 1H), 5.26 (s, 2H).; Mixture of two conformers 9:1 ratio. TFA salt | 3.8 (408.1)+ |
| 206 | C25H20N4O4S | 472.52 | 1H NMR (300 MHz, DMSO-d6) 12.82 (s, 1H), 9.73 (s, 1H), 8.80 (d, J = 4.3, 1.8 Hz, 1H), 8.39 (dd, J = 8.3, 1.8 Hz, 1H), 8.13 (d, J = 8.5 Hz, 1H), 7.96 (d, J = 1.6 Hz, 1H), 7.85 (br.s, 1H), 7.60 (d, J = 8.5 Hz, 1H), 7.54-7.47 (m, 2H), 7.45 (dd, J = 7.7, 1.5 Hz, 1H), 7.38-7.28 (m, 2H), 7.06 (td, J = 7.6, 1.2 Hz, 1H), 2.91 (s, 3H), 2.87 (s, 3H). | 7.7 (473.1)+ |
| 207 | C27H21N3O5S | 499.54 | 1H NMR (400 MHz, DMSO-d6): 13.47 (s, 1H), 8.99 (s, 1H), 8.82 (s, 1H), 8.70 (dd, J = 4.3, 1.8 Hz, 1H), 8.50 (dd, J = 8.5, 1.8 Hz, 1H), 8.36 (d, J = 8.4 Hz, 1H), 7.99 (s, 1H), 7.50-7.41 (m, 2H), 7.38 (dd, J = 7.7, 1.5 Hz, 1H), 7.30 (td, J = 8.5, 8.0, 1.6 Hz, 1H), 7.14 (d, J = 8.5 Hz, 1H), 7.05 (td, J = 7.6, 1.2 Hz, 1H), 5.57-5.52 (m, 2H), 4.03 (s, 3H), 2.19 (d, J = 1.2 Hz, 3H) | 6.8 (500.1)+ |
| 208 | C28H19N3O4S | 493.54 | 1H NMR (400 MHz, DMSO-d6): 13.93 (s, 1H), 9.94 (s, 1H), 8.77 (s, 1H), 8.68-8.62 (m, 2H), 8.39-8.34 (m, 1H), 8.28-8.23 (m, 1H), 8.05 (d, J = 8.5 Hz, 1H), 7.97-7.86 (m, 2H), 7.64-7.59 (m, 1H), 7.57 (d, J = 8.4 Hz, 1H), 7.44-7.40 (m, 1H), 7.39-7.33 (m, 1H), 7.32-7.27 (m, 1H), 7.17-7.12 (m, 1H), 2.86 (s, 3H). | 7.1 (494.2)+ |
| 209 | C28H19N3O5S | 509.54 | 1H NMR (400 MHz, DMSO-d6): 13.90 (s, 1H), 9.35 (s, 1H), 8.70 (s, 1H), 8.66-8.62 (m, 2H), 8.30-8.29 (m, 1H), 8.28-8.27 (m, 1H), 8.27-8.24 (m, 1H), 7.93-7.86 (m, 2H), 7.57 (dd, J = 7.7, 1.4 Hz, 1H), 7.41-7.34 (m, 2H), 7.29-7.25 (m, 1H), 7.19-7.14 (m, 1H), 7.07 (d, J = 8.5 Hz, 1H), 3.98 (s, 3H). | 6.9 (508.0) |
| 210 | C25H19N3O5S | 473.51 | 1H NMR (400 MHz, DMSO-d6): 9.79 (s, 1H), 8.84 (t, J = 1.5 Hz, 1H), 8.80 (dd, J = 4.5, 1.8 Hz, 1H), 8.44-8.37 (m, 1H), 8.23 (d, J = 9.3 Hz, 1H), 8.13 (d, J = 1.5 Hz, 2H), 7.70 (d, J = 9.3 Hz, 1H), 7.52 (dd, J = 8.4, 1.0 Hz, 1H), 7.45 (ddd, J = 12.6, 8.0, 3.0 Hz, 2H), 7.32 (ddd, J = 8.7, 7.5, 1.6 Hz, 1H), 7.05 (td, J = 7.6, 1.1 Hz, 1H), 4.38 (q, J = 7.0 Hz, 2H), 1.38 (t, J = 6.9 Hz, 3H) | 5.2 (474.1)+ |
| 211 | C26H21N3O5S | 487.53 | 1H NMR (400 MHz, DMSO-d6): 9.69 (s, 1H), 8.86 (t, J = 1.5 Hz, 1H), 8.77 (dd, J = 4.4, 1.8 Hz, 1H), 8.38 (dd, J = 8.3, 1.8 Hz, 1H), 8.20 (d, J = 9.3 Hz, 1H), 8.15 (d, J = 1.4 Hz, 2H), 7.71 (d, J = 9.4 Hz, 1H), 7.55 (dd, J = 8.4, 1.0 Hz, 1H), 7.44 (ddd, J = 12.6, 8.0, 3.0 Hz, 2H), 7.30 (ddd, J = 8.6, 7.5, 1.6 Hz, 1H), 7.03 (td, J = 7.6, 1.1 Hz, 1H), 5.03 (hept, J = 6.1 Hz, 1H), 1.35 (d, J = 6.0 Hz, 6H) | 5.8 (488.1)+ |
| 212 | C25H20N4O5S | 488.52 | 1H NMR (300 MHz, DMSO-d6) 12.66 (s, 1H), 9.14 (s, 1H), 8.78 (dd, J = 4.3, 1.8 Hz, 1H), 8.51 (dd, J = 8.5, 1.7 Hz, 1H), 8.32 (d, J = 8.4 Hz, 1H), 7.91 (d, J = 1.6 Hz, 1H), 7.85 (br. s, 1H), 7.55-7.44 (m, 2H), 7.40 (dd, J = 7.8, 1.5 Hz, 1H), 7.33 (td, J = 7.9, 1.6 Hz, 1H), 7.24 (d, J = 1.7 Hz, 1H), 7.18-7.02 (m, 2H), 4.03 (s, 3H), 2.90 (s, 3H). | 7.4 (489.1)+ |
| 213 | C29H22N2O4 | 462.50 | H NMR (300 MHz, DMSO-d6): 8.72 (d, J = 2.0 Hz, 1H), 8.48 (s, 1H), 8.14-8.01 (m, 1H), 7.97 (dd, J = 8.1, 2.1 Hz, 1H), 7.70 (dd, J = 7.7, 1.4 Hz, 1H), 7.61-7.47 (m, 4H), 7.45-7.36 (m, 5H), 7.11 (s, 2H), 5.04 (s, 2H), 3.65 (s, 3H). | 6.8 (463.1)+ |
| 214 | C24H16IN3O5S | 585.38 | 1H NMR (300 MHz, DMSO-d6): 9.32 (s, 1H), 8.76 (dd, J = 4.3, 1.8 Hz, 1H), 8.74-8.72 (m, 1H), 8.51 (dd, J = 8.5, 1.8 Hz, 1H), 8.31 (d, J = 8.4 Hz, 1H), 8.12 (dd, J = 8.1, 0.9 Hz, 1H), 8.03 (dd, J = 8.1, 2.1 Hz, 1H), 7.77 (d, J = 2.1 Hz, 1H), 7.69 (dd, J = 8.7, 2.1 Hz, 1H), 7.48 (dd, J = 8.5, 4.3 Hz, 1H), 7.27 (d, J = 8.7 Hz, 1H), 7.13 (d, J = 8.5 Hz, 1H), 4.03 (s, 3H). | 7.3 (586.0)+ |
| 215 | C30H24N2O5 | 492.53 | 1H NMR (300 MHz, DMSO-d6): 8.61 (s, 1H), 8.51 (s, 1H), 7.73 (s, 1H), 7.69-7.64 (m, 1H), 7.52 (dd, J = 3.9, 2.0 Hz, 2H), 7.35-7.29 (m, | 5.9 (493.1)+ |

TABLE 2-continued

| Cpd. No. | Formula | Mass | NMR | LCMS (M + H) |
|---|---|---|---|---|
| | | | 5H), 7.18 (dd, J = 7.5, 1.8 Hz, 1H), 7.07 (dd, J = 8.4, 1.1 Hz, 1H), 7.02-6.91 (m, 1H), 5.12 (s, 2H), 4.05 (s, 3H), 3.70 (s, 3H). | |
| 216 | C24H18N4O5S | 474.49 | 1H NMR (300 MHz, DMSO-d6) 11.58 (br. s, 1H), 9.19 (br. s, 2 × —NH—, 2H), 8.76 (dd, J = 4.3, 1.8 Hz, 1H), 8.66 (t, J = 1.5 Hz, 1H), 8.50 (dd, J = 8.6, 1.8 Hz, 1H), 8.31 (d, J = 8.4 Hz, 1H), 8.04 (d, J = 1.5 Hz, 2H), 7.54-7.43 (m, 2H), 7.40 (dd, J = 7.7, 1.5 Hz, 1H), 7.32 (td, J = 8.3, 7.9, 1.6 Hz, 1H), 7.17-7.02 (m, 2H), 4.02 (s, 3H). | 6.8 (475.1)+ |
| 217 | C26H22N4O4S | 486.55 | 1H NMR (300 MHz, DMSO-d6) 9.17 (br. s, 1H), 8.79 (dd, J = 4.3, 1.8 Hz, 1H), 8.63 (d, J = 2.0 Hz, 1H), 8.51 (dd, J = 8.5, 1.7 Hz, 1H), 8.32 (d, J = 8.4 Hz, 1H), 7.99 (dd, J = 8.1, 2.1 Hz, 1H), 7.65 (d, J = 8.0 Hz, 1H), 7.55-7.43 (m, 2H), 7.40 (dd, J = 7.6, 1.4 Hz, 1H), 7.36-7.27 (m, 1H), 7.13 (d, J = 8.5 Hz, 1H), 7.07 (t, J = 7.6 Hz, 1H), 4.03 (s, 3H), 3.05 (s, 3H), 3.01 (s, 3H). | 6.1 (487.1)+ |
| 218 | C25H19N3O5S | 473.51 | 1H NMR (400 MHz, DMSO-d6): 13.44 (br, 1H), 9.65 (s, 1H), 8.83 (s, 1H), 8.77 (dd, J = 4.3, 1.8 Hz, 1H), 8.41 (dd, J = 8.3, 1.8 Hz, 1H), 8.23-8.06 (m, 3H), 7.62 (d, J = 8.5 Hz, 1H), 7.50 (dd, J = 8.3, 4.3 Hz, 1H), 7.39 (d, J = 8.7 Hz, 1H), 7.09 (d, J = 2.5 Hz, 1H), 6.65 (dd, J = 8.6, 2.5 Hz, 1H), 3.70 (s, 3H), 2.90 (s, 3H). | 6.4 (474.1)+ |
| 219 | C23H25N3O5S | 455.53 | 1H NMR (300 MHz, DMSO-d6): 8.87 (s, 1H), 8.76 (s, 1H), 7.75 (s, 1H), 7.65-7.53 (m, 2H), 7.46 (td, J = 7.9, 1.6 Hz, 1H), 7.22 (td, J = 7.5, 1.2 Hz, 1H), 4.07 (s, 3H), 3.60 (dt, J = 8.8, 5.7 Hz, 1H), 2.12-1.94 (m, 1H), 1.89-1.70 (m, 1H), 1.70-1.53 (m, 1H), 1.52-1.34 (m, 3H), 1.30-1.19 (m, 2H), 1.06-0.96 (m, 1H). | 6.5 (456.2)+ |
| 220 | C27H19N3O3 | 433.47 | 1H NMR (400 MHz, DMSO-d6): 8.82-8.72 (m, 1H), 8.56-8.52 (m, 1H), 8.50-8.48 (m, 1H), 8.08-8.04 (m, 1H), 8.02-7.98 (m, 1H), 7.95-7.91 (m, 2H), 7.88-7.82 (m, 1H), 7.81-7.73 (m, 1H), 7.71-7.67 (m, 1H), 7.64-7.55 (m, 2H), 7.52-7.28 (m, 4H), 5.13-5.07 (m, 2H). | 5.4 (434.2)+ |
| 221 | C24H27N3O5S | 469.56 | 1H NMR (300 MHz, DMSO-d6): 8.76 (d, J = 2.8 Hz, 2H), 7.75 (s, 1H), 7.62-7.40 (m, 3H), 7.19 (td, J = 7.5, 1.4 Hz, 1H), 3.83 (dd, J = 12.8, 4.4 Hz, 1H), 2.84 (td, J = 13.1, 11.8, 3.0 Hz, 1H), 2.79-2.69 (m, 1H), 2.27-2.20 (m, 1H), 1.60-1.18 (m, 9H), 1.12-0.75 (m, 3H). | 7.1 (470.1)+ |
| 222 | C25H29N3O5S | 483.59 | 1H NMR (400 MHz, DMSO-d6): 9.03 (s, 1H), 8.76 (d, J = 1.9 Hz, 2H), 8.74 (s, 1H), 7.75 (d, J = 1.2 Hz, 2H), 7.62-7.50 (m, 4H), 7.48-7.41 (m, 2H), 7.26-7.14 (m, 2H), 4.08 (s, 3H), 4.07 (s, 3H), 3.89-3.73 (m, 1H), 3.65-3.51 (m, 1H), 3.41-3.22 (m, 1H), 2.97-2.84 (m, 2H), 2.76 (td, J = 10.8, 9.6, 3.5 Hz, 2H), 2.29-2.17 (m, 2H), 1.96-1.73 (m, 1H), 1.66-1.47 (m, 5H), 1.40-1.22 (m, 4H), 1.17-1.09 (m, 1H), 0.86 (d, J = 6.6 Hz, 3H), 0.79 (d, J = 5.8 Hz, 3H), 0.68 (d, J = 12.3 Hz, 1H). | 7.8 (484.3)+ |
| 223 | C27H24N4O5S | 516.58 | 1H NMR (300 MHz, DMSO-d6) 9.03 (s, 1H), 8.70 (dd, J = 4.3, 1.8 Hz, 1H), 8.57-8.48 (m, 2H), 8.42 (d, J = 8.4 Hz, 1H), 7.57-7.51 (m, 1H), 7.51-7.47 (m, 1H), 7.38 (s, 1H), 7.34 (dd, J = 7.7, 1.5 Hz, 1H), 7.31-7.23 (m, 1H), 7.17 (d, J = 8.5 Hz, 1H), 7.05-6.92 (m, 1H), 4.09 (s, 3H), 4.05 (s, 3H), 3.05 (s, 3H), 3.01 (s, 3H). | 6.2 (517.2)+ |
| 224 | C25H20N4O6S | 504.52 | 1H NMR (300 MHz, DMSO-d6) 11.51 (s, 1H), 9.21 (br. s, 2H), 8.67 (dd, J = 4.3, 1.8 Hz, 1H), 8.56 (s, 1H), 8.52 (dd, J = 8.6, 1.7 Hz, 1H), 8.43 (d, J = 8.4 Hz, 1H), 7.73 (s, 1H), 7.59-7.43 (m, 2H), 7.35 (dd, J = 7.8, 1.5 Hz, 1H), 7.31-7.23 (m, 1H), 7.17 (d, J = 8.5 Hz, 1H), 7.06-6.93 (m, 1H), 4.15 (s, 3H), 4.05 (s, 3H). | 7.1 (505.1)+ |
| 225 | C24H27N3O4S | 453.56 | 1H NMR (400 MHz, DMSO-d6): 9.42 (s, 1H), 8.71 (d, J = 1.9 Hz, 1H), 8.04 (d, J = 1.9 Hz, 1H), 7.58 (td, J = 8.2, 1.3 Hz, 2H), 7.47-7.38 (m, 1H), 7.21 (td, J = 7.5, 1.2 Hz, 1H), 3.91-3.64 (m, 1H), 2.84-2.64 (m, 2H), 2.37-2.23 (m, 1H), 1.64-1.38 (m, 7H), 1.28 (dd, J = 13.3, 10.0 Hz, 1H), 1.14-0.90 (m, 2H), 0.88-0.76 (m, 1H). | 7.7 (454.2)+ |

TABLE 2-continued

| Cpd. No. | Formula | Mass | NMR | LCMS (M + H) |
|---|---|---|---|---|
| 226 | C30H21N3O4S | 519.58 | 1H NMR (400 MHz, DMSO-d6): 13.55 (s, 1H), 9.55 (s, 1H), 8.93 (s, 1H), 8.61 (dd, J = 4.3, 1.8 Hz, 1H), 8.35 (dd, J = 8.3, 1.8 Hz, 1H), 8.14 (s, 1H), 8.09 (d, J = 8.5 Hz, 1H), 7.82-7.76 (m, 2H), 7.58 (ddd, J = 7.8, 6.3, 1.2 Hz, 3H), 7.55-7.44 (m, 2H), 7.41 (dd, J = 8.3, 4.3 Hz, 1H), 7.34-7.26 (m, 2H), 7.02 (td, J = 7.6, 1.1 Hz, 1H), 2.87 (s, 3H) | 7.1 (520.2)+ |
| 227 | C27H19N3O4S | 481.53 | 1H NMR (400 MHz, DMSO-d6): 13.25 (s, 1H), 9.89 (s, 1H), 8.60 (dd, J = 2.0, 1.0 Hz, 1H), 8.51 (d, J = 1.8 Hz, 1H), 7.95 (dt, J = 7.9, 0.9 Hz, 1H), 7.84-7.76 (m, 2H), 7.62 (dd, J = 8.7, 1.9 Hz, 1H), 7.58-7.51 (m, 2H), 7.49-7.39 (m, 4H), 7.23 (ddd, J = 7.8, 5.6, 3.0 Hz, 1H), 7.13 (ddd, J = 8.0, 7.1, 1.0 Hz, 1H), 3.81 (s, 3H) | 6.2 (482.2)+ |
| 228 | C24H27N3O4S | 453.56 | 1H NMR (400 MHz, DMSO-d6): 13.39 (s, 2H), 9.60-9.43 (m, 2H), 8.97-8.87 (m, 2H), 8.25-8.17 (m, 2H), 8.17-8.08 (m, 2H), 7.66-7.51 (m, 4H), 7.51-7.40 (m, 2H), 7.29-7.16 (m, 2H), 3.86-3.76 (m, 1H), 3.67-3.56 (m, 1H), 3.27 (d, J = 4.1 Hz, 1H), 2.87-2.65 (m, 3H), 2.39-2.25 (m, 2H), 1.90-1.79 (m, 1H), 1.70-1.41 (m, 8H), 1.40-0.90 (m, 16H), 0.85-0.80 (m, 3H), 0.80-0.75 (m, 3H), 0.73-0.58 (m, 1H). | 17.7 (BCM-30 min) (454.2)+ |
| 229 | C26H20N2O5S | 472.52 | 1H NMR (400 MHz, DMSO-d6): 12.87 (s, 1H), 9.68 (s, 1H), 8.80-8.76 (m, 1H), 8.43-8.39 (m, 1H), 8.16-8.13 (m, 1H), 7.74 (d, 1H), 7.61 (d, 1H), 7.53-7.49 (m, 2H), 7.42 (dd, J = 7.7, 1.5 Hz, 1H), 7.33-7.27 (m, 2H), 7.19 (dd, J = 7.9, 1.4 Hz, 1H), 7.05-7.01 (m, 1H), 3.89 (s, 3H), 2.90 (s, 3H). | 6.7 (473.1)+ |
| 230 | C26H20N2O6S | 488.52 | 1H NMR (400 MHz, DMSO-d6): 12.85 (s, 1H), 9.04 (s, 1H), 8.80-8.73 (m, 1H), 8.53 (dd, J = 8.5, 1.8 Hz, 1H), 8.35 (d, J = 8.4 Hz, 1H), 7.73 (d, J = 7.9 Hz, 1H), 7.56-7.44 (m, 2H), 7.42-7.35 (m, 1H), 7.34-7.26 (m, 1H), 7.26-7.20 (m, 1H), 7.20-7.10 (m, 2H), 7.10-7.00 (m, 1H), 4.04 (s, 3H), 3.88 (s, 3H). | 6.5 (489.1)+ |
| 231 | C24H18N4O4S | 458.50 | 1H NMR (300 MHz, DMSO-d6): 9.43 (s, 1H), 8.88 (dd, J = 4.3, 1.8 Hz, 1H), 8.59 (d, J = 1.8 Hz, 1H), 8.33 (dd, J = 8.3, 1.8 Hz, 1H), 8.07 (dd, J = 8.3, 5.6 Hz, 2H), 7.85 (dd, J = 8.1, 2.1 Hz, 1H), 7.54 (d, J = 8.5 Hz, 1H), 7.43 (dd, J = 8.3, 4.3 Hz, 1H), 6.87 (d, J = 8.7 Hz, 1H), 6.66 (d, J = 2.6 Hz, 1H), 6.54 (dd, J = 8.7, 2.7 Hz, 1H), 2.74 (s, 3H). | 4.7 (459.1)+ |
| 232 | C26H21N3O5S | 487.53 | 1H NMR (300 MHz, DMSO-d6): 9.01 (s, 1H), 8.80 (dd, J = 4.3, 1.8 Hz, 1H), 8.55 (dd, J = 8.5, 1.7 Hz, 1H), 8.37 (d, J = 8.4 Hz, 1H), 7.88 (d, J = 8.1 Hz, 1H), 7.59-7.50 (m, 2H), 7.48 (s, 0H), 7.39 (dd, J = 7.7, 1.5 Hz, 1H), 7.29 (ddd, J = 8.5, 7.5, 1.6 Hz, 1H), 7.16 (d, J = 8.5 Hz, 1H), 7.03 (td, J = 7.6, 1.2 Hz, 1H), 6.83 (d, J = 1.5 Hz, 1H), 6.74 (dd, J = 8.1, 1.5 Hz, 1H), 4.05 (s, 3H), 2.89 (s, 3H). | 7.0 (488.2)+ |
| 233 | C28H18BrN3O4S | 572.44 | 1H NMR (400 MHz, DMSO-d6): 13.97 (s, 1H), 10.00 (s, 1H), 8.75 (s, 1H), 8.67-8.60 (m, 2H), 8.37-8.30 (m, 1H), 8.29-8.22 (m, 1H), 8.05 (d, J = 8.5 Hz, 1H), 7.97-7.84 (m, 3H), 7.60-7.52 (m, 2H), 7.40-7.33 (m, 1H), 7.33-7.25 (m, 1H), 2.85 (s, 3H). | 8.4 (572.2)+ |
| 234 | C28H18ClN3O4S | 527.99 | 1H NMR (400 MHz, DMSO-d6): 13.95 (s, 1H), 10.01 (s, 1H), 8.74 (s, 1H), 8.68-8.60 (m, 2H), 8.37-8.29 (m, 1H), 8.28-8.21 (m, 1H), 8.07-8.00 (m, 1H), 7.97-7.84 (m, 2H), 7.78-7.73 (m, 1H), 7.59-7.52 (m, 1H), 7.48-7.37 (m, 2H), 7.29 (dd, J = 8.2, 4.3 Hz, 1H), 2.85 (s, 3H). | 8.1 (528.1)+ |
| 235 | C28H18BrN3O5S | 588.44 | 1H NMR (400 MHz, DMSO-d6): 13.94 (s, 1H), 9.50 (s, 1H), 8.67 (s, 1H), 8.66-8.59 (m, 2H), 8.33-8.24 (m, 2H), 8.24-8.16 (m, 1H), 7.93-7.85 (m, 2H), 7.83 (d, J = 2.4 Hz, 1H), 7.58 (dd, J = 8.8, 2.4 Hz, 1H), 7.34 (d, J = 8.8 Hz, 1H), 7.28 (dd, J = 8.5, 4.3 Hz, 1H), 7.07 (d, J = 8.5 Hz, 1H), 3.97 (s, 3H). | 8.0 (590.0)+ |

TABLE 2-continued

| Cpd. No. | Formula | Mass | NMR | LCMS (M + H) |
|---|---|---|---|---|
| 236 | C28H18ClN3O5S | 543.98 | 1H NMR (400 MHz, DMSO-d6): 13.94 (s, 1H), 9.52 (s, 1H), 8.68-8.58 (m, 3H), 8.32-8.24 (m, 2H), 8.24-8.15 (m, 1H), 7.94-7.84 (m, 2H), 7.74-7.68 (m, 1H), 7.50-7.36 (m, 2H), 7.31-7.23 (m, 1H), 7.09-7.02 (m, 1H), 3.97 (s, 3H). | 7.8 (544.1)+ |
| 237 | C25H19ClN4O4S | 506.97 | 1H NMR (400 MHz, DMSO-d6): 9.83 (s, 1H), 8.85-8.78 (m, 1H), 8.44-8.37 (m, 1H), 8.18-8.11 (m, 1H), 7.96-7.90 (m, 1H), 7.86 (s, 1H), 7.64-7.54 (m, 2H), 7.54-7.45 (m, 2H), 7.42 (dd, J = 8.9, 2.5 Hz, 1H), 7.29 (d, J = 1.7 Hz, 1H), 2.91 (s, 3H), 2.87 (s, 3H). | 7.3 (507.02)+ |
| 238 | C26H21BrN4O4S | 565.45 | 1H NMR (300 MHz, DMSO-d6) 9.32 (s, 1H), 8.77 (dd, J = 4.3, 1.8 Hz, 1H), 8.59 (dd, J = 2.0 Hz, 1H), 8.50 (dd, J = 8.5, 1.8 Hz, 1H), 8.31 (d, J = 8.4 Hz, 1H), 7.95 (dd, J = 8.1, 2.1 Hz, 1H), 7.65 (dd, J = 8.1 Hz, 1H), 7.62 (d, J = 2.4 Hz, 1H), 7.57-7.45 (m, 2H), 7.39 (d, J = 8.9 Hz, 1H), 7.13 (d, J = 8.5 Hz, 1H), 4.03 (s, 3H), 3.05 (s, 3H), 3.00 (s, 3H). | 6.9 (565.2)+ |
| 239 | C26H21ClN4O4S | 520.99 | 1H NMR (300 MHz, DMSO-d6) 9.34 (s, 1H), 8.77 (dd, J = 4.3, 1.8 Hz, 1H), 8.58 (d, J = 1.9 Hz, 1H), 8.49 (dd, J = 8.5, 1.8 Hz, 1H), 8.30 (d, J = 8.4 Hz, 1H), 7.94 (dd, J = 8.1, 2.1 Hz, 1H), 7.64 (d, J = 8.1 Hz, 1H), 7.55-7.37 (m, 4H), 7.12 (d, J = 8.5 Hz, 1H), 4.03 (s, 3H), 3.05 (s, 3H), 3.00 (s, 3H). | 6.8 (521.2)+ |
| 240 | C26H21N3O4S | 471.53 | 1H NMR (300 MHz, DMSO-d6): 9.68 (s, 1H), 8.80 (dd, J = 4.3, 1.8 Hz, 1H), 8.43 (dd, J = 8.4, 1.8 Hz, 1H), 8.15 (d, J = 8.5 Hz, 1H), 7.90 (d, J = 8.1 Hz, 1H), 7.62 (d, J = 8.5 Hz, 1H), 7.57-7.48 (m, 2H), 7.42 (dd, J = 7.7, 1.5 Hz, 1H), 7.30 (ddd, J = 8.6, 7.5, 1.6 Hz, 1H), 7.02 (td, J = 7.6, 1.1 Hz, 1H), 6.87 (d, J = 1.5 Hz, 1H), 6.77 (dd, J = 8.1, 1.5 Hz, 1H), 2.92 (s, 3H), 2.90 (s, 3H). | 7.2 (472.1)+ |
| 241 | C24H22N2O6S | 466.51 | 1H NMR (400 MHz, DMSO-d6): 13.38 (s, 1H), 9.44 (s, 1H), 8.66 (s, 1H), 7.73 (t, J = 4.4 Hz, 2H), 7.47 (d, J = 7.5 Hz, 1H), 7.37 (dd, J = 4.7, 1.5 Hz, 2H), 7.19-7.14 (m, 1H), 6.87 (d, J = 9.0 Hz, 1H), 4.06 (s, 3H), 3.78 (s, 3H), 2.45 (s, 3H), 1.95 (s, 3H). | 6.2 (467.2)+ |
| 242 | C25H19ClN4O5S | 522.97 | 1H NMR (400 MHz, DMSO-d6): 12.75 (s, 1H), 9.32 (s, 1H), 8.80-8.74 (m, 1H), 8.54-8.46 (m, 1H), 8.33-8.26 (m, 1H), 7.88-7.82 (m, 2H), 7.53-7.38 (m, 4H), 7.20 (d, J = 1.7 Hz, 1H), 7.15-7.08 (m, 1H), 4.02 (s, 3H), 2.89 (s, 3H). | 7.0 (523.2)+ |
| 243 | C24H21ClN2O6S | 500.96 | 1H NMR (300 MHz, DMSO-d6) 13.50 (br. s, 1H), 9.72 (br. s, 1H), 8.65 (s, 1H), 7.82-7.63 (m, 2H), 7.60-7.49 (m, 1H), 7.49-7.41 (m, 1H), 7.37 (d, J = 8.9 Hz, 1H), 6.86 (d, J = 8.9 Hz, 1H), 4.03 (s, 3H), 3.77 (s, 3H), 2.44 (s, 3H), 1.93 (s, 3H). | 8.8 (501.2)+ |
| 244 | C25H18N4O6S | 502.50 | 1H NMR (300 MHz, DMSO-d6): 10.27 (s, 1H), 8.94 (d, J = 1.9 Hz, 1H), 8.77 (dd, J = 4.3, 1.8 Hz, 1H), 8.44 (dd, J = 8.3, 1.8 Hz, 1H), 8.34 (d, J = 2.7 Hz, 1H), 8.30-8.23 (m, 2H), 8.22-8.13 (m, 2H), 7.84 (d, J = 9.3 Hz, 1H), 7.66 (d, J = 8.5 Hz, 1H), 7.52 (dd, J = 8.3, 4.3 Hz, 1H), 3.95 (s, 3H), 2.96 (s, 3H). | 7.0 (503.1)+ |
| 245 | C26H20N4O4S | 484.53 | 1H NMR (400 MHz, DMSO-d6): 9.17 (s, 1H), 8.79-8.71 (m, 2H), 8.53-8.46 (m, 1H), 8.35-8.28 (m, 1H), 8.11 (s, 1H), 7.51-7.38 (m, 3H), 7.38-7.29 (m, 1H), 7.16-7.04 (m, 2H), 4.56 (s, 2H), 4.03 (s, 3H), 3.16 (s, 3H). | 5.7 (485.2)+ |
| 246 | C27H25N5O4S | 515.59 | 1H NMR (300 MHz, DMSO-d6): 9.06 (s, 1H), 8.84-8.75 (m, 1H), 8.57-8.47 (m, 1H), 8.38-8.28 (m, 1H), 7.89-7.82 (m, 1H), 7.56-7.42 (m, 2H), 7.42-7.35 (m, 1H), 7.34-7.26 (m, 1H), 7.17-7.11 (m, 1H), 7.10-7.01 (m, 2H), 6.06-5.95 (m, 1H), 4.04 (s, 3H), 3.04 (s, 3H), 2.96 (s, 3H), 2.80-2.72 (m, 3H). | 6.4 (516.3)+ |
| 247 | C25H19N3O5S | 473.51 | 1H NMR (400 MHz, DMSO-d6): 13.44 (s, 1H), 9.63 (s, 1H), 8.85 (dd, J = 4.3, 1.8 Hz, 1H), 8.67 (dd, J = 2.1, 0.9 Hz, 1H), 8.34 (dd, J = 8.3, 1.8 Hz, 1H), 8.16-8.02 (m, 2H), 7.94 (dd, J = 8.1, 2.1 Hz, 1H), 7.55 (d, J = 8.5 Hz, 1H), 7.43 (dd, J = 8.3, 4.3 Hz, 1H), 7.22 (d, J = 9.0 Hz, 1H), 7.02 (d, J = 3.0 Hz, 1H), 6.93 (dd, J = 9.0, 3.0 Hz, 1H), 3.69 (s, 3H), 2.77 (s, 3H). | 6.1 (474.1)+ |

TABLE 2-continued

| Cpd. No. | Formula | Mass | NMR | LCMS (M + H) |
|---|---|---|---|---|
| 248 | C26H22N4O4S | 486.55 | 1H NMR (400 MHz, Chloroform-d): 9.37 (s, 1H), 8.84 (dd, J = 4.4, 1.8 Hz, 1H), 8.58 (s, 1H), 8.19 (d, J = 8.0 Hz, 1H), 8.08 (dd, J = 8.2, 1.8 Hz, 1H), 7.91 (dd, J = 8.0, 2.0 Hz, 1H), 7.82 (d, J = 8.4 Hz, 1H), 7.41 (d, J = 8.4 Hz, 1H), 7.30 (dd, J = 8.2, 4.3 Hz, 1H), 7.15 (d, J = 9.0 Hz, 1H), 6.72 (d, J = 3.0 Hz, 1H), 6.60 (dd, J = 9.1, 3.0 Hz, 1H), 2.90 (s, 3H), 2.88 (s, 6H). Carboxylic proton not visible. | 6.1 (487.1)+ |
| 249 | C24H21NO5S | 435.50 | 1H NMR (400 MHz, DMSO-d6) d 13.10 (s, 1H), 9.85 (s, 1H), 8.00-7.95 (m, 2H), 7.65 (d, J = 8.9 Hz, 1H), 7.63-7.58 (m, 2H), 7.49-7.44 (m, 1H), 7.39-7.32 (m, 2H), 7.20-7.15 (m, 1H), 6.83 (d, J = 9.0 Hz, 1H), 3.76 (s, 3H), 2.45 (s, 3H), 1.93 (s, 3H). | 1.86 (436.0)* |
| 250 | C23H17NO6S | 435.45 | 1H NMR (300 MHz, DMSO, ppm): 9.87 (s, 1H), 7.93 (d, J = 9 Hz, 2H), 7.60 (d, J = 6 Hz, 2H), 7.47 (m, 1H), 7.39 (m, 1H), 7.30 (m, 1H), 7.23-7.16 (m, 2H), 7.04 (m, 1H), 6.82 (d, J = 9 Hz, 1H), 4.12 (m, 2H), 4.03 (m, 2H). | 2.069 (435.9) |
| 251 | C22H13F2NO6S | 457.41 | 1H NMR (400 MHz, DMSO-d6) d 13.24-12.97 (m, 1H), 10.57 (s, 1H), 7.96-7.91 (m, 2H), 7.54-7.49 (m, 2H), 7.49-7.41 (m, 4H), 7.40-7.36 (m, 1H), 7.34 (td, J = 7.5, 1.4 Hz, 1H), 7.19 (t, J = 8.2 Hz, 1H). | 1.79 (458.0)* |
| 252 | C27H22N2O6S2 | 534.61 | (400 MHz, CD3OD, ppm): 8.52(d, J = 8 Hz, 1H), 8.19(d, J = 8 Hz, 1H), 8.11 (d, J = 8 Hz, 1H), 7.91 (d, J = 8 Hz, 2H), 7.55(d, J = 8 Hz, 1H), 7.36-7.23(m, 6H), 7.12-7.06(m, 1H), 6.80(d, J = 8 Hz, 1H), 3.94(s, 3H), 3.29(s, 3H). | 2.299 (534.9) |
| 253 | C27H19N3O4S | 481.53 | (300 MHz, DMSO, ppm): 10.11(s, 1H), 8.59(d, J = 9 Hz, 1H), 8.17(d, J = 9 Hz, 1H), 8.07(d, J = 9 Hz, 1H), 7.91(d, J = 9 Hz, 2H), 7.48-7.25(m, 7H), 7.17-6.91(m, 3H), 3.95(s, 3H). | |
| 254 | C23H17NO6S | 435.45 | 300 MHz, DMSO-d6 13.12 (s, 1H), 9.48 (s, 1H), 8.02-7.88 (m, 2H), 7.59-7.46 (m, 3H), 7.30 (tt, J = 8.3, 1.7 Hz, 3H), 7.17 (ddd, J = 7.6, 6.9, 1.8 Hz, 1H), 7.02 (dd, J = 8.1, 1.6 Hz, 1H), 6.85 (t, J = 8.0 Hz, 1H), 4.29-3.72 (m, 4H). | 1.348 (433.9) |
| 255 | C26H20FN3O6S2 | 553.59 | 1H NMR (300 MHz, DMSO-d6) 11.86 (s, 1H), 10.21 (s, 1H), 8.56-8.45 (m, 2H), 8.12-8.01 (m, 2H), 7.98-7.79 (m, 2H), 7.49-7.17 (m, 5H), 6.89 (d, J = 8.5 Hz, 1H), 3.90 (s, 3H), 3.37 (s, 3H). | 1.652 (554.1) |
| 256 | C26H17FN4O4S | 500.51 | (300 MHz, CD3OD, ppm): 8.44(m, 1H), 8.30(s, 1H), 8.08-7.98(m, 3H), 7.58-7.47(m, 2H), 7.26-7.23(m, 2H), 7.17-7.10(m, 1H), 6.99-6.96(m, 1H), 6.74(d, J = 6 Hz, 1H), 3.88(s, 3H). | 1.737 (501.1) |
| 258 | C26H19NO5S | 457.50 | 1H NMR (300 MHz, DMSO-d6) 8.10-8.00 (m, 1H), 7.95-7.79 (m, 4H), 7.62-7.46 (m, 2H), 7.46-7.16 (m, 5H), 7.09-6.94 (m, 2H), 3.76 (s, 3H). | 1.478 (458.1) |
| 259 | C22H17NO5S | 407.44 | 1H NMR (400 MHz, DMSO-d6) d 13.30-12.96 (m, 1H), 9.85 (s, 1H), 8.01-7.97 (m, 2H), 7.64-7.62 (m, 2H), 7.62-7.60 (m, 2H), 7.47 (dd, J = 7.7, 1.6 Hz, 1H), 7.42-7.37 (m, 1H), 7.32 (dd, J 8.2, 1.3 Hz, 1H), 7.23 (td, J = 7.5, 1.4 Hz, 1H), 6.93-6.89 (m, 2H), 3.69 (s, 3H). | 1.72 (408.0)* |
| 261 | C26H20N2O4S | 456.52 | 1H NMR (300 MHz, DMSO, ppm): 10.11 (s, 1H), 8.61 (d, J = 9 Hz, 1H), 8.17 (d, J = 9 Hz, 1H), 8.07 (m, 2H), 7.89 (d, J = 9 Hz, 2H), 7.48-7.32 (m, 8H), 7.13 (s, 1H), 6.96 (d, J = 6 Hz, 1H), 3.95 (s, 3H). | 1.634 (457.3) |
| 262 | C24H17N3O4S | 443.48 | 1H NMR (400 MHz, DMSO-d6) d 13.99-12.78 (m, 1H), 9.39 (s, 1H), 8.68-8.64 (m, 1H), 8.61 (d, J = 2.2 Hz, 1H), 8.21 (dd, J = 7.4, 1.4 Hz, 1H), 8.18-8.13 (m, 2H), 8.12-8.08 (m, 1H), 7.96 (dd, J = 8.1, 2.1 Hz, 1H), 7.65 (t, J = 7.8 Hz, 1H), 7.50-7.45 (m, 1H), 7.42 (dd, J = 7.8, 1.6 Hz, 1H), 7.39-7.33 (m, 1H), 7.16-7.10 (m, 1H), 2.27 (s, 3H). | 1.64 (444.0)* |
| 263 | C23H19NO6S | 437.47 | 1H NMR (500 MHz, DMSO-d6) d 13.14 (s, 1H), 9.82 (s, 1H), 7.99-7.96 (m, 2H), 7.61-7.58 (m, 2H), 7.49 (dd, J = 7.7, 1.6 Hz, 1H), 7.43-7.38 (m, 1H), 7.34 (dd, J = 8.2, 1.2 Hz, 1H), 7.27-7.22 (m, 2H), 7.08 (d, J = 2.2 Hz, 1H), 6.93 (d, J = 8.5 Hz, 1H), 3.69 (s, 3H), 3.54 (s, 3H). | 1.66 (438.0)* |
| 264 | C24H17N3O4S | 443.48 | 1H NMR (400 MHz, DMSO-d6) d 9.38 (s, 1H), 8.66 (dd, J = 2.2, 0.7 Hz, 1H), 8.65 (d, J = 4.4 Hz, 1H), 8.38-8.33 (m, 2H), 8.10 (dd, J = 8.1, 0.9 | 1.63 (444.0)* |

TABLE 2-continued

| Cpd. No. | Formula | Mass | NMR | LCMS (M + H) |
|---|---|---|---|---|
| | | | Hz, 1H), 7.96 (dd, J = 8.1, 2.1 Hz, 1H), 7.72 (dd, J = 8.4, 7.4 Hz, 1H), 7.48-7.45 (m, 1H), 7.43 (dd, J = 7.7, 1.6 Hz, 1H), 7.37-7.31 (m, 2H), 7.11 (td, J = 7.5, 1.2 Hz, 1H), 2.65-2.61 (m, 3H). | |
| 265 | C24H17N3O4S | 443.48 | 1H NMR (400 MHz, DMSO-d6) d 14.26-12.32 (m, 1H), 9.38 (s, 1H), 8.74-8.68 (m, 2H), 8.32 (dd, J = 8.5, 1.7 Hz, 1H), 8.20 (d, J = 1.9 Hz, 1H), 8.13-8.08 (m, 1H), 8.02-7.97 (m, 2H), 7.49-7.41 (m, 3H), 7.35 (td, J = 7.9, 1.6 Hz, 1H), 7.12 (td, J = 7.6, 1.2 Hz, 1H), 2.53-2.50 (m, 3H). | 1.68 (444.0)* |
| 266 | C23H14ClN3O4S | 463.90 | 1H NMR (400 MHz, DMSO-d6) d 13.58-13.13 (m, 1H), 9.56 (s, 1H), 8.73 (d, J = 4.8 Hz, 1H), 8.60 (d, J = 2.0 Hz, 1H), 8.44-8.41 (m, 1H), 8.41-8.39 (m, 1H), 8.09-8.03 (m, 1H), 7.88-7.80 (m, 2H), 7.69 (d, J = 4.8 Hz, 1H), 7.46-7.33 (m, 3H), 7.17 (td, J = 7.4, 1.6 Hz, 1H). | 1.69 (464.0)* |
| 267 | C24H17N3O4S | 443.48 | 1H NMR (500 MHz, DMSO-d6) d 14.49-12.20 (m, 1H), 9.28 (s, 1H), 8.60-8.57 (m, 1H), 8.36 (dd, J = 7.3, 1.4 Hz, 1H), 8.28 (d, J = 8.5 Hz, 1H), 8.19 (dd, J = 8.2, 1.4 Hz, 1H), 8.07-8.03 (m, 1H), 7.88 (dd, J = 8.1, 2.1 Hz, 1H), 7.65 (t, J = 7.8 Hz, 1H), 7.47 (dd, J = 7.7, 1.5 Hz, 1H), 7.43-7.39 (m, 2H), 7.35 (td, J = 7.6, 1.6 Hz, 1H), 7.13 (td, J = 7.5, 1.2 Hz, 1H), 2.45 (s, 3H). | 1.63 (444.0)* |
| 269 | C21H13Cl2NO4S | 446.31 | 1H NMR (500 MHz, DMSO-d6) d 13.19 (s, 1H), 10.33 (s, 1H), 8.02-7.97 (m, 2H), 7.67-7.62 (m, 2H), 7.60 (d, J = 2.5 Hz, 1H), 7.59-7.55 (m, 2H), 7.51 (dd, J = 8.7, 2.5 Hz, 1H), 7.47-7.42 (m, 2H), 7.35 (d, J = 8.7 Hz, 1H). | 1.93 (447.0)* |
| 270 | C24H15ClN2O4S | 462.91 | 1H NMR (300 MHz, DMSO-d6) 8.61 (dd, J = 15.8, 2.5 Hz, 2H), 8.23 (ddd, J = 28.2, 7.9, 1.4 Hz, 2H), 7.94 (d, J = 8.0 Hz, 2H), 7.72 (t, J = 7.8 Hz, 1H), 7.51-7.21 (m, 5H), 7.15-7.03 (m, 1H). | 4.285 (463.0) |
| 271 | C23H14ClN3O4S | 463.90 | 400 MHz, DMSO-d6 8.67 (d, J = 2.5 Hz, 1H), 8.56 (dd, J = 6.8, 2.3 Hz, 2H), 8.25 (dd, J = 7.3, 1.4 Hz, 1H), 8.19 (dd, J = 8.4, 1.4 Hz, 1H), 8.02 (d, J = 8.1 Hz, 1H), 7.81 (dd, J = 8.1, 2.1 Hz, 1H), 7.72 (t, J = 7.8 Hz, 1H), 7.46-7.28 (m, 3H), 7.14 (td, J = 7.5, 1.4 Hz, 1H). | 2.611 (464.0) |
| 272 | C24H15ClN2O4S | 462.91 | 300 MHz, DMSO-d6 13.12 (s, 1H), 10.57 (s, 1H), 8.93 (dd, J = 2.3, 0.9 Hz, 1H), 8.65 (d, J = 2.4 Hz, 1H), 8.15 (dt, J = 8.6, 1.1 Hz, 1H), 7.99 (dd, J = 7.5, 1.2 Hz, 1H), 7.89-7.78 (m, 2H), 7.71 (dd, J = 8.5, 7.4 Hz, 1H), 7.44 (dd, J = 3.6, 1.1 Hz, 2H), 7.34 (dt, J = 7.7, 1.2 Hz, 1H), 7.30-7.14 (m, 3H). | 1.345 (463.0) |
| 275 | C19H11Cl2NO4S2 | 452.33 | 1H NMR (400 MHz, DMSO-d6): 13.11 (s, 1H), 10.64 (s, 1H), 8.01-7.96 (m, 2H), 7.63-7.57 (m, 3H), 7.49 (t, J = 7.6 Hz, 1H), 7.44 (s, 1H), 7.41-7.34 (m, 2H). | 2.54 (451.9)' |
| 276 | C23H15NO4S2 | 433.50 | 1H NMR (400 MHz, DMSO-d6) d 13.09 (s, 1H), 10.47 (s, 1H), 7.87 (m, 5H), 7.51 (dd, J = 7.7, 1.5 Hz, 1H), 7.48-7.35 (m, 6H), 7.31 (td, J = 7.4, 1.6 Hz, 1H). | 2.44-2.61 (434.0)' |
| 277 | C24H22N2O5S | 450.51 | 1H NMR (500 MHz, DMSO-d6) d 13.77-12.75 (m, 1H), 9.84 (s, 1H), 8.73 (dd, J = 2.1, 0.9 Hz, 1H), 8.09 (dd, J = 8.1, 0.9 Hz, 1H), 8.01 (dd, J = 8.1, 2.1 Hz, 1H), 7.51-7.48 (m, 1H), 7.43-7.41 (m, 2H), 7.28-7.22 (m, 1H), 6.61 (s, 1H), 3.73 (s, 3H), 2.38 (s, 3H), 2.34 (s, 3H), 1.82 (s, 3H). | 1.72 (451.0)* |
| 278 | C21H14N4O4S | 418.43 | 1H NMR (300 MHz, DMSO-d6) 8.82 (m, 1H), 8.70 (m, 1H), 8.15-8.05 (m, 2H), 7.97 (m, 1H), 7.86 (d, J = 7.3 Hz, 1H), 7.64 (d, J = 1.6 Hz, 1H), 7.54-7.37 (m, 3H), 7.34-7.07 (m, 2H). | 0.651 (419.3) |
| 279 | C24H15FN2O4S | 446.46 | 1H NMR (500 MHz, DMSO-d6) d 10.38 (s, 1H), 8.69-8.66 (m, 1H), 8.36-8.34 (m, 1H), 8.14-8.11 (m, 1H), 8.01-7.98 (m, 1H), 7.93-7.90 (m, 1H), 7.69-7.66 (m, 1H), 7.52-7.35 (m, 7H), 7.25-7.20 (m, 1H). | 1.65 (447.0)* |
| 280 | C20H12Cl2N2O4S | 447.30 | 1H NMR (400 MHz, DMSO-d6) d 13.45-13.32 (m, 1H), 10.33 (s, 1H), 8.74 (dd, J = 2.1, 0.9 Hz, 1H), 8.12 (dd, J = 8.1, 0.9 Hz, 1H), 8.03 (dd, J = 8.1, 2.1 Hz, 1H), 7.67-7.62 (m, 3H), 7.54 (dd, J = 8.7, 2.6 Hz, 1H), 7.48-7.43 (m, 2H), 7.38 (d, J = 8.7 Hz, 1H). | 1.76 (447.0)* |
| 281 | C23H14ClNO4S2 | 467.95 | 1H NMR (500 MHz, DMSO-d6) d 13.11 (s, 1H), 10.59 (s, 1H), 7.94 (d, J = 8.8 Hz, 1H), 7.90-7.86 (m, 2H), 7.85 (s, 1H), 7.79 (d, J = 2.1 Hz, | 2.54 (468.0)' |

TABLE 2-continued

| Cpd. No. | Formula | Mass | NMR | LCMS (M + H) |
|---|---|---|---|---|
| | | | 1H), 7.52 (dd, J = 7.7, 1.6 Hz, 1H), 7.48 (td, J = 7.7, 1.6 Hz, 1H), 7.42 (dt, J = 8.4, 1.7 Hz, 2H), 7.37-7.31 (m, 3H). | |
| 282 | C24H17N3O4S3 | 507.61 | 1H NMR (500 MHz, DMSO-d6) d 13.02 (s, 1H), 10.43 (s, 1H), 8.58 (d, J = 5.2 Hz, 1H), 7.88 (d, J = 4.0 Hz, 1H), 7.80-7.76 (m, 2H), 7.58 (d, J = 5.2 Hz, 1H), 7.53 (dd, J = 7.7, 1.5 Hz, 1H), 7.51 (dd, J = 8.0, 1.8 Hz, 1H), 7.49-7.43 (m, 3H), 7.36 (td, J = 7.5, 1.4 Hz, 1H), 7.23 (d, J = 4.0 Hz, 1H), 2.44 (s, 3H). | 2.37 (508.0)' |
| 283 | C25H15F3N2O4S | 496.46 | 1H NMR (400 MHz, DMSO-d6) d 10.35 (s, 1H), 8.71-8.66 (m, 1H), 8.62 (d, J = 1.8 Hz, 1H), 8.18 (d, J = 1.7 Hz, 1H), 8.11-8.08 (m, 1H), 7.94 (dd, J = 7.4, 1.2 Hz, 1H), 7.87-7.83 (m, 1H), 7.55-7.51 (m, 1H), 7.49-7.44 (m, 2H), 7.42-7.33 (m, 2H), 7.32-7.27 (m, 2H), 7.23 (td, J = 7.5, 1.4 Hz, 1H). | 1.75 (497.0)* |
| 284 | C26H20N2O5S | 472.52 | 1H NMR (400 MHz, DMSO-d6) d 13.92-12.52 (m, 1H), 10.14 (s, 1H), 8.57-8.53 (m, 2H), 8.13-8.10 (m, 1H), 8.04 (dd, J = 8.1, 0.8 Hz, 1H), 8.00 (d, J = 8.4 Hz, 1H), 7.82 (dd, J = 8.1, 2.1 Hz, 1H), 7.45 (dd, J = 8.2, 1.4 Hz, 1H), 7.43-7.32 (m, 4H), 7.21-7.16 (m, 1H), 6.90 (d, J = 8.5 Hz, 1H), 4.16 (q, J = 7.0 Hz, 2H), 1.42 (t, J = 6.9 Hz, 3H). | 1.77 (473.0) |
| 285 | C24H15FN2O4S | 446.46 | 1H NMR (400 MHz, DMSO-d6) d 14.15-12.43 (m, 1H), 10.67 (s, 1H), 8.70-8.66 (m, 1H), 8.59-8.57 (m, 1H), 8.17-8.14 (m, 1H), 8.10 (dd, J = 7.5, 1.2 Hz, 1H), 8.06 (dd, J = 8.1, 0.7 Hz, 1H), 7.96-7.93 (m, 1H), 7.85 (dd, J = 8.1, 2.1 Hz, 1H), 7.56-7.51 (m, 1H), 7.46-7.37 (m, 3H), 7.29 (dd, J = 10.5, 2.6 Hz, 1H), 7.08 (td, J = 8.4, 2.6 Hz, 1H). | 1.71 (447.0)* |
| 286 | C26H16N2O5S | 468.49 | 1H NMR (400 MHz, DMSO-d6) d 13.60-12.33 (m, 1H), 10.10 (s, 1H), 8.61-8.59 (m, 1H), 8.54-8.52 (m, 1H), 7.99-7.95 (m, 1H), 7.83-7.78 (m, 2H), 7.70-7.66 (m, 1H), 7.65-7.61 (m, 2H), 7.52-7.43 (m, 4H), 7.31-7.26 (m, 2H). | 1.71 (439.0)* |
| 287 | C21H15ClN2O5S | 442.88 | 1H NMR (400 MHz, DMSO-d6) d 10.21-9.93 (m, 1H), 8.79-8.75 (m, 1H), 8.11-8.07 (m, 1H), 8.05 (dd, J = 8.2, 2.0 Hz, 1H), 7.81 (d, J = 8.9 Hz, 1H), 7.55-7.51 (m, 1H), 7.44-7.35 (m, 2H), 7.28-7.22 (m, 1H), 7.04 (d, J = 2.5 Hz, 1H), 6.92 (dd, J = 8.9, 2.6 Hz, 1H), 3.73 (s, 3H). | 1.62 (443.0)* |
| 288 | C25H19N3O4S | 457.51 | 1H NMR (500 MHz, DMSO-d6) d 13.40 (s, 1H), 10.42 (s, 1H), 9.07 (s, 1H), 8.48 (dd, J = 2.1, 0.8 Hz, 1H), 8.03 (dd, J = 8.1, 0.8 Hz, 1H), 8.01 (d, J = 1.7 Hz, 1H), 7.98 (s, 1H), 7.93 (s, 1H), 7.72 (dd, J = 8.1, 2.1 Hz, 1H), 7.54-7.50 (m, 2H), 7.36 (dd, J = 7.4, 1.2 Hz, 1H), 7.29 (ddd, J = 7.7, 5.5, 3.1 Hz, 1H), 2.33 (s, 3H), 2.31 (s, 3H). | 1.84-2.06 (458.0)' |
| 289 | C24H15ClN2O4S | 462.91 | 1H NMR (500 MHz, DMSO-d6) d 10.49 (s, 1H), 8.68 (dd, J = 8.7, 1.0 Hz, 1H), 8.49 (dd, J = 2.1, 0.8 Hz, 1H), 8.37 (dt, J = 8.5, 1.1 Hz, 1H), 8.10 (dd, J = 7.4, 1.2 Hz, 1H), 8.02 (dd, J = 8.1, 0.9 Hz, 1H), 7.71 (dd, J = 8.1, 2.1 Hz, 1H), 7.66 (dd, J = 8.5, 7.4 Hz, 1H), 7.56 (dd, J = 7.5, 0.9 Hz, 1H), 7.45-7.42 (m, 2H), 7.39 (dt, J = 8.7, 1.2 Hz, 2H), 7.28-7.20 (m, 1H). | 2.37-3.01 (463.0)' |
| 290 | C21H14N4O4S2 | 450.49 | 1H NMR (400 MHz, Chloroform-d) d 8.86 (dd, J = 2.1, 0.9 Hz, 1H), 8.50 (s, 1H), 8.35-8.29 (m, 1H), 8.17 (dd, J = 8.1, 2.0 Hz, 1H), 8.00 (d, J = 9.0 Hz, 1H), 7.70-7.64 (m, 1H), 7.48 (d, J = 9.0 Hz, 1H), 7.36 (dd, J = 7.7, 1.6 Hz, 1H), 7.29-7.26 (m, 1H), 6.99 (td, J = 7.6, 1.1 Hz, 1H), 2.96 (s, 3H). | 1.61 (451.0)' |
| 291 | C26H18N2O4S | 454.50 | 1H NMR (400 MHz, Chloroform-d) d 8.65 (dd, J = 2.0, 0.9 Hz, 1H), 8.22 (dd, J = 8.1, 0.9 Hz, 1H), 7.96 (dd, J = 8.1, 2.0 Hz, 1H), 7.86-7.81 (m, 2H), 7.66 (d, J = 8.3 Hz, 1H), 7.63-7.59 (m, 2H), 7.52-7.47 (m, 2H), 7.47-7.36 (m, 6H), 7.15 (td, J = 7.6, 1.2 Hz, 1H), 7.09 (s, 1H). | 1.74 (455.0)' |
| 292 | C20H12N4O4S2 | 436.47 | 1H NMR (500 MHz, DMSO-d6) d 10.29 (s, 1H), 8.53 (dd, J = 2.1, 0.8 Hz, 1H), 8.22 (dd, J = 8.8, 1.0 Hz, 1H), 8.10 (dd, J = 7.1, 1.0 Hz, 1H), 8.05 (dd, J = 8.1, 0.9 Hz, 1H), 7.81 (dd, J = 8.1, 2.1 Hz, 1H), 7.71 (dd, J = 8.8, 7.1 Hz, 1H), 7.48- | 1.52-1.55 (437.0)' |

TABLE 2-continued

| Cpd. No. | Formula | Mass | NMR | LCMS (M + H) |
|---|---|---|---|---|
| | | | 7.41 (m, 2H), 7.39 (dd, J = 7.3, 1.2 Hz, 1H), 7.26 (ddd, J = 7.8, 6.1, 2.5 Hz, 1H). | |
| 293 | C27H20N2O4S | 468.53 | 1H NMR (500 MHz, DMSO-d6) d 10.14 (s, 1H), 8.75 (dd, J = 1.9, 1.1 Hz, 1H), 8.11-8.03 (m, 2H), 7.74-7.68 (m, 2H), 7.53 (dd, J = 7.7, 1.5 Hz, 1H), 7.48 (ddd, J = 8.7, 7.1, 1.6 Hz, 1H), 7.44 (dd, J = 8.2, 1.5 Hz, 1H), 7.37-7.33 (m, 2H), 7.30 (td, J = 7.4, 1.6 Hz, 1H), 7.28-7.22 (m, 2H), 7.19-7.15 (m, 1H), 6.90 (dd, J = 7.5, 1.2 Hz, 1H), 1.99 (s, 3H). | 1.81 . 1.82 (469.0)' |
| 294 | C23H14FN3O4S | 447.44 | 1H NMR (500 MHz, DMSO-d6) d 13.92-12.85 (m, 1H), 9.68 (s, 1H), 8.77 (dd, J = 4.2, 1.7 Hz, 1H), 8.64 (dd, J = 2.1, 0.8 Hz, 1H), 8.38 (dd, J = 8.4, 1.7 Hz, 1H), 8.17 (dd, J = 8.0, 2.9 Hz, 1H), 8.11-8.06 (m, 2H), 7.93 (dd, J = 8.1, 2.1 Hz, 1H), 7.52 (dd, J = 8.4, 4.2 Hz, 1H), 7.47-7.43 (m, 1H), 7.42-7.36 (m, 2H), 7.20-7.16 (m, 1H). | 1.64 (448.0)* |
| 295 | C27H22N2O5S | 486.55 | 1H NMR (500 MHz, DMSO-d6) d 13.93-12.71 (m, 1H), 10.14 (s, 1H), 8.58 (dd, J = 2.1, 0.8 Hz, 1H), 8.54-8.51 (m, 1H), 8.12-8.09 (m, 1H), 8.04 (dd, J = 8.1, 0.8 Hz, 1H), 8.01 (d, J = 8.4 Hz, 1H), 7.84 (dd, J = 8.0, 2.1 Hz, 1H), 7.46 (dd, J = 8.3, 1.3 Hz, 1H), 7.43-7.31 (m, 4H), 7.19 (td, J = 7.5, 1.4 Hz, 1H), 6.95 (d, J = 8.5 Hz, 1H), 4.79 (hept, J = 6.0 Hz, 1H), 1.33 (d, J = 6.0 Hz, 6H). | 1.82 (487.0)* |
| 296 | C23H17N3O4S | 431.47 | 1H NMR (400 MHz, DMSO-d6) d 10.41 (s, 1H), 8.77 (d, J = 1.9 Hz, 1H), 8.09 (d, J = 8.1 Hz, 1H), 8.02 (dd, J = 8.1, 2.1 Hz, 1H), 7.83 (dd, J = 7.9, 1.1 Hz, 1H), 7.70 (dd, J = 7.7, 1.1 Hz, 1H), 7.58-7.54 (m, 1H), 7.36 (td, J = 8.9, 8.0, 2.3 Hz, 3H), 7.21 (ddd, J = 8.3, 6.6, 2.1 Hz, 1H), 7.08 (t, J = 7.8 Hz, 1H), 6.58 (d, J = 3.1 Hz, 1H), 4.19 (s, 3H). | 2.30-2.40 (432.0)' |
| 297 | C22H14N2O5S | 418.43 | 1H NMR (400 MHz, DMSO-d6) d 13.35 (s, 1H), 10.06 (s, 1H), 8.68 (d, J = 1.9 Hz, 1H), 8.07 (d, J = 8.1 Hz, 2H), 8.02 (d, J = 2.2 Hz, 1H), 7.96 (dd, J = 8.1, 2.1 Hz, 1H), 7.61-7.54 (m, 2H), 7.45 (ddd, J = 12.2, 7.5, 1.5 Hz, 2H), 7.40 (dd, J = 8.2, 1.4 Hz, 1H), 7.26 (td, J = 7.4, 1.5 Hz, 1H), 6.87 (d, J = 2.2 Hz, 1H). | 2.14 (419.0)' |
| 298 | C23H13Cl2N3O4S | 498.34 | 1H NMR (500 MHz, DMSO-d6) d 13.35 (s, 1H), 9.78 (s, 1H), 8.81 (s, 1H), 8.50 (dd, J = 2.2, 0.8 Hz, 1H), 8.40 (dd, J = 8.5, 1.4 Hz, 1H), 8.32 (dd, J = 7.4, 1.4 Hz, 1H), 8.04 (dd, J = 8.1, 0.8 Hz, 1H), 7.86 (dd, J = 8.5, 7.4 Hz, 1H), 7.75 (dd, J = 8.1, 2.1 Hz, 1H), 7.45-7.40 (m, 3H), 7.26-7.20 (m, 1H). | 2.37 (498.0)' |
| 299 | C22H18N2O6S | 438.46 | 1H NMR (400 MHz, DMSO-d6) d 9.29 (s, 1H), 8.78-8.76 (m, 1H), 8.07 (d, J = 1.1 Hz, 1H), 8.06 (d, J = 1.9 Hz, 1H), 7.67 (d, J = 8.7 Hz, 1H), 7.54-7.51 (m, 1H), 7.38-7.35 (m, 2H), 7.20-7.15 (m, 1H), 6.57-6.51 (m, 2H), 3.74 (s, 3H), 3.59 (s, 3H). | 1.57 (439.0)* |
| 300 | C24H21N3O6S | 479.51 | 1H NMR (500 MHz, DMSO-d6) d 9.91 (s, 1H), 8.86 (s, 1H), 8.72 (dd, J = 2.1, 0.9 Hz, 1H), 8.59-8.56 (m, 1H), 8.05 (d, J = 8.1, 0.9 Hz, 1H), 8.01 (dd, J = 8.1, 2.1 Hz, 1H), 7.48 (dd, J = 7.7, 1.5 Hz, 1H), 7.45-7.41 (m, 1H), 7.39 (dd, J = 8.2, 1.4 Hz, 1H), 7.25 (td, J = 7.5, 1.4 Hz, 1H), 7.21 (dd, J = 8.6, 2.4 Hz, 1H), 6.96 (d, J = 8.7 Hz, 1H), 4.03 (q, J = 7.0 Hz, 2H), 2.00 (s, 3H), 1.29 (t, J = 7.0 Hz, 3H). | 1.48 (480.0)* |
| 301 | C26H16N2O5S | 468.49 | 1H NMR (400 MHz, DMSO-d6) d 13.69-12.58 (m, 1H), 10.10 (s, 1H), 8.61-8.60 (m, 1H), 8.54-8.52 (m, 1H), 7.98-7.95 (m, 1H), 7.83-7.78 (m, 2H), 7.70-7.67 (m, 1H), 7.65-7.61 (m, 2H), 7.52-7.43 (m, 4H), 7.31-7.26 (m, 2H). | 1.71 (469.0)* |
| 302 | C23H13Cl2N3O4S | 498.34 | 1H NMR (500 MHz, DMSO-d6) d 13.55-13.21 (m, 1H), 9.93 (s, 1H), 8.83 (d, J = 4.8 Hz, 1H), 8.59 (dd, J = 2.1, 0.8 Hz, 1H), 8.31 (d, J = 9.1 Hz, 1H), 8.05 (dd, J = 8.1, 0.9 Hz, 1H), 7.87-7.84 (m, 2H), 7.72 (d, J = 4.8 Hz, 1H), 7.51-7.48 (m, 1H), 7.41-7.37 (m, 2H), 7.23-7.18 (m, 1H). | 1.75 (499.0)* |

TABLE 2-continued

| Cpd. No. | Formula | Mass | NMR | LCMS (M + H) |
|---|---|---|---|---|
| 303 | C23H17N3O4S | 431.47 | 1H NMR (400 MHz, DMSO-d6) d 9.91 (s, 1H), 8.55 (d, J = 2.1 Hz, 1H), 8.05 (d, J = 8.0 Hz, 1H), 7.83 (dd, J = 8.1, 2.1 Hz, 1H), 7.60 (d, J = 8.2 Hz, 1H), 7.39 (m, 4H), 7.25 (d, J = 3.1 Hz, 1H), 7.19 (td, J = 7.3, 1.6 Hz, 1H), 7.11 (t, J = 7.8 Hz, 1H), 6.72 (d, J = 3.0 Hz, 1H), 3.67 (s, 3H). | 2.14-2.15 (432.0)' |
| 304 | C18H11ClN2O4S2 | 418.88 | 1H NMR (500 MHz, DMSO-d6) d 10.46 (s, 1H), 8.80 (dd, J = 2.0, 0.9 Hz, 1H), 8.10 (qd, J = 8.1, 1.5 Hz, 2H), 7.59 (dd, J = 7.7, 1.6 Hz, 1H), 7.51 (td, J = 7.8, 1.6 Hz, 1H), 7.41 (dd, J = 8.2, 1.2 Hz, 1H), 7.37 (td, J = 7.6, 1.3 Hz, 1H), 7.21 (d, J = 4.1 Hz, 1H), 7.06 (d, J = 4.1 Hz, 1H). | 2.23 (419.0)' |
| 305 | C26H21N3O4S | 471.53 | 1H NMR (400 MHz, DMSO-d6) d 10.02-9.95 (m, 1H), 8.75 (dd, J = 4.2, 1.6 Hz, 1H), 8.74 (dd, J = 2.1, 0.9 Hz, 1H), 8.53 (dd, J = 8.7, 1.7 Hz, 1H), 8.11 (dd, J = 8.1, 0.9 Hz, 1H), 8.03 (dd, J = 8.1, 2.1 Hz, 1H), 7.48-7.43 (m, 3H), 7.35-7.29 (m, 1H), 7.07 (td, J = 7.6, 1.1 Hz, 1H), 2.85 (s, 3H), 2.60 (s, 3H), 2.40 (s, 3H). | 1.75 (472.0)* |
| 306 | C23H13Cl2N3O4S | 498.34 | 1H NMR (700 MHz, DMSO-d6) d 13.41 (s, 1H), 9.93 (s, 1H), 8.99 (dd, J = 4.3, 1.7 Hz, 1H), 8.62 (d, J = 2.0 Hz, 1H), 8.52 (dd, J = 8.6, 1.7 Hz, 1H), 8.07 (d, J = 8.0 Hz, 1H), 8.02 (s, 1H), 7.89 (dd, J = 8.0, 2.1 Hz, 1H), 7.67 (dd, J = 8.5, 4.2 Hz, 1H), 7.52-7.47 (m, 1H), 7.41-7.36 (m, 2H), 7.20 (ddd, J = 8.3, 6.0, 2.5 Hz, 1H). | 2.46 (498.0)' |
| 307 | C25H18FN3O4S | 475.50 | 1H NMR (500 MHz, DMSO-d6) d 13.30 (s, 1H), 9.78 (s, 1H), 8.82 (dd, J = 4.3, 1.8 Hz, 1H), 8.46 (d, J = 2.0 Hz, 1H), 8.35 (dd, J = 8.3, 1.8 Hz, 1H), 8.10 (d, J = 8.4 Hz, 1H), 7.72 (dd, J = 2.0, 0.9 Hz, 1H), 7.56 (d, J = 8.5 Hz, 1H), 7.34 (dd, J = 8.7, 3.0 Hz, 1H), 7.22 (ddd, J = 9.2, 8.3, 3.1 Hz, 1H), 2.81 (s, 3H), 2.51 (s, 3H). | 1.78 (476.0)* |
| 308 | C27H19FN2O4S | 486.52 | 1H NMR (400 MHz, DMSO-d6) d 10.12 (s, 1H), 8.52 (d, J = 1.8 Hz, 1H), 7.73-7.67 (m, 3H), 7.67-7.62 (m, 2H), 7.47-7.32 (m, 8H), 2.37 (s, 3H). | 1.86-1.87 (487.0)* |
| 309 | C27H17FN2O5S | 500.50 | 1H NMR (500 MHz, DMSO-d6) Î' 13.17-12.97 (m, 1H), 10.08 (s, 1H), 8.53-8.52 (m, 1H), 8.41-8.39 (m, 1H), 7.95-7.92 (m, 1H), 7.69-7.66 (m, 1H), 7.66-7.63 (m, 1H), 7.58 (dd, J = 8.7, 2.0 Hz, 1H), 7.52-7.48 (m, 1H), 7.48-7.44 (m, 2H), 7.38-7.31 (m, 2H), 7.31-7.27 (m, 1H), 2.28 (s, 3H). | 1.84 (201.0)* |
| 310 | C25H19N3O4S | 457.51 | 1H NMR (400 MHz, DMSO-d6) Î' 13.50-13.25 (m, 1H), 9.84-9.77 (m, 1H), 8.72-8.70 (m, 1H), 8.63 (d, J = 4.4 Hz, 1H), 8.22 (d, J = 8.7 Hz, 1H), 8.13-8.09 (m, 1H), 8.02 (dd, J = 8.1, 2.1 Hz, 1H), 7.59 (d, J = 8.7 Hz, 1H), 7.52-7.49 (m, 1H), 7.45 (dd, J = 7.7, 1.3 Hz, 1H), 7.37-7.32 (m, 1H), 7.29-7.26 (m, 1H), 7.08 (td, J = 7.6, 1.0 Hz, 1H), 2.86 (s, 3H), 2.61 (s, 3H). | 1.71 (458.0)* |
| 311 | C25H18FN3O5S | 491.50 | 1H NMR (400 MHz, DMSO-d6) d 9.31 (s, 1H), 8.77 (dd, J = 4.3, 1.8 Hz, 1H), 8.46 (dd, J = 8.5, 1.8 Hz, 1H), 8.40-8.38 (m, 1H), 8.25 (d, J = 8.4 Hz, 1H), 7.64 (dd, J = 1.9, 0.7 Hz, 1H), 7.44 (dd, J = 8.5, 4.3 Hz, 1H), 7.40 (dd, J = 9.1, 5.2 Hz, 1H), 7.29 (dd, J = 8.8, 3.0 Hz, 1H), 7.26-7.20 (m, 1H), 7.08 (d, J = 8.5 Hz, 1H), 4.01 (s, 3H), 2.49-2.48 (m, 3H). | 1.73 (492.0)* |
| 312 | C26H20FN3O4S | 489.52 | 1H NMR (400 MHz, DMSO-d6) d 9.79 (s, 1H), 8.82 (dd, J = 4.3, 1.8 Hz, 1H), 8.47-8.46 (m, 1H), 8.35 (dd, J = 8.3, 1.8 Hz, 1H), 8.10 (d, J = 8.5 Hz, 1H), 7.75-7.74 (m, 1H), 7.56 (d, J = 8.5 Hz, 1H), 7.46-7.39 (m, 2H), 7.35 (dd, J = 8.8, 3.0 Hz, 1H), 7.26-7.20 (m, 1H), 3.91 (s, 3H), 2.81 (s, 3H), 2.51-2.49 (m, 3H). | 1.91 (490.0)* |
| 313 | C28H21FN2O4S | 500.55 | 1H NMR (400 MHz, DMSO-d6) d 10.11 (s, 1H), 8.53-8.50 (m, 1H), 7.72-7.67 (m, 3H), 7.65-7.60 (m, 2H), 7.46-7.33 (m, 8H), 3.89 (s, 3H), 2.35 (s, 3H). | 1.97 (501.0)* |
| 314 | C23H13Cl2N3O4S | 498.34 | 1H NMR (700 MHz, DMSO-d6) d 13.37 (s, 1H), 9.68 (s, 1H), 8.49 (dd, J = 7.5, 1.4 Hz, 1H), 8.41 (d, J = 1.9 Hz, 1H), 8.34 (dd, J = 8.4, 1.3 Hz, 1H), 7.99 (d, J = 8.0 Hz, 1H), 7.88 (s, 1H), 7.86-7.82 (m, 1H), 7.70 (dd, J = 8.0, 2.1 Hz, 1H), 7.49-7.44 (m, 2H), 7.44-7.40 (m, 1H), 7.21 (t, J = 7.5 Hz, 1H). | 2.36 (498.0)' |

TABLE 2-continued

| Cpd. No. | Formula | Mass | NMR | LCMS (M + H) |
|---|---|---|---|---|
| 315 | C23H13BrClN3O4S | 542.80 | 1H NMR (700 MHz, DMSO-d6) d 13.40 (s, 1H), 9.41 (s, 1H), 8.64 (d, J = 2.4 Hz, 1H), 8.47 (d, J = 8.6 Hz, 1H), 8.14 (d, J = 8.7 Hz, 1H), 8.07 (d, J = 8.0 Hz, 1H), 8.02 (d, J = 8.7 Hz, 1H), 7.94 (dd, J = 8.0, 2.1 Hz, 1H), 7.62 (d, J = 8.6 Hz, 1H), 7.52 (dd, J = 7.7, 1.5 Hz, 1H), 7.44 (d, J = 8.2 Hz, 1H), 7.40 (td, J = 8.4, 7.9, 1.5 Hz, 1H), 7.17 (td, J = 7.5, 1.3 Hz, 1H). | 2.36 (544.0)' |
| 316 | C26H20FN3O5S | 505.52 | 1H NMR (700 MHz, DMSO-d6) d 9.33 (s, 1H), 8.76 (dd, J = 4.3, 1.8 Hz, 1H), 8.45 (dd, J = 8.5, 1.8 Hz, 1H), 8.40-8.38 (m, 1H), 8.24 (d, J = 8.8 Hz, 1H), 7.66-7.65 (m, 1H), 7.43 (dd, J = 8.5, 4.2 Hz, 1H), 7.40 (dd, J = 9.1, 5.1 Hz, 1H), 7.28 (dd, J = 8.7, 3.1 Hz, 1H), 7.25-7.22 (m, 1H), 7.08 (d, J = 8.4 Hz, 1H), 4.01 (s, 3H), 3.91 (s, 3H), 2.48 (s, 3H). | 1.86 (506.0)* |
| 317 | C24H16ClN3O4S | 477.93 | 1H NMR (700 MHz, DMSO-d6) d 13.38 (s, 1H), 9.58 (s, 1H), 8.49 (d, J = 1.9 Hz, 1H), 8.28 (d, J = 2.4 Hz, 1H), 8.24-8.19 (m, 2H), 8.02 (dd, J = 8.0, 0.8 Hz, 1H), 7.77 (dd, J = 8.0, 2.1 Hz, 1H), 7.47 (dd, J = 7.7, 1.3 Hz, 1H), 7.44-7.39 (m, 3H), 7.20 (ddd, J = 8.6, 6.8, 1.9 Hz, 1H), 2.39 (s, 3H). | 2.41 (478.0)' |
| 318 | C28H19FN2O5S | 514.53 | 1H NMR (400 MHz, DMSO-d6) d 10.09 (s, 1H), 8.53-8.52 (m, 1H), 8.39-8.37 (m, 1H), 7.94-7.91 (m, 1H), 7.69-7.66 (m, 1H), 7.65-7.62 (m, 1H), 7.55 (dd, J = 8.7, 2.0 Hz, 1H), 7.52-7.45 (m, 3H), 7.40-7.31 (m, 2H), 7.30-7.25 (m, 1H), 3.87 (s, 3H), 2.26 (s, 3H). | 1.95 (515.0)* |
| 319 | C23H13BrClN3O4S | 542.80 | 1H NMR (700 MHz, DMSO-d6) d 13.40 (s, 1H), 9.91 (s, 1H), 8.82 (d, J = 4.8 Hz, 1H), 8.60 (d, J = 2.1 Hz, 1H), 8.20 (d, J = 9.0 Hz, 1H), 8.05 (t, J = 8.9 Hz, 2H), 7.86 (dd, J = 8.1, 2.1 Hz, 1H), 7.74 (d, J = 4.8 Hz, 1H), 7.52-7.48 (m, 1H), 7.39 (dd, J = 6.8, 1.7 Hz, 2H), 7.21 (ddd, J = 8.1, 6.5, 2.2 Hz, 1H). | 2.43 (543.0) |
| 320 | C23H13ClFN3O4S | 481.89 | 1H NMR (700 MHz, DMSO-d6) d 13.40 (s, 1H), 9.88 (s, 1H), 8.79 (d, J = 4.8 Hz, 1H), 8.60 (d, J = 2.0 Hz, 1H), 8.44 (dd, J = 9.4, 5.0 Hz, 1H), 8.06 (d, J = 8.0 Hz, 1H), 7.86 (dd, J = 8.0, 2.1 Hz, 1H), 7.75 (t, J = 9.9 Hz, 1H), 7.68 (d, J = 4.8 Hz, 1H), 7.48 (d, J = 7.5 Hz, 1H), 7.42-7.37 (m, 2H), 7.21 (ddd, J = 8.3, 5.2, 3.4 Hz, 1H). | 2.28 (482.0) |
| 321 | C23H19FN2O5S | 454.48 | 1H NMR (400 MHz, DMSO-d6) d 10.05 (s, 1H), 8.51 (d, J = 1.9 Hz, 1H), 7.81 (dd, J = 2.0, 0.8 Hz, 1H), 7.41-7.28 (m, 4H), 7.15-7.10 (m, 2H), 7.06 (ddd, J = 8.4, 2.6, 1.0 Hz, 1H), 3.89 (s, 3H), 3.55(s, 3H). | 1.78 (455.0)* |
| 322 | C22H17FN2O5S | 440.45 | 1H NMR (400 MHz, DMSO-d6) d 13.64-12.84 (m, 1H), 10.06 (s, 1H), 8.51-8.50 (m, 1H), 7.80-7.78 (m, 1H), 7.41-7.30 (m, 4H), 7.16-7.14 (m, 1H), 7.14-7.10 (m, 1H), 7.09-7.05 (m, 1H), 3.55 (s, 3H), 2.49 (s, 3H). | 1.65 (441.0)* |
| 323 | C23H13Cl2N3O4S | 498.34 | 1H NMR (500 MHz, DMSO-d6) d 9.67 (s, 1H), 8.74 (d, J = 4.7 Hz, 1H), 8.46 (d, J = 1.7 Hz, 1H), 8.44-8.39 (m, 2H), 7.94 (d, J = 1.7 Hz, 1H), 7.84 (dd, J = 8.4, 7.4 Hz, 1H), 7.69 (d, J = 4.7 Hz, 1H), 7.46-7.36 (m, 3H), 7.20 (ddd, J = 8.6, 6.8, 2.0 Hz, 1H). | 2.37 (498.0)' |
| 324 | C24H17N3O5S | 459.48 | 1H NMR (500 MHz, DMSO-d6) d 13.71-13.15 (m, 1H), 9.58-9.24 (m, 1H), 8.65 (dd, J = 2.0, 0.7 Hz, 1H), 8.63 (d, J = 5.3 Hz, 1H), 8.36 (dd, J = 8.4, 1.4 Hz, 1H), 8.31 (dd, J = 7.3, 1.5 Hz, 1H), 8.10 (dd, J = 8.1, 0.7 Hz, 1H), 7.97 (dd, J = 8.1, 2.1 Hz, 1H), 7.65 (dd, J = 8.3, 7.4 Hz, 1H), 7.46-7.42 (m, 2H), 7.37-7.33 (m, 1H), 7.12 (td, J = 7.7, 1.2 Hz, 1H), 6.96 (d, J = 5.4 Hz, 1H), 3.97 (s, 3H). | 1.60-1.61 (460.0)* |
| 325 | C24H15BrFN3O5S | 556.37 | 1H NMR (400 MHz, DMSO-d6) d 9.64-9.48 (m, 1H), 8.72 (dd, J = 4.3, 1.8 Hz, 1H), 8.70 (dd, J = 2.0, 0.7 Hz, 1H), 8.51 (dd, J = 8.5, 1.8 Hz, 1H), 8.38 (d, J = 8.4 Hz, 1H), 8.11 (dd, J = 8.1, 0.7 Hz, 1H), 8.01 (dd, J = 8.1, 2.1 Hz, 1H), 7.82 (d, J = 7.6 Hz, 1H), 7.50-7.46 (m, 2H), 7.14 (d, J = 8.5 Hz, 1H), 4.03 (s, 3H). | 1.89 (558.0)* |
| 326 | C22H16N2O4S | 404.44 | 1H NMR (500 MHz, DMSO-d6) d 13.33 (s, 1H), 9.84 (s, 1H), 8.82 (dd, J = 2.1, 0.9 Hz, 1H), 8.06 | 2.20 (405.0)' |

TABLE 2-continued

| Cpd. No. | Formula | Mass | NMR | LCMS (M + H) |
|---|---|---|---|---|
| | | | (dd, J = 8.1, 2.1 Hz, 1H), 8.00 (dd, J = 8.1, 0.9 Hz, 1H), 7.59 (dt, J = 7.8, 1.1 Hz, 1H), 7.56-7.51 (m, 2H), 7.48-7.45 (m, 2H), 7.37-7.31 (m, 1H), 7.31-7.23 (m, 5H). | |
| 327 | C25H19N3O5S | 473.51 | 1H NMR (300 MHz, DMSO-d6)8.85-7.87 (m, 8H), 7.80-7.04 (m, 3H), 6.99 (d, J = 2.4 Hz, 1H), 6.59 (s, 1H), 3.91 (t, J = 6.7 Hz, 2H), 1.24 (t, J = 6.9 Hz, 3H). | 1.243 (474.2) |
| 328 | C24H16BrN3O5S | 538.38 | 1H NMR (700 MHz, DMSO-d6) d 13.44 (s, 1H), 9.38 (s, 1H), 8.76 (dd, J = 4.3, 1.8 Hz, 1H), 8.71 (d, J = 2.0 Hz, 1H), 8.50 (dd, J = 8.5, 1.7 Hz, 1H), 8.31 (d, J = 8.4 Hz, 1H), 8.11 (d, J = 8.1 Hz, 1H), 8.01 (dd, J = 8.0, 2.1 Hz, 1H), 7.64 (d, J = 2.4 Hz, 1H), 7.55 (dd, J = 8.8, 2.4 Hz, 1H), 7.47 (dd, J = 8.5, 4.3 Hz, 1H), 7.41 (d, J = 8.9 Hz, 1H), 7.12 (d, J = 8.4 Hz, 1H), 4.02 (s, 3H). | 1.1 (540.0)* |
| 329 | C25H19N3O5S | 473.51 | 1H NMR (300 MHz, DMSO-d6): 8.76 (d, J = 44.1 Hz, 1H), 8.64-8.31 (m, 1H), 8.31-7.92 (m, 4H), 7.84 (s, 1H), 7.74-7.01 (m, 3H), 7.03-6.72 (m, 2H), 4.27-3.68 (m, 2H), 1.29-1.14 (m, 3H). | 1.360 (474.2) |
| 330 | C28H25N3O7S | 547.59 | 1H NMR (700 MHz, DMSO-d6) d 14.51-12.31 (m, 1H), 9.49-9.39 (m, 1H), 8.68-8.67 (m, 1H), 8.62 (d, J = 5.3 Hz, 1H), 8.36 (dd, J = 8.3, 1.5 Hz, 1H), 8.32 (dd, J = 7.3, 1.5 Hz, 1H), 8.11-8.09 (m, 1H), 7.98 (dd, J = 8.0, 2.1 Hz, 1H), 7.69-7.66 (m, 1H), 7.45-7.43 (m, 2H), 7.36-7.33 (m, 1H), 7.14-7.11 (m, 1H), 7.01 (d, J = 5.4 Hz, 1H), 4.33-4.30 (m, 2H), 3.87-3.85 (m, 2H), 3.64-3.62 (m, 2H), 3.47-3.44 (m, 2H), 3.21 (s, 3H). | 1.59 (547.0)* |
| 331 | C34H36N4O9S | 676.74 | 1H NMR (400 MHz, DMSO-d6)8.88-8.67 (m, 1H), 8.67-8.37 (m, 1H), 8.29-8.09 (m, 3H), 8.01 (d, J = 14.3 Hz, 1H), 7.87 (d, J = 7.7 Hz, 1H), 7.82-7.65 (m, 1H), 7.60-7.12 (m, 2H), 7.02-6.88 (m, 2H), 6.73 (t, J = 5.5 Hz, 1H), 4.07-3.86 (m, 2H), 3.73-3.56 (m, 2H), 3.56-3.42 (m, 6H), 3.04 (q, J = 6.1 Hz, 2H), 1.34 (d, J = 3.1 Hz, 9H). | 2.469 (677.2) |
| 332 | C29H28N4O7S | 576.63 | (300 MHz, DMSO, ppm)8.81-8.70 (m, 2H), 8.47 (dd, J = 8.4, 1.7 Hz, 1H), 8.37 (d, J = 7.3, 1.4 Hz, 1H), 8.28 (dd, J = 8.4, 1.4 Hz, 1H), 8.16-8.00 (m, 2H), 7.73 (t, J = 7.8 Hz, 1H), 7.51 (dd, J = 8.4, 4.3 Hz, 1H), 7.32 (d, J = 8.7 Hz, 1H), 6.98 (d, J = 2.4 Hz, 1H), 6.68 (dd, J = 8.7, 2.5 Hz, 1H), 5.33(s, 2H), 4.00 (s, 2H), 3.66 (t, J = 4.4 Hz, 2H), 3.63-3.49 (m, 6H), 2.90 (t, J = 5.3 Hz, 2H). | 0.922 (577.2) |
| 333 | C29H28N4O7S | 576.63 | 1H NMR (300 MHz, DMSO-d6)8.80 (dd, J = 4.4, 1.7 Hz, 1H), 8.47 (s, 1H), 8.42-8.30 (m, 1H), 8.21 (dd, J = 15.7, 7.7 Hz, 2H), 7.89 (d, J = 8.0 Hz, 1H), 7.63 (dt, J = 7.7, 3.8 Hz, 2H), 7.44 (dd, J = 8.4, 4.2 Hz, 1H), 7.14 (d, J = 9.0 Hz, 1H), 6.91 (d, J = 2.9 Hz, 1H), 6.83 (dd, J = 9.0, 2.9 Hz, 1H), 3.95 (d, J = 4.9 Hz, 2H), 3.74-3.06 (m, 10H), 2.96 (t, J = 5.5 Hz, 2H). | 0.942 (577.3) |
| 334 | C23H17NO4S | 403.46 | 1H NMR (500 MHz, DMSO-d6) d 13.14 (s, 1H), 9.80 (s, 1H), 7.95-7.88 (m, 2H), 7.67-7.62 (m, 2H), 7.57 (ddd, J = 9.4, 7.5, 1.3 Hz, 3H), 7.47-7.43 (m, 2H), 7.39-7.34 (m, 1H), 7.33-7.21 (m, 5H). | 2.44 (404.0)' |
| 335 | C24H16ClN3O4S | 477.93 | 1H NMR (500 MHz, DMSO-d6) d 14.02 (s, 1H), 9.48 (s, 1H), 8.71 (dd, J = 4.3, 1.7 Hz, 1H), 8.53 (d, J = 1.7 Hz, 1H), 8.31 (dd, J = 8.4, 1.7 Hz, 1H), 8.18 (d, J = 1.9 Hz, 1H), 8.03 (d, J = 1.7 Hz, 1H), 7.99 (dd, J = 2.0, 1.1 Hz, 1H), 7.48-7.43 (m, 2H), 7.42 (dd, J = 7.7, 1.5 Hz, 1H), 7.40-7.34 (m, 1H), 7.14 (td, J = 7.6, 1.2 Hz, 1H), 3.68 (s, 3H). | 2.34 (478.0)' |
| 336 | C25H19N3O5S | 473.51 | 1H NMR (500 MHz, DMSO-d6) d 13.44 (s, 1H), 9.20 (s, 1H), 8.76 (dd, J = 4.3, 1.8 Hz, 1H), 8.73 (dd, J = 2.2, 0.8 Hz, 1H), 8.50 (dd, J = 8.5, 1.8 Hz, 1H), 8.30 (d, J = 8.4 Hz, 1H), 8.11 (dd, J = 8.1, 0.8 Hz, 1H), 8.02 (dd, J = 8.1, 2.1 Hz, 1H), 7.50-7.44 (m, 2H), 7.42 (dd, J = 7.7, 1.5 Hz, 1H), 7.34 (ddd, J = 8.6, 7.5, 1.6 Hz, 1H), 7.12-7.07 (m, 2H), 4.27 (q, J = 7.0 Hz, 2H), 1.45 (t, J = 7.0 Hz, 3H). | 1.71-1.72 (474.0)* |
| 339 | C26H21N3O5S | 487.53 | 1H NMR (500 MHz, DMSO-d6) d 9.04 (dd, J = 4.4, 1.8 Hz, 1H), 8.59-8.57 (m, 1H), 8.54 (dd, | 1.79 (488.0)* |

TABLE 2-continued

| Cpd. No. | Formula | Mass | NMR | LCMS (M + H) |
|---|---|---|---|---|
| | | | J = 8.5, 1.9 Hz, 1H), 8.34 (d, J = 8.3 Hz, 1H), 7.89-7.84 (m, 2H), 7.53 (dd, J = 8.5, 4.3 Hz, 1H), 7.18 (dd, J = 7.6, 1.7 Hz, 1H), 7.14-7.11 (m, 1H), 7.09 (d, J = 8.4 Hz, 1H), 6.90-6.86 (m, 1H), 6.45-6.41 (m, 1H), 4.89 (hept, J = 6.0 Hz, 1H), 1.39 (d, J = 6.0 Hz, 6H). | |
| 340 | C24H16BrN3O4S | 522.38 | 1H NMR (500 MHz, DMSO-d6) d 13.46 (s, 1H), 9.82 (s, 1H), 8.80 (dd, J = 4.3, 1.8 Hz, 1H), 8.78 (dd, J = 2.1, 0.8 Hz, 1H), 8.39 (dd, J = 8.3, 1.8 Hz, 1H), 8.07 (dd, J = 8.1, 2.1 Hz, 1H), 7.69 (d, J = 2.4 Hz, 1H), 7.60 (d, J = 8.5 Hz, 1H), 7.54 (dd, J = 8.9, 2.4 Hz, 1H), 7.47 (dd, J = 8.3, 4.3 Hz, 1H), 7.44 (d, J = 8.9 Hz, 1H), 2.86 (s, 3H). | 2.54 (524.0)' |
| 341 | C24H15BrFN3O4S | 540.37 | 1H NMR (400 MHz, DMSO-d6) d 10.03 (s, 1H), 8.76 (dd, J = 4.4, 1.8 Hz, 2H), 8.40 (dd, J = 8.3, 1.8 Hz, 1H), 8.14 (dd, J = 10.0, 8.3 Hz, 2H), 8.07 (dd, J = 8.1, 2.1 Hz, 1H), 7.89 (d, J = 7.6 Hz, 1H), 7.62 (d, J = 8.5 Hz, 1H), 7.51-7.43 (m, 2H), 2.88 (s, 3H). | 2.64 (542.0)' |
| 342 | C25H19N3O4S | 457.51 | 1H NMR (500 MHz, DMSO-d6) d 9.83 (s, 1H), 8.82 (dd, J = 4.3, 1.8 Hz, 1H), 8.75 (dd, J = 2.1, 0.9 Hz, 1H), 8.37 (dd, J = 8.3, 1.8 Hz, 1H), 8.15 (d, J = 8.5 Hz, 1H), 8.12 (dd, J = 8.1, 0.8 Hz, 1H), 8.03 (dd, J = 8.1, 2.1 Hz, 1H), 7.60 (d, J = 8.5 Hz, 1H), 7.48 (ddd, J = 7.7, 4.7, 1.3 Hz, 2H), 7.44 (dd, J = 8.2, 4.3 Hz, 1H), 7.35 (ddd, J = 8.6, 7.5, 1.6 Hz, 1H), 7.11 (td, J = 7.6, 1.1 Hz, 1H), 3.30 (q, J = 7.4 Hz, 2H), 1.21 (t, J = 7.5 Hz, 3H). | 2.36 (458.0)' |
| 345 | C25H19N3O4S | 457.51 | (400 MHz, DMSO, ppm): 8.79 (dd, J = 4.2, 1.8 Hz, 1H), 8.49-8.43 (m, 2H), 8.37 (dd, J = 7.3, 1.4 Hz, 1H), 8.28 (dd, J = 8.2, 1.4 Hz, 1H), 7.80-7.69 (m, 2H), 7.51 (dd, J = 8.3, 4.3 Hz, 1H), 7.48-7.40 (m, 2H), 7.33 (td, J = 8.4, 7.9, 1.6 Hz, 1H), 7.11 (td, J = 7.6, 1.2 Hz, 1H), 2.82 (q, J = 7.5 Hz, 2H), 1.23 (t, J = 7.5 Hz, 3H). | |
| 346 | C25H18ClN3O5S | 507.95 | 1H NMR (500 MHz, DMSO-d6) d 9.42 (s, 1H), 8.99 (dd, J = 4.2, 1.8 Hz, 1H), 8.28 (dd, J = 8.5, 1.8 Hz, 1H), 8.17 (dd, J = 2.1, 0.8 Hz, 1H), 8.12 (d, J = 8.3 Hz, 1H), 7.90 (dd, J = 8.1, 0.8 Hz, 1H), 7.50 (dd, J = 8.5, 4.2 Hz, 1H), 7.45 (dd, J = 2.6, 0.8 Hz, 1H), 7.41 (dd, J = 2.5, 0.7 Hz, 1H), 7.38 (dd, J = 8.1, 2.1 Hz, 1H), 6.97 (d, J = 8.4 Hz, 1H), 3.94 (s, 3H), 2.20 (s, 3H). | 2.31 (508.0)' |
| 347 | C24H17N3O5S | 459.48 | 1H NMR (500 MHz, DMSO-d6) d 9.92-9.79 (m, 1H), 8.84-8.80 (m, 2H), 8.46-8.41 (m, 1H), 8.28 (d, J = 9.3 Hz, 1H), 8.14-8.08 (m, 2H), 7.73 (d, J = 9.3 Hz, 1H), 7.51-7.43 (m, 3H), 7.34-7.29 (m, 1H), 7.09-7.04 (m, 1H), 4.05 (s, 3H). | 1.37 (460.0)* |
| 348 | C25H19N3O5S | 473.51 | 1H NMR (700 MHz, DMSO-d6) d 13.45 (s, 1H), 9.44 (s, 1H), 8.65-8.60 (m, 2H), 8.36 (dd, J = 8.3, 1.5 Hz, 1H), 8.31 (d, J = 7.4, 1.5 Hz, 1H), 8.09 (d, J = 8.1 Hz, 1H), 7.94 (dd, J = 8.0, 2.1 Hz, 1H), 7.69-7.63 (m, 1H), 7.48-7.42 (m, 2H), 7.36 (td, J = 7.9, 1.6 Hz, 1H), 7.14 (t, J = 7.6 Hz, 1H), 6.95 (d, J = 5.4 Hz, 1H), 4.22 (q, J = 7.0 Hz, 2H), 1.44 (t, J = 7.0 Hz, 3H). | 2.32-2.51 (474.0)' |
| 349 | C26H21N3O5S | 487.53 | 1H NMR (700 MHz, DMSO-d6) d 13.44 (s, 1H), 9.43 (s, 1H), 8.71 (d, J = 2.1 Hz, 1H), 8.60 (d, J = 5.4 Hz, 1H), 8.36 (dd, J = 8.4, 1.4 Hz, 1H), 8.32 (dd, J = 7.4, 1.5 Hz, 1H), 8.11 (d, J = 8.0 Hz, 1H), 8.00 (dd, J = 8.0, 2.1 Hz, 1H), 7.67-7.63 (m, 1H), 7.50-7.44 (m, 2H), 7.36 (td, J = 8.0, 1.6 Hz, 1H), 7.13 (t, J = 7.5 Hz, 1H), 7.01 (d, J = 5.5 Hz, 1H), 4.86 (q, J = 6.0 Hz, 1H), 1.37 (d, J = 6.0 Hz, 5H). | 2.43 (488.0)' |
| 350 | C30H21N3O5S | 535.58 | 1H NMR (400 MHz, DMSO-d6) d 9.03 (dd, J = 4.3, 1.9 Hz, 1H), 8.62 (t, J = 1.5 Hz, 1H), 8.58-8.52 (m, 1H), 8.37 (dd, J = 8.3 Hz, 1H), 7.89 (d, J = 1.5 Hz, 2H), 7.58-7.50 (m, 4H), 7.34 (t, J = 7.7 Hz, 2H), 7.24 (d, J = 1.4 Hz, 2H), 7.23-7.16 (m, 1H), 7.07 (d, J = 8.4 Hz, 1H), 4.02 (s, 3H). | 1.87 (536.0)* |
| 351 | C24H16ClN3O5S | 493.92 | 1H NMR (700 MHz, DMSO-d6) d 9.01 (dd, J = 4.3, 1.9 Hz, 1H), 8.61-8.59 (m, 1H), 8.54 (dd, J = 8.5, 1.9 Hz, 1H), 8.33 (d, J = 8.3 Hz, 1H), 7.92-7.86 (m, 2H), 7.54 (dd, J = 8.5, 4.3 Hz, 1H), 7.09-7.07 (m, 1H), 7.05 (d, J = 8.3 Hz, 1H), 6.86-6.83 (m, 1H), 6.57-6.54 (m, 1H), 4.01 (s, 3H). | 1.73 (494.0)* |

TABLE 2-continued

| Cpd. No. | Formula | Mass | NMR | LCMS (M + H) |
|---|---|---|---|---|
| 352 | C25H18BrN3O5S | 552.41 | 1H NMR (400 MHz, DMSO-d6) d 9.73 (s, 1H), 8.66 (dd, J = 4.3, 1.8 Hz, 1H), 8.65 (s, 1H), 8.39 (dd, J = 8.3, 1.8 Hz, 1H), 8.15 (d, J = 8.4 Hz, 1H), 7.79 (s, 1H), 7.63 (d, J = 8.5 Hz, 1H), 7.59 (t, J = 1.4 Hz, 1H), 7.51-7.42 (m, 3H), 4.12 (s, 3H), 2.94 (s, 3H). | 2.40 (554.0)' |
| 353 | C25H17BrFN3O5S | 570.40 | 1H NMR (500 MHz, DMSO-d6) d 9.92 (s, 1H), 8.65 (d, J = 5.5 Hz, 2H), 8.42 (dd, J = 8.3, 1.8 Hz, 1H), 8.18 (d, J = 8.5 Hz, 1H), 7.86-7.76 (m, 2H), 7.66 (d, J = 8.5 Hz, 1H), 7.51-7.44 (m, 2H), 4.12 (s, 3H), 2.95 (s, 3H). | 2.50 (572) |
| 354 | C26H17N3O5S | 483.50 | 1H NMR (400 MHz, DMSO-d$_6$) δ 8.72 (dd, J = 2.2, 0.9 Hz, 1H), 8.66 (d, J = 5.4 Hz, 1H), 8.40-8.35 (m, 2H), 8.12 (dd, J = 8.1, 0.9 Hz, 1H), 8.03 (dd, J = 8.1, 2.2 Hz, 1H), 7.72-7.67 (m, 1H), 7.47-7.43 (m, 2H), 7.37-7.32 (m, 1H), 7.12 (td, J = 7.6, 1.2 Hz, 1H), 7.08 (d, J = 5.4 Hz, 1H), 5.09 (d, J = 2.4 Hz, 2H), 2.34 (m, 2H), 1.92 (s, 1H) | 1.66 (484) |
| 356 | C25H18BrN3O6S | 568.41 | 1H NMR (400 MHz, DMSO-d6) d 9.13 (s, 1H), 8.67 (dd, J = 4.3, 1.8 Hz, 1H), 8.63 (s, 1H), 8.53 (dd, J = 8.5, 1.7 Hz, 1H), 8.41 (d, J = 8.4 Hz, 1H), 7.79 (s, 1H), 7.57 (d, J = 2.0 Hz, 1H), 7.53-7.45 (m, 3H), 7.18 (d, J = 8.5 Hz, 1H), 4.14 (s, 3H), 4.06 (s, 3H). | 2.33 (570) |
| 358 | C25H17BrFN3O6S | 586.40 | 1H NMR (400 MHz, DMSO-d6) d 8.65 (dd, J = 4.3, 1.8 Hz, 1H), 8.63 (s, 1H), 8.54 (dd, J = 8.5, 1.8 Hz, 1H), 8.48 (d, J = 8.4 Hz, 1H), 7.80 (s, 1H), 7.77 (d, J = 7.6 Hz, 1H), 7.54-7.46 (m, 2H), 7.19 (d, J = 8.5 Hz, 1H), 4.14 (s, 3H), 4.07 (s, 3H). | 2.43 (588) |
| 359 | C24H16ClN3O5S | 493.92 | 1H NMR (400 MHz, DMSO-d6) d 9.45-9.32 (m, 1H), 8.76 (dd, J = 4.3, 1.8 Hz, 1H), 8.70 (d, J = 1.9 Hz, 1H), 8.50 (dd, J = 8.5, 1.8 Hz, 1H), 8.30 (d, J = 8.4 Hz, 1H), 8.11 (d, J = 8.2 Hz, 1H), 8.00 (dd, J = 8.1, 2.1 Hz, 1H), 7.55-7.40 (m, 4H), 7.12 (d, J = 8.5 Hz, 1H), 4.03 (s, 3H). | 1.77 (494) |
| 360 | C25H18ClN3O6S | 523.95 | 1H NMR (500 MHz, DMSO-d6) d 9.13 (s, 1H), 8.66 (dd, J = 4.3, 1.8 Hz, 1H), 8.62 (s, 1H), 8.52 (dd, J = 8.5, 1.8 Hz, 1H), 8.40 (d, J = 8.4 Hz, 1H), 7.78 (s, 1H), 7.53 (d, J = 9.0 Hz, 1H), 7.49 (dd, J = 8.5, 4.3 Hz, 1H), 7.45 (d, J = 2.5 Hz, 1H), 7.37 (dd, J = 8.9, 2.5 Hz, 1H), 7.17 (d, J = 8.5 Hz, 1H), 4.13 (s, 3H), 4.05 (s, 3H). | 1.68 (524) |
| 361 | C25H18ClN3O5S | 507.95 | 1H NMR (500 MHz, DMSO-d6) d 9.83-9.65 (m, 1H), 8.67 (dd, J = 4.3, 1.8 Hz, 1H), 8.66 (s, 1H), 8.39 (dd, J = 8.3, 1.8 Hz, 1H), 8.15 (d, J = 8.4 Hz, 1H), 7.81 (s, 1H), 7.63 (d, J = 8.5 Hz, 1H), 7.54 (d, J = 9.0 Hz, 1H), 7.50-7.46 (m, 2H), 7.37 (dd, J = 9.0, 2.5 Hz, 1H), 4.13 (s, 3H). | 1.71 (508) |
| 362 | C26H21N3O6S | 503.53 | 1H NMR (400 MHz, DMSO-d6) d 9.06 (s, 1H), 8.67 (dd, J = 4.2, 1.8 Hz, 1H), 8.64 (s, 1H), 8.53 (dd, J = 8.4, 1.9 Hz, 1H), 8.40 (d, J = 8.4 Hz, 1H), 7.79 (s, 1H), 7.54 (d, J = 8.4 Hz, 1H), 7.50 (dd, J = 8.5, 4.3 Hz, 1H), 7.37 (dd, J = 7.7, 1.5 Hz, 1H), 7.30 (td, J = 8.0, 1.6 Hz, 1H), 7.15 (d, J = 8.5 Hz, 1H), 7.01 (t, J = 7.6 Hz, 1H), 4.31 (q, J = 6.9 Hz, 2H), 4.15 (s, 3H), 1.46 (t, J = 7.0 Hz, 3H). | 1.61 (504) |
| 363 | C24H16ClN3O4S | 477.93 | 1H NMR (500 MHz, DMSO-d6) d 13.91-12.95 (m, 1H), 9.90-9.77 (m, 1H), 8.80 (dd, J = 4.3, 1.8 Hz, 1H), 8.77 (dd, J = 2.1, 0.9 Hz, 1H), 8.38 (dd, J = 8.3, 1.8 Hz, 1H), 8.14-8.11 (m, 2H), 8.06 (dd, J = 8.1, 2.1 Hz, 1H), 7.59 (d, J = 8.5 Hz, 1H), 7.57 (d, J = 2.5 Hz, 1H), 7.49 (d, J = 8.9 Hz, 1H), 7.46 (dd, J = 8.3, 4.3 Hz, 1H), 7.42 (dd, J = 9.0, 2.5 Hz, 1H), 2.85 (s, 3H). | 1.81 (478) |
| 364 | C27H22N2O6S | 502.54 | 1H NMR (500 MHz, TCE-d2) delta 8.67 (dd, J = 4.4, 1.8 Hz, 1H), 8.60 (dd, J = 8.5, 1.8 Hz, 1H), 8.41 (d, J = 8.4 Hz, 1H), 8.08-8.07 (m, 1H), 7.67-7.64 (m, 1H), 7.38 (dd, J = 7.7, 1.5 Hz, 1H), 7.34 (dd, J = 8.5, 4.4 Hz, 1H), 7.28-7.24 (m, 2H), 7.01-6.97 (m, 1H), 6.89 (d, J = 8.4 Hz, 1H), 4.14 (s, 3H), 4.06 (s, 3H), 2.49 (s, 3H). | 1.82 (503) |
| 365 | C27H22N2O5S | 486.55 | 1H NMR (400 MHz, DMSO-d6) d 13.24-11.96 (m, 1H), 9.69-9.65 (m, 1H), 8.68 (dd, J = 4.3, 1.8 Hz, 1H), 8.39 (dd, J = 8.4, 1.8 Hz, 1H), 8.13 (d, J = 8.4 Hz, 1H), 7.64-7.63 (m, 1H), 7.61 (d, J = 8.5 Hz, 1H), 7.49-7.45 (m, 2H), 7.43 (dd, J = | 1.86 (487) |

| Cpd. No. | Formula | Mass | NMR | LCMS (M + H) |
|---|---|---|---|---|
| | | | 7.7, 1.6 Hz, 1H), 7.32-7.26 (m, 1H), 7.24 (s, 1H), 7.03 (td, J = 7.5, 1.0 Hz, 1H), 3.86 (s, 3H), 2.90 (s, 3H), 2.46 (s, 3H). | |
| 366 | C24H17N3O5S | 459.48 | 1H NMR (400 MHz, DMSO-d6) d 9.25-9.17 (m, 1H), 8.70 (dd, J = 4.3, 1.7 Hz, 1H), 8.64 (s, 1H), 8.46 (td, J = 8.6, 8.0, 1.6 Hz, 2H), 8.29 (dd, J = 8.2, 1.4 Hz, 1H), 7.79 (s, 1H), 7.78-7.73 (m, 1H), 7.56-7.51 (m, 2H), 7.38 (dd, J = 7.7, 1.5 Hz, 1H), 7.32-7.26 (m, 1H), 7.02 (td, J = 7.5, 1.1 Hz, 1H), 4.14 (s, 3H). | 1.48 (460) |
| 367 | C26H20ClN3O6S | 537.98 | 1H NMR (500 MHz, DMSO-d6) d 9.13 (s, 1H), 8.66 (dd, J = 4.3, 1.8 Hz, 1H), 8.61 (s, 1H), 8.52 (dd, J = 8.5, 1.8 Hz, 1H), 8.37 (d, J = 8.4 Hz, 1H), 7.79 (s, 1H), 7.53 (d, J = 8.9 Hz, 1H), 7.49 (dd, J = 8.5, 4.3 Hz, 1H), 7.44 (d, J = 2.5 Hz, 1H), 7.37 (dd, J = 9.0, 2.5 Hz, 1H), 7.13 (d, J = 8.5 Hz, 1H), 4.30 (q, J = 7.0 Hz, 2H), 4.13 (s, 3H), 1.46 (t, J = 7.0 Hz, 3H). | 1.79 (538-542) |
| 368 | C23H14ClN3O4S | 463.90 | 1H NMR (400 MHz, DMSO-d6) d 8.79 (dd, J = 4.3, 1.7 Hz, 1H), 8.66 (d, J = 2.1 Hz, 1H), 8.43 (dd, J = 8.4, 1.8 Hz, 1H), 8.35 (d, J = 7.3 Hz, 1H), 8.26 (d, J = 8.0 Hz, 1H), 8.10 (d, J = 8.1 Hz, 1H), 7.95 (dd, J = 8.1, 2.1 Hz, 1H), 7.75-7.69 (m, 1H), 7.54 (d, J = 1.4 Hz, 1H), 7.51 (dd, J = 8.3, 4.2 Hz, 1H), 7.44 (s, 2H). | 1.73-1.74 (464) |
| 369 | C26H21N3O5S | 487.53 | 1H NMR (500 MHz, DMSO-d6) d 9.80 (s, 1H), 8.69 (dd, J = 4.3, 1.8 Hz, 1H), 8.65 (s, 1H), 8.37 (dd, J = 8.3, 1.8 Hz, 1H), 8.16 (d, J = 8.5 Hz, 1H), 7.79 (s, 1H), 7.64 (d, J = 8.5 Hz, 1H), 7.56 (dd, J = 8.4, 1.0 Hz, 1H), 7.46 (dd, J = 8.2, 4.3 Hz, 1H), 7.40 (dd, J = 7.7, 1.5 Hz, 1H), 7.30 (ddd, J = 8.6, 7.5, 1.6 Hz, 1H), 7.02 (td, J = 7.6, 1.1 Hz, 1H), 4.12 (s, 3H), 3.40 (q, J = 7.5 Hz, 2H), 1.32 (t, J = 7.4 Hz, 3H). | 2.18 (488) |
| 370 | C26H21N3O6S | 503.53 | 1H NMR (300 MHz, Methanol-d4):: 8.74 (d, J = 4.0 Hz, 1H), 8.52 (d, J = 8.5 Hz, 1H), 8.35 (d, J = 8.6 Hz, 2H), 7.57 (dd, J = 8.4, 1.0 Hz, 1H), 7.43: 7.27 (m, 2H), 7.23 (ddd, J = 8.3, 7.5, 1.6 Hz, 1H), 7.07: 6.93 (m, 2H), 4.16 (s, 3H), 4.06 (s, 3H), 2.42 (s, 3H). | .6.40 (504.3) |
| 371 | C27H23N3O5S | 501.56 | 1-H NMR (300 MHz, MeOD-d4, ppm) δ: 8.72-8.64 (m, 1 H), 8.58-8.48 (m, 1 H), 8.46-8.40 (m, 1 H), 8.33 (d, J = 8.4 Hz 1 H), 7.80 (d, J = 1.7 Hz, 1 H), 7.59 (d, J = 8.4 Hz, 1 H), 7.31 (dd, J = 8.3, 3.8 Hz, 2 H), 7.23 (t, J = 8.2 Hz, 1 H), 7.04-6.93 (m, 2 H), 4.31 (q, J = 7.0 Hz, 2 H), 3.09 (q, J = 7.6 Hz, 2 H), 1.51 (t, J = 7.0 Hz, 3 H), 1.31 (t, J = 7.5 Hz, 3 H) | 7.304 (502.1) |
| 372 | C26H21N3O6S | 503.53 | 1-H NMR (300 MHz, DMSO-d6, ppm) δ: 8.70-8.66 (m, 2 H), 8.57-8.29 (m, 2 H), 7.82 (s, 1 H), 7.53 (d, J = 8.2 Hz, 1 H), 7.30-7.21 (m, 3 H), 6.94-6.90 (m, 2 H), 4.10 (s, 3 H), 3.94 (s, 3 H), 2.91 (s, 3 H) | 2.780 (504.2) |
| 373 | C27H23ClN4O5S | 551.02 | 1H NMR (400 MHz, DMSO-d6) delta 9.10 (s, 1H), 8.69 (dd, J = 4.3, 1.8 Hz, 1H), 8.54-8.50 (m, 2H), 8.40 (d, J = 8.4 Hz, 1H), 7.54-7.49 (m, 2H), 7.42 (d, J = 2.5 Hz, 1H), 7.38-7.34 (m, 2H), 7.17 (d, J = 8.5 Hz, 1H), 4.07 (s, 3H), 4.05 (s, 3H), 3.05 (s, 3H), 3.00 (s, 3H). | 1.88 (551-555) |
| 374 | C24H17N3O4S | 443.48 | 1H NMR (500 MHz, DMSO-d6) d 9.10 (dd, J = 4.2, 1.8 Hz, 1H), 8.58 (d, J = 1.6 Hz, 1H), 8.46 (dd, J = 8.6, 1.8 Hz, 1H), 8.33 (d, J = 7.4 Hz, 1H), 7.84 (s, 2H), 7.58 (dd, J = 8.5, 4.3 Hz, 1H), 7.50-7.46 (m, 1H), 7.17 (d, J = 7.6, 1.7 Hz, 1H), 7.12 (dd, J = 8.5, 1.1 Hz, 1H), 6.87 (ddd, J = 8.7, 7.2, 1.8 Hz, 1H), 6.43 (td, J = 7.4, 1.1 Hz, 1H), 2.65 (s, 3H). | 1.64 (444.00) |
| 375 | C27H23N3O4S | 485.56 | (300 MHz, DMSO-d6): 8.79 (s, 1H), 8.42 (s, 1H), 8.31 (d, J = 8.5 Hz, 1H), 8.09 (d, J = 8.5 Hz, 1H), 7.76 (s, 1H), 7.56 (d, J = 8.6 Hz, 1H), 7.45 (dd, J = 19.1, 8.2 Hz, 3H), 7.29 (t, J = 7.9 Hz, 1H), 7.06 (t, J = 7.6 Hz, 1H), 3.33 (q, J = 7.4 Hz, 2H), 2.45(s, 2H) 1.24 (td, J = 7.5, 3.7 Hz, 6H). | 0.946 (486.2) |
| 376 | C26H22N4O5S | 502.55 | 1H NMR (400 MHz, DMSO-d6) delta 9.15-9.10 (m, 1H), 8.77 (dd, J = 4.3, 1.8 Hz, 1H), 8.51 (dd, J = 8.5, 1.7 Hz, 1H), 8.32 (d, J = 8.4 Hz, 1H), 7.91 (d, J = 1.6 Hz, 1H), 7.93-7.71 (m, 1H), 7.51- | 1.72 (503.0)[D] |

TABLE 2-continued

| Cpd. No. | Formula | Mass | NMR | LCMS (M + H) |
|---|---|---|---|---|
| | | | 7.45 (m, 2H), 7.40 (dd, J = 7.8, 1.5 Hz, 1H), 7.35-7.30 (m, 1H), 7.29 (d, J = 1.7 Hz, 1H), 7.12 (d, J = 8.5 Hz, 1H), 7.08 (td, J = 7.5, 1.2 Hz, 1H), 4.03 (s, 3H), 3.27 (q, J = 7.1 Hz, 2H), 1.24 (t, J = 7.1 Hz, 3H). | |
| 377 | C26H22N4O5S | 502.55 | 1H NMR (500 MHz, DMSO-d6) d 9.13 (s, 1H), 8.78 (dd, J = 4.3, 1.8 Hz, 1H), 8.51 (dd, J = 8.5, 2.0 Hz, 1H), 8.30 (d, J = 8.4 Hz, 1H), 7.89 (d, J = 1.8 Hz, 1H), 7.49 (dd, J = 8.5, 4.3 Hz, 1H), 7.46 (d, J = 8.2 Hz, 1H), 7.41 (d, J = 7.3 Hz, 1H), 7.36-7.31 (m, 1H), 7.22 (d, J = 1.7 Hz, 1H), 7.09 (dd, J = 8.3, 5.9 Hz, 2H), 4.28 (q, J = 7.0 Hz, 2H), 2.90 (s, 4H), 1.45 (t, J = 7.0 Hz, 3H). | 1.71-1.74 (503.0)$^D$ |
| 378 | C24H23N3O5S | 465.53 | 1H NMR (500 MHz, DMSO-d6) delta 10.10-9.56 (m, 1H), 8.08-7.88 (m, 1H), 7.91 (d, J = 1.6 Hz, 1H), 7.63 (d, J = 8.9 Hz, 1H), 7.48-7.44 (m, 1H), 7.41-7.32 (m, 2H), 7.25-7.23 (m, 1H), 7.20-7.12 (m, 1H), 6.81 (d, J = 9.0 Hz, 1H), 3.75 (s, 3H), 2.87 (s, 3H), 2.45 (s, 3H), 1.93 (s, 3H). | 1.74 (466.0)$^D$ |
| 379 | C25H25N3O5S | 479.55 | 1H NMR (500 MHz, DMSO-d6) d 9.88 (s, 1H), 7.94 (d, J = 1.7 Hz, 1H), 7.63 (d, J = 8.9 Hz, 1H), 7.49 (dd, J = 7.4, 1.3 Hz, 1H), 7.43-7.34 (m, 3H), 7.21 (ddd, J = 8.3, 6.5, 2.2 Hz, 1H), 6.81 (d, J = 8.9 Hz, 1H), 3.75 (s, 4H), 3.27 (q, J = 7.1 Hz, 8H), 2.45 (s, 3H), 1.93 (s, 3H), 1.25 (t, J = 7.1 Hz, 3H). | 1.81. (480.0)$^D$ |
| 380 | C26H22N4O4S | 486.55 | 1H NMR (500 MHz, DMSO-d6) d 9.84 (s, 1H), 8.83 (dd, J = 4.3, 1.8 Hz, 1H), 8.39 (dd, J = 8.3, 1.8 Hz, 1H), 8.16 (d, J = 8.5 Hz, 1H), 7.92 (d, J = 1.7 Hz, 1H), 7.62 (d, J = 8.5 Hz, 1H), 7.51-7.44 (m, 3H), 7.35 (ddd, J = 8.6, 7.5, 1.6 Hz, 1H), 7.27 (d, J = 1.7 Hz, 1H), 7.10 (m, 1H), 3.3 (q, J = 7.5 Hz, 2H), 2.91 (s, 3H), 1.23 (t, J = 7.5 Hz, 3H). | 1.78 (487.0)$^D$ |
| 381 | C25H19N3O4S | 457.51 | 1H NMR (500 MHz, DMSO-d6) d 9.66 (s, 1H), 8.81-8.76 (m, 2H), 8.44 (dd, J = 8.5, 1.7 Hz, 1H), 8.13 (dd, J = 8.1, 0.9 Hz, 1H), 8.07 (dd, J = 8.1, 2.1 Hz, 1H), 7.53-7.43 (m, 4H), 7.34 (ddd, J = 8.6, 7.5, 1.6 Hz, 1H), 7.07 (td, J = 7.6, 1.1 Hz, 1H), 2.82 (s, 3H), 2.62 (s, 3H). | 1.74 (458.0)$^D$ |
| 382 | C25H16F3N3O5S | 527.48 | 1H NMR (300 MHz, DMSO-d6) d 9.67 (s, 1H), 8.89 (dd, J = 4.2, 1.7 Hz, 1H), 8.48 (dd, J = 8.6, 1.7 Hz, 1H), 8.46-8.29 (m, 2H), 7.75-7.69 (m, 1H), 7.66-7.54 (m, 2H), 7.45-7.38 (m, 2H), 7.20 (td, J = 7.1, 6.7, 2.0 Hz, 1H), 2.54 (s, 2H). | 7.10 (528.20)$^S$ |
| 383 | C25H19N3O5S | 473.51 | 1H NMR (300 MHz, DMSO-d6): 9.10 (s, 1H), 8.78 (dd, J = 4.3, 1.7 Hz, 1H), 8.74-8.69 (m, 1H), 8.49 (dd, J = 8.5, 1.7 Hz, 1H), 8.27 (d, J = 8.4 Hz, 1H), 8.11 (d, J = 8.1 Hz, 1H), 8.00 (dd, J = 8.1, 2.1 Hz, 1H), 7.46 (dd, J = 8.5, 4.3 Hz, 1H), 7.31 (d, J = 8.4 Hz, 1H), 7.25-7.20 (m, 1H), 7.16-7.08 (m, 2H), 4.02 (s, 3H), 2.17 (s, 3H). | 6.50 (474.20)$^S$ |
| 384 | C24H14F3N3O5S | 513.45 | 1H NMR (300 MHz, DMSO-d6): 9.72 (s, 1H), 8.88 (dd, J = 4.3, 1.7 Hz, 1H), 8.60 (d, J = 1.9 Hz, 1H), 8.49 (dd, J = 8.6, 1.7 Hz, 1H), 8.41 (d, J = 8.3 Hz, 1H), 8.06 (d, J = 8.0 Hz, 1H), 7.86 (dd, J = 8.1, 2.1 Hz, 1H), 7.71 (dd, J = 8.3, 1.8 Hz, 1H), 7.63 (dd, J = 8.6, 4.3 Hz, 1H), 7.51-7.39 (m, 2H), 7.26-7.11 (m, 1H) | 6.7 (514.1)+ |
| 385 | C29H26N4O3S | 511.3 | 1H NMR (300 MHz, DMSO-d6): 9.71 (s, 1H), 8.83 (dd, J = 4.3, 1.8 Hz, 1H), 8.72-8.60 (m, 1H), 8.39 (dd, J = 8.4, 1.8 Hz, 1H), 8.14 (d, J = 8.5 Hz, 1H), 8.04 (dd, J = 8.1, 2.1 Hz, 1H), 7.70-7.57 (m, 2H), 7.54-7.42 (m, 3H), 7.33 (td, J = 8.4, 7.9, 1.6 Hz, 1H), 7.08 (td, J = 7.5, 1.2 Hz, 1H), 3.72-3.57 (m, 2H), 3.42-3.35 (m, 1H), 2.88 (s, 3H), 1.78-1.50 (m, 4H). | 7.0 (511.3)+ |
| 386 | C28H24N4O4S | 513.3 | 1H NMR (300 MHz, DMSO-d6) 9.15 (s, 1H), 8.77 (dd, J = 4.2, 1.7 Hz, 1H), 8.64 (d, J = 2.1 Hz, 1H), 8.51 (dd, J = 8.5, 1.8 Hz, 1H), 8.32 (d, J = 8.4 Hz, 1H), 7.99 (dd, J = 8.1, 2.2 Hz, 1H), 7.81 (d, J = 8.1 Hz, 1H), 7.55-7.43 (m, 2H), 7.40 (d, J = 7.7 Hz, 1H), 7.32 (t, J = 7.9 Hz, 1H), 7.13 (d, J = 8.5 Hz, 1H), 7.08 (t, J = 7.5 Hz, 1H), 4.03 (s, 3H), 3.75-3.62 (m, 2H), 3.61-3.46 (m, 2H), 1.96-1.79 (m, 4H). | 6.6 (513.3)+ |
| 387 | C23H19ClN2O5S | 470.92 | 1H NMR (300 MHz, DMSO-d6) 13.43 (br, 1H), 10.16 (s, 1H), 8.78 (s, 1H), 8.12 (d, J = 8.2 Hz, | 7.0 (471.1)+ |

TABLE 2-continued

| Cpd. No. | Formula | Mass | NMR | LCMS (M + H) |
|---|---|---|---|---|
| | | | 1H), 8.07 (dd, J = 8.1, 2.0 Hz, 1H), 7.67-7.56 (m, 2H), 7.48 (dd, J = 8.8, 2.5 Hz, 1H), 7.41 (d, J = 8.8 Hz, 1H), 6.83 (d, J = 8.9 Hz, 1H), 3.75 (s, 3H), 2.43 (s, 3H), 1.91 (s, 3H). | |
| 388 | C22H17ClN2O6S | 472.9 | 1H NMR (400 MHz, DMSO-d6): 13.47 (br, 1H), 9.73 (br, 1H), 8.64 (s, 1H), 7.71 (s, 1H), 7.66-7.59 (m, 2H), 7.53 (d, J = 2.5 Hz, 1H), 7.49 (dd, J = 8.7, 2.5 Hz, 1H), 7.36 (d, J = 8.7 Hz, 1H), 6.95-6.88 (m, 2H), 4.04 (s, 3H), 3.71 (s, 3H) | 6.0 (473.1)+ |
| 389 | C25H16F3N3O6S | 543.47 | 1H NMR (300 MHz, DMSO-d6): 1H NMR (300 MHz, DMSO-d6): 9.34 (s, 1H), 8.82 (dd, J = 4.3, 1.7 Hz, 1H), 8.58 (s, 1H), 8.56-8.48 (m, 2H), 7.84-7.75 (m, 2H), 7.65 (dd, J = 8.6, 4.3 Hz, 1H), 7.52 (d, J = 8.3 Hz, 1H), 7.44-7.30 (m, 2H), 7.09 (t, J = 7.5 Hz, 1H), 4.10 (s, 3H). | 6.4 (544.1)+ |
| 390 | C21H15ClN2O5S | 442.87 | 1H NMR (400 MHz, DMSO-d6): 13.43 (br, 1H), 10.07 (s, 1H), 8.76 (dd, J = 2.0, 0.9 Hz, 1H), 8.12 (dd, J = 8.1, 0.9 Hz, 1H), 8.07 (dd, J = 8.1, 2.1 Hz, 1H), 7.62-7.56 (m, 3H), 7.52 (dd, J = 8.8, 2.6 Hz, 1H), 7.38 (d, J = 8.7 Hz, 1H), 6.93-6.86 (m, 2H), 3.67 (s, 3H) | 6.3 (443.1)+ |
| 391 | C22H18N2O6S | 438.45 | 1H NMR (400 MHz, DMSO-d6): 13.44 (br, 1H), 9.51 (s, 1H), 8.65 (s, 1H), 7.72 (s, 1H), 7.68-7.60 (m, 2H), 7.49-7.33 (m, 3H), 7.22 (td, J = 7.4, 1.6 Hz, 1H), 6.96-6.88 (m, 2H), 4.05 (s, 3H), 3.71 (s, 3H). | 5.3 (439.1)+ |
| 392 | C27H24N4O4S | 501.3 | 1H NMR (400 MHz, DMSO-d6): 9.18 (s, 1H), 8.76 (dd, J = 4.3, 1.7 Hz, 1H), 8.71 (dd, J = 2.0, 0.9 Hz, 1H), 8.59 (d, J = 8.4 Hz, 1H), 8.51 (dd, J = 8.5, 1.7 Hz, 1H), 8.32 (d, J = 8.4 Hz, 1H), 8.12-8.04 (m, 2H), 7.50-7.44 (m, 2H), 7.41 (dd, J = 7.7, 1.3 Hz, 1H), 7.35-7.30 (m, 1H), 7.14-7.05 (m, 2H), 4.21-4.11 (m, 1H), 4.02 (s, 3H), 1.22 (d, J = 6.6 Hz, 6H) | 7.2 (501.3)+ |
| 393 | C25H19N3O4S | 457.5 | 1H NMR (400 MHz, DMSO-d6): 13.47 (s, 1H), 9.64 (s, 1H), 8.89-8.70 (m, 2H), 8.37 (d, J = 8.2 Hz, 1H), 8.19-7.98 (m, 3H), 7.58 (d, J = 8.2 Hz, 1H), 7.51-7.42 (m, 1H), 7.39-7.23 (m, 2H), 7.14 (d, J = 8.2 Hz, 1H), 2.84 (s, 3H), 2.16 (s, 3H). | 6.6 (458.1)+ |
| 394 | C25H20N4O4S | 472.52 | 1H NMR (500 MHz, DMSO-d6) delta 9.36-9.31 (m, 1H), 8.80 (dd, J = 4.3, 1.8 Hz, 1H), 8.45 (dd, J = 8.4, 1.7 Hz, 1H), 8.37 (dd, J = 7.4, 1.4 Hz, 1H), 8.27 (dd, J = 8.3, 1.4 Hz, 1H), 7.99-7.77 (m, 1H), 7.89 (d, J = 1.7 Hz, 1H), 7.74-7.70 (m, 1H), 7.54 (dd, J = 8.3, 4.3 Hz, 1H), 7.45-7.41 (m, 2H), 7.35-7.31 (m, 1H), 7.29 (d, J = 1.7 Hz, 1H), 7.10 (td, J = 7.5, 1.2 Hz, 1H), 3.27 (q, J = 7.2 Hz, 2H), 1.24 (t, J = 7.1 Hz, 3H). | 1.70 (473.00) |
| 395 | C27H22N2O5S | 486.54 | 1H NMR (400 MHz, DMSO-d6): 13.85 (s, 1H), 10.03 (s, 1H), 8.76 (s, 1H), 8.66-8.57 (m, 1H), 8.37-8.30 (m, 1H), 7.94 (ddd, J = 8.3, 6.9, 1.3 Hz, 1H), 7.86 (ddd, J = 8.3, 6.9, 1.3 Hz, 1H), 7.70-7.65 (m, 1H), 7.63 (d, J = 8.9 Hz, 1H), 7.43 (ddd, J = 8.8, 7.4, 1.6 Hz, 1H), 7.34 (dd, J = 8.2, 1.2 Hz, 1H), 7.28 (td, J = 7.5, 1.3 Hz, 1H), 6.76 (d, J = 8.9 Hz, 1H), 3.66 (s, 3H), 2.39 (s, 3H), 1.72 (s, 3H). | 7.1 (487.2)+ |
| 396 | C27H23N3O6S | 517.56 | 1H NMR (300 MHz, DMSO-d6): 9.73 (s, 1H), 8.84 (dd, J = 2.1, 0.9 Hz, 1H), 8.80 (dd, J = 4.3, 1.8 Hz, 1H), 8.39 (dd, J = 8.4, 1.8 Hz, 1H), 8.25-8.10 (m, 3H), 7.60 (d, J = 8.5 Hz, 1H), 7.53-7.44 (m, 3H), 7.40-7.30 (m, 1H), 7.15-7.02 (m, 1H), 5.09 (d, J = 5.3 Hz, 1H), 4.76 (t, J = 5.7 Hz, 1H), 4.40 (dd, J = 11.2, 4.0 Hz, 1H), 4.27 (dd, J = 11.2, 6.5 Hz, 1H), 3.93-3.76 (m, 1H), 3.55-3.44 (m, 2H), 2.88 (s, 3H). | 5.6 (518.2)+ |
| 397 | C25H19N3O6S | 489.50 | 1H NMR (400 MHz, DMSO-d6): 13.42 (br, 1H), 9.14 (s, 1H), 8.80 (dd, J = 4.2, 1.8 Hz, 1H), 8.69-8.57 (m, 1H), 8.45 (dd, J = 8.5, 1.8 Hz, 1H), 8.20 (d, J = 8.4 Hz, 1H), 8.13-8.00 (m, 1H), 7.90 (dd, J = 8.1, 2.1 Hz, 1H), 7.42 (dd, J = 8.5, 4.3 Hz, 1H), 7.21 (d, J = 8.9 Hz, 1H), 7.08 (d, J = 8.5 Hz, 1H), 6.96 (d, J = 2.9 Hz, 1H), 6.92 (dd, J = 8.9, 3.0 Hz, 1H), 4.01 (s, 3H), 3.69 (s, 3H). | 5.90 (490.10) |
| 398 | C27H21BrN2O5S | 565.44 | 1H NMR (400 MHz, DMSO-d6): 13.89 (br, 1H), 10.20 (s, 1H), 8.78 (s, 1H), 8.61 (d, J = 8.4 Hz, 1H), 8.35 (d, J = 8.3 Hz, 1H), 8.02-7.90 (m, 2H), | 8.1 (567.0)+ |

TABLE 2-continued

| Cpd. No. | Formula | Mass | NMR | LCMS (M + H) |
|---|---|---|---|---|
| | | | 7.87 (t, J = 7.6 Hz, 1H), 7.63 (d, J = 8.9 Hz, 2H), 7.31 (d, J = 8.7 Hz, 1H), 6.78 (d, J = 8.9 Hz, 1H), 3.67 (s, 3H), 2.40 (s, 3H), 1.70 (s, 3H). | |
| 399 | C25H19N3O5S | 473.5 | 1H NMR (300 MHz, DMSO-d6) 9.71 (s, 1H), 8.91-8.64 (m, 2H), 8.40 (d, J = 8.2 Hz, 1H), 8.30-8.01 (m, 2H), 7.61 (d, J = 8.5 Hz, 1H), 7.56-7.42 (m, 3H), 7.33 (td, J = 8.5, 8.0, 1.6 Hz, 1H), 7.06 (t, J = 7.5 Hz, 1H), 5.70 (s, 1H). 4.88 (d, 2H), 2.90 (d, 3H). Carboxylic proton not visible.. | 5.8 (474.1)+ |
| 400 | C27H21ClN2O5S | 520.98 | 1H NMR (400 MHz, DMSO-d6): 13.89 (br, 1H), 10.20 (s, 1H), 8.77 (s, 1H), 8.66-8.55 (m, 1H), 8.39-8.30 (m, 1H), 7.94 (ddd, J = 8.3, 6.9, 1.3 Hz, 1H), 7.87 (ddd, J = 8.3, 6.9, 1.3 Hz, 1H), 7.81 (d, J = 2.5 Hz, 1H), 7.62 (d, J = 8.9 Hz, 1H), 7.50 (dd, J = 8.8, 2.6 Hz, 1H), 7.37 (d, J = 8.8 Hz, 1H), 6.77 (d, J = 9.0 Hz, 1H), 3.66 (s, 3H), 2.39 (s, 3H), 1.70 (s, 3H). | 7.9 (521.1)+ |
| 401 | C25H17N3O4S | 455.49 | 1H NMR (300 MHz, DMSO-d6) 9.76 (s, 1H), 8.94-8.85 (m, 1H), 8.80 (dd, J = 4.4, 1.8 Hz, 1H), 8.37 (dd, J = 8.3, 1.8 Hz, 1H), 8.30-8.20 (m, 1H), 8.12 (d, J = 8.5 Hz, 1H), 7.59 (d, J = 8.5 Hz, 1H), 7.54-7.42 (m, 3H), 7.41-7.30 (m, 1H), 7.10 (t, J = 7.6 Hz, 1H), 5.53 (s, 2H), 2.86 (s, 3H). | 6.4 (456.1)+ |
| 402 | C23H21N3O5S | 451.5 | 1H NMR (400 MHz, DMSO-d6): 9.95 (s, 1H), 7.92 (d, J = 1.7 Hz, 1H), 7.64 (d, J = 8.9 Hz, 1H), 7.48 (d, J = 7.5 Hz, 1H), 7.40-7.35 (m, 2H), 7.32 (d, J = 1.8 Hz, 1H), 7.21-7.16 (m, 1H), 6.83 (d, J = 9.0 Hz, 1H), 3.76 (s, 3H), 2.45 (s, 3H), 1.96 (s, 3H). | 6.0 (452.1)+ |
| 403 | C24H22ClN3O5S | 499.97 | 1H NMR (300 MHz, DMSO-d6) 10.10 (br, 1H), 7.94 (d, J = 1.7 Hz, 1H), 7.81 (br, 1H), 7.64-7.56 (m, 2H), 7.50-7.44 (m, 1H), 7.41 (d, J = 8.8 Hz, 1H), 7.31 (d, J = 1.7 Hz, 1H), 6.82 (d, J = 9.0 Hz, 1H), 3.75 (s, 3H), 2.88 (s, 3H), 2.45 (s, 3H), 1.91 (s, 3H). Carboxylic proton not visible. | 7.2 (500.2)+ |
| 404 | C30H27N3O6S | 557.62 | 1H NMR (300 MHz, DMSO-d6): 9.69 (s, 1H), 8.77 (dd, J = 4.3, 1.8 Hz, 1H), 8.41 (dd, J = 8.4, 1.8 Hz, 1H), 8.15 (d, J = 8.5 Hz, 1H), 8.09 (d, J = 8.4 Hz, 2H), 7.73 (d, J = 8.4 Hz, 1H), 7.62 (d, J = 8.5 Hz, 1H), 7.55-7.48 (m, 2H), 7.44 (dd, J = 7.8, 1.5 Hz, 1H), 7.32 (ddd, J = 8.5, 7.5, 1.6 Hz, 1H), 7.05 (td, J = 7.6, 1.1 Hz, 1H), 4.56-4.39 (m, 2H), 4.32 (dd, J = 12.2, 6.4 Hz, 1H), 4.13 (dd, J = 8.4, 6.4 Hz, 1H), 3.86 (dd, J = 8.5, 5.7 Hz, 1H), 2.90 (s, 3H), 1.38 (s, 3H), 1.32 (s, 3H). | 8.0 (557.2)+ |
| 405 | C28H25N3O7S | 547.58 | 1H NMR (400 MHz, DMSO-d6): 9.07 (s, 1H), 8.70-8.63 (m, 2H), 8.51 (dd, J = 8.5, 1.8 Hz, 1H), 8.43 (d, J = 8.4 Hz, 1H), 7.79 (s, 1H), 7.54 (d, J = 8.2 Hz, 1H), 7.49 (dd, J = 8.5, 4.3 Hz, 1H), 7.37 (dd, J = 7.8, 1.5 Hz, 1H), 7.33-7.25 (m, 1H), 7.17 (d, J = 8.5 Hz, 1H), 7.04-6.96 (m, 1H), 4.52-4.44 (m, 2H), 4.16 (s, 3H), 4.05 (s, 3H), 3.75-3.62 (m, 2H), 3.33 (s, 3H) | 6.6 (548.2)+ |
| 406 | C31H29N3O7S | 587.65 | 1H NMR (300 MHz, DMSO-d6): 9.70 (s, 1H), 8.71 (s, 1H), 8.67 (dd, J = 4.3, 1.8 Hz, 1H), 8.38 (dd, J = 8.3, 1.8 Hz, 1H), 8.14 (d, J = 8.5 Hz, 1H), 7.83 (s, 1H), 7.63 (d, J = 8.5 Hz, 1H), 7.55 (d, J = 8.4 Hz, 1H), 7.48 (dd, J = 8.3, 4.3 Hz, 1H), 7.40 (dd, J = 7.8, 1.5 Hz, 1H), 7.35-7.26 (m, 1H), 7.00 (td, J = 7.6, 1.1 Hz, 1H), 4.54-4.42 (m, 2H), 4.41-4.33 (m, 1H), 4.15 (s, 3H), 4.14-4.07 (m, 1H), 3.85 (dd, J = 8.5, 5.7 Hz, 1H), 2.96 (s, 3H), 1.39 (s, 3H), 1.32 (s, 3H). | 7.1 (588.3)+ |
| 407 | C30H30N4O4S | 542.65 | 1H NMR (300 MHz, DMSO-d6) d 9.68 (s, 1H), 8.77 (dd, J = 4.3, 1.8 Hz, 1H), 8.41 (dd, J = 8.4, 1.8 Hz, 1H), 8.15 (d, J = 8.5 Hz, 1H), 8.08 (d, J = 8.4 Hz, 1H), 7.72 (d, J = 8.4 Hz, 2H), 7.62 (d, J = 8.5 Hz, 1H), 7.54-7.48 (m, 2H), 7.44 (dd, J = 7.7, 1.6 Hz, 1H), 7.31 (ddd, J = 8.5, 7.5, 1.6 Hz, 1H), 7.04 (td, J = 7.6, 1.2 Hz, 1H), 4.34 (t, J = 6.5 Hz, 2H), 2.91 (s, 3H), 2.36-2.24 (m, 2H), 2.14 (s, 6H), 1.77 (p, J = 6.7 Hz, 2H), 1.64-1.49 (m, 2H). | 1.32 (542.70) |
| 408 | C28H25N3O7S | 547.58 | 1H NMR (300 MHz, DMSO-d6): 9.70 (s, 1H), 8.70 (s, 1H), 8.67 (dd, J = 4.3, 1.8 Hz, 1H), 8.39 (dd, J = 8.3, 1.8 Hz, 1H), 8.14 (d, J = 8.5 Hz, 1H), 7.84 (s, 1H), 7.63 (d, J = 8.4 Hz, 1H), 7.55 (d, J = | 5.6 (548.1)+ |

| Cpd. No. | Formula | Mass | NMR | LCMS (M + H) |
|---|---|---|---|---|
| | | | 8.4 Hz, 1H), 7.49 (dd, J = 8.3, 4.3 Hz, 1H), 7.40 (dd, J = 7.7, 1.5 Hz, 1H), 7.34-7.26 (m, 1H), 7.04-6.95 (m, 1H), 5.09 (d, J = 5.3 Hz, 1H), 4.75 (t, J = 5.7 Hz, 1H), 4.41 (dd, J = 11.2, 4.0 Hz, 1H), 4.27 (dd, J = 11.2, 6.6 Hz, 1H), 4.16 (s, 3H), 3.95-3.80 (m, 1H), 3.74-3.61 (m, 1H), 3.54-3.44 (m, 1H), 2.96 (s, 3H). | |
| 409 | C28H25N3O6S | 531.58 | 1H NMR (300 MHz, DMSO-d6): 9.69 (s, 1H), 8.78 (dd, J = 4.3, 1.8 Hz, 1H), 8.42 (dd, J = 8.3, 1.8 Hz, 1H), 8.15 (d, J = 8.5 Hz, 1H), 8.08 (d, J = 8.3 Hz, 1H), 7.72 (d, J = 8.4 Hz, 1H), 7.62 (d, J = 8.5 Hz, 1H), 7.58-7.48 (m, 2H), 7.44 (dd, J = 7.8, 1.5 Hz, 1H), 7.37-7.27 (m, 1H), 7.10-6.99 (m, 1H), 4.71-4.60 (m, 1H), 4.52-4.40 (m, 2H), 3.83-3.76 (m, 2H), 3.59-3.50 (m, 4H), 2.91 (s, 3H). Sulfonamide proton not visible. | 6.8 (531.1)+ |
| 410 | C27H23N3O5S | 501.56 | 1H NMR (300 MHz, DMSO-d6): 9.68 (s, 1H), 8.78 (dd, J = 4.3, 1.8 Hz, 1H), 8.41 (dd, J = 8.3, 1.8 Hz, 1H), 8.14 (d, J = 8.5 Hz, 1H), 8.08 (d, J = 8.4 Hz, 2H), 7.72 (d, J = 8.4 Hz, 2H), 7.61 (d, J = 8.5 Hz, 1H), 7.57-7.48 (m, 2H), 7.44 (dd, J = 7.8, 1.6 Hz, 1H), 7.32 (ddd, J = 8.5, 7.5, 1.6 Hz, 1H), 7.04 (td, J = 7.6, 1.1 Hz, 1H), 4.51-4.39 (m, 2H), 3.78-3.66 (m, 2H), 3.34 (s, 3H), 2.91 (s, 3H). Signal at 3.34 overlapped with signal of water | 7.7 (501.1)+ |
| 411 | C25H19N3O4 | 457.50 | 1H NMR (500 MHz, DMSO-d6) delta 13.81-12.79 (m, 1H), 9.32 (s, 1H), 8.77 (dd, J = 4.2, 1.6 Hz, 1H), 8.70 (dd, J = 2.1, 0.9 Hz, 1H), 8.56 (dd, J = 8.7, 1.7 Hz, 1H), 8.29 (d, J = 7.6 Hz, 1H), 8.10 (dd, J = 8.1, 0.9 Hz, 1H), 7.99 (dd, J = 8.1, 2.1 Hz, 1H), 7.57-7.55 (m, 1H), 7.52 (dd, J = 8.6, 4.2 Hz, 1H), 7.49-7.46 (m, 1H), 7.43 (dd, J = 7.7, 1.6 Hz, 1H), 7.37-7.33 (m, 1H), 7.11 (td, J = 7.5, 1.2 Hz, 1H), 3.09 (q, J = 7.5 Hz, 2H), 1.25 (t, J = 7.5 Hz, 3H). | 1.72 (458.00) |
| 412 | C28H25N3O6S | 531.58 | 1H NMR (300 MHz, DMSO-d6): 9.70 (s, 1H), 8.70 (s, 1H), 8.67 (dd, J = 4.3, 1.8 Hz, 1H), 8.38 (dd, J = 8.4, 1.8 Hz, 1H), 8.14 (d, J = 8.5 Hz, 1H), 7.81 (s, 1H), 7.63 (d, J = 8.5 Hz, 1H), 7.57-7.52 (m, 1H), 7.48 (dd, J = 8.3, 4.3 Hz, 1H), 7.40 (dd, J = 7.7, 1.5 Hz, 1H), 7.30 (ddd, J = 8.5, 7.5, 1.6 Hz, 1H), 6.99 (td, J = 7.6, 1.1 Hz, 1H), 4.53-4.43 (m, 2H), 4.16 (s, 3H), 3.76-3.68 (m, 2H), 2.96 (s, 3H). Signal for 3H (OMe) is overlapped with H2O (3.33 ppm) | 6.7 (532.2)+ |
| 413 | C24H22N2O5S | 450.51 | 1H NMR (400 MHz, DMSO-d6): 13.38 (s, 1H), 9.87 (s, 1H), 8.75 (s, 1H), 8.15-7.99 (m, 2H), 7.60 (d, J = 8.9 Hz, 1H), 7.33-7.25 (m, 2H), 7.20 (dd, J = 8.5, 1.8 Hz, 1H), 6.80 (d, J = 9.0 Hz, 1H), 3.73 (s, 3H), 2.41 (s, 3H), 2.24 (s, 3H), 1.88 (s, 3H). | 6.7 (451.1)+ |
| 414 | C26H21N3O4S | 471.53 | 1H NMR (500 MHz, DMSO-d6) d 13.79-12.91 (m, 1H), 9.35-9.30 (m, 1H), 8.77 (dd, J = 4.2, 1.6 Hz, 1H), 8.69 (dd, J = 2.2, 0.9 Hz, 1H), 8.56 (dd, J = 8.7, 1.7 Hz, 1H), 8.28 (d, J = 7.6 Hz, 1H), 8.10 (dd, J = 8.1, 0.9 Hz, 1H), 7.98 (dd, J = 8.1, 2.1 Hz, 1H), 7.54 (d, J = 7.6 Hz, 1H), 7.52 (dd, J = 8.6, 4.2 Hz, 1H), 7.47 (dd, J = 8.3, 1.1 Hz, 1H), 7.43 (dd, J = 7.7, 1.6 Hz, 1H), 7.37-7.32 (m, 1H), 7.11 (td, J = 7.5, 1.2 Hz, 1H), 3.05-3.00 (m, 2H), 1.66-1.57 (m, 2H), 0.92 (t, J = 7.3 Hz, 3H). | 1.80 (472.00) |
| 415 | C26H21N5O4S | 499.55 | 1H NMR (400 MHz, DMSO-d6): 9.76 (s, 1H), 8.80 (dd, J = 4.2, 1.8 Hz, 1H), 8.40 (s, 1H), 8.29 (dd, J = 8.3, 1.7 Hz, 1H), 8.13 (s, 1H), 8.08 (d, J = 8.5 Hz, 1H), 7.55 (d, J = 8.5 Hz, 1H), 7.53-7.43 (m, 3H), 7.41-7.33 (m, 2H), 7.17-7.11 (m, 1H), 3.55-3.51 (m, 2H), 3.47-3.43 (m, 2H), 2.76 (s, 3H). | 5.0 (500.1)+ |
| 416 | C27H23N3O4S | 485.56 | 1H NMR (300 MHz, DMSO-d6): 13.45 (s, 1H), 9.70 (s, 1H), 8.83-8.74 (m, 2H), 8.43-8.34 (m, 1H), 8.15-8.03 (m, 3H), 7.59 (d, J = 8.5 Hz, 1H), 7.52-7.41 (m, 1H), 7.41-7.32 (m, 2H), 7.28-7.18 (m, 1H), 2.85 (s, 3H), 2.81-2.71 (m, 1H), 1.10 (d, J = 6.9 Hz, 6H). | 7.5 (486.1)+ |
| 417 | C26H21N3O4S | 471.53 | 1H NMR (300 MHz, DMSO-d6): 13.46 (br s, 1H), 9.67 (s, 1H), 8.87-8.73 (m, 2H), 8.38 (d, J = 7.8 | 7.1 (472.1)+ |

TABLE 2-continued

| Cpd. No. | Formula | Mass | NMR | LCMS (M + H) |
|---|---|---|---|---|
| | | | Hz, 1H), 8.19-8.01 (m, 3H), 7.59 (d, J = 8.5 Hz, 1H), 7.51-7.41 (m, 1H), 7.42-7.27 (m, 2H), 7.24-7.13 (m, 1H), 2.84 (s, 3H), 2.47-2.41 (m, 3H), 1.07 (t, J = 7.5 Hz, 3H). | |
| 418 | C26H22N4O5S | 502.54 | 1H NMR (300 MHz, DMSO-d6, ppm) 8.50 (s, 1H), 8.40-8.30 (m, 2H), 8.27 (d, J = 5.3 Hz, 1H), 7.68 (s, 1H), 7.64-7.40 (m, 3H), 7.41-7.33 (m, 1H), 7.33-7.22 (m, 1H), 7.04-6.93 (m, 1H), 6.76 (d, J = 5.4 Hz, 1H), 4.06 (s, 3H), 2.98 (s, 5H), 2.85 (s, 1H). | 8.73 (503.2) |
| 419 | C25H20N4O5S | 488.52 | 1H NMR (300 MHz, Methanol-d4, ppm) 8.80 (s, 1 H), 8.65-8.56 (m, 1 H), 8.34-8.21 (m, 2 H), 8.11 (s, 1 H), 7.72-7.60 (m, 1 H), 7.57-7.41 (m, 3 H), 7.40-7.29 (m, 1 H), 6.74 (d, J = 7.4 Hz, 1 H), 4.34 (s, 3 H), 3.15 (s, 3 H). | 4.02 (489.1) |
| 420 | C25H20N4O4 | 472.52 | 1H NMR (300 MHz, Methanol-d4, ppm) 8.56-8.12 (m, 6H), 7.63-7.32 (m, 5H), 6.87-6.78 (m, 1H), 3.46-3.39 (m, 6H). | 2.27 (472.1) |
| 421 | C26H22N4O4S | 486.55 | 1H NMR (400 MHz, DMSO-d6, ppm) 11.07 (s, 1H), 8.53-8.46 (m, 1H), 8.36 (s, 1H), 8.28 (d, J = 7.3 Hz, 1H), 8.07-8.01 (m, 1H), 7.94 (s, 1H), 7.63-7.55 (m, 1H), 7.55-7.47 (m, 2H), 7.47-7.39 (m, 1H), 7.39-7.32 (m, 1H), 6.68-6.62 (m, 1H), 3.29 (s, 6H), 2.30 (s, 3H). | 1.04 (487.0) |
| 422 | C27H22N4O5S | 514.56 | 1H NMR (300 MHz, DMSO-d6, ppm) 8.54-8.43 (m, 2H), 8.31-8.22 (m, 1H), 8.19-8.11 (m, 1H), 8.09-8.00 (m, 1H), 7.93-7.84 (m, 1H), 7.66-7.55 (m, 1H), 7.53-7.33 (m, 3H), 7.28-7.17 (m, 1H), 6.92-6.86 (m, 1H), 4.05-3.59 (m, 4H), 3.45-3.23 (m, 4H). | 0.93 (515.1) |
| 423 | C24H18N4O4S | 458.50 | 1H NMR (400 MHz, DMSO-d6, ppm) 12.50-12.45 (m, 1H), 11.15-11.11 (m, 1H), 9.93-9.89 (m, 1H), 8.80-8.73 (m, 1H), 8.53-8.23 (m, 2H), 8.02-7.91 (m, 2H), 7.83-7.76 (m, 1H), 7.69-7.60 (m, 1H), 7.59-7.49 (m, 2H), 7.49-7.44 (m, 1H), 7.44-7.33 (m, 1H), 6.47-6.41 (m, 1H), 2.96-2.90 (m, 3H). | 0.84 (459.1) |
| 424 | C21H16N2O3S | 376.43 | 1H NMR (500 MHz, DMSO-d6) delta 14.88-11.81 (m, 1H), 8.89-8.87 (m, 1H), 8.14 (dd, J = 8.1, 2.1 Hz, 1H), 8.11-8.08 (m, 1H), 8.06-8.03 (m, 2H), 7.72-7.67 (m, 1H), 7.65-7.61 (m, 2H), 7.47 (dd, J = 7.7, 1.6 Hz, 1H), 7.17-7.13 (m, 1H), 7.03-7.00 (m, 1H), 6.89 (td, J = 7.5, 1.1 Hz, 1H), 3.48 (s, 3H). | 1.51 (377) |
| 425 | C25H20N4O4S | 472.52 | 1H NMR (300 MHz, DMSO-d6, ppm) 8.95-8.86 (m, 1H), 8.60 (s, 1H), 8.34-8.25 (m, 1H), 8.01 (s, 1H), 7.97-7.88 (m, 1H), 7.69-7.32 (m, 5H), 6.43-6.34 (m, 1H), 2.89 (s, 3H), 2.24 (s, 3H). | 1.27 (473.0) |
| 426 | C25H20N4O4S | 472.52 | 1H NMR (400 MHz, DMSO-d6, ppm) 8.89-8.81 (m, 1H), 8.51-8.45 (m, 1H), 8.33-8.28 (m, 1H), 8.03-7.95 (m, 1H), 7.93-7.87 (m, 1H), 7.87-7.80 (m, 1H), 7.63-7.57 (m, 1H), 7.55-7.48 (m, 1H), 7.47-7.41 (m, 2H), 7.38-7.31 (m, 1H), 6.56-6.50 (m, 1H), 3.37-3.23 (m, 2H), 3.07-2.97 (m, 1H), 1.27-1.07 (m, 5H). | 0.67 (473.0) |
| 427 | C26H22N4O4S | 486.55 | DMSO-d6, ppm) 9.36-9.16 (m, 0H), 9.00-8.81 (m, 1H), 8.61-8.40 (m, 1H), 8.37-8.21 (m, 1H), 8.06-7.90 (m, 2H), 7.87-7.77 (m, 1H), 7.67-7.56 (m, 1H), 7.56-7.40 (m, 3H), 7.38-7.24 (m, 1H), 6.70-6.49 (m, 1H), 3.91-3.73 (m, 1H), 3.20-3.05 (m, 7H), 2.08-1.95 (m, 1H), 1.32-1.10 (m, 6H). | 1.45 (487.0) |
| 428 | C22H18N2O4S | 406.46 | 1H NMR (500 MHz, DMSO-d6) delta 14.18-12.22 (m, 1H), 8.87 (dd, J = 2.1, 0.9 Hz, 1H), 8.14 (dd, J = 8.1, 2.1 Hz, 1H), 8.09 (dd, J = 8.1, 0.9 Hz, 1H), 7.96-7.92 (m, 2H), 7.46 (dd, J = 7.7, 1.6 Hz, 1H), 7.16-7.12 (m, 3H), 7.02-6.99 (m, 1H), 6.88 (td, J = 7.5, 1.1 Hz, 1H), 3.83 (s, 3H), 3.43 (s, 3H). | 1.53 (407) |
| 429 | C24H17N3O3S | 427.48 | 1H NMR (400 MHz, DMSO-d6) δ 8.96 (dd, J = 4.2, 1.8 Hz, 1H), 8.79 (dd, J = 2.1, 0.9 Hz, 1H), 8.61 (dd, J = 7.4, 1.5 Hz, 1H), 8.52 (dd, J = 8.4, 1.8 Hz, 1H), 8.33 (dd, J = 8.2, 1.5 Hz, 1H), 8.09 (dd, J = 8.1, 0.9 Hz, 1H), 8.03 (dd, J = 8.1, 2.1 Hz, 1H), 7.79 (dd, J = 8.2, 7.4 Hz, 1H), 7.66-7.58 (m, 3H), 7.58-7.52 (m, 1H), 7.34 (dd, J = 7.7, 1.6 Hz, 1H), 7.08 (ddd, | 0.91 (427) |

TABLE 2-continued

| Cpd. No. | Formula | Mass | NMR | LCMS (M + H) |
|---|---|---|---|---|
| | | | J = 8.2, 7.3, 1.7 Hz, 1H), 6.99 (dd, J = 8.3, 1.2 Hz, 1H), 6.80 (td, J = 7.4, 1.2 Hz, 1H), 3.97 (s, 3H). | |
| 430 | C23H20N2O5S | 436.49 | 1H NMR (500 MHz, DMSO-d6) δ 9.36 (s, 1H), 8.74-8.71 (m, 1H), 8.06 (d, J = 8.1 Hz, 1H), 7.99 (dd, J = 8.2, 2.0 Hz, 1H), 7.85 (dd, J = 7.9, 1.3 Hz, 1H), 7.80 (dd, J = 7.8, 1.3 Hz, 1H), 7.69 (m, J = 7.6, 1.3 Hz, 1H), 7.59 (td, J = 7.7, 1.3 Hz, 1H), 6.72 (d, J = 8.7 Hz, 1H), 6.58 (d, J = 8.8 Hz, 1H), 3.60 (s, 3H), 1.98 (s, 3H), 1.90 (s, 3H). | 1.59 (437) |
| 431 | C21H15FN2O3S | 394.43 | 1H NMR (500 MHz, DMSO-d6) delta 13.84-12.73 (m, 1H), 8.88 (dd, J = 2.1, 0.9 Hz, 1H), 8.14 (dd, J = 8.1, 2.1 Hz, 1H), 8.11-8.07 (m, 3H), 7.51-7.45 (m, 3H), 7.18-7.14 (m, 1H), 7.02-6.99 (m, 1H), 6.91 (td, J = 7.5, 1.1 Hz, 1H), 3.50 (s, 3H). | 0.92 (395) |
| 432 | C23H15N3O4S | 429.46 | 1H NMR (500 MHz, DMSO-d6) δ 9.94 (s, 1H), 8.99 (dd, J = 2.2, 0.9 Hz, 1H), 8.46 (dd, J = 4.3, 1.7 Hz, 1H), 8.33 (m, 2H), 8.22 (m, 2H), 7.76-7.72 (m, 1H), 7.68-7.64 (m, 2H), 7.62 (m, 3H), 7.56-7.52 (m, 2H), 7.48-7.45 (m, 1H). | 1.65-1.67 (430) |
| 433 | C22H18N2O4S | 406.46 | 1H NMR (500 MHz, DMSO-d6) delta 14.00-12.53 (m, 1H), 8.82 (t, J = 1.5 Hz, 1H), 8.08 (d, J = 1.5 Hz, 2H), 8.01 (dd, J = 7.9, 1.7 Hz, 1H), 7.65-7.61 (m, 1H), 7.42 (dd, J = 7.7, 1.6 Hz, 1H), 7.23-7.21 (m, 1H), 7.15-7.11 (m, 1H), 7.11-7.07 (m, 1H), 6.95-6.92 (m, 1H), 6.84 (td, J = 7.4, 1.1 Hz, 1H), 3.82 (s, 3H), 3.53 (s, 3H). | 0.90 (407) |
| 434 | C22H18N2O4S | 406.46 | 1H NMR (500 MHz, DMSO-d6) delta 14.21-12.25 (m, 1H), 8.88 (dd, J = 2.2, 0.9 Hz, 1H), 8.15 (dd, J = 8.1, 2.1 Hz, 1H), 8.08 (dd, J = 8.1, 0.9 Hz, 1H), 7.61-7.58 (m, 1H), 7.54 (t, J = 8.0 Hz, 1H), 7.54 (d, J = 4.4 Hz, 1H), 7.47 (dd, J = 7.7, 1.6 Hz, 1H), 7.26-7.23 (m, 1H), 7.18-7.14 (m, 1H), 7.05 (dd, J = 8.2, 1.0 Hz, 1H), 6.90 (td, J = 7.4, 1.1 Hz, 1H), 3.76 (s, 3H), 3.48 (s, 3H). | 0.94 (391) |
| 435 | C22H18N2O3S | 390.46 | 1H NMR (400 MHz, DMSO-d6) d 14.28-12.10 (m, 1H), 8.88 (dd, J = 2.1, 0.9 Hz, 1H), 8.15 (dd, J = 8.1, 2.1 Hz, 1H), 8.09 (dd, J = 8.1, 0.9 Hz, 1H), 7.90-7.88 (m, 1H), 7.85-7.80 (m, 1H), 7.53-7.49 (m, 2H), 7.48-7.45 (m, 1H), 7.19-7.13 (m, 1H), 7.05-7.02 (m, 1H), 6.90 (td, J = 7.5, 1.2 Hz, 1H), 3.45 (s, 3H), 2.33 (s, 3H). | 0.94 (391) |
| 436 | C21H15FN2O3S | 394.43 | 1H NMR (400 MHz, DMSO-d6) d 13.60-13.14 (m, 1H), 8.89 (dd, J = 2.2, 0.9 Hz, 1H), 8.15 (dd, J = 8.1, 2.1 Hz, 1H), 8.08 (dd, J = 8.1, 0.9 Hz, 1H), 7.89-7.85 (m, 2H), 7.72-7.66 (m, 1H), 7.60-7.54 (m, 1H), 7.48 (dd, J = 7.8, 1.6 Hz, 1H), 7.20-7.15 (m, 1H), 7.04 (dd, J = 8.3, 1.1 Hz, 1H), 6.92 (td, J = 7.5, 1.2 Hz, 1H), 3.54 (s, 3H). | 0.93 (395) |
| 437 | C21H15FN2O3S | 394.43 | 1H NMR (500 MHz, DMSO-d6) d 13.99-12.43 (m, 1H), 8.82 (t, J = 1.5 Hz, 1H), 8.08 (d, J = 1.5 Hz, 2H), 8.02-7.98 (m, 1H), 7.76-7.71 (m, 1H), 7.46-7.41 (m, 3H), 7.17-7.13 (m, 1H), 6.99 (dd, J = 8.3, 1.0 Hz, 1H), 6.91 (td, J = 7.5, 1.1 Hz, 1H), 3.62 (s, 3H). | 0.91 (395) |
| 438 | C22H18N2O3S | 390.46 | 1H NMR (500 MHz, DMSO-d6) d 13.96-12.40 (m, 1H), 8.82 (dd, J = 1.9, 1.1 Hz, 1H), 8.13 (dd, J = 8.0, 1.4 Hz, 1H), 8.10-8.06 (m, 2H), 7.57 (td, J = 7.4, 1.4 Hz, 1H), | 0.94 (391) |
| 439 | C20H14N2O4S | 378.41 | 1H NMR (400 MHz, DMSO-d6) d 13.50-13.23 (m, 1H), 10.37 (s, 1H), 8.90 (dd, J = 2.1, 0.9 Hz, 1H), 8.20 (dd, J = 8.1, 2.1 Hz, 1H), 8.13 (dd, J = 8.1, 0.9 Hz, 1H), 8.02-7.99 (m, 1H), 7.83-7.79 (m, 1H), 7.68 (td, J = 7.6, 1.5 Hz, 1H), 7.62 (td, J = 7.7, 1.5 Hz, 1H), 7.22-7.17 (m, 2H), 7.10-7.06 (m, 2H), 7.01-6.96 (m, 1H). | 1.51 (379) |
| 440 | C21H16N2O4S | 392.43 | 1H NMR (400 MHz, DMSO-d6) d 8.51 (dd, J = 2.2, 0.9 Hz, 1H), 7.92-7.88 (m, 1H), 7.82 (dd, J = 7.8, 1.4 Hz, 1H), 7.78-7.73 (m, 2H), 7.71 (td, J = 7.6, 1.3 Hz, 1H), 7.57 (td, J = 7.7, 1.4 Hz, 1H), 7.28-7.22 (m, 2H), 7.20-7.12 (m, 3H), 3.30 (s, 3H). | 1.56 (393.0) |
| 441 | C27H16ClN3O4S | 513.96 | 1H NMR (500 MHz, DMSO-d6) d 14.17-13.52 (m, 1H), 9.68 (s, 1H), 8.67-8.62 (m, 1H), 8.59 | 1.09 (514.0) |

TABLE 2-continued

| Cpd. No. | Formula | Mass | NMR | LCMS (M + H) |
|---|---|---|---|---|
| | | | (d, J = 4.7 Hz, 1H), 8.56 (s, 1H), 8.38 (dd, J = 7.3, 1.4 Hz, 1H), 8.24 (dd, J = 8.5, 1.4 Hz, 1H), 8.12-8.08 (m, 1H), 7.89-7.84 (m, 2H), 7.77 (dd, J = 8.5, 7.4 Hz, 1H), 7.58 (dd, J = 7.7, 1.5 Hz, 1H), 7.41 (d, J = 4.8 Hz, 1H), 7.42-7.38 (m, 1H), 7.35 (dd, J = 8.3, 1.3 Hz, 1H), 7.25 (td, J = 7.5, 1.4 Hz, 1H). | |
| 442 | C29H21N3O5S | 523.57 | 1H NMR (500 MHz, DMSO-d6) d 14.26-13.52 (m, 1H), 9.32-9.29 (m, 1H), 8.66 (s, 1H), 8.63-8.61 (m, 2H), 8.27 (dd, J = 8.5, 1.8 Hz, 1H), 8.27 (d, J = 8.4 Hz, 1H), 8.22-8.19 (m, 1H), 7.91-7.87 (m, 1H), 7.88-7.84 (m, 1H), 7.56 (dd, J = 7.7, 1.5 Hz, 1H), 7.41 (dd, J = 8.4, 1.2 Hz, 1H), 7.38-7.34 (m, 1H), 7.26 (dd, J = 8.5, 4.3 Hz, 1H), 7.16 (td, J = 7.5, 1.3 Hz, 1H), 7.03 (d, J = 8.5 Hz, 1H), 4.21 (q, J = 7.0 Hz, 2H), 1.42 (t, J = 6.9 Hz, 3H). | 1.09 (524) |
| 443 | C35H34N4O8S | 670.74 | 1H NMR (500 MHz, DMSO-d6) d 9.66-9.47 (m, 1H), 8.66-8.65 (m, 1H), 8.66-8.63 (m, 1H), 8.45 (d, J = 5.3 Hz, 1H), 8.32 (dd, J = 7.3, 1.4 Hz, 1H), 8.24 (dd, J = 8.4, 1.5 Hz, 1H), 8.23-8.20 (m, 1H), 7.91-7.86 (m, 2H), 7.85-7.70 (m, 3H), 7.64 (dd, J = 8.4, 7.3 Hz, 1H), 7.60-7.58 (m, 1H), 7.42-7.39 (m, 1H), 7.39-7.35 (m, 1H), 7.21-7.17 (m, 1H), 6.75-6.73 (m, 1H), 4.20-4.17 (m, 2H), 3.84-3.81 (m, 2H), 3.63 (dd, J = 5.9, 3.6 Hz, 2H), 3.58-3.52 (m, 8H), 2.97-2.90 (m, 2H). | 0.77 (671) |
| 444 | C28H19N3O4S | 493.54 | 1H NMR (500 MHz, DMSO-d6) δ 9.39 (s, 1H), 8.63-8.58 (m, 1H), 8.56 (s, 1H), 8.34 (dd, J = 7.4, 1.4 Hz, 1H), 8.18-8.15 (m, 1H), 8.13-8.08 (m, 2H), 7.91-7.83 (m, 2H), 7.62 (t, J = 7.7 Hz, 2H), 7.41-7.36 (m, 2H), 7.24-7.21 (m, 1H), 7.21-7.18 (m, 1H), 2.35 (s, 3H). | 1.06 (494) |
| 445 | C29H21N3O4S | 507.57 | 1H NMR (500 MHz, DMSO-d6) d 14.67-12.71 (m, 1H), 10.02 (s, 1H), 8.71 (s, 1H), 8.67-8.65 (m, 1H), 8.66-8.64 (m, 1H), 8.35-8.32 (m, 1H), 8.21 (dd, J = 8.3, 1.8 Hz, 1H), 8.05 (d, J = 8.5 Hz, 1H), 7.95-7.91 (m, 1H), 7.91-7.87 (m, 1H), 7.64-7.60 (m, 1H), 7.57 (d, J = 8.5 Hz, 1H), 7.40-7.38 (m, 1H), 7.38-7.34 (m, 1H), 7.26 (dd, J = 8.3, 4.3 Hz, 1H), 7.19-7.15 (m, 1H), 3.30 (q, J = 7.5 Hz, 2H), 1.20 (t, J = 7.4 Hz, 3H). | 1.10 (508) |
| 446 | C29H21N3O4S | 507.57 | 1H NMR (500 MHz, DMSO-d6) d 14.20-13.55 (m, 1H), 9.87 (s, 1H), 8.72 (s, 1H), 8.66-8.64 (m, 1H), 8.63 (dd, J = 4.3, 1.7 Hz, 1H), 8.29-8.26 (m, 1H), 8.24 (dd, J = 8.5, 1.7 Hz, 1H), 7.93-7.89 (m, 1H), 7.90-7.86 (m, 1H), 7.59 (dd, J = 7.7, 1.5 Hz, 1H), 7.46 (dd, J = 8.4, 1.1 Hz, 1H), 7.38-7.37 (m, 1H), 7.39-7.35 (m, 1H), 7.26 (dd, J = 8.5, 4.3 Hz, 1H), 7.14 (td, J = 7.5, 1.2 Hz, 1H), 2.81 (s, 3H), 2.53-2.52 (m, 3H). | 1.10 (5.08.0) |
| 447 | C30H23N3O5S | 537.59 | 1H NMR (400 MHz, DMSO-d6) d 9.31 (s, 1H), 8.72 (s, 1H), 8.66-8.63 (m, 1H), 8.60 (dd, J = 4.3, 1.8 Hz, 1H), 8.32 (dd, J = 8.5, 1.8 Hz, 1H), 8.30-8.27 (m, 1H), 8.28 (d, J = 8.4 Hz, 1H), 7.94-7.85 (m, 2H), 7.58 (dd, J = 7.7, 1.5 Hz, 1H), 7.42 (dd, J = 8.3, 1.3 Hz, 1H), 7.36 (td, J = 8.3, 7.8, 1.5 Hz, 1H), 7.27 (dd, J = 8.5, 4.3 Hz, 1H), 7.16 (td, J = 7.4, 1.4 Hz, 1H), 7.10 (d, J = 8.6 Hz, 1H), 4.92-4.82 (m, 1H), 1.36 (d, J = 6.0 Hz, 6H). | 1.13 (538) |
| 448 | C28H19N3O3S | 477.54 | 1H NMR (500 MHz, DMSO-d6) d 14.57-12.64 (m, 1H), 9.09-9.06 (m, 1H), 8.75 (s, 1H), 8.70-8.67 (m, 1H), 8.68-8.66 (m, 1H), 8.65 (dd, J = 7.4, 1.5 Hz, 1H), 8.45 (dd, J = 8.4, 1.8 Hz, 1H), 8.31 (dd, J = 8.3, 1.5 Hz, 1H), 8.00-7.96 (m, 1H), 7.90-7.86 (m, 1H), 7.84-7.80 (m, 1H), 7.52 (dd, J = 8.3, 4.3 Hz, 1H), 7.40-7.37 (m, 1H), 7.07-7.04 (m, 2H), 6.81-6.75 (m, 1H), 4.07 (s, 3H). | 0.99 (478) |
| 449 | C26H20N2O4S | 456.52 | 1H NMR (500 MHz, DMSO-d6) d 14.36-13.08 (m, 1H), 8.82 (s, 1H), 8.76-8.73 (m, 1H), 8.67-8.65 (m, 1H), 8.00-7.97 (m, 1H), 7.93-7.90 (m, 2H), 7.88-7.84 (m, 1H), 7.58-7.56 (m, 1H), 7.16-7.12 (m, 1H), 7.13-7.09 (m, 2H), 7.02-6.99 (m, 1H), 6.90 (td, J = 7.4, 1.1 Hz, 1H), 3.80 (s, 3H), 3.53 (s, 3H). | 1.01 (457) |

TABLE 2-continued

| Cpd. No. | Formula | Mass | NMR | LCMS (M + H) |
|---|---|---|---|---|
| 450 | C24H16N2O4S | 428.47 | 1H NMR (500 MHz, DMSO-d6) d 13.76-12.88 (m, 1H), 10.27 (s, 1H), 8.67 (dd, J = 2.1, 0.9 Hz, 1H), 8.11-8.07 (m, 1H), 8.04 (dd, J = 8.1, 0.9 Hz, 1H), 7.92 (dd, J = 8.0, 1.3 Hz, 1H), 7.89 (dd, J = 8.1, 2.1 Hz, 1H), 7.81-7.78 (m, 1H), 7.73 (dd, J = 7.7, 1.4 Hz, 1H), 7.70-7.67 (m, 1H), 7.65 (td, J = 7.5, 1.4 Hz, 1H), 7.57 (td, J = 7.7, 1.4 Hz, 1H), 7.46-7.41 (m, 1H), 7.41-7.37 (m, 1H), 7.34-7.30 (m, 1H), 7.25-7.22 (m, 1H). | 0.95 (429) |
| 451 | C26H21N3O5S | 487.53 | 1H NMR (300 MHz, DMSO-d6, ppm) 8.77-8.70 (m, 1H), 8.53-8.40 (m, 2H), 8.36-8.28 (m, 1H), 7.75-7.69 (m, 1H), 7.52-7.42 (m, 2H), 7.42-7.25 (m, 2H), 7.17-7.00 (m, 2H), 4.04-3.98 (m, 3H), 2.85-2.72 (m, 2H), 1.27-1.16 (m, 3H). | 0.98 (488) |
| 452 | C26H21N3O4S | 471.54 | 1H NMR (300 MHz, DMSO-d6, ppm) 8.54-8.05 (m, 3H), 7.69-7.59 (m, 2H), 7.51-7.29 (m, 3H), 7.15-7.07 (m, 1H), 3.29-3.23 (m, 1H), 2.81-2.75 (m, 1H), 2.48-2.42 (m, 1H), 2.34-2.28 (m, 1H), 1.24-1.13 (m, 2H). | 0.97 (472) |
| 453 | C24H14F3N3O5S | 513.45 | 1H NMR (300 MHz, DMSO-d6) d 9.72 (s, 1H), 8.88 (dd, J = 4.3, 1.7 Hz, 1H), 8.60 (d, J = 1.9 Hz, 1H), 8.49 (dd, J = 8.6, 1.7 Hz, 1H), 8.41 (d, J = 8.3 Hz, 1H), 8.06 (d, J = 8.0 Hz, 1H), 7.86 (dd, J = 8.1, 2.1 Hz, 1H), 7.71 (dd, J = 8.3, 1.8 Hz, 1H), 7.63 (dd, J = 8.6, 4.3 Hz, 1H), 7.51-7.39 (m, 2H), 7.26-7.11 (m, 1H). | 1.64 (514) |
| 454 | C25H16F3N3O6S | 543.48 | 1H NMR (300 MHz, DMSO-d6) d 9.34 (s, 1H), 8.82 (dd, J = 4.3, 1.7 Hz, 1H), 8.58 (s, 1H), 8.56-8.48 (m, 2H), 7.84-7.75 (m, 2H), 7.65 (dd, J = 8.6, 4.3 Hz, 1H), 7.52 (d, J = 8.3 Hz, 1H), 7.44-7.30 (m, 2H), 7.09 (t, J = 7.5 Hz, 1H), 4.10 (s, 3H). | 1.70 (544) |
| 455 | C25H16F3N3O5S | 527.48 | 1H NMR (300 MHz, DMSO-d6, ppm) 9.36-9.30 (m, 1H), 8.86-8.78 (m, 1H), 8.74-8.68 (m, 1H), 8.49-8.40 (m, 1H), 8.39-8.30 (m, 1H), 8.15-8.06 (m, 1H), 8.04-7.95 (m, 1H), 7.60-7.49 (m, 1H), 7.48-7.22 (m, 4H), 7.18-7.06 (m, 1H), 5.15-5.01 (m, 2H). | 0.77 (528) |
| 456 | C25H15ClF3N3O5S | 561.92 | 1H NMR (300 MHz, DMSO-d6, ppm) 9.57-9.51 (m, 1H), 8.84-8.76 (m, 1H), 8.68-8.61 (m, 1H), 8.47-8.38 (m, 1H), 8.37-8.28 (m, 1H), 8.14-8.05 (m, 1H), 7.99-7.89 (m, 1H), 7.58-7.49 (m, 2H), 7.49-7.41 (m, 2H), 7.31-7.22 (m, 1H), 5.14-4.99 (m, 2H). | 1.61 (562) |
| 457 | C26H18F3N3O6S | 557.50 | 1H NMR (300 MHz, DMSO-d6, ppm) 9.16-9.10 (m, 1H), 8.76-8.68 (m, 1H), 8.68-8.62 (m, 1H), 8.53-8.42 (m, 2H), 7.82-7.76 (m, 1H), 7.61-7.50 (m, 2H), 7.43-7.27 (m, 3H), 7.08-6.97 (m, 1H), 5.18-5.04 (m, 2H), 4.17-4.11 (m, 3H). | 1.27 (558) |
| 458 | C26H17ClF3N3O6S | 591.95 | 1H NMR (300 MHz, DMSO-d6, ppm) 8.67-8.61 (m, 1H), 8.50-8.18 (m, 3H), 7.89-7.78 (m, 1H), 7.57-7.44 (m, 2H), 7.42-7.23 (m, 4H), 5.20-4.96 (m, 2H), 4.15-4.09 (m, 3H), 1.27-1.21 (m, 1H). | 1.44 (592) |
| 459 | C26H21N3O4S | 471.54 | 1H NMR (400 MHz, DMSO-d$_6$, ppm) δ 9.73 (s, 1H), 8.82-8.76 (m, 1H), 8.59-8.53 (m, 1H), 8.42-8.34 (m, 1H), 8.16-8.09 (m, 1H), 7.93-7.88 (m, 1H), 7.63-7.56 (m, 1H), 7.53-7.41 (m, 3H), 7.38-7.29 (m, 1H), 7.11-7.03 (m, 1H), 2.92-2.82 (m, 5H), 1.28-1.19 (m, 3H). | — |

BIOLOGICAL ACTIVITY

Biological activity of the compounds of the present invention is determined utilizing the assays described herein below.

Extracellular Lactate Production Inhibition after 4 h

For measuring changes in lactate level released to growth medium after compound treatment, MDA-MB-231, SNU398 and MIA PaCa-2 cell lines were used. Cells were plated in growth media supplemented with 10% FBS, followed by overnight recovery at 37° C., 5% CO$_2$. On the following day, assay plates were washed twice with LCIS buffer, pre-treated with test compounds for 30 min at RT and then stimulated with D-(+)-glucose to a final concentration of 25 mM in 30 μl/well total volume. Plates were then moved for 4 h incubation at 37° C., 5% CO$_2$ with subsequent 20 μl media transfer to empty 384-well transparent plates. Later on, freshly reconstituted lactate reagent was added to readout wells with keeping appropriate sample:reagent volume ratio of 1:1. Plates were short-spun and measured kinetically in absorbance mode (530 nm, 12 min measurement time with 2-minute intervals between subsequent readouts at 30° C.). Differences in the signal between T8 min and T0min were normalized to vehicle (cells w/ 0.25% DMSO)

and quasi-positive (LCIS buffer w/ 0.25% DMSO) controls and plotted against logarithmically-transformed test compound concentrations with fitting the 4-parameter model in GraphPad Prism software.

MTS & Extracellular Lactate Production Inhibition after 144 h

In order to test cytostatic vs cytotoxic effect of test compounds in parallel to lactate release, 144 h treatment time was selected. MDA-MB-231, SNU398 and MIA PaCa-2 cells were plated in growth media supplemented with 10% FBS, followed by overnight recovery at 37° C., 5% $CO_2$. On the following day, assay plates were washed twice with sterile PBS buffer and respective media supplemented with 2.5% dialyzed FBS were added to a final volume of 50 μL per well. After this part of experimental procedure, test compounds were dispensed into plates, which were then moved for 144 h incubation at 37° C., 5% $CO_2$. On day 6, 4 μL of media from above the cells were collected and transferred into the new, transparent 384-well plates. 26 μL of LCIS buffer per well was then added (final volume 30 μL per well) and the procedure with lactate reagent addition and kinetic measurement was continued as described above. 5 μL of MTS/PMS solution in PBS buffer were then added to the remaining cell plates and absorbance signal at 490 nm was read after 3 h of incubation at 37° C./5% $CO_2$. Data from MTS assay part were normalized to cells w/ 1 μM staurosporine (−100% ctrl) and vehicle control (100%) with the reference to the signal from additional "T0" plate (0% ctrl), which was measured after backfilling plated cells with 0.25% DMSO on the day of compound dispensing to the actual test plates.

IC50 values of compounds of the present invention are shown in Table 3 below.

Compounds are classified according to their IC50 values in the assays described above in three groups:

TABLE 3

| Cpd. No. | $IC_{50}$ | Cpd. No. | $IC_{50}$ |
| --- | --- | --- | --- |
| 1 | C | 211 | B |
| 2 | D | 212 | A |
| 3 | D | 213 | B |
| 4 | C | 214 | A |
| 5 | D | 215 | A |
| 6 | C | 216 | C |
| 7 | C | 217 | D |
| 8 | C | 218 | C |
| 9 | D | 219 | C |
| 10 | C | 220 | C |
| 11 | C | 221 | A |
| 12 | D | 222 | B |
| 13 | D | 223 | D |
| 14 | C | 224 | C |
| 15 | C | 225 | B |
| 16 | D | 226 | B |
| 17 | C | 227 | B |
| 18 | C | 228 | B |
| 19 | C | 229 | C |
| 20 | D | 230 | C |
| 21 | D | 231 | D |
| 22 | C | 232 | C |
| 23 | C | 233 | B |
| 24 | D | 234 | B |
| 25 | C | 235 | A |
| 26 | C | 236 | B |
| 27 | D | 237 | A |
| 28 | C | 238 | D |
| 29 | D | 239 | D |
| 30 | C | 240 | B |
| 31 | C | 241 | B |
| 32 | C | 242 | A |
| 33 | C | 243 | A |

TABLE 3-continued

| Cpd. No. | $IC_{50}$ | Cpd. No. | $IC_{50}$ |
| --- | --- | --- | --- |
| 34 | D | 244 | B |
| 35 | D | 245 | D |
| 36 | D | 246 | D |
| 37 | C | 247 | B |
| 38 | C | 248 | C |
| 39 | D | 249 | C |
| 40 | D | 250 | D |
| 41 | C | 251 | D |
| 42 | C | 252 | D |
| 43 | C | 253 | D |
| 44 | C | 254 | D |
| 45 | C | 255 | D |
| 46 | C | 256 | D |
| 47 | C | 258 | C |
| 48 | C | 259 | D |
| 49 | C | | |
| 50 | D | 261 | D |
| 51 | D | 262 | C |
| 52 | C | 263 | D |
| 53 | C | 264 | C |
| 54 | D | 265 | C |
| 55 | D | 266 | B |
| 56 | C | 267 | C |
| 57 | D | | |
| 58 | C | 269 | D |
| 59 | C | 270 | C |
| 60 | D | 271 | C |
| 61 | C | 272 | D |
| 62 | C | | |
| 63 | C | | |
| 64 | D | 275 | D |
| 65 | D | 276 | D |
| 66 | D | 277 | C |
| 67 | C | 278 | D |
| 68 | C | 279 | D |
| 69 | C | 280 | D |
| 70 | C | 281 | C |
| 71 | D | 282 | D |
| 72 | D | 283 | D |
| 73 | C | 284 | B |
| 74 | C | 285 | C |
| 75 | C | 286 | C |
| 76 | D | 287 | D |
| 77 | B | 288 | D |
| 78 | C | 289 | C |
| 79 | B | 290 | D |
| 80 | C | 291 | B |
| 81 | C | 292 | D |
| 82 | D | 293 | C |
| 83 | C | 294 | C |
| 84 | D | 295 | B |
| | | 296 | D |
| 86 | D | 297 | D |
| 87 | C | 298 | B |
| 88 | C | 299 | D |
| 89 | D | 300 | C |
| 90 | D | 301 | C |
| 91 | D | 302 | B |
| 92 | B | 303 | C |
| 93 | D | 304 | D |
| 94 | D | 305 | B |
| 95 | D | 306 | B |
| 96 | C | 307 | B |
| 97 | C | 308 | C |
| 98 | D | 309 | C |
| 99 | C | 310 | B |
| 100 | D | 311 | C |
| 101 | D | 312 | D |
| 102 | B | 313 | D |
| 103 | C | 314 | C |
| 104 | C | 315 | B |
| 105 | D | 316 | D |
| 106 | D | 317 | C |
| 107 | B | 318 | D |
| 108 | B | 319 | B |
| 109 | C | 320 | B |
| 110 | B | 321 | D |
| 111 | C | 322 | D |

TABLE 3-continued

| Cpd. No. | IC$_{50}$ | Cpd. No. | IC$_{50}$ | Cpd. No. | IC$_{50}$ | Cpd. No. | IC$_{50}$ |
|---|---|---|---|---|---|---|---|
| 112 | B | 323 | D | 190 | B | 405 | C |
| 113 | D | 324 | C | 191 | B | 406 | B |
| 114 | C | 325 | A | 192 | A | 407 | D |
| 115 | C | 326 | D | 193 | D | 408 | B |
| 116 | C | 327 | D | 194 | C | 409 | C |
| 117 | C | 328 | A | 195 | C | 410 | C |
| 118 | C | 329 | C | 196 | D | 411 | C |
| 119 | C | 330 | D | 197 | C | 412 | B |
| 120 | D | 331 | D | 198 | C | 413 | B |
| 121 | C | 332 | D | 199 | B | 414 | B |
| 122 | B | 333 | D | 200 | C | 415 | C |
| 123 | D | 334 | C | 201 | B | 416 | C |
| 124 | C | 335 | D | 202 | B | 417 | A |
| 125 | C | 336 | B | 203 | C | 418 | C |
| 126 | C | 339 | B | 204 | B | 419 | D |
| 127 | C | 340 | A | 205 | D | 420 | D |
| 128 | C | 341 | A | 206 | A | 421 | C |
| 129 | B | 342 | A | 207 | B | 422 | D |
| 130 | D | 345 | B | 208 | C | 423 | D |
| 131 | C | 346 | C | 209 | C | 424 | D |
| 132 | B | 347 | C | 210 | B | 425 | D |
| 133 | C | 348 | B | 426 | D | 427 | D |
| 134 | B | 349 | C | 428 | D | 429 | D |
| 135 | C | 350 | C | 430 | D | 431 | D |
| 136 | D | 351 | C | 432 | D | 433 | D |
| 137 | C | 352 | A | 434 | C | 435 | D |
| 138 | C | 353 | B | 436 | D | 437 | D |
| 139 | C | 354 | C | 438 | D | 439 | D |
| 140 | C | 355 | D | 440 | D | 441 | C |
| 141 | C | 356 | A | 442 | B | 443 | D |
| 142 | C | 357 | D | 444 | D | 445 | D |
| 143 | B | 358 | A | 446 | C | 447 | C |
| 144 | B | 359 | A | 448 | C | 449 | D |
| 145 | D | 360 | A | 450 | D | 451 | B |
| 146 | B | 361 | A | 452 | | 453 | |
| 147 | C | 362 | A | 454 | | 455 | |
| 148 | B | 363 | D | 456 | | 457 | |
| 149 | B | 364 | D | 458 | | 459 | |
| 150 | C | 365 | C | | | | |
| 151 | C | 366 | B | | | | |
| 152 | B | 367 | A | | | | |
| 153 | C | 368 | B | | | | |
| 154 | D | 369 | A | | | | |
| | | 370 | C | | | | |
| 156 | D | 371 | A | | | | |
| 157 | B | 372 | A | | | | |
| 158 | B | 373 | D | | | | |
| 159 | B | 374 | C | | | | |
| 160 | B | 375 | A | | | | |
| 161 | C | 376 | A | | | | |
| 162 | B | 377 | A | | | | |
| 163 | C | 378 | B | | | | |
| 164 | A | 379 | B | | | | |
| 165 | B | 380 | | | | | |
| 166 | B | 381 | B | | | | |
| 167 | B | 382 | B | | | | |
| 168 | B | 383 | A | | | | |
| 169 | B | 384 | B | | | | |
| 170 | D | 385 | D | | | | |
| 171 | C | 386 | D | | | | |
| 172 | B | 387 | B | | | | |
| 173 | D | 388 | B | | | | |
| 174 | D | 389 | A | | | | |
| 175 | D | 390 | C | | | | |
| 176 | B | 391 | C | | | | |
| 177 | C | 392 | C | | | | |
| 178 | C | 393 | A | | | | |
| 179 | C | 394 | A | | | | |
| 180 | B | 395 | C | | | | |
| 181 | C | 396 | A | | | | |
| 182 | C | 397 | B | | | | |
| 183 | B | 398 | B | | | | |
| 184 | D | 399 | C | | | | |
| 185 | B | 400 | B | | | | |
| 186 | C | 401 | B | | | | |
| 187 | C | 402 | B | | | | |
| 188 | C | 403 | B | | | | |
| 189 | C | 404 | C | | | | |

Group A IC50 is in the range of ≥1 nM to <10 nM
Group B IC50 is in the range of ≥10 nM to <100 nM
Group C IC50 is in the range of ≥100 nM to ≤1 μM
Group D IC50 is in the range of >1 μM to ≤100 μM Selective MCT4 Inhibition and Dual MCT4 and MCT1 Inhibition:

IC50 values of compounds of formula (I) were tested in different cell lines with different expression levels of MCT1 and MCT, respectively. In SNU-398 cells, the ratio of MCT4/MCT1 is 0.02 (mRNA MCT4: 22; MCT1: 874), while in MDA-MB231 cells this ratio is 120 (mRNA MCT4: 2750; MCT1: 23). Mia PaCa-2 cells express both MCT1 and MCT4 with MCT4/MCT1 ratio equal to 0.9 (mRNA MCT4: 1000; MCT1: 940). While most of the compounds of the present invention show sub-micromolar IC50 values in MDA-MB231 cells only but second digit micromolar IC50 values in both SNU-398 and Mia PaCa-2 cells which indicates that they are selective MCT4 inhibitors, some of them show sub-micromolar activity in SNU-398 and Mia PaCa-2 cells indicating that they are dual inhibitors of both MCT4 and MCT1 (see Table 4).

TABLE 4

| Cpd. No. | IC50 (SNU-398) | IC50 (MDA-MB231) | IC50 (MiaPACa) |
|---|---|---|---|
| 44 | >50 μM | C | >50 μM |
| 208 | <1 μM | <1 μM | <1 μM |
| 217 | <1 μM | <1 μM | <1 μM |

525

The following examples relate to medicaments:

Example A: Injection Vials

A solution of 100 g of an active ingredient of the formula (I) and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula (I) with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula (I), 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula (I) are mixed with 99.5 g of Vaseline under aseptic conditions.

Example E: Tablets

A mixture of 1 kg of active ingredient of the formula (I), 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, traga-canth and dye.

Example G: Capsules 2 kg of active ingredient of the formula (I) are introduced into hard gelatine capsules in a conventional manner in such a way that each capsule contains 20 mg of the active ingredient.

Example H: Ampoules

A solution of 1 kg of active ingredient of the formula (I) in 60 l of bidistilled water is sterile filtered, transferred into ampoules, lyophilised under sterile conditions and sealed under sterile conditions. Each ampoule contains 10 mg of active ingredient.

526

The invention claimed is:
1. A compound of formula (I)

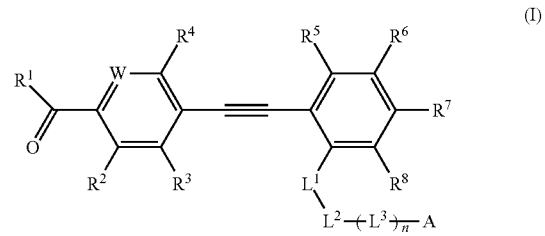

wherein
W denotes $CR^{W1}$ or N;
$R^{W1}$ is H, halogen, $R^a$ or $—OR^a$;
$R^1$ is —OH, $—OR^a$, $—NH_2$, $—NHR^a$, $—NR^aR^b$, —N(H)OH, —N(H)O—$R^a$, —N(H)CN, —N(H)—C(=O)—$R^a$ or —N(H)—$SO_2$—$R^a$; or $R^1$ together with $R^2$ forms a divalent —O—$CH_2$— or —N—$CH_2$— radical;
$R^2$ is H, halogen, —CN, $R^a$, —OH, $—OR^a$, $NH_2$, —NH—$R^a$ or $—NR^aR^b$;
$R^3$ is H, halogen, $R^a$, —OH, $—OR^a$, $NH_2$, —NH—$R^a$, $—NR^aR^b$, $—NO_2$ or unsubstituted or substituted phenyl;
or
$R^2$ and $R^3$ form together with the carbon atoms to which they are attached to an unsubstituted or substituted six-membered aromatic ring; or form together a divalent —NH—$CH_2$—$CH_2$—NH— radical;
$R^4$ is H or $R^a$;
$R^5$ is H or halogen;
$R^6$ is H, halogen, $R^a$, $—OR^a$, $NH_2$, $—NHR^a$, $—NR^aR^b$, $—NO_2$ or $Ar^4$;
$R^7$ is H, halogen, $R^a$, $—OR^a$, $NH_2$, $—NHR^a$, $—NR^aR^b$, —N(H)—C(=O)—$R^a$ or —C(=O)—$NHR^a$;
$R^8$ is H, halogen or $R^a$;
n is an integer selected from 0 and 1;
$L^1$ is a divalent —NH—, —N($R^a$)— or —$CH_2$— radical; and
$L^2$ is a divalent —$SO_2$— radical; and
$L^3$ is a divalent —CH=CH— radical;
or
$L^1$ is a divalent —N(CHO)—, —N(C(=O)—$R^a$)—, —N(C(=O)—$NH_2$)—, —N(C(=O)—$NHR^a$)— or —N(C(=O)—$NR^aR^b$)— radical; and
$L^2$ is a divalent —$CH_2$— radical; and
$L^3$ is a divalent —$CH_2$— radical;
or
$L^1$ is a divalent —$CH_2$— radical;
$L^2$ is a divalent —N(CHO)—, —N(C(=O)—$R^a$)—, —N(C(=O)—$NH_2$)—, —N(C(=O)—$NHR^a$)— or —N(C(=O)—$NR^aR^b$)— radical; and
$L^3$ is a single bond;
or
$L^1$ is a divalent —N=radical;
$L^2$ is a divalent =S(=O)($R^a$)— radical; and
$L^3$ is a single bond;
A is a ring selected from the group consisting of $Ar^4$, $Hetar^4$, $Cyc^4$ and $Hetcyc^4$;
$Ar^4$ is a mono-, bi- or tricyclic aryl with 5, 6, 7, 8, 9, 10, 11, 12, 13, 14 ring carbon atoms, wherein that aryl may be unsubstituted or substituted with substituents $R^{41}$, $R^{42}$, $R^{43}$, $R^{44}$, $R^{45}$, $R^{46}$ and/or $R^{47}$ which may be the same or different, with the proviso that $Ar^4$ is not 4-methylphenyl;

Hetar$^A$ is a mono-, bi- or tricyclic heteroaryl with 5, 6, 7, 8, 9, 10, 11, 12, 13, 14 ring atoms wherein 1, 2, 3, 4, 5 of said ring atoms is/are a hetero atom(s) selected from N, O and/or S and the remaining are carbon atoms, wherein that heteroaryl may be unsubstituted or substituted with substituents R$^{A1}$, R$^{A2}$, R$^{A3}$, R$^{A4}$R$^{A5}$, R$^{A6}$ and/or R$^{A7}$ which may be the same or different;

Cyc$^A$ is a saturated or partially unsaturated, mono-, bi- or tricyclic carbocycle with 3, 4, 5, 6, 7, 8, 9, 10, 11, 12, 13, 14, 15 ring carbon atoms, wherein that carbocycle may be unsubstituted or substituted with R$^{A8}$, R$^{A9}$, R$^{A10}$ and/or R$^{A11}$ which may be the same or different;

Hetcyc$^A$ is a saturated or partially unsaturated, mono-, bi- or tricyclic heterocycle with 3, 4, 5, 6, 7, 8, 9, 10, 11, 12, 13, 14, 15 ring atoms wherein 1, 2, 3, 4, 5 of said ring atoms is/are a hetero atom(s) selected from N, O and/or S and the remaining are carbon atoms, wherein that heterocycle may be unsubstituted or substituted with R$^{A8}$, R$^{A9}$, R$^{A10}$ and/or R$^{A11}$ which may be the same or different;

R$^{A1}$, R$^{A2}$, R$^{A3}$, R$^{A4}$, R$^{A5}$, R$^{A6}$, R$^{A7}$ are independently from each other H, halogen, R$^a$, —OR$^a$, —NH$_2$, —NHR$^a$, —NR$^a$R$^b$, —N(H)—C(=O)—R$^a$, Ar$^B$, —O—Ar$^B$, Hetar$^B$, Cyc$^B$ or Hetcyc$^B$; and/or two adjacent R$^{A1}$, R$^{A2}$, R$^{A3}$, R$^{A4}$, R$^{A5}$, R$^{A6}$, R$^{A7}$ may form together a divalent —C$_{1-3}$-alkylene-O— or —O—C$_{1-3}$-alkylene-O— radical which C$_{1-3}$-alkylene may be unsubstituted or mono- or disubstituted with R$^a$ or halogen; or may form together with the ring atoms to which they are attached to a Cyc$^C$;

R$^{A8}$, R$^{A9}$, R$^{A10}$, R$^{11}$ are independently from each other H or R$^a$; or a pair of R$^{A8}$, R$^{A9}$, R$^{A10}$ and/or R$^{A11}$ form a =O radical;

Ar$^B$ is a phenyl ring, wherein that phenyl ring may be unsubstituted or substituted with substituents R$^{B1}$, R$^{B2}$ and/or R$^{B3}$ which may be the same or different;

Hetar$^B$ is a monocyclic heteroaryl with 5, 6, 7 ring atoms wherein 1, 2, 3, 4 of said ring atoms is/are a hetero atom(s) selected from N, O and/or S and the remaining are carbon atoms, wherein that heteroryl may be unsubstituted or substituted with substituents R$^{B1}$, R$^{B2}$ and/or R$^{B3}$ which may be the same or different;

Cyc$^B$ is a mono- or bicyclic saturated or partially unsaturated carbocycle with 5, 6, 7, 8, 9, 10 ring carbon atoms wherein that carbocycle may be unsubstituted or mono-, di- or trisubstituted with R$^{B4}$, R$^{B5}$ and/or R$^{B6}$ which may be the same or different;

Hetcyc$^B$ is a saturated or partially unsaturated monocyclic heterocycle with 3, 4, 5, 6, 7 ring atoms wherein 1, 2 of said ring atoms is/are a hetero atom(s) selected from N, O and/or S and the remaining are carbon atoms, wherein that heterocycle may be unsubstituted or mono-, di- or trisubstituted with R$^{B4}$, R$^{B5}$ and/or R$^{B6}$ which may be the same or different;

Cyc$^C$ is a mono- or bicyclic saturated or partially unsaturated carbocycle with 5, 6, 7, 8, 9, 10 ring carbon atoms wherein that carbocycle is fused to Ar$^A$ or Hetar$^A$ via 2 adjacent ring atoms of said Ar$^A$ or Hetar$^A$ and wherein that carbocycle may be unsubstituted or substituted with R$^{C1}$, R$^{C2}$, R$^{C3}$, R$^{C4}$, R$^{C5}$, R$^{C6}$ which may be the same or different;

R$^{B1}$, R$^{B2}$ and/or R$^{B3}$ are independently from each other H, halogen, R$^a$, —OR$^a$ or —SR$^a$;

R$^{B4}$, R$^{B5}$, R$^{B6}$, R$^{C1}$, R$^{C2}$, R$^{C3}$, R$^{C4}$, R$^{C5}$, R$^{C6}$ are independently from each other H or R$^a$;

R$^a$, R$^b$ are independently from each other unsubstituted or substituted, straight-chain or branched C$_{1-6}$-aliphatic or may form together with the nitrogen atom to which they are attached to an unsubstituted or substituted saturated, partially unsaturated or aromatic heterocycle with 4, 5, 6, 7 ring atoms wherein 1, 2 of said ring atoms is/are a hetero atom(s) selected from N, O and/or S and the remaining are carbon atoms;

or derivatives, N-oxides, prodrugs, solvates, tautomers or stereoisomers thereof and/or the pharmaceutically acceptable salts of each of the foregoing;

with the proviso that (a) 4-{2-[5-chloro-2-(4-chlorobenzenesulfonamido)phenyl]ethynyl}-benzoic acid;

(b) methyl 4-{2-[5-chloro-2-(4-chlorobenzenesulfonamido)phenyl]-ethynyl}benzoate; and (c) methyl 4-{2-[2-(N-benzyl-2,2,2-trifluoroacetamido)phenyl]ethynyl}-benzoate are excluded.

2. A compound of formula (I)

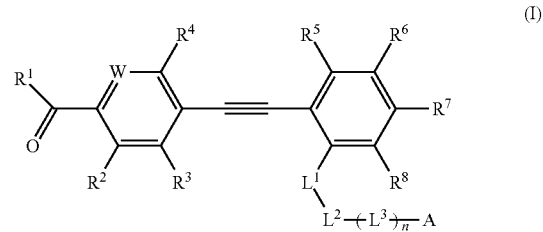

wherein

W denotes CR$^{W1}$ or N;

R$^{W1}$ is H, halogen, R$^a$ or —OR$^a$;

R$^1$ is —OH, —OR$^a$, —NH$_2$, —NHR$^a$, —NR$^a$R$^b$, —N(H)OH, —N(H)O—R$^a$, —N(H)CN, —N(H)—C(=O)—R$^a$ or —N(H)—SO$_2$—R$^a$; or R$^1$ together with R$^2$ forms a divalent —O—CH$_2$— or —N—CH$_2$— radical;

R$^2$ is H, halogen, —CN, R$^a$, —OH, —OR$^a$, NH$_2$, —NH—R$^a$ or —NR$^a$R$^b$;

R$^3$ is H, halogen, R$^a$, —OH, —OR$^a$, NH$_2$, —NH—R$^a$, —NR$^a$R$^b$, —NO$_2$ or unsubstituted or substituted phenyl;

or

R$^2$ and R$^3$ form together with the carbon atoms to which they are attached to an unsubstituted or substituted six-membered aromatic ring; or form together a divalent —NH—CH$_2$—CH$_2$—NH— radical;

R$^4$ is H or R$^a$;

R$^5$ is H or halogen;

R$^6$ is H, halogen, R$^a$, —OR$^a$, NH$_2$, —NHR$^a$, —NR$^a$R$^b$, —NO$_2$ or Ar$^A$;

R$^7$ is H, halogen, R$^a$, —OR$^a$, NH$_2$, —NHR$^a$, —NR$^a$R$^b$, —N(H)—C(=O)—R$^a$ or —C(=O)—NHR$^a$;

R$^8$ is H, halogen or R$^a$;

n is an integer selected from 0 and 1;

L$^1$ is a divalent —NH—, —N(R$^a$)— or —CH$_2$— radical; and

L$^2$ is a divalent —SO$_2$— radical; and

L$^3$ is a divalent —CH=CH— radical;

or

L$^1$ is a divalent —N(CHO)—, —N(C(=O)—R$^a$)—, —N(C(=O)—NH$_2$)—, —N(C(=O)—NHR$^a$)— or —N(C(=O)—NR$^a$R$^b$)— radical; and

529

L² is a divalent —CH₂— radical; and
L³ is a divalent —CH₂— radical;
or
L¹ is a divalent —CH₂— radical;
L² is a divalent —N(CHO)—, —N(C(=O)—Rᵃ)—, —N(C(=O)—NH₂)—, —N(C(=O)—NHRᵃ)— or —N(C(=O)—NRᵃRᵇ)— radical; and
L³ is a single bond;
A is a ring selected from the group consisting of Ar^A, Hetar^A, Cyc^A and Hetcyc^A;
Ar^A is a mono-, bi- or tricyclic aryl with 5, 6, 7, 8, 9, 10, 11, 12, 13, 14 ring carbon atoms, wherein that aryl may be unsubstituted or substituted with substituents $R^{A1}$, $R^{A2}$, $R^{A3}$, $R^{A4}$, $R^{A5}$, $R^{A6}$ and/or $R^{A7}$ which may be the same or different, with the proviso that Ar^A is not 4-methylphenyl;
Hetar^A is a mono-, bi- or tricyclic heteroaryl with 5, 6, 7, 8, 9, 10, 11, 12, 13, 14 ring atoms wherein 1, 2, 3, 4, 5 of said ring atoms is/are a hetero atom(s) selected from N, O and/or S and the remaining are carbon atoms, wherein that heteroaryl may be unsubstituted or substituted with substituents $R^{A1}$, $R^{A2}$, $R^{A3}$, $R^{A4}R^{A5}$, $R^{A6}$ and/or $R^{A7}$ which may be the same or different;
Cyc^A is a saturated or partially unsaturated, mono-, bi- or tricyclic carbocycle with 3, 4, 5, 6, 7, 8, 9, 10, 11, 12, 13, 14, 15 ring carbon atoms, wherein that carbocycle may be unsubstituted or substituted with $R^{A8}$, $R^{A9}$, $R^{A10}$ and/or $R^{A11}$ which may be the same or different;
Hetcyc^A is a saturated or partially unsaturated, mono-, bi- or tricyclic heterocycle with 3, 4, 5, 6, 7, 8, 9, 10, 11, 12, 13, 14, 15 ring atoms wherein 1, 2, 3, 4, 5 of said ring atoms is/are a hetero atom(s) selected from N, O and/or S and the remaining are carbon atoms, wherein that heterocycle may be unsubstituted or substituted with $R^{A8}$, $R^{A9}$, $R^{A10}$ and/or $R^{A11}$ which may be the same or different;
$R^{A1}$, $R^{A2}$, $R^{A3}$, $R^{A4}$, $R^{A5}$, $R^{A6}$, $R^{A7}$ are independently from each other H, halogen, $R^a$, —OR^a, —NH₂, —NHR^a, —NR^aR^b, —N(H)—C(=O)—R^a, Ar^B, —O—Ar^B, Hetar^B, Cyc^B or Hetcyc^B;
and/or
two adjacent $R^{A1}$, $R^{A2}$, $R^{A3}$, $R^{A4}$, $R^{A5}$, $R^{A6}$, $R^{A7}$ may form together a divalent —C₁₋₃-alkylene-O— or —O—C₁₋₃-alkylene-O— radical which C₁₋₃-alkylene may be unsubstituted or mono- or disubstituted with R^a or halogen; or may form together with the ring atoms to which they are attached to a Cyc^C;
$R^{A8}$, $R^{A9}$, $R^{A10}$, $R^{A11}$ are independently from each other H or R^a; or a pair of $R^{A8}$, $R^{A9}$, $R^{A10}$ and/or $R^{A11}$ form a =O radical;
Ar^B is a phenyl ring, wherein that phenyl ring may be unsubstituted or substituted with substituents $R^{B1}$, $R^{B2}$ and/or $R^{B3}$ which may be the same or different;
Hetar^B is a monocyclic heteroaryl with 5, 6, 7 ring atoms wherein 1, 2, 3, 4 of said ring atoms is/are a hetero atom(s) selected from N, O and/or S and the remaining are carbon atoms, wherein that heteroryl may be unsubstituted or substituted with substituents $R^{B1}$, $R^{B2}$ and/or $R^{B3}$ which may be the same or different;
Cyc^B is a mono- or bicyclic saturated or partially unsaturated carbocycle with 5, 6, 7, 8, 9, 10 ring carbon atoms wherein that carbocycle may be unsubstituted or mono-, di- or trisubstituted with $R^{B4}$, $R^{B5}$ and/or $R^{B6}$ which may be the same or different;
Hetcyc^B is a saturated or partially unsaturated monocyclic heterocycle with 3, 4, 5, 6, 7 ring atoms wherein 1, 2 of said ring atoms is/are a hetero atom(s) selected from

530

N, O and/or S and the remaining are carbon atoms, wherein that heterocycle may be unsubstituted or mono-, di- or trisubstituted with $R^{B4}$, $R^{B5}$ and/or $R^{B6}$ which may be the same or different;
Cyc^C is a mono- or bicyclic saturated or partially unsaturated carbocycle with 5, 6, 7, 8, 9, 10 ring carbon atoms wherein that carbocycle is fused to Ar^A or Hetar^A via 2 adjacent ring atoms of said Ar^A or Hetar^A and wherein that carbocycle may be unsubstituted or substituted with $R^{C1}$, $R^{C2}$, $R^{C3}$, $R^{C4}$, $R^{C5}$, $R^{C6}$ which may be the same or different;
$R^{B1}$, $R^{B2}$ and/or $R^{B3}$ are independently from each other H, halogen, R^a, —OR^a or —SR^a
$R^{B4}$, $R^{B5}$, $R^{B6}$, $R^{C1}$, $R^{C2}$, $R^{C3}$, $R^{C4}$, $R^{C5}$, $R^{C6}$ are independently from each other H or R^a;
R^a, R^b are independently from each other unsubstituted or substituted, straight-chain or branched C₁₋₆-aliphatic or may form together with the nitrogen atom to which they are attached to an unsubstituted or substituted saturated, partially unsaturated or aromatic heterocycle with 4, 5, 6, 7 ring atoms wherein 1, 2 of said ring atoms is/are a hetero atom(s) selected from N, O and/or S and the remaining are carbon atoms;
or derivatives, N-oxides, prodrugs, solvates, tautomers or stereoisomers thereof and/or the pharmaceutically acceptable salts of each of the foregoing;
with the proviso that
(a) 4-{2-[5-chloro-2-(4-chlorobenzenesulfonamido)phenyl]ethynyl}-benzoic acid;
(b) methyl 4-{2-[5-chloro-2-(4-chlorobenzenesulfonamido)phenyl]-ethynyl}benzoate; and
(c) methyl 4-{2-[2-(N-benzyl-2,2,2-trifluoroacetamido)phenyl]ethynyl}-benzoate
are excluded.

3. The Compound according to claim 1, or derivatives, N-oxides, prodrugs, solvates, tautomers or stereoisomers thereof and/or the pharmaceutically acceptable salts of each of the foregoing, wherein
$R^5$ is H;
$R^6$ is H, halogen, R^a, —OR^a, —NH₂, —NHR^a— or NR^aR^b;
$R^7$ is H, halogen, R^a or —OR^a; and
$R^8$ is H or halogen.

4. The Compound according to claim 1, or derivatives, N-oxides, prodrugs, solvates, tautomers or stereoisomers thereof and/or the pharmaceutically acceptable salts of each of the foregoing, wherein
W denotes CR^{W1} or N;
$R^{W1}$ is H, R^a or —OR^a;
$R^1$ is —OH, OR^a, NHR^a or NH—OH;
$R^2$ is H, halogen, R^a, —OR^a, —NH₂, —NHR^a or —NR^aR^b;
$R^3$ is H, halogen, R^a, —OR^a, —NH₂, —NHR^a, —NR^aR^b, —NO₂ or phenyl;
or
$R^2$ and $R^3$ form together with the carbon atoms to which they are attached to a benzo ring; and
$R^4$ is H.

5. The Compound according to claim 1, or derivatives, N-oxides, prodrugs, solvates, tautomers or stereoisomers thereof and/or the pharmaceutically acceptable salts of each of the foregoing, wherein
W is N; and
$R^2$ is H, halogen, R^a, —OR^a, —NH₂, —NHR^a or —NR^aR^b;
$R^3$ is H, halogen, R^a, —OR^a, —NH₂, —NHR^a, —NR^aR^b, —NO₂ or phenyl;

thereby forming a compound of formula (I-a)

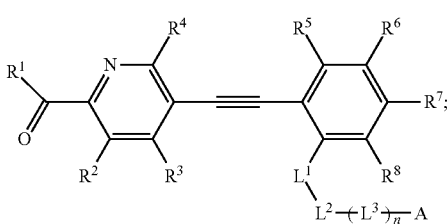

or
R² and R³ form together with the carbon atoms to which they are attached to a benzo ring thereby forming a compound of formula (I-b)

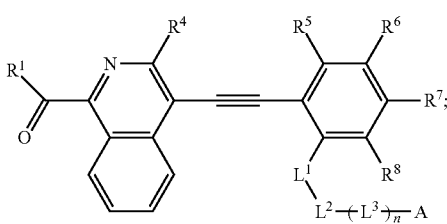

wherein R¹, R⁴, R⁵, R⁶, R⁷, R⁸, n, L¹, L², L³ and A are as defined in claim 1.

6. The Compound according to claim 1, or derivatives, N-oxides, prodrugs, solvates, tautomers or stereoisomers thereof and/or the pharmaceutically acceptable salts of each of the foregoing, wherein
n is 0;
L¹ is a divalent —NH— radical; and
L² is a divalent —SO₂— radical;
or
L¹ is a divalent —N(CHO)— radical; and
L² is a divalent —CH₂— radical.

7. The Compound according to claim 1, or derivatives, N-oxides, prodrugs, solvates, tautomers or stereoisomers thereof and/or the pharmaceutically acceptable salts of each of the foregoing, wherein
A is a ring selected from the group consisting of $Ar^A$, $Hetar^A$, $Hetcyc^A$ and $Cyc^A$;
$Ar^A$ is a phenyl or naphthyl radical which radical may be unsubstituted or substituted with substituents $R^{A1}$, $R^{A2}$, $R^{A3}$, $R^{A4}$, $R^{A5}$, $R^{A6}$ and/or $R^{A7}$ which may be the same or different, with the proviso that $Ar^A$ is not 4-methylphenyl;
$Hetar^A$ is a monocyclic heteroaryl with 5 or 6 ring atoms, a bicyclic heteroaryl with 9 or 10 ring atoms or a tricyclic heteroaryl with 13 ring atoms wherein 1, 2 or 3 of said ring atoms is/are a hetero atom(s) selected from N, O and/or S and the remaining are carbon atoms, wherein that heteroryl may be unsubstituted or substituted with substituents $R^{A1}$, $R^{A2}$, $R^{A3}$, $R^{A4}$, $R^{A5}$, $R^{A6}$ and/or $R^{A7}$ which may be the same or different;
$Cyc^A$ is a saturated or partially unsaturated, monocyclic carbocycle with 5, 6 or 7 ring carbon atoms or a bicyclic carbocycle with 9 or 10 ring carbon atoms, wherein that carbocycle may be unsubstituted or substituted with $R^{A8}$, $R^{A9}$, $R^{A10}$ and/or $R^{A11}$ which may be the same or different;

$Hetcyc^A$ is a saturated or partially unsaturated, monocyclic heterocycle with 5 or 6 ring atoms or a saturated or partially unsaturated, bicyclic heterocycle with 9 or 10 ring atoms wherein 1 or 2 of said ring atoms is/are a hetero atom(s) selected from N, O and/or S and the remaining are carbon atoms, wherein that heterocycle may be unsubstituted or substituted with $R^{A8}$, $R^{A9}$, $R^{A10}$ and/or $R^{A11}$ which may be the same or different;
$R^{A1}$, $R^{A2}$, $R^{A3}$, $R^{A4}$, $R^{A5}$, $R^{A6}$, $R^{A7}$ are independently from each other H, halogen, $R^a$, —$OR^a$, —$NH_2$, —$NHR^a$, —$NR^aR^b$, —N(H)—C(=O)—$R^a$, $Ar^B$, $Hetar^B$ or $Cyc^B$;
and/or
two adjacent $R^{A1}$, $R^{A2}$, $R^{A3}$, $R^{A4}$, $R^{A5}$, $R^{A6}$, $R^{A7}$ may form together a divalent —$C_{1-3}$-alkylen-O— or —O—$C_{1-3}$-alkylene-O— radical; or may form together with the ring atoms to which they are attached to a $Cyc^C$;
$R^{A8}$, $R^{A9}$, $R^{A10}$ and/or $R^{A11}$ are independently from each other H or $R^a$; or
a pair of $R^{A8}$, $R^{A9}$, $R^{A10}$ and $R^{A11}$ form a =O radical;
$Ar^B$ is a phenyl ring, wherein that phenyl ring may be unsubstituted or substituted with substituents $R^{B1}$, $R^{B2}$ and/or $R^{B3}$ which may be the same or different;
$Hetar^B$ is a monocyclic heteroaryl with 5 or 6 ring atoms wherein 1 or 2 of said ring atoms is/are a hetero atom(s) selected from N, O and/or S and the remaining are carbon atoms, wherein that heteroryl may be unsubstituted or substituted with substituents $R^{B1}$, $R^{B2}$ and/or $R^{B3}$ which may be the same or different;
$Cyc^B$ is a monocyclic 6-membered or bicyclic 9-membered saturated or partially unsaturated carbocycle wherein that carbocycle is unsubstituted;
$Cyc^C$ is a monocyclic 6-membered or bicyclic 9-membered carbocycle wherein that carbocycle is fused to a $Ar^A$ or $Hetar^A$ via 2 adjacent ring atoms of said $Ar^A$ or $Hetar^A$;
$R^{B1}$, $R^{B2}$ and/or $R^{B3}$ are independently from each other H, $R^a$, —$OR^a$ or —$SR^a$; and
$R^a$ is unsubstituted or substituted, straight-chain or branched $C_{1-6}$-aliphatic.

8. The Compound according to claim 1, or derivatives, N-oxides, prodrugs, solvates, tautomers or stereoisomers thereof and/or the pharmaceutically acceptable salts of each of the foregoing, wherein
A is a ring selected from the group consisting of $Ar^A$, $Hetar^A$, $Hetcyc^A$ and $Cyc^A$;
$Ar^A$ is selected from the group consisting of phenyl or naphthyl each of which is unsubstituted or substituted with 1, 2, 3 or 4 substituents independently from each other selected from the group consisting of $R^{A1}$, $R^{A2}$, $R^{A3}$, $R^{A4}$, $R^{A5}$, $R^{A6}$, and $R^{A7}$, with the proviso that $Ar^A$ is not 4-methylphenyl; 5,6,7,8-tetrahydronaphthyl (tetralinyl) or 9H-fluorenyl each of which is unsubstituted or substituted with 1, 2 or 3 substituents on the aromatic part of said tetrahydronaphthyl or fluorenyl radical independently from each other selected from the group consisting of $R^{A1}$, $R^{A2}$, $R^{A3}$, $R^{A4}$, $R^{A5}$, $R^{A6}$ and $R^{A7}$ and/or 1, 2 or 3 substituents on the non-aromatic part of said tetrahydronaphthyl or fluorenyl radical independently from each other selected from the group consisting of $R^{C1}$, $R^{C2}$, $R^{C3}$, $R^{C4}$, $R^{C5}$, and $R^{C6}$;
$Hetar^A$ is selected from the group consisting of pyrrolyl, furanyl, thienyl, pyrazolyl, imidazolyl, pyridinyl, indolyl, benzofuranyl, benzothienyl, benzothiazolyl, benzoxadiazolyl, benzofuranzanyl, benzothiadiazolyl, imidazopyridinyl, quinolinyl, isoquinolinyl, quinoxalinyl, dibenzofuranyl, 9H-carbazolyl and azatricyclotridecapentaendionyl each of which is unsubstituted or substituted with 1, 2 or 3 substituents independently from each other selected from the group consisting of $R^{A1}$, $R^{A2}$, $R^{A3}$, $R^{A4}$, $R^{A5}$, $R^{A6}$, and $R^{A7}$, Cyc$^A$ is selected from the group consisting of cyclohexenyl, 1,4-dihydronaphth-1-yl 1,4-dihydronaphth-2-yl, 2,3-dihydronaphth-1-yl, 2,3-dihydronaphth-2-yl, 2,3-dihydronaphth-3-yl, 2,3-dihydronaphth-4-yl, indan-1-yl, and indan-2-yl each of which is unsubstituted or substituted with 1, 2 or 3 substituents independently from each other selected from the group consisting of $R^{A8}$, $R^{A9}$, $R^{A10}$ and $R^{A11}$, Hetcyc$^A$ is selected from the group consisting of decahydroquinolinyl, decahydroisoquinolinyl, octahydro-1H-indolyl, 2,3-dihydro-1H-indolyl, 1H,2H,3H-pyrrolopyridinyl, 1,2,3,4-tetrahydroisoquinolinyl, and 1,2,3,4-tetrahydronaphthridinyl, each of which is unsubstituted or substituted with 1, 2 or 3 substituents independently from each other selected from the group consisting of $R^{A8}$, $R^{A9}$, $R^{A10}$ and $R^{A11}$;

$R^{A1}$, $R^{A2}$, $R^{A3}$, $R^{A4}$, $R^{A5}$, $R^{A6}$, $R^{A7}$ are independently from each other H, halogen, $R^a$, —$OR^a$, —$NR^aR^b$, —N(H)—C(=O)—$R^a$, Ar$^B$, —O—Ar$^B$, Hetar$^B$ or Cyc$^B$;

and/or two adjacent $R^{A1}$, $R^{A2}$, $R^{A3}$, $R^{A4}$, $R^{A5}$, $R^{A6}$, $R^{A7}$ may form together a divalent —$C_{1-3}$-alkylene-O— or —O—$C_{1-3}$-alkylene-O— radical which $C_1$-3-alkylene may be unsubstituted or mono- or disubstituted with $R^a$ $R^{A8}$, $R^{A9}$, $R^{A10}$, $R^{A11}$ are independently from each other H or $R^a$; or a pair of $R^{A8}$, $R^{A9}$, $R^{A10}$ and/or $R^{A11}$ form a =O radical;

Ar$^B$ is phenyl which is unsubstituted or substituted with 1, 2 or 3 substituents independently from each other selected from the group consisting of $R^{B1}$, $R^{B2}$ and $R^{B3}$;

Hetar$^B$ is pyrrolyl, furanyl, thienyl, pyrazolyl, imidazolyl, pyridinyl or pyrimidinyl, each of which is unsubstituted or substituted with 1, 2 or 3 substituents independently from each other selected from the group consisting of $R^{B1}$, $R^{B2}$ and $R^{B3}$;

Cyc$^B$ is cyclohexenyl;

$R^{B1}$, $R^{B2}$ and/or $R^{B3}$ are independently from each other H, $R^a$, —$OR^a$ or —$SR^a$;

$R^a$ is unsubstituted or substituted, straight-chain or branched $C_{1-6}$-aliphatic; and halogen is F, Cl or Br.

9. The Compound according to claim 1, or derivatives, N-oxides, prodrugs, solvates, tautomers or stereoisomers thereof and/or the pharmaceutically acceptable salts of each of the foregoing, wherein W denotes $CR^{W1}$ or N;

$R^{W1}$ is H or —$OCH_3$;

$R^1$ is —OH, —$OC_{1-4}$-alkyl, —$OCH_2CH(OH)$—$CH_2OH$, —$O(CH_2)_2O(CH_2)_2OH$, —$O(CH_2)_2OCH_3$,

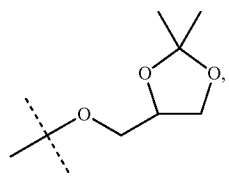

—$OCH_2$-phenyl or —$NHCH(CH_3)_2$;

$R^2$ is H, F, Cl, $CH_3$, $C_2H_5$, —$CH_2OH$, —$OCH_3$, —$OC_2H_5$, —$NH_2$, —$NHCH_3$ or —$NHC_2H_5$;

$R^3$ is H, F, Cl, $CH_3$, —C(=$CH_2$)$CH_3$, —$OCH_3$, —$OC_2H_5$, phenyl, —N($CH_3$)$_2$ or —$NO_2$;

or $R^2$ and $R^3$ form together with the carbon atoms to which they are attached to a benzo ring;

$R^4$ is H;

$R^5$ is H;

$R^6$ is H, F, Cl, Br, I, —$CH_3$, —$C_2H_5$, —$CH(CH_3)_2$, —$OCH_3$ or —N($CH_3$)$_2$;

$R^7$ is H, F, Cl, Br, $CH_3$, $CF_3$ or —$OCH_3$;

$R^8$ is H or F;

n is 0;

$L^1$ is a divalent —NH— or —N($CH_3$)— radical; and $L^2$ is a divalent —$SO_2$— radical;

or $L^1$ is a divalent —N(CHO)— radical; and $L^2$ is a divalent —$CH_2$— radical; and A is a ring selected from the group consisting of Ar$^A$, Hetar$^A$, Cyc$^A$ and Hetcyc$^A$;

Ar$^A$ is selected from the group consisting of 4-methoxyphenyl, 4-methoxy-2-methylphenyl, 4-methoxy-3-methylphenyl, 2,3-dimethyl-4-methoxyphenyl, 2,3,6-trimethyl-4-methoxyphenyl, 2,3-dichloro-4-methoxyphenyl, 3-acetamido-4-ethoxyphenyl, 4-(cyclohex-1-en-1-yl)phenyl, 1,1'-biphenyl-2-yl, 1,1'-biphenyl-3-yl, 1,1'-biphenyl-4-yl, 2'-methyl-1,1'-biphenyl-4-yl, 2-methoxy-1,1'-biphenyl-4-yl, 3-methoxy-1,1'-biphen-4-yl, 2'-methoxy-1,1'-biphenyl-2-yl, 2'-methoxy-1,1'-biphenyl-3-yl, 2'-methoxy-1,1'-biphenyl-4-yl, 3-phenoxyphenyl, 4-(1H-pyrazol-1-yl)phenyl, 3-(pyridin-2-yl)phenyl, 3-(pyridin-3-yl)phenyl, 3-(6-methoxypyridin-2-yl)phenyl, 3-(2,6-dimethoxypyridin-3-yl)phenyl, naphth-1-yl, naphth-2-yl, 4-bromonaphth-1-yl, 4-methylnaphth-1-yl, 1-methylnaphth-2-yl, 4-methoxynaphth-1-yl, 4-methoxynaphth-2-yl, 4-ethoxynaphth-1-yl, 4-propan-2-yloxynaphth-1-yl, 5-chloronaphth-1-yl, 6-chloronaphth-2-yl, 5,6,7,8-tetrahydronaphth-2-yl, 4-methoxy-5,6,7,8-tetrahydronaphth-1-yl, and 9H-fluoren-2-yl;

Hetar$^A$ is selected from the group consisting of 5-bromo-6-methoxypyridin-3-yl, 6-phenylpyridin-3-yl, 1-methylindol-4-yl, 1-benzofuran-2-yl, 1-benzothiophen-3-yl, 5-chloro-1-benzothiophen-2-yl, 5-chloro-3-methyl-1-benzothiophen-2-yl, 1,3-benzothiazol-4-yl, quinolin-2-yl, quinolin-8-yl, 2-methylquinolin-8-yl, 3-methylquinolin-8-yl, 4-methylquinolin-8-yl, 6-methylquinolin-8-yl, 7-methylquinolin-8-yl, 4,7-dimethylquinolin-8-yl, 5,7-dimethylquinolin-8-yl, 5,6,7-trimethylquinolin-8-yl, 5-ethylquinolin-8-yl, 5-(n-propyl-)quinolin-8-yl, 2-methoxyquinolin-8-yl, 4-methoxyquinolin-8-yl, 5-methoxyquinolin-8-yl, 5-trifluormethoxyquinolin-8-yl, 5-ethoxyquinolin-8-yl, 7-ethoxyquinolin-8-yl, 5-(propan-2-yloxy)quinolin-8-yl, 7-(propan-2-yloxy)quinolin-8-yl, 4-prop-2-yn-1-oxyquinolin-8-yl, 3-chloroquinolin-8-yl, 4-chloroquinolin-8-yl, 6-fluorooquinolin-8-yl, 2,4-dichloroquinolin-8-yl, 3,4-dichloroquinolin-8-yl, 4,7-dichloroquinolin-8-yl, 5,7-dichloroquinolin-8-yl, 7-bromo-2-chloroquinolin-8-yl, 4-chloro-7-fluoroquinolin-8-yl, 7-bromo-4-chloroquinolin-8-yl, 6-chloro-2-methylquinolin-8-yl, 4-dimethyl-aminoquinolin-8-yl, 9H-carbazol-2-yl, 9-methyl-9H-carbazol-3-yl, 9-methyl-9H-carbazol-4-yl, dibenzofuran-2-yl, and dibenzofuran-3-yl;

Cyc$^A$ is 3,4-dihydronaphth-2-yl; and

Hetcyc$^A$ is selected from the group consisting of 2,3-dihydro-1H-indol-1-yl, octahydro-1H-indol-1-yl, decahydroquinolin-1-yl, 4a,8a-trans-decahydroquinolin-1- yl, 4aR,8aS-decahydroquinolin-1-yl, decahydroquinolin-2-yl, 4-methyldecahydroquinolin-1-yl, and 1,2,3,4-tetrahydro-1,8-naphthyridin-1-yl.

10. The Compound according to claim 1, or derivatives, N-oxides, prodrugs, solvates, tautomers or stereoisomers thereof and/or the pharmaceutically acceptable salts of each of the foregoing, wherein the compound is selected from the group consisting of
4-methoxy-5-{2-[2-(7-methylquinoline-8-sulfonamido) phenyl]ethynyl}pyridine-2-carboxylic acid;
5-(2-{2-[N-({[1,1'-biphenyl]-4-yl}methyl)formamido] phenyl}ethynyl)-4-methoxypyridine-2-carboxylic acid;
3-(methylamino)-5-{2-[2-(7-methylquinoline-8-sulfonamido)phenyl]-ethynyl}pyridine-2-carboxylic acid;
5-{2-[2-(5-methoxyquinoline-8-sulfonamido)phenyl] ethynyl}-3-(methylamino)pyridine-2-carboxylic acid;
5-{2-[5-iodo-2-(5-methoxyquinoline-8-sulfonamido)phenyl]ethynyl}pyridine-2-carboxylic acid;
4-methoxy-5-(2-{2-[N-({2'-methoxy-[1,1'-biphenyl]-4-yl}methyl)formamido]phenyl}ethynyl)pyridine-2-carboxylic acid;
5-[2-(2-{[(4a,8a-trans)-decahydroquinoline-1-sulfonyl] amino}phenyl)ethynyl]-4-methoxypyridine-2-carboxylic acid;
4-{2-[5-bromo-2-(5-methoxyquinoline-8-sulfonamido) phenyl]ethynyl}-isoquinoline-1-carboxylic acid;
5-{2-[5-chloro-2-(7-methylquinoline-8-sulfonamido) phenyl]ethynyl}-3-(methylamino)pyridine-2-carboxylic acid;
5-{2-[5-chloro-2-(5-methoxyquinoline-8-sulfonamido) phenyl]ethynyl}-3-(methylamino)pyridine-2-carboxylic acid;
5-{2-[5-chloro-2-(4-methoxy-2,3-dimethylbenzenesulfonamido)phenyl]-ethynyl}-4-methoxypyridine-2-carboxylic acid;
5-{2-[5-bromo-4-fluoro-2-(5-methoxyquinoline-8-sulfonamido)phenyl]-ethynyl}pyridine-2-carboxylic acid;
5-{2-[5-bromo-2-(5-methoxyquinoline-8-sulfonamido) phenyl]ethynyl}pyridine-2-carboxylic acid;
5-{2-[5-bromo-2-(5-methoxyquinoline-8-sulfonamido) phenyl]ethynyl}-4-methoxypyridine-2-carboxylic acid;
5-{2-[5-bromo-4-fluoro-2-(5-methoxyquinoline-8-sulfonamido)phenyl]ethynyl}-4-methoxypyridine-2-carboxylic acid;
5-{2-[5-chloro-2-(5-methoxyquinoline-8-sulfonamido) phenyl]ethynyl}pyridine-2-carboxylic acid;
5-{2-[5-chloro-2-(5-methoxyquinoline-8-sulfonamido) phenyl]ethynyl}-4-methoxypyridine-2-carboxylic acid;
5-{2-[5-chloro-2-(7-methylquinoline-8-sulfonamido) phenyl]ethynyl}-4-methoxypyridine-2-carboxylic acid;
5-{2-[5-chloro-2-(5-ethoxyquinoline-8-sulfonamido)phenyl]ethynyl}-4-methoxypyridine-2-carboxylic acid;
5-[2-(5-Methoxy-quinoline-8-sulfonylamino)-5-methyl-phenylethynyl]-pyridine-2-carboxylic acid;
4-Methoxy-5-[2-(5-trifluoromethoxy-quinoline-8-sulfonylamino)-phenyl-ethynyl]-pyridine-2-carboxylic acid;
5-[5-Methyl-2-(7-methyl-quinoline-8-sulfonylamino)-phenylethynyl]-pyridine-2-carboxylic acid;
3-(ethylamino)-5-{2-[2-(quinoline-8-sulfonamido)phenyl]ethynyl}pyridine-2-carboxylic acid;
2,3-dihydroxypropyl 5-{2-[2-(7-methylquinoline-8-sulfonamido)phenyl]-ethynyl}pyridine-2-carboxylate;
5-{2-[5-ethyl-2-(7-methylquinoline-8-sulfonamido)phenyl]ethynyl}pyridine-2-carboxylic acid;
5-{2-[2-(7-methylquinoline-8-sulfonamido)phenyl] ethynyl}pyridine-2-carboxylic acid;
5-{2-[2-(5-methoxyquinoline-8-sulfonamido)phenyl] ethynyl}-3-methylpyridine-2-carboxylic acid;
5-{2-[2-(9H-fluorene-2-sulfonamido)phenyl] ethynyl}pyridine-2-carboxylic acid;
3-methyl-5-{2-[2-(7-methylquinoline-8-sulfonamido) phenyl]ethynyl}pyridine-2-carboxylic acid;
4-methyl-5-{2-[2-(7-methylquinoline-8-sulfonamido) phenyl]ethynyl}pyridine-2-carboxylic acid;
5-[2-(2-{8-oxatricyclo[7.4.0.0$^{2,7}$]trideca-1(9),2(7),3,5,10,12-hexaene-6-sulfonamido}phenyl)ethynyl]pyridine-2-carboxylic acid;
5-{2-[2-(5-methoxyquinoline-8-sulfonamido)phenyl] ethynyl}-4-methylpyridine-2-carboxylic acid;
5-{2-[5-fluoro-2-(7-methylquinoline-8-sulfonamido)phenyl]ethynyl}pyridine-2-carboxylic acid;
methyl 5-{2-[2-(5-methoxyquinoline-8-sulfonamido) phenyl]ethynyl}-4-methylpyridine-2-carboxylate;
methyl 5-{2-[2-(5-methoxyquinoline-8-sulfonamido) phenyl]ethynyl}pyridine-2-carboxylate;
methyl 5-{2-[2-(9H-fluorene-2-sulfonamido)phenyl] ethynyl}pyridine-2-carboxylate;
methyl 5-{2-[5-fluoro-2-(7-methylquinoline-8-sulfonamido)-phenyl]ethynyl}pyridine-2-carboxylate;
methyl 5-{2-[2-(7-methylquinoline-8-sulfonamido)phenyl]ethynyl}pyridine-2-carboxylate;
5-(2-{2-[(decahydroquinoline-1-sulfonyl)amino] phenyl}ethynyl)pyridine-2-carboxylic acid;
methyl 5-{2-[5-fluoro-2-(7-methylquinoline-8-sulfonamido)phenyl]ethynyl}-4-methylpyridine-2-carboxylate;
5-{2-[5-fluoro-2-(7-methylquinoline-8-sulfonamido)phenyl]ethynyl}-4-methylpyridine-2-carboxylic acid;
4-chloro-5-{2-[2-(7-methylquinoline-8-sulfonamido) phenyl]ethynyl}pyridine-2-carboxylic acid;
methyl 4-chloro-5-{2-[2-(7-methylquinoline-8-sulfonamido)-phenyl]ethynyl}pyridine-2-carboxylate;
methyl 4-chloro-5-{2-[2-(5-methoxyquinoline-8-sulfonamido)-phenyl]ethynyl}pyridine-2-carboxylate;
5-{2-[2-(7-methylquinoline-8-sulfonamido)phenyl]ethynyl}-4-(prop-1-en-2-yl)pyridine-2-carboxylic acid;
4-chloro-5-{2-[2-(5-methoxyquinoline-8-sulfonamido) phenyl]ethynyl}pyridine-2-carboxylic acid;
4-{2-[2-(7-methylquinoline-8-sulfonamido)phenyl] ethynyl}benzoic acid;
5-[2-(2-{[(4aR,8aS)-decahydroquinoline-1-sulfonyl] amino}phenyl)ethynyl]pyridine-2-carboxylic acid;
ethyl 5-{2-[2-(5-methoxyquinoline-8-sulfonamido)phenyl]ethynyl}pyridine-2-carboxylate;
propyl 5-{2-[2-(5-methoxyquinoline-8-sulfonamido)phenyl]ethynyl}pyridine-2-carboxylate;
propan-2-yl 5-{2-[2-(5-methoxyquinoline-8-sulfonamido)phenyl]ethynyl}-pyridine-2-carboxylate;
butyl 5-{2-[2-(5-methoxyquinoline-8-sulfonamido)phenyl]ethynyl}pyridine-2-carboxylate;
4-methoxy-5-{2-[2-(5-methoxyquinoline-8-sulfonamido) phenyl]ethynyl}-pyridine-2-carboxylic acid;
benzyl 5-{2-[2-(5-methoxyquinoline-8-sulfonamido)phenyl]ethynyl}pyridine-2-carboxylate;
4-ethoxy-5-{2-[2-(5-methoxyquinoline-8-sulfonamido) phenyl]ethynyl}pyridine-2-carboxylic acid;
4-ethoxy-5-{2-[2-(7-methylquinoline-8-sulfonamido) phenyl]ethynyl}pyridine-2-carboxylic acid;

5-(2-{2-[N-({[1,1'-biphenyl]-4-yl}methyl)formamido]phenyl}ethynyl)pyridine-2-carboxylic acid;
5-{2-[5-fluoro-2-(5-methoxyquinoline-8-sulfonamido)phenyl]ethynyl}pyridine-2-carboxylic acid;
5-{2-[4,5-dichloro-2-(5-methoxyquinoline-8-sulfonamido)phenyl]ethynyl}-pyridine-2-carboxylic acid;
5-(2-{2-[N-({2'-methoxy-[1,1'-biphenyl]-4-yl}methyl)formamido]phenyl}-ethynyl)pyridine-2-carboxylic acid;
5-{2-[4-chloro-2-(5-methoxyquinoline-8-sulfonamido)phenyl]ethynyl}pyridine-2-carboxylic acid;
5-(2-{2-[N-({2-methoxy-[1,1'-biphenyl]-4-yl}methyl)formamido]phenyl}-ethynyl)pyridine-2-carboxylic acid;
5-[2-(2-{[N-(naphthalen-2-yl)formamido]methyl}phenyl)ethynyl]pyridine-2-carboxylic acid;
5-{2-[4,5-dichloro-2-(7-methylquinoline-8-sulfonamido)phenyl]ethynyl}-pyridine-2-carboxylic acid;
5-{2-[2-(5-methoxyquinoline-8-sulfonamido)phenyl]ethynyl}-3-(methylamino)pyridine-2-carboxylic acid;
5-{2-[2-(7-ethoxyquinoline-8-sulfonamido)phenyl]ethynyl}pyridine-2-carboxylic acid;
5-(2-{2-[7-(propan-2-yloxy)quinoline-8-sulfonamido]phenyl}ethynyl)pyridine-2-carboxylic acid;
5-(2-{2-[N-({3-methoxy-[1,1'-biphenyl]-4-yl}methyl)formamido]phenyl}ethynyl)pyridine-2-carboxylic acid;
4-methoxy-5-[2-(2-{[(4-methyl-decahydroquinolin-1-yl)sulfonyl]amino}phenyl)ethynyl]pyridine-2-carboxylic acid;
5-[2-(2-{[(4a,8a-trans)-decahydroquinoline-1-sulfonyl]amino}phenyl)ethynyl]-3-methylpyridine-2-carboxylic acid;
5-{2-[2-(7-methylquinoline-8-sulfonamido)phenyl]ethynyl}-4-phenylpyridine-2-carboxylic acid;
5-{2-[2-(9-methyl-9H-carbazole-3-sulfonamido)phenyl]ethynyl}pyridine-2-carboxylic acid;
5-[2-(2-{[(4-methyl-decahydroquinolin-1-yl)sulfonyl]amino}phenyl)-ethynyl]pyridine-2-carboxylic acid;
4-{2-[5-bromo-2-(7-methylquinoline-8-sulfonamido)phenyl]ethynyl}-isoquinoline-1-carboxylic acid;
4-{2-[5-chloro-2-(7-methylquinoline-8-sulfonamido)phenyl]ethynyl}-isoquinoline-1-carboxylic acid;
4-{2-[5-chloro-2-(5-methoxyquinoline-8-sulfonamido)phenyl]ethynyl}-isoquinoline-1-carboxylic acid;
2-(methylamino)-4-{2-[2-(7-methylquinoline-8-sulfonamido)phenyl]-ethynyl}benzoic acid;
4-methoxy-5-{2-[2-(4-methoxy-2, 3-dimethylbenzenesulfonamido)phenyl]ethynyl}pyridine-2-carboxylic acid methyl 5-{2-[2-(7-methylquinoline-8-sulfonamido)-5-nitrophenyl]ethynyl}-pyridine-2-carboxylate;
5-{2-[5-methoxy-2-(7-methylquinoline-8-sulfonamido)phenyl]ethynyl}pyridine-2-carboxylic acid;
5-[2-(4-Chloro-quinoline-8-sulfonylamino)-phenylethynyl]-pyridine-2-carboxylic acid;
5-{2-[2-(4-ethoxynaphthalene-1-sulfonamido)phenyl]ethynyl}pyridine-2-carboxylic acid;
5-[2-(2-{[1,1'-biphenyl]-4-sulfonamido}phenyl)ethynyl]pyridine-2-carboxylic acid;
5-(2-{2-[4-(propan-2-yloxy)naphthalene-1-sulfonamido]phenyl}ethynyl)-pyridine-2-carboxylic acid;
5-{2-[2-(3,4-dichloroquinoline-8-sulfonamido)phenyl]ethynyl}pyridine-2-carboxylic acid;
5-{2-[2-(4,7-dichloroquinoline-8-sulfonamido)phenyl]ethynyl}pyridine-2-carboxylic acid;
5-{2-[2-(5,6,7-trimethylquinoline-8-sulfonamido)phenyl]ethynyl}pyridine-2-carboxylic acid;
5-{2-[2-(5,7-dichloroquinoline-8-sulfonamido)phenyl]ethynyl}pyridine-2-carboxylic acid;
5-{2-[5-fluoro-2-(7-methylquinoline-8-sulfonamido)phenyl]ethynyl}-3-methylpyridine-2-carboxylic acid;
5-{2-[2-(4,7-dimethylquinoline-8-sulfonamido)phenyl]ethynyl}pyridine-2-carboxylic acid;
5-{2-[2-(7-bromo-2-chloroquinoline-8-sulfonamido)phenyl]ethynyl}pyridine-2-carboxylic acid;
5-{2-[2-(7-bromo-4-chloroquinoline-8-sulfonamido)phenyl]ethynyl}pyridine-2-carboxylic acid;
5-{2-[2-(4-chloro-7-fluoroquinoline-8-sulfonamido)phenyl]ethynyl}pyridine-2-carboxylic acid;
5-{2-[2-(5-ethoxyquinoline-8-sulfonamido)phenyl]ethynyl}pyridine-2-carboxylic acid;
3-Ethyl-5-[2-(quinoline-8-sulfonylamino)-phenylethynyl]-pyridine-2-carboxylic acid;
5-{2-[5-bromo-4-fluoro-2-(7-methylquinoline-8-sulfonamido)phenyl]ethynyl}-4-methoxypyridine-2-carboxylic acid;
4-methoxy-5-{2-[2-(quinoline-8-sulfonamido)phenyl]ethynyl}pyridine-2-carboxylic acid;
3-Methyl-5-[2-(5-trifluoromethoxy-quinoline-8-sulfonylamino)-phenylethynyl]-pyridine-2-carboxylic acid;
5-[2-(5-Trifluoromethoxy-quinoline-8-sulfonylamino)-phenylethynyl]-pyridine-2-carboxylic acid;
5-[5-Chloro-2-(4-methoxy-2,3-dimethyl-benzenesulfonylamino)-phenyl-ethynyl]-pyridine-2-carboxylic acid;
5-[5-Chloro-2-(4-methoxy-benzenesulfonylamino)-phenylethynyl]-4-methoxy-pyridine-2-carboxylic acid;
5-[5-Methoxy-2-(5-methoxy-quinoline-8-sulfonylamino)-phenylethynyl]-pyridine-2-carboxylic acid;
4-{2-[5-bromo-2-(4-methoxy-2,3-dimethylbenzenesulfonamido)phenyl]-ethynyl}isoquinoline-1-carboxylic acid;
4-[5-Chloro-2-(4-methoxy-2,3-dimethyl-benzenesulfonylamino)-phenyl-ethynyl]-isoquinoline-1-carboxylic acid;
7-methyl-N-[2-(2-{7-oxo-5H,7H-furo[3,4-b]pyridin-3-yl}ethynyl)phenyl]-quinoline-8-sulfonamide;
3-amino-5-{2-[2-(4-methoxy-2,3-dimethylbenzenesulfonamido)phenyl]-ethynyl}pyridine-2-carboxylic acid;
5-{2-[5-chloro-2-(4-methoxy-2,3-dimethylbenzenesulfonamido)phenyl]-ethynyl}-3-(methylamino)pyridine-2-carboxylic acid;
(2,2-dimethyl-1,3-dioxolan-4-yl)methyl 4-methoxy-5-{2-[2-(7-methylquinoline-8-sulfonamido)phenyl]ethynyl}pyridine-2-carboxylate;
2,3-dihydroxypropyl 4-methoxy-5-{2-[2-(7-methylquinoline-8-sulfonamido)phenyl]ethynyl}pyridine-2-carboxylate;
5-{2-[2-(4-methoxy-2,3-dimethylbenzenesulfonamido)-5-methylphenyl]-ethynyl}pyridine-2-carboxylic acid;
5-{2-[2-(5-propylquinoline-8-sulfonamido)phenyl]ethynyl}pyridine-2-carboxylic acid;
3-{2-[2-(naphthalene-2-sulfonamido)phenyl]ethynyl}benzoic acid;
4-{2-[2-(naphthalene-2-sulfonamido)phenyl]ethynyl}benzoic acid;
4-{2-[2-(N-methylnaphthalene-2-sulfonamido)phenyl]ethynyl}benzoic acid;
4-(2-{2-[(naphthalene-2-sulfonyl)methyl]phenyl}ethynyl)benzoic acid;
4-{2-[2-(5,6,7,8-tetrahydronaphthalene-2-sulfonamido)phenyl]ethynyl}benzoic acid;
4-{2-[2-(4-methoxynaphthalene-1-sulfonamido)phenyl]ethynyl}benzoic acid;

2-methyl-4-{2-[2-(naphthalene-2-sulfonamido)phenyl]ethynyl}benzoic acid;
4-{2-[2-(4-methoxy-5,6,7,8-tetrahydronaphthalene-1-sulfonamido)-phenyl]ethynyl}benzoic acid;
2-fluoro-4-{2-[2-(naphthalene-2-sulfonamido)phenyl]ethynyl}benzoic acid;
4-{2-[5-fluoro-2-(naphthalene-2-sulfonamido)phenyl]ethynyl}benzoic acid;
4-{2-[2-(naphthalene-2-sulfonamido)-4-(trifluoromethyl)phenyl]ethynyl}-benzoic acid;
4-{2-[2-(4-methoxynaphthalene-1-sulfonamido)phenyl]ethynyl}-2-methylbenzoic acid;
4-{2-[4-methoxy-2-(naphthalene-2-sulfonamido)phenyl]ethynyl}benzoic acid;
4-{2-[2-(5-chloro-3-methyl-1-benzothiophene-2-sulfonamido)phenyl]-ethynyl}benzoic acid;
4-{2-[2-(2,3-dichloro-4-methoxybenzenesulfonamido)phenyl]ethynyl}benzoic acid;
4-{2-[5-fluoro-2-(4-methoxynaphthalene-1-sulfonamido)phenyl]ethynyl}-benzoic acid;
4-{2-[2-(5-methoxyquinoline-8-sulfonamido)phenyl]ethynyl}benzoic acid;
2-chloro-4-{2-[2-(naphthalene-2-sulfonamido)phenyl]ethynyl}benzoic acid;
3-fluoro-4-{2-[2-(naphthalene-2-sulfonamido)phenyl]ethynyl}benzoic acid;
5-{2-[2-(4-methoxynaphthalene-1-sulfonamido)phenyl]ethynyl}pyridine-2-carboxylic acid;
4-{2-[3-fluoro-2-(naphthalene-2-sulfonamido)phenyl]ethynyl}benzoic acid;
2-methoxy-4-{2-[2-(4-methoxynaphthalene-1-sulfonamido)phenyl]ethynyl}benzoic acid;
5-{2-[5-fluoro-2-(4-methoxynaphthalene-1-sulfonamido)phenyl]ethynyl}-pyridine-2-carboxylic acid;
4-{2-[2-(quinoline-8-sulfonamido)phenyl]ethynyl}benzoic acid;
4-{2-[6-methyl-2-(naphthalene-2-sulfonamido)pyridin-3-yl]ethynyl}benzoic acid;
5-{2-[2-(4-methoxy-2,3-dimethylbenzenesulfonamido)phenyl]ethynyl}pyridine-2-carboxylic acid;
4-{2-[2-(6-chloronaphthalene-2-sulfonamido)phenyl]ethynyl}benzoic acid;
5-{2-[2-(5-methoxyquinoline-8-sulfonamido)phenyl]ethynyl}pyridine-2-carboxylic acid;
2-fluoro-4-{2-[2-(4-methoxynaphthalene-1-sulfonamido)phenyl]ethynyl}-benzoic acid;
4-{2-[4-methyl-2-(naphthalene-2-sulfonamido)phenyl]ethynyl}benzoic acid;
4-{2-[2-(4-methoxy-2-methylbenzenesulfonamido)phenyl]ethynyl}benzoic acid;
4-{2-[2-(5-bromo-6-methoxypyridine-3-sulfonamido)phenyl]ethynyl}benzoic acid;
3-methyl-5-{2-[2-(naphthalene-2-sulfonamido)phenyl]ethynyl}pyridine-2-carboxylic acid;
5-{2-[2-(quinoline-8-sulfonamido)phenyl]ethynyl}pyridine-2-carboxylic acid;
4-{2-[2-(naphthalene-1-sulfonamido)phenyl]ethynyl}benzoic acid;
4-{2-[2-(4-methoxy-3-methylbenzenesulfonamido)phenyl]ethynyl}benzoic acid;
2-ethoxy-4-{2-[2-(4-methoxynaphthalene-1-sulfonamido)phenyl]-ethynyl}benzoic acid;
3-methyl-5-{2-[2-(quinoline-8-sulfonamido)phenyl]ethynyl}pyridine-2-carboxylic acid;
4-methyl-5-{2-[2-(quinoline-8-sulfonamido)phenyl]ethynyl}pyridine-2-carboxylic acid;
2-methoxy-4-{2-[2-(naphthalene-1-sulfonamido)phenyl]ethynyl}benzoic acid;
5-{2-[2-(4-methoxynaphthalene-1-sulfonamido)phenyl]ethynyl}-3-methylpyridine-2-carboxylic acid;
2-methoxy-4-{2-[2-(4-methoxy-2-methylbenzenesulfonamido)-phenyl]ethynyl}benzoic acid;
4-{2-[5-fluoro-2-(naphthalene-1-sulfonamido)phenyl]ethynyl}benzoic acid;
2-fluoro-4-{2-[2-(naphthalene-1-sulfonamido)phenyl]ethynyl}benzoic acid;
5-{2-[2-(naphthalene-1-sulfonamido)phenyl]ethynyl}pyridine-2-carboxylic acid;
4-{2-[2-(1-benzofuran-2-sulfonamido)phenyl]ethynyl}benzoic acid 3-methyl-5-{2-[2-(naphthalene-1-sulfonamido)phenyl]ethynyl}pyridine-2-carboxylic acid;
4-{2-[2-(4-methylnaphthalene-1-sulfonamido)phenyl]ethynyl}benzoic acid;
4-{2-[2-(3,4-dihydronaphthalene-2-sulfonamido)phenyl]ethynyl}benzoic acid;
2-methyl-4-{2-[2-(naphthalene-1-sulfonamido)phenyl]ethynyl}benzoic acid;
5-{2-[2-(3,4-dihydronaphthalene-2-sulfonamido)phenyl]ethynyl}pyridine-2-carboxylic acid;
4-{2-[2-(1-benzothiophene-3-sulfonamido)phenyl]ethynyl}benzoic acid
4-{2-[2-(9H-fluorene-2-sulfonamido)phenyl]ethynyl}benzoic acid
4-methyl-5-{2-[2-(naphthalene-1-sulfonamido)phenyl]ethynyl}pyridine-2-carboxylic acid;
5-[2-(2-{[1,1'-biphenyl]-3-sulfonamido}phenyl)ethynyl]pyridine-2-carboxylic acid;
5-{2-[2-(1-methylnaphthalene-2-sulfonamido)phenyl]ethynyl}pyridine-2-carboxylic acid;
5-(2-{2-[(decahydroisoquinoline-2-sulfonyl)amino]phenyl}ethynyl)pyridine-2-carboxylic acid;
5-{2-[2-(1-benzothiophene-3-sulfonamido)phenyl]ethynyl}pyridine-2-carboxylic acid;
5-{2-[2-(1,3-benzothiazole-4-sulfonamido)phenyl]ethynyl}pyridine-2-carboxylic acid;
5-{2-[5-fluoro-2-(quinoline-8-sulfonamido)phenyl]ethynyl}pyridine-2-carboxylic acid;
5-[2-(2-{2'-methoxy-[1,1'-biphenyl]-3-sulfonamido}phenyl)ethynyl]pyridine-2-carboxylic acid;
5-[2-(2-{N-[(naphthalen-2-yl)methyl]formamido}phenyl)ethynyl]pyridine-2-carboxylic acid;
5-[2-(2-{N-[(naphthalen-2-yl)methyl]acetamido}phenyl)ethynyl]pyridine-2-carboxylic acid;
5-{2-[2-(2-methoxyquinoline-8-sulfonamido)phenyl]ethynyl}pyridine-2-carboxylic acid;
5-{2-[2-(9H-fluorene-2-sulfonamido)phenyl]ethynyl}-3-methylpyridine-2-carboxylic acid;
5-{2-[2-(9H-fluorene-2-sulfonamido)phenyl]ethynyl}-4-methylpyridine-2-carboxylic acid;
5-[2-(2-{N-[(quinolin-2-yl)methyl]acetamido}phenyl)ethynyl]pyridine-2-carboxylic acid;
5-{2-[2-(9H-carbazole-2-sulfonamido)phenyl]ethynyl}pyridine-2-carboxylic acid;
5-(2-{2-[3-(2,6-dimethoxypyridin-3-yl)benzenesulfonamido]phenyl}ethynyl)pyridine-2-carboxylic acid;
5-(2-{2-[(2,3-dihydro-1H-indole-1-sulfonyl)amino]phenyl}ethynyl)pyridine-2-carboxylic acid;
5-(2-{2-[3-(6-methoxypyridin-2-yl)benzenesulfonamido]phenyl}ethynyl)-pyridine-2-carboxylic acid;

5-{2-[2-(4-bromonaphthalene-1-sulfonamido)phenyl]ethynyl}pyridine-2-carboxylic acid;

methyl 5-(2-{2-[3-(pyridin-3-yl)benzenesulfonamido]phenyl}ethynyl)pyridine-2-carboxylate;

methyl 5-(2-{2-[4-(1H-pyrazol-1-yl)benzenesulfonamido]phenyl}ethynyl)-pyridine-2-carboxylate;

methyl 5-[2-(2-{[1,1'-biphenyl]-2-sulfonamido}phenyl)ethynyl]pyridine-2-carboxylate;

methyl 4-methyl-5-{2-[2-(7-methylquinoline-8-sulfonamido)phenyl]ethynyl}pyridine-2-carboxylate;

5-[2-(2-{[1,1'-biphenyl]-4-sulfonamido}-5-fluorophenyl)ethynyl]-4-methyl-pyridine-2-carboxylic acid;

methyl 5-[2-(2-{[1,1'-biphenyl]-4-sulfonamido}-5-fluorophenyl)ethynyl]-4-methylpyridine-2-carboxylate;

methyl 5-[2-(2-{carbamoyl[(naphthalen-2-yl)methyl]amino}phenyl)-ethynyl]pyridine-2-carboxylate;

5-[2-(2-{[1,1'-biphenyl]-2-sulfonamido}phenyl)ethynyl]pyridine-2-carboxylic acid;

5-(2-{2-[4-(1H-pyrazol-1-yl)benzenesulfonamido]phenyl}ethynyl)pyridine-2-carboxylic acid;

5-[2-(2-{carbamoyl[(naphthalen-2-yl)methyl]amino}phenyl)ethynyl]pyridine-2-carboxylic acid;

5-{2-[2-(9-methyl-9H-carbazole-2-sulfonamido)phenyl]ethynyl}pyridine-2-carboxylic acid;

5-(2-{2-[(1,2,3,4-tetrahydro-1,8-naphthyridine-1-carbonyl)amino]phenyl}-ethynyl)pyridine-2-carboxylic acid;

4-[2-(2-{[1,1'-biphenyl]-4-sulfonamido}phenyl)ethynyl]benzoic acid;

5-[2-(2-{[N-(naphthalen-1-yl)acetamido]methyl}phenyl)ethynyl]pyridine-2-carboxylic acid;

3-(dimethylamino)-5-{2-[2-(7-methylquinoline-8-sulfonamido)phenyl]ethynyl}pyridine-2-carboxylic acid;

3-methoxy-5-{2-[2-(7-methylquinoline-8-sulfonamido)phenyl]ethynyl}pyridine-2-carboxylic acid;

5-(2-{2-[4-(cyclohex-1-en-1-yl)benzenesulfonamido]phenyl}ethynyl)pyridine-2-carboxylic acid;

5-[2-(2-{N-[(quinolin-8-yl)methyl]formamido}phenyl)ethynyl]pyridine-2-carboxylic acid;

5-(2-{2-[N-({2'-methoxy-[1,1'-biphenyl]-3-yl}methyl)formamido]phenyl}ethynyl)pyridine-2-carboxylic acid;

5-(2-{2-[N-({[1,1'-biphenyl]-3-yl}methyl)formamido]phenyl}ethynyl)pyridine-2-carboxylic acid;

5-{2-[4-bromo-2-(5-methoxyquinoline-8-sulfonamido)phenyl]ethynyl}pyridine-2-carboxylic acid;

5-{2-[4-bromo-2-(7-methylquinoline-8-sulfonamido)phenyl]ethynyl}pyridine-2-carboxylic acid;

4-(dimethylamino)-5-{2-[2-(7-methylquinoline-8-sulfonamido)phenyl]ethynyl}pyridine-2-carboxylic acid;

3-ethoxy-5-{2-[2-(7-methylquinoline-8-sulfonamido)phenyl]ethynyl}pyridine-2-carboxylic acid;

5-(2-{2-[N-({2'-methoxy-[1,1'-biphenyl]-2-yl}methyl)formamido]phenyl}-ethynyl)pyridine-2-carboxylic acid;

5-(2-{2-[N-({[1,1'-biphenyl]-4-yl}methyl)formamido]phenyl}ethynyl)-3-methylpyridine-2-carboxylic acid;

3-methyl-5-[2-(2-{N-[(naphthalen-2-yl)methyl]formamido}phenyl)-ethynyl]pyridine-2-carboxylic acid;

5-{2-[4-methoxy-2-(5-methoxyquinoline-8-sulfonamido)phenyl]ethynyl}-pyridine-2-carboxylic acid;

5-{2-[2-(9-methyl-9H-carbazole-4-sulfonamido)phenyl]ethynyl}pyridine-2-carboxylic acid;

5-[2-(2-{N-[2-(naphthalen-1-yl)ethyl]formamido}phenyl)ethynyl]pyridine-2-carboxylic acid;

N-(2-{2-[6-(3-hydroxyoxetan-3-yl)pyridin-3-yl]ethynyl}phenyl)-7-methylquinoline-8-sulfonamide;

5-[2-(2-{N-[(3-phenoxyphenyl)methyl]formamido}phenyl)ethynyl]pyridine-2-carboxylic acid 4-[2-(7-methylquinoline-8-sulfonamido)phenyl]ethynyl}isoquinoline-1-carboxylic acid;

4-{2-[2-(5-methoxyquinoline-8-sulfonamido)phenyl]ethynyl}isoquinoline-1-carboxylic acid;

N-hydroxy-5-{2-[2-(5-methoxyquinoline-8-sulfonamido)phenyl]-ethynyl}pyridine-2-carboxamide;

5-{2-[4-methoxy-2-(7-methylquinoline-8-sulfonamido)phenyl]ethynyl}pyridine-2-carboxylic acid;

4-methoxy-5-(2-{2-[(octahydro-1H-indole-1-sulfonyl)amino]phenyl}ethynyl)pyridine-2-carboxylic acid;

5-[2-(2-{N-[(6-phenylpyridin-3-yl)methyl]formamido}phenyl)ethynyl]pyridine-2-carboxylic acid;

N-hydroxy-4-methoxy-5-{2-[2-(5-methoxyquinoline-8-sulfonamido)phenyl]ethynyl}pyridine-2-carboxamide;

2-methoxy-4-{2-[2-(7-methylquinoline-8-sulfonamido)phenyl]ethynyl}benzoic acid;

2-methoxy-4-{2-[2-(5-methoxyquinoline-8-sulfonamido)phenyl]ethynyl}-benzoic acid;

4-{2-[2-(5-methoxyquinoline-8-sulfonamido)phenyl]ethynyl}-2-(methylamino)benzoic acid;

5-{2-[5-(dimethylamino)-2-(7-methylquinoline-8-sulfonamido)phenyl]ethynyl}pyridine-2-carboxylic acid;

4-[2-(4-Methoxy-2,3-dimethyl-benzenesulfonylamino)-phenylethynyl]-benzoic acid;

4-Methoxy-naphthalene-1-sulfonic acid [4-fluoro-2-(6-methanesulfonylaminocarbonyl-pyridin-2-ylethynyl)-phenyl]-amide;

4-[2-(4-Methoxy-naphthalene-2-sulfonylamino)-phenylethynyl]-benzoic acid;

5-[2-(3-Methyl-quinoline-8-sulfonylamino)-phenylethynyl]-pyridine-2-carboxylic acid;

5-[2-(4-Methyl-quinoline-8-sulfonylamino)-phenylethynyl]-pyridine-2-carboxylic acid;

5-[2-(6-Methyl-quinoline-8-sulfonylamino)-phenylethynyl]-pyridine-2-carboxylic acid;

5-[2-(2-Methyl-quinoline-8-sulfonylamino)-phenylethynyl]-pyridine-2-carboxylic acid;

4-[2-(3-Chloro-quinoline-8-sulfonylamino)-phenylethynyl]-benzoic acid

5-[2-(3-Chloro-quinoline-8-sulfonylamino)-phenylethynyl]-pyridine-2-carboxylic acid;

5-{2-[2-(4-methoxy-2,3,6-trimethylbenzenesulfonamido)phenyl]ethynyl}-pyridine-2-carboxylic acid;

4-{2-[2-(5-chloro-1-benzothiophene-2-sulfonamido)phenyl]ethynyl}benzoic acid;

5-{2-[4-fluoro-2-(naphthalene-1-sulfonamido)phenyl]ethynyl}pyridine-2-carboxylic acid;

5-[2-(2-{8-oxatricyclo[7.4.0.0$^{2,7}$]trideca-1(9),2(7),3,5,10,12-hexaene-4-sulfonamido}phenyl)ethynyl]pyridine-2-carboxylic acid;

5-{2-[2-(5-chloronaphthalene-1-sulfonamido)phenyl]ethynyl}pyridine-2-carboxylic acid;

5-[2-(2-{2'-methyl-[1,1'-biphenyl]-4-sulfonamido}phenyl)ethynyl]pyridine-2-carboxylic acid;

5-{2-[2-(6-fluoroquinoline-8-sulfonamido)phenyl]ethynyl}pyridine-2-carboxylic acid;

5-{2-[2-(3-acetamido-4-ethoxybenzenesulfonamido)phenyl]ethynyl}pyridine-2-carboxylic acid;

5-[2-(2-{8-oxatricyclo[7.4.0.0$^{2,7}$]trideca-1(9),2(7),3,5,10,12-hexaene-5-sulfonamido}phenyl)ethynyl]pyridine-2-carboxylic acid;

5-{2-[2-(1-methyl-1H-indole-4-sulfonamido)phenyl]ethynyl}pyridine-2-carboxylic acid;

5-[2-(2-{[1,1'-biphenyl]-4-sulfonamido}-5-fluorophenyl)ethynyl]-3-methylpyridine-2-carboxylic acid;

5-[2-(5-fluoro-2-{8-oxatricyclo[7.4.0.0²,⁷]trideca-1(9),2(7),3,5,10,12-hexaene-5-sulfonamido}phenyl)ethynyl]-3-methylpyridine-2-carboxylic acid;

5-{2-[5-fluoro-2-(5-methoxyquinoline-8-sulfonamido)phenyl]ethynyl}-3-methylpyridine-2-carboxylic acid;

5-{2-[2-(2,4-dichloroquinoline-8-sulfonamido)phenyl]ethynyl}pyridine-2-carboxylic acid;

5-{2-[2-(6-chloro-2-methylquinoline-8-sulfonamido)phenyl]ethynyl}pyridine-2-carboxylic acid;

5-{2-[2-(4-methoxyquinoline-8-sulfonamido)phenyl]ethynyl}pyridine-2-carboxylic acid;

5-[5-Ethoxy-2-(quinoline-8-sulfonylamino)-phenylethynyl]-pyridine-2-carboxylic acid;

4-(2-{2-[(E)-2-phenylethenesulfonamido]phenyl}ethynyl)benzoic acid 5-(2-{2-[4-(prop-2-yn-1-yloxy)quinoline-8-sulfonamido]phenyl}-ethynyl)pyridine-2-carboxylic acid;

2-methoxy-5-methyl-4-{2-[2-(7-methylquinoline-8-sulfonamido)phenyl]-ethynyl}benzoic acid;

5-[5-Chloro-2-(4-methoxy-benzenesulfonylamino)-phenylethynyl]-pyridine-2-carboxylic acid;

4-Methoxy-5-[2-(4-methoxy-benzenesulfonylamino)-phenylethynyl]-pyridine-2-carboxylic acid;

5-[2-(5-Methoxy-quinoline-8-sulfonylamino)-phenylethynyl]-pyridine-2-carboxylic acid isopropylamide;

4-[2-(4-Methoxy-2,3-dimethyl-benzenesulfonylamino)-phenylethynyl]-isoquinoline-1-carboxylic acid;

3-(hydroxymethyl)-5-{2-[2-(7-methylquinoline-8-sulfonamido)phenyl]-ethynyl}pyridine-2-carboxylic acid;

(2,2-dimethyl-1,3-dioxolan-4-yl)methyl 5-{2-[2-(7-methylquinoline-8-sulfonamido)phenyl]ethynyl}pyridine-2-carboxylate;

2-methoxyethyl 4-methoxy-5-{2-[2-(5-methoxyquinoline-8-sulfonamido)-phenyl]ethynyl}pyridine-2-carboxylate;

2-(2-hydroxyethoxy)ethyl 5-{2-[2-(7-methylquinoline-8-sulfonamido)-phenyl]ethynyl}pyridine-2-carboxylate;

2-methoxyethyl 5-{2-[2-(7-methylquinoline-8-sulfonamido)-phenyl]ethynyl}pyridine-2-carboxylate;

5-{2-[2-(5-ethylquinoline-8-sulfonamido)phenyl]ethynyl}pyridine-2-carboxylic acid;

8-{2-[2-(7-methylquinoline-8-sulfonamido)phenyl]ethynyl}-1H,2H,3H,4H-pyrido[3,4-b]pyrazine-5-carboxylic acid;

5-{2-[2-(7-methylquinoline-8-sulfonamido)-5-(propan-2-yl)phenyl]ethynyl}pyridine-2-carboxylic acid;

5-[2-(4-Dimethylamino-quinoline-8-sulfonylamino)-phenylethynyl]-4-methoxy-pyridine-2-carboxylic acid;

5-(2-{2-[5-(propan-2-yloxy)quinoline-8-sulfonamido]phenyl}ethynyl)pyridine-2-carboxylic acid;

5-{2-[5-bromo-2-(7-methylquinoline-8-sulfonamido)phenyl]ethynyl}pyridine-2-carboxylic acid;

5-{2-[5-bromo-4-fluoro-2-(7-methylquinoline-8-sulfonamido)phenyl]ethynyl}pyridine-2-carboxylic acid;

5-{2-[2-(7-ethylquinoline-8-sulfonamido)phenyl]ethynyl}pyridine-2-carboxylic acid;

5-{2-[5-chloro-2-(5-methoxyquinoline-8-sulfonamido)-3-methylphenyl]-ethynyl}pyridine-2-carboxylic acid;

5-{2-[2-(7-methoxyquinoline-8-sulfonamido)phenyl]ethynyl}pyridine-2-carboxylic acid;

5-{2-[2-(4-ethoxyquinoline-8-sulfonamido)phenyl]ethynyl}pyridine-2-carboxylic acid;

5-(2-{2-[4-(propan-2-yloxy)quinoline-8-sulfonamido]phenyl}ethynyl)pyridine-2-carboxylic acid;

5-{2-[4-(5-methoxyquinoline-8-sulfonamido)-[1,1'-biphenyl]-3-yl]ethynyl}pyridine-2-carboxylic acid;

5-{2-[2-chloro-6-(5-methoxyquinoline-8-sulfonamido)phenyl]ethynyl}pyridine-2-carboxylic acid;

5-{2-[5-bromo-2-(7-methylquinoline-8-sulfonamido)phenyl]ethynyl}-4-methoxypyridine-2-carboxylic acid;

5-{2-[2-(5-ethoxyquinoline-8-sulfonamido)phenyl]ethynyl}-4-methoxypyridine-2-carboxylic acid;

5-{2-[5-chloro-2-(7-methylquinoline-8-sulfonamido)phenyl]ethynyl}pyridine-2-carboxylic acid;

3-Ethyl-5-[2-(7-ethyl-quinoline-8-sulfonylamino)-phenylethynyl]-pyridine-2-carboxylic acid;

3-(ethylamino)-5-{2-[2-(4-methoxy-2,3-dimethylbenzenesulfonamido)-phenyl]ethynyl}pyridine-2-carboxylic acid;

5-{2-[2-(7-ethylquinoline-8-sulfonamido)phenyl]ethynyl}-3-(methylamino)pyridine-2-carboxylic acid;

5-{2-[2-(5,7-dimethylquinoline-8-sulfonamido)phenyl]ethynyl}pyridine-2-carboxylic acid;

2-methoxyethyl 4-methoxy-5-{2-[2-(7-methylquinoline-8-sulfonamido)phenyl]ethynyl}pyridine-2-carboxylate;

4-Methoxy-5-[2-(4-methylamino-quinoline-8-sulfonylamino)-phenylethynyl]-pyridine-2-carboxylic acid;

5-[2-(4-Dimethylamino-quinoline-8-sulfonylamino)-phenylethynyl]-4-methyl-pyridine-2-carboxylic acid;

5-[2-(2-{[(3-methoxyphenyl)(methyl)oxo-λ6-sulfanylidene]amino}-phenyl)ethynyl]pyridine-2-carboxylic acid;

4-{2-[2-(4-chloroquinoline-8-sulfonamido)phenyl]ethynyl}isoquinoline-1-carboxylic acid;

4-{2-[2-(5-ethoxyquinoline-8-sulfonamido)phenyl]ethynyl}isoquinoline-1-carboxylic acid;

4-{2-[2-(5,7-dimethylquinoline-8-sulfonamido)phenyl]ethynyl}isoquinoline-1-carboxylic acid;

4-(2-{2-[5-(propan-2-yloxy)quinoline-8-sulfonamido]phenyl}ethynyl)-isoquinoline-1-carboxylic acid;

4-[2-(2-{[methyl(oxo)(quinolin-8-yl)-λ6-sulfanylidene]amino}phenyl)ethynyl]isoquinoline-1-carboxylic acid 3-Ethyl-5-[2-(5-methoxy-quinoline-8-sulfonylamino)-phenylethynyl]-pyridine-2-carboxylic acid;

3-Ethyl-5-[2-(2-methyl-quinoline-8-sulfonylamino)-phenylethynyl]-pyridine-2-carboxylic acid;

5-[2-(5-Trifluoromethoxy-quinoline-8-sulfonylamino)-phenylethynyl]-pyridine-2-carboxylic acid;

4-Methoxy-5-[2-(5-trifluoromethoxy-quinoline-8-sulfonylamino)-phenylethynyl]-pyridine-2-carboxylic acid;

5-{2-[5-(2,2,2-Trifluoro-ethoxy)-quinoline-8-sulfonylamino]-phenylethynyl}-pyridine-2-carboxylic acid;

5-{5-Chloro-2-[5-(2,2,2-trifluoro-ethoxy)-quinoline-8-sulfonylamino]-phenylethynyl}-pyridine-2-carboxylic acid;

4-Methoxy-5-{2-[5-(2,2,2-trifluoro-ethoxy)-quinoline-8-sulfonylamino]-phenylethynyl}-pyridine-2-carboxylic acid;

5-{5-Chloro-2-[5-(2,2,2-trifluoro-ethoxy)-quinoline-8-sulfonylamino]-phenylethynyl}-4-methoxy-pyridine-2-carboxylic acid; and 3-Ethyl-5-[2-(7-methyl-quinoline-8-sulfonylamino)-phenylethynyl]-pyridine-2-carboxylic acid.

11. The Compound according to claim 10, or derivatives, N-oxides, prodrugs, solvates, tautomers or stereoisomers thereof and/or the pharmaceutically acceptable salts of each of the foregoing, wherein the compound is selected from the group consisting of 4-methoxy-5-{2-[2-(7-methylquinoline-8-sulfonamido)phenyl]ethynyl}pyridine-2-carboxylic acid;

5-(2-{2-[N-({[1,1'-biphenyl]-4-yl}methyl)formamido]phenyl}ethynyl)-4-methoxypyridine-2-carboxylic acid;

3-(methylamino)-5-{2-[2-(7-methylquinoline-8-sulfonamido)phenyl]-ethynyl}pyridine-2-carboxylic acid;

5-{2-[2-(5-methoxyquinoline-8-sulfonamido)phenyl]ethynyl}-3-(methylamino)pyridine-2-carboxylic acid;

5-{2-[5-iodo-2-(5-methoxyquinoline-8-sulfonamido)phenyl]ethynyl}pyridine-2-carboxylic acid;

4-methoxy-5-(2-{2-[N-({2'-methoxy-[1,1'-biphenyl]-4-yl}methyl)formamido]phenyl}ethynyl)pyridine-2-carboxylic acid;

5-[2-(2-{[(4a,8a-trans)-decahydroquinoline-1-sulfonyl]amino}phenyl)ethynyl]-4-methoxypyridine-2-carboxylic acid;

4-{2-[5-bromo-2-(5-methoxyquinoline-8-sulfonamido)phenyl]-ethynyl}isoquinoline-1-carboxylic acid;

5-{2-[5-chloro-2-(7-methylquinoline-8-sulfonamido)phenyl]ethynyl}-3-(methylamino)pyridine-2-carboxylic acid;

5-{2-[5-chloro-2-(5-methoxyquinoline-8-sulfonamido)phenyl]ethynyl}-3-(methylamino)pyridine-2-carboxylic acid;

5-{2-[5-chloro-2-(4-methoxy-2,3-dimethylbenzenesulfonamido)phenyl]ethynyl}-4-methoxypyridine-2-carboxylic acid;

5-{2-[5-bromo-4-fluoro-2-(5-methoxyquinoline-8-sulfonamido)phenyl]ethynyl}pyridine-2-carboxylic acid;

5-{2-[5-bromo-2-(5-methoxyquinoline-8-sulfonamido)phenyl]ethynyl}pyridine-2-carboxylic acid;

5-{2-[5-bromo-2-(5-methoxyquinoline-8-sulfonamido)phenyl]ethynyl}-4-methoxypyridine-2-carboxylic acid;

5-{2-[5-bromo-4-fluoro-2-(5-methoxyquinoline-8-sulfonamido)phenyl]ethynyl}-4-methoxypyridine-2-carboxylic acid;

5-{2-[5-chloro-2-(5-methoxyquinoline-8-sulfonamido)phenyl]ethynyl}pyridine-2-carboxylic acid;

5-{2-[5-chloro-2-(5-methoxyquinoline-8-sulfonamido)phenyl]ethynyl}-4-methoxypyridine-2-carboxylic acid;

5-{2-[5-chloro-2-(7-methylquinoline-8-sulfonamido)phenyl]ethynyl}-4-methoxypyridine-2-carboxylic acid;

5-{2-[5-chloro-2-(5-ethoxyquinoline-8-sulfonamido)phenyl]ethynyl}-4-methoxypyridine-2-carboxylic acid;

5-[2-(5-Methoxy-quinoline-8-sulfonylamino)-5-methyl-phenylethynyl]-pyridine-2-carboxylic acid;

4-Methoxy-5-[2-(5-trifluoromethoxy-quinoline-8-sulfonylamino)-phenylethynyl]-pyridine-2-carboxylic acid;

5-[5-Methyl-2-(7-methyl-quinoline-8-sulfonylamino)-phenylethynyl]-pyridine-2-carboxylic acid;

3-(ethylamino)-5-{2-[2-(quinoline-8-sulfonamido)phenyl]ethynyl}pyridine-2-carboxylic acid;

2,3-dihydroxypropyl 5-{2-[2-(7-methylquinoline-8-sulfonamido)phenyl]-ethynyl}pyridine-2-carboxylate 5-{2-[5-ethyl-2-(7-methylquinoline-8-sulfonamido)phenyl]ethynyl}pyridine-2-carboxylic acid;

5-{2-[2-(7-methylquinoline-8-sulfonamido)phenyl]ethynyl}pyridine-2-carboxylic acid;

5-{2-[2-(5-methoxyquinoline-8-sulfonamido)phenyl]ethynyl}-3-methylpyridine-2-carboxylic acid;

5-{2-[2-(9H-fluorene-2-sulfonamido)phenyl]ethynyl}pyridine-2-carboxylic acid;

3-methyl-5-{2-[2-(7-methylquinoline-8-sulfonamido)phenyl]ethynyl}pyridine-2-carboxylic acid;

4-methyl-5-{2-[2-(7-methylquinoline-8-sulfonamido)phenyl]ethynyl}pyridine-2-carboxylic acid;

5-[2-(2-{8-oxatricyclo[7.4.0.0$^{2,7}$]trideca-1(9),2(7),3,5,10,12-hexaene-6-sulfonamido}phenyl)ethynyl]pyridine-2-carboxylic acid;

5-{2-[2-(5-methoxyquinoline-8-sulfonamido)phenyl]ethynyl}-4-methylpyridine-2-carboxylic acid;

5-{2-[5-fluoro-2-(7-methylquinoline-8-sulfonamido)phenyl]ethynyl}pyridine-2-carboxylic acid;

methyl 5-{2-[2-(5-methoxyquinoline-8-sulfonamido)phenyl]ethynyl}-4-methylpyridine-2-carboxylate;

methyl 5-{2-[2-(5-methoxyquinoline-8-sulfonamido)phenyl]ethynyl}pyridine-2-carboxylate;

methyl 5-{2-[2-(9H-fluorene-2-sulfonamido)phenyl]ethynyl}pyridine-2-carboxylate;

methyl 5-{2-[5-fluoro-2-(7-methylquinoline-8-sulfonamido)phenyl]ethynyl}pyridine-2-carboxylate;

methyl 5-{2-[2-(7-methylquinoline-8-sulfonamido)phenyl]ethynyl}pyridine-2-carboxylate;

5-(2-{2-[(decahydroquinoline-1-sulfonyl)amino]phenyl}ethynyl)pyridine-2-carboxylic acid;

methyl 5-{2-[5-fluoro-2-(7-methylquinoline-8-sulfonamido)phenyl]ethynyl}-4-methylpyridine-2-carboxylate;

5-{2-[5-fluoro-2-(7-methylquinoline-8-sulfonamido)phenyl]ethynyl}-4-methylpyridine-2-carboxylic acid;

4-chloro-5-{2-[2-(7-methylquinoline-8-sulfonamido)phenyl]ethynyl}pyridine-2-carboxylic acid;

methyl 4-chloro-5-{2-[2-(7-methylquinoline-8-sulfonamido)phenyl]ethynyl}pyridine-2-carboxylate;

methyl 4-chloro-5-{2-[2-(5-methoxyquinoline-8-sulfonamido)phenyl]ethynyl}pyridine-2-carboxylate;

5-{2-[2-(7-methylquinoline-8-sulfonamido)phenyl]ethynyl}-4-(prop-1-en-2-yl)pyridine-2-carboxylic acid;

4-chloro-5-{2-[2-(5-methoxyquinoline-8-sulfonamido)phenyl]ethynyl}pyridine-2-carboxylic acid;

4-{2-[2-(7-methylquinoline-8-sulfonamido)phenyl]ethynyl}benzoic acid;

5-[2-(2-{[(4aR,8aS)-decahydroquinoline-1-sulfonyl]amino}phenyl)ethynyl]pyridine-2-carboxylic acid;

ethyl 5-{2-[2-(5-methoxyquinoline-8-sulfonamido)phenyl]ethynyl}pyridine-2-carboxylate;

propyl 5-{2-[2-(5-methoxyquinoline-8-sulfonamido)phenyl]ethynyl}pyridine-2-carboxylate;

propan-2-yl 5-{2-[2-(5-methoxyquinoline-8-sulfonamido)phenyl]ethynyl}pyridine-2-carboxylate;

butyl 5-{2-[2-(5-methoxyquinoline-8-sulfonamido)phenyl]ethynyl}pyridine-2-carboxylate;

4-methoxy-5-{2-[2-(5-methoxyquinoline-8-sulfonamido)phenyl]ethynyl}pyridine-2-carboxylic acid;

benzyl 5-{2-[2-(5-methoxyquinoline-8-sulfonamido)phenyl]ethynyl}pyridine-2-carboxylate;

4-ethoxy-5-{2-[2-(5-methoxyquinoline-8-sulfonamido)phenyl]ethynyl}pyridine-2-carboxylic acid;

4-ethoxy-5-{2-[2-(7-methylquinoline-8-sulfonamido)phenyl]ethynyl}pyridine-2-carboxylic acid;

5-(2-{2-[N-({[1,1'-biphenyl]-4-yl}methyl)formamido]phenyl}ethynyl)pyridine-2-carboxylic acid;

5-{2-[5-fluoro-2-(5-methoxyquinoline-8-sulfonamido)phenyl]ethynyl}pyridine-2-carboxylic acid;

5-{2-[4,5-dichloro-2-(5-methoxyquinoline-8-sulfonamido)phenyl]ethynyl}pyridine-2-carboxylic acid;

5-(2-{2-[N-({2'-methoxy-[1,1'-biphenyl]-4-yl}methyl)formamido]phenyl}ethynyl)pyridine-2-carboxylic acid;

5-{2-[4-chloro-2-(5-methoxyquinoline-8-sulfonamido)phenyl]ethynyl}pyridine-2-carboxylic acid;

5-(2-{2-[N-({2'-methoxy-[1,1'-biphenyl]-4-yl}methyl)formamido]phenyl}ethynyl)pyridine-2-carboxylic acid;

5-[2-(2-{[N-(naphthalen-2-yl)formamido]methyl}phenyl)ethynyl]pyridine-2-carboxylic acid;

5-{2-[4,5-dichloro-2-(7-methylquinoline-8-sulfonamido)phenyl]ethynyl}pyridine-2-carboxylic acid;

5-{2-[2-(5-methoxyquinoline-8-sulfonamido)phenyl]ethynyl}-3-(methylamino)pyridine-2-carboxylic acid;

5-{2-[2-(7-ethoxyquinoline-8-sulfonamido)phenyl]ethynyl}pyridine-2-carboxylic acid;

5-(2-{2-[7-(propan-2-yloxy)quinoline-8-sulfonamido]phenyl}ethynyl)pyridine-2-carboxylic acid 5-(2-{2-[N-({3-methoxy-[1,1'-biphenyl]-4-yl}methyl)formamido]phenyl}ethynyl)pyridine-2-carboxylic acid;

4-methoxy-5-[2-(2-{[(4-methyl-decahydroquinolin-1-yl)sulfonyl]amino}phenyl)ethynyl]pyridine-2-carboxylic acid;

5-[2-(2-{[(4a,8a-trans)-decahydroquinoline-1-sulfonyl]amino}phenyl)ethynyl]-3-methylpyridine-2-carboxylic acid;

5-{2-[2-(7-methylquinoline-8-sulfonamido)phenyl]ethynyl}-4-phenylpyridine-2-carboxylic acid;

5-{2-[2-(9-methyl-9H-carbazole-3-sulfonamido)phenyl]ethynyl}pyridine-2-carboxylic acid;

5-[2-(2-{[(4-methyl-decahydroquinolin-1-yl)sulfonyl]amino}phenyl)ethynyl]pyridine-2-carboxylic acid;

4-{2-[5-bromo-2-(7-methylquinoline-8-sulfonamido)phenyl]ethynyl}isoquinoline-1-carboxylic acid;

4-{2-[5-chloro-2-(7-methylquinoline-8-sulfonamido)phenyl]ethynyl}isoquinoline-1-carboxylic acid;

4-{2-[5-chloro-2-(5-methoxyquinoline-8-sulfonamido)phenyl]ethynyl}isoquinoline-1-carboxylic acid;

2-(methylamino)-4-{2-[2-(7-methylquinoline-8-sulfonamido)phenyl]ethynyl}benzoic acid;

4-methoxy-5-{2-[2-(4-methoxy-2,3-dimethylbenzenesulfonamido)-phenyl]ethynyl}pyridine-2-carboxylic acid;

methyl 5-{2-[2-(7-methylquinoline-8-sulfonamido)-5-nitrophenyl]ethynyl}-pyridine-2-carboxylate;

5-{2-[5-methoxy-2-(7-methylquinoline-8-sulfonamido)phenyl]ethynyl}pyridine-2-carboxylic acid;

5-[2-(4-Chloro-quinoline-8-sulfonylamino)-phenylethynyl]-pyridine-2-carboxylic acid;

5-{2-[2-(4-ethoxynaphthalene-1-sulfonamido)phenyl]ethynyl}pyridine-2-carboxylic acid;

5-[2-(2-{[1,1'-biphenyl]-4-sulfonamido}phenyl)ethynyl]pyridine-2-carboxylic acid;

5-(2-{2-[4-(propan-2-yloxy)naphthalene-1-sulfonamido]phenyl}ethynyl)pyridine-2-carboxylic acid;

5-{2-[2-(3,4-dichloroquinoline-8-sulfonamido)phenyl]ethynyl}pyridine-2-carboxylic acid;

5-{2-[2-(4,7-dichloroquinoline-8-sulfonamido)phenyl]ethynyl}pyridine-2-carboxylic acid;

5-{2-[2-(5,6,7-trimethylquinoline-8-sulfonamido)phenyl]ethynyl}pyridine-2-carboxylic acid;

5-{2-[2-(5,7-dichloroquinoline-8-sulfonamido)phenyl]ethynyl}pyridine-2-carboxylic acid;

5-{2-[5-fluoro-2-(7-methylquinoline-8-sulfonamido)phenyl]ethynyl}-3-methylpyridine-2-carboxylic acid;

5-{2-[2-(4,7-dimethylquinoline-8-sulfonamido)phenyl]ethynyl}pyridine-2-carboxylic acid;

5-{2-[2-(7-bromo-2-chloroquinoline-8-sulfonamido)phenyl]ethynyl}pyridine-2-carboxylic acid;

5-{2-[2-(7-bromo-4-chloroquinoline-8-sulfonamido)phenyl]ethynyl}pyridine-2-carboxylic acid;

5-{2-[2-(4-chloro-7-fluoroquinoline-8-sulfonamido)phenyl]ethynyl}pyridine-2-carboxylic acid;

5-{2-[2-(5-ethoxyquinoline-8-sulfonamido)phenyl]ethynyl}pyridine-2-carboxylic acid;

3-Ethyl-5-[2-(quinoline-8-sulfonylamino)-phenylethynyl]-pyridine-2-carboxylic acid;

5-{2-[5-bromo-4-fluoro-2-(7-methylquinoline-8-sulfonamido)phenyl]ethynyl}-4-methoxypyridine-2-carboxylic acid;

4-methoxy-5-{2-[2-(quinoline-8-sulfonamido)phenyl]ethynyl}pyridine-2-carboxylic acid;

3-Methyl-5-[2-(5-trifluoromethoxy-quinoline-8-sulfonylamino)-phenylethynyl]-pyridine-2-carboxylic acid;

5-[2-(5-Trifluoromethoxy-quinoline-8-sulfonylamino)-phenylethynyl]-pyridine-2-carboxylic acid;

5-[5-Chloro-2-(4-methoxy-2,3-dimethyl-benzenesulfonylamino)-phenylethynyl]-pyridine-2-carboxylic acid;

5-[5-Chloro-2-(4-methoxy-benzenesulfonylamino)-phenylethynyl]-4-methoxy-pyridine-2-carboxylic acid;

5-[5-Methoxy-2-(5-methoxy-quinoline-8-sulfonylamino)-phenylethynyl]-pyridine-2-carboxylic acid;

4-{2-[5-bromo-2-(4-methoxy-2,3-dimethylbenzenesulfonamido)phenyl]-ethynyl}isoquinoline-1-carboxylic acid;

4-[5-Chloro-2-(4-methoxy-2,3-dimethyl-benzenesulfonylamino)-phenylethynyl]-isoquinoline-1-carboxylic acid;

7-methyl-N-[2-(2-{7-oxo-5H,7H-furo[3,4-b]pyridin-3-yl}ethynyl)phenyl]-quinoline-8-sulfonamide;

3-amino-5-{2-[2-(4-methoxy-2,3-dimethylbenzenesulfonamido)phenyl]-ethynyl}pyridine-2-carboxylic acid;

5-{2-[5-chloro-2-(4-methoxy-2,3-dimethylbenzenesulfonamido)phenyl]-ethynyl}-3-(methylamino)pyridine-2-carboxylic acid;

(2,2-dimethyl-1,3-dioxolan-4-yl)methyl 4-methoxy-5-{2-[2-(7-methylquinoline-8-sulfonamido)phenyl]ethynyl}pyridine-2-carboxylate 2,3-dihydroxypropyl 4-methoxy-5-{2-[2-(7-methylquinoline-8-sulfonamido)phenyl]ethynyl}pyridine-2-carboxylate;

5-{2-[2-(4-methoxy-2,3-dimethylbenzenesulfonamido)-5-methylphenyl]-ethynyl}pyridine-2-carboxylic acid;

5-{2-[2-(5-propylquinoline-8-sulfonamido)phenyl]ethynyl}pyridine-2-carboxylic acid;

5-(2-{2-[5-(propan-2-yloxy)quinoline-8-sulfonamido]phenyl}ethynyl)pyridine-2-carboxylic acid;

5-{2-[5-bromo-2-(7-methylquinoline-8-sulfonamido)phenyl]ethynyl}pyridine-2-carboxylic acid;

5-{2-[5-bromo-4-fluoro-2-(7-methylquinoline-8-sulfonamido)phenyl]ethynyl}pyridine-2-carboxylic acid;

5-{2-[2-(7-ethylquinoline-8-sulfonamido)phenyl]ethynyl}pyridine-2-carboxylic acid;

5-{2-[2-(4-ethoxyquinoline-8-sulfonamido)phenyl]ethynyl}pyridine-2-carboxylic acid;

5-{2-[5-bromo-2-(7-methylquinoline-8-sulfonamido)phenyl]ethynyl}-4-methoxypyridine-2-carboxylic acid;

5-{2-[2-(5-ethoxyquinoline-8-sulfonamido)phenyl]ethynyl}-4-methoxypyridine-2-carboxylic acid;

5-{2-[5-chloro-2-(7-methylquinoline-8-sulfonamido)phenyl]ethynyl}pyridine-2-carboxylic acid;

3-Ethyl-5-[2-(7-ethyl-quinoline-8-sulfonylamino)-phenylethynyl]-pyridine-2-carboxylic acid;

3-(ethylamino)-5-{2-[2-(4-methoxy-2,3-dimethylbenzenesulfonamido)-phenyl]ethynyl}pyridine-2-carboxylic acid;

5-{2-[2-(7-ethylquinoline-8-sulfonamido)phenyl]ethynyl}-3-(methylamino)pyridine-2-carboxylic acid;

5-{2-[2-(5,7-dimethylquinoline-8-sulfonamido)phenyl]ethynyl}pyridine-2-carboxylic acid;

2-methoxyethyl 4-methoxy-5-{2-[2-(7-methylquinoline-8-sulfonamido)phenyl]ethynyl}pyridine-2-carboxylate;

4-Methoxy-5-[2-(4-methylamino-quinoline-8-sulfonylamino)-phenylethynyl]-pyridine-2-carboxylic acid;

4-{2-[2-(5-ethoxyquinoline-8-sulfonamido)phenyl]ethynyl}isoquinoline-1-carboxylic acid;

3-Ethyl-5-[2-(5-methoxy-quinoline-8-sulfonylamino)-phenylethynyl]-pyridine-2-carboxylic acid;

3-Ethyl-5-[2-(2-methyl-quinoline-8-sulfonylamino)-phenylethynyl]-pyridine-2-carboxylic acid;

5-[2-(5-Trifluoromethoxy-quinoline-8-sulfonylamino)-phenylethynyl]-pyridine-2-carboxylic acid;

4-Methoxy-5-[2-(5-trifluoromethoxy-quinoline-8-sulfonylamino)-phenylethynyl]-pyridine-2-carboxylic acid;

5-{2-[5-(2,2,2-Trifluoro-ethoxy)-quinoline-8-sulfonylamino]-phenylethynyl}-pyridine-2-carboxylic acid;

5-{5-Chloro-2-[5-(2,2,2-trifluoro-ethoxy)-quinoline-8-sulfonylamino]-phenylethynyl}-pyridine-2-carboxylic acid;

4-Methoxy-5-{2-[5-(2,2,2-trifluoro-ethoxy)-quinoline-8-sulfonylamino]-phenylethynyl}-pyridine-2-carboxylic acid;

5-{5-Chloro-2-[5-(2,2,2-trifluoro-ethoxy)-quinoline-8-sulfonylamino]-phenylethynyl}-4-methoxy-pyridine-2-carboxylic acid; and 3-Ethyl-5-[2-(7-methyl-quinoline-8-sulfonylamino)-phenylethynyl]-pyridine-2-carboxylic acid.

12. A method of treatment and/or prevention of a medical condition or disease that is affected by inhibiting monocarboxylate transporters (MCT), the method comprising administering to a subject the Compound according to claim 1, or derivatives, N-oxides, prodrugs, solvates, tautomers or stereoisomers thereof and/or the pharmaceutically acceptable salts of each of the foregoing.

13. The method of claim 12 wherein the medical condition or disease is selected from the group consisting of: adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, Wilms' tumor, Crohn's disease, ulcerative colitis, idiopathic pulmonary fibrosis, muscular dystrophy, rheumatoid arthritis, systemic sclerosis (scleroderma), and Huntington's disease.

14. A pharmaceutical composition comprising at least one compound according to claim 1, or derivatives, N-oxides, prodrugs, solvates, tautomers or stereoisomers thereof and/or the pharmaceutically acceptable salts of each of the foregoing, including mixtures thereof in all ratios, as active ingredient, together with a pharmaceutically acceptable carrier.

15. The pharmaceutical composition comprising at least one compound according to claim 1, or derivatives, N-oxides, prodrugs, solvates, tautomers or stereoisomers thereof and/or the pharmaceutically acceptable salts of each of the foregoing, including mixtures thereof in all ratios, as active ingredient, together with a pharmaceutically acceptable carrier, that further comprises a second active ingredient or its derivatives, N-oxides, prodrugs, solvates, tautomers or stereoisomers thereof as well as the pharmaceutically acceptable salts of each of the foregoing, including mixtures thereof in all ratios, wherein that second active ingredient is other than a compound of formula (I) as defined in claim 1.

16. A kit comprising separate packs of
a) a composition comprising an effective amount of a compound of formula (I) according to claim 1, or its derivatives, N-oxides, prodrugs, solvates, tautomers or stereoisomers thereof as well as the pharmaceutically acceptable salts of each of the foregoing, including mixtures thereof in all ratios; and
b) an effective amount of a further active ingredient that further active ingredient not being a compound of formula (I) as defined in claim 1.

17. A Process for manufacturing a compound according to claim 1, or derivatives, N-oxides, prodrugs, solvates, tautomers or stereoisomers thereof as well as the pharmaceutically acceptable salts of each of the foregoing, the process being characterized in that either
(A)
(a) a compound of formula (II)

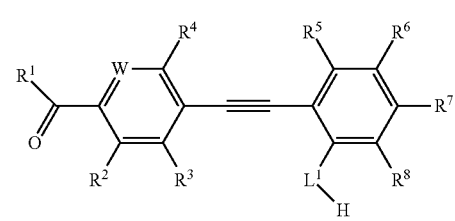

II wherein
$R^1$ is —$OR^a$;
$L^1$ is NH or $NR^a$; and
W, $R^2$, $R^3$, $R^4$, $R^5$, $R^6$, $R^7$, $R^8$ and $R^a$ are as defined in claim 1;
is reacted with a compound of formula (III)

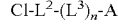

III wherein
n is an integer selected from 0 and 1;
$L^3$ is a divalent —CH=CH— radical;
to form a compound of formula (I)

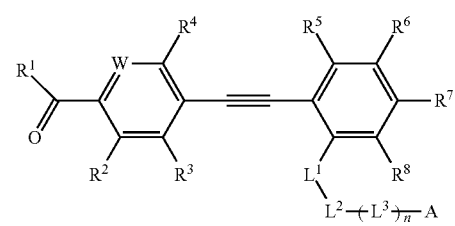

I wherein R¹ is OR$^a$;
(b) which compound of formula (I) optionally be converted into another compound of formula (I) wherein R¹ is —OH, —NH$_2$, —NHR$^a$, —NR$^a$R$^b$, —N(H)OH, —N(H)O—R$^a$, —N(H)CN, —N(H)—C(=O)—R$^a$, —N(H)—SO$_2$—R$^a$;

or (B)

(a) a compound of formula (IV)

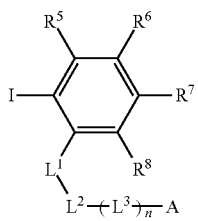

wherein
n is an integer selected from 0 and 1;
L¹ is —N(CHO)—, —N(C(=O)R$^a$)—, —N(C(=O)—NH$_2$)—, —N(C(=O)—NHR$^a$)— or —N(C(=O)—NR$^a$R$^b$)—;
L² is a divalent —CH$_2$— radical;
L³ is a divalent —CH$_2$— radical; or
L¹ is a divalent —CH$_2$— radical;
L² is —N(CHO)—, —N(C(=O)R$^a$)—, —N(C(=O)—NH$_2$)—, —N(C(=O)—NHR$^a$)— or —N(C(=O)—NR$^a$R$^b$)—;
R⁵, R⁶, R⁷, R⁸ and A are as defined in claim 1;
is reacted under suitable C—C-coupling reaction conditions with a compound of formula (V)

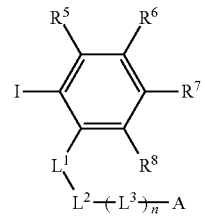

wherein
R¹ is OR$^a$; and
W, R², R³, R⁴ and R$^a$ are as defined in claim 1;
to form a compound of formula (I) as defined above; and
(b) which optionally be converted into a compound of formula (I) wherein R¹ is —OH, —NH$_2$, —NHR$^a$, —NR$^a$R$^b$, —N(H)OH, —N(H)O—R$^a$, —N(H)CN, —N(H)—C(=O)—R$^a$, —N(H)—SO$_2$—R$^a$;

or (C)

(a) a compound of formula (IV)

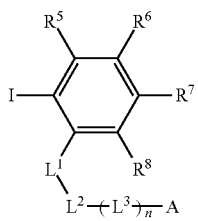

wherein
n is an integer selected from 0 and 1;
L² is a divalent —N(PG)- radical with PG being a suitable protecting group, e.g., tert.-butyloxy carbonyl (BOC); and
R⁵, R⁶, R⁷, R⁸ and A are as defined for claim 1;
is reacted under suitable C—C-coupling reaction conditions with a compound of formula (V)

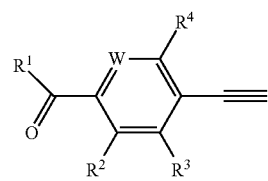

wherein
R¹ is OR$^a$; and
W, R², R³, R⁴ and R$^a$ are as defined in claim 1;
to form a compound of formula (VI)

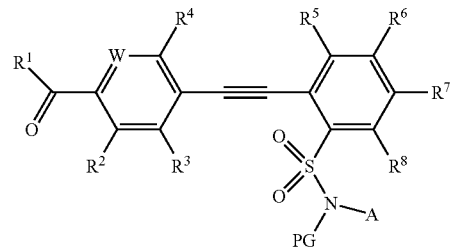

wherein
R¹ is OR$^a$
PG is that suitable protecting group, e.g. BOC; and
A, W, R², R³, R⁴, R⁵, R⁶, R⁷, R⁸ and R$^a$ are as defined in claim 1; and
(b) which is converted into a compound of formula (VII)

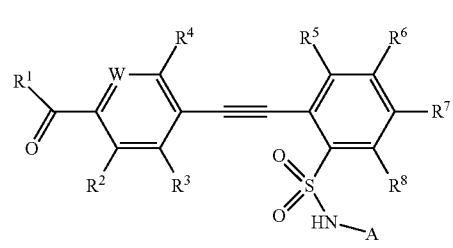

wherein
R¹ is OR$^a$; and
A; W, R², R³, R⁴, R⁵, R⁶, R⁷, R⁸ and R$^a$ are as defined in claim 1; and
(c) which optionally be converted into a compound of formula (I) wherein R¹ is —OH, —NH₂, —NHR$^a$, —NR$^a$R$^b$, —N(H)OH, —N(H)O—R$^a$, —N(H)CN, —N(H)—C(=O)—R$^a$, —N(H)—SO₂—R$^a$;
or
(D)
a compound of formula VIII

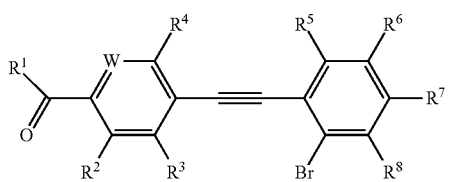

VIII wherein R¹ is —OR$^a$; and
W, R², R³, R⁴, R⁵, R⁶, R⁷, R⁸ and R$^a$ are as defined in claim 1;
is reacted with a compound of formula (IX)

H-L¹-L²-A          IX wherein
L¹ is a divalent —N=radical; and
L² is a divalent =S(=O)(R$^a$)— radical;
A is as defined in claim 1;
to form a compound of formula (I)

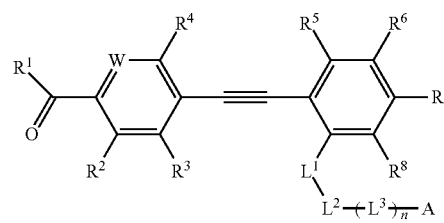

I wherein R¹ is OR$^a$; and
n is 0;
(b) which compound of formula (I) optionally be converted into another compound of formula (I) wherein R1 is —OH, —NH2, —NHRa, —NRaRb, —N(H)OH, —N(H)O—Ra, —N(H)CN, —N(H)—C(=O)—Ra, —N(H)—SO2-Ra.

* * * * *